United States Patent
Honda et al.

(10) Patent No.: US 6,340,702 B1
(45) Date of Patent: Jan. 22, 2002

(54) NEURAMINIC ACID DERIVATIVES, THEIR PREPARATION AND THEIR MEDICAL USE

(75) Inventors: Takeshi Honda, Tokyo; Yoshiyuki Kobayashi, Sagamihara; Takeshi Masuda, Tokyo; Makoto Yamashita, Urawa; Masami Arai, Kanagawa-ken, all of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/301,672

(22) Filed: Apr. 28, 1999

Related U.S. Application Data

(63) Continuation-in-part of application No. 09/249,420, filed on Feb. 12, 1999, which is a continuation-in-part of application No. 09/232,539, filed on Jan. 18, 1999, which is a continuation of application No. PCT/JP97/02810, filed on Aug. 12, 1997, which is a continuation of application No. 08/895,952, filed on Jul. 17, 1997.

(30) Foreign Application Priority Data

| Jul. 22, 1996 | (JP) | ............................................ 8-191862 |
| Aug. 13, 1996 | (JP) | ............................................ 8-213456 |
| Apr. 4, 1997 | (JP) | ............................................ 9-86888 |

(51) Int. Cl.⁷ ......................... A01N 43/16; C07D 315/00
(52) U.S. Cl. ..................... 514/451; 514/459; 514/460; 549/417; 549/419
(58) Field of Search ................................ 549/419, 417; 514/459, 460, 451

(56) References Cited

U.S. PATENT DOCUMENTS

| 5,360,817 A | 11/1994 | Von Itzstein et al. ....... 514/459 |
| 5,627,290 A | 5/1997 | Iida et al. .................... 549/419 |
| 5,639,786 A | 6/1997 | Von Itzstein et al. ....... 514/459 |
| 5,648,379 A | 7/1997 | Von Itzstein et al. ....... 514/459 |

FOREIGN PATENT DOCUMENTS

| EP | 0 539 204 A1 | 4/1993 | .................. 514/459 |
| EP | 823 428 A2 | 2/1998 | .................. 514/459 |
| WO | WO 91/16320 | 10/1991 | .................. 514/459 |
| WO | WO 95/16680 | 6/1995 | .................. 514/459 |
| WO | WO 95/18800 | 7/1995 | .................. 514/459 |
| WO | WO 95/20583 | 8/1995 | .................. 514/459 |
| WO | WO 97/06157 | 2/1997 | .................. 514/459 |

*Primary Examiner*—Alan L. Rotman
*Assistant Examiner*—Raymond Covington
(74) *Attorney, Agent, or Firm*—Frishauf, Holtz, Goodman, Langer & Chick, P.C.

(57) ABSTRACT

Compounds of formula (I) or their salts or esters:

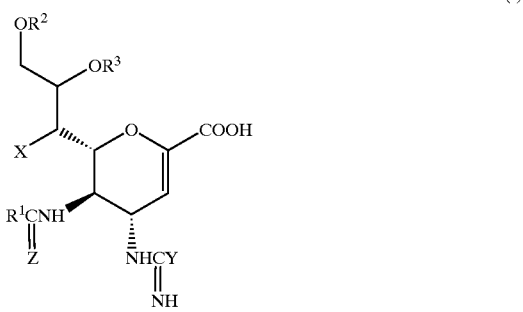

have excellent sialidase inhibitory activity and are therefore useful for the treatment and prevention of influenza and other viral diseases where the replication of the virus is susceptible to sialidase inhibitors.

71 Claims, No Drawings

NEURAMINIC ACID DERIVATIVES, THEIR PREPARATION AND THEIR MEDICAL USE

This application is:
(1) a C-I-P of Ser. No. 09/232,539 filed Jan. 18, 1999, which is a continuation of Ser. No. 08/895,952 filed Jul. 17, 1997; and
(2) a C-I-P of Ser. No. 09/249,420 filed Feb. 12, 1999, which is a continuation of International Application No. PCT/JP97/02810 filed Aug. 12, 1997.

BACKGROUND OF THE INVENTION

The present invention relates to a series of new neuraminic acid derivatives which have excellent sialidase inhibitory activity and which are therefore useful for the treatment and prevention of influenza and other viral diseases where the replication of the virus is susceptible to sialidase inhibitors. The invention also provides methods and compositions using these compounds for the treatment or prevention of influenza and similar viral infections, as well as processes for the preparation of these compounds.

The compounds of the present invention have a 2-deoxy-2,3-didehydro-N-acylneuraminic acid structure. Sialic acid is N-acetylneuraminic acid.

The influenza virus, as well as a number of other types of virus, have sialidase on the surface of the virus particles. As one of the processes by which such viruses proliferate, subviruses that have budded on the cell surface dissociate from the cell. Such subviruses are coupled to sialic acid on the cell surface mediated by hemagglutinin of the subvirus surface. Subviruses dissociate from the cell as a result of sialidase on the subvirus surface breaking down the sialic acid, thereby resulting in secondary infection of surrounding cells. Thus, inhibition of sialidase would make it possible to inhibit dissociation of subviruses from the cell surface, thereby preventing secondary infection. Accordingly, a substance that has the effect of inhibiting sialidase is considered to be effective in treating or preventing (but preferably treating) influenza.

A number of compounds having a sialidase inhibitory activity and a 2-deoxy-2,3-didehydro-N-acylneuraminic acid backbone are known from WO91/16320 (equivalent to Japanese Patent Publication (Kokoku) No. Hei 5-507068). Other such compounds are known from WO96/26933. These compounds (described in WO91/16320 (Japanese PCT Application (Kokai) No. Hei 5-507068)) include Compound A (GG-167), represented by the following formula which is being developed as a drug for the treatment of influenza.

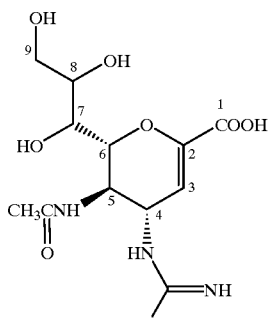

Compound A (GG-167)

We have now discovered a series of new compounds having a 2-deoxy-2,3-didehydro-N-acylneuraminic acid backbone which have excellent sialidase inhibitory activity, which is significantly greater than that of the prior art compounds referred to above, and which can thus be used for the treatment and prevention of influenza and other diseases caused by sialidase-bearing viruses.

BRIEF SUMMARY OF INVENTION

It is, therefore, an object of the present invention to provide a series of novel compounds having sialidase inhibitory activity.

Other objects and advantages of the present invention will become apparent as the description proceeds.

The compounds of the present invention are those compounds of formula (I):

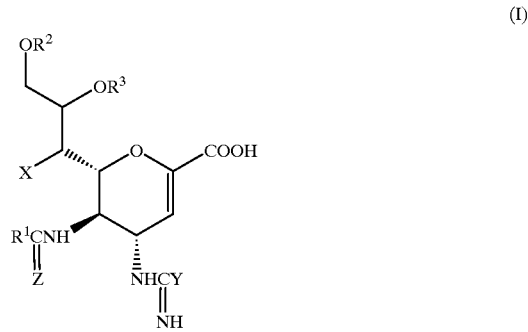

(I)

wherein:
  $R^1$ represents an alkyl group having from 1 to 4 carbon atoms or a haloalkyl group having from 1 to 4 carbon atoms;
  $R^2$ and $R^3$ are the same as or different from each other and each represents a hydrogen atom or an aliphatic acyl group having from 2 to 25 carbon atoms;
  X represents a hydroxy group, a halogen atom, an alkoxy group having from 1 to 4 carbon atoms, or a group of formula $R^aO$—, where $R^a$ represents an aliphatic acyl group having from 2 to 25 carbon atoms;
  Y represents a group of formula $R^bR^cN$— or $R^bR^cN$—O—, where $R^b$ and $R^c$ are the same as or different from each other and each represents a hydrogen atom or an alkyl group having from 1 to 4 carbon atoms; and
  Z represents an oxygen atom or a sulfur atom;
and pharmaceutically acceptable salts and esters thereof.

The invention also provides a pharmaceutical composition for the treatment or prevention of infections in a mammal, which may be human, caused by sialidase-bearing viruses, such as viruses of the influenza family, which composition comprises a sialidase inhibitory compound in admixture with a pharmaceutically acceptable carrier or diluent, wherein the sialidase inhibitory compound is at least one compound selected from the group consisting of compounds of formula (1) and pharmaceutically acceptable salts and esters thereof The invention still further provides a method of treating or preventing an infection in a mammal, which may be human, caused by a sialidase-bearing virus, such as a virus of the influenza family, which method comprises administering to said mammal an effective amount of a sialidase inhibitory compound, wherein the sialidase inhibitory compound is at least one compound selected from the group consisting of compounds of formula (I) and pharmaceutically acceptable salts and esters thereof.

The invention also provides processes for the preparation of the compounds of the present invention which processes are described in greater detail hereafter.

DETAILED DESCRIPTION OF THE INVENTION

In a first embodiment, there is provided a compound of formula (I):

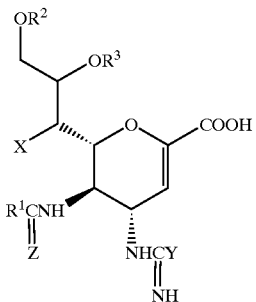

(I)

wherein:

$R^1$ represents an alkyl group having from 1 to 4 carbon atoms or a haloalkyl group having from 1 to 4 carbon atoms;

$R^2$ and $R^3$ are the same as or different from each other and each represents a hydrogen atom or an aliphatic acyl group having from 2 to 25 carbon atoms;

X represents a hydroxy group, a halogen atom, an alkoxy group having from 1 to 4 carbon atoms, or a group of formula $R^a$O—, where $R^a$ represents an aliphatic acyl group having from 2 to 25 carbon atoms;

Y represents a group of formula $R^b R^c$N— or $R^b R^c$N—O—, where $R^b$ and $R^c$ are the same as or different from each other and each represents a hydrogen atom or an alkyl group having from 1 to 4 carbon atoms; and Z represents an oxygen atom or a sulfur atom;

PROVIDED THAT, when Y represents an amino group and Z represents an oxygen atom, then X represents a halogen atom or an alkoxy group;

and pharmaceutically acceptable salts and esters thereof.

The compounds of the present invention are named on the basis of saccharide terminology, in which the main positions are numbered as shown in the following formula:

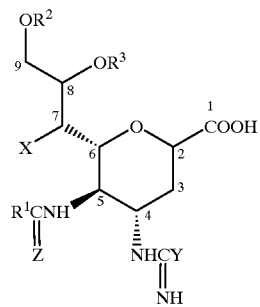

(I)

The compounds are named as derivatives of the unsaturated sugar non-2-enopyranosoic acid, of formula:

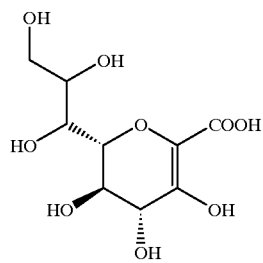

The configurations of the carbon atoms at the 4 to 7 positions are D-galacto, while that of the carbon atom at the 8 position is D-glycero, as can be seen from the following partial formula:

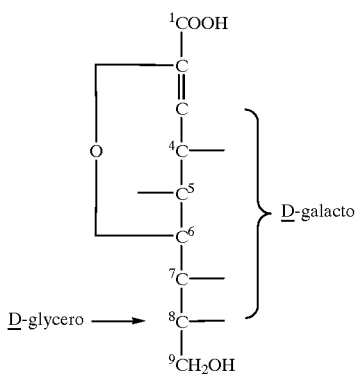

In the compounds of the present invention, where $R^1$ represents an alkyl group, this may be a straight or branched chain group having from 1 to 4 carbon atoms, and examples of such groups include the methyl, ethyl, propyl, isopropyl, butyl, isobutyl, sec-butyl and t-butyl groups, of which we prefer the methyl group.

Where $R^1$ represents a haloalkyl group, the halogen atom may be a fluorine, chlorine, bromine or iodine atom, preferably a fluorine, chlorine or bromine atom, and more preferably a fluorine atom. The alkyl part of this haloalkyl group may be any of the alkyl groups having from 1 to 4 carbon atoms listed above. Specific examples of such haloalkyl groups include the fluoromethyl, difluoromethyl, trifluoromethyl, 1-fluoroethyl, 2-fluoroethyl, 1-fluoropropyl, 2-fluoropropyl, 3-fluoropropyl, 4fluorobutyl, chloromethyl, 1-chloroethyl, 2-chloroethyl, 1-chloropropyl, 2-chloropropyl, 3-chloropropyl, bromomethyl, 1-bromoethyl, 2-bromoethyl, 1-bromopropyl, 2-bromopropyl, and 3-bromopropyl groups, of which we prefer a methyl group substituted with at least one fluorine atom, particularly the fluoromethyl or difluoromethyl groups.

More preferably $R^1$ represents a methyl group or a halomethyl group, particularly a methyl, fluoromethyl or difluoromethyl group, more preferably a methyl group.

Where $R^2$, $R^3$ or $R^a$ represents an aliphatic carboxylic acyl group having from 2 to 25 carbon atoms, this may be a straight or branched chain group; and is preferably an alkanoyl (alkylcarbonyl) group having from 2 to 25 carbon atoms. Specific examples of such groups include the acetyl, propionyl, butyryl, isobutyryl, pivaloyl, valeryl, isovaleryl, octanoyl, nonylcarbonyl, decylcarbonyl, 3-methylnonylcarbonyl, 8-methylnonylcarbonyl, 3-ethyloctylcarbonyl, 3,7direthyloctylcarbonyl, undecylcarbonyl, dodecylcarbonyl, tridecylcarbonyl, tetradecylcarbonyl, pentadecylcarbonyl, hexadecylcarbonyl, 1-methylpentadecylcarbonyl, 14methylpentadecylcarbonyl, 13,13-dimethyltetradecylcarbonyl, heptadecylcarbonyl, 15-methylhexadecylcarbonyl, octadecylcarbonyl, 1-methylheptadecylcarbonyl, nonadecylcarbonyl, icosylcarbonyl and tricosylcarbonyl groups. Of these, we prefer those alkylcarbonyl group having from 6 to 25 carbon atoms, more preferably those alkylcarbonyl groups having from 8 to 16 carbon atoms.

$R^2$ preferably represents a hydrogen atom or an aliphatic carboxylic acyl group having from 6 to 25 carbon atoms, more preferably an aliphatic carboxylic acyl group having from 8 to 16 carbon atoms, particularly an octanoyl, nonylcarbonyl, undecylcarbonyl, tridecylcarbonyl or pentadecylcarbonyl group.

$R^3$ preferably represents a hydrogen atom or an aliphatic carboxylic acyl group having from 6 to 25 carbon atoms, more preferably a hydrogen atom or an aliphatic carboxylic acyl group having from 8 to 16 carbon atoms, particularly an octanoyl, nonylcarbonyl, undecylcarbonyl, tridecylcarbonyl or pentadecylcarbonyl group.

Still more preferably, $R^2$ represents an aliphatic acyl group having from 8 to 16 carbon atoms (particularly an octanoyl, nonylcarbonyl, undecylcarbonyl, tridecylcarbonyl or pentadecylcarbonyl group), and $R^3$ represents a hydrogen atom.

Where X represents a halogen atom, this may be a fluorine, chlorine, bromine or iodine atom, preferably a fluorine, chlorine or bromine atom, and more preferably a fluorine atom;

Where X represents an alkoxy group having from 1 to 4 carbon atoms, this may be a straight or branched chain group, and examples include the methoxy, ethoxy, propoxy, isopropoxy, butoxy, isobutoxy, sec-butoxy and t-butoxy groups, of which we prefer the methoxy and ethoxy groups.

X preferably represents a fluorine atom, or a methoxy or ethoxy group.

Where Y represents a group of formula $R^bR^cN$— or $R^bR^cN$—O— and $R^b$ and/or $R^c$ represents an alkyl group having from 1 to 4 carbon atoms, this may be a straight or branched chain group, and examples include the methyl, ethyl, propyl, isopropyl, butyl, isobutyl, sec-butyl and t-butyl groups, of which we prefer the methyl group. However, we most prefer that at least one, and preferably both, of $R^b$ and $R^c$ should represent a hydrogen atom. Thus, the preferred group represented by $R^bR^cN$—O— is a group of formula $NH_2$—O—, and the preferred group represented by $R^bR^cN$— is $NH_2$—, i.e. an amino group.

Y preferably represents a group of formula $NH_2$ or $NH_2$—O—, more preferably an amino group of formula $NH_2$.

Z preferably represents an oxygen atom.

The compounds of the present invention contain a carboxy group, and can, therefore, form salts with cations. There is no particular restriction on the nature of these salts, provided that, where the compounds are to be used medically, the salts should be pharmaceutically acceptable, that is they should not be more toxic (or unacceptably more toxic) than the free acid, nor should they be less active (or unacceptably less active) than the free acid. When the compound is to be used for other purposes, for example as intermediates in the preparation of other, and possibly more active compounds, even this restriction does not apply. Examples of such salts include: alkali metal salts, such as the sodium salt, potassium and lithium salts; alkaline earth metal salts, such as the calcium and magnesium salts; other metal salts, such as the aluminum, iron, zinc, copper, nickel and cobalt salts; other inorganic salts, such as the ammonium salt; amine salts, such as the t-octylamine, dibenzylamine, morpholine, glucosamine, phenylglycine alkyl ester, ethylenediamine, methylglucanine, guanidine, diethylamine, triethylamine, dicyclohexylamine, N,N'-dibenzylethylenediamine, chloroprocaine, procaine, diethanolamine, benzyl-phenethylamine, piperazine, tetramethylammonium and tris(hydroxymethyl)aminomethane salts.

Furthermore, when the compound of the present invention contains a guadinino group, it can be also converted to a salt. Such salts, likewise, are not particularly restricted, except that, where they are for medical use, they should be pharmaceutically acceptable. Examples of such salts include: hydrohalides, such as the hydrofluoride, hydrochloride, hydrobromide or hydroiodide; other inorganic acid salts, such as the nitrate, perchlorate, a sulfate or phosphate; lower alkanesulfonates, such as the methanesulfonate, trifluoromethanesulfonate or ethanesulfonate; arylsulfonates, such as the benzenesulfonate or p-toluenesulfonate; organic acid salts, especially carboxylic acid salts, such as the acetate, trifluoroacetate, malate, fumarate, succinate, citrate, tartarate, oxalate or maleate; and amino acid salts, such as the glycine, lysine, arginine, ornithine, glutamic acid salt or aspartic acid salt. Of these, we prefer the alki metal salts, such as the sodium, potassium and lithium salts, organic acid salts, such as the acetate and trifluoroacetate and inorganic acid salts, such as the hydrochloride and sulfate.

Since the compounds of the present invention contain a carboxy group, they can form esters. There is no particular restriction on the nature of these esters, provided that, where the compounds are to be used medically, the esters should be pharmaceutically acceptable, that is they should not be more toxic (or unacceptably more toxic) than the free acid, nor should they be less active (or unacceptably less active) than the free acid. When the compound is to be used for other purposes, for example as intermediates in the preparation of other, and possibly more active compounds, even this restriction does not apply. Examples of groups which can form such esters include:

alkyl groups, preferably having from 1 to 30, more preferably from 1 to 25 carbon atoms, such as the methyl, ethyl, propyl, isopropyl, butyl, isobutyl, sec-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methypentyl, 3,3-dimethylbutyl, 2,2dimethylbutyl, 1,1-dimethylbutyl, 1,2dimethylbutyl, 1,3dimethylbutyl, 2,3-dimethylbutyl, 2-ethylbutylheptyl, 1-methylhexyl 2-methylhexyl, 3-methylhexyl, 4-methylhexyl, 5-methylhexyl, 1-propylbutyl, 4,4imethylpentyl, octyl, 1-methylheptyl, 2-methylheptyl, 3-methylheptyl, 4-methylheptyl, 5-methylheptyl, 6methylheptyl, 1-propylpentyl, 2-ethylhexyl, 5,5-dimethylhexyl, nonyl, 3-methyloctyl, 4-methyloctyl, 5-methyloctyl, 6-methyloctyl, 1-propylhexyl, 2-ethylheptyl, 6,6dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8imethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, 3.7,11,15-tetramethylhexadecyl, henicosyl and docosyl groups;

alkenyl groups, preferably having from 2 to 10, and more preferably from 2 to 8 carbon atoms, such as the ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl4pentenyl, 2-methylpentenyl, 1-hexenyl, 2-hexenyl, 3-hexenyl, 4-hexenyl and 5-hexenyl groups;

alkynyl groups, preferably having from 2 to 10, and more preferably from 2 to 8 carbon atoms, such as the ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl4pentynyl, 2-methyl4pentynyl, 2-hexynyl, 3-hexynyl, 4-hexynyl and 5-hexynyl groups;

haloalkyl groups, preferably having from 1 to 6, more preferably from 1 to 4, carbon atoms, such as the trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl and 2,2dibromoethyl groups;

hydroxyalkyl groups, preferably having from 1 to 6, more preferably from 1 to 4, carbon atoms, such as the 2-hydroxyethyl, 2,3dihydroxypropyl, 3-hydroxypropyl, 3,4-dihydroxybutyl and 4-hydroxybutyl groups;

aliphatic acyl-substituted alkyl groups, in which the alkyl part preferably has from 1 to 6 carbon atoms, and may be any such group of those listed above, and the aliphatic acyl group, such as those exemplified above in relation to $R^2$, and especially those having from 2 to 5 carbon atoms, such as the acetylmethyl group;

aralkyl groups in which an alkyl group having from 1 to 6 carbon atoms is substituted with from 1 to 3 unsubstituted carbocyclic aryl groups, such as the benzyl, phenethyl, 3-phenylpropyl, α-naphthylnethyl, β-naphthylmethyl, diphenylmethyl, triphenylmethyl, 6-phenylhexyl, α-naphthyldiphenylmethyl and 9-anthrylmethyl groups;

aralkyl groups in which an alkyl group having from 1 to 6 carbon atoms is substituted with from 1 to 3 substituted carbocyclic aryl groups, the subsituents being, for example, the alkyl, alkoxy, nitro, halogen, cyano oralkoxycarbonyl groups, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl, piperonyl and 4-methoxycarbonylbenzyl groups;

silyl groups, including trialkylsilyl, dialkylarylsilyl and alkyldiarylsilyl groups (the alkyl groups preferably having from 1 to 6 carbon atoms), such as the trimethylsilyl, triethylsilyl, isopropyldimethylsilyl, t-butyldimethylsilyl, methyldiisopropylsilyl, methyldi-t-butylsilyl, triisopropylsilyl, methyldiphenylsilyl, isopropyldiphenylsilyL butyldiphenylsilyl and phenyldiisopropylsilyl groups;

alkoxyalkyl groups in which the alkoxy and alkyl parts both have from 1 to 6, preferably from 1 to 4, carbon atoms, such as the methoxymethyl, 1-ethoxyethyl, 1-methyl-1-methoxyethyl, 1-(isopropoxy)ethyl, 2-methoxyethyl, 2-ethoxyethyl, 1,1-dimethyl-1-methoxymethyl, ethoxymethyl, propoxymethyl, isopropoxymethyl, butoxymethyl and t-butoxymethyl groups;

alkoxyalkoxyalkyl groups in which each of the alkoxy parts and the alkyl part all have from 1 to 6, preferably from 1 to 4, carbon atoms, such as the 2-methoxyethoxymethyl group;

aryloxyalkyl groups in which the alkyl part has from 1 to 6, preferably from 1 to 4, carbon atoms, such as the phenoxymethyl group;

halogenated alkoxyalkyl groups in which the alkoxy and alkyl parts both have from 1 to 6, preferably from 1 to 4, carbon atoms, such as the 2,2,2-trichloroethoxymethyl and bis(2-chloroethoxy)methyl groups;

alkoxycarbonylalkyl groups in which the alkoxy and alkyl parts both have from 1 to 6, preferably from 1 to 4, carbon atoms, such as the methoxycarbonylmethyl group;

cyanoalkyl groups in which the alkyl part has from 1 to 6, preferably front 1 to 4, carbon atoms, such as the cyanomethyl and 2-cyanoethyl groups;

alkylthiomethyl groups in which the alkyl part has from 1 to 6, preferably from 1 to 4, carbon atoms, such as the methylthiomethyl and ethylthiomethyl groups;

arylthiomethyl groups, such as the phenylthiomethyl and naphthylthiomethyl groups;

alkylsulfonylalkyl groups in which each of the alkyl parts has from 1 to 6, preferably from 1 to 4, carbon atoms and which may be substituted with one or more halogen atoms, such as the 2-methanesulfonylethyl and 2-trifluoromethanesulfonylethyl groups;

arylsulfonylalkyl groups in which the alkyl part has from 1 to 6, preferably from 1 to 4, carbon atoms, such as the 2-benzenesulfonylethyl and 2-toluenesulfonylethyl groups;

acyloxyalkyl groups, including
  aliphatic carboxylic acyloxyalkyl groups in which the alkyl part has from 1 to 6, preferably from 1 to 4, carbon atoms and the aliphatic acyl part has from 1 to 8, preferably from 2 to 5, carbon atoms, such as the formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl groups;

cycloalkylcarbonyloxyalkyl groups in which the alkyl part has from 1 to 6, preferably from 1 to 4, carbon atoms and the cycloalkyl part has from 3 to 8, preferably 5 or 6, carbon atoms, such as the cyclopentanecarbonyloxymethyl, cyclohexanecarbonyloxymethyl, 1-cyclopentanecarbonyloxyethyl, 1-cyclohexanecarbonyloxyethyl, 1-cyclopentanecarbonyloxypropyl, 1-cyclohexanecarbonyloxypropyl, 1-cyclopentanecarbonyloxybutyl and 1-cyclohexanecarbonyloxybutyl groups; aromatic acyloxyalkyl groups in which the alkyl part has from 1 to 6, preferably from 1 to 4, carbon atoms, such as the benzoyloxymethyl group;

(alkoxycarbonyloxy)alkyl groups in which the alkoxy and alkyl parts both have from 1 to 6, preferably from 1 to 4, carbon atoms, such as the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, 1-(methoxycarbonyloxy)ethyl, 1-(ethoxycarbonyloxy)ethyl, 1-propoxycarbonyloxyethyl, 1-(isopropoxycarbonyloxy)ethyl, 1-butoxycarbonyloxyethyl, 1-isobutoxycarbonyloxyethyl, 1tert-butoxycarbonyloxy)ethyl, 1-pentyloxycarbonyloxyethyl, 1-hexyloxycarbonyloxyethyl, 1-(ethoxycarbonyloxy)propyl, 2-methoxycarbonyloxyethyl, 2-ethoxycarbonyloxyethyl, 2-propoxycarbonyloxyethyl, 2-isopropoxycarbonyloxyethyl 2-butoxycarbonyloxyethyl, 2-isobutoxycarbonyloxyethyl 2-pentyloxycarbonyloxyethyl, 2-hexyloxycarbonyloxyethyl, 1-methoxycarbonyloxypropyl, 1-ethoxycarbonyloxypropyl, 1-propoxycarbonyloxypropyl, 1-isopropoxycarbonyloxypropyl, 1-butoxycarbonyloxypropyl, 1-isobutoxycarbonyloxypropyl, 1-pentyloxycarbonyloxypropyl, 1-hexyloxycarbonyloxypropyl, 1-methoxycarbonyloxybutyl, 1-ethoxycarbonyloxybutyl, 1-propoxycarbonyloxybutyl, 1-isopropoxycarbonyloxybutyl, 1-butoxycarbonyloxybutyl, 1-isobutoxycarbonyloxybutyl, 1-methoxycarbonyloxypentyl, 1-ethoxycarbonyloxypentyl, 1-methoxycarbonyloxyhexyl and 1-ethoxycarbonyloxyhexyl groups;

(cycloalkyloxycarbonyloxy)alkyl and (cycloalkyloxycarbonyloxy)(cycloalkyl)alkyl groups in which the alkyl part has from 1 to 6, preferably from 1 to 4, carbon atoms and the cycloalkyl part has from 3 to 8, preferably 5 or 6, carbon atoms, such as the cyclohexyloxycarbonyloxymethyl, cyclohexyloxycarbonyloxy(cyclohexyl)methyl, 1-cyclopentyloxycarbonyloxyethyl, 1-cyclopentyloxycarbonyloxypropyl, 1-cyclohexyloxycarbonyloxypropyl, 1-cyclopentyloxycarbonyloxybutyl, 1-cyclohexyloxycarbonyloxybutyl and 1-(cyclohexyloxycarbonyloxy)ethyl groups;

carbonyloxyalkyl groups in which the alkyl part has from 1 to 6, preferably from 1 to 4, carbon atoms, including oxodioxolenylmethyl groups, such as the (5-phenyl-2-oxo-1,3-dioxolen4-yl)methyl, [5-(4-methylphenyl)-2-oxo-1,3-dioxolen4-yl]methyl, [5-(4-methoxyphenyl)-2-oxo-1,3ioxolen 4-yl]methyl, [5-(4-fluorophenyl)2-oxo-1,3-ioxolen4-yl]methyl, [5-(4-chlorophenyl)-2-oxo-1,3-dioxolen4-yl]methyl, (2-oxo-1,3-dioxolen4-yl)methyl, (5-methyl-2-oxo-1,3-dioxolen 4-yl)methyl, (5-ethyl-2-oxo-1,3-dioxolen-4yl)methyl, (5-propyl-2-oxo-1,3dioxolen-4-yl)methyl, (5-isopropyl-2-oxo-1,3-dioxolen-4-yl)methyl and (5-butyl-2-oxo-1,3ioxolen 4-yl)methyl groups;

phthalidyl and substituted phthalidyl groups, such as the phthalidyl, dimethylphthalidyl and dimethoxyphthalidyl groups;

aryl groups, preferably having from 6 to 14 carbon atoms in one or more carbocyclic rings, such as the phenyl and indanyl groups;

carboxyalkyl groups in which the alkyl part has from 1 to 6, preferably from 1 to 4, carbon atoms, such as the carboxymethyl group; and amide forming residues of amino acid.

Of the ester groups listed above, the following are cleavable by a biological method such as hydrolysis in a living body;. that is the esters produce free acids or salts by hydrolysis or a similar reaction in a human body, specifically:

alkyl groups, alkoxyalkyl groups, alkoxyalkoxyalkyl groups, aryloxyalkyl groups, halogenated alkoxyalkyl groups, alkoxycarbonylalkyl groups, cyanoalkyl groups, alkylthiomethyl groups, alkylsulfonylalkyl groups, arylsulfonylalkyl groups, acyloxyalkyl groups, (alkoxycarbonyloxy)alkyl groups, (cycloalkyloxycarbonyloxy)alkyl groups, (cycloalkyloxycarbonyloxy)(cycloalkyl)alkyl groups, carbonyloxyalkyl groups, phthalidyl and substituted phthalidyl groups, aryl groups, carboxyalkyl groups, and amide forming residues of amino acid.

Of these, we prefer the straight or branched alkyl groups having from 6 to 25 carbon atoms, more preferably an alkyl group having 16 to 25 carbon atoms.

The compound of the present invention, when it is allowed to stand in the atmosphere, may absorb some moisture, and it may, as a result, be associated with adsorption water or it may be converted to a hydrate. Such hydrates also form part of the present invention.

Preferred classes of compounds of the present invention are those compounds of formula (I) and pharmaceutically acceptable salts and esters thereof in which:

(A) $R^1$ represents a methyl or halomethyl group.

(B) $R^2$ represents a hydrogen atom or an aliphatic carboxylic acyl group having from 6 to 25 carbon atoms.

(C) $R^3$ represents a hydrogen atom or an aliphatic carboxylic acyl group having from 6 to 25 carbon atoms.

(D) X represents a halogen atom or an alkoxy group having from 1 to 4 carbon atoms.

(E) Y represents an amino group or a group of formula $R^b R^c N-O-$, where $R^b$ and $R^c$ are as defined above.

Of the above compounds, we particularly prefer those compounds of formula (I) and pharmaceutically acceptable salts and esters thereof wherein $R^1$ is as defined in (A) above, $R^2$ is as defined in (B) above, $R^3$ is as defined in (C) above, X is as defined in (D) above, and Y is as defined in E) above, especially those in which $R^1$ is as defined in (A) above, $R^2$ is as defined in (B) above, $R^3$ is as defined in (C) above, X is as defined in (I) above, Y is as defined in (E) above, and Z represents an oxygen atom.

More preferred classes of compounds of the present invention are those compounds of formula (I) and pharmaceutically acceptable salts and esters thereof wherein:

(F) $R^1$ represents a methyl group or a methyl group having at least one flourine substituent.

(G) $R^2$ represents a hydrogen atom or an aliphatic carboxylic acyl group having from 8 to 16 carbon atoms.

(H) $R^3$ represents a hydrogen atom or an aliphatic carboxylic acyl group having from 8 to 16 carbon atoms.

(I) X represents a fluorine atom, a methoxy group or an ethoxy group.

(J) Y represents an amino group or an aminooxy group.

(K) Z represents an oxygen atom.

Of the above compounds, we particularly prefer those compounds of formula (I) and pharmaceutically acceptable salts and esters thereof wherein $R^1$ is as defined in (F) above, $R^2$ is as defined in (G) above, $R^3$ is as defined in (H) above, X is as defined in (I) above, Y is as defined in (J) above, and Z is as defined in (K) above.

A still more preferred class of compounds of the present invention are those compounds of formula (I) and pharmaceutically acceptable salts and esters thereof wherein:

(L) $R^2$ represents a hydrogen atom or an aliphatic carboxylic acyl group having from 8 to 16 carbon atoms and $R^3$ represents a hydrogen atom.

Of the above compounds, we particularly prefer those compounds of formula (I) and pharmaceutically acceptable salts and esters thereof wherein $R^1$ is as defined in (F) above, $R^2$ and $R^3$ are as defined in (L) above, X is as defined in (I) above, Y is as defined in (J) above, and Z is as defined in (K) above.

Further more preferred classes of compounds of the present invention are those compounds of formula (I) and pharmaceutically acceptable salts and esters thereof wherein:

(M) $R^1$ represents a methyl, fluoromethyl or difluoromethyl group.

(N) $R^2$ represents an octanoyl, decanoyl, dodecanoyl, myristoyl or paimitoyl group.

(O) $R^3$ represents a hydrogen atom, or an octanoyl, decanoyl, dodecanoyl, myristoyl or palmitoyl group.

(P) Y represents an amino group.

Of the above compounds, we particularly prefer those compounds of formula (I) and pharmaceutically acceptable salts and esters thereof wherein $R^1$ is as defined in (M) above, $R^2$ is as defined in (N) above, $R^3$ is as defined in (O) above, X is as defined in (I) above, Y is as defined in (P) above, and Z is as defined in (K) above.

Further more preferred classes of compounds of the present invention are those compounds of formula (I) and pharmaceutically acceptable salts and esters thereof wherein:

(Q) $R^1$ represents a methyl group.

(R) $R^2$ represents an octanoyl, decanoyl, dodecanoyl, myristoyl or palmitoyl group and $R^3$ represents a hydrogen atom.

Of the above compounds, we particularly prefer those compounds of formula (I) and pharmaceutically acceptable salts and esters thereof wherein $R^1$ is as defined in (Q) above, $R^2$ and $R^3$ are as defined in (R) above, X is as defined in (I) above, Y is as defined in (P) above, and Z is as defined in (K) above.

Specific compounds of the present invention are exemplified below by the following formula (I'), in which the substituent groups are as defined in the following Tables 1 and 2. Any individual compound may be defined by taking the combination of definitions of $R^1$, X, Y and Z in any row of Table 1 and combining them with the combination of definitions of $R^2$, $R^3$ and W in any row of Table 2. The compound may then be identified by a number in the form α-β, where α is the number of the respective row of Table 1 and β is the number of the respective row of Table 2. Thus, for example, the compound of formula (I"), given below, which is a compound of formula (I') in which $R^1$ represents a methyl group, X represents a fluorine atom, Y represents an amino group, Z represents an oxygen atom (row 1 of Table 1), $R^2$ represents a hydrogen atom, $R^3$ represents a hydrogen atom and W represents an undecyl group (row 4 of Table 2) is Compound No. 1-4.

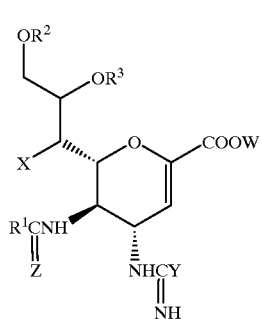

(I')

-continued

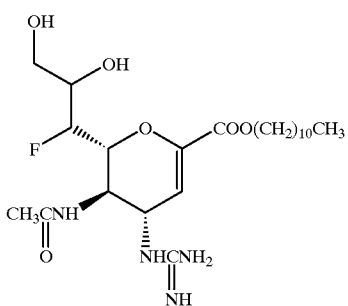

(I'')

In the Tables, the following abbreviations are used:

| | |
|---|---|
| Bu | butyl |
| iBu | isobutyl |
| Et | ethyl |
| Me | methyl |
| Pr | propyl |
| iPr | isopropyl |

TABLE 1

| Cpd. No. | R¹ | X | Y | Z |
|---|---|---|---|---|
| 1 | $CH_3$ | F | $NH_2$ | O |
| 2 | $CF_2H$ | F | $NH_2$ | O |
| 3 | $CFH_2$ | F | $NH_2$ | O |
| 4 | $CH_3$ | F | $NH_2$ | S |
| 5 | $CF_2H$ | F | $NH_2$ | S |
| 6 | $CFH_2$ | F | $NH_2$ | S |
| 7 | $CH_3$ | F | $ONH_2$ | O |
| 8 | $CF_2H$ | F | $ONH_2$ | O |
| 9 | $CFH_2$ | F | $ONH_2$ | O |
| 10 | $CH_3$ | F | $ONH_2$ | S |
| 11 | $CF_2H$ | F | $ONH_2$ | S |
| 12 | $CFH_2$ | F | $ONH_2$ | S |
| 13 | $CH_3$ | F | ONHMe | O |
| 14 | $CF_2H$ | F | ONHEt | O |
| 15 | $CFH_2$ | F | ONHPr | O |
| 16 | $CH_3$ | F | ONHMe | S |
| 17 | $CF_2H$ | F | ONHBU | S |
| 18 | $CFH_2$ | F | ONHMe | S |
| 19 | $CH_3$ | F | $ON(Me)_2$ | O |
| 20 | $CF_2H$ | F | $ON(Et)_2$ | O |
| 21 | $CFH_2$ | F | $ON(Pr)_2$ | O |
| 22 | $CH_3$ | F | $ON(Me)_2$ | S |
| 23 | $CF_2H$ | F | $ON(Bu)_2$ | S |
| 24 | $CFH_2$ | F | ON(Me)Et | S |
| 25 | $CH_3$ | Cl | $NH_2$ | O |
| 26 | $CF_2H$ | Br | $NH_2$ | O |
| 27 | $CFH_2$ | Br | $NH_2$ | O |
| 28 | $CH_3$ | Cl | $NH_2$ | S |
| 29 | $CF_2H$ | Cl | $NH_2$ | S |
| 30 | $CFH_2$ | Br | $NH_2$ | S |
| 31 | $CH_3$ | OH | $NH_2$ | S |
| 32 | $CF_2H$ | OH | $NH_2$ | S |
| 33 | $CFH_2$ | OH | $NH_2$ | S |
| 34 | $CH_3$ | OH | $ONH_2$ | O |
| 35 | $CF_2H$ | OH | $ONH_2$ | O |
| 36 | $CFH_2$ | OH | $ONH_2$ | O |
| 37 | $CH_3$ | OH | $ONH_2$ | S |
| 38 | $CF_2H$ | OH | $ONH_2$ | S |
| 39 | $CFH_2$ | OH | $ONH_2$ | S |
| 40 | $CH_3$ | OH | ONHMe | O |
| 41 | $CF_2H$ | OH | ONHEt | O |
| 42 | $CFH_2$ | OH | ONHPr | O |
| 43 | $CH_3$ | OH | ONHMe | S |
| 44 | $CF_2H$ | OH | ONHBu | S |
| 45 | $CFH_2$ | OH | ONHMe | S |

TABLE 1-continued

| Cpd. No. | R¹ | X | Y | Z |
|---|---|---|---|---|
| 46 | $CH_3$ | OH | $ON(Me)_2$ | O |
| 47 | $CF_2H$ | OH | $ON(Et)_2$ | O |
| 48 | $CFH_2$ | OH | $ON(Pr)_2$ | O |
| 49 | $CH_3$ | OH | $ON(Me)_2$ | S |
| 50 | $CF_2H$ | OH | $ON(Bu)_2$ | S |
| 51 | $CFH_2$ | OH | ON(Me)Et | S |
| 52 | Et | F | $NH_2$ | O |
| 53 | $CF_3CH_2$ | F | $NH_2$ | O |
| 54 | Pr | F | $NH_2$ | O |
| 55 | Bu | F | $NH_2$ | S |
| 56 | iPr | F | $NH_2$ | S |
| 57 | iBu | F | $NH_2$ | S |
| 58 | Bu | OH | $NH_2$ | S |
| 59 | iPr | OH | $NH_2$ | S |
| 60 | iBu | OH | $NH_2$ | S |
| 61 | Et | F | $ONH_2$ | O |
| 62 | $CF_3CH_2$ | F | $ONH_2$ | O |
| 63 | Pr | F | $ONH_2$ | O |
| 64 | Bu | F | $ONH_2$ | S |
| 65 | iPr | F | $ONH_2$ | S |
| 66 | iBu | F | $ONH_2$ | S |
| 67 | Et | $CH_3(CH_2)_4COO$ | $ONH_2$ | O |
| 68 | $CF_3CH_2$ | $CH_3(CH_2)_4COO$ | $ONH_2$ | O |
| 69 | Pr | $CH_3(CH_2)_4COO$ | $ONH_2$ | O |
| 70 | Bu | $CH_3(CH_2)_4COO$ | $ONH_2$ | S |
| 71 | iPr | $CH_3(CH_2)_4COO$ | $ONH_2$ | S |
| 72 | iBu | $CH_3(CH_2)_4COO$ | $ONH_2$ | S |
| 73 | $CH_3$ | $CH_3(CH_2)_4COO$ | $NH_2$ | S |
| 74 | $CF_2H$ | $CH_3(CH_2)_4COO$ | $NH_2$ | S |
| 75 | $CFH_2$ | $CH_3(CH_2)_4COO$ | $NH_2$ | S |
| 76 | $CH_3$ | $CH_3(CH_2)_4COO$ | $ONH_2$ | O |
| 77 | $CF_2H$ | $CH_3(CH_2)_4COO$ | $ONH_2$ | O |
| 78 | $CFH_2$ | $CH_3(CH_2)_4COO$ | $ONH_2$ | O |
| 79 | $CH_3$ | $CH_3(CH_2)_4COO$ | $ONH_2$ | S |
| 80 | $CF_2H$ | $CH_3(CH_2)_4COO$ | $ONH_2$ | S |
| 81 | $CFH_2$ | $CH_3(CH_2)_4COO$ | $ONH_2$ | S |
| 82 | $CH_3$ | $CH_3(CH_2)_4COO$ | ONHMe | O |
| 83 | $CF_2H$ | $CH_3(CH_2)_4COO$ | ONHEt | O |
| 84 | $CFH_2$ | $CH_3(CH_2)_4COO$ | ONHPr | O |
| 85 | $CH_3$ | $CH_3(CH_2)_4COO$ | ONHMe | S |
| 86 | $CF_2H$ | $CH_3(CH_2)_4COO$ | ONHBu | S |
| 87 | $CFH_2$ | $CH_3(CH_2)_4COO$ | ONHMe | S |
| 88 | $CH_3$ | $CH_3(CH_2)_4COO$ | $ON(Me)_2$ | O |
| 89 | $CF_2H$ | $CH_3(CH_2)_4COO$ | $ON(Et)_2$ | O |
| 90 | $CFH_2$ | $CH_3(CH_2)_4COO$ | $ON(Pr)_2$ | O |
| 91 | $CH_3$ | $CH_3(CH_2)_4COO$ | $ON(Me)_2$ | S |
| 92 | $CF_2H$ | $CH_3(CH_2)_4COO$ | $ON(Bu)_2$ | S |
| 93 | $CFH_2$ | $CH_3(CH_2)_4COO$ | ON(Me)Et | S |
| 94 | Bu | $CH_3(CH_2)_4COO$ | $NH_2$ | S |
| 95 | iPr | $CH_3(CH_2)_4COO$ | $NH_2$ | S |
| 96 | iBu | $CH_3(CH_2)_4COO$ | $NH_2$ | S |
| 97 | Et | $CH_3(CH_2)_4COO$ | $ONH_2$ | O |
| 98 | $CF_3CH_2$ | $CH_3(CH_2)_4COO$ | $ONH_2$ | O |
| 99 | Pr | $CH_3(CH_2)_4COO$ | $ONH_2$ | O |
| 100 | Bu | $CH_3(CH_2)_4COO$ | $ONH_2$ | S |
| 101 | iPr | $CH_3(CH_2)_4COO$ | $ONH_2$ | S |
| 102 | iBu | $CH_3(CH_2)_4COO$ | $ONH_2$ | S |
| 103 | $CH_3$ | $CH_3(CH_2)_{12}COO$ | $NH_2$ | S |
| 104 | $CF_2H$ | $CH_3(CH_2)_{12}COO$ | $NH_2$ | S |
| 105 | $CFH_2$ | $CH_3(CH_2)_{12}COO$ | $NH_2$ | S |
| 106 | $CH_3$ | $CH_3(CH_2)_{12}COO$ | $ONH_2$ | O |
| 107 | $CF_2H$ | $CH_3(CH_2)_{12}COO$ | $ONH_2$ | O |
| 108 | $CFH_2$ | $CH_3(CH_2)_{12}COO$ | $ONH_2$ | O |
| 109 | $CH_3$ | $CH_3(CH_2)_{12}COO$ | $ONH_2$ | S |
| 110 | $CF_2H$ | $CH_3(CH_2)_{12}COO$ | $ONH_2$ | S |
| 111 | $CFH_2$ | $CH_3(CH_2)_{12}COO$ | $ONH_2$ | S |
| 112 | $CH_3$ | $CH_3(CH_2)_{12}COO$ | ONHMe | O |
| 113 | $CF_2H$ | $CH_3(CH_2)_{12}COO$ | ONHEt | O |
| 114 | $CFH_2$ | $CH_3(CH_2)_{12}COO$ | ONHPr | O |
| 115 | $CH_3$ | $CH_3(CH_2)_{12}COO$ | ONHMe | S |
| 116 | $CF_2H$ | $CH_3(CH_2)_{12}COO$ | ONHBu | S |
| 117 | $CFH_2$ | $CH_3(CH_2)_{12}COO$ | ONHMe | S |
| 118 | $CH_3$ | $CH_3(CH_2)_{12}COO$ | $ON(Me)_2$ | O |
| 119 | $CF_2H$ | $CH_3(CH_2)_{12}COO$ | $ON(Et)_2$ | O |
| 120 | $CFH_2$ | $CH_3(CH_2)_{12}COO$ | $ON(Pr)_2$ | O |
| 121 | $CH_3$ | $CH_3(CH_2)_{12}COO$ | $ON(Me)_2$ | S |
| 122 | $CF_2H$ | $CH_3(CH_2)_{12}COO$ | $ON(Bu)_2$ | S |

TABLE 1-continued

| Cpd. No. | R¹ | X | Y | Z |
|---|---|---|---|---|
| 123 | CFH₂ | CH₃(CH₂)₁₂COO | ON(Me)Et | S |
| 124 | Bu | CH₃(CH₂)₁₂COO | NH₂ | S |
| 125 | iPr | CH₃(CH₂)₁₂COO | NH₂ | S |
| 126 | iBu | CH₃(CH₂)₁₂COO | NH₂ | S |
| 127 | Et | CH₃(CH₂)₁₂COO | ONH₂ | O |
| 128 | CF₃CH₂ | CH₃(CH₂)₁₂COO | ONH₂ | O |
| 129 | Pr | CH₃(CH₂)₁₂COO | ONH₂ | O |
| 130 | Bu | CH₃(CH₂)₁₂COO | ONH₂ | S |
| 131 | iPr | CH₃(CH₂)₁₂COO | ONH₂ | S |
| 132 | iBu | CH₃(CH₂)₁₂COO | ONH₂ | S |
| 133 | CH₃ | CH₃(CH₂)₂COO | NH₂ | S |
| 134 | CF₂H | CH₃(CH₂)₃COO | NH₂ | S |
| 135 | CFH₂ | CH₃(CH₂)₅COO | NH₂ | S |
| 136 | CH₃ | CH₃(CH₂)₆COO | ONH₂ | O |
| 137 | CF₂H | CH₃(CH₂)₈COO | ONH₂ | O |
| 138 | CFH₂ | CH₃(CH₂)₁₀COO | ONH₂ | O |
| 139 | CH₃ | CH₃(CH₂)₁₄COO | ONH₂ | S |
| 140 | CF₂H | CH₃(CH₂)₁₆COO | ONH₂ | S |
| 141 | CFH₂ | CH₃(CH₂)₁₈COO | ONH₂ | S |
| 142 | CH₃ | CH₃(CH₂)₂₀COO | ONHMe | O |
| 143 | CF₂H | CH₃(CH₂)₂₂COO | ONHEt | O |
| 144 | CFH₂ | CH₃CH₂COO | ONHPr | O |
| 145 | CH₃ | CH₃(CH₂)₂COO | ONHMe | S |
| 146 | CF₂H | CH₃(CH₂)₃COO | ONHBu | S |
| 147 | CFH₂ | CH₃(CH₂)₅COO | ONHMe | S |
| 148 | CH₃ | CH₃(CH₂)₆COO | ON(Me)₂ | O |
| 149 | CF₂H | CH₃(CH₂)₈COO | ON(Et)₂ | O |
| 150 | CFH₂ | CH₃(CH₂)₁₀COO | ON(Pr)₂ | O |
| 151 | CH₃ | CH₃(CH₂)₁₄COO | ON(Me)₂ | S |
| 152 | CF₂H | CH₃(CH₂)₁₆COO | ON(Bu)₂ | S |
| 153 | CFH₂ | CH₃(CH₂)₁₈COO | ON(Me)Et | S |
| 154 | Bu | CH₃(CH₂)₂COO | NH₂ | S |
| 155 | iPr | CH₃(CH₂)₃COO | NH₂ | S |
| 156 | iBu | CH₃(CH₂)₅COO | NH₂ | S |
| 157 | Et | CH₃(CH₂)₆COO | ONH₂ | O |
| 158 | CF₃CH₂ | CH₃(CH₂)₈COO | ONH₂ | O |
| 159 | Pr | CH₃(CH₂)₁₀COO | ONH₂ | O |
| 160 | Bu | CH₃(CH₂)₁₄COO | ONH₂ | S |
| 161 | ipr | CH₃(CH₂)₁₆COO | ONH₂ | S |
| 162 | iBu | CH₃(CH₂)₁₈COO | ONH₂ | S |
| 163 | CH₃ | OMe | NH₂ | O |
| 164 | CF₂H | OMe | NH₂ | O |
| 165 | CFH₂ | OMe | NH₂ | O |
| 166 | CH₃ | OMe | NH₂ | S |
| 167 | CF₂H | OMe | NH₂ | S |
| 168 | CFH₂ | OMe | NH₂ | S |
| 169 | CH₃ | OMe | ONH₂ | O |
| 170 | CF₂H | OMe | ONH₂ | O |
| 171 | CFH₂ | OMe | ONH₂ | O |
| 172 | CH₃ | OMe | ONH₂ | S |
| 173 | CF₂H | OMe | ONH₂ | S |
| 174 | CFH₂ | OMe | ONH₂ | S |
| 175 | CH₃ | OMe | ONHMe | O |
| 176 | CF₂H | OMe | ONHEt | O |
| 177 | CFH₂ | OMe | ONHPr | O |
| 178 | CH₃ | OMe | ONHMe | S |
| 179 | CF₂H | OMe | ONHBu | S |
| 180 | CFH₂ | OMe | ONHMe | S |
| 181 | CH₃ | OMe | ON(Me)₂ | O |
| 182 | CF₂H | OMe | ON(Et)₂ | O |
| 183 | CFH₂ | OMe | ON(Pr)₂ | O |
| 184 | CH₃ | OMe | ON(Me)₂ | S |
| 185 | CF₂H | OMe | ON(Bu)₂ | S |
| 186 | CFH₂ | OMe | ON(Me)Et | S |
| 187 | Et | OMe | NH₂ | O |
| 188 | CF₃CH₂ | OMe | NH₂ | O |
| 189 | Pr | OMe | NH₂ | O |
| 190 | Bu | OMe | NH₂ | S |
| 191 | iPr | OMe | NH₂ | S |
| 192 | iBu | OMe | NH₂ | S |
| 193 | Et | OMe | ONH₂ | O |
| 194 | CF₃CH₂ | OMe | ONH₂ | O |
| 195 | Pr | OMe | ONH₂ | O |
| 196 | Bu | OMe | ONH₂ | S |
| 197 | iPr | OMe | ONH₂ | S |
| 198 | iBu | OMe | ONH₂ | S |
| 199 | CH₃ | OEt | NH₂ | O |
| 200 | CF₂H | OEt | NH₂ | O |
| 201 | CFH₂ | OEt | NH₂ | O |
| 202 | CH₃ | OEt | NH₂ | S |
| 203 | CF₂H | OEt | NH₂ | S |
| 204 | CFH₂ | OEt | NH₂ | S |
| 205 | CH₃ | OEt | ONH₂ | O |
| 206 | CF₂H | OEt | ONH₂ | O |
| 207 | CFH₂ | OEt | ONH₂ | O |
| 208 | CH₃ | OEt | ONH₂ | S |
| 209 | CF₂H | OEt | ONH₂ | S |
| 210 | CFH₂ | OEt | ONH₂ | S |
| 211 | CH₃ | OEt | ONHMe | O |
| 212 | CF₂H | OEt | ONHEt | O |
| 213 | CFH₂ | OEt | ONHPr | O |
| 214 | CH₃ | OEt | ONHMe | S |
| 215 | CF₂H | OEt | ONHBu | S |
| 216 | CFH₂ | OEt | ONHMe | S |
| 217 | CH₃ | OEt | ON(Me)₂ | O |
| 218 | CF₂H | OEt | ON(Et)₂ | O |
| 219 | CFH₂ | OEt | ON(Pr)₂ | O |
| 220 | CH₃ | OEt | ON(Me)₂ | S |
| 221 | CF₂H | OEt | ON(Bu)₂ | S |
| 222 | CFH₂ | OEt | ON(Me)Et | S |
| 223 | Et | OEt | NH₂ | O |
| 224 | CF₃CH₂ | OEt | NH₂ | O |
| 225 | Pr | OEt | NH₂ | O |
| 226 | Bu | OEt | NH₂ | S |
| 227 | iPr | OEt | NH₂ | S |
| 228 | iBu | OEt | NH₂ | S |
| 229 | Et | OEt | ONH₂ | O |
| 230 | CF₃CH₂ | OEt | ONH₂ | O |
| 231 | Pr | OEt | ONH₂ | O |
| 232 | Bu | OEt | ONH₂ | S |
| 233 | iPr | OEt | ONH₂ | S |
| 234 | iBu | OEt | ONH₂ | S |

TABLE 2

| Cpd. No. | R² | R³ | W |
|---|---|---|---|
| 1 | H | H | H |
| 2 | H | H | CH₃ |
| 3 | H | H | (CH₂)₅CH₃ |
| 4 | H | H | (CH₂)₁₀CH₃ |
| 5 | H | H | (CH₂)₁₃CH₃ |
| 6 | H | H | (CH₂)₁₅CH₃ |
| 7 | H | H | (CH₂)₁₇CH₃ |
| 8 | H | H | (CH₂)₂₁CH₃ |
| 9 | H | CH₃CO | H |
| 10 | H | CH₃CH₂CO | H |
| 11 | H | CH₃(CH₂)₂CO | H |
| 12 | H | CH₃(CH₂)₃CO | H |
| 13 | H | CH₃(CH₂)₄CO | H |
| 14 | H | CH₃(CH₂)₅CO | H |
| 15 | H | CH₃(CH₂)₆CO | H |
| 16 | H | CH₃(CH₂)₈CO | H |
| 17 | H | CH₃(CH₂)₁₀CO | H |
| 18 | H | CH₃(CH₂)₁₂CO | H |
| 19 | H | CH₃(CH₂)₁₄CO | H |
| 20 | H | CH₃(CH₂)₁₆CO | H |
| 21 | H | CH₃(CH₂)₁₈CO | H |
| 22 | H | CH₃(CH₂)₂₀CO | H |
| 23 | H | CH₃(CH₂)₂₂CO | H |
| 24 | H | CH₃(CH₂)₄CO | CH₃ |
| 25 | H | CH₃(CH₂)₄CO | (CH₂)₅CH₃ |
| 26 | H | CH₃(CH₂)₄CO | (CH₂)₁₀CH₃ |
| 27 | H | CH₃(CH₂)₄CO | (CH₂)₁₃CH₃ |
| 28 | H | CH₃(CH₂)₁₂CO | CH₃ |
| 29 | H | CH₃(CH₂)₁₂CO | (CH₂)₅CH₃ |
| 30 | H | CH₃(CH₂)₁₂CO | (CH₂)₁₀CH₃ |
| 31 | H | CH₃(CH₂)₁₂CO | (CH₂)₁₃CH₃ |
| 32 | CH₃CO | H | H |
| 33 | CH₃CH₂CO | H | H |
| 34 | CH₃(CH₂)₂CO | H | H |

TABLE 2-continued

| Cpd. No. | R² | R³ | W |
|---|---|---|---|
| 35 | CH₃(CH₂)₃CO | H | H |
| 36 | CH₃(CH₂)₄CO | H | H |
| 37 | CH₃(CH₂)₅CO | H | H |
| 38 | CH₃(CH₂)₆CO | H | H |
| 39 | CH₃(CH₂)₈CO | H | H |
| 40 | CH₃(CH₂)₁₀CO | H | H |
| 41 | CH₃(CH₂)₁₂CO | H | H |
| 42 | CH₃(CH₂)₁₄CO | H | H |
| 43 | CH₃(CH₂)₁₆CO | H | H |
| 44 | CH₃(CH₂)₁₈CO | H | H |
| 45 | CH₃(CH₂)₂₀CO | H | H |
| 46 | CH₃(CH₂)₄CO | H | CH₃ |
| 47 | CH₃(CH₂)₄CO | H | (CH₂)₅CH₃ |
| 48 | CH₃(CH₂)₄CO | H | (CH₂)₁₀CH₃ |
| 49 | CH₃(CH₂)₄CO | H | (CH₂)₁₃CH₃ |
| 50 | CH₃(CH₂)₁₂CO | H | CH₃ |
| 51 | CH₃(CH₂)₁₂CO | H | (CH₂)₅CH₃ |
| 52 | CH₃(CH₂)₁₂CO | H | (CH₂)₁₀CH₃ |
| 53 | CH₃(CH₂)₁₂CO | H | (CH₂)₁₃CH₃ |
| 54 | CH₃CO | CH₃CO | H |
| 55 | CH₃CH₂CO | CH₃CH₂CO | H |
| 56 | CH₃(CH₂)₂CO | CH₃(CH₂)₂CO | H |
| 57 | CH₃(CH₂)₃CO | CH₃(CH₂)₃CO | H |
| 58 | CH₃(CH₂)₄CO | CH₃(CH₂)₄CO | H |
| 59 | CH₃(CH₂)₅CO | CH₃(CH₂)₅CO | H |
| 60 | CH₃(CH₂)₆CO | CH₃(CH₂)₆CO | H |
| 61 | CH₃(CH₂)₈CO | CH₃(CH₂)₈CO | H |
| 62 | CH₃(CH₂)₁₀CO | CH₃(CH₂)₁₀CO | H |
| 63 | CH₃(CH₂)₁₂CO | CH₃(CH₂)₁₂CO | H |
| 64 | CH₃(CH₂)₁₄CO | CH₃(CH₂)₁₄CO | H |
| 65 | CH₃(CH₂)₁₆CO | CH₃(CH₂)₁₆CO | H |
| 66 | CH₃(CH₂)₁₈CO | CH₃(CH₂)₁₈CO | H |
| 67 | CH₃(CH₂)₂₀CO | CH₃(CH₂)₂₀CO | H |
| 68 | CH₃(CH₂)₂₂CO | CH₃(CH₂)₂₂CO | H |
| 69 | CH₃(CH₂)₁₂CO | CH₃(CH₂)₆CO | H |
| 70 | CH₃(CH₂)₄CO | CH₃(CH₂)₁₂CO | H |
| 71 | CH₃(CH₂)₄CO | CH₃(CH₂)₄CO | CH₃ |
| 72 | CH₃(CH₂)₄CO | CH₃(CH₂)₄CO | (CH₂)₅CH₃ |
| 73 | CH₃(CH₂)₄CO | CH₃(CH₂)₄CO | (CH₂)₁₀CH₃ |
| 74 | CH₃(CH₂)₄CO | CH₃(CH₂)₄CO | (CH₂)₁₃CH₃ |
| 75 | CH₃(CH₂)₁₂CO | CH₃(CH₂)₁₂CO | CH₃ |
| 76 | CH₃(CH₂)₁₂CO | CH₃(CH₂)₁₂CO | (CH₂)₅CH₃ |
| 77 | CH₃(CH₂)₁₂CO | CH₃(CH₂)₁₂CO | (CH₂)₁₀CH₃ |
| 78 | CH₃(CH₂)₁₂CO | CH₃(CH₂)₁₂CO | (CH₂)₁₃CH₃ |
| 79 | CH₃(CH₂)₄CO | CH₃(CH₂)₁₂CO | CH₃ |
| 80 | CH₃(CH₂)₄CO | CH₃(CH₂)₁₂CO | (CH₂)₅CH₃ |
| 81 | CH₃(CH₂)₄CO | CH₃(CH₂)₁₂CO | (CH₂)₁₀CH₃ |
| 82 | CH₃(CH₂)₄CO | CH₃(CH₂)₁₂CO | (CH₂)₁₃CH₃ |
| 83 | CH₃(CH₂)₁₂CO | CH₃(CH₂)₄CO | CH₃ |
| 84 | CH₃(CH₂)₁₂CO | CH₃(CH₂)₄CO | (CH₂)₅CH₃ |
| 85 | CH₃(CH₂)₁₂CO | CH₃(CH₂)₄CO | (CH₂)₁₀CH₃ |
| 86 | CH₃(CH₂)₁₂CO | CH₃(CH₂)₄CO | (CH₂)₁₃CH₃ |
| 87 | CH₃(CH₂)₆CO | H | CH₃ |
| 88 | CH₃(CH₂)₈CO | H | CH₃ |
| 89 | CH₃(CH₂)₁₀CO | H | CH₃ |
| 90 | CH₃(CH₂)₁₄CO | H | CH₃ |
| 91 | CH₃(CH₂)₁₆CO | H | CH₃ |
| 92 | CH₃(CH₂)₆CO | H | CH₂CH₃ |
| 93 | CH₃(CH₂)₈CO | H | CH₂CH₃ |
| 94 | CH₃(CH₂)₁₀CO | H | CH₂CH₃ |
| 95 | CH₃(CH₂)₁₂CO | H | CH₂CH₃ |
| 96 | CH₃(CH₂)₁₄CO | H | CH₂CH₃ |
| 97 | CH₃(CH₂)₁₆CO | H | CH₂CH₃ |

Thus, the following compounds are disclosed: Compounds No., 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-24, 1-25, 1-26, 1-27, 1-28, 1-29, 1-30, 1-31, 1-32, 1-33, 1-34, 1-35, 1-36, 1-37, 1-38, 1-39, 1-40, 1-41, 1-42, 1-43, 1-44, 1-45, 1-46, 1-47, 1-48, 1-49, 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 2-1, 2-2, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-34, 2-35, 2-36, 2-37, 2-38, 2-39, 2-40, 2-41, 2-42, 2-43, 2-44, 2-45, 2-46, 2-47, 2-48, 2-49, 2-50, 2-51, 2-52, 2-53, 2-54, 2-55, 2-56, 2-57, 2-58, 2-59, 2-60, 2-61, 2-62, 2-63, 2-64, 2-65, 2-66, 2-67, 2-68, 2-69, 2-70, 2-71, 2-72, 2-73, 2-74, 2-75, 2-76, 2-77, 2-78, 2-79, 2-80, 2-81, 2-82, 2-83, 2-84, 2-85, 2-86, 2-87, 2-88, 2-89, 2-90, 2-91, 2-92, 2-93, 2-94, 2-95, 2-96, 2-97, 3-1, 3-2, 3-3, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 3-37, 3-38, 3-39, 3-40, 3-41, 3-42, 3-43, 3-44, 3-45, 3-46, 3-47, 3-48, 3-49, 3-50, 3-51, 3-52, 3-53, 3-54, 3-55, 3-56, 3-57, 3-58, 3-59, 3-60, 3-61, 3-62, 3-63, 3-64, 3-65, 3-66, 3-67, 3-68, 3-69, 3-70, 3-71, 3-72, 3-73, 3-74, 3-75, 3-76, 3-77, 3-78, 3-79, 3-80, 3-81, 3-82, 3-83, 3-84, 3-85, 3-86, 3-87, 3-88, 3-89, 3-90, 3-91, 3-92, 3-93, 3-94, 3-95, 3-96, 3-97, 4-1, 4-2, 4-3, 4-4, 4-5, 4-6, 4-7, 4-8, 4-9, 4-10, 4-11, 4-12, 4-13, 4-15, 4-16, 4-17, 4-18, 4-19, 4-20, 4-21, 4-22, 4-23, 4-24, 4-25, 4-26, 4-27, 4-28, 4-29, 4-30, 4-31, 4-32, 4-33, 4-34, 4-35, 4-36, 4-37, 4-38, 4-39, 4-40, 4-41, 4-42, 4-43, 4-44, 4-45, 4-46, 4-47, 4-48, 4-49, 4-50, 4-51, 4-52, 4-53, 4-54, 4-55, 4-56, 4-57, 4-58, 4-59, 4-60, 4-61, 4-62, 4-63, 4-64, 4-65, 4-66, 4-67, 4-68, 4-69, 4-70, 4-71, 4-72, 4-73, 4-74, 4-75, 4-76, 4-77, 4-78, 4-79, 4-80, 4-81, 4-82, 4-83, 4-84, 4-85, 4-86, 4-87, 4-88, 4-89, 4-90, 4-91, 4-92, 4-93, 4-94, 4-95, 4-96, 4-97, 5-1, 5-2, 5-3, 5-4, 5-5, 5-6, 5-7, 5-8, 5-9, 5-10, 5-11, 5-12, 5-13, 5-14, 5-15, 5-16, 5-17, 5-18, 5-19, 5-20, 5-21, 5-22, 5-23, 5-24, 5-25, 5-26, 5-27, 5-28, 5-29, 5-30, 5-31, 5-32, 5-33, 5-34, 5-35, 5-36, 5-37, 5-38, 5-39, 5-40, 5-41, 5-42, 5-43, 5-44, 5-45, 5-46, 5-47, 5-48, 5-49, 5-50, 5-51, 5-52, 5-53, 5-54, 5-55, 5-56, 5-57, 5-58, 5-59, 5-60, 5-61, 5-62, 5-63, 5-64, 5-65, 5-66, 5-67, 5-68, 5-69, 5-70, 5-71, 5-72, 5-73, 5-74, 5-75, 5-76, 5-77, 5-78, 5-79, 5-80, 5-81, 5-82, 5-83, 5-84, 5-86, 5-87, 5-88, 5-89, 5-90, 5-91, 5-92, 5-93, 5-94, 5-95, 5-96, 5-97, 6-1, 6-2, 6-3, 6-4, 6-5, 6-6, 6-7, 6-8, 6-9, 6-10, 6-11, 6-12, 6-13, 6-14, 6-15, 6-16, 6-17, 6-18, 6-19, 6-20, 6-21, 6-22, 6-23, 6-24, 6-25, 6-26, 6-27, 6-28, 6-29, 6-30, 6-31, 6-32, 6-33, 6-34, 6-35, 6-36, 6-37, 6-38, 6-39, 6-40, 6-41, 6-42, 6-43, 6-44, 6-45, 6-46, 6-47, 6-48, 6-49, 6-50, 6-51, 6-52, 6-53, 6-54, 6-55, 6-56, 6-57, 6-58, 6-59, 6-60, 6-61, 6-62, 6-63, 6-64, 6-65, 6-66, 6-67, 6-68, 6-69, 6-70, 6-71, 6-72, 6-73, 6-74, 6-75, 6-76, 6-77, 6-78, 6-79, 6-80, 6-81, 6-82, 6-83, 6-84, 6-85, 6-86, 6-87, 6-88, 6-89, 6-90, 6-91, 6-92, 6-93, 6-94, 6-95, 6-96, 6-97, 7-1, 7-2, 7-3, 7-4, 7-5, 7-6, 7-7, 7-8, 7-9, 7-10, 7-11, 7-12, 7-11, 7-12, 7-13, 7-14, 7-15, 7-16, 7-17, 7-18, 7-19, 7-20, 7-21, 7-22, 7-23, 7-24, 7-25, 7-26, 7-27, 7-28, 7-29, 7-30, 7-31, 7-32, 7-33, 7-34, 7-35, 7-36, 7-37, 7-38, 7-39, 7-40, 7-41, 7-42, 7-43, 7-44, 7-45, 7-46, 7-47, 7-48, 7-49, 7-50, 7-51, 7-52, 7-53, 7-54, 7-55, 7-56, 7-57, 7-58, 7-59, 7-60, 7-61, 7-62, 7-63, 7-64, 7-65, 7-66, 7-67, 7-68, 7-69, 7-70, 7-71, 7-72, 7-73, 7-74, 7-75, 7-76, 7-77, 7-78, 7-79, 7-80, 7-81, 7-82, 7-83, 7-84, 7-85, 7-86 7-87, 7-88, 7-89, 7-90, 7-91, 7-92, 7-93, 7-94, 7-95, 7-96, 7-97, 8-1, 8-2, 8-3, 8-4, 8-5, 8-6, 8-7, 8-8, 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-20, 8-31, 8-32, 8-33, 8-34, 8-35, 8-36, 8-37, 8-38, 8-39, 8-40, 8-41, 8-42, 8-43, 8-44, 8-45, 8-46, 8-47, 8-48, 8-49, 8-50, 8-51, 8-52, 8-53, 8-54, 8-55, 8-56, 8-57, 8-58, 8-59, 8-60, 8-61, 8-62, 8-63, 8-64, 8-65, 8-66, 8-67, 8-68, 8-69, 8-70, 8-71, 8-72, 8-73, 8-74, 8-75, 8-76, 8-77, 8-78, 8-79, 8-80, 8-81, 8-82, 8-83, 8-84, 8-85, 8-86, 8-87, 8-88, 8-89, 8-90, 8-91, 8-92, 8-93, 8-94, 8-95, 8-96, 8-97, 9-1, 9-2, 9-3, 9-4, 9-5, 9-6, 9-7, 9-8, 9-9, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 9-31, 9-32, 9-33, 9-34, 9-35, 9-36, 9-37, 9-38, 9-39, 9-40, 9-41, 9-42, 9-43, 9-44, 9-45, 9-46, 9-47, 9-48, 9-49, 9-50, 9-51, 9-52, 9-53, 9-54, 9-55, 9-56, 9-57, 9-58, 9-59, 9-60, 9-61, 9-62, 9-63, 9-64, 9-65, 9-66, 9-67, 9-68, 9-69, 9-70, 9-71, 9-72, 9-73, 9-74, 9-75, 9-76, 9-77, 9-78, 9-79, 9-80, 9-81, 9-82, 9-83, 9-84, 9-85, 9-86, 9-87, 9-88, 9-89, 9-90, 9-91, 9-92, 9-93, 9-94, 9-95, 9-96, 9-97, 10-1, 10-2, 10-3, 10-4, 10-5, 10-6, 10-7, 10-8, 10-9, 10-10, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 10-31, 10-32, 10-33, 10-34, 10-35, 10-36, 10-37, 10-38, 10-39, 10-40, 10-41, 10-42, 10-43, 10-44, 10-45, 10-46, 10-47, 10-48, 10-49, 10-50, 10-51, 10-52, 10-53, 10-54, 10-55, 10-56, 10-57, 10-58, 10-59, 10-60, 10-61, 10-62, 10-63, 10-64, 10-65, 10-66, 10-67, 10-68, 10-69, 10-70, 10-71, 10-72, 10-73, 10-74, 10-75, 10-76, 10-77, 10-78, 10-79, 10-80, 10-81, 10-82, 10-83, 10-84, 10-85, 10-86, 10-87, 10-88, 10-89, 10-90, 10-91, 10-92, 10-93, 10-94, 10-95, 10-96, 10-97, 11-1, 11-2, 11-3, 11-4, 11-5, 11-6, 11-7, 11-8, 11-9, 11-10, 11-11, 11-12, 11-13, 11-14, 11-15, 11-16, 11-17, 11-18, 11-19, 11-20, 11-21, 11-22, 11-23, 11-23, 11-24, 11-25, 11-26, 11-27, 11-28, 11-29, 11-30, 11-31, 11-32, 11-33, 11-34, 11-35, 11-36, 11-37, 11-38, 11-39, 11-40, 11-41, 11-42, 11-43, 11-44, 11-45, 11-46, 11-47, 11-48, 11-49, 11-50, 11-51, 11-52, 11-53, 11-54, 11-55, 11-56, 11-57, 11-58, 11-59, 11-60, 11-61, 11-62, 11-63, 11-64, 11-65, 11-66, 11-67, 11-68, 11-69, 11-70, 11-71, 11-72, 11-73, 11-74, 11-75, 11-76, 11-77, 11-78, 11-79, 11-80, 11-81, 11-82, 11-83, 11-84, 11-85, 11-86, 11-87, 11-88, 11-89, 11-90, 11-91, 11-92, 11-93, 11-94, 11-95, 11-96, 11-97, 12-1, 12-2, 12-3, 12-4, 12-5, 12-6, 12-7, 12-8, 12-9, 12-10, 12-11, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 12-31, 12-32, 12-33, 12-34, 12-35, 12-36, 12-37, 12-38, 12-39, 12-40, 12-41, 12-42, 12-43, 12-44, 12-45, 12-46, 12-47, 12-48, 12-49, 12-50, 12-51, 12-52, 12-53, 12-54, 12-55, 12-56, 12-57, 12-58, 12-59, 12-60, 12-61, 12-62, 12-63, 12-64, 12-65, 12-66, 12-67, 12-68, 12-69, 12-70, 12-71, 12-72, 12-73, 12-74, 12-75, 12-76, 12-77, 12-78, 12-79, 12-80, 12-81, 12-82, 12-83, 12-84, 12-85, 12-86, 12-87, 12-88, 12-89, 12-90, 12-91, 12-92, 12-93, 12-94, 12-95, 12-96, 12-97, 13-1, 13-2, 13-3, 13-4, 13-5, 13-6, 13-7, 13-8, 13-9, 13-10, 13-11, 13-12, 13-13, 13-14, 13-15, 13-16, 13-17, 13-18, 13-19, 13-20, 13-21, 13-22, 13-23, 13-24, 13-25, 13-26, 13-27, 13-28, 13-29, 13-30, 13-31, 13-32, 13-33, 13-34, 13-35, 13-36, 13-37, 13-38, 13-39, 13-40, 13-41, 13-42, 13-43, 13-44, 13-45, 13-46, 13-47, 13-48, 13-49, 13-50, 13-51, 13-52, 13-53, 13-54, 13-55, 13-56, 13-57, 13-58, 13-59, 13-60, 13-61, 13-62, 13-63, 13-64, 13-65, 13-66, 13-67, 13-68, 13-69, 13-70, 13-71, 13-72, 13-73, 13-74, 13-75, 13-76, 13-77, 13-78, 13-79, 13-80, 13-81, 13-82, 13-83, 13-84, 13-85, 13-86, 13-87, 13-88, 13-89, 13-90, 13-91, 13-92, 13-93, 13-94, 13-95, 13-96, 13-97, 14-1, 14-2, 14-3, 14-4, 14-5, 14-6, 14-7, 14-8, 14-9, 14-10, 14-11, 14-12, 14-13, 14-14, 14-15, 14-16, 14-17, 14-18, 14-19, 14-20, 14-21, 14-22, 14-23, 14-24, 14-25, 14-26, 14-27, 14-28, 14-29, 14-30, 14-31, 14-32, 14-33, 14-34, 14-35, 14-36, 14-37, 14-38, 14-39, 14-40, 14-41, 14-42, 14-43, 14-44, 14-45, 14-46, 14-47, 14-48, 14-49, 14-50, 14-51, 14-52, 14-53, 14-54, 14-55, 14-56, 14-57, 14-58, 14-59, 14-60, 14-61, 14-62, 14-63, 14-64, 14-65, 14-66, 14-67, 14-68, 14-69, 14-70, 14-71, 14-72, 14-73, 14-74, 14-75, 14-76, 14-77, 14-78, 14-79, 14-80, 14-81, 14-82, 14-83, 14-84, 14-85, 14-86, 14-87, 14-88, 14-89, 14-90, 14-91, 14-92, 14-93, 14-94, 14-95, 14-96, 14-97, 15-1, 15-2, 15-3, 15-4, 15-5, 15-6, 15-7, 15-8, 15-9, 15-10, 15-11, 15-12, 15-13, 15-14, 15-15, 15-16, 15-17, 15-18, 15-19, 15-20, 15-21, 15-22, 15-23, 15-24, 15-25, 15-26, 15-27, 15-28, 15-29, 15-30, 15-31, 15-32, 15-33, 15-34, 15-35, 15-36, 15-37, 15-38, 15-39, 15-40, 15-41, 15-42, 15-43, 15-44, 15-45, 15-46, 15-47, 15-48, 15-49, 15-50, 15-51, 15-52, 15-53, 15-54, 15-55, 15-56, 15-57, 15-58, 15-59, 15-60, 15-61, 15-62, 15-63, 15-64, 15-65, 15-66, 15-67, 15-68, 15-69, 15-70, 15-71, 15-72, 15-73, 15-74, 15-75, 15-76, 15-77, 15-78, 15-79, 15-80, 15-81, 15-82, 15-83, 15-84, 15-85, 15-86, 15-87, 15-88, 15-89, 15-90, 15-91, 15-92, 15-93, 15-94, 15-95, 15-96, 15-97, 16-1, 16-2, 16-3, 16-4, 16-5, 16-6, 16-7, 16-8, 16-9, 16-10, 16-11, 16-12, 16-13, 16-14, 16-15, 16-16, 16-17, 16-18, 16-19, 16-20, 16-21, 16-22, 16-23, 16-24, 16-25, 16-26, 16-27, 16-28, 16-29, 16-30, 16-31, 16-32, 16-33, 16-34, 16-35, 16-36, 16-37, 16-38, 16-39, 1640, 16-41, 16-42, 16-43, 16-44, 16-45, 16-46, 16-47, 16-48, 16-49, 16-50, 16-51, 16-52, 16-53, 16-54, 16-55, 16-56, 16-57, 16-58, 16-59, 16-60, 16-61, 16-62, 16-63, 16-64, 16-65, 16-66, 16-67, 16-68, 16-69, 16-70, 16-71, 16-72, 16-73, 16-74, 16-75, 16-76, 16-77, 16-78, 16-79, 16-80, 16-81, 16-82, 16-83, 16-84, 16-85, 16-86, 16-87, 16-88, 16-89, 16-90, 16-91, 16-92, 16-93, 16-94, 16-95, 16-96, 16-97, 17-1, 17-2, 17-3, 174, 17-5, 17-6, 17-7, 17-8, 17-9, 17-10, 17-11, 17-12, 17-13, 17-14, 17-15, 17-16, 17-17, 17-18, 17-19, 17-20, 17-21, 17-22, 17-23, 17-24, 17-25, 17-26, 17-27, 17-28, 17-29, 17-30, 17-31, 17-32, 17-33, 17-34, 17-35, 17-36, 17-37, 17-38, 17-39, 17-40, 17-41, 17-42, 17-43, 17-44, 17-45, 17-46, 17-47, 17-48, 17-49, 17-50, 17-51, 17-52, 17-53, 17-54, 17-55, 17-56, 17-57, 17-58, 17-59, 17-60, 17-61, 17-62, 17-63, 17-64, 17-65, 17-66, 17-67, 17-68, 17-69, 17-70, 17-71, 17-72, 17-73, 17-74, 17-75, 17-76, 17-77, 17-78, 17-79, 17-80, 17-81, 17-82, 17-83, 17-84, 17-85, 17-86, 17-87, 17-88, 17-89, 17-90, 17-91, 17-92, 17-93, 17-94, 17-95, 17-96, 17-97, 18-1, 18-2, 18-3, 18-4, 18-5, 18-6, 18-7, 18-8, 18-9, 18-10, 18-11, 18-12, 18-13, 18-14, 18-15, 18-16, 18-17, 18-18, 18-19, 18-20, 18-21, 18-22, 18-23, 18-24, 18-25, 18-26, 18-27, 18-28, 18-29, 18-30, 18-31, 18-32, 18-33, 18-34, 18-35, 18-36, 18-37, 18-38, 18-39, 18-40, 18-41, 18-42, 18-43, 18-44, 18-45, 18-46, 18-47, 18-48, 18-49, 18-50, 18-51, 18-52, 18-53, 18-54, 18-55, 18-56, 18-57, 18-58, 18-59, 18-60, 18-61, 18-62, 18-63, 18-64, 18-65, 18-66, 18-67, 18-68, 18-69, 18-70, 18-71, 18-72, 18-73, 18-74, 18-75, 18-76, 18-77, 18-78, 18-79, 18-80, 18-81, 18-82, 18-83, 18-84, 18-85, 18-86, 18-87, 18-88, 18-89, 18-90, 18-91, 18-92, 18-93, 18-94, 18-95, 18-96, 18-97, 19-1, 19-2, 19-3, 19-4, 19-5, 19-6, 19-7, 19-8, 19-9, 19-10, 19-11, 19-12, 19-13, 19-14, 19-15, 19-16, 19-17, 19-18, 19-19, 19-20, 19-21, 19-22, 19-23, 19-24, 19-25, 19-26, 19-27, 19-28, 19-29, 19-30, 19-31, 19-32, 19-33, 19-34, 19-35, 19-36, 19-37, 19-38, 19-39, 19-40, 19-41, 19-42, 19-43, 19-44, 19-45, 19-46, 19-47, 19-48, 19-49, 19-50, 19-51, 19-52, 19-53, 19-54, 19-55, 19-56, 19-57, 19-58, 19-59, 19-60, 19-61, 19-62, 19-63, 19-64, 19-65, 19-66, 19-67, 19-68, 19-69, 19-70, 19-71, 19-72, 19-73, 19-74, 19-75, 19-76, 19-77, 19-78, 19-79, 19-80, 19-81, 19-82, 19-83, 19-84, 19-85, 19-86, 19-87, 19-88, 19-89, 19-90, 19-91, 19-92, 19-93, 19-94, 19-95, 19-96, 19-97, 20-1, 20-2, 20-3, 20-4, 20-5, 20-6, 20-7, 20-8, 20-9, 20-10, 20-11, 20-12, 20-13, 20-14, 20-15, 20-16, 20-17, 20-18, 20-19, 20-20, 20-21, 20-22, 20-23, 20-24, 20-25, 20-26, 20-27, 20-28, 20-29, 20-30, 20-31, 20-32, 20-33, 20-34, 20-35, 20-36, 20-37, 20-38, 20-39, 20-40, 20-41, 20-42, 20-43, 20-44, 20-45, 20-46, 20-47, 20-48, 20-49, 20-50, 20-51, 20-52, 20-53, 20-54, 20-55, 20-56, 20-57, 20-58, 20-59, 20-60, 20-61, 20-62, 20-63, 20-64, 20-65, 20-66, 20-67, 20-68, 20-69, 20-70, 20-71, 20-72, 20-73, 20-74, 20-75, 20-76, 20-77, 20-78, 20-79, 20-80, 20-81, 20-82, 20-83, 20-84, 20-85, 20-86, 20-87, 20-88, 20-89, 20-90, 20-91, 20-92, 20-93, 20-94, 20-95, 20-96, 20-97, 21-1, 21-2, 21-3, 21-4, 21-5, 21-6, 21-7, 21-8, 21-9, 21-10, 21-11, 21-12, 21-13, 21-14, 21-15, 21-16, 21-17, 21-18, 21-19, 21-20, 21-21, 21-22, 21-23, 21-24, 21-25, 21-26, 21-27, 21-28, 21-29, 21-30, 21-31, 21-32, 21-33, 21-34, 21-35, 21-36, 21-37, 21-38, 21-39, 21-40, 21-41, 21-42, 21-43, 21-44, 21-45, 21-46, 21-47, 21-48, 21-49, 21-50, 21-51, 21-52, 21-53, 21-54, 21-55, 21-56, 21-57, 21-58, 21-59, 21-60, 21-61, 21-62, 21-63, 21-64, 21-65, 21-66, 21-67, 21-68, 21-69, 21-70, 21-71, 21-72, 21-73, 21-74, 21-75, 21-76, 21-77, 21-78, 21-79, 21-80, 21-81, 21-82, 21-83, 21-84, 21-85, 21-86, 21-87, 21-88, 21-89, 21-90, 21-91, 21-92, 21-93, 21-94, 21-95, 21-96, 21-97, 22-1, 22-2, 22-3, 22-4, 22-5, 22-6, 22-7, 22-8, 22-9, 22-10, 22-11, 22-12, 21-13, 22-14, 22-15, 22-16, 22-17, 22-18, 22-19, 22-20, 22-21, 22-22, 22-23, 22-24, 22-25, 22-26, 22-27, 22-28, 22-29, 22-30, 22-31, 22-32, 22-33, 22-34, 22-35, 22-36, 22-37, 22-38, 22-39, 22-40, 22-41, 22-42, 22-43, 22-44, 22-45, 22-46, 22-47, 22-48, 22-49, 22-50, 22-51, 22-52, 22-53, 22-54, 22-55, 22-56, 22-57, 22-58, 22-59, 22-60, 22-61, 22-62, 22-63, 22-64, 22-65, 22-66, 22-67, 22-68, 22-69, 22-70, 22-71, 22-72, 22-73, 22-74, 22-75, 22-76, 22-77, 22-78, 22-79, 22-80, 22-81, 22-82, 22-83, 22-84, 22-85, 22-86, 22-87, 22-88, 22-89, 22-90, 22-91, 22-92, 22-93, 22-94, 22-95, 22-96, 22-97, 23-1, 23-2, 23-3, 234, 23-5, 23-6, 23-7, 23-8, 23-9, 23-10, 23-11, 23-12, 23-13, 23-14, 23-15, 23-16, 23-17, 23-18, 23-19, 23-20, 23-21, 23-22, 23-23, 23-24, 23-25, 23-26, 23-27, 23-28, 23-29, 23-30, 23-31, 23-32, 23-33, 23-34, 23-35, 23-36, 23-37, 23-38, 23-39, 23-40, 23-41, 23-42, 23-43, 23-44, 23-45, 23-46, 23-47, 23-48, 23-49, 23-50, 23-51, 23-52, 23-53, 23-54, 23-55, 23-56, 23-57, 23-58, 23-59, 23-60, 23-61, 23-62, 23-63, 23-64, 23-65, 23-66, 23-67, 23-68, 23-69, 23-70, 23-71, 23-72, 23-73, 23-74, 23-75, 23-76, 23-77, 23-78, 23-79, 23-80, 23-81, 23-82, 23-83, 23-84, 23-85, 23-86, 23-87, 23-88, 23-89, 23-90, 23-91, 23-92, 23-93, 23-94, 23-95, 23-96, 23-97, 24-1, 24-2, 24-3, 24-4, 24-5, 24-6, 24-7, 24-8, 24-9, 24-10, 24-11, 24-12, 24-13, 24-14, 24-15, 24-16, 24-17, 24-18, 24-19, 24-20, 24-21, 24-22, 24-23, 24-24, 24-25, 24-26, 24-27, 24-28, 24-29, 24-30, 24-31, 24-32, 24-33, 24-34, 24-35, 24-36, 24-37, 24-38, 24-39, 24-40, 24-41, 24-42, 24-43, 24-44, 24-45, 24-46, 24-47, 24-48, 24-49, 24-50, 24-51, 24-52, 24-53, 24-54, 24-55, 24-56, 24-57, 24-58, 24-59, 24-60, 24-61, 24-62, 24-63, 24-64, 24-65, 24-66, 24-67, 24-68, 24-69, 24-70, 24-71, 24-72, 24-73, 24-74, 24-75, 24-76, 24-77, 24-78, 24-79, 24-80, 24-81, 24-82, 24-83, 24-84, 24-85, 24-86, 24-87, 24-88, 24-89, 24-90, 24-91, 24-92, 24-93, 24-94, 24-95, 24-96, 24-97, 25-1, 25-2, 25-3, 25-4, 25-5, 25-6, 25-7, 25-8, 25-9, 25-10, 25-11, 25-12, 25-13, 25-14, 25-15, 25-16, 25-17, 25-18, 25-19, 25-20, 25-21, 25-22, 25-23, 25-24, 25-25, 25-26, 25-27, 25-28, 25-29, 25-30, 25-31, 25-32, 25-33, 25-34, 25-35, 25-36, 25-37, 25-38, 25-39, 25-40, 25-41, 25-42, 25-43, 25-44, 25-45, 25-46, 25-47, 25-48, 25-49, 25-50, 25-51, 25-52, 25-53, 25-54, 25-55, 25-56, 25-57, 25-58, 25-59, 25-60, 25-61, 25-62, 25-63, 25-64, 25-65, 25-66, 25-67, 25-68, 25-69, 25-70, 25-71, 25-72, 25-73, 25-74, 25-75, 25-76, 25-77, 25-78, 25-79, 25-80, 25-81, 25-82, 25-83, 25-84, 25-85, 25-86, 25-87, 25-88, 25-89, 25-90, 25-91, 25-92, 25-93, 25-94, 25-95, 25-96, 25-97, 26-1, 26-2, 26-3, 26-4, 26-5, 26-6, 26-7, 26-8, 26-9, 26-10, 26-11, 26-12, 26-13, 26-14, 26-15, 26-16, 26-17, 26-18, 26-19, 26-20, 26-21, 26-22, 26-23, 26-24, 26-25, 26-26, 26-27, 26-28, 26-29, 26-30, 26-31, 26-32, 26-33, 26-34, 26-35, 26-36, 26-37, 26-38, 26-39, 26-40, 26-41, 26-42, 26-43, 26-44, 26-45, 26-46, 26-47, 26-48, 26-49, 26-50, 26-51, 26-52, 26-53, 26-54, 26-55, 26-56, 26-57, 26-58, 26-59, 26-60, 26-61, 26-62, 26-63, 26-64, 26-65, 26-66, 26-67, 26-68, 26-69, 26-70, 26-71, 26-72, 26-73, 26-74, 26-75, 26-76, 26-77, 26-78, 26-79, 26-80, 26-81, 26-82, 26-83, 26-84, 26-85, 26-86, 26-87, 26-88, 26-89, 26-90, 26-91, 26-92, 26-93, 26-94, 26-95, 26-96, 26-97, 27-1, 27-2, 27-3, 27-4, 27-5, 27-6, 27-7, 27-8, 27-9, 27-10, 27-11, 27-12, 27-13, 27-14, 27-15, 27-16, 27-17, 27-18, 27-19, 27-20, 27-21, 27-22, 27-23, 27-24, 27-25, 27-26, 27-27, 27-28, 27-29, 27-30, 27-31, 27-32, 27-33, 27-34, 27-35, 27-36, 27-37, 27-38, 27-39, 27-40, 27-41, 27-42, 27-43, 27-44, 27-45, 27-46, 27-47, 27-48, 27-49, 27-50, 27-51, 27-52, 27-53, 27-54, 27-55, 27-56, 27-57, 27-58, 27-59, 27-60, 27-61, 27-62, 27-63, 27-64, 27-65, 27-66, 27-67, 27-68, 27-69, 27-70, 27-71, 27-72, 27-73, 27-74, 27-75, 27-76, 27-77, 27-78, 27-79, 27-80, 27-81, 27-82, 27-83, 27-84, 27-85, 27-86, 27-87, 27-88, 27-89, 27-90, 27-91, 27-92, 27-93, 27-94, 27-95, 27-96, 27-97, 28-1, 28-2, 28-3, 28-4, 28-5, 28-6, 28-7, 28-8, 28-9, 28-10, 28-11, 28-12, 28-13, 28-14, 28-15, 28-16, 28-17, 28-18, 28-19, 28-20, 28-21, 28-22, 28-23, 28-24, 28-25, 28-26, 28-27, 28-28, 28-29, 28-30, 28-31, 28-32, 28-33, 28-34, 28-35, 28-36, 28-37, 28-38, 28-39, 28-40, 28-41, 28-42, 28-43, 28-44, 28-45, 28-46, 28-47, 28-48, 28-49, 28-50, 28-51, 28-52, 28-53, 28-54, 28-55, 28-56, 28-57, 28-58, 28-59, 28-60, 28-61, 28-62, 28-63, 28-64, 28-65, 28-66, 28-67, 28-68, 28-69, 28-70, 28-71, 28-72, 28-73, 28-74, 28-75, 28-76, 28-77, 28-78, 28-79, 28-80, 28-81, 28-82, 28-83, 28-84, 28-85, 28-86, 28-87, 28-88, 28-89, 28-90, 28-91, 28-92, 28-93, 28-94, 28-95, 28-96, 28-97, 29-1, 29-2, 29-3, 29-4, 29-5, 29-6, 29-7, 29-8, 29-9, 29-10, 29-11, 29-12, 29-13, 29-14, 29-15, 29-16, 29-17, 29-18, 29-19, 29-20, 29-21, 29-22, 29-23, 29-24, 29-25, 29-26, 29-27, 29-28, 29-29, 29-30, 29-31, 29-32, 29-33, 29-34, 29-35, 29-36, 29-37, 29-38, 29-39, 29-40, 29-41, 29-42, 29-43, 29-44, 29-45, 29-46, 29-47, 29-48, 29-49, 29-50, 29-51, 29-52, 29-53, 29-54, 29-55, 29-56, 29-57, 29-58, 29-59, 29-60, 29-61, 29-62, 29-63, 29-64, 29-65, 29-66, 29-67, 29-68, 29-69, 29-70, 29-71, 29-72, 29-73, 29-74, 29-75, 29-76, 29-77, 29-78, 29-79, 29-80, 29-81, 29-82, 29-83, 29-84, 29-85, 29-86, 29-87, 29-88, 29-89, 29-90, 29-91, 29-92, 29-93, 29-94, 29-95, 29-96, 29-97, 30-1, 30-2, 30-3, 30-4, 30-5, 30-6, 30-7, 30-8, 30-9, 30-10, 30-11, 30-12, 30-13, 30-14, 30-15, 30-16, 30-17, 30-18, 30-19, 30-20, 30-21, 30-22, 30-23, 30-24, 30-25, 30-26, 30-27, 30-28, 30-29, 30-30, 30-31, 30-32, 30-33, 30-34, 30-35, 30-36, 30-37, 30-38, 30-39, 30-40, 30-41, 30-42, 30-43, 30-44, 30-45, 30-46, 30-47, 30-48, 30-49, 30-50, 30-51, 30-52, 30-53, 30-54, 30-55, 30-56, 30-57, 30-58, 30-59, 30-60, 30-61, 30-62, 30-63, 30-64, 30-65, 30-66, 30-67, 30-68, 30-69, 30-70, 30-71, 30-72, 30-73, 30-74, 30-75, 30-76, 30-77, 30-78, 30-79, 30-80, 30-81, 30-82, 30-83, 30-84, 30-85, 30-86, 30-87, 30-88, 30-89, 30-90, 30-91, 30-92, 30-93, 30-94, 30-95, 30-96, 30-97, 31-1, 31-2, 31-3, 31-4, 31-5, 31-6, 31-7, 31-8, 31-9, 31-10, 31-11, 31-12, 31-13, 31-14, 31-15, 31-16, 31-17, 31-18, 31-19, 31-20, 31-21, 31-22, 31-23, 31-24, 31-25, 31-26, 31-27, 31-28, 31-29, 31-30, 31-31, 31-32, 31-33, 31-34, 31-35, 31-36, 31-37, 31-38, 31-39, 31-40, 31-41, 31-42, 31-43, 31-44, 31-45, 31-46, 31-47, 31-48, 31-49, 31-50, 31-51, 31-52, 31-53, 31-54, 31-55, 31-56, 31-57, 31-58, 31-59, 31-60, 31-61, 31-62, 31-63, 31-64, 31-65, 31-66, 31-67, 31-68, 31-69, 31-70, 31-71, 31-72, 31-73, 31-74, 31-75, 31-76, 31-77, 31-78, 31-79, 31-80, 31-81, 31-82, 31-83, 31-84, 31-85, 31-86, 31-87, 31-88, 31-89, 31-90, 31-91, 31-92, 31-93, 31-94, 31-95, 31-96, 31-97, 32-1, 32-2, 32-3, 32-4, 32-5, 32-6, 32-7, 32-8, 32-9, 32-10, 32-11, 32-12, 32-13, 32-14, 32-15, 32-16, 32-17, 32-18, 32-19, 32-20, 32-21, 32-22, 32-23, 32-24, 32-25, 32-26, 32-27, 32-28, 32-29; 32-30; 32-31, 32-32, 32-33, 32-34, 32-35, 32-36, 32-37, 32-38, 32-39, 32-40, 32-41, 32-42, 32-43, 32-44, 32-45, 32-46, 32-47, 32-48, 32-49, 32-50, 32-51, 32-52, 32-53, 32-54, 32-55, 32-56, 32-57, 32-58, 32-59, 32-60, 32-61, 32-62, 32-63, 32-64, 32-65, 32-66, 32-67, 32-68, 32-69, 32-70, 32-71, 32-72, 32-73, 32-74, 32-75, 32-76, 32-77, 32-78, 32-79, 32-80, 32-81, 32-82, 32-83, 32-84, 32-85, 32-86, 32-87, 32-88, 32-89, 32-90, 32-91, 32-92, 32-93, 32-94, 32-95, 32-96, 32-97, 33-1, 33-2, 33-3, 33-4, 33-5, 33-6, 33-7, 33-8, 33-9, 33-10, 33-11, 33-12, 33-13, 33-14, 33-15, 33-16, 33-17, 33-18, 33-19, 33-20, 33-21, 33-22, 33-23, 33-24, 33-25, 33-26, 33-27, 33-28, 33-29, 33-30, 33-31, 33-32, 33-33, 33-34, 33-35, 33-36, 33-37, 33-38, 33-39, 33-40, 33-41, 33-42, 33-43, 33-44, 33-45, 33-46, 33-47, 33-48, 33-49, 33-50, 33-51, 33-52, 33-53, 33-54, 33-55, 33-56, 33-57, 33-58, 33-59, 33-60, 33-61, 33-62, 33-63, 33-64, 33-65, 33-66, 33-67, 33-68, 33-69, 33-70, 33-71, 33-72, 33-73, 33-74, 33-75, 33-76, 33-77, 33-78, 33-79, 33-80, 33-81, 33-82, 33-83, 33-84, 33-85, 33-86, 33-87, 33-88, 33-89, 33-90, 33-91, 33-92, 33-93, 33-94, 33-95, 33-96, 33-97, 34-1, 34-2, 34-3, 34-4, 34-5, 34-6, 34-7, 34-8, 34-9, 34-10, 34-11, 34-12, 33-13, 34-14, 34-15, 34-16, 34-17, 34-18, 34-19, 34-20, 34-21, 34-22, 34-23, 34-24, 34-25, 34-26, 34-27, 34-28, 34-29, 34-30, 34-31, 34-32, 34-33, 34-34, 34-35, 34-36, 34-37, 34-38, 34-39, 34-40, 34-41, 34-42, 34-43, 34-44, 34-45, 34-46, 34-47, 34-48, 34-49, 34-50, 34-51, 34-52, 34-53, 34-54, 34-55, 34-56, 34-57, 34-58, 34-59, 34-60, 34-61, 34-62, 34-63, 34-64, 34-65, 34-66, 34-67, 34-68, 34-69, 34-70, 34-71, 34-72, 34-73, 34-74, 34-75, 34-76, 34-77, 34-78, 34-79, 34-80, 34-81, 34-82, 34-83, 34-84, 34-85, 34-86, 34-87, 34-88, 34-89, 34-90, 34-91, 34-92, 34-93, 34-94, 34-95, 34-96, 34-97, 35-1, 35-2, 35-3, 35-4, 35-5, 35-6, 35-7, 35-8, 35-9, 35-10, 35-11, 35-12, 35-13, 35-14, 35-15, 35-16, 35-17, 35-18, 35-19, 35-20, 35-21, 35-22, 35-23, 35-24, 35-25, 35-26, 35-27, 35-28, 35-29, 35-30, 35-31, 35-32, 35-33, 35-34, 35-35, 35-36, 35-37, 35-38, 35-39, 35-40, 35-41, 35-42, 35-43, 35-44, 35-45, 35-46, 35-47, 35-48, 35-49, 35-50, 35-51, 35-52, 35-53, 35-54, 35-55, 35-56, 35-57, 35-58, 35-59, 35-60, 35-61, 35-62, 35-63, 35-64, 35-65, 35-66, 35-67, 35-68, 35-69, 35-70, 35-71, 35-72, 35-73, 35-74, 35-75, 35-76, 35-77, 35-78, 35-79, 35-80, 35-81, 35-82, 35-83, 35-84, 35-85, 35-86, 35-87, 35-88, 35-89, 35-90, 35-91, 35-92, 35-93, 35-94, 35-95, 35-96, 35-97, 36-1, 36-2, 36-3, 36-4, 36-5, 36-6, 36-7, 36-8, 36-9, 36-10, 36-11, 36-12, 36-13, 36-14, 36-15, 36-16, 36-17, 36-18, 36-19, 36-20, 36-21, 36-22, 36-23, 36-24, 36-25, 36-26, 36-27, 36-28, 36-29, 36-30, 36-31, 36-32, 36-33, 36-34, 36-35, 36-36, 36-37, 36-38, 36-39, 36-40, 36-41, 36-42, 36-43, 36-44, 36-45, 36-46, 36-47, 36-48, 36-49, 36-50, 36-51, 36-52, 36-53, 36-54, 36-55, 36-56, 36-57, 36-58, 36-59, 36-60, 36-61, 36-62, 36-63, 36-64, 36-65, 36-66, 36-67, 36-68, 36-69, 36-70, 36-71, 36-72, 36-73, 36-74, 36-75, 36-76, 36-77, 36-78, 36-79, 36-80, 36-81, 36-82, 36-83, 36-84, 36-85, 36-86, 36-87, 36-88, 36-89, 36-90, 36-91, 36-92, 36-93, 36-94, 36-95, 36-96, 36-97, 37-1, 37-2, 37-3, 37-4, 37-5, 37-6, 37-7, 37-8, 37-9, 37-10, 37-11, 37-12, 37-13, 37-14, 37-15, 37-16, 37-17, 37-18, 37-19, 37-20, 37-21, 37-22, 37-23, 37-24, 37-25, 37-26, 37-27, 37-28, 37-29, 37-30, 37-31, 37-32, 37-33, 37-34, 37-35, 37-36, 37-37, 37-38, 37-39, 3740, 37-41, 37-42, 37-43, 37-44, 37-45, 37-46, 37-47, 37-48, 37-49, 37-50, 37-51, 37-52, 37-53, 37-54, 37-55, 37-56, 37-57, 37-58, 37-59, 37-60, 37-61, 37-62, 37-63, 37-64, 37-65, 37-66, 37-67, 37-68, 37-69, 37-70, 37-71, 37-72, 37-73, 37-74, 37-75, 37-76, 37-77, 37-78, 37-79, 37-80, 37-81, 37-82, 37-83, 37-84, 37-85, 37-86, 37-87, 37-88, 37-89, 37-90, 37-91, 37-92, 37-93, 37-94, 37-95, 37-96, 37-97, 38-1, 38-2, 38-3, 38-4, 38-5, 38-6, 38-7, 38-8, 38-9, 38-10, 38-11, 38-12, 38-13, 38-14, 38-15, 38-16, 38-17, 38-18, 38-19, 38-20, 38-21, 38-22, 38-23, 38-24, 38-25, 38-26, 38-27, 38-28, 38-29, 38-30, 38-31, 38-32, 38-33, 38-34, 38-35, 38-36, 38-37, 38-38, 38-39, 38-40, 38-41, 38-42, 38-43, 38-44, 38-45, 38-46, 38-47, 38-48, 38-49, 38-50, 38-51, 38-52, 38-53, 38-54, 38-55, 38-56, 38-57, 38-58, 38-59, 38-60, 38-61, 38-62, 38-63, 38-64, 38-65, 38-66, 38-67, 38-68, 38-69, 38-70, 38-71, 38-72, 38-73, 38-74, 38-75, 38-76, 38-77, 38-78, 38-79, 38-80, 38-81, 38-82, 38-83, 38-84, 38-85, 38-86, 38-87, 38-88, 38-89, 38-90, 38-91, 38-92, 38-93, 38-94, 38-95, 38-96, 38-97, 39-1, 39-2, 39-3, 39-4, 39-5, 39-6, 39-7, 39-8, 39-9, 39-10, 39-11, 39-12, 39-13, 39-14, 39-15, 39-16, 39-17, 39-18, 39-19, 39-20, 39-21, 39-22, 39-23, 39-24, 39-25, 39-26, 39-27, 39-28, 39-29, 39-30, 39-31, 39-32, 39-33, 39-34, 39-35, 39-36, 39-37, 39-38, 39-39, 39-40, 39-41, 39-42, 39-43, 39-44, 39-45, 39-46, 39-47, 39-48, 39-49, 39-50, 39-51, 39-52, 39-53, 39-54, 39-55, 39-56, 39-57, 39-58, 39-59, 39-60, 39-61, 39-62, 39-63, 39-64, 39-65, 39-66, 39-67, 39-68, 39-69, 39-70, 39-71, 39-72, 39-73, 39-74, 39-75, 39-76, 39-77, 39-78, 39-79, 39-80, 39-81, 39-82, 39-83, 39-84, 39-85, 39-86, 39-87, 39-88, 39-89, 39-90, 39-91, 39-92, 39-93, 39-94, 39-95, 39-96, 39-97, 40-1, 40-2, 40-3, 40-4, 40-5, 40-6, 40-7, 40-8, 40-9, 40-10, 40-11, 40-12, 40-13, 40-14, 40-15, 40-16, 40-17, 40-18, 40-19, 40-20, 40-21, 40-22, 40-23, 40-24, 40-25, 40-26, 40-27, 40-28, 40-29, 40-30, 40-31, 40-32, 40-33, 40-34, 40-35, 40-36, 40-37, 40-38, 40-39, 40-40, 40-41, 40-42, 40-43, 40-44, 40-45, 40-46, 40-47, 40-48, 40-49, 40-50, 40-51, 40-52, 40-53, 40-54, 40-55, 40-56, 40-57, 40-58, 40-59, 40-60, 40-61, 40-62, 40-63, 40-64, 40-65, 40-66, 40-67, 40-68, 40-69, 40-70, 40-71, 40-72, 40-73, 40-74, 40-75, 40-76, 40-77, 40-78, 40-79, 40-80, 40-81, 40-82, 40-83, 40-84, 40-85, 40-86, 40-87, 40-88, 40-89, 40-90, 40-91, 40-92, 40-93, 40-94, 40-95, 40-96, 40-97, 41-1, 41-2, 41-3, 41-4, 41-5, 41-6, 41-7, 41-8, 41-9, 41-10, 41-11, 41-12, 41-13, 41-14, 41-15, 41-16, 41-17, 41-18, 41-19, 41-20, 41-21, 41-22, 41-23, 41-24, 41-25, 41-26, 41-27, 41-28, 41-29, 41-30, 41-31, 41-32, 41-33, 41-34, 41-35, 41-36, 41-37, 41-38, 41-39, 41-40, 41-41, 41-42, 41-43, 41-44, 41-45, 41-46, 41-47, 41-48, 41-49, 41-50, 41-51, 41-52, 41-53, 41-54, 41-55, 41-56, 41-57, 41-58, 41-59, 41-60, 41-61, 41-62, 41-63, 41-64, 41-65, 41-66, 41-67, 41-68, 41-69, 41-70, 41-71, 41-72, 41-73, 41-74, 41-75, 41-76, 41-77, 41-78, 41-79, 41-80, 41-81, 41-82, 41-83, 41-84, 41-85, 41-86, 41-87, 41-88, 41-89, 41-90, 41-91, 41-92, 41-93, 41-94, 41-95, 41-96, 41-97, 42-1, 42-2, 42-3, 42-4, 42-5, 42-6, 42-7, 42-8, 42-9, 42-10, 42-11, 42-12, 42-13, 42-14, 42-15, 42-16, 42-17, 42-18, 42-19, 42-20, 42-21, 42-22, 42-23, 42-24, 42-25, 42-26, 42-27, 42-28, 42-29, 42-30, 42-31, 42-32, 42-33, 42-34, 42-35, 42-36, 42-37, 42-38, 42-39, 42-40, 42-41, 42-42, 42-43, 42-44, 42-45, 42-46, 42-47, 42-48, 42-49, 42-50, 42-51, 42-52, 42-53, 42-54, 42-55, 42-56, 42-57, 42-58, 42-59, 42-60, 42-61, 42-62, 42-63, 42-64, 42-65, 42-66, 42-67, 42-68, 42-69, 42-70, 42-71, 42-72, 42-73, 42-74, 42-75, 42-76, 42-77, 42-78, 42-79, 42-80, 42-81, 42-82, 42-83, 42-84, 42-85, 42-86, 42-87, 42-88, 42-89, 42-90, 42-91, 42-92, 42-93, 42-94, 42-95, 42-96, 42-97, 43-1, 43-2, 43-3, 43-4, 43-5, 43-6, 43-7, 43-8, 43-9, 43-10, 43-11, 43-12, 43-13, 43-14, 43-15, 43-16, 43-17, 43-18, 43-19, 43-20, 43-21, 43-22, 43-23, 43-24, 43-25, 43-26, 43-27, 43-28, 43-29, 43-30, 43-31, 43-32, 43-33, 43-34, 43-35, 43-36, 43-37, 43-38, 43-39, 43-40, 43-41, 4342, 43-43, 43-44, 43-45, 43-46, 43-47, 43-48, 43-49, 43-50, 43-51, 43-52, 43-53, 43-54, 43-55, 43-56, 43-57, 43-58, 43-59, 43-60, 43-61, 43-62, 43-63, 43-64, 43-65, 43-66, 43-67, 43-68, 43-69, 43-70, 43-71, 43-72, 43-73, 43-74, 43-75, 43-76, 43-77, 43-78, 43-79, 43-80, 43-81, 43-82, 43-83, 43-84, 43-85, 43-86, 43-87, 43-88, 43-89, 43-90, 43-91, 43-92, 43-93, 43-94, 43-95, 43-96, 43-97, 44-1, 44-2, 44-3, 44-4, 44-5, 44-6, 44-7, 44-8, 44-9, 44-10, 44-11, 44-12, 44-13, 44-14, 44-15, 44-16, 44-17, 44-18, 44-19, 44-20, 44-21, 44-22, 44-23, 44-24, 44-25, 44-26, 44-27, 44-28, 44-29, 44-30, 44-31, 44-32, 44-33, 44-34, 44-35, 44-36, 44-37, 44-38, 44-39, 44-40, 44-41, 44-42, 44-43, 44-44, 44-45, 44-46, 44-47, 44-48, 44 49, 44-50, 44-51, 44-52, 44-53, 44-54, 44-55, 44-56, 44-57, 44-58, 44-59, 44-60, 44-61, 44-62, 44-63, 44-64, 44-65, 44-66, 44-67, 44-68, 44-69, 44-70, 44-71, 44-72, 44-73, 44-74, 44-75, 44-76, 44-77, 44-78, 44-79, 44-80, 44-81, 44-82, 44-83, 44-84, 44-85, 44-86, 44-87, 44-88, 44-89, 44-90, 44-91, 44-92, 44-93, 44-94, 44-95, 44-96, 44-97, 45-1, 45-2, 45-3, 45-4, 45-5, 45-6, 45-7, 45-8, 45-9, 45-10, 45-11, 45-12, 45-13, 45-14, 45-15, 45-16, 45-17, 45-18, 45-19, 45-20, 45-21, 45-22, 45-23, 45-24, 45-25, 45-26, 45-27, 45-28, 45-29, 45-30, 45-31, 45-32, 45-33, 45-34, 45-35, 45-36, 45-37, 45-38, 45-39, 45-40, 45-41, 45-42, 45-43, 45-44, 45-45, 45-46, 45-47, 45-48, 45-49, 45-50, 45-51, 45-52, 45-53, 45-54, 45-55, 45-56, 45-57, 45-58, 45-59, 45-60, 45-61, 45-62, 45-63, 45-64, 45-65, 45-66, 45-67, 45-68, 45-69, 45-70, 45-71, 45-72, 45-73, 45-74, 45-75, 45-76, 45-77, 45-78, 45-79, 45-80, 45-81, 45-82, 45-83, 45-84, 45-85, 45-86, 45-87, 45-88, 45-89, 45-90, 45-91, 45-92, 45-93, 45-94, 45-95, 45-96, 45-97, 46-1, 46-2, 46-3, 46-4, 46-5, 46-6, 46-7, 46-8, 46-9, 46-10, 46-11, 46-12, 46-13, 46-14, 46-15, 46-16, 46-17, 46-18, 46-19, 46-20, 46-21, 46-22, 46-23, 46-24, 46-25, 46-26, 46-27, 46-28, 46-29, 46-30, 46-31, 46-32, 46-33, 46-34, 46-35, 46-36, 46-37, 46-38, 46-39, 46-40, 46-41, 46-42, 46-43, 46-44, 46-45, 46-46, 46-47, 46-48, 46-49, 46-50, 46-51, 46-52, 46-53, 46-54, 46-55, 46-56, 46-57, 46-58, 46-59, 46-60, 46-61, 46-62, 46-63, 46-64, 46-65, 46-66, 46-67, 46-68, 46-69, 46-70, 46-71, 46-72, 46-73, 46-74, 46-75, 46-76, 46-77, 46-78, 46-79, 46-80, 46-81, 46-82, 46-83, 46-84, 46-85, 46-86, 46-87, 46-88, 46-89, 46-90, 46-91, 46-92, 46-93, 46-94, 46-95, 46-96, 46-97, 47-1, 47-2, 47-3, 47-4, 47-5, 47-6, 47-7, 47-8, 47-9, 47-10, 47-11, 47-12, 47-13, 47-14, 47-15, 47-16, 47-17, 47-18, 47-19, 47-20, 47-21, 47-22, 47-23, 47-24, 47-25, 47-26, 47-27, 47-28, 47-29, 47-30, 47-31, 47-32, 47-33, 47-34, 47-35, 47-36, 47-37, 47-38, 47-39, 47-40, 47-41, 47-42, 47-43, 47-44, 47-45, 47-46, 47-47, 47-48, 47-49, 47-50, 47-51, 47-52, 47-53, 47-54, 47-55, 47-56, 47-57, 47-58, 47-59, 47-60, 47-61, 47-62, 47-63, 47-64, 47-65, 47-66, 47-67, 47-68, 47-69, 47-70, 47-71, 47-72, 47-73, 47-74, 47-75, 47-76, 47-77, 47-78, 47-79, 47-80, 47-81, 47-82, 47-83, 47-84, 47-85, 47-86, 47-87, 47-88, 47-89, 47-90, 47-91, 47-92, 47-93, 47-94, 47-95, 47-96, 47-97, 48-1, 48-2, 48-3, 48-4, 48-5, 48-6, 48-7, 48-8, 48-9, 48-10, 48-11, 48-12, 48-13, 48-14, 48-15, 48-16, 48-17, 48-18, 48-19, 48-20, 48-21, 48-22, 48-23, 48-24, 48-25, 48-26, 48-27, 48-28, 48-29, 48-30, 48-31, 48-32, 48-33, 48-34, 48-35, 48-36, 48-37, 48-38, 48-39, 48-40, 48-41, 48-42, 48-43, 48-44, 48-45, 48-46, 48-47, 48-48, 48-49, 48-50, 48-51, 48-52, 48-53, 48-54, 48-55, 48-56, 48-57, 48-58, 48-59, 48-60, 48-61, 48-62, 48-63, 48-64, 48-65, 48-66, 48-67, 48-68, 48-69, 48-70, 48-71, 48-72, 48-73, 48-74, 48-75, 48-76, 48-77, 48-78, 48-79, 48-80, 48-81, 48-82, 48-83, 48-84, 48-85, 48-86, 48-87, 48-88, 48-89, 48-90, 48-91, 48-92, 48-93, 48-94, 48-95, 48-96, 48-97, 49-1, 49-2, 49-3, 49-4, 49-5, 49-6, 49-7, 49-8, 49-9, 49-10, 49-11, 49-12, 49-13, 49-14, 49-15, 49-16, 49-17, 49-18, 49-19, 49-20, 49-21, 49-22, 49-23, 49-24, 49-25, 49-26, 49-27, 49-28, 49-29, 49-30, 49-31, 49-32, 49-33, 49-34, 49-35, 49-36, 49-37, 49-38, 49-39, 49-40, 49-41, 49-42, 49-43, 49-44, 49-45, 49-46, 49-47, 49-48, 49-49, 49-50, 49-51, 49-52, 49-53, 49-54, 49-55, 49-56, 49-57, 49-58, 49-59, 49-60, 49-61, 49-62, 49-63, 49-64, 49-65, 49-66, 49-67, 49-68, 49-69, 49-70, 49-71, 49-72, 49-73, 49-74, 49-75, 49-76, 49-77, 49-78, 49-79, 49-80, 49-81, 49-82, 49-83, 49-84, 49-85, 49-86, 49-87, 49-88, 49-89, 49-90, 49-91, 49-92, 49-93, 49-94, 49-95, 49-96, 49-97, 50-1, 50-2, 50-3, 50-4, 50-5, 50-6, 50-7, 50-8, 50-9, 50-10, 50-11, 50-12, 50-13, 50-14, 50-15, 50-16, 50-17, 50-18, 50-19, 50-20, 50-21, 50-22, 50-23, 50-24, 50-25, 50-26, 50-27, 50-28, 50-29, 50-30, 50-31, 50-32, 50-33, 50-34, 50-35, 50-36, 50-37, 50-38, 50-39, 50-40, 50-41, 50-42, 50-43, 50-44, 50-45, 50-46, 50-47, 50-48, 50-49, 50-50, 50-51, 50-52, 50-53, 50-54, 50-55, 50-56, 50-57, 50-58, 50-59, 50-60, 50-61, 50-62, 50-63, 50-64, 50-65, 50-66, 50-67, 50-68, 50-69, 50-70, 50-71, 50-72, 50-73, 50-74, 50-75, 50-76, 50-77, 50-78, 50-79, 50-80, 50-81, 50-82, 50-83, 50-84, 50-85, 50-86, 50-87, 50-88, 50-89, 50-90, 50-91, 50-92, 50-93, 50-94, 50-95, 50-96, 50-97, 51-1, 51-2, 51-3, 514, 51-5, 51-6, 51-7, 51-8, 51-9, 51-10, 51-11, 51-12, 51-13, 51-14, 51-15, 51-16, 51-17, 51-18, 51-19, 51-20, 51-21, 51-22, 51-23, 51-24, 51-25, 51-26, 51-27, 51-28, 51-29, 51-30, 51-31, 51-32, 51-33, 51-34, 51-35, 51-36, 51-37, 51-38, 51-39, 51-40, 51-41, 51-42, 51-43, 51-44, 51-45, 51-46, 51-47, 51-48, 51-49, 51-50, 51-51, 51-52, 51-53, 51-54, 51-55, 51-56, 51-57, 51-58, 51-59, 51-60, 51-61, 51-62, 51-63, 51-64, 51-65, 51-66, 51-67, 51-68, 51-69, 51-70, 51-71, 51-72, 51-73, 51-74, 51-75, 51-76, 51-77, 51-78, 51-79, 51-80, 51-81, 51-82, 51-83, 51-84, 51-85, 51-86, 51-87, 51-88, 51-89, 51-90, 51-91, 51-92, 51-93, 51-94, 51-95, 51-96, 51-97, 52-1, 52-2, 52-3, 52-4, 52-5, 52-6, 52-7, 52-8, 52-9, 52-10, 52-11, 52-12, 52-13, 52-14, 52-15, 52-16, 52-17, 52-18, 52-19, 52-20, 52-21, 52-22, 52-23, 52-24, 52-25, 52-26, 52-27, 52-28, 52-29, 52-30, 52-31, 52-32, 52-33, 52-34, 52-35, 52-36, 52-37, 52-38, 52-39, 52-40, 52-41, 52-42, 52-43, 52-44, 52-45, 52-46, 52-47, 52-48, 52-49, 52-50, 52-51, 52-52, 52-53, 52-54, 52-55, 52-56, 52-57, 52-58, 52-59, 52-60, 52-61, 52-62, 52-63, 52-64, 52-65, 52-66, 52-67, 52-68, 52-69, 52-70, 52-71, 52-72, 52-73, 52-74, 52-75, 52-76, 52-77, 52-78, 52-79, 52-80, 52-81, 52-82, 52-83, 52-84, 52-85, 52-86, 52-87, 52-88, 52-89, 52-90, 52-91, 52-92, 52-93, 52-94, 52-95, 52-96, 52-97, 53-1, 53-2, 53-3, 53-4, 53-5, 53-6, 53-7, 53-8, 53-9, 53-10, 53-11, 53-12, 53-13, 53-14, 53-15, 53-16, 53-17, 53-18, 53-19, 53-20, 53-21, 53-22, 53-23, 53-24, 53-25, 53-26, 53-27, 53-28, 53-29, 53-30, 53-31, 53-32, 53-33, 53-34, 53-35, 53-36, 53-37, 53-38, 53-39, 53-40, 53-41, 53-42, 53-43, 53-44, 53-45, 53-46, 53-47, 53-48, 53-49, 53-50, 53-51, 53-52, 53-53, 53-54, 53-55, 53-56, 53-57, 53-58, 53-59, 53-60, 53-61, 53-62, 53-63, 53-64, 53-65, 53-66, 53-67, 53-68, 53-69, 53-70, 53-71, 53-72, 53-73, 53-74, 53-75, 53-76, 53-77, 53-78, 53-79, 53-80, 53-81, 53-82, 53-83, 53-84, 53-85, 53-86, 53-87, 53-88, 53-89, 53-90, 53-91, 53-92, 53-93, 53-94, 53-95, 53-96, 53-97, 54-1, 54-2, 54-3, 54-4, 54-5, 54-6, 54-7, 54-8, 54-9, 54-10, 54-11, 54-12, 54-13, 54-14, 54-15, 54-16, 54-17, 54-18, 54-19, 54-20, 54-21, 54-22, 54-23, 54-24, 54-25, 54-26, 54-27, 54-28, 54-29, 54-30, 54-31, 54-32, 54-33, 54-34, 54-35, 54-36, 54-37, 54-38, 54-39, 54-40, 54-41, 54-42, 54-43, 54-44, 54-45, 54-46, 54-47, 54-48, 54-49, 54-50, 54-51, 54-52, 54-53, 54-54, 54-55, 54-56, 54-57, 54-58, 54-59, 54-60, 54-61, 54-62, 54-63, 54-64, 54-65, 54-66, 54-67, 54-68, 54-69, 54-70, 54-71, 54-72, 54-73, 54-74, 54-75, 54-76, 54-77, 54-78, 54-79, 54-80, 54-81, 54-82, 54-83, 54-84, 54-85, 54-86, 54-87, 54-88, 54-89, 54-90, 54-91, 54-92, 54-93, 54-94, 54-95, 54-96, 54-97, 55-1, 55-2, 55-3, 55-4, 55-5, 55-6, 55-7, 55-8, 55-9, 55-10, 55-11, 55-12, 55-13, 55-14, 55-15, 55-16, 55-17, 55-18, 55-19, 55-20, 55-21, 55-22, 55-23, 55-24, 55-25, 55-26, 55-27, 55-28, 55-29, 55-30, 55-31, 55-32, 55-33, 55-34, 55-35, 55-36, 55-37, 55-38, 55-39, 55-40, 55-41, 55-42, 55-43, 55-44, 55-45, 55-46, 55-47, 55-48, 55-49, 55-50, 55-51, 55-52, 55-53, 55-54, 55-55, 55-56, 55-57, 55-58, 55-59, 55-60, 55-61, 55-62, 55-63, 55-64, 55-65, 55-66, 55-67, 55-68, 55-69, 55-70, 55-71, 55-72, 55-73, 55-74, 55-75, 55-76, 55-77, 55-78, 55-79, 55-80, 55-81, 55-82, 55-83, 55-84, 55-85, 55-86, 55-87, 55-88, 55-89, 55-90, 55-91, 55-92, 55-93, 55-94, 55-95, 55-96, 55-97, 56-1, 56-2, 56-3, 56-4, 56-5, 56-6, 56-7, 56-8, 56-9, 56-10, 56-11, 56-12, 56-13, 56-14, 56-15, 56-16, 56-17, 56-18, 56-19, 56-20, 56-21, 56-22, 56-23, 56-24, 56-25, 56-26, 56-27, 56-28, 56-29, 56-30, 56-31, 56-32, 56-33, 56-34, 56-35, 56-36, 56-37, 56-38, 56-39, 56-40, 56-41, 56-42, 56-43, 56-44, 56-45, 56-46, 56-47, 56-48, 56-49, 56-50, 56-51, 56-52, 56-53, 56-54, 56-55, 56-56, 56-57, 56-58, 56-59, 56-60, 56-61, 56-62, 56-63, 56-64, 56-65, 56-66, 56-67, 56-68, 56-69, 56-70, 56-71, 56-72, 56-73, 56-74, 56-75, 56-76, 56-77, 56-78, 56-79, 56-80, 56-81, 56-82, 56-83, 56-84, 56-85, 56-86, 56-87, 56-88, 56-89, 56-90, 56-91, 56-92, 56-93, 56-94, 56-95, 56-96, 56-97, 57-1, 57-2, 57-3, 57-4, 57-5, 57-6, 57-7, 57-8, 57-9, 57-10, 57-11, 57-12, 57-13, 57-14, 57-15, 57-16, 57-17, 57-18, 57-19, 57-20, 57-21, 57-22, 57-23, 57-24, 57-25, 57-26, 57-27, 57-28, 57-29, 57-30, 57-31, 57-32, 57-33, 57-34, 57-35, 57-36, 57-37, 57-38, 57-39, 57-40, 57-41, 57-42, 57-43, 57-44, 57-45, 57-46, 57-47, 57-48, 57-49, 57-50, 57-51, 57-52, 57-53, 57-54, 57-55, 57-56, 57-57, 57-58, 57-59, 57-60, 57-61, 57-62, 57-63, 57-64, 57-65, 57-66; 57-67, 57-68, 57-69, 57-70, 57-71, 57-72, 57-73, 57-74, 57-75, 57-76, 57-77, 57-78, 57-79, 57-80, 57-81, 57-82, 57-83, 57-84, 57-85, 57-86, 57-87, 57-88, 57-89, 57-90, 57-91, 57-92, 57-93, 57-94, 57-95, 57-96, 57-97, 58-1, 58-2, 58-3, 58-4, 58-5, 58-6, 58-7, 58-8, 58-9, 58-10, 58-11, 58-12, 58-13, 58-14, 58-15, 58-16, 58-17, 58-18, 58-19, 58-20, 58-21, 58-22, 58-23, 58-24, 58-25, 58-26, 58-27, 58-28, 58-29, 58-30, 58-31, 58-32, 58-33, 58-34, 58-35, 58-36, 58-37, 58-38, 58-39, 58-40, 58-41, 58-42, 58-43, 58-44, 58-45, 58-46, 58-47, 58-48, 58-49, 58-50, 58-51, 58-52, 58-53, 58-54, 58-55, 58-56, 58-57, 58-58, 58-59, 58-60, 58-61, 58-62, 58-63, 58-64, 58-65, 58-66, 58-67, 58-68, 58-69, 58-70, 58-71, 58-72, 58-73, 58-74, 58-75, 58-76, 58-77, 58-78, 58-79, 58-80, 58-81, 58-82, 58-83, 58-84, 58-85, 58-86, 58-87, 58-88, 58-89, 58-90, 58-91, 58-92, 58-93, 58-94, 58-95, 58-96, 58-97, 59-1, 59-2, 59-3, 59-4, 59-5, 59-6, 59-7, 59-8, 59-9, 59-10, 59-11, 59-12, 59-13, 59-14, 59-15, 59-16, 59-17, 59-18, 59-19, 59-20, 59-21, 59-22, 59-23, 59-24, 59-25, 59-26, 59-27, 59-28, 59-29, 59-30, 59-31, 59-32, 59-33, 59-34, 59-35, 59-36, 59-37, 59-38, 59-39, 59-40, 59-41, 59-42, 59-43, 59-44, 59-45, 59-46, 59-47, 59-48, 59-49, 59-50, 59-51, 59-52, 59-53, 59-54, 59-55, 59-56, 59-57, 59-58, 59-59, 59-60, 59-61, 59-62, 59-63, 59-64, 59-65, 59-66, 59-67, 59-68, 59-69, 59-70, 59-71, 59-72, 59-73, 59-74, 59-75, 59-76, 59-77, 59-78, 59-79, 59-80, 59-81, 59-82, 59-83, 59-84, 59-85, 59-86, 59-87, 59-88, 59-89, 59-90, 59-91, 59-92, 59-93, 59-94, 59-95, 59-96, 59-97, 60-1, 60-2, 60-3, 60-4, 60-5, 60-6, 60-7, 60-8, 60-9, 60-10, 60-11, 60-12, 60-13, 60-14, 60-15, 60-16, 60-17, 60-18, 60-19, 60-20, 60-21, 60-22, 60-23, 60-24, 60-25, 60-26, 60-27, 60-28, 60-29, 60-30, 60-31, 60-32, 60-33, 60-34, 60-35, 60-36, 60-37, 60-38, 60-39, 60-40, 60-41, 60-42, 60-43, 60-44, 60-45, 60-46, 60-47, 60-48, 60-49, 60-50, 60-51, 60-52, 60-53, 60-54, 60-55, 60-56, 60-57, 60-58, 60-59, 60-60, 60-61, 60-62, 60-63, 60-64, 60-65, 60-66, 60-67, 60-68, 60-69, 60-70, 60-71, 60-72, 60-73, 60-74, 60-75, 60-76, 60-77, 60-78, 60-79, 60-80, 60-81, 60-82, 60-83, 60-84, 60-85, 60-86, 60-87, 60-88, 60-89, 60-90, 60-91, 60-92, 60-93, 60-94, 60-95, 60-96, 60-97, 61-1, 61-2, 61-3, 61-4, 61-5, 61-6, 61-7, 61-8, 61-9, 61-10, 61-11, 61-12, 61-13, 61-14, 61-15, 61-16, 61-17, 61-18, 61-19, 61-20, 61-21, 61-22, 61-23, 61-24, 61-25, 61-26, 61-27, 61-28, 61-29, 61-30, 61-31, 61-32, 61-33, 61-34, 61-35, 61-36, 61-37, 61-38, 61-39, 61-40, 61-41, 61-42, 61-43, 61-44, 61-45, 61-46, 61-47, 61-48, 61-49, 61-50, 61-51, 61-52, 61-53, 61-54, 61-55, 61-56, 61-57, 61-58, 61-59, 61-60, 61-61, 61-62, 61-63, 61-64, 61-65, 61-66, 61-67, 61-68, 61-69, 61-70, 61-71, 61-72, 61-73, 61-74, 61-75, 61-76, 61-77, 61-78, 61-79, 61-80, 61-81, 61-82, 61-83, 61-84, 61-85, 61-86, 61-87, 61-88, 61-89, 61-90, 61-91, 61-92, 61-93, 61-94, 61-95, 61-96, 61-97, 62-1, 62-2, 62-3, 62-4, 62-5, 62-6, 62-7, 62-8, 62-9, 62-10, 62-11, 62-12, 62-13, 62-14, 62-15, 62-16, 62-17, 62-18, 62-19, 62-20, 62-21, 62-22, 62-23, 62-24, 62-25, 62-26, 62-27, 62-28, 62-29, 62-30, 62-31, 62-32, 62-33, 62-34, 62-35, 62-36, 62-37, 62-38, 62-39, 62-40, 62-41, 62-42, 62-43, 62-44, 62-45, 62-46, 62-47, 62-48, 62-49, 62-50, 62-51, 62-52, 62-53, 62-54, 62-55, 62-56, 62-57, 62-58, 62-59, 62-60, 62-61, 62-62, 62-63, 62-64, 62-65, 62-66, 62-67, 62-68, 62-69, 62-70, 62-71, 62-72, 62-73, 62-74, 62-75, 62-76, 62-77, 62-78, 62-79, 62-80, 62-81, 62-82, 62-83, 62-84, 62-85, 62-86, 62-87, 62-88, 62-89, 62-90, 62-91, 62-92, 62-93, 62-94, 62-95, 62-96, 62-97, 63-1, 63-2, 63-3, 63-4, 63-5, 63-6, 63-7, 63-8, 63-9, 63-10, 63-11, 63-12, 63-13, 63-14, 63-15, 63-16, 63-17, 63-18, 63-19, 63-20, 63-21, 63-22, 63-23, 63-24, 63-25, 63-26, 63-27, 63-28, 63-29, 63-30, 63-31, 63-32, 63-33, 63-34, 63-35, 63-36, 63-37, 63-38, 63-39, 63-40, 63-41, 63-42, 63-43, 63-44, 63-45, 63-46, 63-47, 63-48, 63-49, 63-50, 63-51, 63-52, 63-53, 63-54, 63-55, 63-56, 63-57, 63-58, 63-59, 63-60, 63-61, 63-62, 63-63, 63-64, 63-65, 63-66, 63-67, 63-68, 63-69, 63-70, 63-71, 63-72, 63-73, 63-74, 63-75, 63-76, 63-77, 63-78, 63-79, 63-80, 63-81, 63-82, 63-83, 63-84, 63-85, 63-86, 63-87, 63-88, 63-89, 63-90, 63-91, 63-92, 63-93, 63-94, 63-95, 63-96, 63-97, 64-1, 64-2, 64-3, 644, 64-5, 64-6, 64-7, 64-8, 64-9, 64-10, 64-11, 64-12, 64-13, 64-14, 64-15, 64-16, 64-17, 64-18, 64-19, 64-20, 64-21, 64-22, 64-23, 64-24, 64-25, 64-26, 64-27, 64-28, 64-29, 64-30, 64-31, 64-32, 64-33, 64-34, 64-35, 64-36, 64-37, 64-38, 64-39, 64-40, 64-41, 64-42, 64-43, 64-44, 64-45, 64-46, 64-47, 64-48, 64-49, 64-50, 64-51, 64-52, 64-53, 64-54, 64-55, 64-56, 64-57, 64-58, 64-59, 64-60, 64-61, 64-62, 64-63, 64-64, 64-65, 64-66, 64-67, 64-68, 64-69, 64-70, 64-71, 64-72, 64-73, 64-74, 64-75, 64-76, 64-77, 64-78, 64-79, 64-80, 64-81, 64-82, 64-83, 64-84, 64-85, 64-86, 64-87, 64-88, 64-89, 64-90, 64-91, 64-92, 64-93, 64-94, 64-95, 64-96, 64-97, 65-1, 65-2, 65-3, 65-4, 65-5, 65-6, 65-7, 65-8, 65-9, 65-10, 65-11, 65-12, 65-13, 65-14, 65-15, 65-16, 65-17, 65-18, 65-19, 65-20, 65-21, 65-22, 65-23, 65-24, 65-25, 65-26, 65-27, 65-28, 65-29, 65-30, 65-31, 65-32, 65-33, 65-34, 65-35, 65-36, 65-37, 65-38, 65-39, 65-40, 65-41, 65-42, 65-43, 65-44, 65-45, 65-46, 65-47, 65-48, 65-49, 65-50, 65-51, 65-52, 65-53, 65-54, 65-55, 65-56, 65-57, 65-58, 65-59, 65-60, 65-61, 65-62, 65-63, 65-64, 65-65, 65-66, 65-67, 65-68, 65-69, 65-70, 65-71, 65-72, 65-73, 65-74, 65-75, 65-76, 65-77, 65-78, 65-79, 65-80, 65-81, 65-82, 65-83, 65-84, 65-85, 65-86, 65-87, 65-88, 65-89, 65-90, 65-91, 65-92, 65-93, 65-94, 65-95, 65-96, 65-97, 66-1, 66-2, 66-3, 66-4, 66-5, 66-6, 66-7, 66-8, 66-9, 66-10, 66-11, 66-12, 66-13, 66-14, 66-15, 66-16, 66-17, 66-18, 66-19, 66-20, 66-21, 66-22, 66-23, 66-24, 66-25, 66-26, 66-27, 66-28, 66-29, 66-30, 66-31, 66-32, 66-33, 66-34, 66-35, 66-36, 66-37, 66-38, 66-39, 66-40, 66-41, 66-42, 66-43, 66-44, 66-45, 66-46, 66-47, 66-48, 66-49, 66-50, 66-51, 66-52, 66-53, 66-54, 66-55, 66-56, 66-57, 66-58, 66-59, 66-60, 66-61, 66-62, 66-63, 66-64, 66-65, 66-66, 66-67, 66-68, 66-69, 66-70, 66-71, 66-72, 66-73, 66-74, 66-75, 66-76, 66-77, 66-78, 66-79, 66-80, 66-81, 66-82, 66-83, 66-84, 66-85, 66-86, 66-87, 66-88, 66-89, 66-90, 66-91, 66-92, 66-93, 66-94, 66-95, 66-96, 66-97, 67-1, 67-2, 67-3, 674, 67-5, 67-6, 67-7, 67-8, 67-9, 67-10, 67-11, 67-12, 67-13, 67-14, 67-15, 67-16, 67-17, 67-18, 67-19, 67-20, 67-21, 67-22, 67-23, 67-24, 67-25, 67-26, 67-27, 67-28, 67-29, 67-30, 67-31, 67-32, 67-33, 67-34, 67-35, 67-36, 67-37, 67-38, 67-39, 67-40, 67-41, 67-42, 67-43, 67-44, 67-45, 67-46, 67-47, 67-48, 67-49, 67-50, 67-51, 67-52, 67-53, 67-54, 67-55, 67-56, 67-57, 67-58, 67-59, 67-60, 67-61, 67-62, 67-63, 67-64, 67-65, 67-66, 67-67, 67-68, 67-69, 67-70, 67-71, 67-72, 67-73, 67-74, 67-75, 67-76, 67-77, 67-78, 67-79, 67-80, 67-81, 67-82, 67-83, 67-84, 67-85, 67-86, 67-87, 67-88, 67-89, 67-90, 67-91, 67-92, 67-93, 67-94, 67-95, 67-96, 67-97, 68-1, 68-2, 68-3, 68-4, 68-5, 68-6, 68-7, 68-8, 68-9, 68-10, 68-11, 68-12, 68-13, 68-14, 68-15, 68-16, 68-17, 68-18, 68-19, 68-20, 68-21, 68-22, 68-23, 68-24, 68-25, 68-26, 68-27, 68-28, 68-29, 68-30, 68-31, 68-32, 68-33, 68-34, 68-35, 68-36, 68-37, 68-38, 68-39, 68-40, 68-41, 68-42, 68-43, 68-44, 68-45, 68-46, 68-47, 68-48, 68-49, 68-50, 68-51, 68-52, 68-53, 68-54, 68-55, 68-56, 68-57, 68-58, 68-59, 68-60, 68-61, 68-62, 68-63, 68-64, 68-65, 68-66, 68-67, 68-68, 68-69, 68-70, 68-71, 68-72, 68-73, 68-74, 68-75, 68-76, 68-77, 68-78, 68-79, 68-80, 68-81, 68-82, 68-83, 68-84, 68-85, 68-86, 68-87, 68-88, 68-89, 68-90, 68-91, 68-92, 68-93, 68-94, 68-95, 68-96, 68-97, 69-1, 69-2, 69-3, 694, 69-5, 69-6, 69-7, 69-8, 69-9, 69-10, 69-11, 69-12, 69-13, 69-14, 69-15, 69-16, 69-17, 69-18, 69-19, 69-20, 69-21, 69-22, 69-23, 69-24, 69-25, 69-26, 69-27, 69-28, 69-29, 69-30, 69-31, 69-32, 69-33, 69-34, 69-35, 69-36, 69-37, 69-38, 69-39, 69-40, 69-41, 69-42, 69-43, 69-44, 69-45, 69-46, 69-47, 69-48, 69-49, 69-50, 69-51, 69-52, 69-53, 69-54, 69-55, 69-56, 69-57, 69-58, 69-59, 69-60, 69-61, 69-62, 69-63, 69-64, 69-65, 69-66, 69-67, 69-68, 69-69, 69-70, 69-71, 69-72, 69-73, 69-74, 69-75, 69-76, 69-77, 69-78, 69-79, 69-80, 69-81, 69-82, 69-83, 69-84, 69-85, 69-86, 69-87, 69-88, 69-89, 69-90, 69-91, 69-92, 69-93, 69-94, 69-95, 69-96, 69-97, 70-1, 70-2, 70-3, 70-4, 70-5, 70-6, 70-7, 70-8, 70-9, 70-10, 70-11, 70-12, 70-13, 70-14, 70-15, 70-16, 70-17, 70-18, 70-19, 70-20, 70-21, 70-22, 70-23, 70-24, 70-25, 70-26, 70-27, 70-28, 70-29, 70-30, 70-31, 70-32, 70-33, 70-34, 70-35, 70-36, 70-37, 70-38, 70-39, 70-40, 70-41, 70-42, 70-43, 70-44, 70-45, 70-46, 70-47, 70-48, 70-49, 70-50, 70-51, 70-52, 70-53, 70-54, 70-55, 70-56, 70-57, 70-58, 70-59, 70-60, 70-61, 70-62, 70-63, 70-64, 70-65, 70-66, 70-67, 70-68, 70-69, 70-70, 70-71, 70-72, 70-73, 70-74, 70-75, 70-76, 70-77, 70-78, 70-79, 70-80, 70-81, 70-82, 70-83, 70-84, 70-85, 70-86, 70-87, 70-88, 70-89, 70-90, 70-91, 70-92, 70-93, 70-94, 70-95, 70-96, 70-97, 71-1, 71-2, 71-3, 714, 71-5, 71-6, 71-7, 71-8, 71-9, 71-10, 71-11, 71-12, 71-13, 71-14, 71-15, 71-16, 71-17, 71-18, 71-19, 71-20, 71-21, 71-22, 71-23, 71-24, 71-25, 71-26, 71-27, 71-28, 71-29, 71-30, 71-31, 71-32, 71-33, 71-34, 71-35, 71-36, 71-37, 71-38, 71-39, 71-40, 71-41, 71-42, 71-43, 71-44, 71-45, 71-46, 71-47, 71-48, 71-49, 71-50, 71-51, 71-52, 71-53, 71-54, 71-55, 71-56, 71-57, 71-58, 71-59, 71-60, 71-61, 71-62, 71-63, 71-64, 71-65, 71-66, 71-67, 71-68, 71-69, 71-70, 71-71, 71-72, 71-73, 71-74, 71-75, 71-76, 71-77, 71-78, 71-79, 71-80, 71-81, 71-82, 71-83, 71-84, 71-85, 71-86, 71-87, 71-88, 71-89, 71-90, 71-91, 71-92, 71-93, 71-94, 71-95, 71-96, 71-97, 72-1, 72-2, 72-3, 72-4, 72-5, 72-6, 72-7, 72-8, 72-9, 72-10, 72-11, 72-12, 72-13, 72-14, 72-15, 72-16, 72-17, 72-18, 72-19, 72-20, 72-21, 72-22, 72-23, 72-24, 72-25, 72-26, 72-27, 72-28, 72-29, 72-30, 72-31, 72-32, 72-33, 72-34, 72-35, 72-36, 72-37, 72-38, 72-39, 72-40, 72-41, 72-42, 72-43, 72-44, 72-45, 72-46, 72-47, 72-48, 72-49, 72-50, 72-51, 72-52, 72-53, 72-54, 72-55, 72-56, 72-57, 72-58, 72-59, 72-60, 72-61, 72-62, 72-63, 72-64, 72-65, 72-66, 72-67, 72-68, 72-69, 72-70, 72-71, 72-72, 72-73, 72-74, 72-75, 72-76, 72-77, 72-78, 72-79, 72-80, 72-81, 72-82, 72-83, 72-84, 72-85, 72-86, 72-87, 72-88, 72-89, 72-90, 72-91, 72-92, 72-93, 72-94, 72-95, 72-96, 72-97,

73-1, 73-2, 73-3, 73-4, 73-5, 73-6, 73-7, 73-8, 73-9, 73-10, 73-11, 73-12, 73-13, 73-14, 73-15, 73-16, 73-17, 73-18, 73-19, 73-20, 73-21, 73-22, 73-23, 73-24, 73-25, 73-26, 73-27, 73-28, 73-29, 73-30, 73-31, 73-32, 73-33, 73-34, 73-35, 73-36, 73-37, 73-38, 73-39, 73-40, 73-41, 73-42, 73-43, 73-44, 73-45, 73-46, 73-47, 73-48, 73-49, 73-50, 73-51, 73-52, 73-53, 73-54, 73-55, 73-56, 73-57, 73-58, 73-59, 73-60, 73-61, 73-62, 73-63, 73-64, 73-65, 73-66, 73-67, 73-68, 73-69, 73-70, 73-71, 73-72, 73-73, 73-74, 73-75, 73-76, 73-77, 73-78, 73-79, 73-80, 73-81, 73-82, 73-83, 73-84, 73-85, 73-86, 73-87, 73-88, 73-89, 73-90, 73-91, 73-92, 73-93, 73-94, 73-95, 73-96, 73-97, 74-1, 74-2, 74-3, 74-4, 74-5, 74-6, 74-7, 74-8, 74-9, 74-10, 74-11, 74-12, 74-13, 74-14, 74-15, 74-16, 74-17, 74-18, 74-19, 74-20, 74-21, 74-22, 74-23, 74-24, 74-25, 74-26, 74-27, 74-28, 74-29, 74-30, 74-31, 74-32, 74-33, 74-34, 74-35, 74-36, 74-37, 74-38, 74-39, 74-40, 74-41, 74-42, 74-43, 74-44, 74-45, 74-46, 74-47, 74-48, 74-49, 74-50, 74-51, 74-52, 74-53, 74-54, 74-55, 74-56, 74-57, 74-58, 74-59, 74-60, 74-61, 74-62, 74-63, 74-64, 74-65, 74-66, 74-67, 74-68, 74-69, 74-70, 74-71, 74-72, 74-73, 74-74, 74-75, 74-76, 74-77, 74-78, 74-79, 74-80, 74-81, 74-82, 74-83, 74-84, 74-85, 74-86, 74-87, 74-88, 74-89, 74-90, 74-91, 74-92, 74-93, 74-94, 74-95, 74-96, 74-97, 75-1, 75-2, 75-3, 75-4, 75-5, 75-6, 75-7, 75-8, 75-9, 75-10, 75-11, 75-12, 75-13, 75-14, 75-15, 75-16, 75-17, 75-18, 75-19, 75-20, 75-21, 75-22, 75-23, 75-24, 75-25, 75-26, 75-27, 75-28, 75-29, 75-30, 75-31, 75-32, 75-33, 75-34, 75-35, 75-36, 75-37, 75-38, 75-39, 75-40, 75-41, 75-42, 75-43, 75-44, 75-45, 75-46, 75-47, 75-48, 75-49, 75-50, 75-51, 75-52, 75-53, 75-54, 75-55, 75-56, 75-57, 75-58, 75-59, 75-60, 75-61, 75-62, 75-63, 75-64, 75-65, 75-66, 75-67, 75-68, 75-69, 75-70, 75-71, 75-72, 75-73, 75-74, 75-75, 75-76, 75-77, 75-78, 75-79, 75-80, 75-81, 75-82, 75-83, 75-84, 75-85, 75-86, 75-87, 75-88, 75-89, 75-90, 75-91, 75-92, 75-93, 75-94, 75-95, 75-96, 75-97, 76-1, 76-2, 76-3, 76-4, 76-5, 76-6, 76-7, 76-8, 76-9, 76-10, 76-11, 76-12, 76-13, 76-14, 76-15, 76-16, 76-17, 76-18, 76-19, 76-20, 76-21, 76-22, 76-23, 76-24, 76-25, 76-26, 76-27, 76-28, 76-29, 76-30, 76-31, 76-32, 76-33, 76-34, 76-35, 76-36, 76-37, 76-38, 76-39, 76-40, 76-41, 76-42, 76-43, 76-44, 76-45, 76-46, 76-47, 76-48, 76-49, 76-50, 76-51, 76-52, 76-53, 76-54, 76-55, 76-56, 76-57, 76-58, 76-59, 76-60, 76-61, 76-62, 76-63, 76-64, 76-65, 76-66, 76-67, 76-68, 76-69, 76-70, 76-71, 76-72, 76-73, 76-74, 76-75, 76-76, 76-77, 76-78, 76-79, 76-80, 76-81, 76-82, 76-83, 76-84, 76-85, 76-86, 76-87, 76-88, 76-89, 76-90, 76-91, 76-92, 76-93, 76-94, 76-95, 76-96, 76-97, 77-1, 77-2, 77-3, 77-4, 77-5, 77-6, 77-7, 77-8, 77-9, 77-10, 77-11, 77-12, 77-13, 77-14, 77-15, 77-16, 77-17, 77-18, 77-19, 77-20, 77-21, 77-22, 77-23, 77-24, 77-25, 77-26, 77-27, 77-28, 77-29, 77-30, 77-31, 77-32, 77-33, 77-34, 77-35, 77-36, 77-37, 77-38, 77-39, 77-40, 77-41, 77-42, 77-43, 77-44, 77-45, 77-46, 77-47, 77-48, 77-49, 77-50, 77-51, 77-52, 77-53, 77-54, 77-55, 77-56, 77-57, 77-58, 77-59, 77-60, 77-61, 77-62, 77-63, 77-64, 77-65, 77-66, 77-67, 77-68, 77-69, 77-70, 77-71, 77-72, 77-73, 77-74, 77-75, 77-76, 77-77, 77-78, 77-79, 77-80, 77-81, 77-82, 77-83, 77-84, 77-85, 77-86, 77-87, 77-88, 77-89, 77-90, 77-91, 77-92, 77-93, 77-94, 77-95, 77-96, 77-97, 78-1, 78-2, 78-3, 784, 78-5, 78-6, 78-7, 78-8, 78-9, 78-10, 78-11, 78-12, 78-13, 78-14, 78-15, 78-16, 78-17, 78-18, 78-19, 78-20, 78-21, 78-22, 78-23, 78-24, 78-25, 78-26, 78-27, 78-28, 78-29, 78-30, 78-31, 78-32, 78-33, 78-34, 78-35, 78-36, 78-37, 78-38, 78-39, 78-40, 78-41, 78-42, 78-43, 78-44, 78-45, 78-46, 78-47, 78-48, 78-49, 78-50, 78-51, 78-52, 78-53, 78-54, 78-55, 78-56, 78-57, 78-58, 78-59, 78-60, 78-61, 78-62, 78-63, 78-64, 78-65, 78-66, 78-67, 78-68, 78-69, 78-70, 78-71, 78-72, 78-73, 78-74, 78-75, 78-76, 78-77, 78-78, 78-79, 78-80, 78-81, 78-82, 78-83, 78-84, 78-85, 78-86, 78-87, 78-88, 78-89, 78-90, 78-91, 78-92, 78-93, 78-94, 78-95, 78-96, 78-97, 79-1, 79-2, 79-3, 79-4, 79-5, 79-6, 79-7, 79-8, 79-9, 79-10, 79-11, 79-12, 79-13, 79-14, 79-15, 79-16, 79-17, 79-18, 79-19, 79-20, 79-21, 79-22, 79-23, 79-24, 79-25, 79-26, 79-27, 79-28, 79-29, 79-30, 79-31, 79-32, 79-33, 79-34, 79-35, 79-36, 79-37, 79-38, 79-39, 79-40, 79-41, 79-42, 79-43, 79-44, 79-45, 79-46, 79-47, 79-48, 79-49, 79-50, 79-51, 79-52, 79-53, 79-54, 79-55, 79-56, 79-57, 79-58, 79-59, 79-60, 79-61, 79-62, 79-63, 79-64, 79-65, 79-66, 79-67, 79-68, 79-69, 79-70, 79-71, 79-72, 79-73, 79-74, 79-75, 79-76, 79-77, 79-78, 79-79, 79-80, 79-81, 79-82, 79-83, 79-84, 79-85, 79-86, 79-87, 79-88, 79-89, 79-90, 79-91, 79-92, 79-93, 79-94, 79-95, 79-96, 79-97, 80-1, 80-2, 80-3, 80-4, 80-5, 80-6, 80-7, 80-8, 80-9, 80-10, 80-11, 80-12, 80-13, 80-14, 80-15, 80-16, 80-17, 80-18, 80-19, 80-20, 80-21, 80-22, 80-23, 80-24, 80-25, 80-26, 80-27, 80-28, 80-29, 80-30, 80-31, 80-32, 80-33, 80-34, 80-35, 80-36, 80-37, 80-38, 80-39, 80-40, 80-41, 80-42, 80-43, 80-44, 80-45, 80-46, 80-47, 80-48, 80-49, 80-50, 80-51, 80-52, 80-53, 80-54, 80-55, 80-56, 80-57, 80-58, 80-59, 80-60, 80-61, 80-62, 80-63, 80-64, 80-65, 80-66, 80-67, 80-68, 80-69, 80-70, 80-71, 80-72, 80-73, 80-74, 80-75, 80-76, 80-77, 80-78, 80-79, 80-80, 80-81, 80-82, 80-83, 80-84, 80-85, 80-86, 80-87, 80-88, 80-89, 80-90, 80-91, 80-92, 80-93, 80-94, 80-95, 80-96, 80-97, 81-1, 81-2, 81-3, 814, 81-5, 81-6, 81-7, 81-8, 81-9, 81-10, 81-11, 81-12, 81-13, 81-14, 81-15, 81-16, 81-17, 81-18, 81-19, 81-20, 81-21, 81-22, 81-23, 81-24, 81-25, 81-26, 81-27, 81-28, 81-29, 81-30, 81-31, 81-32, 81-33, 81-34, 81-35, 81-36, 81-37, 81-38, 81-39, 81-40, 81-41, 81-42, 81-43, 81-44, 81-45, 81-46, 81-47, 81-48, 81-49, 81-50, 81-51, 81-52, 81-53, 81-54, 81-55, 81-56, 81-57, 81-58, 81-59, 81-60, 81-61, 81-62, 81-63, 81-64, 81-65, 81-66, 81-67, 81-68, 81-69, 81-70, 81-71, 81-72, 81-73, 81-74, 81-75, 81-76, 81-77, 81-78, 81-79, 81-80, 81-81, 81-82, 81-83, 81-84, 81-85, 81-86, 81-87, 81-88, 81-89, 81-90, 81-91, 81-92, 81-93, 81-94, 81-95, 81-96, 81-97, 82-1, 82-2, 82-3, 824, 82-5, 82-6, 82-7, 82-8, 82-9, 82-10, 82-11, 82-12, 82-13, 82-14, 82-15, 82-16, 82-17, 82-18, 82-19, 82-20, 82-21, 82-22, 82-23, 82-24, 82-25, 82-26, 82-27, 82-28, 82-29, 82-30, 82-31, 82-32, 82-33, 82-34, 82-35, 82-36, 82-37, 82-38, 82-39, 82-40, 82-41, 82-42, 82-43, 82-44, 82-45, 82-46, 82-47, 82-48, 82-49, 82-50, 82-51, 82-52, 82-53, 82-54, 82-55, 82-56, 82-57, 82-58, 82-59, 82-60, 82-61, 82-62, 82-63, 82-64, 82-65, 82-66, 82-67, 82-68, 82-69, 82-70, 82-71, 82-72, 82-73, 82-74, 82-75, 82-76, 82-77, 82-78, 82-79, 82-80, 82-81, 82-82, 82-83, 82-84, 82-85, 82-86, 82-87, 82-88, 82-89, 82-90, 82-91, 82-92, 82-93, 82-94, 82-95, 82-96, 82-97, 83-1, 83-2, 83-3, 83-4, 83-5, 83-6, 83-7, 83-8, 83-9, 83-10, 83-11, 83-12, 83-13, 83-14, 83-15, 83-16, 83-17, 83-18, 83-19, 83-20, 83-21, 83-22, 83-23, 83-24, 83-25, 83-26, 83-27, 83-28, 83-29, 83-30, 83-31, 83-32, 83-33, 83-34, 83-35, 83-36, 83-37, 83-38, 83-39, 83-40, 83-41, 83-42, 83-43, 83-44, 83-45, 83-46, 83-47, 83-48, 83-49, 83-50, 83-51, 83-52, 83-53, 83-54, 83-55, 83-56, 83-57, 83-58, 83-59, 83-60, 83-61, 83-62, 83-63, 83-64, 83-65, 83-66, 83-67, 83-68, 83-69, 83-70, 83-71, 83-72, 83-73, 83-74, 83-75, 83-76, 83-77, 83-78, 83-79, 83-80, 83-81, 83-82, 83-83, 83-84, 83-85, 83-86, 83-87, 83-88, 83-89, 83-90, 83-91, 83-92, 83-93, 83-94, 83-95, 83-96, 83-97, 84-1, 84-2, 84-3, 84-4, 84-5, 84-6, 84-7, 84-8, 84-9, 84-10, 84-11, 84-12, 84-13, 84-14, 84-15, 84-16, 84-17, 84-18, 84-19, 84-20, 84-21, 84-22, 84-23, 84-24, 84-25, 84-26, 84-27, 84-28, 84-29, 84-30, 84-31, 84-32, 84-33, 84-34, 84-35, 84-36, 84-37, 84-38, 84-39, 84-40, 84-41, 84-42, 84-43, 84-44, 84-45, 84-46, 84-47, 84-48, 84-49, 84-50, 84-51, 84-52, 84-53, 84-54, 84-55, 84-56, 84-57, 84-58, 84-59, 84-60, 84-61, 84-62, 84-63, 84-64, 84-65, 84-66, 84-67, 84-68, 84-69, 84-70, 84-71, 84-72, 84-73, 84-74, 84-75, 84-76, 84-77, 84-78, 84-79, 84-80, 84-81, 84-82, 84-83, 84-84, 84-85, 84-86, 84-87, 84-88, 84-89, 84-90, 84-91, 84-92, 84-93, 84-94, 84-95, 84-96, 84-97, 85-1, 85-2, 85-3, 85-4, 85-5, 85-6, 85-7, 85-8, 85-9, 85-10, 85-11, 85-12, 85-13, 85-14, 85-15, 85-16, 85-17, 85-18, 85-19, 85-20, 85-21, 85-22, 85-23, 85-24, 85-25, 85-26, 85-27, 85-28, 85-29, 85-30, 85-31, 85-32, 85-33, 85-34, 85-35, 85-36, 85-37, 85-38, 85-39, 85-40, 85-41, 85-42, 85-43, 85-44, 85-45, 85-46, 85-47, 85-48, 85-49, 85-50, 85-51, 85-52, 85-53, 85-54, 85-55, 85-56, 85-57, 85-58, 85-59, 85-60, 85-61, 85-62, 85-63, 85-64, 85-65, 85-66, 85-67, 85-68, 85-69, 85-70, 85-71, 85-72, 85-73, 85-74, 85-75, 85-76, 85-77, 85-78, 85-79, 85-80, 85-81, 85-82, 85-83, 85-84, 85-85, 85-86, 85-87, 85-88, 85-89, 85-90, 85-91, 85-92, 85-93, 85-94, 85-95, 85-96, 85-97, 86-1, 86-2, 86-3, 86-4, 86-5, 86-6, 86-7, 86-8, 86-9, 86-10, 86-11, 86-12, 86-13, 86-14, 86-15, 86-16, 86-17, 86-18, 86-19, 86-20, 86-21, 86-22, 86-23, 86-24, 86-25, 86-26, 86-27, 86-28, 86-29, 86-30, 86-31, 86-32, 86-33, 86-34, 86-35, 86-36, 86-37, 86-38, 86-39, 86-40, 86-41, 86-42, 86-43, 86-44, 86-45, 86-46, 86-47, 86-48, 86-49, 86-50, 86-51, 86-52, 86-53, 86-54, 86-55, 86-56, 86-57, 86-58, 86-59, 86-60, 86-61, 86-62, 86-63, 86-64, 86-65, 86-66, 86-67, 86-68, 86-69, 86-70, 86-71, 86-72, 86-73, 86-74, 86-75, 86-76, 86-77, 86-78, 86-79, 86-80, 86-81, 86-82, 86-83, 86-84, 86-85, 86-86, 86-87, 86-88, 86-89, 86-90, 86-91, 86-92, 86-93, 86-94, 86-95, 86-96, 86-97, 87-1, 87-2, 87-3, 874, 87-5, 87-6, 87-7, 87-8, 87-9, 87-10, 87-11, 87-12, 87-13, 87-14, 87-15, 87-16, 87-17, 87-18, 87-19, 87-20, 87-21, 87-22, 87-23, 87-24, 87-25, 87-26, 87-27, 87-28, 87-29, 87-30, 87-31, 87-32, 87-33, 87-34, 87-35, 87-36, 87-37, 87-38, 87-39, 87-40, 87-41, 87-42, 87-43, 87-44, 87-45, 87-46, 87-47, 87-48, 87-49, 87-50, 87-51, 87-52, 87-53, 87-54, 87-55, 87-56, 87-57, 87-58, 87-59, 87-60, 87-61, 87-62, 87-63, 87-64, 87-65, 87-66, 87-67, 87-68, 87-69, 87-70, 87-71, 87-72, 87-73, 87-74, 87-75, 87-76, 87-77, 87-78, 87-79, 87-80, 87-81, 87-82, 87-83, 87-84, 87-85, 87-86, 87-87, 87-88, 87-89, 87-90, 87-91, 87-92, 87-93, 87-94, 87-95, 87-96, 87-97, 88-1, 88-2, 88-3, 884, 88-5, 88-6, 88-7, 88-8, 88-9, 88-10, 88-11, 88-12, 88-13, 88-14, 88-15, 88-16, 88-17, 88-18, 88-19, 88-20, 88-21, 88-22, 88-23, 88-24, 88-25, 88-26, 88-27, 88-28, 88-29, 88-30, 88-31, 88-32, 88-33, 88-34, 88-35, 88-36, 88-37, 88-38, 88-39, 88-40, 88-41, 88-42, 88-43, 88-44, 88-45, 88-46, 88-47, 88-48, 88-49, 88-50, 88-51, 88-52, 88-53, 88-54, 88-55, 88-56, 88-57, 88-58, 88-59, 88-60, 88-61, 88-62, 88-63, 88-64, 88-65, 88-66, 88-67, 88-68, 88-69, 88-70, 88-71, 88-72, 88-73, 88-74, 88-75, 88-76, 88-77, 88-78, 88-79, 88-80, 88-81, 88-82, 88-83, 88-84, 88-85, 88-86, 88-87, 88-88, 88-89, 88-90, 88-91, 88-92, 88-93, 88-94, 88-95, 88-96, 88-97, 89-1, 89-2, 89-3, 89-4, 89-5, 89-6, 89-7, 89-8, 89-9, 89-10, 89-11, 89-12, 89-13, 89-14, 89-15, 89-16, 89-17, 89-18, 89-19, 89-20, 89-21, 89-22, 89-23, 89-24, 89-25, 89-26, 89-27, 89-28, 89-29, 89-30, 89-31, 89-32, 89-33, 89-34, 89-35, 89-36, 89-37, 89-38, 89-39, 89-40, 89-41, 89-42, 89-43, 89-44, 89-45, 89-46, 89-47, 89-48, 89-49, 89-50, 89-51, 89-52, 89-53, 89-54, 89-55, 89-56, 89-57, 89-58, 89-59, 89-60, 89-61, 89-62, 89-63, 89-64, 89-65, 89-66, 89-67, 89-68, 89-69, 89-70, 89-71, 89-72, 89-73, 89-74, 89-75, 89-76, 89-77, 89-78, 89-79, 89-80, 89-81, 89-82, 89-83, 89-84, 89-85, 89-86, 89-87, 89-88, 89-89, 89-90, 89-91, 89-92, 89-93, 89-94, 89-95, 89-96, 89-97, 90-1, 90-2, 90-3, 90-4, 90-5, 90-6, 90-7, 90-8, 90-9, 90-10, 90-11, 90-12, 90-13, 90-14, 90-15, 90-16, 90-17, 90-18, 90-19, 90-20, 90-21, 90-22, 90-23, 90-24, 90-25, 90-26, 90-27, 90-28, 90-29, 90-30, 90-31, 90-32, 90-33, 90-34, 90-35, 90-36, 90-37, 90-38, 90-39, 90-40, 90-41, 90-42, 90-43, 90-44, 90-45, 90-46, 90-47, 90-48, 90-49, 90-50, 90-51, 90-52, 90-53, 90-54, 90-55, 90-56, 90-57, 90-58, 90-59, 90-60, 90-61, 90-62, 90-63, 90-64, 90-65, 90-66, 90-67, 90-68, 90-69, 90-70, 90-71, 90-72, 90-73, 90-74, 90-75, 90-76, 90-77, 90-78, 90-79, 90-80, 90-81, 90-82, 90-83, 90-84, 90-85, 90-86, 90-87, 90-88, 90-89, 90-90, 90-91, 90-92, 90-93, 90-94, 90-95, 90-96, 90-97, 91-1, 91-2, 91-3, 914, 91-5, 91-6, 91-7, 91-8, 91-9, 91-10, 91-11, 91-12, 91-13, 91-14, 91-15, 91-16, 91-17, 91-18, 91-19, 91-20, 91-21, 91-22, 91-23, 91-24, 91-25, 91-26, 91-27, 91-28, 91-29, 91-30, 91-31, 91-32, 91-33, 91-34, 91-35, 91-36, 91-37, 91-38, 91-39, 91-40, 91-41, 91-42, 91-43, 91-44, 91-45, 91-46, 91-47, 91-48, 91-49, 91-50, 91-51, 91-52, 91-53, 91-54, 91-55, 91-56, 91-57, 91-58, 91-59, 91-60, 91-61, 91-62, 91-63, 91-64, 91-65, 91-66, 91-67, 91-68, 91-69, 91-70, 91-71, 91-72, 91-73, 91-74, 91-75, 91-76, 91-77, 91-78, 91-79, 91-80, 91-81, 91-82, 91-83, 91-84, 91-85, 91-86, 91-87, 91-88, 91-89, 91-90, 91-91, 91-92, 91-93, 91-94, 91-95, 91-96, 91-97, 92-1, 92-2, 92-3, 92-4, 92-5, 92-6, 92-7, 92-8, 92-9, 92-10, 92-11, 92-12, 92-13, 92-14, 92-15, 92-16, 92-17, 92-18, 92-19, 92-20, 92-21, 92-22, 92-23, 92-24, 92-25, 92-26, 92-27, 92-28, 92-29, 92-30, 92-31, 92-32, 92-33, 92-34, 92-35, 92-36, 92-37, 92-38, 92-39, 92-40, 92-41, 92-42, 92-43, 92-44, 92-45, 92-46, 92-47, 92-48, 92-49, 92-50, 92-51, 92-52, 92-53, 92-54, 92-55, 92-56, 92-57, 92-58, 92-59, 92-60, 92-61, 92-62, 92-63, 92-64, 92-65, 92-66, 92-67, 92-68, 92-69, 92-70, 92-71, 92-72, 92-73, 92-74, 92-75, 92-76, 92-77, 92-78, 92-79, 92-80, 92-81, 92-82, 92-83, 92-84, 92-85, 92-86, 92-87, 92-88; 92-89, 92-90, 92-91, 92-92, 92-93, 92-94, 92-95, 92-96, 92-97, 93-1, 93-2, 93-3, 93-4, 93-5, 93-6, 93-7, 93-8, 93-9, 93-10, 93-11, 93-12, 93-13, 93-14, 93-15, 93-16, 93-17, 93-18, 93-19, 93-20, 93-21, 93-22, 93-23, 93-24, 93-25, 93-26, 93-27, 93-28, 93-29, 93-30, 93-31, 93-32, 93-33, 93-34, 93-35, 93-36, 93-37, 93-38, 93-39, 93-40, 93-41, 93-42, 93-43, 93-44, 93-45, 93-46, 93-47, 93-48, 93-49, 93-50, 93-51, 93-52, 93-53, 93-54, 93-55, 93-56, 93-57, 93-58, 93-59, 93-60, 93-61, 93-62, 93-63, 93-64, 93-65, 93-66, 93-67, 93-68, 93-69, 93-70, 93-71, 93-72, 93-73, 93-74, 93-75, 93-76, 93-77, 93-78, 93-79, 93-80, 93-81, 93-82, 93-83, 93-84, 93-85, 93-86, 93-87, 93-88, 93-89, 93-90, 93-91, 93-92, 93-93, 93-94, 93-95, 93-96, 93-97, 94-1, 94-2, 94-3, 94-4, 94-5, 94-6, 94-7, 94-8, 94-9, 94-10, 94-11, 94-12, 94-13, 94-14, 94-15, 94-16, 94-17, 94-18, 94-19, 94-20, 94-21, 94-22, 94-23, 94-24, 94-25, 94-26, 94-27, 94-28, 94-29, 94-30, 94-31, 94-32, 94-33, 94-34, 94-35, 94-36, 94-37, 94-38, 94-39, 94-40, 94-41, 94-42, 94-43, 94-44, 94-45, 94-46, 94-47, 94-48, 94-49, 94-50, 94-51, 94-52, 94-53, 94-54, 94-55, 94-56, 94-57, 94-58, 94-59, 94-60, 94-61, 94-62, 94-63, 94-64, 94-65, 94-66, 94-67, 94-68, 94-69, 94-70, 94-71, 94-72, 94-73, 94-74, 94-75, 94-76, 94-77, 94-78, 94-79, 94-80, 94-81, 94-82, 94-83, 94-84, 94-85, 94-86, 94-87, 94-88, 94-89, 94-90, 94-91, 94-92, 94-93, 94-94, 94-95, 94-96, 94-97, 95-1, 95-2, 95-3, 954, 95-5, 95-6, 95-7, 95-8, 95-9, 95-10, 95-11, 95-12, 95-13, 95-14, 95-15, 95-16, 95-17, 95-18, 95-19, 95-20, 95-21, 95-22, 95-23, 95-24, 95-25, 95-26, 95-27, 95-28, 95-29, 95-30, 95-31, 95-32, 95-33, 95-34, 95-35, 95-36, 95-37, 95-38, 95-39, 95-40, 95-41, 95-42, 95-43, 95-44, 95-45, 95-46, 95-47, 95-48, 95-49, 95-50, 95-51, 95-52, 95-53, 95-54, 95-55, 95-56, 95-57, 95-58, 95-59, 95-60, 95-61, 95-62, 95-63, 95-64, 95-65, 95-66, 95-67, 95-68, 95-69, 95-70, 95-71, 95-72, 95-73, 95-74, 95-75, 95-76, 95-77, 95-78, 95-79, 95-80, 95-81, 95-82, 95-83, 95-84, 95-85, 95-86, 95-87, 95-88, 95-89, 95-90, 95-91, 95-92, 95-93, 95-94, 95-95, 95-96, 95-97, 96-1, 96-2, 96-3, 96-4, 96-5, 96-6, 96-7, 96-8, 96-9, 96-10, 96-11, 96-12, 96-13, 96-14, 96-15, 96-16, 96-17, 96-18, 96-19, 96-20, 96-21, 96-22, 96-23, 96-24, 96-25, 96-26, 96-27, 96-28, 96-29, 96-30, 96-31, 96-32, 96-33, 96-34, 96-35, 96-36, 96-37, 96-38, 96-39, 96-40, 96-41, 96-42, 96-43, 96-44, 96-45, 96-46, 96-47, 96-48, 96-49, 96-50, 96-51, 96-52, 96-53, 96-54, 96-55, 96-56, 96-57, 96-58, 96-59, 96-60, 96-61, 96-62, 96-63, 96-64, 96-65, 96-66, 96-67, 96-68, 96-69, 96-70, 96-71, 96-72, 96-73, 96-74, 96-75, 96-76, 96-77, 96-78, 96-79, 96-80, 96-81, 96-82, 96-83, 96-84, 96-85, 96-86, 96-87, 96-88, 96-89, 96-90, 96-91, 96-92, 96-93, 96-94, 96-95, 96-96, 96-97, 97-1, 97-2, 97-3, 974, 97-5, 97-6, 97-7, 97-8, 97-9, 97-10, 97-11, 97-12, 97-13, 97-14, 97-15, 97-16, 97-17, 97-18, 97-19, 97-20, 97-21, 97-22, 97-23, 97-24, 97-25, 97-26, 97-27, 97-28, 97-29, 97-30, 97-31, 97-32, 97-33, 97-34, 97-35, 97-36, 97-37, 97-38, 97-39, 97-40, 97-41, 97-42, 97-43, 97-44, 97-45, 97-46, 97-47, 97-48, 97-49, 97-50, 97-51, 97-52, 97-53, 97-54, 97-55, 97-56, 97-57, 97-58, 97-59, 97-60, 97-61, 97-62, 97-63, 97-64, 97-65, 97-66, 97-67, 97-68, 97-69, 97-70, 97-71, 97-72, 97-73, 97-74, 97-75, 97-76, 97-77, 97-78, 97-78, 97-80, 97-81, 97-82, 97-83, 97-84, 97-85, 97-86, 97-87, 97-88, 97-89, 97-90, 97-91, 97-92, 97-93, 97-94, 97-95, 97-96, 97-97, 98-1, 98-2, 98-3, 98-4, 98-5, 98-6, 98-7, 98-8, 98-9, 98-10, 98-11, 98-12, 98-13, 98-14, 98-15, 98-16, 98-17, 98-18, 98-19, 98-20, 98-21, 98-22, 98-23, 98-24, 98-25, 98-26, 98-27, 98-28, 98-29, 98-30, 98-31, 98-32, 98-33, 98-34, 98-35, 98-36, 98-37, 98-38, 98-39, 98-40, 98-41, 98-42, 98-43, 98-44, 98-45, 98-46, 98-47, 98-48, 98-49, 98-50, 98-51, 98-52, 98-53, 98-54, 98-55, 98-56, 98-57, 98-58, 98-59, 98-60, 98-61, 98-62, 98-63, 98-64, 98-65, 98-66, 98-67, 98-68, 98-69, 98-70, 98-71, 98-72, 98-73, 98-74, 98-75, 98-76, 98-77, 98-78, 98-79, 98-80, 98-81, 98-82, 98-83, 98-84, 98-85, 98-86, 98-87, 98-88, 98-89, 98-90, 98-91, 98-92, 98-93, 98-94, 98-95, 98-96, 98-97, 99-1, 99-2, 99-3, 99-4, 99-5, 99-6, 99-7, 99-8, 99-9, 99-10, 99-11, 99-12, 99-13, 99-14, 99-15, 99-16, 99-17, 99-18, 99-19, 99-20, 99-21, 99-22, 99-23, 99-24, 99-25, 99-26, 99-27, 99-28, 99-29, 99-30, 99-31, 99-32, 99-33, 99-34, 99-35, 99-36, 99-37, 99-38, 99-39, 99-40, 99-41, 99-42, 99-43, 99-44, 99-45, 99-46, 99-47, 99-48, 99-49, 99-50, 99-51, 99-52, 99-53, 99-54, 99-55, 99-56, 99-57, 99-58, 99-59, 99-60, 99-61, 99-62, 99-63, 99-64, 99-65, 99-66, 99-67, 99-68, 99-69, 99-70, 99-71, 99-72, 99-73, 99-74, 99-75, 99-76, 99-77, 99-78, 99-79, 99-80, 99-81, 99-82, 99-83, 99-84, 99-85, 99-86, 99-87, 99-88, 99-89, 99-90, 99-91, 99-92, 99-93, 99-94, 99-95, 99-96, 99-97, 100-1, 100-2, 100-3, 100-4, 100-5, 100-6, 100-7, 100-8, 100-9, 100-10, 100-11, 100-12, 100-13, 100-14, 100-15, 100-16, 100-17, 100-18, 100-19, 100-20, 100-21, 100-22, 100-23, 100-24, 100-25, 100-26, 100-27, 100-28, 100-29, 100-30, 100-31, 100-32, 100-33, 100-34, 100-35, 100-36, 100-37, 100-38, 100-39, 100-40, 100-41, 100-42, 100-43, 100-44, 100-45, 100-46, 100-47, 100-48, 100-49, 100-50, 100-51, 100-52, 100-53, 100-54, 100-55, 100-56, 100-57, 100-58, 100-59, 100-60, 100-61, 100-62, 100-63, 100-64, 100-65, 100-66, 100-67, 100-68, 100-69, 100-70, 100-71, 100-72, 100-73, 100-74, 100-75, 100-76, 100-77, 100-78, 100-79, 100-80, 100-81, 100-82, 100-83, 100-84, 100-85, 100-86, 100-87, 100-88, 100-89, 100-90, 100-91, 100-92, 100-93, 100-94, 100-95, 100-96, 100-97, 101-1, 101-2, 101-3, 101-4, 101-5, 101-6, 101-7, 101-8, 101-9, 101-10, 101-11, 101-12, 101-13, 101-14, 101-15, 101-16, 101-17, 101-18, 101-19, 101-20, 101-21, 101-22, 101-23, 101-24, 101-25, 101-26, 101-27, 101-28, 101-29, 101-30, 101-31, 101-32, 101-33, 101-34, 101-35, 101-36, 101-37, 101-38, 101-39, 101-40, 101-41, 101-42, 101-43, 101-44, 101-45, 101-46, 101-47, 101-48, 101-49, 101-50, 101-51, 101-52, 101-53, 101-54, 101-55, 101-56, 101-57, 101-58, 101-59, 101-60, 101-61, 101-62, 101-63, 101-64, 101-65, 101-66, 101-67, 101-68, 101-69, 101-70, 101-71, 101-72, 101-73, 101-74, 101-75, 101-76, 101-77, 101-78, 101-79, 101-80, 101-81, 101-82, 101-83, 101-84, 101-85, 101-86, 101-87, 101-88, 101-89, 101-90, 101-91, 101-92, 101-93, 101-94, 101-95, 101-96, 101-97, 102-1, 102-2, 102-3, 102-4, 102-5, 102-6, 102-7, 102-8, 102-9, 102-10, 102-11, 102-12, 102-13, 102-14, 102-15, 102-16, 102-17, 102-18, 102-19, 102-20, 102-21, 102-22, 102-23, 102-24, 102-25, 102-26, 102-27, 102-28, 102-29, 102-30, 102-31, 102-32, 102-33, 102-34, 102-35, 102-36, 102-37, 102-38, 102-39, 102-40, 102-41, 102-42, 102-43, 102-44, 102-45, 102-46, 102-47, 102-48, 102-49, 102-50, 102-51, 102-52, 102-53, 102-54, 102-55, 102-56, 102-57, 102-58, 102-59, 102-60, 102-61, 102-62, 102-63, 102-64, 102-65, 102-66, 102-67, 102-68, 102-69, 102-70, 102-71, 102-72, 102-73, 102-74, 102-75, 102-76, 102-77, 102-78, 102-79, 102-80, 102-81, 102-82, 102-83, 102-84, 102-85, 102-86, 102-87, 102-88, 102-89, 102-90, 102-91, 102-92, 102-93, 102-94, 102-95, 102-96, 102-97, 103-1, 103-2, 103-3, 103-4, 103-5, 103-6, 103-7, 103-8, 103-9, 103-10, 103-11, 103-12, 103-13, 103-14, 103-15, 103-16, 103-17, 103-18, 103-19, 103-20, 103-21, 103-22, 103-23, 103-24, 103-25, 103-26, 103-27, 103-28, 103-29, 103-30, 103-31, 103-32, 103-33, 103-34, 103-35, 103-36, 103-37, 103-38, 103-39, 103-40, 103-41, 103-42, 103-43, 103-44, 103-45, 103-46, 103-47, 103-48, 103-49, 103-50, 103-51, 103-52, 103-53, 103-

54, 103-55, 103-56, 103-57, 103-58, 103-59, 103-60, 103-61, 103-62, 103-63, 103-64, 103-65, 103-66, 103-67, 103-68, 103-69, 103-70, 103-71, 103-72, 103-73, 103-74, 103-75, 103-76, 103-77, 103-78, 103-79, 103-80, 103-81, 103-82, 103-83, 103-84, 103-85, 103-86, 103-87, 103-88, 103-89, 103-90, 103-91, 103-92, 103-93, 103-94, 103-95, 103-96, 103-97, 104-1, 104-2, 104-3, 104-4, 104-5, 104-6, 104-7, 104-8, 104-9, 104-10, 104-11, 104-12, 104-13, 104-14, 104-15, 104-16, 104-17, 104-18, 104-19, 104-20, 104-21, 104-22, 104-23, 104-24, 104-25, 104-26, 104-27, 104-28, 104-29, 104-30, 104-31, 104-32, 104-33, 104-34, 104-35, 104-36, 104-37, 104-38, 104-39, 104-40, 104-41, 104-42, 104-43, 104-44, 104-45, 104-46, 104-47, 104-48, 104-49, 104-50, 104-51, 104-52, 104-53, 104-54, 104-55, 104-56, 104-57, 104-58, 104-59, 104-60, 104-61, 104-62, 104-63, 104-64, 104-65, 104-66, 104-67, 104-68, 104-69, 104-70, 104-71, 104-72, 104-73, 104-74, 104-75, 104-76, 104-77, 104-78, 104-79, 104-80, 104-81, 104-82, 104-83, 104-84, 104-85, 104-86, 104-87, 104-88, 104-89, 104-90, 104-91, 104-92, 104-93, 104-94, 104-95, 104-96, 104-97, 105-1, 105-2, 105-3, 105-4, 105-5, 105-6, 105-7, 105-8, 105-9, 105-10, 105-11, 105-12, 105-13, 105-14, 105-15, 105-16, 105-17, 105-18, 105-19, 105-20, 105-21, 105-22, 105-23, 105-24, 105-25, 105-26, 105-27, 105-28, 105-29, 105-30, 105-31, 105-32, 105-33, 105-34, 105-35, 105-36, 105-37, 105-38, 105-39, 105-40, 105-41, 105-42, 105-43, 105-44, 105-45, 105-46, 105-47, 105-48, 105-49, 105-50, 105-51, 105-52, 105-53, 105-54, 105-55, 105-56, 105-57, 105-58, 105-59, 105-60, 105-61, 105-62, 105-63, 105-64, 105-65, 105-66, 105-67, 105-68, 105-69, 105-70, 105-71, 105-72, 105-73, 105-74, 105-75, 105-76, 105-77, 105-78, 105-79, 105-80, 105-81, 105-82, 105-83, 105-84, 105-85, 105-86, 105-87, 105-88, 105-89, 105-90, 105-91, 105-92, 105-93, 105-94, 105-95, 105-96, 105-97, 106-1, 106-2, 106-3, 106-4, 106-5, 106-6, 106-7, 106-8, 106-9, 106-10, 106-11, 106-12, 106-13, 106-14, 106-15, 106-16, 106-17, 106-18, 106-19, 106-20, 106-21, 106-22, 106-23, 106-24, 106-25, 106-26, 106-27, 106-28, 106-29, 106-30, 106-31, 106-32, 106-33, 106-34, 106-35, 106-36, 106-37, 106-38, 106-39, 106-40, 106-41, 106-42, 106-43, 106-44, 106-45, 106-46, 106-47, 106-48, 106-49, 106-50, 106-51, 106-52, 106-53, 106-54, 106-55, 106-56, 106-57, 106-58, 106-59, 106-60, 106-61, 106-62, 106-63, 106-64, 106-65, 106-66, 106-67, 106-68, 106-69, 106-70, 106-71, 106-72, 106-73, 106-74, 106-75, 106-76, 106-77, 106-78, 106-79, 106-80, 106-81, 106-82, 106-83, 106-84, 106-85, 106-86, 106-87, 106-88, 106-89, 106-90, 106-91, 106-92, 106-93, 106-94, 106-95, 106-96, 106-97, 107-1, 107-2, 107-3, 107-4, 107-5, 107-6, 107-7, 107-8, 107-9, 107-10, 107-11, 107-12, 107-13, 107-14, 107-15, 107-16, 107-17, 107-18, 107-19, 107-20, 107-21, 107-22, 107-23, 107-24, 107-25, 107-26, 107-27, 107-28, 107-29, 107-30, 107-31, 107-32, 107-33, 107-34, 107-35, 107-36, 107-37, 107-38, 107-39, 107-40, 107-41, 107-42, 107-43, 107-44, 107-45, 107-46, 107-47, 107-48, 107-49, 107-50, 107-51, 107-52, 107-53, 107-54, 107-55, 107-56, 107-57, 107-58, 107-59, 107-60, 107-61, 107-62, 107-63, 107-64, 107-65, 107-66, 107-67, 107-68, 107-69, 107-70, 107-71, 107-72, 107-73, 107-74, 107-75, 107-76, 107-77, 107-78, 107-79, 107-80, 107-81, 107-82, 107-83, 107-84, 107-85, 107-86, 107-87, 107-88, 107-89, 107-90, 107-91, 107-92, 107-93, 107-94, 107-95, 107-96, 107-97, 108-1, 108-2, 108-3, 108-4, 108-5, 108-6, 108-7, 108-8, 108-9, 108-10, 108-11, 108-12, 108-13, 108-14, 108-15, 108-16, 108-17, 108-48, 108-19, 108-20, 108-21, 108-22, 108-23, 108-24, 108-25, 108-26, 108-27, 108-28, 108-29, 108-30, 108-31, 108-32, 108-33, 108-34, 108-35, 108-36, 108-37, 108-38, 108-39, 108-40, 108-41, 108-42, 108-43, 108-44, 108-45, 108-46, 108-47, 108-48, 108-49, 108-50, 108-51, 108-52, 108-53, 108-54, 108-55, 108-56, 108-57, 108-58, 108-59, 108-40, 108-61, 108-62, 108-63, 108-64, 108-65, 108-66, 108-67, 108-68, 108-69, 108-70, 108-71, 108-72, 108-73, 108-74, 108-75, 108-76, 108-77, 108-78, 108-79, 108-80, 108-81, 108-82, 108-83, 108-84, 108-85, 108-86, 108-87, 108-88, 108-89, 108-90, 108-91, 108-92, 108-93, 108-94, 108-95, 108-96, 108-97, 109-1, 109-2, 109-3, 109-4, 109-5, 109-6, 109-7, 109-8, 109-9, 109-10, 109-11, 109-12, 109-13, 109-14, 109-15, 109-16, 109-17, 109-18, 109-19, 109-20, 109-21, 109-22, 109-23, 109-24, 109-25, 109-26, 109-27, 109-28, 109-29, 109-30, 109-31, 109-32, 109-33, 109-34, 109-35, 109-36, 109-37, 109-38, 109-39, 109-40, 109-41, 109-42, 109-43, 109-44, 109-45, 109-46, 109-47, 109-48, 109-49, 109-50, 109-51, 109-52, 109-53, 109-54, 109-55, 109-56, 109-57, 109-58, 109-59, 109-60, 109-61, 109-62, 109-63, 109-64, 109-65, 109-66, 109-67, 109-68, 109-69, 109-70, 109-71, 109-72, 109-73, 109-74, 109-75, 109-76, 109-77, 109-78, 109-79, 109-80, 109-81, 109-82, 109-83, 109-84, 109-85, 109-86, 109-87, 109-88, 109-89, 109-90, 109-91, 109-92, 109-93, 109-94, 109-95, 109-96, 109-97, 110-1, 110-2, 110-3, 110-4, 110-5, 110-6, 110-7, 110-8, 110-9, 110-10, 110-11, 110-12, 110-13, 110-14, 110-15, 110-16, 110-17, 110-18, 110-19, 110-20, 110-21, 110-22, 110-23, 110-24, 110-25, 110-26, 110-27, 110-28, 110-29, 110-30, 110-31, 110-32, 110-33, 110-34, 110-35, 110-36, 110-37, 110-38, 110-39, 110-40, 110-41, 110-42, 110-43, 110-44, 110-45, 110-46, 110-47, 110-48, 110-49, 110-50, 110-51, 110-52, 110-53, 110-54, 110-55, 110-56, 110-57, 110-58, 110-59, 110-60, 110-61, 110-62, 110-63, 110-64, 110-65, 110-66, 110-67, 110-68, 110-69, 110-70, 110-71, 110-72, 110-73, 110-74, 110-75, 110-76, 110-77, 110-78, 110-79, 110-80, 110-81, 110-82, 110-83, 110-84, 110-85, 110-86, 110-87, 110-88, 110-89, 110-90, 110-91, 110-92, 110-93, 110-94, 110-95, 110-96, 110-97, 111-1, 111-2, 111-3, 111-4, 111-5, 111-6, 111-7, 111-8, 111-9, 111-10, 111-11, 111-12, 111-13, 111-14, 111-15, 111-16, 111-17, 111-18, 111-19, 111-20, 111-21, 111-22, 111-23, 111-24, 111-25, 111-26, 111-27, 111-28, 111-29, 111-30, 111-31, 111-32, 111-33, 111-34, 111-35, 111-36, 111-37, 111-38, 111-39, 111-40, 111-41, 111-42, 111-43, 111-44, 111-45, 111-46, 111-47, 111-48, 111-49, 111-50, 111-51, 111-52, 111-53, 111-54, 111-55, 111-56, 111-57, 111-58, 111-59, 111-60, 111-61, 111-62, 111-63, 111-64, 111-65, 111-66, 111-67, 111-68, 111-69, 111-70, 111-71, 111-72, 111-73, 111-74, 111-75, 111-76, 111-77, 111-78, 111-79, 111-80, 111-81, 111-82, 111-83, 111-84, 111-85, 111-86, 111-87, 111-88, 111-89, 111-90, 111-91, 111-92, 111-93, 111-94, 111-95, 111-96, 111-97, 112-1, 112-2, 112-3, 1124, 112-5, 112-6, 112-7, 112-8, 112-9, 112-10, 112-11, 112-12, 112-13, 112-14, 112-15, 112-16, 112-17, 112-18, 112-19, 112-20, 112-21, 112-22, 112-23, 112-24, 112-25, 112-26, 112-27, 112-28, 112-29, 112-30, 112-31, 112-32, 112-33, 112-34, 112-35, 112-36, 112-37, 112-38, 112-39, 112-40, 112-41, 112-42, 112-43, 112-44, 112-45, 112-46, 112-47, 112-

48, 112-49, 112-50, 112-51, 112-52, 112-53, 112-54, 112-55, 112-56, 112-57, 112-58, 112-59, 112-60, 112-61, 112-62, 112-63, 112-64, 112-65, 112-66, 112-67, 112-68, 112-69, 112-70, 112-71, 112-72, 112-73, 112-74, 112-75, 112-76, 112-77, 112-78, 112-79, 112-80, 112-81, 112-82, 112-83, 112-84, 112-85, 112-86, 112-87, 112-88, 112-89, 112-90, 112-91, 112-92, 112-93, 112-94, 112-95, 112-96, 112-97, 113-1, 113-2, 113-3, 113-4, 113-5, 113-6, 113-7, 113-8, 113-9, 113-10, 113-11, 113-12, 113-13, 113-14, 113-15, 113-16, 113-17, 113-18, 113-19, 113-20, 113-21, 113-22, 113-23, 113-24, 113-25, 113-26, 113-27, 113-28, 113-29, 113-30, 113-31, 113-32, 113-33, 113-34, 113-35, 113-36, 113-37, 113-38, 113-39, 113-40, 113-41, 113-42, 113-43, 113-44, 113-45, 113-46, 113-47, 113-48, 113-49, 113-50, 113-51, 113-52, 113-53, 113-54, 113-55, 113-56, 113-57, 113-58, 113-59, 113-60, 113-61, 113-62, 113-63, 113-64, 113-65, 113-66, 113-67, 113-68, 113-69, 113-70, 113-71, 113-72, 113-73, 113-74, 113-75, 113-76, 113-77, 113-78, 113-79, 113-80, 113-81, 113-82, 113-83, 113-84, 113-85, 113-86, 113-87, 113-88, 113-89, 113-90, 113-91, 113-92, 113-93, 113-94, 113-95, 113-96, 113-97, 114-1, 114-2, 114-3, 114-4, 114-5, 114-6, 114-7, 114-8, 114-9, 114-10, 114-11, 114-12, 114-13, 114-14, 114-15, 114-16, 114-17, 114-18, 114-19, 114-20, 114-21, 114-22, 114-23, 114-24, 114-25, 114-26, 114-27, 114-28, 114-29, 114-30, 114-31, 114-32, 114-33, 114-34, 114-35, 114-36, 114-37, 114-38, 114-39, 114-40, 114-41, 114-42, 114-43, 114-44, 114-45, 114-46, 114-47, 114-48, 114-49, 114-50, 114-51, 114-52, 114-53, 114-54, 114-55, 114-56, 114-57, 114-58, 114-59, 114-60, 114-61, 114-62, 114-63, 114-64, 114-65, 114-66, 114-67, 114-68, 114-69, 114-70, 114-71, 114-72, 114-73, 114-74, 114-75, 114-76, 114-77, 114-78, 114-79, 114-80, 114-81, 114-82, 114-83, 114-84, 114-85, 114-86, 114-87, 114-88, 114-89, 114-90, 114-91, 114-92, 114-93, 114-94, 114-95, 114-96, 114-97, 115-1, 115-2, 115-3, 115-4, 115-5, 115-6, 115-7, 115-8, 115-9, 115-10, 115-11, 115-12, 115-13, 115-14, 115-15, 115-16, 115-17, 115-18, 115-19, 115-20, 115-21, 115-22, 115-23, 115-24, 115-25, 115-26, 115-27, 115-28, 115-29, 115-30, 115-31, 115-32, 115-33, 115-34, 115-35, 115-36, 115-37, 115-38, 115-39, 115-40, 115-41, 115-42, 115-43, 115-44, 115-45, 115-46, 115-47, 115-48, 115-49, 115-50, 115-51, 115-52, 115-53, 115-54, 115-55, 115-56, 115-57, 115-58, 115-59, 115-60, 115-61, 115-62, 115-63, 115-64, 115-65, 115-66, 115-67, 115-68, 115-69, 115-70, 115-71, 115-72, 115-73, 115-74, 115-75, 115-76, 115-77, 115-78, 115-79, 115-80, 115-81, 115-82, 115-83, 115-84, 115-85, 115-86, 115-87, 115-88, 115-89, 115-90, 115-91, 115-92, 115-93, 115-94, 115-95, 115-96, 115-97, 116-1, 116-2, 116-3, 116-4, 116-5, 116-6, 116-7, 116-8, 116-9, 116-10, 116-11, 116-12, 116-13, 116-14, 116-15, 116-16, 116-17, 116-18, 116-19, 116-20, 116-21, 116-22, 116-23, 116-24, 116-25, 116-26, 116-27, 116-28, 116-29, 116-30, 116-31, 116-32, 116-33, 116-34, 116-35, 116-36, 116-37, 116-38, 116-39, 116-40, 116-41, 116-42, 116-43, 116-44, 116-45, 116-46, 116-47, 116-48, 116-49, 116-50, 116-51, 116-52, 116-53, 116-54, 116-55, 116-56, 116-57, 116-58, 116-59, 116-60, 116-61, 116-62, 116-63, 116-64, 116-65, 116-66, 116-67, 116-68, 116-69, 116-70, 116-71, 116-72, 116-73, 116-74, 116-75, 116-76, 116-77, 116-78, 116-79, 116-80, 116-81, 116-82, 116-83, 116-84, 116-85, 116-86, 116-87, 116-88, 116-89, 116-90, 116-91, 116-92, 116-93, 116-94, 116-95, 116-96, 116-97, 117-1, 117-2, 117-3, 117-4, 117-5, 117-6, 117-7, 117-8, 117-9, 117-10, 117-11, 117-12, 117-13, 117-14, 117-15, 117-16, 117-17, 117-18, 117-19, 117-20, 117-21, 117-22, 117-23, 117-24, 117-25, 117-26, 117-27, 117-28, 117-29, 117-30, 117-31, 117-32, 117-33, 117-34, 117-35, 117-36, 117-37, 117-38, 117-39, 117-40, 117-41, 117-42, 117-43, 117-44, 117-45, 117-46, 117-47, 117-48, 117-49, 117-50, 117-51, 117-52, 117-53, 117-54, 117-55, 117-56, 117-57, 117-58, 117-59, 117-60, 117-61, 117-62, 117-63, 117-64, 117-65, 117-66, 117-67, 117-68, 117-69, 117-70, 117-71, 117-72, 117-73, 117-74, 117-75, 117-76, 117-77, 117-78, 117-79, 117-80, 117-81, 117-82, 117-83, 117-84, 117-85, 117-86, 117-87, 117-88, 117-89, 117-90, 117-91, 117-92, 117-93, 117-94, 117-95, 117-96, 117-97, 118-1, 118-2, 118-3, 118-4, 118-5, 118-6, 118-7, 118-8, 118-9, 118-10, 118-11, 118-12, 118-13, 118-14, 118-15, 118-16, 118-17, 118-18, 118-19, 118-20, 118-21, 118-22, 118-23, 118-24, 118-25, 118-26, 118-27, 118-28, 118-29, 118-30, 118-31, 118-32, 118-33, 118-34, 118-35, 118-36, 118-37, 118-38, 118-39, 118-40, 118-41, 118-42, 118-43, 118-44, 118-45, 118-46, 118-47, 118-48, 118-49, 118-50, 118-51, 118-52, 118-53, 118-54, 118-55, 118-56, 118-57, 118-58, 118-59, 118-60, 118-61, 118-62, 118-63, 118-64, 118-65, 118-66, 118-67, 118-68, 118-69, 118-70, 118-71, 118-72, 118-73, 118-74, 118-75, 118-76, 118-77, 118-78, 118-79, 118-80, 118-81, 118-82, 118-83, 118-84, 118-85, 118-86, 118-87, 118-88, 118-89, 118-90, 118-91, 118-92, 118-93, 118-94, 118-95, 118-96, 118-97, 119-1, 119-2, 119-3, 119-4, 119-5, 119-6, 119-7, 119-8, 119-9, 119-10, 119-11, 119-12, 119-13, 119-14, 119-15, 119-16, 119-17, 119-18, 119-19, 119-20, 119-21, 119-22, 119-23, 119-24, 119-25, 119-26, 119-27, 119-28, 119-29, 119-30, 119-31, 119-32, 119-33, 119-34, 119-35, 119-36, 119-37, 119-38, 119-39, 119-40, 119-41, 119-42, 119-43, 119-44, 119-45, 119-46, 119-47, 119-48, 119-49, 119-50, 119-51, 119-52, 119-53, 119-54, 119-55, 119-56, 119-57, 119-58, 119-59, 119-60, 119-61, 119-62, 119-63, 119-64, 119-65, 119-66, 119-67, 119-68, 119-69, 119-70, 119-71, 119-72, 119-73, 119-74, 119-75, 119-76, 119-77, 119-78, 119-79, 119-80, 119-81, 119-82, 119-83, 119-84, 119-85, 119-86, 119-87, 119-88, 119-89, 119-90, 119-91, 119-92, 119-93, 119-94, 119-95, 119-96, 119-97, 120-1, 120-2, 120-3, 120-4, 120-5, 120-6, 120-7, 120-8, 120-9, 120-10, 120-11, 120-12, 120-13, 120-14, 120-15, 120-16, 120-17, 120-18, 120-19, 120-20, 120-21, 120-22, 120-23, 120-24, 120-25, 120-26, 120-27, 120-28, 120-29, 120-30, 120-31, 120-32, 120-33, 120-34, 120-35, 120-36, 120-37, 120-38, 120-39, 120-40, 120-41, 120-42, 120-43, 120-44, 120-45, 120-46, 120-47, 120-48, 120-49, 120-50, 120-51, 120-52, 120-53, 120-54, 120-55, 120-56, 120-57, 120-58, 120-59, 120-60, 120-61, 120-62, 120-63, 120-64, 120-65, 120-66, 120-67, 120-68, 120-69, 120-70, 120-71, 120-72, 120-73, 120-74, 120-75, 120-76, 120-77, 120-78, 120-79, 120-80, 120-81, 120-82, 120-83, 120-84, 120-85, 120-86, 120-87, 120-88, 120-89, 120-90, 120-91, 120-92, 120-93, 120-94, 120-95, 120-96, 120-97, 121-1, 121-2, 121-3, 121-4, 121-5, 121-6, 121-7, 121-8, 121-9, 121-10, 121-11, 121-12, 121-13, 121-14, 121-15, 121-16, 121-17, 121-18, 121-19, 121-20, 121-21, 121-22, 121-23, 121-24, 121-25, 121-26, 121-27, 121-28, 121-29, 121-30, 121-31, 121-32, 121-33, 121-34, 121-35, 121-36, 121-37, 121-38, 121-39, 121-40, 121-41, 121-42, 121-43, 121-44, 121-45, 121-46, 12-147, 12-148, 121-49, 121-50, 121-51, 121-52, 121-53, 121-54, 121-55, 121-56, 121-57, 121-58, 121-59, 121-60, 121-61, 121-62, 121-63, 121-64, 121-65, 121-66, 121-67, 121-68, 121-69, 121-70, 121-71, 121-72, 121-73, 121-74, 121-75, 121-76, 121-77, 121-78, 121-79, 121-80, 121-81, 121-82, 121-83, 121-84, 121-85, 121-86, 121-87, 121-88, 121-89, 121-90, 121-91, 121-92, 121-93, 121-94, 121-95, 121-96, 121-97, 122-1, 122-2, 122-3, 1224, 122-5, 122-6, 122-7, 122-8, 122-9, 122-10, 122-11, 122-12, 122-13, 122-14, 122-15, 122-16, 122-17, 122-18, 122-19, 122-20, 122-21, 122-22, 122-23, 122-24, 122-25, 122-26, 122-27, 122-28, 122-29, 122-30, 122-31, 122-32, 122-33, 122-34, 122-35, 122-36, 122-37, 122-38, 122-39, 122-40, 122-41, 122-42, 122-43, 122-44, 122-45, 122-46, 122-47, 122-48, 122-49, 122-50, 122-51, 122-52, 122-53, 122-54, 122-55, 122-56, 122-57, 122-58, 122-59, 122-60, 122-61, 122-62, 122-63, 122-64, 122-65, 122-66, 122-67, 122-68, 122-69, 122-70, 122-71, 122-72, 122-73, 122-74, 122-75, 122-76, 122-77, 122-78, 122-79, 122-80, 122-81, 122-82, 122-83, 122-84, 122-85, 122-86, 122-87, 122-88, 122-89, 122-90, 122-91, 122-92, 122-93, 122-94, 122-95, 122-96, 122-97, 123-1, 123-2, 123-3, 123-4, 123-5, 123-6, 123-7, 123-8, 123-9, 123-10, 123-11, 123-12, 123-13, 123-14, 123-15, 123-16, 123-17, 123-18, 123-19, 123-20, 123-21, 123-22, 123-23, 123-24, 123-25, 123-26, 123-27, 123-28, 123-29, 123-30, 123-31, 123-32, 123-33, 123-34, 123-35, 123-36, 123-37, 123-38, 123-39, 123-40, 123-41, 123-42, 123-43, 123-44, 123-45, 123-46, 123-47, 123-48, 123-49, 123-50, 123-51, 123-52, 123-53, 123-54, 123-55, 123-56, 123-57, 123-58, 123-59, 123-60, 123-61, 123-62, 123-63, 123-64, 123-65, 123-66, 123-67, 123-68, 123-69, 123-70, 123-71, 123-72, 123-73, 123-74, 123-75, 123-76, 123-77, 123-78, 123-79, 123-80, 123-81, 123-82, 123-83, 123-84, 123-85, 123-86, 123-87, 123-88, 123-89, 123-90, 123-91, 123-92, 123-93, 123-94, 123-95, 123-96, 123-97, 124-1, 124-2, 124-3, 124-4, 124-5, 124-6, 124-7, 124-8, 124-9, 124-10, 124-11, 124-12, 124-13, 124-14, 124-15, 124-16, 124-17, 124-18, 124-19, 124-20, 124-21, 124-22, 124-23, 124-24, 124-25, 124-26, 124-27, 124-28, 124-29, 124-30, 124-31, 124-32, 124-33, 124-34, 124-35, 124-36, 124-37, 124-38, 124-39, 124-40, 124-41, 124-42, 124-43, 124-44, 124-45, 124-46, 124-47, 124-48, 124-49, 124-50, 124-51, 124-52, 124-53, 124-54, 124-55, 124-56, 124-57, 124-58, 124-59, 124-60, 124-6 124-62, 124-63, 124-64, 124-65, 124-66, 124-67, 124-68, 124-69, 124-70, 124-71, 124-72, 124-73, 124-74, 124-75, 124-76, 124-77, 124-78, 124-79, 124-80, 124-81, 124-82, 124-83, 124-84, 124-85, 124-86, 124-87, 124-88, 124-89, 124-90, 124-91, 124-92, 124-93, 124-94, 124-95, 124-96, 124-97, 125-1, 125-2, 125-3, 125-4, 125-5, 125-6, 125-7, 125-8, 125-9, 125-10, 125-11, 125-12, 125-13, 125-14, 125-15, 125-16, 125-17, 125-18, 125-19, 125-20, 125-21, 125-22, 125-23, 125-24, 125-25, 125-26, 125-27, 125-28, 125-29, 125-30, 125-31, 125-32, 125-33, 125-34, 125-35, 125-36, 125-37, 125-38, 125-39, 125-40, 125-41, 125-42, 125-43, 125-44, 125-45, 125-46, 125-47, 125-48, 125-49, 125-50, 125-51, 125-52, 125-53, 125-54, 125-55, 125-56, 125-57, 125-58, 125-59, 125-60, 125-61, 125-62, 125-63, 125-64, 125-65, 125-66, 125-67, 125-68, 125-69, 125-70, 125-71, 125-72, 125-73, 125-74, 125-75, 125-76, 125-77, 125-78, 125-79, 125-80, 125-81, 125-82, 125-83, 125-84, 125-85, 125-86, 125-87, 125-88, 125-89, 125-90, 125-91, 125-92, 125-93, 125-94, 125-95, 125-96, 125-97, 126-1, 126-2, 126-3, 126-4, 126-5, 126-6, 126-7, 126-8, 126-9, 126-10, 126-11, 126-12, 126-13, 126-14, 126-15, 126-16, 126-17, 126-18, 126-19, 126-20, 126-21, 126-22, 126-23, 126-24, 126-25, 126-26, 126-27, 126-28, 126-29, 126-30, 126-31, 126-32, 126-33, 126-34, 126-35, 126-36, 126-37, 126-38, 126-39, 126-40, 126-41, 126-42, 126-43, 126-44, 126-45, 126-46, 126-47, 126-48, 126-49, 126-50, 126-51, 126-52, 126-53, 126-54, 126-55, 126-56, 126-57, 126-58, 126-59, 126-60, 126-61, 126-62, 126-63, 126-64, 126-65, 126-66, 126-67, 126-68, 126-69, 126-70, 126-71, 126-72, 126-73, 126-74, 126-75, 126-76, 126-77, 126-78, 126-79, 126-80, 126-81, 126-82, 126-83, 126-84, 126-85, 126-86, 126-87, 126-88, 126-89, 126-90, 126-91, 126-92, 126-93, 126-94, 126-95, 126-96, 126-97, 127-1, 127-2, 127-3, 127-4, 127-5, 127-6, 127-7, 127-8, 127-9, 127-10, 127-11, 127-12, 127-13, 127-14, 127-15, 127-16, 127-17, 127-18, 127-19, 127-20, 127-21, 127-22, 127-23, 127-24, 127-25, 127-26, 127-27, 127-28, 127-29, 127-30, 127-31, 127-32, 127-33, 127-34, 127-35, 127-36, 127-37, 127-38, 127-39, 127-40, 127-41, 127-42, 127-43, 127-44, 127-45, 127-46, 127-47, 127-48, 127-49, 127-50, 127-51, 127-52, 127-53, 127-54, 127-55, 127-56, 127-57, 127-58, 127-59, 127-60, 127-61, 127-62, 127-63, 127-64, 127-65, 127-66, 127-67, 127-68, 127-69, 127-70, 127-71, 127-72, 127-73, 127-74, 127-75, 127-76, 127-77, 127-78, 127-79, 127-80, 127-81, 127-82, 127-83, 127-84, 127-85, 127-86, 127-87, 127-88, 127-89, 127-90, 127-91, 127-92, 127-93, 127-94, 127-95, 127-96, 127-97, 128-1, 128-2, 128-3, 1284, 128-5, 128-6, 128-7, 128-8, 128-9, 128-10, 128-11, 128-12, 128-13, 128-14, 128-15, 128-16, 128-17, 128-18, 128-19, 128-20, 128-21, 128-22, 128-23, 128-24, 128-25, 128-26, 128-27, 128-28, 128-29, 128-30, 128-31, 128-32, 128-33, 128-34, 128-35, 128-36, 128-37, 128-38, 128-39, 128-40, 128-41, 128-42, 128-43, 128-44, 128-45, 128-46, 128-47, 128-48, 128-49, 128-50, 128-51, 128-52, 128-53, 128-54, 128-55, 128-56, 128-57, 128-58, 128-59, 128-60, 128-61, 128-62, 128-63, 128-64, 128-65, 128-66, 128-67, 128-68, 128-69, 128-70, 128-71, 128-72, 128-73, 128-74, 128-75, 128-76, 128-77, 128-78, 128-79, 128-80, 128-81, 128-82, 128-83, 128-84, 128-85, 128-86, 128-87, 128-88, 128-89, 128-90, 128-91, 128-92, 128-93, 128-94, 128-95, 128-96, 128-97, 129-1, 129-2, 129-3, 129-4, 129-5, 129-6, 129-7, 129-8, 129-9, 129-10, 129-11, 129-12, 129-13, 129-14, 129-15, 129-16, 129-17, 129-18, 129-19, 129-20, 129-21, 129-22, 129-23, 129-24, 129-25, 129-26, 129-27, 129-28, 129-29, 129-30, 129-31, 129-32, 129-33, 129-34, 129-35, 129-36, 129-37, 129-38, 129-39, 129-40, 129-41, 129-42, 129-43, 129-44, 129-45, 129-46, 129-47, 129-48, 129-49, 129-50, 129-51, 129-52, 129-53, 129-54, 129-55, 129-56, 129-57, 129-58, 129-59, 129-60, 129-61, 129-62, 129-63, 129-64, 129-65, 129-66, 129-67, 129-68, 129-69, 129-70, 129-71, 129-72, 129-73, 129-74, 129-75, 129-76, 129-77, 129-78, 129-79, 129-80, 129-81, 129-82, 129-83, 129-84, 129-85, 129-86, 129-87, 129-88, 129-89, 129-90, 129-91, 129-92, 129-93, 129-94, 129-95, 129-96, 129-97, 130-1, 130-2, 130-3, 130-4, 130-5, 130-6, 130-7, 130-8, 130-9, 130-10, 130-11, 130-12, 130-13, 130-14, 130-15, 130-16, 130-17, 130-18, 130-19, 130-20, 130-21, 130-22, 130-23, 130-24, 130-25, 130-26, 130-27, 130-28, 130-29, 130-30, 130-31, 130-32, 130-33, 130-34, 130-35, 130-36, 130-37, 130-38, 130-39, 130-40, 130-41, 130-42, 130-43, 130-44, 130-45, 130-46, 130-47, 130-48, 130-49, 130-50, 130-51, 130-52, 130-53, 130-54, 130-55, 130-56, 130-57, 130-58, 130-59, 130-60, 130-61, 130-62, 130-63, 130-64, 130-65, 130-66, 130-67, 130-68, 130-69, 130-70, 130-71, 130-72, 130-73, 130-74, 130-75, 130-76, 130-77, 130-78, 130-79, 130-80, 130-81, 130-82, 130-83, 130-84, 130-85, 130-86, 130-87, 130-88, 130-89, 130-90, 130-91, 130-92, 130-93, 130-94, 130-95, 130-96, 130-97, 131-1, 131-2, 131-3, 131-4, 131-5, 131-6, 131-7, 131-8, 131-9, 131-10, 131-11, 131-12, 131-13, 131-14, 131-15, 131-16, 131-17, 131-18, 131-19, 131-20, 131-21, 131-22, 131-23, 131-24, 131-25, 131-26, 131-27, 131-28, 131-29, 131-30, 131-31, 131-32, 131-33, 131-34, 131-35, 131-36, 131-37, 131-38, 131-39, 131-40, 131-41, 131-42, 131-43, 131-44, 131-45, 131-46, 131-47, 131-48, 131-49, 131-50, 131-51, 131-52, 131-53, 131-54, 131-55, 131-56, 131-57, 131-58, 131-59, 131-60, 131-61, 131-62, 131-63, 131-64, 131-65, 131-66, 131-67, 131-68, 131-69, 131-70, 131-71, 131-72, 131-73, 131-74, 131-75, 131-76, 131-77, 131-78, 131-79, 131-80, 131-81, 131-82, 131-83, 131-84, 131-85, 131-86, 131-87, 131-88, 131-89, 131-90, 131-91, 131-92, 131-93, 131-94, 131-95, 131-96, 131-97, 132-1, 132-2, 132-3, 1324, 132-5, 132-6, 132-7, 132-8, 132-9, 132-10, 132-11, 132-12, 132-13, 132-14, 132-15, 132-16, 132-17, 132-18, 132-19, 132-20, 132-21, 132-22, 132-23, 132-24, 132-25, 132-26, 132-27, 132-28, 132-29, 132-30, 132-31, 132-32, 132-33, 132-34, 132-35, 132-36, 132-37, 132-38, 132-39, 132-40, 132-41, 132-42, 132-43, 132-44, 132-45, 132-46, 132-47, 132-48, 132-49, 132-50, 132-51, 132-52, 132-53, 132-54, 132-55, 132-56, 132-57, 132-58, 132-59, 132-60, 132-61, 132-62, 132-63, 132-64, 132-65, 132-66, 132-67, 132-68, 132-69, 132-70, 132-71, 132-72, 132-73, 132-74, 132-75, 132-76, 132-77, 132-78, 132-79, 132-80, 132-81, 132-82, 132-83, 132-84, 132-85, 132-86, 132-87, 132-88, 132-89, 132-90, 132-91, 132-92, 132-93, 132-94, 132-95, 132-96, 132-97, 133-1, 133-2, 133-3, 1334, 133-5, 133-6, 133-7, 133-8, 133-9, 133-10, 133-11, 133-12, 133-13, 133-14, 133-15, 133-16, 133-17, 133-18, 133-19, 133-20, 133-21, 133-22, 133-23, 133-24, 133-25, 133-26, 133-27, 133-28, 133-29, 133-30, 133-31, 133-32, 133-33, 133-34, 133-35, 133-36, 133-37, 133-38, 133-39, 133-40, 133-41, 133-42, 133-43, 133-44, 133-45, 133-46, 133-47, 133-48, 133-49, 133-50, 133-51, 133-52, 133-53, 133-54, 133-55, 133-56, 133-57, 133-58, 133-59, 133-60, 133-61, 133-62, 133-63, 133-64, 133-65, 133-66, 133-67, 133-68, 133-69, 133-70, 133-71, 133-72, 133-73, 133-74, 133-75, 133-76, 133-77, 133-78, 133-79, 133-80, 133-81, 133-82, 133-83, 133-84, 133-85, 133-86, 133-87, 133-88, 133-89, 133-90, 133-91, 133-92, 133-93, 133-94, 133-95, 133-96, 133-97, 134-1, 134-2, 134-3, 134-4, 134-5, 134-6, 134-7, 134-8, 134-9, 134-10, 134-11, 134-12, 134-13, 134-14, 134-15, 134-16, 134-17, 134-18, 134-19, 134-20, 134-21, 134-22, 134-23, 134-24, 134-25, 134-26, 134-27, 134-28, 134-29, 134-30, 134-31, 134-32, 134-33, 134-34, 134-35, 134-36, 134-37, 134-38, 134-39, 134-40, 134-41, 134-42, 134-43, 134-44, 134-45, 134-46, 134-47, 134-48, 134-49, 134-50, 134-51, 134-52, 134-53, 134-54, 134-55, 134-56, 134-57, 134-58, 134-59, 134-60, 134-61, 134-62, 134-63, 134-64, 134-65, 134-66, 134-67, 134-68, 134-69, 134-70, 134-71, 134-72, 134-73, 134-74, 134-75, 134-76, 134-77, 134-78, 134-79, 134-80, 134-81, 134-82, 134-83, 134-84, 134-85, 134-86, 134-87, 134-88, 134-89, 134-90, 134-91, 134-92, 134-93, 134-94, 134-95, 134-96, 134-97, 135-1, 135-2, 135-3, 135-4, 135-5, 135-6, 135-7, 135-8, 135-9, 135-10, 135-11, 135-12, 135-13, 135-14, 135-15, 135-16, 135-17, 135-18, 135-19, 135-20, 135-21, 135-22, 135-23, 135-24, 135-25, 135-26, 135-27, 135-28, 135-29, 135-30, 135-31, 135-32, 135-33, 135-34, 135-35, 135-36, 135-37, 135-38, 135-39, 135-40, 135-41, 135-42, 135-43, 135-44, 135-45, 135-46, 135-47, 135-48, 135-49, 135-50, 135-51, 135-52, 135-53, 135-54, 135-55, 135-56, 135-57, 135-58, 135-59, 135-60, 135-61, 135-62, 135-63, 135-64, 135-65, 135-66, 135-67, 135-68, 135-69, 135-70, 135-71, 135-72, 135-73, 135-74, 135-75, 135-76, 135-77, 135-78, 135-79, 135-80, 135-81, 135-82, 135-83, 135-84, 135-85, 135-86, 135-87, 135-88, 135-89, 135-90, 135-91, 135-92, 135-93, 135-94, 135-95, , 135-96, 135-97, 136-1, 136-2, 136-3, 136-4, 136-5, 136-6, 136-7, 136-8, 136-9, 136-10, 136-11, 136-12, 136-13, 136-14, 136-15, 136-16, 136-17, 136-18, 136-19, 136-20, 136-21, 136-22, 136-23, 136-24, 136-25, 136-26, 136-27, 136-28, 136-29, 136-30, 136-31, 136-32, 136-33, 136-34, 136-35, 136-36, 136-37, 136-38, 136-39, 136-40, 136-41, 136-42, 136-43, 136-44, 136-45, 136-46, 136-47, 136-48, 136-49, 136-50, 136-51, 136-52, 136-53, 136-54, 136-55, 136-56, 136-57, 136-58, 136-59, 136-60, 136-61, 136-62, 136-63, 136-64, 136-65, 136-66, 136-67, 136-68, 136-69, 136-70, 136-71, 136-72, 136-73, 136-74, 136-75, 136-76, 136-77, 136-78, 136-79, 136-80, 136-81, 136-82, 136-83, 136-84, 136-85, 136-86, 136-87, 136-88, 136-89, 136-90, 136-91, 136-92, 136-93, 136-94, 136-95, 136-96, 136-97, 137-1, 137-2, 137-3, 137-4, 137-5, 137-6, 137-7, 137-8, 137-9, 137-10, 137-11, 137-12, 137-13, 137-14, 137-15, 137-16, 137-17, 137-18, 137-19, 137-20, 137-21, 137-22, 137-23, 137-24, 137-25, 137-26, 137-27, 137-28, 137-29, 137-30, 137-31, 137-32, 137-33, 137-34, 137-35, 137-36, 137-37, 137-38, 137-39, 137-40, 137-41 137-42, 137-43, 137-44, 137-45, 137-46, 137-47, 137-48, 137-49, 137-50, 137-51, 137-52, 137-53, 137-54, 137-55, 137-56, 137-57, 137-58, 137-59, 137-60, 137-61, 137-62, 137-63, 137-64, 137-65, 137-66, 137-67, 137-68, 137-69, 137-70, 137-71, 137-72, 137-73, 137-74, 137-75, 137-76, 137-77, 137-78, 137-79, 137-80, 137-81, 137-82, 137-83, 137-84, 137-85, 137-86, 137-87, 137-88, 137-89, 137-90, 137-91, 137-92, 137-93, 137-94, 137-95, 137-96, 137-97, 138-1, 138-2, 138-3, 138-4, 138-5, 138-6, 138-7, 138-8, 138-9, 138-10, 138-11, 138-12, 138-13, 138-14, 138-15, 138-16, 138-17, 138-18, 138-19, 138-20, 138-21, 138-22, 138-23, 138-24, 138-25, 138-26, 138-27, 138-28, 138-29, 138-30, 138-31, 138-32, 138-33, 138-34, 138-35, 138-36, 138-37, 138-38, 138-39, 138-40, 138-41, 138-42, 138-43, 138-44, 138-45, 138-46, 138-47, 138-48, 138-49, 138-50, 138-51, 138-52, 138-53, 138-54, 138-55, 138-56, 138-57, 138-58, 138-59, 138-60, 138-61, 138-62, 138-63, 138-64, 138-65, 138-66, 138-67, 138-68, 138-69, 138-70, 138-71, 138-72, 138-73, 138-74, 138-75, 138-76, 138-77, 138-78, 138-79, 138-80, 138-81, 138-82, 138-83, 138-84, 138-85, 138-86, 138-87, 138-88, 138-89, 138-90, 138-91, 138-92, 138-93, 138-94, 138-95, 138-96, 138-97, 139-1, 139-2, 139-3, 1394, 139-5, 139-6, 139-7, 139-8, 139-9, 139-10, 139-11, 139-12, 139-13, 139-14, 139-15, 139-16, 139-17, 139-18, 139-19, 139-20, 139-21, 139-22, 139-23, 139-24, 139-25, 139-26, 139-27, 139-28, 139-29, 139-30, 139-31, 139-32, 139-33, 139-34, 139-35, 139-36, 139-37, 139-38, 139-39, 139-40, 139-41, 139-42, 139-43, 139-44, 139-45, 139-46, 139-47, 139-48, 139-49, 139-50, 139-51, 139-52, 139-53, 139-54, 139-55, 139-56, 139-57, 139-58, 139-59, 139-60, 139-61, 139-62, 139-63, 139-64, 139-65, 139-66, 139-67, 139-68, 139-69, 139-70, 139-71, 139-72, 139-73, 139-74, 139-75, 139-76, 139-77, 139-78, 139-79, 139-80, 139-81, 139-82, 139-83, 139-84, 139-85, 139-86, 139-87, 139-88, 139-89, 139-90, 139-91, 139-92, 139-93, 139-94, 139-95, 139-96, 139-97, 140-1, 140-2, 140-3, 140-4, 140-5, 1406, 140-7, 140-8, 140-9, 140-10, 140-11, 140-12, 140-13, 140-14, 140-15, 140-16, 140-17, 140-18, 140-19, 140-20, 140-21, 140-22, 140-23, 140-24, 140-25, 140-26, 140-27, 140-28, 140-29, 140-30, 140-31, 140-32, 140-33, 140-34, 140-35, 140-36, 140-37, 140-38, 140-39, 140-40, 140-41, 140-42, 140-43, 140-44, 140-45, 140-46, 140-47, 140-48, 140-49, 140-50, 140-51, 140-52, 140-53, 140-54, 140-55, 140-56, 140-57, 140-58, 140-59, 140-60, 140-61, 140-62, 140-63, 140-64, 140-65, 140-66, 140-67, 140-68, 140-69, 140-70, 140-71, 140-72, 140-73, 140-74, 140-75, 140-76, 140-77, 140-78, 140-79, 140-80, 140-81, 140-82, 140-83, 140-84, 140-85, 140-86, 140-87, 140-88, 140-89, 140-90, 140-91, 140-92, 140-93, 140-94, 140-95, 140-96, 140-97, 141-1, 141-2, 141-3, 141-4, 141-5, 141-6, 141-7, 141-8, 141-9, 141-10, 141-11, 141-12, 141-13, 141-14, 141-15, 141-16, 141-17, 141-18, 141-19, 141-20, 141-21, 141-22, 141-23, 141-24, 141-25, 141-26, 141-27, 141-28, 141-29, 141-30, 141-31, 141-32, 141-33, 141-34, 141-35, 141-36, 141-37, 141-38, 141-39, 141-40, 141-41, 141-42, 141-43, 141-44, 141-45, 141-46, 141-47, 141-48, 141-49, 141-50, 141-51, 141-52, 141-53, 141-54, 141-55, 141-56, 141-57, 141-58, 141-59, 141-60, 141-61, 141-62, 141-63, 141-64, 141-65, 141-66, 141-67, 141-68, 141-69, 141-70, 141-71, 141-72, 141-73, 141-74, 141-75, 141-76, 141-77, 141-78, 141-79, 141-80, 141-81, 141-82, 141-83, 141-84, 141-85, 141-86, 141-87, 141-88, 141-89, 141-90, 141-91, 141-92, 141-93, 141-94, 141-95, 141-96, 141-97, 142-1, 142-2, 142-3, 1424, 142-5, 142-6, 142-7, 142-8, 142-9, 142-10, 142-11, 142-12, 142-13, 142-14, 142-15, 142-16, 142-17, 142-18, 142-19, 142-20, 142-21, 142-22, 142-23, 142-24, 142-25, 142-26, 142-27, 142-28, 142-29, 142-30, 142-31, 142-32, 142-33, 142-34, 142-35, 142-36, 142-37, 142-38, 142-39, 142-40, 142-41, 142-42, 142-43, 142-44, 14-245, 142-46, 142-47, 142-48, 142-49, 142-50, 142-51, 142-52, 142-53, 142-54, 142-55, 142-56, 142-57, 142-58, 142-59, 142-60, 142-61, 142-62, 142-63, 142-64, 142-65, 142-66, 142-67, 142-68, 142-69, 142-70, 142-71, 142-72, 142-73, 142-74, 142-75, 142-76, 142-77, 142-78, 142-79, 142-80, 142-81, 142-82, 142-837 142-84, 142-85, 142-86, 142-87, 142-88, 142-89, 142-90, 142-91, 142-92, 142-93, 142-94, 142-95, 142-96, 142-97, 143-1, 143-2, 143-3, 143-4, 143-5, 143-6, 143-7, 143-8, 143-9, 143-10, 143-11, 143-12, 143-13, 143-14, 143-15, 143-16, 143-17, 143-18, 143-19, 143-20, 143-21, 143-22, 143-23, 143-24, 143-25, 143-26, 143-27, 143-28, 143-29, 143-30, 143-31, 143-32, 143-33, 143-34, 143-35, 143-36, 143-37, 143-38, 143-39, 143-40, 143-41, 143-42, 143-43, 143-44, 143-45, 143-46, 143-47, 143-48, 143-49, 143-50, 143-51, 143-52, 143-53, 143-54, 143-55, 143-56, 143-57, 143-58, 143-59, 143-60, 143-61, 143-62, 143-63, 143-64, 143-65, 143-66, 143-67, 143-68, 143-69, 143-70, 143-71, 143-72, 143-73, 143-74, 143-75, 143-76, 143-77, 143-78, 143-79, 143-80, 143-81, 143-82, 143-83, 143-84, 143-85, 143-86, 143-87, 143-88, 143-89, 143-90, 143-91, 143-92, 143-93, 143-94, 143-95, 143-96, 143-97, 144-1, 144-2, 144-3, 1444, 144-5, 144-6, 144-7, 144-8, 144-9, 144-10, 144-11, 144-12, 144-13, 144-14, 144-15, 144-16, 144-17, 144-18, 144-19, 144-20, 144-21, 144-22, 144-23, 144-24, 144-25, 144-26, 144-27, 144-28, 144-29, 144-30, 144-31, 144-32, 144-33, 144-34, 144-35, 144-36, 144-37, 144-38, 144-39, 144-40, 144-41, 144-42, 144-43, 144-44, 144-45, 141-46, 144-47, 144-48, 144-49, 144-50, 144-51, 144-52, 144-53, 144-54, 144-55, 144-56, 144-57, 144-58, 144-59, 144-60, 144-61, 144-62, 144-63, 144-64, 144-65, 144-66, 144-67, 144-68, 144-69, 144-70, 144-71, 144-72, 144-73, 144-74, 144-75, 144-76, 144-77, 144-78, 144-79, 144-80, 144-81, 144-82, 144-83, 144-84, 144-85, 144-86, 144-87, 144-88, 144-89, 144-90, 144-91, 144-92, 144-93, 144-94, 144-95, 144-96, 144-97, 145-1, 145-2, 145-3, 145-4, 145-5, 145-6, 145-7, 145-8, 145-9, 145-10, 145-11, 145-12, 145-13, 145-14, 145-15, 145-16, 145-17, 145-18, 145-19, 145-20, 145-21, 145-22, 145-23, 145-24, 145-25, 145-26, 145-27, 145-28, 145-29, 145-30, 145-31, 145-32, 145-33, 145-34, 145-35, 145-36, 145-37, 145-38, 145-39, 145-40, 145-41, 145-42, 145-43, 145-44, 145-45, 145-46, 145-47, 145-48, 145-49, 145-50, 145-51, 145-52, 145-53, 145-54, 145-55, 145-56, 145-57, 145-58, 145-59, 145-60, 145-61, 145-62, 145-63, 145-64, 145-65, 145-66, 145-67, 145-68, 145-69, 145-70, 145-71, 145-72, 145-73, 145-74, 145-75, 145-76, 145-77, 145-78, 145-79, 145-80, 145-81, 145-82, 145-83, 145-84, 145-85, 145-86, 145-87, 145-88, 145-89, 145-90, 145-91, 145-92, 145-93, 145-94, 145-95, 145-96, 145-97, 146-1, 146-2, 146-3, 146-4, 146-5, 146-6, 146-7, 146-8, 146-9, 146-10, 146-11, 146-12, 146-13, 146-14, 146-15, 146-16, 146-17, 146-18, 146-19, 146-20, 146-21, 146-22, 146-23, 146-24, 146-25, 146-26, 146-27, 146-28, 146-29, 146-30, 146-31, 146-32, 146-33, 146-34, 146-35, 146-36, 146-37, 146-38, 146-39, 146-40, 146-41, 146-42, 146-43, 146-44, 146-45, 146-46, 146-47, 146-48, 146-49, 146-50, 146-51, 146-52, 146-53, 146-54, 146-55, 146-56, 146-57, 146-58, 146-59, 146-60, 146-61, 146-62, 146-63, 146-64, 146-65, 146-66, 146-67, 146-68, 146-69, 146-70, 146-71, 146-72, 146-73, 146-74, 146-75, 146-76, 146-77, 146-78, 146-79, 146-80, 146-81, 146-82, 146-83, 146-84, 146-85, 146-86, 146-87, 146-88, 146-89, 146-90, 146-91, 146-92, 146-93, 146-94, 146-95, 146-96, 146-97, 147-1, 147-2, 147-3, 1474, 147-5, 147-6, 147-7, 147-8, 147-9, 147-10, 147-11, 147-12, 147-13, 147-14, 147-15, 147-16, 147-17, 147-18, 147-19, 147-20, 147-21, 147-22, 147-23, 147-24, 147-25, 147-26, 147-27, 147-28, 147-29, 147-30, 147-31, 147-32, 147-33, 147-34, 147-35, 147-36, 147-37, 147-38, 147-39, 147-40, 147-41, 147-42, 147-43, 147-44, 147-45, 147-46, 147-47, 147-48, 147-49, 147-50, 147-51, 147-52, 147-53, 147-54, 147-55, 147-56, 147-57, 147-58, 147-59, 147-60, 147-61, 147-62, 147-63, 147-64, 147-65, 147-66, 147-67, 147-68, 147-69, 147-70, 147-71, 147-72, 147-73, 147-74, 147-75, 147-76, 147-77, 147-78, 147-79, 147-80, 147-81, 147-82, 147-83, 147-84, 147-85, 147-86, 147-87, 147-88, 147-89, 147-90, 147-91, 147-92, 147-93, 147-94, 147-95, 147-96, 147-97, 148-1, 148-2, 148-3, 148-4, 148-5, 148-6, 148-7, 148-8, 148-9, 148-10, 148-11, 148-12, 148-13, 148-14, 148-15, 148-16, 148-17, 148-18, 148-19, 148-20, 148-21, 148-22, 148-23, 148-24, 148-25, 148-26, 148-27, 148-28, 148-29, 148-30, 148-31, 148-32, 148-33, 148-34, 148-35, 148-36, 148-37, 148-38, 148-39, 148-40, 148-41, 148-42, 148-43, 148-44, 148-45, 148-46, 148-47, 148-48, 148-49, 148-50, 148-51, 148-52, 148-53, 148-54, 148-55, 148-56, 148-57, 148-58, 148-59, 148-60, 148-61, 148-62, 148-63, 148-64, 148-65, 148-66, 148-67, 148-68, 148-69, 148-70, 148-71, 148-72, 148-73, 148-74, 148-75, 148-76, 148-77, 148-78, 148-79, 148-80, 148-81, 148-82, 148-83, 148-84, 148-85, 148-86, 148-87, 148-88, 148-89, 148-90, 148-91, 148-92, 148-93, 148-94, 148-95, 148-96, 148-97, 149-1, 149-2, 149-3, 149-4, 149-5, 149-6, 149-7, 149-8, 149-9, 149-10, 149-11, 149-12, 149-13, 149-14, 149-15, 149-16, 149-17, 149-18, 149-19, 149-20, 149-21, 149-22, 149-23, 149-24, 149-25, 149-26, 149-27, 149-28, 149-29, 149-30, 149-31, 149-32, 149-33, 149-34, 149-35, 149-36, 149-37, 149-38, 149-39, 149-40, 149-41, 149-42, 149-43, 149-44, 149-45, 149-46, 149-47, 149-48, 149-49, 149-50, 149-51, 149-52, 149-53, 149-54, 149-55, 149-56, 149-57, 149-58, 149-59, 149-60, 149-61, 149-62, 149-63, 149-64, 149-65, 149-66, 149-67, 149-68, 149-69, 149-70, 149-71, 149-72, 149-73, 149-74, 149-75, 149-76, 149-77, 149-78, 149-79, 149-80, 149-81, 149-82, 149-83, 149-84, 149-85, 149-86, 149-87, 149-88, 149-89, 149-90, 149-91, 149-92, 149-93, 149-94, 149-95, 149-96, 149-97, 150-1, 150-2, 150-3, 150-4, 150-5, 150-6, 150-7, 150-8, 150-9, 150-10, 150-11, 150-12, 150-13, 150-14, 150-15, 150-16, 150-17, 150-18, 150-19, 150-20, 150-21, 150-22, 150-23, 150-24, 150-25, 150-26, 150-27, 150-28, 150-29, 150-30, 150-31, 150-32, 150-33, 150-34, 150-35, 150-36, 150-37, 150-38, 150-39, 150-40, 150-41, 150-42, 150-43, 150-44, 150-45, 150-46, 150-47, 150-48, 150-49, 150-50, 150-51, 150-52, 150-53, 150-54, 150-55, 150-56, 150-57, 150-58, 150-59, 150-60, 150-61, 150-62, 150-63, 150-64, 150-65, 150-66, 150-67, 150-68, 150-69, 150-70, 150-71, 150-72, 150-73, 150-74, 150-75, 150-76, 150-77, 150-78, 150-79, 150-80, 150-81, 150-82, 150-83, 150-84, 150-85, 150-86, 150-87, 150-88, 150-89, 150-90, 150-91, 150-92, 150-93, 150-94, 150-95, 150-96, 150-97, 151-1, 151-2, 151-3, 151-4, 151-5, 151-6, 151-7, 151-8, 151-9, 151-10, 151-11, 151-12, 151-13, 151-14, 151-15, 151-16, 151-17, 151-18, 151-19, 151-20, 151-21, 151-22, 151-23, 151-24, 151-25, 151-26, 151-27, 151-28, 151-29, 151-30, 151-31, 151-32, 151-33, 151-34, 151-35, 151-36, 151-37, 151-38, 151-39, 151-40, 151-41, 151-42, 151-43, 151-44, 151-45, 151-46, 151-47, 151-48, 151-49, 151-50, 151-51, 151-52, 151-53, 151-54, 151-55, 151-56, 151-57, 151-58, 151-59, 151-60, 151-61, 151-62, 151-63, 151-64, 151-65, 151-66, 151-67, 151-68, 151-69, 151-70, 151-71, 151-72, 151-73, 151-74, 151-75, 151-76, 151-77, 151-78, 151-79, 151-80, 151-81, 151-82, 151-83, 151-84, 151-85, 151-86, 151-87, 151-88, 151-89, 151-90, 151-91, 151-92, 151-93, 151-94, 151-95, 151-96, 151-97, 152-1, 152-2, 152-3, 152-4, 152-5, 152-6, 152-7, 152-8, 152-9, 152-10, 152-11, 152-12, 152-13, 152-14, 152-15, 152-16, 152-17, 152-18, 152-19, 152-20, 152-21, 152-22, 152-23, 152-24, 152-25, 152-26, 152-27, 152-28, 152-29, 152-30, 152-31, 152-32, 152-33, 152-34, 152-35, 152-36, 152-37, 152-38, 152-39, 152-40, 152-41, 152-42, 152-43, 152-44, 152-45, 152-46, 152-47, 152-48, 152-49, 152-50, 152-51, 152-52, 152-53, 152-54, 152-55, 152-56, 152-57, 152-58, 152-59, 152-60, 152-61, 152-62, 152-63, 152-64, 152-65, 152-66, 152-67, 152-68, 152-69, 152-70, 152-71, 152-72, 152-73, 152-74, 152-75, 152-76, 152-77, 152-78, 152-79, 152-80, 152-81, 152-82, 152-83, 152-84, 152-85, 152-86, 152-87, 152-88, 152-89, 152-90, 152-91, 152-92, 152-93, 152-94, 152-95, 152-96, 152-97, 153-1, 153-2, 153-3, 1534, 153-5, 153-6, 153-7, 153-8, 153-9, 153-10, 153-11, 153-12, 153-13, 153-14, 153-15, 153-16, 153-17, 153-18, 153-19, 153-20, 153-21, 153-22, 153-23, 153-24, 153-25, 153-26, 153-27, 153-28, 153-29, 153-30, 153-31, 153-32, 153-33, 153-34, 153-35, 153-36, 153-37, 153-38, 153-39, 153-40, 153-41, 153-42, 153-43, 153-44, 153-45, 153-46, 153-47, 153-48, 153-49, 153-50, 153-51, 153-52; 153-53, 153-54, 153-55, 153-56, 153-57, 153-58, 153-59, 153-60, 153-61, 153-62, 153-63, 153-64, 153-65, 153-66, 153-67, 153-68, 153-69, 153-70, 153-71, 153-72, 153-73, 153-74, 153-75, 153-76, 153-77, 153-78, 153-79, 153-80, 153-81, 153-82, 153-83, 153-84, 153-85, 153-86, 153-87, 153-88, 153-89, 153-90, 153-91, 153-92, 153-93, 153-94, 153-95, 153-96, 153-97, 154-1, 154-2, 154-3, 154-4, 154-5, 154-6, 154-7, 154-8, 154-9, 154-10, 154-11, 154-12, 154-13, 154-14, 154-15, 154-16, 154-17, 154-18, 154-19, 154-20, 154-21, 154-22, 154-23, 154-24, 154-25, 154-26, 154-27, 154-28, 154-29, 154-30, 154-31, 154-32, 154-33, 154-34, 154-35, 154-36, 154-37, 154-38, 154-39, 154-40, 154-41, 154-42, 154-43, 154-44, 154-45, 154-46, 154-47, 154-48, 154-49, 154-50, 154-51, 154-52, 154-53, 154-54, 154-55, 154-56, 154-57, 154-58, 154-59, 154-60, 154-61, 154-62, 154-63, 154-64, 154-65, 154-66, 154-67, 154-68, 154-69, 154-70, 154-71, 154-72, 154-73, 154-74, 154-75, 154-76, 154-77, 154-78, 154-79, 154-80, 154-81, 154-82, 154-83, 154-84, 154-85, 154-86, 154-87, 154-88, 154-89, 154-90, 154-91, 154-92, 154-93, 154-94, 154-95, 154-96, 154-97, 155-1, 155-2, 155-3, 155-4, 155-5, 155-6, 155-7, 155-8, 155-9, 155-10, 155-11, 155-12, 155-13, 155-14, 155-15, 155-16, 155-17, 155-18, 155-19, 155-20, 155-21, 155-22, 155-23, 155-24, 155-25, 155-26, 155-27, 155-28, 155-29, 155-30, 155-31, 155-32, 155-33, 155-34, 155-35, 155-36, 155-37, 155-38, 155-39, 155-40, 155-41, 155-42, 155-43, 155-44, 155-45, 155-46, 155-47, 155-48, 155-49, 155-50, 155-51, 155-52, 155-53, 155-54, 155-55, 155-56, 155-57, 155-58, 155-59, 155-60, 155-61, 155-62, 155-63, 155-64, 155-65, 155-66, 155-67, 155-68, 155-69, 155-70, 155-71, 155-72, 155-73, 155-74, 155-75, 155-76, 155-77, 155-78, 155-79, 155-80, 155-81, 155-82, 155-83, 155-84, 155-85, 155-86, 155-87, 155-88, 155-89, 155-90, 155-91, 155-92, 155-93, 155-94, 155-95, 155-96, 155-97, 156-1, 156-2, 156-3, 156-4, 156-5, 156-6, 156-7, 156-8, 156-9, 156-10, 156-11, 156-12, 156-13, 156-14, 156-15, 156-16, 156-17, 156-18, 156-19, 156-20, 156-21, 156-22, 156-23, 156-24, 156-25, 156-26, 156-27, 156-28, 156-29, 156-30, 156-31, 156-32, 156-33, 156-34, 156-35, 156-36, 156-37, 156-38, 156-39, 156-40, 156-41, 156-42, 156-43, 156-44, 156-45, 156-46, 156-47, 156-48, 156-49, 156-50, 156-51, 156-52, 156-53, 156-54, 156-55, 156-56, 156-57, 156-58, 156-59, 156-60, 156-61, 156-62, 156-63, 156-64, 156-65, 156-66, 156-67, 156-68, 156-69, 156-70, 156-71, 156-72, 156-73, 156-74, 156-75, 156-76, 156-77, 156-78, 156-79, 156-80, 156-81, 156-82, 156-83, 156-84, 156-85, 156-86, 156-87, 156-88, 156-89, 156-90, 156-91, 156-92, 156-93, 156-94, 156-95, 156-96, 156-97, 157-1, 157-2, 157-3, 157-4, 157-5, 157-6, 157-7, 157-8, 157-9, 157-10, 157-11, 157-12, 157-13, 157-14, 157-15, 157-16, 157-17, 157-18, 157-19, 157-20, 157-21, 157-22, 157-23, 157-24, 157-25, 157-26, 157-27, 157-28, 157-29, 157-30, 157-31, 157-32, 157-33, 157-34, 157-35, 157-36, 157-37, 157-38, 157-39, 157-40, 157-41, 157-42, 157-43, 157-44, 157-45, 157-46, 157-47, 157-48, 157-49, 157-50, 157-51, 157-52, 157-53, 157-54, 157-55, 157-56, 157-57, 157-58, 157-59, 157-60, 157-61, 157-62, 157-63, 157-64, 157-65, 157-66, 157-67, 157-68, 157-69, 157-70, 157-71, 157-72, 157-73, 157-74, 157-75, 157-76, 157-77, 157-78, 157-79, 157-80, 157-81, 157-82, 157-83, 157-84, 157-85, 157-86, 157-87, 157-88, 157-89, 157-90, 157-91, 157-92, 157-93, 157-94, 157-95, 157-96, 157-97, 158-1, 158-2, 158-3, 158-4, 158-5, 158-6, 158-7, 158-8, 158-9, 158-10, 158-11, 158-12, 158-13, 158-14, 158-15, 158-16, 158-17, 158-18, 158-19, 158-20, 158-21, 158-22, 158-23, 158-24, 158-25, 158-26, 158-27, 158-28, 158-29, 158-30, 158-31, 158-32, 158-33, 158-34, 158-35, 158-36, 158-37, 158-38, 158-39, 158-40, 158-41, 158-42, 158-43, 158-44, 158-45, 158-46, 158-47, 158-48, 158-49, 158-50, 158-51, 158-52, 158-53, 158-54, 158-55, 158-56, 158-57, 158-58, 158-59, 158-60, 158-61, 158-62, 158-63, 158-64, 158-65, 158-66, 158-67, 158-68, 158-69, 158-70, 158-71, 158-72, 158-73, 158-74, 158-75, 158-76, 158-77, 158-78, 158-79, 158-80, 158-81, 158-82, 158-83, 158-84, 158-85, 158-86, 158-87, 158-88, 158-89, 158-90, 158-91, 158-92, 158-93, 158-94, 158-95, 158-96, 158-97, 159-1, 159-2, 159-3, 159-4, 159-5, 159-6, 159-7, 159-8, 159-9, 159-10, 159-11, 159-12, 159-13, 159-14, 159-15, 159-16, 159-17, 159-18, 159-19, 159-20, 159-21, 159-22, 159-23, 159-24, 159-25, 159-26, 159-27, 159-28, 159-29, 159-30, 159-31, 159-32, 159-33, 159-34, 159-35, 159-36, 159-37, 159-38, 159-39, 159-40, 159-41, 159-42, 159-43, 159-44, 159-45, 159-46, 159-47, 159-48, 159-49, 159-50, 159-51, 159-52, 159-53, 159-54, 159-55, 159-56, 159-57, 159-58, 159-59, 159-60, 159-61, 159-62, 159-63, 159-64, 159-65, 159-66, 159-67, 159-68, 159-69, 159-70, 159-71, 159-72, 159-73, 159-74, 159-75, 159-76, 159-77, 159-78, 159-79, 159-80, 159-81, 159-82, 159-83, 159-84, 159-85, 159-86, 159-87, 159-88, 159-89, 159-90, 159-91, 159-92, 159-93, 159-94, 159-95, 159-96, 159-97, 160-1, 160-2, 160-3, 1604, 160-5, 160-6, 160-7, 160-8, 160-9, 160-10, 160-11, 160-12, 160-13, 160-14, 160-15, 160-16, 160-17, 160-18, 160-19, 160-20, 160-21, 160-22, 160-23, 160-24, 160-25, 160-26, 160-27, 160-28, 160-29, 160-30, 160-31, 160-32, 160-33, 160-34, 160-35, 160-36, 160-37, 160-38, 160-39, 160-40, 160-41, 160-42, 160-43, 160-44, 160-45, 160-46, 160-47, 160-48, 160-49, 160-50, 160-51, 160-52, 160-53, 160-54, 160-55, 160-56, 160-57, 160-58, 160-59, 160-60, 160-61, 160-62, 160-63, 160-64, 160-65, 160-66, 160-67, 160-68, 160-69, 160-70, 160-71, 160-72, 160-73, 160-74, 160-75, 160-76, 160-77, 160-78, 160-79, 160-80, 160-81, 160-82, 160-83, 160-84, 160-85, 160-86, 160-87, 160-88, 160-89, 160-90, 160-91, 160-92, 160-93, 160-94, 160-95, 160-96, 160-97, 161-1, 161-2, 161-3, 161-4, 161-5, 161-6, 161-7, 161-8, 161-9, 161-10, 161-11, 161-12, 161-13, 161-14, 161-15, 161-16, 161-17, 161-18, 161-19, 161-20, 161-21, 161-22, 161-23, 161-24, 161-25, 161-26, 161-27, 161-28, 161-29, 161-30, 161-31, 161-32, 161-33, 161-34, 161-35, 161-36, 161-37, 161-38, 161-39, 161-40, 161-41, 161-42, 161-43, 161-44, 161-45, 161-46, 161-47, 161-48, 161-49, 161-50, 161-51, 161-52, 161-53, 161-54, 161-55, 161-56, 161-57, 161-58, 161-59, 161-60, 161-61, 161-62, 161-63, 161-64, 161-65, 161-66, 161-67, 161-68, 161-69, 161-70, 161-71, 161-72, 161-73, 161-74, 161-75, 161-76, 161-77, 161-78, 161-79, 161-80, 161-81, 161-82, 161-83, 161-84, 161-85, 161-86, 161-87, 161-88, 161-89, 161-90, 161-91, 161-92, 161-93, 161-94, 161-95, 161-96, 161-97, 162-1, 162-2, 162-3, 162-4, 162-5, 162-6, 162-7, 162-8, 162-9, 162-10, 162-11, 162-12, 162-13, 162-14, 162-15, 162-16, 162-17, 162-18, 162-19, 162-20, 162-21, 162-22, 162-23, 162-24, 162-25, 162-26, 162-27, 162-28, 162-29, 162-30, 162-31, 162-32, 162-33, 162-34, 162-35, 162-36, 162-37, 162-38, 162-39, 162-40, 162-41, 162-42, 162-43, 162-44, 162-45, 162-46, 162-47, 162-48, 162-49, 162-50, 162-51, 162-52, 162-53, 162-54, 162-55, 162-56, 162-57, 162-58, 162-59, 162-60, 162-61, 162-62, 162-63, 162-64, 162-65, 162-66, 162-67, 162-68, 162-69, 162-70, 162-71, 162-72, 162-73, 162-74, 162-75, 162-76, 162-77, 162-78, 162-79, 162-80, 162-81, 162-82, 162-83, 162-84, 162-85, 162-86, 162-87, 162-88, 162-89, 162-90, 162-91, 162-92, 162-93, 162-94, 162-95, 162-96, 162-97, 163-1, 163-2, 163-3, 163-4, 163-5, 163-6, 163-7, 163-8, 163-9, 163-10, 163-11, 163-12, 163-13, 163-14, 163-15, 163-16, 163-17, 163-18, 163-19, 163-20, 163-21, 163-22, 163-23, 163-24, 163-25, 163-26, 163-27, 163-28, 163-29, 163-30, 163-31, 163-32, 163-33, 163-34, 163-35, 163-36, 163-37, 163-38, 163-39, 163-40, 163-41, 163-42, 163-43, 163-44, 163-45, 163-46, 163-47, 163-48, 163-49, 163-50, 163-51, 163-52, 163-53, 163-54, 163-55, 163-56, 163-57, 163-58, 163-59, 163-60, 163-61, 163-62, 163-63, 163-64, 163-65, 163-66, 163-67, 163-68, 163-69, 163-70, 163-71, 163-72, 163-73, 163-74, 163-75, 163-76, 163-77, 163-78, 163-79, 163-80, 163-81, 163-82, 163-83, 163-84, 163-85, 163-86, 163-87, 163-88, 163-89, 163-90, 163-91, 163-92, 163-93, 163-94, 163-95, 163-96, 163-97, 164-1, 164-2, 164-3, 164-4, 164-5, 164-6, 164-7, 164-8, 164-9, 164-10, 164-11, 164-12, 164-13, 164-14, 164-15, 164-16, 164-17, 164-18, 164-19, 164-20, 164-21, 164-22, 164-23, 164-24, 164-25, 164-26, 164-27, 164-28, 164-29, 164-30, 164-31, 164-32, 164-33, 164-34, 164-35, 164-36, 164-37, 164-38, 164-39, 164-40, 164-41, 164-42, 164-43, 164-44, 164-45, 164-46, 164-47, 164-48, 164-49, 164-50, 164-51, 164-52, 164-53, 164-54, 164-55, 164-56, 164-57, 164-58, 164-59, 164-60, 164-61, 164-62, 164-63, 164-64, 164-65, 164-66, 164-67, 164-68, 164-69, 164-70, 164-71, 164-72, 164-73, 164-74, 164-75, 164-76, 164-77, 164-78, 164-79, 164-80, 164-81, 164-82, 164-83, 164-84, 164-85, 164-86, 164-87, 164-88, 164-89, 164-90, 164-91, 164-92, 164-93, 164-94, 164-95, 164-96, 164-97, 165-1, 165-2, 165-3, 165-4, 165-5, 165-6, 165-7, 165-8, 165-9, 165-10, 165-11, 165-12, 165-13, 165-14, 165-15, 165-16, 165-17, 165-18, 165-19, 165-20, 165-21, 165-22, 165-23, 165-24, 165-25, 165-26, 165-27, 165-28, 165-29, 165-30, 165-31, 165-32, 165-33, 165-34, 165-35, 165-36, 165-37, 165-38, 165-39, 165-40, 165-41, 165-42, 165-43, 165-44, 165-45, 165-46, 165-47, 165-48, 165-49, 165-50, 165-51, 165-52, 165-53, 165-54, 165-55, 165-56, 165-57, 165-58, 165-59, 165-60, 165-61, 165-62, 165-63, 165-64, 165-65, 165-66, 165-67, 165-68, 165-69, 165-70, 165-71, 165-72, 165-73, 165-74, 165-75, 165-76, 165-77, 165-78, 165-79, 165-80, 165-81, 165-82, 165-83, 165-84, 165-85, 165-86, 165-87, 165-88, 165-89, 165-90, 165-91, 165-92, 165-93, 165-94, 165-95, 165-96, 165-97, 166-1, 166-2, 166-3, 166-4, 166-5, 166-6, 166-7, 166-8, 166-9, 166-10, 166-11, 166-12, 166-13, 166-14, 166-15, 166-16, 166-17, 166-18, 166-19, 166-20, 166-21, 166-22, 166-23, 166-24, 166-25, 166-26, 166-27, 166-28, 166-29, 166-30, 166-31, 166-32, 166-33, 166-34, 166-35, 166-36, 166-37, 166-38, 166-39, 166-40, 166-41, 166-42, 166-43, 166-44, 166-45, 166-46, 166-47, 166-48, 166-49, 166-50, 166-51, 166-52, 166-53, 166-54, 166-55, 166-56, 166-57, 166-58, 166-59, 166-60, 166-61, 166-62, 166-63, 166-64, 166-65, 166-66, 166-67, 166-68, 166-69, 166-70, 166-71, 166-72, 166-73, 166-74, 166-75, 166-76, 166-77, 166-78, 166-79, 166-80, 166-81, 166-82, 166-83, 166-84, 166-85, 166-86, 166-87, 166-88, 166-89, 166-90, 166-91, 166-92, 166-93, 166-94, 166-95, 166-96, 166-97, 167-1, 167-2, 167-3, 167-4, 167-5, 167-6, 167-7, 167-8, 167-9, 167-10, 167-11, 167-12, 167-13, 167-14, 167-15, 167-16, 167-17, 167-18, 167-19, 167-20, 167-21, 167-22, 167-23, 167-24, 167-25, 167-26, 167-27, 167-28, 167-29, 167-30, 167-31, 167-32, 167-33, 167-34, 167-35, 167-36, 167-37, 167-38, 167-39, 167-40, 167-41, 167-42, 167-43, 167-44, 167-45, 167-46, 167-47, 167-48, 167-49, 167-50, 167-51, 167-52, 167-53, 167-54, 167-55, 167-56, 167-57, 167-58, 167-59, 167-60, 167-61, 167-62, 167-63, 167-64, 167-65, 167-66, 167-67, 167-68, 167-69, 167-70, 167-71, 167-72, 167-73, 167-74, 167-75, 167-76, 167-77, 167-78, 167-79, 167-80, 167-81, 167-82, 167-83, 167-84, 167-85, 167-86, 167-87, 167-88, 167-89, 167-90, 167-91, 167-92, 167-93, 167-94, 167-95, 167-96, 167-97, 168-1, 168-2, 168-3, 168-4, 168-5, 168-6, 168-7, 168-8, 168-9, 168-10, 168-11, 168-12, 168-13, 168-14, 168-15, 168-16, 168-17, 168-18, 168-19, 168-20, 168-21, 168-22, 168-23, 168-24, 168-25, 168-26, 168-27, 168-28, 168-29, 168-30, 168-31, 168-32, 168-33, 168-34, 168-35, 168-36, 168-37, 168-38, 168-39, 168-40, 168-41, 168-42, 168-43, 168-44, 168-45, 168-46, 168-47, 168-48, 168-49, 168-50, 168-51, 168-52, 168-53, 168-54, 168-55, 168-56, 168-57, 168-58, 168-59, 168-60, 168-61, 168-62, 168-63, 168-64, 168-65, 168-66, 168-67, 168-68, 168-69, 168-70, 168-71, 168-72, 168-73, 168-74, 168-75, 168-76, 168-77, 168-78, 168-79, 168-80, 168-81, 168-82, 168-83, 168-84, 168-85, 168-86, 168-87, 168-88, 168-89, 168-90, 168-91, 168-92, 168-93, 168-94, 168-95, 168-96, 168-97, 169-1, 169-2, 169-3, 169-4, 169-5, 169-6, 169-7, 169-8, 169-9, 169-10, 169-11, 169-12, 169-13, 169-14, 169-15, 169-16, 169-17, 169-18, 169-19, 169-20, 169-21, 169-22, 169-23, 169-24, 169-25, 169-26, 169-27, 169-28, 169-29, 169-30, 169-31, 169-32, 169-33, 169-34, 169-35, 169-36, 169-37, 169-38, 169-39, 169-40, 169-41, 169-42, 169-43, 169-44, 169-45, 169-46, 169-47, 169-48, 169-49, 169-50, 169-51, 169-52, 169-53, 169-54, 169-55, 169-56, 169-57, 169-58, 169-59, 169-60, 169-61, 169-62, 169-63, 169-64, 169-65, 169-66, 169-67, 169-68, 169-69, 169-70, 169-71, 169-72, 169-73, 169-74, 169-75, 169-76, 169-77, 169-78, 169-79, 169-80, 169-81, 169-82, 169-83, 169-84, 169-85, 169-86, 169-87, 169-88, 169-89, 169-90, 169-91, 169-92, 169-93, 169-94, 169-95, 169-96, 169-97, 170-1, 170-2, 170-3, 170-4, 17-5, 170-6, 170-7, 170-8, 170-9, 170-10, 170-11, 170-12, 170-13, 170-14, 170-15, 170-16, 170-17, 170-18, 170-19, 170-20, 170-21, 170-22, 170-23, 170-24, 170-25, 170-26, 170-27, 170-28, 170-29, 170-30, 170-31, 170-32, 170-33, 170-34, 170-35, 170-36, 170-37, 170-38, 170-39, 170-40, 170-41, 170-42, 170-43, 170-44, 170-45, 170-46, 170-47, 170-48, 170-49, 170-50, 170-51, 170-52, 170-53, 170-54, 170-55, 170-56, 170-57, 170-58, 170-59, 170-60, 170-61, 170-62, 170-63, 170-64, 170-65, 170-66, 170-67, 170-68, 170-69, 170-70, 170-71, 170-72, 170-73, 170-74, 170-75, 170-76, 170-77, 170-78, 170-79, 170-80, 170-81, 170-82, 170-83, 170-84, 170-85, 170-86, 170-87, 170-88, 170-89, 170-90, 170-91, 170-92, 170-93, 170-94, 170-95, 170-96, 170-97, 171-1, 171-2, 171-3, 171-4, 171-5, 171-6, 171-7, 171-8, 171-9, 171-10, 171-11, 171-12, 171-13, 171-14, 171-15, 171-16, 171-17, 171-18, 171-19, 171-20, 171-21, 171-22, 171-23, 171-24, 171-25, 171-26, 171-27, 171-28, 171-29, 171-30, 171-31, 171-32, 171-33, 171-34, 171-35, 171-36, 171-37, 171-38, 171-39, 171-40, 171-41, 171-42, 171-43, 171-44, 171-45, 171-46, 171-47, 171-48, 171-49, 171-50, 171-51, 171-52, 171-53, 171-54, 171-55, 171-56, 171-57, 171-58, 171-59, 171-60, 171-61, 171-62, 171-63, 171-64, 171-65, 171-66, 171-67, 171-68, 171-69, 171-70, 171-71, 171-72, 171-73, 171-74, 171-75, 171-76, 171-77, 171-78, 171-79, 171-80, 171-81, 171-82, 171-83, 171-84, 171-85, 171-86, 171-87, 171-88, 171-89, 171-90, 171-91, 171-92, 171-93, 171-94, 171-95, 171-96, 171-97, 172-1, 172-2, 172-3, 172-4, 172-5, 172-6, 172-7, 172-8, 172-9, 172-10, 172-11, 172-12, 172-13, 172-14, 172-15, 172-16, 172-17, 172-18, 172-19, 172-20, 172-21, 172-22, 172-23, 172-24, 172-25, 172-26, 172-27, 172-28, 172-29, 172-30, 172-31, 172-32, 172-33, 172-34, 172-35, 172-36, 172-37, 172-38, 172-39, 172-40, 172-41, 172-42, 172-43, 172-44, 172-45, 172-46, 172-47, 172-48, 172-49, 172-50, 172-51, 172-52, 172-53, 172-54, 172-55, 172-56, 172-57, 172-58, 172-59, 172-60, 172-61, 172-62, 172-63, 172-64, 172-65, 172-66, 172-67, 172-68, 172-69, 172-70, 172-71, 172-72, 172-73, 172-74, 172-75, 172-76, 172-77, 172-78, 172-79, 172-80, 172-81, 172-82, 172-83, 172-84, 172-85, 172-86, 172-87, 172-88, 172-89, 172-90, 172-91, 172-92, 172-93, 172-94, 172-95, 172-96, 172-97, 173-1, 173-2, 173-3, 173-4, 173-5, 173-6, 173-7, 173-8, 173-9, 173-10, 173-11, 173-12, 173-13, 173-14, 173-15, 173-16, 173-17, 173-18, 173-19, 173-20, 173-21, 173-22, 173-23, 173-24, 173-25, 173-26, 173-27, 173-28, 173-29, 173-30, 173-31, 173-32, 173-33, 173-34, 173-35, 173-36, 173-37, 173-38, 173-39, 173-40, 173-41, 173-42, 173-43, 173-44, 173-45, 173-46, 173-47, 173-48, 173-49, 173-50, 173-51, 173-52, 173-53, 173-54, 173-55, 173-56, 173-57, 173-58, 173-59, 173-60, 173-61, 173-62, 173-63, 173-64, 173-65, 173-66, 173-67, 173-68, 173-69, 173-70, 173-71, 173-72, 173-73, 173-74, 173-75, 173-76, 173-77, 173-78, 173-79, 173-80, 173-81, 173-82, 173-83, 173-84, 173-85, 173-86, 173-87, 173-88, 173-89, 173-90, 173-91, 173-92, 173-93, 173-94, 173-95, 173-96, 173-97, 174-1, 174-2, 174-3, 174-4, 174-5, 174-6, 174-7, 174-8, 174-9, 174-10, 174-11, 174-12, 174-13, 174-14, 174-15, 174-16, 174-17, 174-18, 174-19, 174-20, 174-21, 174-22, 174-23, 174-24, 174-25, 174-26, 174-27, 174-28, 174-29, 174-30, 174-31, 174-32, 174-33, 174-34, 174-35, 174-36, 174-37, 174-38, 174-39, 174-40, 174-41, 174-42, 174-43, 174-44, 174-45, 174-46, 174-47, 174-48, 174-49, 174-50, 174-51, 174-52, 174-53, 174-54, 174-55, 174-56, 174-57, 174-58, 174-59, 174-60, 174-61, 174-62, 174-63, 174-64, 174-65, 174-66, 174-67, 174-68, 174-69, 174-70, 174-71, 174-72, 174-73, 174-74, 174-75, 174-76, 174-77, 174-78, 174-79, 174-80, 174-81, 174-82, 174-83, 174-84, 174-85, 174-86, 174-87, 174-88, 174-89, 174-90, 174-91, 174-92, 174-93, 174-94, 174-95, 174-96, 174-97, 175-1, 175-2, 175-3, 175-4, 175-5, 175-6, 175-7, 175-8, 175-9, 175-10, 175-11, 175-12, 175-13, 175-14, 175-15, 175-16, 175-17, 175-18, 175-19, 175-20, 175-21, 175-22, 175-23, 175-24, 175-25, 175-26, 175-27, 175-28, 175-29, 175-30, 175-31, 175-32, 175-33, 175-34, 175-35, 175-36, 175-37, 175-38, 175-39, 175-40, 175-41, 175-42, 175-43, 175-44, 175-45, 175-46, 175-47, 175-48, 175-49, 175-50, 175-51, 175-52, 175-53, 175-54, 175-55, 175-56, 175-57, 175-58, 175-59, 175-60, 175-61, 175-62, 175-63, 175-64, 175-65, 175-66, 175-67, 175-68, 175-69, 175-70, 175-71, 175-72, 175-73, 175-74, 175-75, 175-76, 175-77, 175-78, 175-79, 175-80, 175-81, 175-82, 175-83, 175-84, 175-85, 175-86, 175-87, 175-88, 175-89, 175-90, 175-91, 175-92, 175-93, 175-94, 175-95, 175-96, 175-97, 176-1, 176-2, 176-3, 176-4, 1765, 176-6, 176-7, 176-8, 176-9, 176-10, 176-11, 176-12, 176-13, 176-14, 176-15, 176-16, 176-17, 176-18, 176-19, 176-20, 176-21, 176-22, 176-23, 176-24, 176-25, 176-26, 176-27, 176-28, 176-29, 176-30, 176-31, 176-32, 176-33, 176-34, 176-35, 176-36, 176-37, 176-38, 176-39, 176-40, 176-41, 176-42, 176-43, 176-44, 176-45, 176-46, 176-47, 176-48, 176-49, 176-50, 176-51, 176-52, 176-53, 176-54, 176-55, 176-56, 176-57, 176-58, 176-59, 176-60, 176-61, 176-62, 176-63, 176-64, 176-65, 176-66, 176-67, 176-68, 176-69, 176-70, 176-71, 176-72, 176-73, 176-74, 176-75, 176-76, 176-77, 176-78, 176-79, 176-80, 176-81, 176-82, 176-83, 176-84, 176-85, 176-86, 176-87, 176-88, 176-89, 176-90, 176-91, 176-92, 176-93, 176-94, 176-95, 176-96, 176-97, 177-1, 177-2, 177-3, 1774, 177-5, 177-6, 177-7, 177-8, 177-9, 177-10, 177-11, 177-12, 177-13, 177-14, 177-15, 177-16, 177-17, 177-18, 177-19, 177-20, 177-21, 177-22, 177-23, 177-24, 177-25, 177-26, 177-27, 177-28, 177-29, 177-30, 177-31, 177-32, 177-33, 177-34, 177-35, 177-36, 177-37, 177-38, 177-39, 177-40, 177-41, 177-42, 177-43, 177-44, 177-45, 177-46, 177-47, 177-48, 177-49, 177-50, 177-51, 177-52, 177-53, 177-54, 177-55, 177-56, 177-57, 177-58, 177-59, 177-60, 177-61, 177-62, 177-63, 177-64, 177-65, 177-66, 177-67, 177-68, 177-69, 177-70, 177-71, 177-72, 177-73, 177-74, 177-75, 177-76, 177-77, 177-78, 177-79, 177-80, 177-81, 177-82, 177-83, 177-84, 177-85, 177-86, 177-87, 177-88, 177-89, 177-90, 177-91, 177-92, 177-93, 177-94, 177-95, 177-96, 177-97, 178-1, 178-2, 178-3, 178-4, 178-5, 178-6, 178-7, 178-8, 178-9, 178-10, 178-11, 178-12, 178-13, 178-14, 178-15, 178-16, 178-17, 178-18, 178-19, 178-20, 178-21, 178-22, 178-23, 178-24, 178-25, 178-26, 178-27, 178-28, 178-29, 178-30, 178-31, 178-32, 178-33, 178-34, 178-35, 178-36, 178-37, 178-38, 178-39, 178-40, 178-41, 178-42, 178-43, 177-84, 178-45, 178-46, 178-47, 178-48, 178-49, 178-50, 178-51, 178-52, 178-53, 178-54, 178-55, 178-56, 178-57, 178-58, 178-59, 178-60, 178-61, 178-62, 178-63, 178-64, 178-65, 178-66, 178-67, 178-68, 178-69, 178-70, 178-71, 178-72, 178-73, 178-74, 178-75, 178-76, 178-77, 178-78, 178-79, 178-80, 178-81, 178-82, 178-83, 178-84, 178-85, 178-86, 178-87, 178-88, 178-89, 178-90, 178-91, 178-92, 178-93, 178-94, 178-95, 178-96, 178-97, 179-1, 179-2, 179-3, 179-4, 179-5, 179-6, 179-7, 179-8, 179-9, 179-10, 179-11, 179-12, 179-13, 179-14, 179-15, 179-16, 179-17, 179-18, 179-19, 179-20, 179-21, 179-22, 179-23, 179-24, 179-25, 179-26, 179-27, 179-28, 179-29, 179-30, 179-31, 179-32, 179-33, 179-34, 179-35, 179-36, 179-37, 179-38, 179-39, 179-40, 179-41, 179-42, 179-43, 179-44, 179-45, 179-46, 179-47, 179-48, 179-49, 179-50, 179-51, 179-52, 179-53, 179-54, 179-55, 179-56, 179-57, 179-58, 179-59, 179-60, 179-61, 179-62, 179-63, 179-64, 179-65, 179-66, 179-67, 179-68, 179-69, 179-70, 179-71, 179-72, 179-73, 179-74, 179-75, 179-76, 179-77, 179-78, 179-79, 179-80, 179-81, 179-82, 179-83, 179-84, 179-85, 179-86, 179-87, 179-88, 179-89, 179-90, 179-91, 179-92, 179-93, 179-94, 179-95, 179-96, 179-97, 180-1, 180-2, 180-3, 180-4, 180-5, 180-6, 180-7, 180-8, 180-9, 180-10, 180-11, 180-12, 180-13, 180-14, 180-15, 180-16, 180-17, 180-18, 180-19, 180-20, 180-21, 180-22, 180-23, 180-24, 180-25, 180-26, 180-27, 180-28, 180-29, 180-30, 180-31, 180-32, 180-33, 180-34, 180-35, 180-36, 180-37, 180-38, 180-39, 180-40, 180-41, 180-42, 180-43, 180-44, 180-45, 180-46, 180-47, 180-48, 180-49, 180-50, 180-51, 180-52, 180-53, 180-54, 180-55, 180-56, 180-57, 180-58, 180-59, 180-60, 180-61, 180-62, 180-63, 180-64, 180-65, 180-66, 180-67, 180-68, 180-69, 180-70, 180-71, 180-72, 180-73, 180-74, 180-75, 180-76, 180-77, 180-78, 180-79, 180-80, 180-81, 180-82, 180-83, 180-84, 180-85, 180-86, 180-87, 180-88, 180-89, 180-90, 180-91, 180-92, 180-93, 180-94, 180-95, 180-96, 180-97, 181-1, 181-2, 181-3, 181-4, 181-5, 181-6, 181-7, 181-8, 181-9, 181-10, 181-11, 181-12, 181-13, 181-14, 181-15, 181-16, 181-17, 181-18, 181-19, 181-20, 181-21, 181-22, 181-23, 181-24, 181-25, 181-26, 181-27, 181-28, 181-29, 181-30, 181-31, 181-32, 181-33, 181-34, 181-35, 181-36, 181-37, 181-38, 181-39, 181-40, 181-41, 181-42, 181-43, 181-44, 181-45, 181-46, 181-47, 181-48, 181-49, 181-50, 181-51, 181-52, 181-53, 181-54, 181-55, 181-56, 181-57, 181-58, 181-59, 181-60, 181-61, 181-62, 181-63, 181-64, 181-65, 181-66, 181-67, 181-68, 181-69, 181-70, 181-71, 181-72, 181-73, 181-74, 181-75, 181-76, 181-77, 181-78, 181-79, 181-80, 181-81, 181-82, 181-83, 181-84, 181-85, 181-86, 181-87, 181-88, 181-89, 181-90, 181-91, 181-92, 181-93, 181-94, 181-95, 181-96, 181-97, 182-1, 182-2, 182-3, 182-4, 182-5, 182-6, 182-7, 182-8, 182-9, 182-10, 182-11, 182-12, 182-13, 182-14, 182-15, 182-16, 182-17, 182-18, 182-19, 182-20, 182-21, 182-22, 182-23, 182-24, 182-25, 182-26, 182-27, 182-28, 182-29, 182-30, 182-31, 182-32, 182-33, 182-34, 182-35, 182-36, 182-37, 182-38, 182-39, 18240, 182-41, 182-42, 182-43, 182-44, 182-45, 182-46, 182-47, 182-48, 182-49, 182-50, 182-51, 182-52; 182-53, 182-54, 182-55, 182-56, 182-57, 182-58, 182-59, 182-60, 182-61, 182-62, 182-63, 182-64, 182-65, 182-66, 182-67, 182-68, 182-69, 182-70, 182-71, 182-72, 182-73, 182-74, 182-75, 182-76, 182-77, 182-78, 182-79, 182-80, 182-81, 182-82, 182-83, 182-84, 182-85, 182-86, 182-87, 182-88, 182-89, 182-90, 182-91, 182-92, 182-93, 182-94, 182-95, 182-96, 182-97, 183-1, 183-2, 183-3, 183-4, 183-5, 183-6, 183-7, 183-8, 183-9, 183-10, 183-11, 183-12, 183-13, 183-14, 183-15, 183-16, 183-17, 183-18, 183-19, 183-20, 183-21, 183-22, 183-23, 183-24, 183-25, 183-26, 183-27, 183-28, 183-29, 183-30, 183-31, 183-32, 183-33, 183-34, 183-35, 183-36, 183-37, 183-38, 183-39, 183-40, 183-41, 183-42, 183-43, 183-44, 183-45, 183-46, 183-47, 183-48, 183-49, 183-50, 183-51, 183-52, 183-53, 183-54, 183-55, 183-56, 183-57, 183-58, 183-59, 183-60, 183-61, 183-62, 183-63, 183-64, 183-65, 183-66, 183-67, 183-38, 183-69, 183-70, 183-71, 183-72, 183-73, 183-74, 183-75, 183-76, 183-77, 183-78, 183-79, 183-80, 183-81, 183-82, 183-83, 183-84, 183-85, 183-86, 183-87, 183-88, 183-89, 183-90, 183-91, 183-92, 183-93, 183-94, 183-95, 183-96, 183-97, 184-1, 184-2, 184-3, 184-4, 184-5, 184-6, 184-7, 184-8, 184-9, 184-10, 184-11, 184-12, 184-13, 184-14, 184-15, 184-16, 184-17, 184-18, 184-19, 184-20, 184-21, 184-22, 184-23, 184-24, 184-25, 184-26, 184-27, 184-28, 184-29, 184-30, 184-31, 184-32, 184-33, 184-34, 184-35, 184-36, 184-37, 184-38, 184-39, 184-40, 184-41, 184-42, 184-43, 184-44, 184-45, 184-46, 184-47, 184-48, 184-49, 184-50, 184-51, 184-52, 184-53, 184-54, 184-55, 184-56, 184-57, 184-58, 184-59, 184-60, 184-61, 184-62, 184-63, 184-64, 184-65, 184-66, 184-67, 184-68, 184-69, 184-70, 184-71, 184-72, 184-73, 184-74, 184-75, 184-76, 184-77, 184-78, 184-79, 184-80, 184-81, 184-82, 184-83, 184-84, 184-85, 184-86, 184-87, 184-88, 184-89, 184-90, 184-91, 184-92, 184-93, 184-94, 184-95, 184-96, 184-97, 185-1, 185-2, 185-3, 185-4, 185-5, 185-6, 185-7, 185-8, 185-9, 185-10, 185-11, 185-12, 185-13, 185-14, 185-15, 185-16, 185-17, 185-18, 185-19, 185-20, 185-21, 185-22, 185-23, 185-24, 185-25, 185-26, 185-27, 185-28, 185-29, 185-30, 185-31, 185-32, 185-33, 185-34, 185-35, 185-36, 185-37, 185-38, 185-39, 185-40, 185-41, 185-42, 185-43, 185-44, 185-45, 185-46, 185-47, 185-48, 185-49, 185-50, 185-51, 185-52, 185-53, 185-54, 185-55, 185-56, 185-57, 185-58, 185-59, 185-60, 185-61, 185-62, 185-63, 185-64, 185-65, 185-66, 185-67, 185-68, 185-69, 185-70, 185-71, 185-72, 185-73, 185-74, 185-75, 185-76, 185-77, 185-78, 185-79, 185-80, 185-81, 185-82, 185-83, 185-84, 185-85, 185-86, 185-87, 185-88, 185-89, 185-90, 185-91, 185-92, 185-93, 185-94, 185-95, 185-96, 185-97, 186-1, 186-2, 186-3, 186-4, 186-5, 186-6, 186-7, 186-8, 186-9, 186-10, 186-11, 186-12, 186-13, 186-14, 186-15, 186-16, 186-17, 186-18, 186-19, 186-20, 186-21, 186-22, 186-23, 186-24, 186-25, 186-26, 186-27, 186-28, 186-29, 186-30, 186-31, 186-32, 186-33, 186-34, 186-35, 186-36, 186-37, 186-38, 186-39, 186-40, 186-41, 186-42, 186-43, 186-44, 186-45, 186-46, 186-47, 186-48, 186-49, 186-50, 186-51, 186-52, 186-53, 186-54, 186-55, 186-56, 186-57, 186-58, 186-59, 186-60, 186-61, 186-62, 186-63, 186-64, 186-65, 186-66, 186-67, 186-68, 186-69, 186-70, 186-71, 186-72, 186-73, 186-74, 186-75, 186-76, 186-77, 186-78, 186-79, 186-80, 186-81, 186-82, 186-83, 186-84, 186-85, 186-86, 186-87, 186-88, 186-89, 186-90, 186-91, 186-92, 186-93, 186-94, 186-95, 186-96, 186-97, 187-1, 187-2, 187-3, 187-4, 187-5, 187-6, 187-7, 187-8, 187-9, 187-10, 187-11, 187-12, 187-13, 187-14, 187-15, 187-16, 187-17, 187-18, 187-19, 187-20, 187-21, 187-22, 187-23, 187-24, 187-25, 187-26, 187-27, 187-28, 187-29, 187-30, 187-31, 187-32, 187-33, 187-34, 187-35, 187-36, 187-37, 187-38, 187-39, 187-40, 187-41, 187-42, 187-43, 187-44, 187-45, 187-46, 187-47, 187-48, 187-49, 187-50, 187-51, 187-52, 187-53, 187-54, 187-55, 187-56, 187-57, 187-58, 187-59, 187-60, 187-61, 187-62, 187-63, 187-64, 187-65, 187-66, 187-67, 187-68, 187-69, 187-70, 187-71, 187-72, 187-73, 187-74, 187-75, 187-76, 187-77, 187-78, 187-79, 187-80, 187-81, 187-82, 187-83, 187-84, 187-85, 187-86, 187-87, 187-88, 187-89, 187-90, 187-91, 187-92, 187-93, 187-94, 187-95, 187-96, 187-97, 188-1, 188-2, 188-3, 188-4, 188-5, 188-6, 188-7, 188-8, 188-9, 188-10, 188-11, 188-12, 188-13, 188-14, 188-15, 188-16, 188-17, 188-18, 188-19, 188-20, 188-21, 188-22, 188-23, 188-24, 188-25, 188-26, 188-27, 188-28, 188-29, 188-30, 188-31, 188-32, 188-33, 188-34, 188-35, 188-36, 188-37, 188-38, 188-39, 188-40, 188-41, 188-42, 188-43, 188-44, 188-45, 188-46, 188-47, 188-48, 188-49, 188-50, 188-51, 188-52, 188-53, 188-54, 188-55, 188-56, 188-57, 188-58, 188-59, 188-60, 188-61, 188-62, 188-63, 188-64, 188-65, 188-66, 188-67, 188-68, 188-69, 188-70, 188-71, 188-72, 188-73, 188-74, 188-75, 188-76, 188-77, 188-78, 188-79, 188-80, 188-81, 188-82, 188-83, 188-84, 188-85, 188-86, 188-87, 188-88, 188-89, 188-90, 188-91, 188-92, 188-93, 188-94, 188-95, 188-96, 188-97, 189-1, 189-2, 189-3, 189-4, 189-5, 189-6, 189-7, 189-8, 189-9, 189-10, 189-11, 189-12, 189-13, 189-14, 189-15, 189-16, 189-17, 189-18, 189-19, 189-20, 189-21, 189-22, 189-23, 189-24, 189-25, 189-26, 189-27, 189-28, 189-29, 189-30, 189-31, 189-32, 189-33, 189-34, 189-35, 189-36, 189-37, 189-38, 189-39, 189-40, 189-41, 189-42, 189-43, 189-44, 189-45, 189-46, 189-47, 189-48, 189-49, 189-50, 189-51, 189-52, 189-53, 189-54, 189-55, 189-56, 189-57, 189-58, 189-59, 189-60, 189-61, 189-62, 189-63, 189-64, 189-65, 189-66, 189-67, 189-68, 189-69, 189-70, 189-71, 189-72, 189-73, 189-74, 189-75, 189-76, 189-77, 189-78, 189-79, 189-80, 189-81, 189-82, 189-83, 189-84, 189-85, 189-86, 189-87, 189-88, 189-89, 189-90, 189-91, 189-92, 189-93, 189-94, 189-95, 189-96, 189-97, 190-1, 190-2, 190-3, 190-4, 190-5, 190-6, 190-7, 190-8, 190-9, 190-10, 190-11, 190-12, 190-13, 190-14, 190-15, 190-16, 190-17, 190-18, 190-19, 190-20, 190-21, 190-22, 190-23, 190-24, 190-25, 190-26, 190-27, 190-28, 190-29, 190-30, 190-31, 190-32, 190-33, 190-34, 190-35, 190-36, 190-37, 190-38, 190-39, 190-40, 190-41, 190-42, 190-43, 190-44, 190-45, 190-46, 190-47, 190-48, 190-49, 190-50, 190-51, 190-52, 190-53, 190-54, 190-55, 190-56, 190-57, 190-58, 190-59, 190-60, 190-61, 190-62, 190-63, 190-64, 190-65, 190-66, 190-67, 190-68, 190-69, 190-70, 190-71, 190-72, 190-73, 190-74, 190-75, 190-76, 190-77, 190-78, 190-79, 190-80, 190-81, 190-82, 190-83, 190-84, 190-85, 190-86, 190-87, 190-88, 190-89, 190-90, 190-91, 190-92, 190-93, 190-94, 190-95, 190-96, 190-97, 191-1, 191-2, 191-3, 191-4, 191-5, 191-6, 191-7, 191-8, 191-9, 191-10, 191-11, 191-12, 191-13, 191-14, 191-15, 191-16, 191-17, 191-18, 191-19, 191-20, 191-21, 191-22, 191-23, 191-24, 191-25, 191-26, 191-27, 191-28, 191-29, 191-30, 191-31, 191-32, 191-33, 191-34, 191-35, 191-36, 191-37, 191-38, 191-39, 191-40, 191-41, 191-42, 191-43, 191-44, 191-45, 191-46, 191-47, 191-48, 191-49, 191-50, 191-51, 191-52, 191-53, 191-54, 191-55, 191-56, 191-57, 191-58, 191-59, 191-60, 191-61, 191-62, 191-63, 191-64, 191-65, 191-66, 191-67, 191-68, 191-69, 191-70, 191-71, 191-72, 191-73, 191-74, 191-75, 191-76, 191-77, 191-78, 191-79, 191-80, 191-81, 191-82, 191-83, 191-84, 191-85, 191-86, 191-87, 191-88, 191-89, 191-90, 191-91, 191-92, 191-93, 191-94, 191-95, 191-96, 191-97, 192-1, 192-2, 192-3, 192-4, 192-5, 192-6, 192-7, 192-8, 192-9, 192-10, 192-11, 192-12, 192-13, 192-14, 192-15, 192-16, 192-17, 192-18, 192-19, 192-20, 192-21, 192-22, 192-23, 192-24, 192-25, 192-26, 192-27, 192-28, 192-29, 192-30, 192-31, 192-32, 192-33, 192-34, 192-35, 192-36, 192-37, 192-38, 192-39, 192-40, 192-41, 192-42, 192-43, 192-44, 192-45, 192-46, 192-47, 192-48, 192-49, 192-50, 192-51, 192-52, 192-53, 192-54, 192-55, 192-56, 192-57, 192-58, 192-59, 192-60, 192-61, 192-62, 192-63, 192-64, 192-65, 192-66, 192-67, 192-68, 192-69, 192-70, 192-71, 192-72, 192-73, 192-74, 192-75, 192-76, 192-77, 192-78, 192-79, 192-80, 192-81, 192-82, 192-83, 192-84, 192-85, 192-86, 192-87, 192-88, 192-89, 192-90, 192-91, 192-92, 192-93, 192-94, 192-95, 192-96, 192-97, 193-1, 193-2, 193-3, 193-4, 193-5, 193-6, 193-7, 193-8, 193-9, 193-10, 193-11, 193-12, 193-13, 193-14, 193-15, 193-16, 193-17, 193-18, 193-19, 193-20, 193-21, 193-22, 193-23, 193-24, 193-25, 193-26, 193-27, 193-28, 193-29, 193-30, 193-31, 193-32, 193-33, 193-34, 193-35, 193-36, 193-37, 193-38, 193-39, 193-40, 193-41, 193-42, 193-43, 193-44, 193-45, 193-46, 193-47, 193-48, 193-49, 193-50, 193-51, 193-52, 193-53, 193-54, 193-55, 193-56, 193-57, 193-58, 193-59, 193-60, 193-61, 193-62, 193-63, 193-64, 193-65, 193-66, 193-67, 193-68, 193-69, 193-70, 193-71, 193-72, 193-73, 193-74, 193-75, 193-76, 193-77, 193-78, 193-79, 193-80, 193-81, 193-82, 193-83, 193-84, 193-85, 193-86, 193-87, 193-88, 193-89, 193-90, 193-91, 193-92, 193-93, 193-94, 193-95, 193-96, 193-97, 194-1, 194-2, 194-3, 194-4, 194-5, 194-6, 194-7, 194-8, 194-9, 194-10, 194-11, 194-12, 194-13, 194-14, 194-15, 194-16, 194-17, 194-18, 194-19, 194-20, 194-21, 194-22, 194-23, 194-24, 194-25, 194-26, 194-27, 194-28, 194-29, 194-30, 194-31, 194-32, 194-33, 194-34, 194-35, 194-36, 194-37, 194-38, 194-39, 194-40, 194-41, 194-42, 194-43, 194-42, 194-45, 194-46, 194-47, 194-48, 194-49, 194-50, 194-51, 194-52, 194-53, 194-54, 194-55, 194-56, 194-57, 194-58, 194-59, 194-60, 194-61, 194-62, 194-63, 194-64, 194-65, 194-66, 194-67, 194-68, 194-69, 194-70, 194-71, 194-72, 194-73, 194-74, 194-75, 194-76, 194-77, 194-78, 194-79, 194-80, 194-81, 194-82, 194-83, 194-84, 194-85, 194-86, 194-87, 194-88, 194-89, 194-90, 194-91, 194-92, 194-93, 194-94, 194-95, 194-96, 194-97, 195-1, 195-2, 195-3, 195-4, 195-5, 195-6 195-7, 195-8, 195-9, 195-10, 195-11, 195-12, 195-13, 195-14, 195-15, 195-16, 195-17, 195-18, 195-19, 195-20, 195-21, 195-22, 195-23, 195-24, 195-25, 195-26, 195-27, 195-28, 195-29, 195-30, 195-31, 195-32, 195-33, 195-34, 195-35, 195-36, 195-37, 195-38, 195-39, 195-40, 195-41, 195-42, 195-43, 195-44, 195-45, 195-46, 195-47, 195-48, 195-49, 195-50, 195-51, 195-52, 195-53, 195-54, 195-55, 195-56, 195-57, 195-58, 195-59, 195-60, 195-61, 195-62, 195-63, 195-64, 195-65, 195-66, 195-67, 195-68, 195-69, 195-70, 195-71, 195-72, 195-73, 195-74, 195-75, 195-76, 195-77, 195-78, 195-79, 195-80, 195-81, 195-82, 195-83, 195-84, 195-85, 195-86, 195-87, 195-88, 195-89, 195-90, 195-91, 195-92, 195-93, 195-94, 195-95, 195-96, 195-97, 196-1, 196-2, 196-3, 196-4, 196-5, 196-6, 196-7, 196-8, 196-9, 196-10, 196-11, 196-12, 196-13, 196-14, 196-15, 196-16, 196-17, 196-18, 196-19, 196-20, 196-21, 196-22, 196-23, 196-24, 196-25, 196-26, 196-27, 196-28, 196-29, 196-30, 196-31, 196-32, 196-33, 196-34, 196-35, 196-36, 196-37, 196-38, 196-39, 196-40, 196-41, 196-42, 196-43, 196-44, 196-45, 196-46, 196-47, 196-48, 196-49, 196-50, 196-51, 196-52, 196-53, 196-54, 196-55, 196-56, 196-57, 196-58, 196-59, 196-60, 196-61, 196-62, 196-63, 196-64, 196-65, 196-66, 196-67, 196-68, 196-69, 196-70, 196-71, 196-72, 196-73, 196-74, 196-75, 196-76, 196-77, 196-78, 196-79, 196-80, 196-81, 196-82, 196-83, 196-84, 196-85, 196-86, 196-87, 196-88, 196-89, 196-90, 196-91, 196-92, 196-93, 196-94, 196-95, 196-96, 196-97, 197-1, 197-2, 197-3, 197-4, 197-5, 197-6, 197-7, 197-8, 197-9, 197-10, 197-11, 197-12, 197-13, 197-14, 197-15, 197-16, 197-17, 197-18, 197-19, 197-20, 197-21, 197-22, 197-23, 197-24, 197-25, 197-26, 197-27, 197-28, 197-29, 197-30, 197-31, 197-32, 197-33, 197-34, 197-35, 197-36, 197-37, 197-38, 197-39, 197-40, 197-41, 197-42, 197-43, 197-44, 197-45, 197-46, 197-47, 197-48, 197-49, 197-50, 197-51, 197-52, 197-53, 197-54, 197-55, 197-56, 197-57, 197-58, 197-59, 197-60, 197-61, 197-62, 197-63, 197-64, 197-65, 197-66, 197-67, 197-68, 197-69, 197-70, 197-71, 197-72, 197-73, 197-74, 197-75, 197-76, 197-77, 197-78, 197-79, 197-80, 197-81, 197-82, 197-83, 197-84, 197-85, 197-86, 197-87, 197-88, 197-89, 197-90, 197-91, 197-92, 197-93, 197-94, 197-95, 197-96, 197-97, 198-1, 198-2, 198-3, 198-4, 198-5, 198-6, 198-7, 198-8, 198-9, 198-10, 198-11, 198-12, 198-13, 198-14, 198-15, 198-16, 198-17, 198-18, 198-19, 198-20, 198-21, 198-22, 198-23, 198-24, 198-25, 198-26, 198-27, 198-28, 198-29, 198-30, 198-31, 198-32, 198-33, 198-34, 198-35, 198-36, 198-37, 198-38, 198-39, 198-40, 198-41, 198-42, 198-43, 198-44, 198-45, 198-46, 198-47, 198-48, 198-49, 198-50, 198-51, 198-52, 198-53, 198-54, 198-55, 198-56, 198-57, 198-58, 198-59, 198-60, 198-61, 198-62, 198-63, 198-64, 198-65, 198-66, 198-67, 198-68, 198-69, 198-70, 198-71, 198-72, 198-73, 198-74, 198-75, 198-76, 198-77, 198-78, 198-79, 198-80, 198-81, 198-82, 198-83, 198-84, 198-85, 198-86, 198-87, 198-88, 198-89, 198-90, 198-91, 198-92, 198-93, 198-94, 198-95, 198-96, 198-97, 199-1, 199-2, 199-3, 199-4, 199-5, 199-6, 199-7, 199-8, 199-9, 199-10, 199-11, 199-12, 199-13, 199-14, 199-15, 199-16, 199-17, 199-18, 199-19, 199-20, 199-21, 199-22, 199-23, 199-24, 199-25, 199-26, 199-27, 199-28, 199-29, 199-30, 199-31, 199-32, 199-33, 199-34, 199-35, 199-36, 199-37, 199-38, 199-39, 199-40, 199-41, 199-42, 199-43, 199-44, 199-45, 199-46, 199-47, 199-48, 199-49, 199-50, 199-51, 199-52, 199-53, 199-54, 199-55, 199-56, 199-57, 199-58, 199-59, 199-60, 199-61, 199-62, 199-63, 199-64, 199-65, 199-66, 199-67, 199-68, 199-69, 199-70, 199-71, 199-72, 199-73, 199-74, 199-75, 199-76, 199-77, 199-78, 199-79, 199-80, 199-81, 199-82, 199-83, 199-84, 199-85, 199-86, 199-87, 199-88, 199-89, 199-90, 199-91, 199-92, 199-93, 199-94, 199-95, 199-96, 199-97, 200-1, 200-2, 200-3, 200-4, 200-5, 200-6, 200-7, 200-8, 200-9, 200-10, 200-11, 200-12, 200-13, 200-14, 200-15, 200-16, 200-17, 200-18, 200-19, 200-20, 200-21, 200-22, 200-23, 200-24, 200-25, 200-26, 200-27, 200-28, 200-29, 200-30, 200-31, 200-32, 200-33, 200-34, 200-35, 200-36, 200-37, 200-38, 200-39, 200-40, 200-41, 200-42, 200-43, 200-44, 200-45, 200-46, 200-47, 200-48, 200-49, 200-50, 200-51, 200-52, 200-53, 200-54, 200-55, 200-56, 200-57, 200-58, 200-59, 200-60, 200-61, 200-62, 200-63, 200-64, 200-65, 200-66, 200-67, 200-68, 200-69, 200-70, 200-71, 200-72, 200-73, 200-74, 200-75, 200-76, 200-77, 200-78, 200-79, 200-80, 200-81, 200-82, 200-83, 200-84, 200-85, 200-86, 200-87, 200-88, 200-89, 200-90, 200-91, 200-92, 200-93, 200-94, 200-95, 200-96, 200-97, 201-1, 201-2, 201-3, 201-4, 201-5, 201-6, 201-7, 201-8, 201-9, 201-10, 201-11, 201-12, 201-13, 201-14, 201-15, 201-16, 201-17, 201-18, 201-19, 201-20, 201-21, 201-22, 201-23, 201-24, 201-25, 201-26, 201-27, 201-28, 201-29, 201-30, 201-31, 201-32, 201-33, 201-34, 201-35, 201-36, 201-37, 201-38, 201-39, 201-40, 201-41, 201-42, 201-43, 201-44, 201-45, 201-46, 201-47, 201-48, 201-49, 201-50, 201-51, 201-52, 201-53, 201-54, 201-55, 201-56, 201-57, 201-58, 201-59, 201-60, 201-61, 201-62, 201-63, 201-64, 201-65, 201-66, 201-67, 201-68, 201-69, 201-70, 201-71, 201-72, 201-73, 201-74, 201-75, 201-76, 201-77, 201-78, 201-79, 201-80, 201-81, 201-82, 201-83, 201-84, 201-85, 201-86, 201-87, 201-88, 201-89, 201-90, 201-91, 201-92, 201-93, 201-94, 201-95, 201-96, 201-97, 202-1, 202-2, 202-3, 202-4, 202-5, 202-6, 202-7, 202-8, 202-9, 202-10, 202-11, 202-12, 202-13, 202-14, 202-15, 202-16, 202-17, 202-18, 202-19, 202-20, 202-21, 202-22, 202-23, 202-24, 202-25, 202-26, 202-27, 202-28, 202-29, 202-30, 202-31, 202-32, 202-33, 202-34, 202-35, 202-36, 202-37, 202-38, 202-39, 202-40, 202-41, 202-42, 202-43, 202-44, 202-45, 202-46, 202-47, 202-48, 202-49, 202-50, 202-51, 202-52, 202-53, 202-54, 202-55, 202-56, 202-57, 202-58, 202-59, 202-60, 202-61, 202-62, 202-63, 202-64, 202-65, 202-66, 202-67, 202-68, 202-69, 202-70, 202-71, 202-72, 202-73, 202-74, 202-75, 202-76, 202-77, 202-78, 202-79, 202-80, 202-81, 202-82; 202-83, 202-84, 202-85, 202-86, 202-87, 202-88, 202-89, 202-90, 202-91, 202-92, 202-93, 202-94, 202-95, 202-96, 202-97, 203-1, 203-2, 203-3, 203-4, 203-5, 203-6, 203-7, 203-8, 203-9, 203-10, 203-11, 203-12, 203-13, 203-14, 203-15, 203-16, 203-17, 203-18, 203-19, 203-20, 203-21, 203-22, 203-23, 203-24, 203-25, 203-26, 203-27, 203-28, 203-29, 203-30, 203-31, 203-32, 203-33, 203-34, 203-35, 203-36, 203-37, 203-38, 203-39, 203-40, 203-41, 203-42, 203-43, 203-44, 203-45, 203-46, 203-47, 203-48, 203-49, 203-50, 203-51, 203-52, 203-53, 203-54, 203-55, 203-56, 203-57, 203-58, 203-59, 203-60, 203-61, 203-62, 203-63, 203-64, 203-65, 203-66, 203-67, 203-68, 203-69, 203-70, 203-71, 203-72, 203-73, 203-74, 203-75, 203-76, 203-77, 203-78, 203-79, 203-80, 203-81, 203-82, 203-83, 203-84, 203-85, 203-86, 203-87, 203-88, 203-89, 203-90, 203-91, 203-92, 203-93, 203-94, 203-95, 203-96, 203-97, 204-1, 204-2, 204-3, 204-4, 204-5, 204-6, 204-7, 204-8, 204-9, 204-10, 204-11, 204-12, 204-13, 204-14, 204-15, 204-16, 204-17, 204-18, 204-19, 204-20, 204-21, 204-22, 204-23, 204-24, 204-25, 204-26, 204-27, 204-28, 204-29, 204-30, 204-31, 204-32, 204-33, 204-34, 204-35, 204-36, 204-37, 204-38, 204-39, 204-40, 204-41, 204-42, 204-43, 204-44, 204-45, 204-46, 204-47, 204-48, 204-49, 204-50, 204-51, 204-52, 204-53, 204-54, 204-55, 204-56, 204-57, 204-58, 204-59, 204-60, 204-61, 204-62, 204-63, 204-64, 204-65, 204-66, 204-67, 204-68, 204-69, 204-70, 204-71, 204-72, 204-73, 204-74, 204-75, 204-76, 204-77, 204-78, 204-79, 204-80, 204-81, 204-82, 204-83, 204-84, 204-85, 204-86, 204-87, 204-88, 204-89, 204-90, 204-91, 204-92, 204-93, 204-94, 204-95, 204-96, 204-97, 205-1, 205-2, 205-3, 205-4, 205-5, 205-6, 205-7, 205-8, 205-9, 205-10, 205-11, 205-12, 205-13, 205-14, 205-15, 205-16, 205-17, 205-18, 205-19, 205-20, 205-21, 205-22, 205-23, 205-24, 205-25, 205-26, 205-27, 205-28, 205-29, 205-30, 205-31, 205-32, 205-33, 205-34, 205-35, 205-36, 205-37, 205-38, 205-39, 205-40, 205-41, 205-42, 205-43, 205-44, 205-45, 205-46, 205-47, 205-48, 205-49, 205-50, 205-51, 205-52, 205-53, 205-54, 205-55, 205-56, 205-57, 205-58, 205-59, 205-60, 205-61, 205-62, 205-63, 205-64, 205-65, 205-66, 205-67, 205-68, 205-69, 205-70, 205-71, 205-72, 205-73, 205-74, 205-75, 205-76, 205-77, 205-78, 205-79, 205-80, 205-81, 205-82, 205-83, 205-84, 205-85, 205-86, 205-87, 205-88, 205-89, 205-90, 205-91, 205-92, 205-93, 205-94, 205-95, 205-96, 205-97, 206-1, 206-2, 206-3, 206-4, 206-5, 206-6, 206-7, 206-8, 206-9, 206-10, 206-11, 206-12, 206-13, 206-14, 206-15, 206-16, 206-17, 206-18, 206-19, 206-20, 206-21, 206-22, 206-23, 206-24, 206-25, 206-26, 206-27, 206-28, 206-29, 206-30, 206-31, 206-32, 206-33, 206-34, 206-35, 206-36, 206-37, 206-38, 206-39, 206-40, 206-41, 206-42, 206-43, 206-44, 206-45, 206-46, 206-47, 206-48, 206-49, 206-50, 206-51, 206-52, 206-53, 206-54, 206-55, 206-56, 206-57, 206-58, 206-59, 206-60, 206-61, 206-62, 206-63, 206-64, 206-65, 206-66, 206-67, 206-68, 206-69, 206-70, 206-71, 206-72, 206-73, 206-74, 206-75, 206-76, 206-77, 206-78, 206-79, 206-80, 206-81, 206-82, 206-83, 206-84, 206-85, 206-86, 206-87, 206-88, 206-89, 206-90, 206-91, 206-92, 206-93, 206-94, 206-95, 206-96, 206-97, 207-1, 207-2, 207-3, 207-4, 207-5, 207-6, 207-7, 207-8, 207-9, 207-10, 207-11, 207-12, 207-13, 207-14, 207-15, 207-16, 207-17, 207-18, 207-19, 207-20, 207-21, 207-22, 207-23, 207-24, 207-25, 207-26, 207-27, 207-28, 207-29, 207-30, 207-31, 207-32, 207-33, 207-34, 207-35, 207-36, 207-37, 207-38, 207-39, 207-40, 207-41, 207-42, 207-43, 207-44, 207-45, 207-46, 207-47, 207-48, 207-49, 207-50, 207-51, 207-52, 207-53, 207-54, 207-55, 207-56, 207-57, 207-58, 207-59, 207-60, 207-61, 207-62, 207-63, 207-64, 207-65, 207-66, 207-67, 207-68, 207-69, 207-70, 207-71, 207-72, 207-73, 207-74, 207-75, 207-76, 207-77, 207-78, 207-79, 207-80, 207-81, 207-82, 207-83, 207-84, 207-85, 207-86, 207-87, 207-88, 207-89, 207-90, 207-91, 207-92, 207-93, 207-94, 207-95, 207-96, 207-97, 208-1, 208-2, 208-3, 208-4, 208-5, 208-6, 208-7, 208-8, 208-9, 208-10, 208-11, 208-12, 208-13, 208-14, 208-15, 208-16, 208-17, 208-18, 208-19, 208-20, 208-21, 208-22, 208-23, 208-24, 208-25, 208-26, 208-27, 208-28, 208-29, 208-30, 208-31, 208-32, 208-33, 208-34, 208-35, 208-36, 208-37, 208-38, 208-39, 208-40, 208-41, 208-42, 208-43, 208-44, 208-45, 208-46, 208-47, 208-48, 208-49, 208-50, 208-51, 208-52, 208-53, 208-54, 208-55, 208-56, 208-57, 208-58, 208-59, 208-60, 208-61, 208-62, 208-63, 208-64, 208-65, 208-66, 208-67, 208-68, 208-69, 208-70, 208-71, 208-72, 208-73, 208-74, 208-75, 208-76, 208-77, 208-78, 208-79, 208-80, 208-81, 208-82, 208-83, 208-84, 208-85, 208-86, 208-87, 208-88, 208-89, 208-90, 208-91, 208-92, 208-93, 208-94, 208-95, 208-96, 208-97, 209-1, 209-2, 209-3, 209-4, 209-5, 209-6, 209-7, 209-8, 209-9, 209-10, 209-11, 209-12, 209-13, 209-14, 209-15, 209-16, 209-17, 209-18, 209-19, 209-20, 209-21, 209-22, 209-23, 209-24, 209-25, 209-26, 209-27, 209-28, 209-29, 209-30, 209-31, 209-32, 209-33, 209-34, 209-35, 209-36, 209-37, 209-38, 209-39, 209-40, 209-41, 209-42, 209-43, 209-44, 209-45, 209-46, 209-47, 209-48, 209-49, 209-50, 209-51, 209-52, 209-53, 209-54, 209-55, 209-56, 209-57, 209-58, 209-59, 209-60, 209-61, 209-62, 209-63, 209-64, 209-65, 209-66, 209-67, 209-68, 209-69, 209-70, 209-71, 209-72, 209-73, 209-74, 209-75, 209-76, 209-77, 209-78, 209-79, 209-80, 209-81, 209-82, 209-83, 209-84, 209-85, 209-86, 209-87, 209-88, 209-89, 209-90, 209-91, 209-92, 209-93, 209-94, 209-95, 209-96, 209-97, 210-1, 210-2, 210-3, 210-4, 210-5, 210-6, 210-7, 210-8, 210-9, 210-10, 210-11, 210-12, 210-13, 210-14, 210-15, 210-16, 210-17, 210-18, 210-19, 210-20, 210-21, 210-22, 210-23, 210-24, 210-25, 210-26, 210-27, 210-28, 210-29, 210-30, 210-31, 210-32, 210-33, 210-34, 210-35, 210-36, 210-37, 210-38, 210-39, 210-40, 210-41, 210-42, 210-43, 210-44, 210-45, 210-46, 210-47, 210-48, 210-49, 210-50, 210-51, 210-52, 210-53, 210-54, 210-55, 210-56, 210-57, 210-58, 210-59, 210-60, 210-61, 210-62, 210-63, 210-64, 210-65, 210-66, 210-67, 210-68, 210-69, 210-70, 210-71, 210-72, 210-73, 210-74, 210-75, 210-76, 210-77, 210-78, 210-79, 210-80, 210-81, 210-82, 210-83, 210-84, 210-85, 210-86, 210-87, 210-88, 210-89, 210-90, 210-91, 210-92, 210-93, 210-94, 210-95, 210-96, 210-97, 211-1, 211-2, 211-3, 211-4, 211-5, 211-6, 211-7, 211-8, 211-9, 211-10, 211-11, 211-12, 211-13, 211-14, 211-15, 211-16, 211-17, 211-18, 211-19, 211-20, 211-21, 211-22, 211-23, 211-24, 211-25, 211-26, 211-27, 211-28, 211-29, 211-30, 211-31, 211-32, 211-33, 211-34, 211-35, 211-36, 211-37, 211-38, 211-39, 211-40, 211-41, 211-42, 211-43, 211-44, 211-45, 211-46, 211-47, 211-

48, 211-49, 211-50, 211-51, 211-52, 211-53, 211-54, 211-55, 211-56, 211-57, 211-58, 211-59, 211-60, 211-61, 211-62, 211-63, 211-64, 211-65, 211-66, 211-67, 211-68, 211-69, 211-70, 211-71, 211-72, 211-73, 211-74, 211-75, 211-76, 211-77, 211-78, 211-79, 211-80, 211-81, 211-82, 211-83, 211-84, 211-85, 211-86, 211-87, 211-88, 211-89, 211-90, 211-91, 211-92, 211-93, 211-94, 211-95, 211-96, 211-97, 212-1, 212-2, 212-3, 212-4, 212-5, 212-6, 212-7, 212-8, 212-9, 212-10, 212-11, 212-12, 212-13, 212-14, 212-15, 212-16, 212-17, 212-18, 212-19, 212-20, 212-21, 212-22, 212-23, 212-24, 212-25, 212-26, 212-27, 212-28, 212-29, 212-30, 212-31, 212-32, 212-33, 212-34, 212-35, 212-36, 212-37, 212-38, 212-39, 212-40, 212-41, 212-42, 212-43, 212-44, 212-45, 212-46, 212-47, 212-48, 212-49, 212-50, 212-51, 212-52, 212-53, 212-54, 212-55, 212-56, 212-57, 212-58, 212-59, 212-60, 212-61, 212-62, 212-63, 212-64, 212-65, 212-66, 212-67, 212-68, 212-69, 212-70, 212-71, 212-72, 212-73, 212-74, 212-75, 212-76, 212-77, 212-78, 212-79, 212-80, 212-81, 212-82, 212-83, 212-84, 212-85, 212-86, 212-87, 212-88, 212-89, 212-90, 212-91, 212-92, 212-93, 212-94, 212-95, 212-96, 212-97, 213-1, 213-2, 213-3, 213-4, 213-5, 213-6, 213-7, 213-8, 213-9, 213-10, 213-11, 213-12, 213-13, 213-14, 213-15, 213-16, 213-17, 213-18, 213-19, 213-20, 213-21, 213-22, 213-23, 213-24, 213-25, 213-26, 213-27, 213-28, 213-29, 213-30, 213-31, 213-32, 213-33, 213-34, 213-35, 213-36, 213-37, 213-38, 213-39, 213-40, 213-41, 213-42, 213-43, 213-44, 213-45, 213-46, 213-47, 213-48, 213-49, 213-50, 213-51, 213-52, 213-53, 213-54, 213-55, 213-56, 213-57, 213-58, 213-59, 213-60, 213-61, 213-62, 213-63, 213-64, 213-65, 213-66, 213-67, 213-68, 213-69, 213-70, 213-71, 213-72, 213-73, 213-74, 213-75, 213-76, 213-77, 213-78, 213-79, 213-80, 213-81, 213-82, 213-83, 213-84, 213-85, 213-86, 213-87, 213-88, 213-89, 213-90, 213-91, 213-92, 213-93, 213-94, 213-95, 213-96, 213-97, 214-1, 214-2, 214-3, 214-4, 214-5, 214-6, 214-7, 214-8, 214-9, 214-10, 214-11, 214-12, 214-13, 214-14, 214-15, 214-16, 214-17, 214-18, 214-19, 214-20, 214-21, 214-22, 214-23, 214-24, 214-25, 214-26, 214-27, 214-28, 214-29, 214-30, 214-31, 214-32, 214-33, 214-34, 214-35, 214-36, 214-37, 214-38, 214-39, 214-40, 214-41, 214-42, 214-43, 214-44, 214-45, 214-46, 214-47, 214-48, 214-49, 214-50, 214-51, 214-52, 214-53, 214-54, 214-55, 214-56, 214-57, 214-58, 214-59, 214-60, 214-61, 214-62, 214-63, 214-64, 214-65, 214-66, 214-67, 214-68, 214-69, 214-70, 214-71, 214-72, 214-73, 214-74, 214-75, 214-76, 214-77, 214-78, 214-79, 214-80, 214-81, 214-82, 214-83, 214-84, 214-85, 214-86, 214-87, 214-88, 214-89, 214-90, 214-91, 214-92, 214-93, 214-94, 214-95, 214-96, 214-97, 215-1, 215-2, 215-3, 215-4, 215-5, 215-6, 215-7, 215-8, 215-9, 215-10, 215-11, 215-12, 215-13, 215-14, 215-15, 215-16, 215-17, 215-18, 215-19, 215-20, 215-21, 215-22, 215-23, 215-24, 215-25, 215-26, 215-27, 215-28, 215-29, 215-30, 215-31, 215-32, 215-33, 215-34, 215-35, 215-36, 215-37, 215-38, 215-39, 215-40, 215-41, 215-42, 215-43, 215-44, 215-45, 215-46, 215-47, 215-48, 215-49, 215-50, 215-51, 215-52, 215-53, 215-54, 215-55, 215-56, 215-57, 215-58, 215-59, 215-60, 215-61, 215-62, 215-63, 215-64, 215-65, 215-66, 215-67, 215-68, 215-69, 215-70, 215-71, 215-72, 215-73, 215-74, 215-75, 215-76, 215-77, 215-78, 215-79, 215-80, 215-81, 215-82, 215-83, 215-84, 215-85, 215-86, 215-87, 215-88, 215-89, 215-90, 215-91, 215-92, 215-93, 215-94, 215-95, 215-96, 215-97, 216-1, 216-2, 216-3, 216-4, 216-5, 216-6, 216-7, 216-8, 216-9, 216-10, 216-11, 216-12, 216-13, 216-14, 216-15, 216-16, 216-17, 216-18, 216-19, 216-20, 216-21, 216-22, 216-23, 216-24, 216-25, 216-26, 216-27, 216-28, 216-29, 216-30, 216-31, 216-32, 216-33, 216-34, 216-35, 216-36, 216-37, 216-38, 216-39, 216-40, 216-41, 216-42, 216-43, 216-44, 216-45, 216-46, 216-47, 216-48, 216-49, 216-50, 216-51, 216-52, 216-53, 216-54, 216-55, 216-56, 216-57, 216-58, 216-59, 216-60, 216-61, 216-62, 216-63, 216-64, 216-65, 216-66, 216-67, 216-68, 216-69, 216-70, 216-71, 216-72, 216-73, 216-74, 216-75, 216-76, 216-77, 216-78, 216-79, 216-80, 216-81, 216-82, 216-83, 216-84, 216-85, 216-86, 216-87, 216-88, 216-89, 216-90, 216-91, 16-92, 216-93, 216-94, 216-95, 216-96, 216-97, 217-1, 217-2, 217-3, 217-4, 217-5, 217-6, 217-7, 217-8, 217-9, 217-10, 217-11, 217-12, 217-13, 217-14, 217-15, 217-16, 217-17, 217-18, 217-19, 217-20, 217-21, 217-22, 217-23, 217-24, 217-25, 217-26, 217-27, 217-28, 217-29, 217-30, 217-31, 217-32, 217-33, 217-34, 217-35, 217-36, 217-37, 217-38, 217-39, 217-40, 217-41, 217-42, 217-43, 217-44, 217-45, 217-46, 217-47, 217-48, 217-49, 217-50, 217-51, 217-52, 217-53, 217-54, 217-55, 217-56, 217-57, 217-58, 217-59, 217-60, 217-61, 217-62, 217-63, 217-64, 217-65, 217-66, 217-67, 217-68, 217-69, 217-70, 217-71, 217-72, 217-73, 217-74, 217-75, 217-76, 217-77, 217-78, 217-79, 217-80, 217-81, 217-82, 217-83, 217-84, 217-85, 217-86, 217-87, 217-88, 217-89, 217-90, 217-91, 217-92, 217-93, 217-94, 217-95, 217-96, 217-97, 218-1, 218-2, 218-3, 218-4, 218-5, 218-6, 218-7, 218-8, 218-9, 218-10, 218-11, 218-12, 218-13, 218-14, 218-15, 218-16, 218-17, 218-18, 218-19, 218-20, 218-21, 218-22, 218-23, 218-24, 218-25, 218-26, 218-27, 218-28, 218-29, 218-30, 218-31, 218-32, 218-33, 218-34, 218-35, 218-36, 218-37, 218-38, 218-39, 218-40, 218-41, 218-42, 218-43, 218-44, 218-45, 218-46, 218-47, 218-48, 218-49, 218-50, 218-51, 218-52, 218-53, 218-54, 218-55, 218-56, 218-57, 218-58, 218-59, 218-60, 218-61, 218-62, 218-63, 218-64, 218-65, 218-66, 218-67, 218-68, 218-69, 218-70, 218-71, 218-72, 218-73, 218-74, 218-75, 218-76, 218-77, 218-78, 218-79, 218-80, 218-81, 218-82, 218-83, 218-84, 218-85, 218-86, 218-87, 218-88, 218-89, 218-90, 218-91, 218-92, 218-93, 218-94, 218-95, 218-96, 218-97, 219-1, 219-2, 219-3, 219-4, 219-5, 219-6, 219-7, 219-8, 219-9, 219-10, 219-11, 219-12, 219-13, 219-14, 219-15, 219-16, 219-17, 219-18, 219-19, 219-20, 219-21, 219-22, 219-23, 219-24, 219-25, 219-26, 219-27, 219-28, 219-29, 219-30, 219-31, 219-32, 219-33, 219-34, 219-35, 219-36, 219-37, 219-38, 219-39, 219-40, 219-41, 219-42, 219-43, 219-44, 219-45, 219-46, 219-47, 219-48, 219-49, 219-50, 219-51, 219-52, 219-53, 219-54, 219-55, 219-56, 219-57, 219-58, 219-59, 219-60, 219-61, 219-62, 219-63, 219-64, 219-65, 219-66, 219-67, 219-68, 219-69, 219-70, 219-71, 219-72, 219-73, 219-74, 219-75, 219-76, 219-77, 219-78, 219-79, 219-80, 219-81, 219-82, 219-83, 219-84, 219-85, 219-86, 219-87, 219-88, 219-89, 219-90, 219-91, 219-92, 219-93, 219-94, 219-95, 219-96, 219-97, 220-1, 220-2, 220-3, 220-4, 220-5, 220-6, 220-7, 220-8, 220-9, 220-10, 220-11, 220-12, 220-13, 220-14, 220-15, 220-16, 220-17, 220-18, 220-19, 220-20, 220-21, 220-22, 220-23, 220-24, 220-25, 220-26, 220-27, 220-28, 220-29, 220-30, 220-31, 220-32, 220-33, 220-34, 220-35, 220-36, 220-37, 220-38, 220-39, 220-40, 220-41, 220-42, 220-43, 220-44, 220-45, 220-46, 220-47, 220-48, 220-49, 220-50, 220-51, 220-52, 220-53, 220-54, 220-55, 220-56, 220-57, 220-58, 220-59, 220-60, 220-61, 220-62, 220-63, 220-64, 220-65, 220-66, 220-67, 220-68, 220-69, 220-70, 220-71, 220-72, 220-73, 220-74, 220-75, 220-76, 220-77, 220-78, 220-79, 220-80, 220-81, 220-82, 220-83, 220-84, 220-85, 220-86, 220-87, 220-88, 220-89, 220-90, 220-91, 220-92, 220-93, 220-94, 220-95, 220-96, 220-97,

221-1, 221-2, 221-3, 221-4, 221-5, 221-6, 221-7, 221-8, 221-9, 221-10, 221-11, 221-12, 221-13, 221-14, 221-15, 221-16, 221-17, 221-18, 221-19, 221-20, 221-21, 221-22, 221-23, 221-24, 221-25, 221-26, 221-27, 221-28, 221-29, 221-30, 221-31, 221-32, 221-33, 221-34, 221-35, 221-36, 221-37, 221-38, 221-39, 221-40, 221-41, 221-42, 221-43, 221-44, 221-45, 221-46, 221-47, 221-48, 221-49, 221-50, 221-51, 221-52, 221-53, 221-54, 221-55, 221-56, 221-57, 221-58, 221-59, 221-60, 221-61, 221-62, 221-63, 221-64, 221-65, 221-66, 221-67, 221-68, 221-69, 221-70, 221-71, 221-72, 221-73, 221-74, 221-75, 221-76, 221-77, 221-78, 221-79, 221-80, 221-81, 221-82, 221-83, 221-84, 221-85, 221-86, 221-87, 221-88, 221-89, 221-90, 221-91, 221-92, 221-93, 221-94, 221-95, 221-96, 221-97, 222-1, 222-2, 222-3, 222-4, 222-5, 222-6, 222-7, 222-8, 222-9, 222-10, 222-11, 222-12, 222-13, 222-14, 222-15, 222-16, 222-17, 222-18, 222-19, 222-20, 222-21, 222-22, 222-23, 222-24, 222-25, 222-26, 222-27, 222-28, 222-29, 222-30, 222-31, 222-32, 222-33, 222-34, 222-35, 222-36, 222-37, 222-38, 222-39, 222-40, 222-41, 222-42, 222-43, 222-44, 222-45, 222-46, 222-47, 222-48, 222-49, 222-50, 222-51, 222-52, 222-53, 222-54, 222-55, 222-56, 222-57, 222-58, 222-59, 222-60, 222-61, 222-62, 222-63, 222-64, 222-65, 222-66, 222-67, 222-68, 222-69, 222-70, 222-71, 222-72, 222-73, 222-74, 222-75, 222-76, 222-77, 222-78, 222-79, 222-80, 222-81, 222-82, 222-83, 222-84, 222-85, 222-86, 222-87, 222-88, 222-89, 222-90, 222-91, 222-92, 222-93, 222-94, 222-95, 222-96, 222-97, 223-1, 223-2, 223-3, 223-4, 223-5, 223-6, 223-7, 223-8, 223-9, 223-10, 223-11, 223-12, 223-13, 223-14, 223-15, 223-16, 223-17, 223-18, 223-19, 223-20, 223-21, 223-22, 223-23, 223-24, 223-25, 223-26, 223-27, 223-28, 223-29, 223-30, 223-31, 223-32, 223-33, 223-34, 223-35, 223-36, 223-37, 223-38, 223-39, 223-40, 223-41, 223-42, 223-43, 223-44, 223-45, 223-46, 223-47, 223-48, 223-49, 223-50, 223-51, 223-52, 223-53, 223-54, 223-55, 223-56, 223-57, 223-58, 223-59, 223-60, 223-61, 223-62, 223-63, 223-64, 223-65, 223-66, 223-67, 223-68, 223-69, 223-70, 223-71, 223-72, 223-73, 223-74, 223-75, 223-76, 223-77, 223-78, 223-79, 223-80, 223-81, 223-82, 223-83, 223-84, 223-85, 223-86, 223-87, 223-88, 223-89, 223-90, 223-91, 223-92, 223-93, 223-94, 223-95, 223-96, 223-97, 224-1, 224-2, 224-3, 224-4, 224-5, 224-6, 224-7, 224-8, 224-9, 224-10, 224-11, 224-12, 224-13, 224-14, 224-15, 224-16, 224-17, 224-18, 224-19, 224-20, 224-21, 224-22, 224-23, 224-24, 224-25, 224-26, 224-27, 224-28, 224-29, 224-30, 224-31, 224-32, 224-33, 224-34, 224-35, 224-36, 224-37, 224-38, 224-39, 224-40, 224-41, 224-42, 224-43, 224-44, 224-45, 224-46, 224-47, 224-48, 224-49, 224-50, 224-51, 224-52, 224-53, 224-54, 224-55, 224-56, 224-57, 224-58, 224-59, 224-60, 224-61, 224-62, 224-63, 224-64, 224-65, 224-66, 224-67, 224-68, 224-69, 224-70, 224-71, 224-72, 224-73, 224-74, 224-75, 224-76, 224-77, 224-78, 224-79, 224-80, 224-81, 224-82, 224-83, 224-84, 224-85, 224-86, 224-87, 224-88, 224-89, 224-90, 224-91, 224-92, 224-93, 224-94, 224-95, 224-96, 224-97, 225-1, 225-2, 225-3, 225-4, 225-5, 225-6, 225-7, 225-8, 225-9, 225-10, 225-11, 225-12, 225-13, 225-14, 225-15, 225-16, 225-17, 225-18, 225-19, 225-20, 225-21, 225-22, 225-23, 225-24, 225-25, 225-26, 225-27, 225-28, 225-29, 225-30, 225-31, 225-32, 225-33, 225-34, 225-35, 225-36, 225-37, 225-38, 225-39, 225-40, 225-41, 225-42, 225-43, 225-44, 225-45, 225-46, 225-47, 225-48, 225-49, 225-50, 225-51, 225-52, 225-53, 225-54, 225-55, 225-56, 225-57, 225-58, 225-59, 225-60, 225-61, 225-62, 225-63, 225-64, 225-65, 225-66, 225-67, 225-68, 225-69, 225-70, 225-71, 225-72, 225-73, 225-74, 225-75, 225-76, 225-77, 225-78, 225-79, 225-80, 225-81, 225-82, 225-83, 225-84, 225-85, 225-86, 225-87, 225-88, 225-89, 225-90, 225-91, 225-92, 225-93, 225-94, 225-95, 225-96, 225-97, 226-1, 226-2, 226-3, 226-4, 226-5, 226-6, 226-7, 226-8, 226-9, 226-10, 226-11, 226-12, 226-13, 226-14, 226-15, 226-16, 226-17, 226-18, 226-19, 226-20, 226-21, 226-22, 226-23, 226-24, 226-25, 226-26, 226-27, 226-28, 226-29, 226-30, 226-31, 226-32, 226-33, 226-34, 226-35, 226-36, 226-37, 226-38, 226-39, 226-40, 226-41, 226-42, 226-43, 226-44, 226-45, 226-46, 226-47, 226-48, 226-49, 226-50, 226-51, 226-52, 226-53, 226-54, 226-55, 226-56, 226-57, 226-58, 226-59, 226-60, 226-61, 226-62, 226-63, 226-64, 226-65, 226-66, 226-67, 226-68, 226-69, 226-70, 226-71, 226-72, 226-73, 226-74, 226-75, 226-76, 226-77, 226-78, 226-79, 226-80, 226-81, 226-82, 226-83, 226-84, 226-85, 226-86, 226-87, 226-88, 226-89, 226-90, 226-91, 226-92, 226-93, 226-94, 226-95, 226-96, 226-97, 227-1, 227-2, 227-3, 227-4, 227-5, 227-6, 227-7, 227-8, 227-9, 227-10, 227-11, 227-12, 227-13, 227-14, 227-15, 227-16, 227-17, 227-18, 227-19, 227-20, 227-21, 227-22, 227-23, 227-24, 227-25, 227-26, 227-27, 227-28, 227-29, 227-30, 227-31, 227-32, 227-33, 227-34, 227-35, 227-36, 227-37, 227-38, 227-39, 227-40, 227-41, 227-42, 227-43, 227-44, 227-45, 227-46, 227-47, 227-48, 227-49, 227-50, 227-51, 227-52, 227-53, 227-54, 227-55, 227-56, 227-57, 227-58, 227-59, 227-60, 227-61, 227-62, 227-63, 227-64, 227-65, 227-66, 227-67, 227-68, 227-69, 227-70, 227-71, 227-72, 227-73, 227-74, 227-75, 227-76, 227-77, 227-78, 227-79, 227-80, 227-81, 227-82, 227-83, 227-84, 227-85, 227-86, 227-87, 227-88, 227-89, 227-90, 227-91, 227-92, 227-93, 227-94, 227-95, 227-96, 227-97, 228-1, 228-2, 228-3, 228-4, 228-5, 228-6, 228-7, 228-8, 228-9, 228-10, 228-11, 228-12, 228-13, 228-14, 228-15, 228-16, 228-17, 228-18, 228-19, 228-20, 228-21, 228-22, 228-23, 228-24, 228-25, 228-26, 228-27, 228-28, 228-29, 228-30, 228-31, 228-32, 228-33, 228-34, 228-35, 228-36, 228-37, 228-38, 228-39, 228-40, 228-41, 228-42, 228-43, 228-44, 228-45, 228-46, 228-47, 228-48, 228-49, 228-50, 228-51, 228-52, 228-53, 228-54, 228-55, 228-56, 228-57, 228-58, 228-59, 228-60, 228-61, 228-62, 228-63, 228-64, 228-65, 228-66, 228-67, 228-68, 228-69, 228-70, 228-71, 228-72, 228-73, 228-74, 228-75, 228-76, 228-77, 228-78, 228-79, 228-80, 228-81, 228-82, 228-83, 228-84, 228-85, 228-86, 228-87, 228-88, 228-89, 228-90, 228-91, 228-92, 228-93, 228-94, 228-95, 228-96, 228-97, 229-1, 229-2, 229-3, 229-4, 229-5, 229-6, 229-7, 229-8, 229-9, 229-10, 229-11, 229-12, 229-13, 229-14, 229-15, 229-16, 229-17, 229-18, 229-19, 229-20, 229-21, 229-22, 229-23, 229-24, 229-25, 229-26, 229-27, 229-28, 229-29, 229-30, 229-31, 229-32, 229-33, 229-34, 229-35, 229-36, 229-37, 229-38, 229-39, 229-40, 229-41, 229-42, 229-43, 229-44, 229-45, 229-46, 229-47, 229-48, 229-49, 229-50, 229-51, 229-52, 229-53, 229-54, 229-55, 229-56, 229-57, 229-58, 229-59, 229-60, 229-61, 229-62, 229-63, 229-64, 229-65, 229-66, 229-67, 229-68, 229-69, 229-70, 229-71, 229-72, 229-73, 229-74, 229-75, 229-76, 229-77, 229-78, 229-79, 229-80, 229-81, 229-82, 229-83, 229-84, 229-85, 229-86, 229-87, 229-88, 229-89, 229-90, 229-91, 229-92, 229-93, 229-94, 229-95, 229-96, 229-97, 230-1, 230-2, 230-3, 230-4, 230-5, 230-6, 230-7, 230-8, 230-9, 230-10, 230-11, 230-12, 230-13, 230-14, 230-15, 230-16, 230-17, 230-18, 230-19, 230-20, 230-21, 230-22, 230-23, 230-24, 230-25, 230-26, 230-27, 230-28, 230-29, 230-30, 230-31, 230-32, 230-33, 230-34, 230-35, 230-36, 230-37, 230-38, 230-39, 230-40, 230-41, 230-42, 230-43, 230-44, 230-45, 230-46, 230-47, 230-48, 230-49, 230-50, 230-51, 230-52, 230-53, 230-54, 230-55, 230-56, 230-57, 230-58, 230-59, 230-60, 230-61, 230-62, 230-63, 230-64, 230-65, 230-66, 230-67, 230-68, 230-69, 230-70, 230-71, 230-72, 230-73, 230-74, 230-75, 230-76, 230-77, 230-78, 230-79, 230-80, 230-81, 230-82, 230-83, 230-84, 230-85, 230-86, 230-87, 230-88, 230-89, 230-90, 230-91, 230-92, 230-93, 230-94, 230-95, 230-96, 230-97, 231-1, 231-2, 231-3, 231-4, 231-5, 231-6, 231-7, 231-8, 231-9, 231-10, 231-11, 231-12, 231-13, 231-14, 231-15, 231-16, 231-17, 231-18, 231-19, 231-20, 231-21, 231-22, 231-23, 231-24, 231-25, 231-26, 231-27, 231-28, 231-29, 231-30, 231-31, 231-32, 231-33, 231-34, 231-35, 231-36, 231-37, 231-38, 231-39, 231-40, 231-41, 231-42, 231-43, 231-44, 231-45, 231-46, 231-47, 231-48, 231-49, 231-50, 231-51, 231-52, 231-53, 231-54, 231-55, 231-56, 231-57, 231-58, 231-59, 231-60, 231-61, 231-62, 231-63, 231-64, 231-65, 231-66, 231-67, 231-68, 231-69, 231-70, 231-71, 231-72, 231-73, 231-74, 231-75, 231-76, 231-77, 231-78, 231-79, 231-80, 231-81, 231-82, 231-83, 231-84, 231-85, 231-86, 231-87, 231-88, 231-89, 231-90, 231-91, 231-92, 231-93, 231-94, 231-95, 231-96, 231-97, 232-1, 232-2, 232-3, 232-4, 232-5, 232-6, 232-7, 232-8, 232-9, 232-10, 232-11, 232-12, 232-13, 232-14, 232-15, 232-16, 232-17, 232-18, 232-19, 232-20, 232-21, 232-22, 232-23, 232-24, 232-25, 232-26, 232-27, 232-28, 232-29, 232-30, 232-31, 232-32, 232-33, 232-34, 232-35, 232-36, 232-37, 232-38, 232-39, 232-40, 232-41, 232-42, 232-43, 232-44, 232-45, 232-46, 232-47, 232-48, 232-49, 232-50, 232-51, 232-52, 232-53, 232-54, 232-55, 232-56, 232-57, 232-58, 232-59, 232-60, 232-61, 232-62, 232-63, 232-64, 232-65, 232-66, 232-67, 232-68, 232-69, 232-70, 232-71, 232-72, 232-73, 232-74, 232-75, 232-76, 232-77, 232-78, 232-79, 232-80, 232-81, 232-82, 232-83, 232-84, 232-85, 232-86, 232-87, 232-88, 232-89, 232-90, 232-91, 232-92, 232-93, 232-94, 232-95, 232-96, 232-97, 233-1, 233-2, 233-3, 233-4, 233-5, 233-6, 233-7, 233-8, 233-9, 233-10, 233-11, 233-12, 233-13, 233-14, 233-15, 233-16, 233-17, 233-18, 233-19, 233-20, 233-21, 233-22, 233-23, 233-24, 233-25, 233-26, 233-27, 233-28, 233-29, 233-30, 233-31, 233-32, 233-33, 233-34, 233-35, 233-36, 233-37, 233-38, 233-39, 233-40, 233-41, 233-42, 233-43, 233-44, 233-45, 233-46, 233-47, 233-48, 233-49, 233-50, 233-51, 233-52, 233-53, 233-54, 233-55, 233-56, 233-57, 233-58, 233-59, 233-60, 233-61, 233-62, 233-63, 233-64, 233-65, 233-66, 233-67, 233-68, 233-69, 233-70, 233-71, 233-72, 233-73, 233-74, 233-75, 233-76, 233-77, 233-78, 233-79, 233-80, 233-81, 233-82, 233-83, 233-84, 233-85, 233-86, 233-87, 233-88, 233-89, 233-90, 233-91, 233-92, 233-93, 233-94, 233-95, 233-96, 233-97, 234-1, 234-2, 234-3, 234-4, 234-5, 234-6, 234-7, 234-8, 234-9, 234-10, 234-11, 234-12, 234-13, 234-14, 234-15, 234-16, 234-17, 234-18, 234-19, 234-20, 234-21, 234-22, 234-23, 234-24, 234-25, 234-26, 234-27, 234-28, 234-29, 234-30, 234-31, 234-32, 234-33, 234-34, 234-35, 234-36, 234-37, 234-38, 234-39, 234-40, 234-41, 234-42, 234-43, 234-44, 234-45, 234-46, 234-47, 234-48, 234-49, 234-50, 234-51, 234-52, 234-53, 234-54, 234-55, 234-56, 234-57, 234-58, 234-59, 234-60, 234-61, 234-62, 234-63, 234-64, 234-65, 234-66, 234-67, 234-68, 234-69, 234-70, 234-71, 234-72, 234-73, 234-74, 234-75, 234-76, 234-77, 234-78, 234-79, 234-80, 234-81, 234-82, 234-83, 234-84, 234-85, 234-86, 234-87, 234-88, 234-89, 234-90, 234-91, 234-92, 234-93, 234-94, 234-95, 234-96, 234-97.

Among the combinations of groups given in Table 1 above, we prefer those identified as Nos. 1, 2, 3, 4, 5, 6, 7, 8, 9, 31, 34, 35, 36, 76, 77, 78, 106, 107, 108, 136, 137, 138, 163 and 199, and more prefer those identified as Nos. 1, 163 and 199.

Among the combinations of groups in Table 2 above, we prefer those identified as Nos. 1 to 8, 32 to 53, and 87 to 97, and more prefer those identified as Nos. 1, 38, 40, 41 and 42.

Among the compounds represented by the combinations of groups selected from Table 1 and Table 2, we prefer Compounds Nos. 1-1, 1-2, 1-3, 14, 1-5, 1-6, 1-7, 1-8, 1-32, 1-33, 1-34, 1-35, 1-36, 1-37, 1-38, 1-39, 1-40, 1-41, 1-42, 1-43, 1-44, 1-45, 1-48, 1-49, 1-50, 1-51, 1-52, 1-53, 7-1, 7-2, 7-3, 7-4, 7-5, 7-6, 7-7, 7-8, 7-32, 7-33, 7-34, 7-35, 7-36, 7-37, 7-38, 7-39, 7-40, 7-41, 7-42, 7-43, 7-44, 7-45, 7-48, 7-49, 7-50, 7-51, 7-52, 7-53, 163-1, 163-38, 163-39, 163-40, 163-41, 163-42, 199-1, 199-38, 199-39, 199-40, 199-41 and 199-42.

The most preferred compounds are Compounds No.:
1-1. 5-acetamido-4-guanidino-2,3,4,5,7-pentadeoxy-7-fluoro-D-glycero-D-galacto-non-2-enopyranosoic acid; IUPAC name: 5-acetamido-6-(1-fluoro-2,3-dihydroxypropyl)-4-(R)-guanidino-2-(S)-3-(R)-diydropyran-2-carboxylic acid;
1-40. 5-acetamido-4-guanidino-9-O-dodecanoyl-2,3,4,5,7-pentadeoxy-7-fluoro-D-glycero-D-galacto-non-2-enopyranosoic acid; IUPAC name: 5-acetamido-6-(1-fluoro-2-hydroxy-3-dodecanoyloxypropyl)-4-(R)-guanidino-2-(S)-3-(R)-dihydropyran-2-carboxylic acid;
1-41. 5-acetamido-4-guanidino-9-O-myristoyl-2,3,4,5,7-pentadeoxy-7-fluoro-D-glycero-D-galacto-non-2-enopyranosoic acid; IUPAC name: 5-acetamido-6-(1-fluoro-2-hydroxy-3-myristoyloxypropyl)-4-(R)-guanidino-2-(S)-3-(R)-dihydropyran-2-carboxylic acid;
1-42. 5-acetamido-4-guanidino-9-O-palmitoyl-2,3,4,5,7-pentadeoxy-7-fluoro-D-glycero-D-galacto-non-2-enopyranosoic acid; IUPAC name: 5-acetamido-6-(1-fluoro-2-hydroxy-3-palmitoyloxypropyl)-4-(R)-guanidino-2-(S)-3-(R)-dihydropyran-2-carboxylic acid;
163-1. 5-acetamido-4-guanidino-2,3,4,5,7-pentadeoxy-7-methoxy-D-glycero-D-galacto-non-2-enopyranosoic acid; IUPAC name: 5-acetamido-6-(2,3-dihydroxy-1-methoxypropyl)-4-(R)-guanidino-2-(S)-3-(R)-dihydropyran-2-carboxylic acid;
163-41. 5-acetamido-4-guanidino-9-O-myristoyl-2,3,4,5,7-pentadeoxy-7-methoxy-D-glycero-D-galacto-non-2-enopyranosoic acid: 5-acetamido-6-(2-hydroxy-1-methoxy-3-myristoyloxypropyl)-4-(R)-guanidino-2-(S)-3-(R)-dihydropyran-2-carboxylic acid;
199-1. 5-acetamido-4-guanidino-2,3,4,5,7-pentadeoxy-7-ethoxy-D-glycero-D-galacto-non-2-enopyranosoic acid; IUPAC name: 5-acetamido-6-(1-ethoxy-2,3- dihydroxypropyl)-4-(R)-guanidino-2-(S)-3-(R)-dihydropyran-2-carboxylic acid;

199-38. 5-acetamido-4-guanidino-9-O-octanoyl-2,3,4,5,7-pentadeoxy-7-ethoxy-D-glycero-D-galacto-non-2-enopyranosoic acid; IUPAC name: 5-acetamido-6-(1-ethoxy-2-hydroxy-3-octanoyloxypropyl)-4-(R)-guanidino-2-(S)-3-(R)-dihydropyran-2-carboxylic acid;

199-40. 5-acetamido-4-guanidino-9-O-dodecanoyl-2,3,4,5,7-pentadeoxy-7-ethoxy-D-glycero-D-galacto-non-2-enopyranosoic acid; IUPAC name: 5-acetamido-6-(1-ethoxy-2-hydroxy-3-dodecanoyloxypropyl)-4-(R)-guanidino-2-(S)-3-(R)-dihydropyran-2-carboxylic acid;

199-41. 5-acetamido-4-guanidino-9-O-myristoyl-2,3,4,5,7-pentadeoxy-7-ethoxy-D-glycero-D-galacto-non-2-enopyranosoic acid; IUPAC name: 5-acetamido-6-(1-ethoxy-2-hydroxy-3-myristoyloxypropyl)-4-(R)-guanidino-2-(S)-3-(R)-dihydropyran-2-carboxylic acid; and 199-42. 5-acetamido-4-guanidino-9-O-palmitoyl-2,3,4,5,7-pentadeoxy-7-ethoxy-D-glycero-D-galacto-non-2-enopyranosoic acid; IUPAC name: 5-acetamido-6-(1-ethoxy-2-hydroxy-3-palmitoyloxypropyl)-4-(R)-guanidino-2-(S)-3-(R)-dihydropyran-2-carboxylic acid;.

The compounds of the present invention may be prepared by a variety of processes well known in the art for the preparation of compounds of this type, for example as illustrated by the following Methods A, B and C.

The compound of formula (2), which is used as a starting material in Method A or B, can be prepared by the following Methods D, E, F or G.

The compound of formula (5), which is used as a starting material in Method C, can be prepared by the following Method H.

Method A

Reaction Scheme A

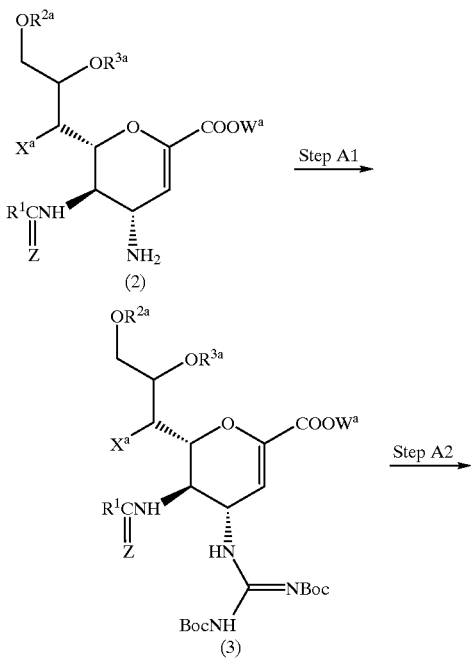

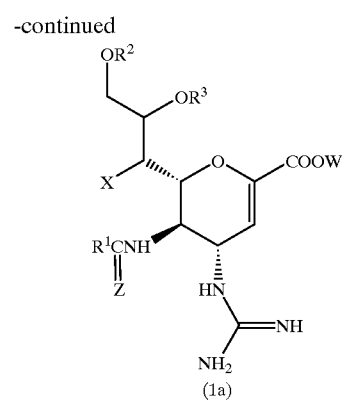

In the above formulae:

$R^1$, $R^2$, $R^3$, X and Z are as defined above;

$R^{2a}$ represents any of the groups or atoms represented by $R^2$ or a hydroxy-protecting group, preferably t-butyldimethylsilyl group;

$R^{3a}$ represents any of the groups or atoms represented by $R^3$ or a hydroxy-protecting group, preferably t-butyldimethylsilyl group;

$X^a$ represents any of the groups or atoms represented by X or a protected hydroxy group, preferably t-butyldimethylsilyloxy group;

W represents a hydrogen atom or an ester residue;

$W^a$ represents any of the groups or atoms represented by W or a carboxy-protecting group, preferably an allyl group, a methoxymethyl group, a methylthiomethyl group, a [2-(trimethylsily)ethoxy]methoxy group or a diphenylmethyl group, more preferably a diphenylmethyl group; and Boc represents a t-butoxycarbonyl group.

In this Method, a compound of formula (1a) is prepared by reacting a compound of formula (2) with N,N'-t-butoxycarbonylthiourea to give a compound of formula (3), which is then deprotected.

Step A1

In this Step, a compound of formula (3) is prepared by reacting the compound of formula (2) with N,N'-di-t-butoxycarbonylthiourea in the presence of a base and mercuric chloride and in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; ethers, such as diethyl ether, diisopropyl ether, tetrahydrofuran, dioxane, dimethoxyethane and diethylene glycol dimethyl ether, and amides, such as N,N-dimethylacetamide, and dimethylformamide. Of these, we prefer the amides, particularly N,N-dimethylacetamide or dimethylformamide.

There is likewise no particular restriction on the nature of the bases used, and any base commonly used in reactions of this type may equally be used here. Examples of such bases include: organic bases, such as triethylamine or dimethylaminopyridine.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 50° C., more preferably from 10 to 30° C. The time required for the reaction may also vary widely, depending on many factors, notably the reaction temperature and the nature of the reagents, base and solvent employed. However, provided that the reaction is effected under the preferred conditions outlined above, a period of from 1 hour to 24 hours, more preferably from 5 to 10 hours, will usually suffice.

After completion of the reaction, the desired compound can be obtained by conventional means. For example, one suitable recovery procedure comprises: filtering the reaction solution under reduced pressure to remove the insolubles; adding a water-immiscible organic solvent, such as ethyl acetate, thereto, separating the organic layer containing the desired compound after washing with water; and distilling off the solvent after the organic layer is dried, for example over anhydrous magnesium sulfate.

The desired compound can, if desired, be further purified by recrystallization or by the various forms of chromatography, such as column chromatography or preparative thin layer chromatography.

Step A2

In this Step, a compound of formula (1a), which is a compound of the present invention, is prepared by treating the compound of formula (3) with a reagent which can remove a t-butoxycarbonyl group, in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; water; or a mixture of any two or more thereof.

There is likewise no particular restriction on the nature of the reagents used to remove the t-butoxycarbonyl group, and any reagent commonly used in reactions of this type may equally be used here. Examples of such reagents include acids, and any acid commonly used as an acid catalyst may be used, for example a Bronsted acid, such as an inorganic acid (e.g. hydrochloric acid, hydrobromic acid, sulfuric acid, perchloric acid or phosphoric acid) or an organic acid (e.g. acetic acid, formic acid, oxalic acid, methanesulfonic acid, p-toluenesulfonic acid, trifluoroacetic acid or trifluoromethanesulfonic acid), preferably an organic acid (particularly acetic acid or trifluoroacetic acid).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 50° C., more preferably from 10 to 30° C. The time required for the reaction may also vary widely, depending on many factors, notably the reaction temperature and the nature of the reagents and solvent employed. However, provided that the reaction is effected under the preferred conditions outlined above, a period of from 15 minutes to 10 hours, more preferably from 1 to 5 hours, will usually suffice.

After completion of the reaction, the desired compound can be recovered from the reaction mixture by conventional means. For example, one suitable recovery procedure comprises: neutralising the reaction solution and purifying the residue obtained by distilling off the solvent under reduced pressure by means of silica gel chromatography.

Where $R^{2a}$ or $R^{3a}$ represents a hydroxy-protecting group, $X^a$ represents a protected hydroxy group or $W^a$ represents a carboxy-protecting group, a compound of the present invention can be prepared by deprotecting these protecting groups further.

The reaction employed for the removal of the protecting group will vary, depending on the nature of the protecting group. However it can be carried out by conventional means, for example, by the method described in "Protective Groups in Organic Synthesis", Second Edition (written by, Greene and Wuts, John Wiley & Sons, Inc., published in 1991), the disclosures of which are incorporated herein by reference.

Where the hydroxy-protecting group is a trialkylsilyl group, such as a t-butyldimethylsilyl group, acetic acid in a mixture of water and tetrahydrofuran or tetrabutylammonium fluoride in tetrahydrofuran can preferably be used. Where the carboxy-protecting group is a diphenylmethyl group, catalytic reduction using hydrogen gas and a catalyst such as palladium black in a mixture of methanol and tetrahydrofuran, trifluoroacetic acid in phenol, acetic acid as an acid and a solvent or trifluoroboran-diethyl ether complex in acetic acid can be used.

Method B

In this Method, a compound of formula (1) is prepared by reacting the compound of formula (2) with ammonia or a hydroxylamine which may be substituted by an alkyl group having from 1 to 4 carbon atoms at the amino moiety, if desired, followed by deprotection.

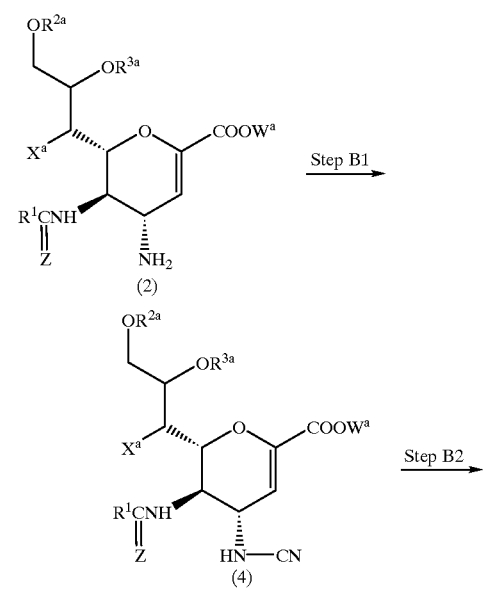

Reaction Scheme B

-continued

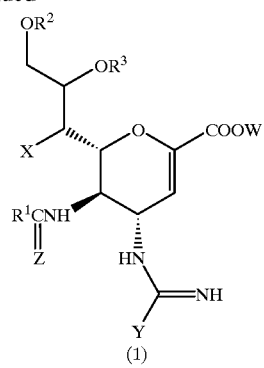

In the above formulae, $R^1$, $R^2$, $R^3$, $R^{2a}$, $R^{3a}$, X, Y, W, Z, $X^a$ and $W^a$ are as defined above.

Step B1

In this Step, a compound of formula (4) is prepared by reacting the compound of formula (2) with a cyanating agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol ethanol, propanol isopropanol, butanol, isobutanol, t-butanol, isoamyl alcohol, diethylene glycol, glycerin, octanol, cyclohexanol and ethylene glycol monomethyl ether (methyl Cellosolve—"Cellosolve" is a trade mark); amides, such as formamide, dimethylformamide, N,N-dimethylacetamide, N-methyl-2-pyrrolidone, N-methylpyrrolidinone and hexamethylphosphoric triamide and sulfoxides, such as dimethyl sulfoxide and sulfolane. Of these, we prefer the alcohols (particularly methanol).

There is likewise no particular restriction on the nature of the cyanating agents used, and any cyanating agent commonly used in reactions of this type may equally be used here. Examples of such cyanating agents include cyanogen bromide, in which case, sodium acetate is simultaneously used as a base.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 50° C., more preferably from 10 to 40° C. The time required for the reaction may also vary widely, depending on many factors, notably the reaction temperature and the nature of the reagents, base and solvent employed. However, provided that the reaction is effected under the preferred conditions outlined above, a period of from 15 minutes to 10 hours, more preferably from 1 to 5 hours, will usually suffice.

After completion of the reaction the desired compound can, for example, be obtained by using silica gel chromatography to purify the residue obtained by distilling off the solvent.

Step B2

In this Step, a compound of formula (1), which is a compound of the present invention, is prepared by reacting the compound of formula (4) with ammonia or a hydroxylamine which may be substituted by an allyl group having from 1 to 4 carbon atoms at the amino moiety, if desired, followed by deprotection.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent Examples of suitable solvents include alcohols (particularly methanol).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 50° C., more preferably from 10 to 40° C. The time required for the reaction may also vary widely, depending on many factors, notably the reaction temperature and the nature of the reagents and solvent employed. However, provided that the reaction is effected under the preferred conditions outlined above, a period of from 15 minutes to 10 hours, more preferably from 1 to 5 hours, will usually suffice.

After completion of the reaction, the desired compound can be recovered from the reaction mixture by conventional means. For example, one suitable recovery procedure comprises using silica gel chromatography to purify the residue obtained by distilling off the solvent.

Where $R^{a2}$ or $R^{3a}$ represents a hydroxy-protecting group, $X^a$ represents a protected hydroxy group or $W^a$ represents a carboxy-protecting group, a compound of the present invention can be prepared by the subsequent removal of these protecting groups as described in Method A.

Method C

In this Method, a compound of formula (1c) is prepared by reacting the compound of formula (5) with an acylating agent, followed by deprotection.

Reaction Scheme C

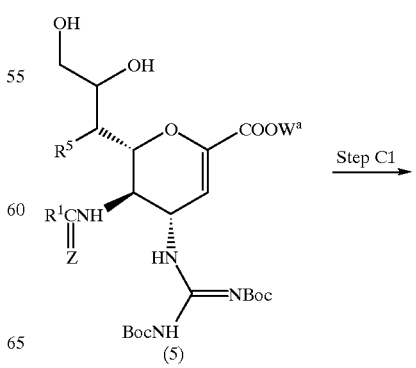

-continued

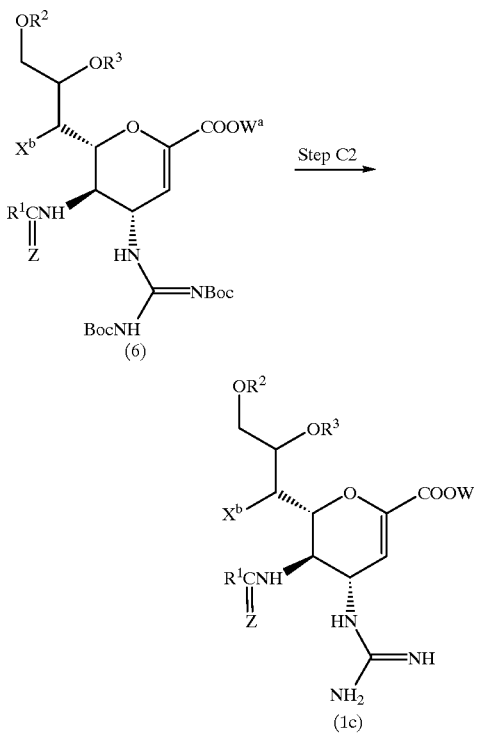

In the above formulae:

R¹, R², R³, W, Z and $W^a$ are as defined above;

R⁵ represents a halogen atom, a hydroxy group or an alkoxy group having from 1 to 4 carbon atoms; and $X^b$ represents a halogen atom, an aliphatic acyloxy group having from 2 to 25 carbon atoms or an alkoxy group having from 1 to 4 carbon atoms.

Step C1

In this Step, a compound of formula (6) is prepared by introducing a desired acyl group into the compound of formula (5) in an inert solvent.

The acylation method may be carried out by any of the following Processes 1, 2 and 3.

Process 1

In this Process, a compound of formula (5) is reacted with a compound of formula RCO—L or a compound of formula RCO—O—COR, wherein R represents an alkyl group having from 1 to 24 carbon atoms; and L represents a leaving group. There is no particular restriction on the nature of the leaving groups used, and any nucleophilic leaving group commonly used in reactions of this type may equally be used here. Examples of such leaving groups include: halogen atoms, such as the chlorine, bromine and iodine atoms; alkoxycarbonyloxy groups having from 1 to 6 carbon atoms in the alkoxy part, such as the methoxycarbonyloxy and ethoxycarbonyloxy groups; halogenated alkanoyloxy groups, such as the chloroacetoxy, dichloroacetoxy, trichloroacetoxy and trifluoroacetoxy groups; alkanesulfonyloxy groups having from 1 to 6 carbon atoms in the alkyl part, such as the methanesulfonyloxy and ethanesulfonyloxy groups; halogenated alkanesulfonyloxy groups having from 1 to 6 carbon atoms in the alkyl part, such as the trifluoromethanesulfonyloxy and pentafluoroethanesulfonyloxy groups; and arylsulfonyloxy groups, such as the benzenesulfonyloxy, p-toluenesulfonyloxy and p-nitrobenzenesulfonyl oxy groups. Of these, we prefer the halogen atoms, halogenated alkanesulfonyloxy groups and arylsulfonyloxy groups.

The reaction may take place in the presence or absence of a base and in a solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether, nitriles, such as acetonitrile and isobutyronitrile; and amides, such as formamide, dimethylformamide, N,N-dimethylacetamide, N-methyl-2-pyrrolidone, N-methylpyrrolidinone and hexamethylphosphoric triamide.

There is likewise no particular restriction on the nature of the bases used, and any base commonly used in reactions of this type may equally be used here. Examples of such bases include: organic bases, such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino) pyridine, 2,6-di(t-butyl)-4-methylpyridine, quinoline, N,N-dimethylaniline and N,N-diethylaniline.

4-(N,N-Dimethylamino)pyridine and 4-pyrrolidinopyridine can be used in a catalytic amount in combination with one or more other bases. In addition, it may facilitate the reaction to carry it out in the presence of one or more of: quaternary ammonium salts, such as benzyltriethylammonium chloride and tetrabutylammonium chloride; and crown ethers, such as dibenzo-18-crown-6.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to the reflux temperature of the solvent used, more preferably from 0° C. to the reflux temperature of the solvent used. The time required for the reaction may also vary widely, depending on many factors, notably the reaction temperature and the nature of the reagents, base and solvent employed. However, provided that the reaction is effected under the preferred conditions outlined above, a period of from 10 minutes to 3 days, more preferably from 1 hour to 6 hours, will usually suffice.

Process 2

In this Process, a compound of formula: RCOOH [wherein R is as defined above] is reacted with the compound of formula (5) in the presence of an esterifying agent and in the presence or absence of a catalytic amount of a base in a solvent. The reaction may also be effected in the presence of a condensing agent.

There is no particular restriction on the nature of the esterifying agents used, and any esterifying agent commonly used in reactions of this type may equally be used here.

Examples of such esterifying agents include active esters, especially: alkyl haloformates, such as methyl chloroformate and ethyl chloroformate; and cyanophosphoric acid diesters, such as diethyl cyanophosphate. Esterification with such active esters preferably takes place in the presence of at least one condensing agent. Specific examples of such condensing agents include: N-hydroxy derivatives, such as N-hydroxysuccinimide, 1-hydroxybenzotriazole and N-hydroxy-5-norbornene-2,3-dicarboximide; disulfide compounds, such as 2,2'-dipyridyl disulfide; succinic acid compounds, such as N,N'-disuccinimidyl carbonate; phosphinic chloride compounds, such as N,N'-bis(2-oxo-3-oxazolidinyl)phosphinic chloride; oxalate derivatives, such as N,N'-disuccinimidyl oxalate (DSO), N,N'-diphthalimidoxalate (DPO), N,N'-bis (norbornenylsuccinimidyl) oxalate (BNO), 1,1'-bis (benzotriazolyl)oxalate (BBTO), 1,1'-bis(6-chlorobenzotriazolyl)oxalate (BCTO) and 1,1'-bis(6-trifluoromethylbenzotriazolyl)oxalate (BTBO); triarylphosphines including triarylphosphines, such as triphenylphosphine, dialkyl azodicarboxylate-triarylphosphines in which the alkyl part has from 1 to 6 carbon atoms, such as diethyl azodicarboxylatetriphenylphosphine; N-alkyl-5-arylisoxazolium-3'-sulfonates in which the alkyl part has from 1 to 6 carbon atoms, such as N-ethyl-5-phenylisoxazolium-3'-sulfonate; carbodiimide derivatives including N',N'-dicycloalkylcarbodiimides, such as N',N''-dicyclohexylcarbodiimide (DCC) and 1-ethyl-3-(3-dimethylaminopropyl)carbodiimide (EDAPC); diheteroaryldiselenides, such as di-2-pyridyldiselenide; arylsulfonyltriazolides, such as p-nitrobenzenesulfonyltriazolide; 2-halo-1-alkylpyridinium halides in which the alkyl part has from 1 to 6 carbon atoms, such as 2-chloro-1-methylpyridinium iodide; diarylphosphorylazides, such as diphenylphosphorylazide (DPPA); imidazole derivatives, such as 1,1'-oxalyldiimidazole and N,N'-carbonyldiimidazole; benzotriazole derivatives, such as 1-hydroxybenzotriazole (HOBT); and dicarboximide derivatives, such as N-hydroxy-5-norbornene-2,3-dicarboximide (HONB), preferably the diarylphosphorylazides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; amides, such as formamide, dimethylformamide, N,N-dimethylacetamide, N-methyl-2-pyrrolidone, N-methylpyrrolidinone and hexamethylphosphoric triamide.

There is likewise no particular restriction on the nature of the bases used, and any base commonly used in reactions of this type may equally be used here. Examples of such bases include those described in relation to Process 1, above.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 80° C., more preferably from 0° C. to room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 1 day, will usually suffice.

Process 3

In this Process, a compound of formula: RCOOH [wherein R is as defined above] is reacted with the compound of formula (5) in the presence of a halogenated phosphoric acid dialkyl ester, such as diethyl chlorophosphate, and a base in a solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitrites, such as acetonitrile and isobutyronitrile; amides, such as formamide, N,N-dimethylformamide, N,N-dimethylacetamide, N-methyl-2-pyrrolidone, N-methylpyrrolidinone and hexamethylphosphoric triamide.

There is likewise no particular restriction on the nature of the bases used, and any base commonly used in reactions of this type may equally be used here. Examples of such bases include those described in relation to Process 1, above.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to the reflux temperature of the solvent used, more preferably from room temperature to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to 1 day, will usually suffice.

The number of acyl groups introduced varies depending on the amount of acylating agent employed.

After completion of the reaction of any of the above Processes, the desired compound of formula (6) may be collected from the reaction mixture by conventional means. For example, the desired compound can be obtained by the following procedure: appropriately neutralising the reaction mixture; adding a water-immiscible organic solvent, such as ethyl acetate, thereto after the insolubles have, if necessary, been removed by filtration; washing with water; separating the organic layer containing the desired compound; drying the organic layer over anhydrous magnesium sulfate; and distilling off the solvent.

The compound thus obtained can be separated and purified, if necessary, by any suitable combination conventional methods, for example, recrystallization, reprecipitation or other methods commonly used for the separation and purification of organic compounds, for example: adsorption column chromatography in which a carrier such as silica gel, alumina or a magnesium silicate gel (such as that available under the trade mark "Florisil") is used; a method in which a synthesis adsorbing agent is used such as partition chromatography, using a carrier such as Sephadex LH-20 (a trade mark for a material produced by Pharmacia Co., Ltd.), Amberlite XAD-11 (a trade mark for a material produced by Rohm & Haas Co., Ltd.) or Diaion HP-20 (a trade mark for a material produced by Mitsubishi Kasei Co., Ltd.); or normal phase or reverse phase column chromatography (preferably high performance liquid chromatography) using silica gel or an alkylated silica gel and elution with a suitable eluent.

Step C2

In this Step, a compound of formula (1c), which is a compound of the present invention is prepared by treating the compound of formula (6) with a reagent which can remove a t-butoxycarbonyl group. The reaction is normally and preferably effected in the presence of an inert solvent.

This reaction is essentially the same as and may be carried out in the same manner as and using the same reagents and reaction conditions as in Step A2 of Method A.

Where $W^a$ represents a carboxy-protecting group, a compound of the present invention can be prepared by the subsequent removal of these protecting groups as mentioned in Step A2.

Method D

This Method illustrates the preparation of a compound of formula (2a), which is one of starting materials used in Methods A and B.

Reaction Scheme D

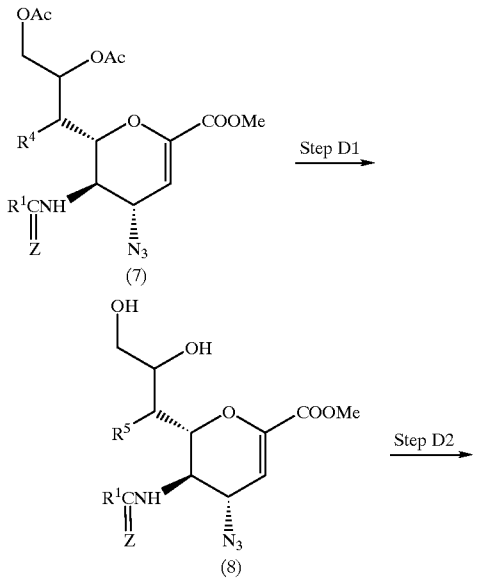

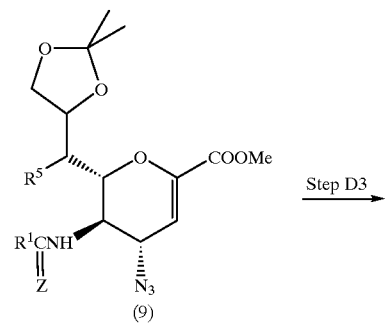

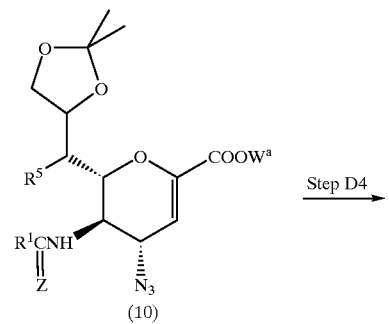

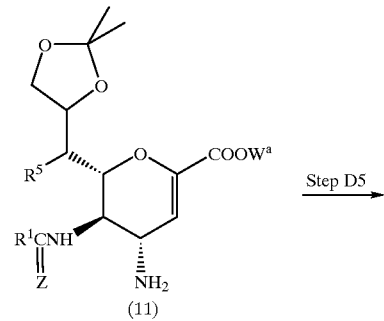

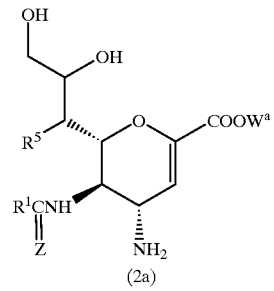

In the above formulae:

$R^1$, $R^5$, Z and $W^a$ are as defined above;

$R^4$ represents a halogen atom, an acetoxy group or an alkoxy group having from 1 to 4 carbon atoms;

Ac represents an acetyl group;

Boc represents a t-butoxycarbonyl group; and

Me represents a methyl group.

Step D1

In this Step, a compound of formula (8) is prepared by reacting the compound of formula (7) with a base in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent.

Examples of suitable solvents include: aliphatic hydrocarbons, such as hexane, heptane, ligroin and petroleum ether, aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether, and alcohols, such as methanol. Of these, we prefer the halogenated hydrocarbons and methanol.

There is likewise no particular restriction on the nature of the bases used, provided that it does not affect other functional groups (for example methyl ester groups), and any base commonly used in reactions of this type may equally be used here. Examples of such bases include the alkali metal methoxides, such as sodium methoxide and potassium methoxide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 50° C., more preferably from 10 to 30° C. The time required for the reaction may also vary widely, depending on many factors, notably the reaction temperature and the nature of the reagents, base and solvent employed. However, provided that the reaction is effected under the preferred conditions outlined above, a period of from 15 minutes to 10 hours, more preferably from 1 to 5 hours, will usually suffice.

After completion of the reaction, the desired compound can be recovered from the reaction mixture by conventional means. For example, one suitable recovery procedure comprises: neutralising the reaction solution with a solution of hydrogen chloride in dioxane; distilling off the solvent under reduced pressure; and purifying the residue thus obtained by silica gel chromatography.

Step D2

In this Step, a compound of formula (9) is prepared by reacting the compound of formula (8) with a reagent for introducing an isopropylidene group.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether, aromatic hydrocarbons, such as benzene, toluene and xylene; ethers, such as diethyl ether, diisopropyl ether, tetrahydrofuran, dioxane, dimethoxyethane and diethylene glycol dimethyl ether, and ketones, such as acetone, methyl ethyl ketone, methyl isobutyl ketone, isophorone and cyclohexanone. Of these, we prefer the ketones (particularly acetone).

The reagent used to introduce an isopropylidene group is preferably 2,2-dimethoxypropane. The reaction is usually effected in the presence of an acid, such as p-toluenesulfonic acid, as a catalyst.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 50° C., more preferably from 10 to 30° C. The time required for the reaction may also vary widely, depending on many factors, notably the reaction temperature and the nature of the reagents, base and solvent employed. However, provided that the reaction is effected under the preferred conditions outlined above, a period of from 15 minutes to 10 hours, more preferably from 1 to 5 hours, will usually suffice.

After completion of the reaction, the desired compound can be recovered from the reaction mixture by conventional means. For example, one suitable recovery procedure comprises: adding a water-immiscible solvent, such as ethyl acetate, and an aqueous solution of sodium hydrogencarbonate to the reaction solution; extracting the desired compound with a solvent such as ethyl acetate; and distilling off the solvent. The desired compound can be further purified by recrystallization or by the various types of chromatography, such as column chromatography or preparative thin layer chromatography, if necessary.

Step D3

This Step may be carried out, if desired, by:

1) converting the methyl group of the carboxylic acid ester into another substituent;
2) hydrolysing the carboxylic acid ester; or
3) carrying out 2) above and then protecting the resulting free carboxylic acid.

1. Ester Conversion

In this Step, a compound of formula (10) is prepared by reacting the compound of formula (9) with an alcohol which is capable of giving the desired ester group, in the presence of a base and in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether, aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, isoamyl alcohol, diethylene glycol, glycerin, octanol, cyclohexanol and ethylene glycol monomethyl ether (such as that available under the trade mark "Methyl Cellosolve"). Of these, we prefer those alcohols which form the desired ester group.

There is likewise no particular restriction on the nature of the bases used, and any base commonly used in reactions of this type may equally be used here. Examples of such bases include organic bases, such as pyridine, triethylamine, diethylamine and 4-N,N-dimethylaminopyridine.

After completion of the reaction, the desired compound can be recovered from the reaction mixture by conventional means. For example, one suitable recovery procedure comprises: neutralising the reaction mixture with an acid; adding a water-immiscible organic solvent such as ethyl acetate; extracting the desired compound with a solvent such as ethyl acetate; washing the extract; and distilling off the solvent. The desired compound can be further purified by recrystallization or the various types of chromatography, such as column chromatography or preparative thin layer chromatography, if necessary.

The same compound of formula (10) can be also obtained by reacting a carboxylic acid [obtained by removing a methyl group of the compound of formula (9)] with an alcohol of formula $W^d$-OH or an alkyl halide of formula $W^d$-Hal (where $W^d$ represents an alkyl group and Hal represents a halogen atom).

2. Hydrolysis

In this Step, the compound of formula (10) is prepared by reacting the compound of formula (9) with a base in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include water or a mixture of water and one or more organic solvents. Suitable such organic solvents include: alcohols, such as methanol and ethanol; and ethers, such as diethyl ether, tetrahydrofuran and dioxane. Of these solvents, we prefer water or a mixture of water and one or more alcohols.

There is likewise no particular restriction on the nature of the bases used, and any base commonly used in reactions of this type may equally be used here. Examples of such bases include alkali metal hydroxides, such as sodium hydroxide and potassium hydroxide.

The reaction can take place over a wide range of temperatures, and the precise reaction temperature is not critical to the invention The preferred reaction temperature will depend upon such factors as the nature of the solvent, and the starting material or reagent used. However, in general, we find it convenient to carry out the reaction at a temperature of from −10 to 50° C., more preferably from 10 to 30° C. The time required for the reaction may also vary widely, depending on many factors, notably the reaction temperature and the nature of the reagents, base and solvent employed. However, provided that the reaction is effected under the preferred conditions outlined above, a period of from 15 minutes to 10 hours, more preferably from 1 to 5 hours, will usually suffice.

After completion of the reaction, the desired compound can be recovered from the reaction mixture by conventional means. For example, one suitable recovery procedure comprises: adding Dowex-50x8 ($H^+$ type) (Dowex is a trade mark) to the reaction solution to neutralize it; distilling off the solvent under reduced pressure; and purifying the residue thus obtained by silica gel chromatography.

3. Diphenylmethylation

In this Step, a compound of formula (10) is prepared by reacting diphenyldiazomethane with the compound of formula (9) in the presence of a Lewis acid and in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent Examples of suitable solvents include: aliphatic hydrocarbons, such as hexane, heptane, ligroin and petroleum ether; aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether, alcohols, such as methanol, ethanol, propanol, isopropanol, butanol, isobutanol, t-butanol, isoamyl alcohol, diethylene glycol, glycerin, octanol, cyclohexanol and ethylene glycol monomethyl ether (such as that available under the trade mark "Methyl Cellosolve"). Of these, we prefer the alcohols (particularly methanol), the halogenated hydrocarbons (particularly dichloromethane) and mixtures thereof.

The Lewis acid which may be employed in this reaction is preferably boron trifluoride-diethyl ether complex.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 10 minutes to 5 hours, more preferably from 1 to 3 hours, will usually suffice.

After completion of the reaction, the desired compound can be recovered from the reaction mixture by conventional means. For example, one suitable recovery procedure comprises: adding an acid, such as acetic acid, to the reaction mixture; distilling off the solvent; and purifying the residue by recrystallization or chromatography.

Step D4

In this Step, a compound of formula (11) is prepared from the compound of formula (10), using a reducing agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; ethers, such as diethyl ether, diisopropyl ether, tetrahydrofuran, dioxane, dimethoxyethane and diethylene glycol dimethyl ether, alcohols, such as methanol, ethanol, propanol, isopropanol, butanol, isobutanol, t-butanol, isoamyl alcohol, diethylene glycol, glycerin, octanol, cyclohexanol and ethylene glycol monomethyl ether (such as that available under the trade mark "Methyl Cellosolve"); ketones, such as acetone, methyl ethyl ketone, methyl isobutyl ketone, isophorone and cyclohexanone; nitrites, such as acetonitrile and isobutyronitrile; amides, such as formamide, dimethylformamide, N,N-dimethylacetamide, N-methyl-2-pyrrolidone, N-methylpyrrolidinone and hexamethylphosphoric triamide; sulfoxides, such as dimethyl sulfoxide and sulfolane; fatty acids, such as acetic acid; and mixtures of water and any one or more of these organic solvents. Of these, we prefer the alcohols (particularly methanol), the ethers, such as tetrahydrofuran and dioxane, the fatty acids, such as acetic acid, and mixtures of one or more of these organic solvents and water.

There is likewise no particular restriction on the nature of the reducing agents used, and any reducing agent commonly used in reactions of this type may equally be used here. Examples of such reducing agents include a hydrogenation catalyst, such as palladium-on-carbon, platinum or Raney nickel, in the presence of hydrogen gas. We particularly prefer to use a Lindlar catalyst (Pd—$BaSO_4$ or Pd—$CaCO_3$ and quinoline or lead acetate in combination).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 50° C., more preferably from 10 to 30° C. The time required for the reaction may also vary widely, depending on many factors, notably the reaction temperature and the nature of the reagents, reducing agent and solvent employed. However, provided that the reaction is effected under the preferred conditions outlined above, a period of from 15 minutes to 10 hours, more preferably from 1 to 5 hours, will usually suffice.

After completion of the reaction, the desired compound can be obtained, for example, by filtering the reaction solution under reduced pressure to remove the catalyst and distilling off the solvent under reduced pressure. The desired compound can be fierier purified by recrystallization or the various types of chromatography, such as column chromatography or preparative thin layer chromatography, if necessary.

Step D5

In this Step, a compound of formula (2a) is prepared by deprotecting the isopropylidene group of a compound of formula (11) in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride or chloroform.

The reagent employed for deprotecting the isopropylidene group is preferably an acid. There is likewise no particular restriction on the nature of the acids used, and any acid commonly used as an acid catalyst in reactions of this type may equally be used here. Examples of such acids include: Bronsted acids, such as inorganic acids (e.g. hydrochloric acid, hydrobromic acid, sulfuric acid, perchloric acid or phosphoric acid) or organic acids (e.g. formic acid, oxalic acid, methanesulfonic acid, p-toluenesulfonic acid, trifluoroacetic acid or trifluoromethanesulfonic acid); Lewis acids, such as zinc chloride, tin tetrachloride, boron trichloride, boron trifluoride or boron tribromide; and acidic ion exchange resins. Of these, we prefer the organic acids (particularly trifluoroacetic acid).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 50° C., more preferably from 10 to 30° C. The time required for the reaction may also vary widely, depending on many factors, notably the reaction temperature and the nature of the reagents and solvent employed. However, provided that the reaction is effected under the preferred conditions outlined above, a period of from 15 minutes to 10 hours, more preferably from 1 to 5 hours, will usually suffice.

After completion of the reaction, the desired compound can be recovered from the reaction mixture by conventional means. For example, one suitable recovery procedure comprises: neutralising the reaction solution; and distilling off the solvent under reduced pressure. The desired compound can, if desired, be farther purified by recrystallization or the various types of chromatography, such as column chromatography or preparative thin layer chromatography.

Method E

In Method E, a compound of formula (2b) or a compound of formula (2c), which are amongst the starting materials which may be used in Method A or B, is prepared.

Reaction Scheme E

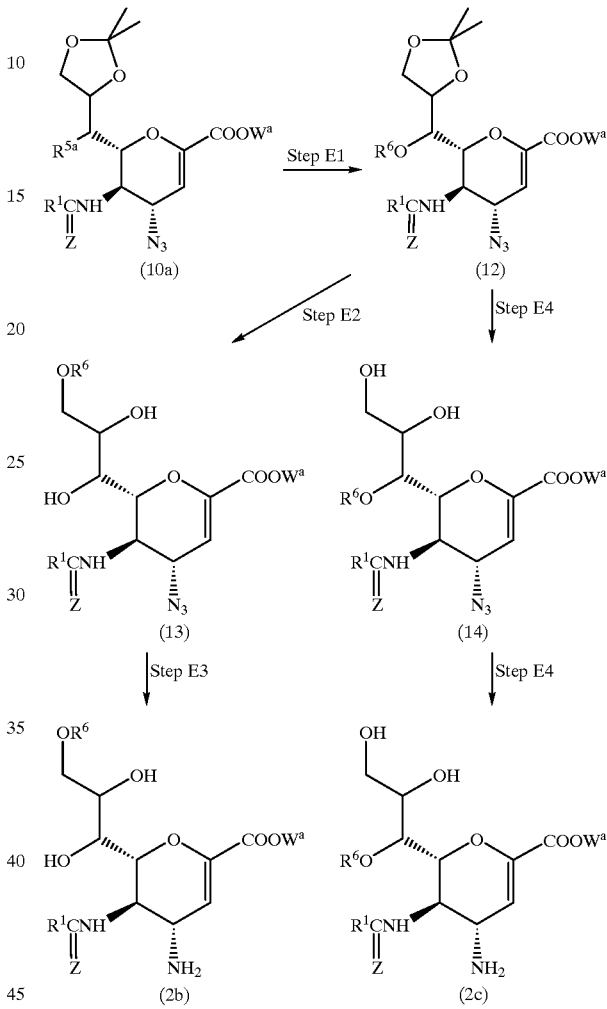

In the above formulae:
R$^1$, Z and W$^a$ are as defined above;
R$^{5a}$ represents a hydroxy group; and
R$^6$ represents an aliphatic acyl group having from 2 to 25 carbon atoms.

Step E1

In this Step, a compound of formula (12) is prepared by introducing a desired acyl group into the compound of formula (10a) in an inert solvent.

This reaction is essentially the same as and may be carried out in the same manner as and using the same reagents and reaction conditions as Step C1 of Method C.

Step E2

In this Step, a compound of formula (13) is prepared by deprotecting the isopropylidene group of a compound of formula (12) in an inert solvent.

This reaction is essentially the same as and may be carried out in the same manner as and using the same reagents and reaction conditions as Step D5 of Method D.

Step E3

In this Step, a compound of formula (2b) is prepared from the compound of formula (13) by using a reducing agent in an inert solvent.

This reaction is essentially the same as and may be carried out in the same manner as and using the same reagents and reaction conditions as Step D4 of Method D.

Step E4

In this Step, a compound of formula (14) is prepared by treating the compound of formula (12) with a reagent which removes an isopropylidene group in the presence of an acid catalyst and in a suitable solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent The solvent employed is preferably a mixture of water and acetic acid (which simultaneously functions as an acid catalyst).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10 to 70° C., more preferably from 30 to 60° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 10 to 20 hours, will usually suffice.

After completion of the reaction, the desired compound can be recovered from the reaction mixture by conventional means. For example, one suitable recovery procedure comprises: distilling off the solvent under reduced pressure; adding a water-immiscible solvent, such as ethyl acetate, and an aqueous solution of sodium hydrogencarbonate to the reaction solution; extracting the desired compound with a suitable solvent, such as ethyl acetate, and distilling off the solvent. The desired compound can, if desired, be further purified by recrystallization or the various types of chromatography, such as column chromatography or preparative thin layer chromatography.

Step E5

In this Step, a compound of formula (2c) is prepared from the compound of formula (14) using a reducing agent in an inert solvent.

This reaction is essentially the same as and may be carried out in the same manner as and using the same reagents and reaction conditions as Step D4 of Method D.

Method F

In Method F, a compound of formula (2d) or a compound of formula (2e), which are amongst the starting materials used in Methods A and B, are prepared.

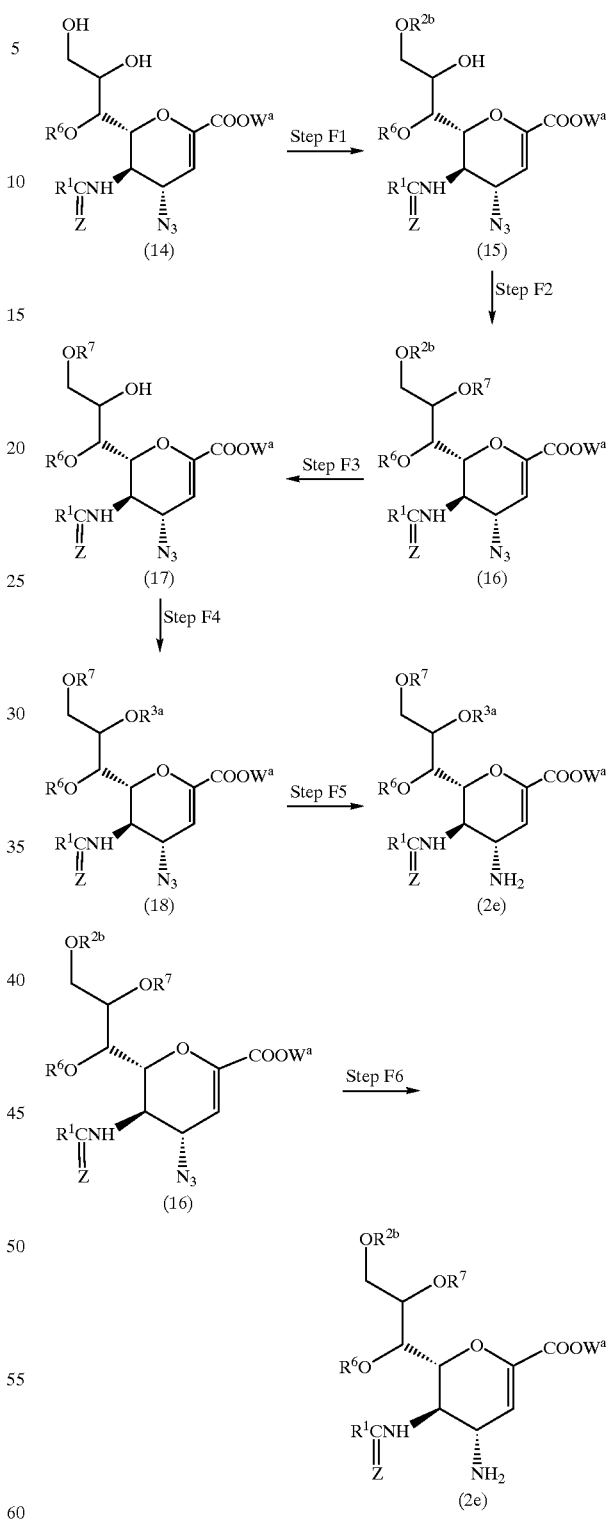

Reaction Scheme F

In the above formulae:
$R^1$, $R^{3a}$, $R^6$, Z and $W^a$ are as defined above;
$R^{2b}$ represents a hydroxy-protecting group, preferably a t-butyldimethylsilyl group; and
$R^7$ represents an aliphatic acyl group having from 2 to 25 carbon atoms.

Step F1

In this Step, a compound of formula (15) is prepared by reacting the compound of formula (14) with a reagent which protects a primary hydroxy group in an inert solvent.

There is no particular restriction on the nature of the protecting group, provided that it can selectively protect a primary hydroxy group, and any hydroxy-protecting group commonly used in organic synthesis can be used here. Examples of such groups include tialkylsilyl, dialkylarylsilyl and alkyldiarylsilyl groups, such as the t-butyldimethylsilyl group and the t-butyldiphenylsilyl group.

Silylation can be carried out by any conventional method. For example, silylation can be carried out by reacting the compound of formula (14) with a t-butyldimethylsilyl halide (particularly the chloride) in the presence of a base, such as triethylamine or 4-(N,N-dimethylamino)pyridine in a solvent such as dimethylformamide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –10 to 50° C., more preferably from 10 to 40° C. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 10 to 20 hours, will usually suffice.

After completion of the reaction, the desired compound can be recovered from the reaction mixture by conventional means. For example, one suitable recovery procedure comprises: adding a water-immiscible solvent, such as ethyl acetate, and an aqueous solution of sodium hydrogencarbonate to the reaction solution; extracting the desired compound with a suitable solvent, such as ethyl acetate; and distilling off the solvent. The desired compound can, if desired, be further purified by recrystallization or the various types of chromatography, such as column chromatography or preparative thin layer chromatography.

Step F2

In this Step, a compound of formula (16) is prepared by introducing a desired acyl group into the compound of formula (15) in an inert solvent This reaction is essentially the same as and may be carried out in the same manner as and using the same reagents and reaction conditions as Step C1 of Method C.

Step F3

In this Step, a compound of formula (17) is prepared by reacting the compound of formula (16) with a reagent which removes the protecting group for the primary hydroxy group.

The reaction is normally and preferably effected in the presence of a solvent there is no particular restriction on the nature of the solvent to be employed, provided that it has no adverse effect on the reaction or on the reagents involved and that it can dissolve the reagents, at least to some extent Examples of suitable solvents include: alcohols, such as methanol and ethanol; water, or a mixture of any two or more of these solvents.

There is likewise no particular restriction on the nature of the deprotecting agents used, and any deprotecting agent commonly used in reactions of this type may equally be used here. Examples of such deprotecting agents include acids. The nature of the acid is not critical, and any acid commonly used in conventional reactions as an acid catalyst may be used here. Examples include: Bronsted acids, such as inorganic acids (e.g. hydrochloric acid, hydrobromic acid, sulfuric acid, perchloric acid and phosphoric acid) and organic acids, such as acetic acid, formic acid, oxalic acid, methanesulfonic acid, p-toluenesulfonic acids trifluoroacetic acid and trifluoromethanesulfonic acid; Lewis acids, such as zinc chloride, tin tetrachloride, boron trichloride, boron trifluoride and boron tribromide; and acidic ion exchange resins. Of these, we prefer the organic acids (particularly acetic acid and trifluoroacetic acid).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –10 to 50° C., more preferably from 10 to 30° C. The time required for the reaction may also vary widely, depending on many factors, notably the reaction temperature and the nature of the reagents and solvent employed. However, provided that the reaction is effected under the preferred conditions outlined above, a period of from 15 minutes to 10 hours, more preferably from 1 to 5 hours, will usually suffice.

After completion of the reaction, the desired compound can be recovered from the reaction mixture by conventional means. For example, one suitable recovery procedure comprises: neutralising the reaction solution; distilling off the solvent under reduced pressure; and purifying the residue thus obtained by silica gel chromatography.

In this step, the acyl group ($R^7$) at the 8-position is shifted to the 9-position.

A reagent for forming a fluoride anion such as tetrabutylammonium fluoride can be used, if desired, as the deprotecting agent.

Step F4

This step may be carried out by:

1) acylating the hydroxy group in the 8-position; or 2) protecting the hydroxy group.

The reaction of step 1) is essentially the same as and may be carried out in the same manner as and using the same reagents and reaction conditions as Step C1 of Method C.

The reaction of step 2) can be carried out by using t-butyldimethylsilyl triflate as the reagent for introducing a protecting group, and using lutidine as a base in methylene chloride as the solvent.

Step F5

In this Step, a compound of formula (2d) is prepared from the compound of formula (18) by using a reducing agent in an inert solvent.

This reaction is essentially the same as and may be carried out in the same manner as and using the same reagents and reaction conditions as Step D4 of Method D.

Step F6

In this Step, a compound of formula (2e) is prepared from the compound of formula (16) by using a reducing agent in an inert solvent.

This reaction is essentially the same as and may be carried out in the same manner as and using the same reagents and reaction conditions as Step D4 of Method D.

Method G

In Method G, a compound of formula (2f) or a compound of formula (2g), which are among the staring materials used in Methods A and B, are prepared.

Reaction Scheme G

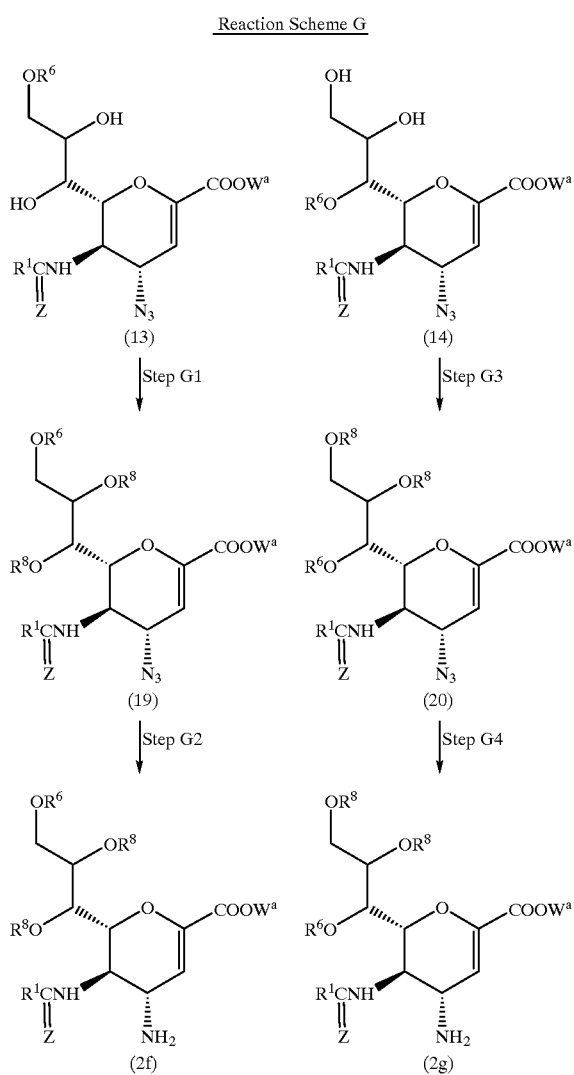

Step G4

In this Step, a compound of formula (2g) is prepared from the compound of formula (20) by using a reducing agent in an inert solvent.

This reaction is essentially the same as and may be carried out in the same manner as and using the same reagents and reaction conditions as Step D4 of Method D.

Method H

In Method H, a compound of formula (5), which is among the starting materials used in Method C is prepared.

Reaction Scheme H

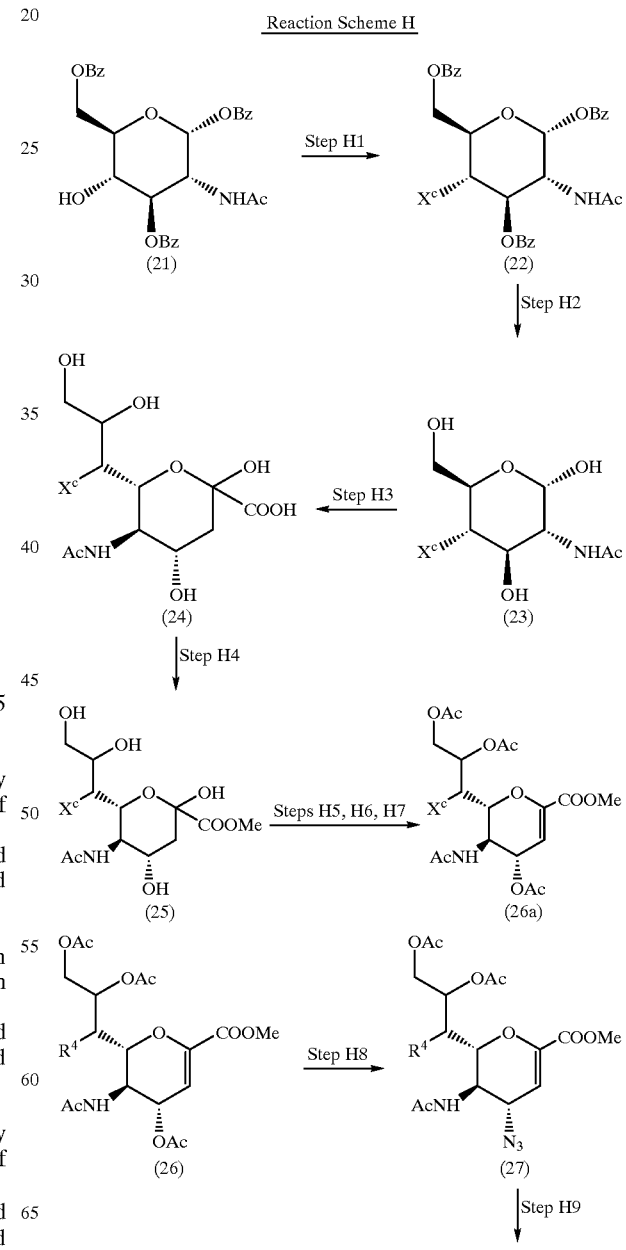

In the above formulae:

$R^1$, $R^6$, Z and $W^a$ are as defined above; and $R^8$ represents an aliphatic acyl group having from 2 to 25 carbon atoms.

Step G1

In this Step, a compound of formula (19) is prepared by introducing a desired acyl group into the compound of formula (13) in an inert solvent.

This reaction is essentially the same as and may be carried out in the same manner as and using the same reagents and reaction conditions as Step C1 of Method C.

Step G2

In this Step, a compound of formula (2f) is prepared from the compound of formula (19) by using a reducing agent in an inert solvent.

This reaction is essentially the same as and may be carried out in the same manner as and using the same reagents and reaction conditions as Step D4 of Method D.

Step G3

In this Step, a compound of formula (20) is prepared by introducing a desired acyl group into the compound of formula (14) in an inert solvent.

This reaction is essentially the same as and may be carried out in the same manner as and using the same reagents and reaction conditions as Step C1 of Method C.

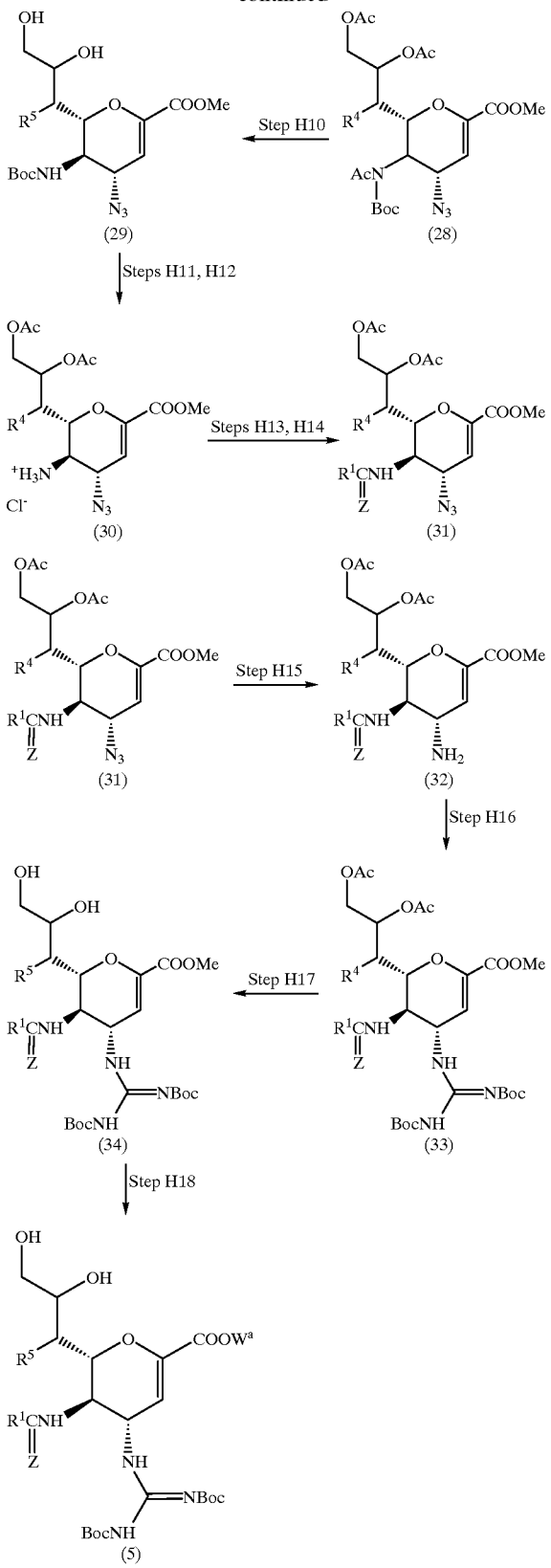

In the above formulae:

R[1], R[4], R[5], Z, W[a], Ac, Boc and Me are as defined above;

X[c] represents an alkoxy group having from 1 to 4 carbon atoms; and

Bz represents a benzyl group.

Step H1

In this Step, a compound of formula (22) is prepared by reacting an alkyl halide with a compound of formula (21) [described in Carbohydrate Research 83, 163–169 (1980)] in the presence of a base and in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptine, ligroin and petroleum ether; aromatic hydrocarbons, such as benzene, toluene and xylene; ethers, such as diethyl ether, diisopropyl ether, tetrrhydrofuran, dioxane, dimethoxyethane and diethylene glycol dimethyl ether; amides, such as formamide, dimethylformamide, N,N-dimethylacetamide, N-methyl-2-pyrrolidone, N-methylpyrrolidinone and hexamnethylphosphoric triamide; and sulfoxides, such as dimethyl sulfoxide and sulfolane. Of these, we prefer the amides (particularly dimethylformamide).

There is likewise no particular restriction on the nature of the bases used, and any base commonly used in reactions of this type may equally be used here. Examples of such bases include: alkali metal hydrides, such as lithium hydride, sodium hydride and potassium hydride; alkali metal alkoxides, such as sodium methoxide, sodium ethoxide, potassium methoxide, potassium ethoxide, potassium t-butoxide and lithium methoxide; pikali metal mercaptans, such as N-methylmercaptan sodium and ethylmercaptan sodium; organic bases, such as N-methylmorpholine, triethylamine, tripropylamine, tributylamine, diisopropylethylamine, dicyclohexylamine, N-methylpiperidine, pyridine, 4-pyrrolidinopyridine, picoline, 4-N,N-dimethylaio)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU); and organic metal bases, such as butyllithium, lithium diisopropylamide and lithium bis(trimethylsilyl)amide. Of these, we prefer the alkali metal hydrides particularly sodium hydride).

There is likewise no particular restriction on the nature of the alkyl halides used, and any alkyl halide commonly used in reactions of this type may equally be used here. Preferred such alkyl halides include the alkyl bromides and alkyl iodides.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 50° C., more preferably at about room temperature. The time required for the reaction may also vary widely, depending on many factors, notably the reaction temperature and the nature of the reagents, base and solvent employed. However, provided that the reaction is effected under the preferred conditions outlined above, a period of from 15 minutes to 24 hours, more preferably from 2 to 10 hours, will usually suffice.

After completion of the reaction, the desired compound can be recovered from the reaction mixture by conventional means. For example, one suitable recovery procedure comprises: adding a water-immiscible solvent, such as ethyl acetate, and an aqueous solution of sodium hydrogencarbonate to the reaction solution; extracting the desired compound with a suitable solvent, such as ethyl acetate; and distilling off the solvent. The desired compound can, if desired, be further purified by recrystallization or the various types of chromatography, such as column chromatography or preparative thin layer chromatography.

Step H2

In this Step, a compound of formula (23) is prepared by reacting a reducing agent with the compound of formula (22) in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as methanol and ethanol; ethers, such as tetrahydrofuran and dioxane; fatty acids, such as acetic acid; or a mixture of any one or more of these organic solvents and water. Of these, we prefer acetic acid.

The reduction is preferably effected by means of hydrogen in the presence of a hydrogenation catalyst. There is likewise no particular restriction on the nature of the hydrogenation catalysts used, and any hydrogenation catalyst commonly used in reactions of this type may equally be used here. Examples of such hydrogenation catalysts include: palladium-on-carbon, platinum and Raney nickel, preferably palladium-on-carbon.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 15 minutes to 24 hours, more preferably from 2 to 10 hours, will usually suffice.

After completion of the reaction, the desired compound can be recovered from the reaction mixture by conventional means. For example, one suitable recovery procedure comprises: removing the hydrogenation catalyst by filtration; distilling off the solvent; and purifying the residue thus obtained by recrystallization or by the various forms of chromatography.

Step H3

In this Step, a compound of formula (24) is prepared by reacting sodium pyruvate with the compound of formula (23) in the presence of N-acetylneuraminic acid aldolase and sodium azide in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. A preferred solvent is water.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 5 hours to 5 days, more preferably from 1 to 3 days, will usually suffice.

After completion of the reaction, the desired compound can be recovered from the reaction mixture by conventional means. For example, one suitable recovery procedure comprises: desalting the compound by means of a cation exchange resin; and purifying the compound by chromatography using an anion exchange resin.

Step H4

In this Step, a compound of formula (25) is prepared by esterifying the compound of formula (24) in the presence of an acid in a methanol solvent.

There is no particular restriction on the nature of the acids used, and any acid commonly used as an acid catalyst in reactions of this type may equally be used here. Examples of such acids include: Bronsted acids, such as inorganic acids (e.g. hydrochloric acid, hydrobromic acid, sulfric acid, perchloric acid or phosphoric acid) or organic acids (e.g. acetic acid, formic acid, oxalic acid, methanesulfonic acid, p-toluenesulfonic acid, trifluoroacetic acid or trifluoromethanesulfonic acid); Lewis acids, such as zinc chloride, stannous tetrachloride, boron trichloride, boron trifluoride and boron tribromide; and cation exchange resins. Of these, we prefer the cation exchange resins.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 1 to 48 hours, more preferably from 5 to 24 hours, will usually suffice.

After completion of the reaction, the desired compound can be recovered from the reaction mixture by conventional means. For example, one suitable recovery procedure comprises: removing the cation exchange resin by filtration; distilling off the solvent; and purifying the residue thus obtained by recrystallization or by the various forms of chromatography.

Step H5

In this Step, a compound of formula (25) is acylated in an inert solvent.

This reaction is essentially the same as and may be carried out in the same manner as and using the same reagents and reaction conditions as Step C1 of Method C.

Step H6

In this Step, the compound obtained in Step H5 is chlorinated by reacting the compound obtained in Step H5 with hydrogen chloride in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent.

Examples of suitable solvents include: aliphatic hydrocarbons, such as hexane, heptane, ligroin and petroleumn ether; aromatic hydrocarbons, such as benzene, toluene and xylene; and ethers, such as diethyl ether, diisopropyl ether, tetrahydroflran, dioxane, dimethoxyethane and diethylene glycol dimethyl ether. Of these, we prefer the ethers (particularly dioxane).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 5 hours to 2 days, more preferably from 10 to 24 hours, will usually suffice.

After completion of the reaction, the solvent and hydrogen chloride are distilled off under reduced pressure and the product is used as such for the next reaction.

Step H7

In this Step, a compound of formula (26a) is prepared by reacting a base with the compound obtained in Step H6 to carry out dehydrochlorination.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; and ethers, such as diethyl ether, diisopropyl ether, tetrahydrofuran, dioxane, dimethoxyethane and diethylene glycol dimethyl ether. Of these, we prefer the aromatic hydrocarbons (particularly benzene).

There is likewise no particular restriction on the nature of the bases used, and any base commonly used in reactions of this type may equally be used here. Examples of such bases include: alkali metal alkoxides, such as sodium methoxide, sodium ethoxide, potassium methoxide, potassium ethoxide, potassium t-butoxide and lithium methoxide; mercaptan alkali metals, such as methylmercaptan sodium and ethylmercaptan sodium; organic bases, such as N-methylmorpholine, triethylamine, tripropylamine, tributylamine, diisopropylethylamine, dicyclohexylamnine, N-methylpiperidine, pyridine, 4-pyrrolidinopyridine, picoline, 4-(N,N-dimethylamino)pyridine, 2,6-di(t-butyl-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) and 1,8-diazabicyclo[5.4.0]undec-7-ene (DBU), more preferably DBU.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 5 hours to 2 days, more preferably from 10 to 24 hours, will usually suffice.

After completion of the reaction, the desired compound can be recovered from the reaction mixture by conventional means. For example, one suitable recovery procedure comprises: adding a water-immiscible solvent, such as methylene chloride, and an aqueous solution of ammonium chloride to the reaction solution; extracting the desired compound; and distilling off the solvent. The desired compound can be purified by ether recrystallization and the various types of chromatography, such as column chromatography or preparative thin layer chromatography.

Step H8

In this Step, a compound of formula (27) is prepared by reacting the compound of formula (26a), prepared as described in Step H7, or another compound of formula (26), which may have been prepared as described in WO95/32955, with an azidating agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride and chloroform; ethers, such as ether, tetaahydrofuran, dioxane and dimethoxyethane, and nitriles, such as acetonitrile.

There is likewise no particular restriction on the nature of the azidating agents used, and any azidating agent commonly used in reactions of this type may equally be used here. Examples of such azidating agents include: diarylphosphoric azide derivatives, such as diphenylphosphoric azide; trialkylsilyl azides, such as trimethylsilyl azide and triethylsilyl azide; and alkali metal azides, such as sodium azide and potassium azide. Of these, we prefer sodium azide.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –10 to 50° C., more preferably from 10 to 30° C. The time required for the reaction may also vary widely, depending on many factors, notably the reaction temperature and the nature of the reagents and solvent employed. However, provided that the reaction is effected under the preferred conditions outlined above, a period of from 15 minutes to 10 hours, more preferably from 1 to 5 hours, will usually suffice.

After completion of the reaction, the desired compound can be recovered from the reaction mixture by conventional means. For example, one suitable recovery procedure comprises: neutaalising the reaction solution with a solution of hydrogen chloride in dioxane; distilling off the solvent under reduced pressure; and purifying the residue thus obtained by silica gel chromatography.

Step H9

In this Step, a compound of formula (28) is prepared by reacting the compound of formula (27) with a t-butoxycarbonylating agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride and chloroform; ethers, such as ether, tetrahydrofuran, dioxane and dimethoxyethane, and amides, such as dimethylformamide.

The t-butoxycarbonylation can be carried out by reacting di-t-butyl dicarbonate or 2-(t-butoxycarbonyloxyimino)-2-phenylacetonitrile in the presence of a base, for example 4-(N,N-dimethylamino)pyridine.

After completion of the reaction, the desired compound can be recovered from the reaction mixture by conventional means. For example, one suitable recovery procedure comprises: neutralising the reaction solution; distilling off the solvent under reduced pressure; adding a water-immiscible solvent, such as ethyl acetate, and water to the residue; extracting the desired compound with a suitable solvent, such as ethyl acetate; and distilling off the solvent. The desired compound can, if desired, be further purified by recrystallization or the various types of chromatography, such as column chromatography or preparative thin layer chromatography.

Step H10

In this Step, a compound of formula (29) is prepared by reacting the compound of formula (28) with a base in an inert solvent.

This reaction is essentially the same as and may be carried out in the same manner as and using the same reagents and reaction conditions as Step D1 of Method D.

Step H11

In this Step, the compound of formula (29) is acetylated in an inert solvent.

The acetylation may be carried out by conventional means, commonly used for the protection of a hydroxy group. For example, the acetylation may be carried out 1) by reacting the compound of formula (29) with acetic anhydride in pyridine or 2) by reacting the compound of formula (29) with an acetyl halide (particularly the chloride) in the presence of a base catalyst (for example, triethylamine, 4-N,N-dimethylaminopyridine) in methylene chloride.

After completion of the reaction, the desired compound can be recovered from the reaction mixture by conventional means. For example, one suitable recovery procedure comprises: distilling off the solvent under reduced pressure; adding a water-immiscible solvent, such as ethyl acetate, and an aqueous solution of sodium hydrogencarbonate to the residue; extracting the desired compound with a suitable solvent, such as ethyl acetate; and distilling off the solvent. The desired compound can, if desired, be further purified by recrystallization or the various types of chromatography, such as column chromatography or preparative thin layer chromatography.

Step H12

In this Step, a compound of formula (30) is prepared by treating the compound obtained in Step H11 with a reagent which eliminates a t-butoxycarbonyl group in an inert solvent.

Elimination of the t-butoxycarbonyl group may be carried out by conventional processes.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent Examples of suitable solvents include: aliphatic hydrocarbons, such as hexane, heptane, ligroin and petroleum ether, aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether, amides, such as formamide, dimethylformamide, N,N-diinethylacetamide, N,N-methyl-2-pyrrolidone, N-methylpyrrolidinone and hexamethylphosphoric triamide; and sulfoxides, such as dimethyl sulfoxide and sulfolane. Of these, we prefer the halogenated hydrocarbons (particularly methylene chloride).

There is likewise no particular restriction on the nature of the reagent used to eliminate the t-butoxycarbonyl group, and any reagent commonly used in reactions of this type may equally be used here. An example of such a reagent is hydrochloric acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −10 to 50° C., more preferably from 10 to 30° C. The time required for the reaction may also vary widely, depending on many factors, notably the reaction temperature and the nature of the reagents and solvent employed. However, provided that the reaction is effected under the a preferred conditions outlined above, a period of from 15 minutes to 24 hours, more preferably from 1 to 10 hours, will usually suffice.

After completion of the reaction, the desired compound can be recovered a from the reaction mixture by conventional means. For example, one suitable recovery procedure comprises: distilling off the solvent under reduced pressure; adding a water-immiscible solvent, such as ethyl acetate, and an aqueous solution of sodium hydrogencarbonate to the reaction solution; extracting the desired compound with a suitable solvent, such as ethyl acetate; and distilling off the solvent. The desired compound can, if desired, be further purified by recrystallization or the various types of chromatography, such as column chromatography or preparative thin layer chromatography.

Step H13

In this Step, an acyl group is introduced into the compound of formula (30) by reaction with an acylating agent in an inert solvent.

This reaction is essentially the same as and may be carried out in the same manner as and using the same reagents and reaction conditions as Step C1 of Method C.

Step H14

In this Step, a compound of formula (31) is prepared by reacting the compound obtained in Step H13 with a reagent which converts a carbonyl group into a thiocarbonyl group in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether, aromatic hydrocarbons, such as benzene, toluene and xylene; halogenated hydrocarbons, such as methylene chloride, chloroform, carbon tetrachloride, dichloroethane, chlorobenzene and dichlorobenzene; and ethers, such as diethyl ether, diisopropyl ether, tetrahydroflran, dioxane, dimethoxyethane and diethylene glycol dimethyl ether. Of these, we prefer the ethers (particularly tetrahydrofuran).

There is no particular restriction on the nature of the reagent employed to convert the carbonyl group into a thiocarbonyl group is preferably Lawesson's reagent.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10 to 100° C., more preferably from 40 to 70° C. The time required for the reaction may also vary widely, depending on many factors, notably the reaction temperature and the nature of the reagents and solvent employed. However, provided that the reaction is effected under the preferred conditions outlined above, a period of from 15 minutes to 10 hours, more preferably from 1 to 5 hours, will usually suffice.

After completion of the reaction, the desired compound can be recovered from the reaction mixture by conventional means. For example, one suitable recovery procedure comprises: adding a water-immiscible solvent, such as ethyl acetate, and an aqueous solution of sodium hydrogencarbonate to the reaction solution; extracting the desired compound with a suitable solvent, such as ethyl acetate; and distilling off the solvent. The desired compound can, if desired, be further purified by recrystallization or the various types of chromatography, such as column chromatography or preparative thin layer chromatography.

Step H15

In this Step, a compound of formula (32) is prepared from the compound of formula (31) by using a reducing agent in an inert solvent.

This reaction is essentially the same as and may be carried out in the same manner as and using the same reagents and reaction conditions as Step D4 of Method D.

Step H16

In this Step, a compound of formula (33) is prepared by reacting the compound of formula (32) with N,N-di-t-butoxycarbonylthiourea in the presence of a base and mercuric chloride in an inert solvent.

This reaction is essentially the same as and may be carried out in the same manner as and using the same reagents and reaction conditions as Step A1 of Method A.

Step H17

In this Step, a compound of formula (34) is prepared by reacting the compound of formula (33) described later with a base in an inert solvent.

This reaction is essentially the same as and may be carried out in the same manner as and using the same reagents and reaction conditions as Step D1 of Method D.

Step H18

The present step may be carried out, if desired, by 1) converting a methyl group of a carboxylic acid ester into another substituent, 2) hydrolysing a carboxylic acid ester or 3) protecting the carboxylic acid after step 2) above.

This reaction is essentially the same as and may be carried out in the same manner as and using the same reagents and reaction conditions as Step D3 of Method D.

In some cases, the compounds of the present invention can be prepared efficiently by carrying out the above steps in a different order, as will be appreciated by the skilled reader.

The compounds of the present invention may be administered alone or in admixture with conventional pharmaceutically acceptable carriers, diluents or adjuvants and in various formulations, as is well known in the art. For example, the compounds of the present invention may be given by oral or intranasal administration as a liquid preparation, such as a solution or suspension (optionally in an aqueous medium or in a mixture or such a medium and an aqueous cosolvent 3), or as an aerosol or a powder preparation. The liquid preparations, such as solutions, optionally including an aqueous cosolvent, may be prepared by conventional means, for example using purified water, a pharmaceutically acceptable organic solvent (for example, ethanol, propylene glycol or PEG400), a stabilizing agent (a paraoxybenzoate, such as methylparaben or propylparaben; an alcohol, such as chlorobutanol, benzyl alcohol or phenylethyl alcohol; a benzalkonium chloride; a phenol, such as phenol or cresol; thimerosal; or dehydroacetic acid). Aerosols may be prepared by conventional means, using a propellant, such as the various Freon (trade mark) gases or nitrogen gas and a surface active agent, such as lecithin. Powder preparations may be prepared by conventional means, using any one or more of an excipient, a lubricant, a stabilizing agent, a corrigent and a diluent. Examples of such excipients include organic excipients including: sugar derivatives, such as lactose, sucrose, glucose, mannitol and sorbitol; starch derivatives, such as corn starch, potato starch, α-starch, dextrin and carboxymethyl starch; cellulose derivatives, such as crystalline cellulose, low substitution hydroxypropyl cellulose, hydroxypropylmethyl cellulose, carboxymethyl cellulose, calcium carboxymethyl cellulose and internally crosslinked sodium carboxymethyl cellulose; gum arabic; dextran; and pullulan. Other excipients include inorganic excipients including: silicate derivatives, such as soft silicic anhydride, synthetic aluminum silicate and magnesium aluminate metasilicate; phosphates, such as calcium phosphate; carbonates, such as calcium carbonate; and sulfates, such as calcium sulfate. Examples of lubricants include: stearic acid; metal salts of stearic acid such as calcium stearate and magnesium stearate; talc; colloid silica; waxes, such as beeswax and sperm whale; boric acid; adipic acid; sulfates, such as sodium sulfate; glycol; fimaric acid; sodium benzoate; DL-leucine; fatty acid sodium salts; laurylsulfates, such as sodium laurylsulfate and magnesium laurylsulfate; silicic acids, such as silicic anhydride and silicic hydrate; and the above starch derivatives. Examples of stabilizing agent include: paraoxybenzoates, such as methylparaben and propylparaben; alcohols, such as chlorobutanol, benzyl alcohol and phenylethyl alcohol; benzalkonium chlorides; phenols, such as phenol and cresol; thimerosal; dehydroacetic acid; and sorbic acid. Examples of corrigents include sweeteners, souring agents and flavors.

The amount of the active component to be used will vary depending on the symptoms, age, and body weight of the patient, as well as upon the mode of administration and the severity of the disease. However, in general, it is desirable to administer the active component in an amount of from 0.1 mg per day (preferably 1 mg) to 1000 mg (preferably 500 mg) in the case of liquid preparations; in the case of dry powder preparations, the active component is preferably administered in an amount of from 0.1 mg per day (preferably 1 mg) to 1000 mg (preferably 500 mg); in the case of aerosols, the active component is preferably administered in an amount of from 0.1 mg per day (preferably 1 mg) to 1000 mg (preferably 500 mg). This may be administered in a single dose or in divided doses, depending on the condition.

BIOLOGICAL ACTIVITY

The 2-deoxy-2,3-didehydro-N-acylneuraminic acid derivatives of the present invention have excellent sialidase inhibitory activity, and are, accordingly, useful in the prophylaxis and therapy of influenza The activity of compounds of the present invention is further illustrated by the following Experiments.

EXPERIMENT 1

Influenza Virus Replication Inhibitory Activity

Influenza virus strain A/Yamagata/32189(H1N1) was proliferated in a live hen's egg, and the virus produced by this technique was then applied to plates of MDCK cells (derived from canine kidney) to obtain plaques. MDCK cells were infected with virus in the presence or absence of various concentrations of test compound. Influenza virus replication inhibitory activity of test compounds could then be calculated by comparing the amounts of plaques in the control and test samples.

The methodology of the present Experiment was generally in accordance with Antimicrobial Agents And Chemotherapy, 17, pp.865–870 (1980).

More specifically, MDCK cells were cultured to a single, confluent layer on the surface of petri-dishes having a diameter of 35 mm. The culture conditions of the MDCK cells on these plates were 37° C. under a sterile atmosphere containing 5% v/v carbon dioxide gas. After the cells had reached confluence, the culture liquid was sucked off. An amount of phosphate buffered physiological saline solution containing 50–100 pfu (plaque forming units) of virus was then added to the plates.

The resulting plates were then left to stand for 1 hour at 37° C. to permit adsorption of the virus, after which time the remaining phosphate buffered physiological saline solution was sucked off and replaced with MEM medium (Gibco BRL) containing 1 µg/ml of trypsin (Cooper Biomedical), 0.01% w/w DEAE dextran (Pharmacia LKB), 0.6% w/w agar (Sigma) together with an amount of between 0.00056 and 5.6 µg/ml of test compound.

Cultivation of the plates was continued at 37° C. for 40 hours under a sterile atmosphere containing 5% carbon dioxide gas, after which time solidified agar medium was recovered. Crystal violet (Merck) was dissolved in 19% methanol to a final concentration of 0.01% and was added to the recovered agar in order to fix and stain the cells, thereby permitting determination of the number of plaques.

The number of plaques formed in the absence of test compound is taken as 100% (the control). It was then possible to calculate $IC_{50}$ (the concentration in nM/ml at which the test compound reduces the number of observed plaques to 50%,) as a measure of influenza virus replication inhibitory activity.

The compounds of the present invention were found to exhibit high influenza virus replication inhibitory activity, as shown in Tables 3 and 4, below.

TABLE 3

| Test Compound | $IC_{50}$ (nM) |
|---|---|
| Compound A | 4.7 |
| Compound of Example 28 | 1.7 |

TABLE 4

| Test Compound | $IC_{50}$ (nM) |
|---|---|
| Compound A | 11 |
| Compound of Example 30 | 0.8 |

Compound A in the above Tables 3 and 4, as well as in Tables 5 and 6 below, is the compound prepared in Example 3 of Toku-Hyo-Hei 5-507068. Its structure is shown below:

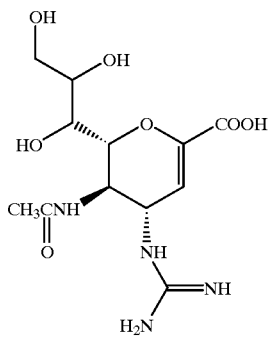

added as a trifluoroacetic acid salt.

EXPERIMENT 2

Influenza Virus Sialidase Inhibitora Activity

In this experiment, a sample of influenza virus strain A/PR/8/34(H1N1) was dissolved by means of a surfactant, after which the virus membrane fraction was purified by centrifugation. The thus purified fraction was used as a crude influenza virus sialidase, and p-nitrophenyl-N-acetylneuraminic acid (Wako Pure Chemical) was used as a substrate to perform similar tests to those described in Analytical Biochemistry, 94, 287–296 (1979).

An enzyme solution was first prepared such that the final enzyme activity was 0.001 1 units/ml (1 unit corresponds to that amount of enzyme which hydrolyzes 1 µmole of substrate in 1 minute). Also prepared beforehand were aqueous solutions of test compound in various concentrations; an aqueous solution of the substrate to a concentration of 33 µg/ml, and a 20 mM 2-(N-morpholino)-ethanesulfonic acid buffer (pH 6.5) containing 50 mM calcium chloride. These solutions were combined to prepare a mixture having a final volume of 150 µl, and which was then left to stand at 37° C. for 20 minutes. The absorbance of any p-nitrophenol formed in the mixture was measured at 415 nm. The absorbance measured at 415 nm where the mixture was prepared by adding water in place of the aqueous solution of test compound was taken as 100%. Thus, $IC_{50}$ (nM) was determined as the concentration of the sample at which the absorbance was reduced by 50%, to provide a measure of influenza virus sialidase inhibitory activity.

The results are shown below in Table 5.

TABLE 5

| Test Compound | IC$_{50}$ (nM) |
|---|---|
| Compound A | 9.0 |
| Compound of Example 28 | 13 |
| Compound of Example 30 | 7.0 |

EXPERIMENT 3

Mouse Infection Test

A solution of 1500 pfu of mouse-adapted influenza virus strain A/PR/8/34 in 50 μl of a 0.42% v/v bovine serum albuminontaining phosphate buffer was prepared, and mice (BALB/C, female, age: 5 to 6 weeks, 20 g) were infected dropwise, intranasally, with the resulting solution. Test compound was suspended in a physiological saline solution to provide a dosage of 0.9 μmol/kg/50 μl. The resulting suspension was administered dropwise intranasally 3 times in total, once 4 hours before the virus infection, once 4 hours after the infection and once at 17 hours after the infection. The result is shown in terms of the number of mice surviving after 6 days, 8 days, 10 days and 15 days from infection. The test was conducted on groups of mice, each group consisting of 12 animals. The results are shown in Table 6 below.

TABLE 6

|  | 6th day | 8th day | 10th day | 15th day |
|---|---|---|---|---|
| Physiological saline only | 2 | 0 | 0 | 0 |
| Compound A | 12 | 2 | 1 | 0 |
| Compound of Example 29 | 12 | 12 | 12 | 12 |
| Compound of Example 34 | 12 | 12 | 11 | 10 |

Thus, it can be seen that the compounds of the present invention greatly enhance the survival rate of animals exposed to the influenza virus.

EXAMPLE 1

5-Acetamido-4-(C-aminooxy-C-iminomethylamino)-7-O-hexanoyl-2,3,4,5-tetradeoxy-D-glycero-D-galacto-non-2-wnopyreaosoic acid (Compound No. 761)

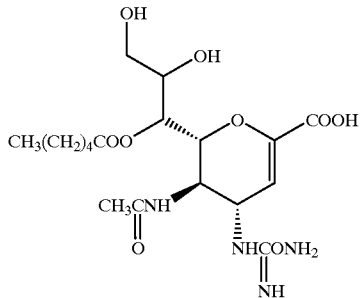

1(i) Methyl 5-acetamido-4-azido-2,3,4,5-tetradeoxy-D-glycero-D-galacto-non-2-enogyranosoate 7 g (15.3 mmol) of methyl 5-acetamido-7,8,9-tri-O-acetylfazido-2,3,4,5-tetradeoxy-D-glycero-D-galacto-non-2-enopyranosoate were dissolved in 20 ml of methanol, and 0.2 ml of a 4.9 M methanolic solution of sodium methoxide (0.98 mmol) was added dropwise to the resulting solution, while stirring at room temperature. The reaction mixture was then stirred at room temperature for 2 hours, after which a 4 M solution of hydrogen chloride in dioxane was added dropwise thereto. The pH of the mixture was adjusted to a value of 6 to 7, and then the mixture was evaporated to dryness under a vacuum. The resulting residue was subjected to silica gel column chromatography, using a 10:1 by volume mixture of methylene chloride and methanol as the eluent, to obtain 3.56 g (yield 69%) of the title compound as a colorless solid.

Rf=0.63 (5:1=methylene chloride: methanol). Mass Spectrum (FAB) mre 331 (M$^+$+H). ("FAB" is "Fast Atom Bombardment".) [α]$D^{25}$+28.4° (c=0.21, methanol). Infrared Absorption Spectrum ν$_{max}$ (cm$^{-1}$): 2100, 1731, 1657. $^1$H-Nuclear Magnetic Resonance Spectrum (CD$_3$OD, 270 MHz) δ (ppm): 5.92 (1H, doublet, J=2.3 Hz); 4.34 (1H, doublet of doublets, J=9.3 & 2.5 Hz); 4.27 (1H, doublet of doublets, J=10.7 & 1.2 Hz); 4.13 (1H, doublet of doublets, J=10.8 & 9.4 Hz); 3.82–3.92 (2H, multiplet); 3.79 (3H, singlet); 3.66 (1H, doublet of doublets, J=11.4 & 5.0 Hz); 3.60 (1H, broad doublet, J=9.3 Hz); 2.03 (3H, singlet).

1(ii) Methyl 5-acetamido-4-azido-8,9-O-isopropylidene-2,3,4,5-tetradeoxt-D-glycero-D-galacto-non-2-enopvranosoate 3.33 g (10.1 mmol) of methyl 5-acetamido4azido-2,3,4,5-tetradeoxy-D-glycero-D-galacto-non-2-enopyranosoate [prepared as described in step (i) above] were dissolved in 10 ml of acetone, and 3.7 ml of 2,2-dimethoxypropane (30.2 mmol) and 100 mg of p-toluenesulfonic acid 1 hydrate (0.52 mmol) were added to the resulting solution while stirring at room temperature. The mixture was then stirred for 30 minutes. At the end of this time, 200 ml of ethyl acetate and 60 ml of a saturated aqueous solution of sodium hydrogencarbonate were added to the reaction mixture, and the mixture was partitioned to separate the organic layer. The organic layer was washed three times, each time with 50 ml of a saturated aqueous solution of sodium hydrogencarbonate, and then once with 50 ml of a saturated aqueous solution of sodium chloride. It was then dried over anhydrous sodium sulfate, and the solvent was removed by distillation under reduced pressure to obtain a residue. This residue was subjected to silica gel column chromatography, using a 2:1 by volume mixture of ethyl acetate and hexane as the eluent, to obtain 3.24 g (yield 87%) of the title compound as a colorless solid.

Rf=0.38 (20:1=methylene chloride: methanol). Mass Spectrum (FAB) m/e 371 (M$^+$+H.) [α]$D^{25}$+160.93° (c=0.32, CHCl$_3$). Infrared Absorption Spectrum ν$_{max}$ (cm$^{-1}$): 2094, 1734, 1656. $^1$H-Nuclear Magnetic Resonance Spectrum (CDCl$_3$, 270 MHz) δ (ppm): 5.98 (1H, doublet, J=2.5 Hz); 5.66 (1H, broad doublet, J=6.9 Hz); 4.32–4.41 (1H, multiplet); 4.03–4.28 (6H, multiplet); 3.81 (3H, singlet); 3.57 (1H, doublet of doublets, J=7.9 & 5.2 Hz); 2.12 (3H, singlet); 1.66 (1H, singlet); 1.39 (3H, singlet); 1.36 (3H, singlet);

1 (iii) Methyl 5-acetamido-4-azido-7-O-hexanal-8,9-O-isopropyidene-2,3,4-tetradeoxy-D-glycero-D-galacto-non-2-enopyranosoate 1.35 g (3.65 mmol) of methyl 5-acetamido-4azido-8,9-O-isopropylidene-2,3,4,5-tetradeoxy-1-glycero-12-galacto-non-2-enopyranosoate [prepared as described in step (ii) above] were dissolved in 30 ml of methylene chloride, and 490 mg (4.01 mmol) of dimethylaminopyridine and 0.61 ml (4.37 mmmol) of hexanoyl chloride were added to the resulting solution while stirring and ice-cooling. The reaction mixture was then stirred at room temperature for 30 minutes, after which 0.56 ml of triethylamine were added dropwise while ice-cooling. The mixture was then stirred at room temperature for a furher 2 days. 200 ml of ethyl acetate and 100 ml of a saturated aqueous solution of sodium hydrogencarbonate were added to the resulting solution, and the mixture was partitioned to separate the organic layer. The organic layer was washed three times, each time with 50 ml of a saturated aqueous solution of sodium chloride and dried over anhydrous sodium sulfate, after which the solvent was removed by distillation under reduced pressure to obtain a residue. This residue was subjected to silica gel column chromatography, using a 100:1 by volume mixture of methylene chloride and methanol as the eluent, to obtain 0.69 g (yield 34%) of the title compound as a yellow oil.

Rf=0.46 (20:1=methylene chloride: methanol). Mass Spectum (FAB) m/e 469 (M$^+$+H). [α]$D^{25}$+87.7° (c=0.26, CHCl$_3$). Infrared Absorption Spectrum $v_{max}$ (cm$^{-1}$): 2099, 1745, 1660. $^1$H-Nuclear Magnetic Resonance Spectrum (CDCl$_3$, 270 MHz) (ppm): 5.95 (1H, doublet, J=2.6 Hz); 5.76 (1H, broad doublet, J=7.8 Hz); 5.34 (1H, doublet of doublets, J=5.3 & 1.8 Hz); 4.85 (1H, doublet of doublets, J=9.0 & 2.7 Hz); 4.73 (1H, doublet of doublets, J=10.4 & 1.7 Hz); 4.39 (1H, doublet of doublets, J=11.4 & 6.1 Hz); 4.14 (1H, doublet of doublets, J=12.3 & 6.3 Hz); 3.95 (1H, doublet of doublets, J=8.8 & 6.2 Hz); 3.81 (3H, singlet); 3.40 (1H, doublet of doublets, J=18.7 & 8.6 Hz); 2.28–2.52 (2H, multiplet); 2.02 (3H, singlet); 1.53–1.72 (2H, multiplet); 1.37 (3H, singlet); 1.35 (3H, singlet); 1.25–1.43 (4H, multiplet); 0.86–0.94 (3H, multiplet).

1(iv) Methyl 5-acetamido-4-amino-7-O-hexanoyl-8,9-O-isopropylidene-2,3,4,5-tetradeoa-D-glycero-D-non-2-enopyanosnate 650 mg (1.38 mmol) of methyl 5-acetamido-4-azido-7-O-hexanoyl-8,9-O-isopropylidene-2,3,4,5-tetradeoxy-D-glycero-D-galacto-non-2-enopyranosoate [prepared as described in step (iii) above] were dissolved in 20 ml of methanol, and 400 mg of a Lindlar catalyst were added to the resulting solution while stirring at room temperature. The reaction system was then deaerated and the air was replaced with hydrogen. The reaction mixture was then stirred at room temperature for 2 hours, after which it was filtered under reduced pressure, and the solvent was removed from the filtrate by distillation under reduced pressure to obtain a residue. The resulting residue was subjected to silica gel column chromatography, using a 20:1 by volume mixture of methylene chloride and methanol, followed by a 10:1 by volume mixture of methylene chloride and methanol, as the eluent, to obtain 0.63 g (yield 100%) of the title compound as a yellow amorphous substance.

Rf=0.17 (10:1=methylene chloride: methanol). Mass Spectrum (FAB) m/e 443 (M$^+$+H). [α]$D^{25}$+30.6° (c=0.32, CHCl$_3$). Infrared Absorption Spectrum $v_{max}$ (cm$^{-1}$): 1743, 1660. $^1$H-Nuclear Magnetic Resonance Spectrum (CDCl$_3$, 270 MHz) δ (ppm): 5.97 (1H, doublet, J=2.3 Hz); 5.51 (1H, broad doublet, J=9.0 Hz); 5.43 (1H, doublet of doublets, J=5.0 & 1.9 Hz); 4.40 (1H, doublet of doublets, J=17.2 & 6.5 Hz); 4.37 (1H, doublet of doublets, J=9.9 & 1.4 Hz); 4.15 (1H, doublet of doublets, J=8.9 & 6.3 Hz); 3.95 (1H, doublet of doublets, J=8.7 & 6.8 Hz); 3.80 (3H, singlet); 3.73–3.80 (1H, multiplet); 3.60 (1H, doublet of doublets, J=19.0 & 9.3 Hz); 2.24–2.49 (2H, multiplet); 2.02 (3H, singlet); 1.53–1.70 (2H, multiplet); 1.37 (3H, singlet); 1.35 (3H, singlet); 1.25–1.43 (4H, multiplet); 0.86–0.94 (3H, multiplet).

1(v) 5-Acetamido-4-amino-7-O-hexanoyl-8,9-O-isopropylidene-2,3,4,5-tetradeoxy-D-glycero-D-galactonon-2-enopyranosok acid 470 mg (1.06 mmol) of methyl 5-acetamido-4-amino-7-Q-hexanoyl-8,9-O-isopropylidene-2,3,4,5-tetradeoxy-D-glycero-D-galacto-non-2-enopyranosoate [prepared as described in step (iv) above] were dissolved in a mixture of 4 ml of methanol and 4 ml of water, and 47 mg (1.12 mmol) of lithium hydroxide 1 hydrate were added to the resulting solution, while stiring at room temperature. The mixture was then stirred for a furter 30 minutes. At the end of this time, Dowex-50Wx8 (H$^+$) resin (Dowex is a trade mark) was gradually added to the mixture, and the pH of the mixture was adjusted to a value of about 7.5. Immediately after the pH adjustment, the resulting suspension was rapidly filtered under reduced pressure. The residue obtained by distilling off the filtrate under reduced pressure was subjected to silica gel column chromatography, using a 2:5:1 by volume mixture of isopropanol, ethyl acetate and water as the eluent, to obtain 375 mg (yield 82%) of the title compound as a colorless solid.

Rf=0.26 (2:5:1=isopropanol: ethyl acetate: methanol). Mass Spectrum (FAB) m/e 429 (M$^+$+H). [α]$D^{25}$+8.3° (c=0.48, CH$_3$OH). Infrared Absorption Spectrum $v_{max}$ (cm$^{-1}$): 1750, 1666. $^1$H-Nuclear Magnetic Resonance Spectrum (CD$_3$OD, 270 MHz) (ppm): 5.60 (1H, doublet, J=2.1 Hz); 5.41 (1H, doublet of doublets, J=5.4 & 1.9 Hz); 4.58 (1H, triplet, J=6.0 Hz); 4.15–4.28 (3H, multiplet); 3.92 (1H, doublet of doublets, J=10.8 & 6.1 Hz); 3.79–3.87 (1H, multiplet); 2.30–2.40 (2H, multiplet); 1.96 (3H, singlet); 1.53–1.70 (2H, multiplet); 1.35 (3H, singlet); 1.32 (3H, singlet); 1.25–1.43 (4H, multiplet); 0.87–0.96 (3H, multiplet).

1(vi) 5-Acetamido-4-amino-7-O-exanoyl-2,3,4,5-tetradeo-D-glycero-D-galacto-non-2-enopyranosoic acid 270 mg (0.63 mmol) of 5-acetamido-4-amino-7-O-hexanoyl-8,9-O-isopropylidene-2,3,4,5-tetradeoxy-D-glycero-D-galacto-non-2-enopyranosoic acid [prepared as described in step (v) above] were dissolved in a mixture of 12 ml of acetic acid and 3 ml of water at room temperature, and the mixture was then stirred at 60° C. for 2.5 hours. At the end of this time, the residue obtained by distilling off the solvent under reduced pressure was subjected to azeotropic distillation with benzene, followed by concentration to dryness under a vacuum. The resulting residue was subjected to silica gel column chromatography, using a 2:5:1 by volume mixture of isopropanol, ethyl acetate and water as the eluent, to obtain 174 mg (yield 71%) of the title compound as a colorless solid.

Rf=0.32 (5:1:1=isopropanol:ethyl acetate:methanol). Mass Spectrum (FAB) m/e 389 (M$^+$+H). [α]$D^{25}$+1.1° (c=0.14, CH$_3$OH). Infrared Absorption Spectrum $v_{max}$ (cm$^{-1}$): 1745, 1662. $^1$H-Nuclear Magnetic Resonance Spectrum (D2O, 270 MHz)δ (ppm): 5.66 (1H, doublet, J=2.2 Hz); 5.13 (1H, doublet of doublets, J=9.3 & 1.7 Hz); 4.47 (1H, doublet of doublets, J=10.5 & 1.3 Hz); 4.17 (1H, triplet, J=10.0 Hz); 4.00–4.10 (2H, multiplet); 3.59 (1H, doublet of doublets, J=12.0 & 3.1 Hz); 3.39 (1H, doublet of doublets, J=12.0 & 6.1 Hz); 2.32–2.39 (2H, multiplet); 1.91 (3H, singlet); 1.45–1.63 (2H, multiplet); 1.20–1.28 (4H, multiplet); 0.78–0.86 (3H, multiplet).

1(vii) 5-Acetamido-4-cyanamido-7-O-hexanoyl-2,3,4,5-tetradeoxy-D-glycero-D-galactonon-2-enopyranosoic acid 155 mg (0.40 mmol) of 5-acetamido-4-amino-7-O-hexanoyl-2,3,4,5-tetradeoxy-D-glycero-D-galacto-non-2-enopyranosoic acid [prepared as described in step (vi) above] were dissolved in 4 ml of methanol, and 65 mg (0.80 mmol) of sodium acetate and 53 mg (0.50 mmol) of cyanogen bromide were added to the resulting solution, while stirring at room temperature. The reaction mixture was then stirred at room temperature for a further 40 minutes, after which the solvent was removed by distillation under reduced pressure. The resulting residue was subjected to silica gel column chromatography, using a 2:5:1 by volume mixture of isopropanol, ethyl acetate and water as the eluent, to obtain 144 mg (yield 85%) of the title compound as a colorless solid.

Rf=0.21 (2:5:1=isopropanol:ethyl acetate:methanol). Mass Spectrum (FAB) m/e 436 (M$^+$+Na), 452 (M$^+$+K). $^1$H-Nuclear Magnetic Resonance Spectrum (CD$_3$OD, 270 MHz) δ (ppm): 5.73 (1H, doublet, J=1.0 Hz); 5.07 (1H, doublet of doublets, J=7.8 & 1.2 Hz); 4.49 (1H, doublet, J=10.6 Hz); 4.47 (1H, doublet of doublets, J=10.5 & 1.3 Hz); 4.05–4.18 (2H, multiplet); 3.85 (1H, doublet of doublets, J=9.8 & 1.8 Hz); 3.63–3.73 (1H, multiplet); 3.48–3.58 (1H, multiplet); 2.28–2.48 (2H, multiplet); 1.95 (3H, singlet); 51.54–1.68 (2H, multiplet); 1.28–1.40 (4H, multiplet); 0.87–0.96 (3H, multiplet).

1(viii) 5-Acetamido-4-(C-aminooxy-C-iminomethylamino)-7-O-hexanoyl-2,3,4,5-tetradegxo-D-glycero-D-galacto-non-2-enopvranosoic acid 88 mg (0.21 mmol) of 5-acetamido-4-cyanamido-7-O-hexanoyl-2,3,4,5-tetradeoxy-D-glycero-D-galacto-non-2-enopyranosoic acid [prepared as described in step (vii) above] were dissolved in 4 ml of methanol, and 15 mg (0.21 mmol) of hydroxylamine hydrochloride were added to the resulting solution, while stirring at room temperature. The reaction mixture was then stirred at room temperature for 2.5 hours, after which the solvent was removed by distillation under reduced pressure. The resulting residue was subjected to silica gel column chromatography, using a 2:5:12 by volume mixture of isopropanol, ethyl acetate and water as the eluent, to obtain 43 mg (yield 45%) of the title compound as a colorless solid.

Rf=0.50 (5:1:1=isopropanol:ethyl acetate:methanol). Mass Spectrum (FAB) m/e 447 (M$^+$+H). [α]D$^{25}$+28.0° (c=0.035, CH$_3$OH). Infrared Absorption Spectrum $v_{max}$ (cm$^{-1}$): 1727, 1661, 1631. $^1$H-Nuclear Magnetic Resonance Spectrum (CD$_3$OD, 270 MHz) (ppm): 5.57 (1H, doublet, J=1.9 Hz); 5.13 (1H, doublet of doublets, J=8.7 & 1.9 Hz); 4.47 (1H, broad doublet, J=10.2 Hz); 4.29 (1H, broad doublet, J=9.3 Hz); 4.21 (1H, triplet, J=9.9 Hz); 4.00–4.09 (1H, multiplet); 3.58 (1H, doublet of doublets, J=8.7 & 3.4 Hz); 3.43 (1H, doublet of doublets, J=11.5 & 5.7 Hz); 2.30–2.40 (2H, multiplet); 1.91 (3H, singlet); 1.52–1.68 (2H, multiplet); 1.28–1.40 (4H, multiplet); 0.88–0.96 (3H, multiplet).

EXAMPLE 2

5-Acetamido-4-(C-aminooxy-C-iminomethylamino)-2,3,4,5-tetradeoxy-D-glycero-D-galacto-non-2-enopyranosoic acid (Compound No. 34-1)

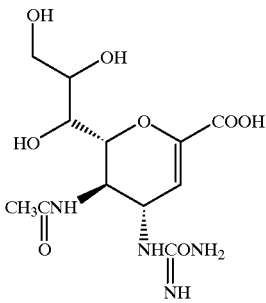

2(i) 5-Acetamido-4-(C-aminooxy-C-iminometbylamino)-2,3,4,5-tetradeox-D-glycero-D-galacto-non-2-enopyranosoic acid 20 mg (0.05 mmol) of 5-acetado-4-(C-aminooxy-C-iminomethylamino)- 7-O-hexanoyl-2,3,4,5-tetradeoxy-D-glycero-D-galacto-non-2-enopyranosoic acid (prepared as described in Example 1) were dissolved in 20 ml of methanol, and 2.1 ml of a 4.9 M methanolic solution of sodium methoxide (0.01 mmol) were added to the resulting solution, while stirring at room temperature. The solution was then stirred at room temperature for a further 2 hours, after which a 4 M solution of hydrogen chloride in dioxane was added, to adjust the pH to a value of 6–7. The mixture was then evaporated to dryness under a vacuum. The resulting residue was applied to a silica gel chromatography column, using a 5:1:1 by volume mixture of isopropanol, ethyl acetate and water, to obtain 7.3 mg (yield 50%) of the title compound as a colorless solid.

Rf=0.30 (4:1:1 isopropanol: ethyl acetate: methanol). Mass Spectrrn (FAB) m/e 325 (M$^+$+H). $^1$H-Nuclear Magnetic Resonance Spectrum (D2O 270 MHz) δ (ppm): 5.58 (1H, doublet, J=2.0 Hz); 4.42 (1H, doublet of doublets, J=10.0 & 2.0 Hz); 4.30 (1H, doublet, J=10.0 Hz); 4.20 (1H, doublet of doublets, J=10.0 & 10.0 Hz); 3.90 (1H, multiplet); 3.95 (1H, doublet of doublets, J=12.0 & 2.2 Hz); 3.55–3.65 (2H, multiplet); 1.99 (3H, singlet).

EXAMPLE 3

5-Acetamido-4-(C-aminooxy-C-iminomethylamino)-9-O-hexanoyl-2,3,4,5-tetradeox-D-glycrid-D-galacto-non-2-enopyranosic acid (Compound No. 3436)

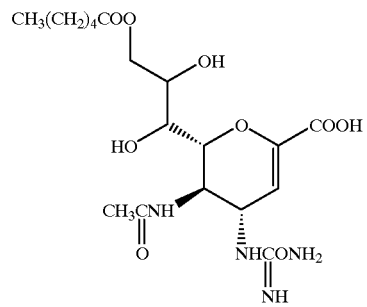

3(i) 5-Acetamido-4-amino-9-O-hexanoyl-2,3,4,5-tetradeoxy-D-glycero-D-galacto-non-2-enopyranosoic acid 80 mg (0.21 mmol) of 5-acetamido-4-amino-7-O-hexanoyl-2,3,4,5-tetradeoxy-D-glycero-D-galacto-non-2-enopyranosoic acid [prepared as described in Example 1 (vi)] were dissolved in a mixture of 3 ml of trifluoroacetic acid and 6 ml of methylene chloride at room temperature, and the mixture was then stirred at room temperature for a further 6 hours. At the end of this time, the solvent was removed by distillation under reduced pressure to obtain a residue. This residue was subjected to azeotropic distillation with benzene, after which it was evaporated to dryness under a vacuum. The resulting residue was then subjected to silica gel column chromatography, using a 2:5:1 by volume mixture of isopropanol, ethyl acetate and water as the eluent, to obtain 55 mg (yield 68%) of the title compound as a colorless solid.

Rf=0.39 (5:1:1=isopropanol: ethyl acetate: methanol). Mass Spectrum (FAB) m/e 389 (M$^+$+H). [a]D$^{25}$+10.0° (c=0.07, CH$_3$OH). Infrared Absorption Spectrum $v_{max}$ (cm$^{-1}$): 1724, 1664. $^1$H-Nuclear Magnetic Resonance Spectrum (CD$_3$OD, 270 MHz) δ (ppm): 5.56 (1H, doublet, J=2.1 Hz); 4.38 (1H, doublet of doublets, J=11.1 & 1.9 Hz); 4.30 (1H, singlet); 4.28 (1H, doublet, J=1.9 Hz); 4.07–4.25 (2H, multiplet); 3.93–4.02 (1H, multiplet); 3.58 (1H, doublet, J=9.3 Hz); 2.37 (2H, triplet, J=7.4 Hz); 2.04 (3H, singlet); 1.57–1.71 (2H, multiplet); 1.27–1.40 (4H, multiplet); 0.88–0.96 (3H, multiplet).

3(ii) 5-Acetamido-4-cyanamido-9-O-hexanoyl-2,3,4,5-tetradeoxy-D-glycero-D-galactonon-2-enopyranosoic acid 46 mg (0.12 mmol) of 5-acetamido-4-amino-9-O-hexanoyl-2,3,4,5-tetradeoxy-D-glycero-D-galacto-non-2-enopyranosoic acid [prepared as described in step (i) above] were dissolved in 10 ml of methanol, and 29 mg (0.35 mmol) of sodium acetate and 17 mg (0.16 mmol) of cyanogen bromide were added to the resulting solution, while stirring at room temperature. The reaction mixture was stirred at room temperature for a further 40 minutes, and then the solvent was removed by distillation under reduced pressure to obtain a residue. This residue was subjected to silica gel column chromatography, using a 2:5:12 by volume mixture of isopropanol, ethyl acetate and water as the eluent, to obtain 29 mg (yield 60%) of the title compound as a colorless solid.

Rf=0.43 (2:5:1=isopropanol:ethyl acetate:methanol).

Mass Spectrum (FAB) m/e 436 (M$^+$+Na), 458 (M$^+$+2Na-H). [α]$_D^{25}$+8.27° (c=0.075, CH$_3$OH). $^1$H-Nuclear Magnetic Resonance Spectrum (CD$_3$OD, 270 MH)δ (ppm): 5.66 (1H, doublet, J=2.0 Hz); 3.95–4.36 (6H, multiplet); 3.67 (1H, doublet, J=7.4 Hz); 2.36 (2H, triplet, J=7.5 Hz); 2.05 (3H, singlet); 1.55–1.71 (2H, multiplet); 1.27–1.40 (4H, multiplet); 0.88–0.96 (3H, multiplet).

3(iii) 5-Acetamido-4-(C-aminooxy-C-iminomethylamino)-9-O-hexanoyl-2,3,4,5-tetradeoxy-D-glycero-D-galacto-non-2-enopyranosoic acid 24 mg (0.06 mmol) of 5-acetamido-4cyanamido-9-O-hexanoyl-2,3,4,5-tetradeoxy-D-glycero-D-galacto-non-2-enopyranosoic acid [prepared as described in step (ii) above] were dissolved in 4 ml of methanol, and 4.5 mg (0.06 mmol) of hydroxylamine hydrochloride were added to the resulting solution, while stirring at room temperature. The reaction mixture was stirred at room temperature for a further 4 hours, and then the solvent was removed by distillation under reduced pressure to obtain a residue. This residue was subjected to silica gel column chromatography, using a 2:5:1 by volume mixture of isopropanol, ethyl acetate and water as the eluent, to obtain 18 mg (yield 70%) of the title compound as a colorless solid.

Rf=0.58 (5:1:1=isopropanol:ethyl acetate:methanol). Mass Spectrun (FAB) m/e 447 (M$^+$+H). [α]$_D^{25}$+39.2° (c=0.025, CH$_3$OH). Infrared Absorption Spectrum $v_{max}$ (cm$^{-1}$): 1723, 1656, 1630. $^1$H-Nuclear Magnetic Resonance Spectrum (D2O, 270 MHz) δ (ppm): 5.57 (1H, doublet, J=2.0 Hz); 4.30–4.46 (3H, multiplet); 4.08–4.25 (3H, multiplet); 3.68 (1H, doublet, J=9.4 Hz); 2.37 (2H, triplet, J=7.3 Hz); 1.98 (3H, singlet); 1.50–1.64 (2H, multiplet); 1.18–1.32 (4H, multiplet); 0.77–0.86 (3H, multiplet).

EXAMPLE 4

5-Acetamido-4-(C-aminooxy-C-iminomethylamino)-7-O-tetradecanoyl-2,3,4,5-tetradeoxy-D-glycero-D-galacto-non-2-enopyranosoic acid (Compound No. 1061)

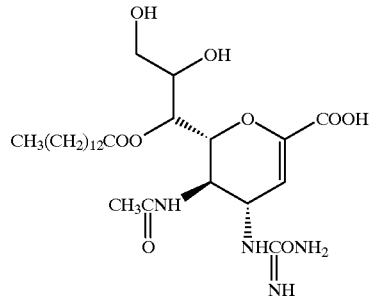

4(i) Methyl 5-acetamidoazido-7-O-tetradecanoyl-8,9-O-isopropyliden-2,3,4,5-tetradeoxy-D-glycer-D-galacto-non-2-enopyranosoate 1.50 g (4.05 mmol) of methyl 5-acetamido 4azido-8,9-O-isopropylidene-2,3,4,5-tetradeoxy-D-glycero-D-galacto-non-2-enopyranosoate [prepared as described in Example 1(ii)] were dissolved in 30 ml of methylene chloride, and 545 mg (4.45 mmol) of dimethylaminopyridine and 1.32 ml (4.86 mmol) of tetradecanoyl chloride were added to the resulting solution, while stirring in an ice bath. The reaction mixture was then stirred at room temperature for 40 minutes, after which 0.62 ml (4.45 mmol) of triethylamine was added dropwise to the mixture in an ice bath. The mixture was then stirred at room temperature for 20 hours. At the end of this time, 200 ml of ethyl acetate and 100 ml of a saturated aqueous solution of sodium hydrogencarbonate.were added to the reaction mixture, and the mixture was partitioned to separate the organic layer. The organic layer was washed three times, each time with 50 ml of a saturated aqueous solution of sodium chloride. It was then dried over anhydrous sodium sulfate anhydride, after which the solvent was removed by distillation under reduced pressure. The resulting residue was subjected to silica gel column chromatography, using a 100:1 by volume mixture of methylene chloride and methanol as the eluent, to obtain 1.57 g (yield 67%) of the title compound as a yellow oil.

Rf=0.49 (20:1=methylene chloride: methanol). Mass Spectrum (FAB) m/e 603 (M$^+$+Na). [α]$_D^{25}$–56.4° (c=0.11, CHCl$_3$). Infrared Absorption Spectrum $v_{max}$ (cm$^{-1}$): 2100, 1745,1661. $^1$H-Nuclear Magnetic Resonance Spectrum (CDCl$_{3, 270}$ MHz) δ (ppm): 6.14 (1H, doublet, J=5.8 Hz); 5.77 (1H, broad doublet, J=9.8 Hz); 5.42 (1H, doublet of doublets, J=5.2 & 2.1 Hz); 4.37–4.53 (2H, multiplet); 4.10–4.27 (3H, multiplet); 3.94 (1H, doublet of doublets, J=8.7 & 6.7 Hz); 3.83 (3H, singlet); 2.21–2.47 (2H, multiplet); 1.99 (3H, singlet); 1.52–1.68 (2H, multiplet); 1.37 (3H, singlet); 1.35 (3H, singlet); 1.20–1.48 (20H, multiplet); 0.85–0.92 (3H, multiplet).

4(ii) Methyl 5-acetamidoamino-7-O-tetradecangyl-8,9-O-isopropylidene-2,3,4,5-tetradeoxy-D-glyacero-D-galacto-non-2enopyranosoate 1.50 g (2.65 mmol) of methyl 5-acetamido-4-azido-7-O-tetradecanoyl-8,9-O-isopropylidene-2,3,4,5-tetradeoxy-D-glycero-D-galacto-non-2-enopyranosoate [prepared as described in step (i) above] were dissolved in 20 ml of methanol, and 600 mg of a Lindlar catalyst were added to the resulting solution, while stirring at room temperature. The atmosphere in the reaction system was then replaced by hydrogen, and the mixture was stirred at room temperature for 2 hours. At the end of this time, it was filtered under reduced pressure using a Celite (trade mark) filter aid, and the solvent was removed from the filtrate by distillation under reduced pressure. The resulting residue was subjected to silica gel column chromatography, using a 20:1 by volume mixture of methylene chloride and methanol and then a 10:1 by volume mixture of methylene chloride and methanol as the eluent, to obtain 710 mg (yield 50%)of the title compound as a yellow amorphous substance.

Rf=0.29 (10:1=methylene chloride: methanol). Mass Spectrum (FAB) m/e 555 W$^+$+H). [α]$D^{25}$+25.2° (c=0.25, CHCl$_3$). Infrared Absorption Spectrum $v_{max}$ (cm$^{-1}$): 1753, 1738, 1660. $^1$H-Nuclear Magnetic Resonance Spectrum (CDCl$_3$, 270 MHz) δ (ppm): 5.98 (1H, doublet, J=2.01 Hz); 5.61 (1H, broad singlet); 5.43 (1H, doublet of doublets, J=5.1 & 1.9 Hz); 4.35–4.45 (2H, multiplet); 4.15 (1H, doublet of doublets, J=8.9 & 6.3 Hz); 3.95 (1H, doublet of doublets, J=8.9 & 6.8 Hz); 3.83 (1H, broad singlet); 3.80 (3H, singlet); 3.64 (1H, broad doublet, J=8.4 Hz); 2.25–2.50 (2H, multiplet); 2.01 (3H, singlet); 1.77 (1H, broad singlet); 1.53–1.69 (2H, multiplet); 1.37 (3H, singlet); 1.35 (3H, singlet); 1.22–1.35 (20H, multiplet); 0.85–0.92 (3H, multiplet).

4(iii) 5-Acetamido-4-amino-7-O-tetradecanoygl-8,9-isopropylidene-2,3,4,5-tetradeoxy-D-glycero-D-galacto-non-2-enopyranosoic acid 710 mg (1.28 mmol) of methyl 5-acetamido-4-amino-7-O-tetradecanoyl-8,9-O-isopropylidene-2,3,4,5-tetradeoxy-D-gycero-D-galacto-non-2-enopyranosoate [prepared as described in step (ii) above] were dissolved in a mixture of 4 ml of methanol and 4 ml of water, and 59 mg (1.41 mmol) of lithium hydroxide 1 hydrate were added to the resulting solution, while stirrng at room temperature. The mixture was then stirred for a further 30 minutes at room temperature. Dowex-50Wx8 (H$^+$) resin (Dowex is a trade mark) was then gradually added to the resulting mixture to adjust the pH to a value of about 7.5. Immediately after the adjustment, the resulting suspension was rapidly filtered under reduced pressure. The residue obtained by distilling the solvent from the filtrate under reduced pressure was subjected to silica gel column chromatography, using a 2:5:1 by volume mixture of isopropanol, ethyl acetate and water as the eluent, to obtain 490 mg (yield 71%) of the title compound as a colorless solid.

Rf=0.29 (2:5:1=isopropanol: ethyl acetate: methanol). Mass Spectrum (FAB) m/e 541 (M$^+$+H). [α]$D^{25}$+10.8° (c=0.12, CH$_3$OH). Infrared Absorption Spectrum $v_{max}$ (cm$^{-1}$): 1750, 1666. $^1$H-Nuclear Magnetic Resonance Spectrum (CDCl$_3$, 270 MHz) δ (ppm): 5.61 (1H, doublet, J=1.9 Hz); 5.41 (1H, doublet of doublets, J=6.0 & 1.4 Hz); 4.59 (1H, doublet of doublets, J=12.0 & 6.2 Hz); 4.13–4.28 (3H, multiplet); 3.93 (1H, doublet of doublets, J=9.0 & 6.4 Hz); 3.79–3.86 (1H, multiplet); 2.28–2.42 (2H, multiplet); 1.96 (3H, singlet); 1.52–1.70 (2H, multiplet); 1.35 (3H, singlet); 1.33 (3H, singlet); 1.26–1.43 (20H, multiplet); 0.87–0.95 (3H, multiplet).

4(iv) 5-Acetamidoamino-7-O-tetradecanoyl-2,3,4,5-tetradeoxy-D-glycero-D-galacto-non-2-enopyranosoic acid 480 mg (0.89 mmol) of 5-acetamido-4-amino-7-O-tetradecanoyl-8,9-O-isopropylidene-2,3,4,5-tetradeoxy-D-glycero-D-galacto-non-2-enopyranosoic acid [prepared as described in step (iii) above] were dissolved in a mixture of 10 ml of acetic acid and 10 ml of water at room temperature, and the mixture was stirred for 5 hours at room temperature. The solvent was then removed by distillation under reduced pressure and the resulting residue was subjected to azeotropic distillation with benzene, after which it was evaporated to dryness under a vacuum. The resulting residue was subjected to silica gel column chromatography, using a 2:5:1 by volume mixture of isopropanol, ethyl acetate and water as the eluent, to obtain 110 mg (yield 25%) of the title compound as a colorless solid.

Rf=0.37 (5:1:1=isopropanol:ethyl acetate:methanol). Mass Spectrum (FAB) m/e 501 (M$^+$+H). [α]$D^{25}$+7.50° (c=0.07, CH$_3$OH). Infrared Absorption Spectrum $v_{max}$ (cm$^{-1}$): 1740, 1661. $^1$H-Nuclear Magnetic Resonance Spectrum (CD$_3$OD, 270 MHz) δ (ppm): 5.59 (1H, doublet, J=2.2 Hz); 5.14 (1H, doublet of doublets, J=9.4 & 1.8 Hz); 4.42 (1H, doublet of doublets, J=10.7 & 1.7 Hz); 4.23 (1H, triplet, J=10.1 Hz); 4.01–4.09 (1H, multiplet); 3.83 (1H, doublet of doublets, J=9.4 & 2.1 Hz); 3.56 (1H, doublet of doublets, J=11.8 & 3.2 Hz); 3.40 (1H, doublet of doublets, J=11.7 & 6.3 Hz); 2.28–2.38 (2H, multiplet); 1.95 (3H, singlet); 1.52–1.68 (2H, multiplet); 1.26–1.38 (20H, multiplet); 0.87–0.95 (3H, multiplet).

4(v) 5-Acetamido-4-cyanamido-7-O-tetradecanoyl-2,3, 4,5-tetradeoxy-D-glycero-D-galacto-non-2-enopyranosoic acid 108 mg (0.22 mmol) of 5-acetamido-4-amino-7-O-tetradecanoyl-2,3, 4,5-tetradeoxy-D-glycero-D-galacto-non-2-enopyranosoic acid [prepared as described in step (iv) above] were dissolved in 4 ml of methanol, and 46 mg (0.56 mmol) of sodium acetate and 31 mg (0.29 mmol) of cyanogen bromide were added to the resulting solution, while stirring at room temperature. The reaction solution was stirred at room temperature for 150 minutes, and then the solvent was removed by distillation under reduced pressure to obtain a residue. This residue was then subjected to azeotropic distillation with benzene. The resulting residue was subjected to silica gel column chromatography, using a 2:5:1 by volume mixture of isopropanol, ethyl acetate and water as the eluent, to obtain 66 mg (yield 58%) of the title compound as a colorless solid.

Rf=0.30 (2:5:1=isopropanol:ethyl acetate:methanol). Mass Spectrum (FAB) m/e 526 (M$^+$+H). [α]$D^{25}$−36.3° (c=0.07, CH$_3$OH). Infared Absorption Spectrum $v_{max}$ (cm$^{-1}$): 2223, 1746, 1662. $^1$H-Nuclear Magnetic Resonance Spectrum (CD$_3$OD, 270 MHz) δ (ppm): 5.71 (1H, doublet, J=2.1 Hz); 5.08 (1H, doublet of doublets, J=8.2 & 1.8 Hz); 4.46 (1H, doublet of doublets, J=10.6 & 1.7 Hz); 4.04–4.20 (2H, multiplet); 3.85 (1H, doublet of doublets, J=9.5 & 2.2 Hz); 3.66 (1H, doublet of doublets, J=11.5 & 3.5 Hz); 3.45–3.54 (1H, multiplet); 2.25–2.50 (2H, multiplet); 1.96 (3H, singlet); 1.53–1.68 (2H, multiplet); 1.26–1.40 (20H, multiplet); 0.87–0.96 (3H, multiplet).

4(vi) 5-Acetamido-4-(C-aminooxy-C-iminomethylamino)-7-O-tetradecanoyl-2,3, 4,5-tetradeoxy-D-glycero-D-galacto-non-2-enopyranosoic acid 51 mg (0.1 mmol) of 5-acetamido-4-cyanamido-7-O-tetradecanoyl-2,3, 4,5-tetradeoxy-D-glycero-D-galacto-non-2-enopyranosoic acid [prepared as described in step (v) above] were dissolved in 4 ml of methanol, and 7.6 mg (0.1 mmol) of hydroxylamine hydrochloride were added to the resulting solution, while stirring at room temperature. The reaction mixture was then stirred at room temperature for a further 3 hours, after which the solvent was removed by distillation under reduced pressure. The resulting residue was subjected to silica gel column chromatography, using a 2:5:1 by volume mixture of isopropanol, ethyl acetate and water as the eluent, to obtain 34 mg (yield 63%) of the title compound as a colorless solid.

Rf=0.37 (5:1:1=isopropanol:ethyl acetate:methanol). Mass Spectrum (FAB) m/e 559 (M$^+$+H). [α]$D^{25}$+22.5° (c=0.065, CH$_3$OH). Infrared Absorption Spectrum $v_{max}$ (cm$^{-1}$): 1743, 1726, 1664, 1633. $^1$H-Nuclear Magnetic Resonance Spectrum (CD$_3$OD, 270 MHz) δ (ppm): 5.55 (1H, doublet, J=1.9 Hz); 5.12 (1H, doublet of doublets, J=9.2 & 2.0 Hz); 4.44 (1H, doublet of doublets, J=10.2 & 1.5 Hz); 4.17–4.33 (2H, multiplet); 3.98–4.08 (1H, multiplet); 3.56 (1H, doublet of doublets, J=11.8 & 3.2 Hz); 3.40 (1H, doublet of doublets, J=11.7 & 6.1 Hz); 2.28–2.42 (2H, multiplet); 1.91 (3H, singlet); 1.53–1.70 (2H, multiplet); 1.26–1.39 (20H, multiplet); 0.87–0.94 (3H, multiplet).

EXAMPLE 5

5-Acetamido-4-(C-aminooxy-C-iminomethylamino)-9-O-tetradecanoyl-2,3, 4,5-tetradeoxy-D-glycero-D-galacto-non-2-enopyranosoic acid (Compound No. 34-41)

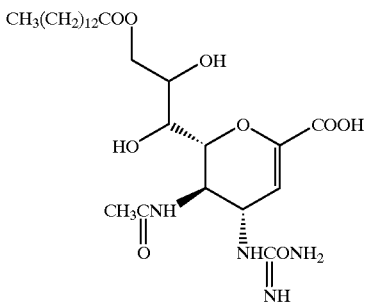

5(i) 5-Acetamido-4-amino-9-O-tetradecanoyl-2,3, 4,5-tetradeoxy-D-glycero-D-galacto-non-2-enopyranosoic acid 55 mg (1.01 mmol) of 5-acetamido-4-amino-7-O-tetradecanoyl-8, 9-O-isopropylidene-2,3,4,5-tetradeoxy-D-glycero-D-galacto-non-2-enopyranosoic acid [prepared as described in Example 4(iii)] were dissolved in a mixture of 2 ml of trifluoroacetic acid and 4 ml of methylene chloride at room temperature, and the mixture was then stirred at room temperature for a further 3 days. At the end of this time, the solvent was removed by distillation under reduced pressure to obtain a residue. This residue was then subjected to azeotropic distillation with benzene, after which it was evaporated to dryness under a vacuum. The resulting residue was subjected to silica gel column chromatography, using a 2:5:1 by volume mixture of isopropanol, ethyl acetate and water as the eluent, to obtain 51 mg (yield 100%) of the title compound as a colorless solid.

Rf=0.49 (5:1:1=isopropanol:ethyl acetate:methanol). Mass Spectrum (FAB) m/e 501 (M$^+$+H). [α]D$^{25}$+3.560 (c=0.09, CH$_3$OH). Infrared Absorption Spectrum v$_{max}$ (cm$^{-1}$): 1734, 1628. $^1$H-Nuclear Magnetic Resonance Spectrum (CD$_3$OD, 270 MHz) δ (ppm): 5.68 (1H, doublet, J=1.9 Hz); 4.01–4.38 (3H, multiplet); 3.84–4.00 (4H, multiplet); 3.71 (1H, doublet, J=7.7 Hz); 2.30–2.42 (2H, multiplet); 2.06 (3H, singlet); 1.53–1.71 (2H, multiplet); 1.26–1.40 (20H, multiplet); 0.87–0.93 (3H, multiplet).

5(ii) 5-Acetamido-4-cyanamido-9-O-tetradecanoyl-2,3, 4,5-tetradeoxy-D-glycero-D-galacto-non-2-enopyranosoic acid 90 mg (0.18 mmol) of 5-acetamido-4-amino-9-O-tetradecanoyl-2,3, 4,5-tetradeoxy-D-glycero-D-galacto-non-2-enopyranosoic acid [prepared as described in step (i) above] were dissolved in 10 ml of methanol, and 44 mg (0.54 mmol) of sodium acetate and 19 mg (0.18 mmol) of cyanogen bromide were added to the resulting solution, while stirring at room temperature. The reaction mixture was then stirred at room temperature for 10 hours, after which the solvent was removed by distillation under reduced pressure. The resulting residue was subjected to silica gel column chromatography, using a 2:5:1 by volume mixture of isopropanol, ethyl acetate and water as the eluent, to obtain 75 mg (yield 79%) of the title compound as a colorless solid.

Rf=0.52 (2:5:1=isopropanol:ethyl acetate:methanol). Mass Spectrum (FAB) mle 526 (M$^+$+H). [α]D$^{25}$–56.7° (c=0.060, CH$_3$OH). $^1$H-Nuclear Magnetic Resonance Spectrum (CD$_3$OD, 270 MHz) δ (ppm): 5.70 (1H, doublet, J=1.9 Hz); 4.05–4.32 (3H, multiplet); 3.78–4.02 (4H, multiplet); 2.32–2.38 (2H, multiplet); 2.06 (3H, singlet); 1.55–1.68 (2H, multiplet); 1.26–1.40 (20H, multiplet); 0.87–0.93 (3H, multiplet).

5(iii) 5-Acetamido-4-(C-aminooxy-C-iminomethylamino)-9-O-tetradecanoyl-2,3, 4,5-tetradeoxy-D-glycero-D-galacto-non-2-enopyranosoic acid 55 mg (0.11 mmol) of 5-acetamido-4cyanamido-9-O-tetradecanoyl-2,3, 4,5-tetradeoxy-D-glycero-D-galacto-non-2-enopyranosoic acid [prepared as described in step (ii) above] were dissolved in 4 ml of methanol, and 27 mg (0.39 mmol) of hydroxylamine hydrochloride were added to the resulting solution, while stirring at room temperature. The reaction mixture was then stirred at room temperature for a further 2 hours, after which the solvent was removed by distillation under reduced pressure. The resulting residue was subjected to silica gel column chromatography, using a 2:5:1 by volume mixture of isopropanol, ethyl acetate and water as the eluent, to obtain 11 mg (yield 19%) of the title compound as a colorless solid.

Rf=0.28 (2:5:1=isopropanol:ethyl acetate:methanol). Mass Spectrum (FAB) m/e 559 (M$^+$+H). [α]D$^{25}$+53.3° (c=0.015, CH$_3$OH). Infrared Absorption Spectrum v$_{max}$ (cm$^{-1}$): 1679. $^1$H-Nuclear Magnetic Resonance Spectrum (CD$_3$OD, 270 MHz) δ (ppm): 5.53 (1H, doublet, J=1.9 Hz); 4.30–4.43 (2H, multiplet); 4.03–4.28 (3H, multiplet); 3.55–3.65 (2H, multiplet); 2.32–2.40 (2H, multiplet); 2.00 (3H, singlet); 1.55–1.68 (2H, multiplet); 1.26–1.37 (20H, multiplet); 0.85–0.93 (3H, multiplet).

EXAMPLE 6

5-Acetamido-4-guanidino-2,3,4,5,7-pentadeoxy-7-fluoro-D-glycero-D-galacto-non-2-enopyranosoic acid trifluoroacetic acid salt (Compound No. 1-1)

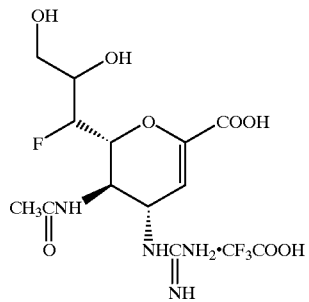

6(i) Methyl 5-acetamido-4-azido-8.9-di-O-acetyl-2,3, 4,5,7-pentadeoxy-7-fluoro-glycero-D-galacto-non-2-enopyranosoate 300 mg (0.70 mmol) of methyl 5-acetamido-4,8,9-tri-O-acetyl-2, 6-anhydro-3,5,7-trideoxy-7-fluoro-D-glycero-D-galacto-non-2-enopyranosoate [prepared according to the procedure described in WO 95/3295 5] were dissolved in 10 ml of anhydrous methylene chloride, and 25 mg (0.78 mmol) of methanol were added to the resulting solution. The atmosphere in the reaction system was replaced by nitrogen, and then 1.0 g (7.0 mmol) of a boron trifluoride diethyl ether complex salt was added to the reaction system, and the mixture was stirred at room temperature for 24 hours. At the end of this time, the reaction mixture was poured into a mixture of 50 ml of water, 10 g of ice, 10 g of solid sodium hydrogencarbonate and 50 ml of ethyl acetate, and the mixture was vigorously stirred for 10 minutes. The organic layer was separated, washed with 10 ml of a saturated aqueous solution of sodium chloride and dried over anhydrous sodium sulfate, after which the solvent was removed by distillation under reduced pressure. The resulting residue (210 mg) was dissolved in 4 ml of dimethylformamide, and 400 mg of a cation exchange resin, Dowex-50×8 (H$^+$) (Dowex is a trade mark) and 100 mg (1.53 mmol) of sodium azide were added to the resulting solution. The mixture was then stirred at 80° C. for 4 hours. At the end of this time, the Dowex-50×8 (H$^+$) was separated by filtration and the solvent was removed by distillation under reduced pressure. 30 ml of ethyl acetate and 20 ml of a saturated aqueous solution of sodium hydrogencarbonate were then added to dissolve the residue. The organic layer was separated, washed with a saturated aqueous solution of sodium chloride and dried over anhydrous sodium sulfate, after which the solvent was removed by distillation under reduced pressure. The resulting residue was purified by silica gel column chromatography, using a 50:1 by volume mixture of methylene chloride and methanol as the eluent, to obtain 170 mg (yield 59%) of the title compound as a colorless viscous substance.

Rf=0.31 (20:1=methylene chloride:methanol). [α]$D^{25}$+ 69.4° (c=0.18, CHCl$_3$). Mass Spectrum (FAB) m/e 417 (M$^+$+H). $^1$H-Nuclear Magnetic Resonance Spectrum (CDCl$_3$, 270 MHz) δ (ppm): 2.07 (9H, singlet); 3.58 (1H, doubled doublet of doublets, J=9.0, 9.0 & 9.0 Hz); 3.80 (3H, singlet); 4.22 (1H, doubled doublet of doublets, J=1.8, 5.2 & 13.0 Hz); 4.65–5.00 (4H, multiplet); 5.45 (1H, multiplet); 5.98 (1H, doublet, J=2.8 Hz); 6.00 (1H, doublet, J=8.5 Hz).

6(ii) Methyl 5-acetamido-4-(N,N'-bis-t-butoxycarbonylguanidino)-8, 9-di-O-acetyl-2,3,4,5,7-pentadeoxy-7-fluoro-D-glycero-D-galacto-non-2-enopyranosoate 36 mg (0.08 mmol) of methyl 5-acetamido-4-azido-8,9-di-O-acetyl-2,3, 4,5,7-pentadeoxy-7-fluoro-D-glycero-D-galacto-non-2-enopyranosoate [prepared as described in step (i) above] were dissolved in 3 ml of methanol, and 10 mg of a Lindlar catalyst were added to the resulting solution. The atmosphere in the reaction system was replaced by hydrogen, and then the mixture was stirred for 2 hours. The catalyst was then separated by filtration, and the solvent was removed by distillation under reduced pressure. The resulting residue was dissolved in 2 ml of dimethylformamide, and 26 mg (0.093 mmol) of N,N'-di-t-butoxycarbonylthiourea, 19 mg (0.186 mmol) of triethylamine and 25 mg (0.093 mmol) of mercuric chloride were added to the resulting solution. The mixture was then stirred at room temperature for 1 hour. The solid was separated by filtration and the filtrate was poured into a 2-layer mixture of 5 ml of ethyl acetate and 3 ml of a saturated aqueous solution of sodium hydrogencarbonate. The organic layer was separated, washed with a saturated aqueous solution of sodium chloride and dried over anhydrous sodium sulfate, after which the solvent was removed by distillation under reduced pressure. The residue was purified by silica gel column chromatography, using a 2:1 by volume mixture of ethyl acetate and hexane as the eluent, to obtain 32 mg (yield 59%) of the title compound as a colorless amorphous substance.

Rf=0.35 (2:1=ethyl acetate:hexane). [α]$D^{25}$+5.6° (c=0.16, CHCl$_3$). Mass Spectrum (FAB) m/e 633 (M$^+$+H).

$^1$H-Nuclear Magnetic Resonance Spectrum (CDCl$_3$, 270 MHz) δ (ppm): 1.49 (9H, singlet); 1.52 (9H, singlet); 1.98 (3H, singlet); 2.05 (3H, singlet); 2.07 (3H, singlet); 3.80 (3H, singlet); 4.00–4.30 (3H, multiplet); 4.75 (1H, doublet of doublets, J=9.2, 50 Hz); 4.78 (1H, doublet, J=18 Hz); 5.23 (1H, doublet of doublets, J=9.0, 9.0 Hz); 5.43 (1H, multiplet); 5.88 (1H, doublet, J=2.8 Hz); 6.80 (1H, doublet, J=8.2 Hz); 8.60 (1H, doublet, J=8.5 Hz).

6(iii) 5-Acetamido-4-guanidino-2,3,4,5,7-pentadeoxy-7-fluoro-D-glycero-D-galacto-non-2-enopyranosoic acid trifluoroacetic acid salt 32 mg (0.05 mmol) of methyl 5-acetamido-4-(N,N '-bis-t-butoxycarbonylguanidino)-8,9-di-O-acetyl-2,3,4,5,7-pentadeoxy-7-fluoro-D-glycero-D-galacto-non-2-enopyranosoate [prepared as described in step (ii) above] were dissolved in 2 ml of methanol, and 0.5 ml of a 0.1 N methanolic solution of sodium methoxide was added to the resulting solution. The mixture was then stirred at room temperature for 1 hour. At the end of this time, the reaction mixture was neutralized with a 4 M solution of hydrogen chloride in dioxane, and the solvent was removed by distillation under reduced pressure. The residue was then dissolved in a 3:1 by volume mixture of methylene chloride-trifluoroacetic acid, and the mixture was stirred at room temperature for 5 hours. At the end of this time, the solvent was removed by distillation under reduced pressure, and the resulting residue was dissolved in 1 ml of distilled water, and then 70 ml of a 1 N aqueous solution of sodium hydroxide were added to the resulting solution. The mixture was then stirred at room temperature for 1 hour. Dowex-50×8 (H$^+$) (Dowex is a trade mark) was added to the resulting mixture to neutralize it, and then the water was removed by distillation. The resulting residue was purified by silica gel column chromatography, using a 5:1:1 by volume mixture of isopropanol, ethyl acetate and water as the eluent, to obtain 16 mg (yield 71%) of the title compound as a colorless solid.

Rf=0.30 (4:1:1=isopropanol:acetic acid:water). [α]$D^{25}$+ 28.0° (c=0.10, H$_2$O). Mass Spectrum (FAB) m/e 335 (M$^+$+ H). $^1$H-Nuclear Magnetic Resonance Spectrum (D$_2$O, 270 MHz) δ (ppm): 2.00 (3H, singlet); 3.65 (1H, doubled doublet of doublets, J=2.4, 5.5 & 12.0 Hz); 3.85 (1H, doubled doublet of doublets, J=2.5, 2.5 & 12 Hz); 4.15 (1H, multiplet); 4.23 (1H, doublet, J=9.0 Hz); 4.30–4.60 (3H, multiplet); 5.63 (1H, singlet).

EXAMPLE 7

Tetradecyl 5-acetamido-4-guanidino-2,3,4,5,7-pentadeoxy-7-fluoro-D-glycero-D-galacto-non-2-enopyranosoate trifluoroacetic acid salt (Compound No. 1-5)

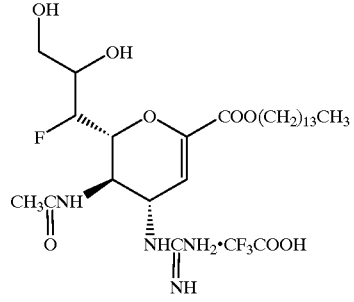

7(i) Methyl 5-acetamido-4-azido-8.9-O-isopropylidene-2,3, 4,5,7-pentadeoxy-7-fluoro-D-glycero-D-galacto-non-2-enopyranosoate 300 mg (0.72 mmol) of methyl 5-acetamido-4-azido-8,9-di-O-acetyl-2,3, 4,5,7-pentadeoxy-7-fluoro-D-glycero-1-galacto-non-2-enopyranosoate [prepared as described in Example 6(i)] were dissolved in 5 ml of methanol, and 0.2 ml of a 1 M methanolic solution of sodium methoxide was added to the resulting solution. The mixture was then stirred at room temperature for 1 hour. At the end of this time, the reaction mixture was neutralized with a 4 M solution of hydrogen chloride in dioxane, and then the solvent was removed by distillation under reduced pressure. The resulting residue was dissolved in 5 ml of acetone, and 400 mg (3.85 mmol) of 2,2-dimethoxypropane and 20 mg (0.11 mmol) of p-toluenesulfonic acid were added to the resulting solution. The mixture was then stirred at room temperature for 3 hours. The solids were separated by filtration and the solvent was removed from the filtrate by distillation under reduced pressure. The residue was purified by silica gel column chromatography, using a 50:1 by volume mixture of methylene chloride and methanol as the eluent, to obtain 140 mg (yield 52%) of the title compound as a colorless amorphous substance.

Rf=0.33 (20:1=methylene chloride:methanol). $[\alpha]_D^{25}$+111° (c=0.13, $CHCl_3$). Mass Spectrum (FAB) m/e 373 ($M^+$+H). $^1$H-Nuclear Magnetic Resonance Spectrum ($CDCl_3$, 270 M 8z) δ (ppm): 1.37 (3H, singlet); 1.42 (3H, singlet); 2.05 (3H, singlet); 3.50 (1H, doubled doublet of doublets, J=7.5, 7.5 & 9.5 Hz); 3.80 (3H, singlet); 4.13 (1H, doubled doublet of doublets, J=1.2, 6.0 & 9.0 Hz); 4.20 (1H, doubled doublet of doublets, J=1.2, 6.0 & 9.0 Hz); 4.45 (1H, multiplet); 4.70 (1H, doubled doublet of doublets, J=1.5, 5.7 & 47.0 Hz); 4.90 (1H, doublet of doublets, J=2.8 & 9.5 Hz); 4.92 (1H, doubled doublet of doublets, J=1.0, 11.0 & 28.0 Hz); 5.90 (1H, doublet, J=7.3 Hz); 5.96 (1H, doublet, J=2.8 Hz).

7(ii) Tetradecyl 5-acetamido-4azido-8.9-O-isopropylidene-2,3, 4,5,7-pentadeoxy-7-fluoro-D-glycero-D-galacto-non-2-enopyranosoate 113 mg (0.31 mmol) of methyl 5-acetamido-4-azido-8,9-O-isopropylidene-2,3, 4,5,7-pentadeoxy-7-fluoro-D-glycero-D-galacto-non-2-enopyranosoate [prepared as described in step (i) above] were dissolved in 4 ml of a 6:1 by volume mixture of methanol and water, and 0.33 ml of a 1 M aqueous solution of potassium hydroxide was added to the resulting solution. The mixture was then stirred at room temperature for 2 hours. At the end of this time, the solvent was removed by distillation under reduced pressure, and the residue was dried over anhydrous sodium sulfate at room temperature and under reduced pressure for 2 hours to obtain a pale yellow solid. The solid was dissolved in 8 ml of acetonitrile, and 80 mg (0.3 mmol) of 18-crown-6 and 415 mg (1.5 mmol) of tetradecyl bromide were added to the resulting solution. The mixture was then stirred at 80° C. for 2 hours. At the end of this time, the reaction mixture was poured into a 2-layer solution of 15 ml of ethyl acetate and 10 ml of a saturated aqueous solution of sodium hydrogencarbonate, and the organic layer was separated, washed with a saturated aqueous solution of sodium chloride and dried over anhydrous sodium sulfate, after which the solvent was removed by distillation under reduced pressure. The residue was purified by silica gel column chromatography, using a 50:1 by volume mixture of methylene chloride and methanol as the eluent, to obtain 110 mg (yield 64%) of the title compound as a colorless viscous substance.

Rf=0.47 (20:1=methylene chloride:methanol). $[\alpha]_D^{25}$+52.9° (c=0.09, $CHCl_3$). Mass Spectrum (FAB) m/e 555 ($M^+$+H). $^1$H-Nuclear Magnetic Resonance Spectrum ($CDCl_3$, 270 MHz) δ (ppm): 0.80–0.95 (3H, singlet); 1.20–1.50 (24H, multiplet); 1.37 (3H, singlet); 1.42 (3H, singlet); 1.60–1.80 (2H, multiplet); 2.05 (3H, singlet); 4.10–4.30 (2H, multiplet); 4.45 (1H, multiplet); 4.72 (1H, doubled doublet of doublets, J=1.5, 5.3 & 38.0 Hz); 4.90 (1H, doublet of doublets, J=2.4 & 9.3 Hz); 4.92 (1H, doubled doublet of doublets, J=1.0, 10.0 & 28.0 Hz); 5.97 (1H, doublet, J=6.5 Hz); 5.95 (1H, doublet, J=2.4 Hz).

7(iii) Tetradecyl 5-acetamido-4-(N,N'-bis-t-butoxycarbanylguanidino)-8, 9-O-isopropylidene-2,3,4,5,7-pentadeoxy-7-fluoro-D-glycero-D-galacto-non-2-enopyranosoate 110 mg (0.20 mmol) of tetradecyl 5-acetamido-4azido-8, 9-O-isopropylidene-2,3, 4,5,7-pentadeoxy-7-fluoro-1-glycero-D-galacto-non-2-enopyranosoate [prepared as described in step (ii) above] were dissolved in 5 ml of methanol, and 30 mg of a Lindlar catalyst were added to the resulting solution. The atmosphere in the reaction system was then replaced by hydrogen. The mixture was then stirred for 2 hours. At the end of this time, the catalyst was separated by filtration and the solvent was removed by distillation under reduced pressure. The residue was dissolved in 4 ml of dimethylfonnamide, and 47 mg (0.17 mmol) of N,N-di-t-butoxycarbonylthiourea, 35 mg (0.342 mmol) of triethylamine and 47 mg (0.17 mmol) of mercuric chloride were added to the resulting solution. The mixture was then stirred at room temperature for 1 hour. The solid was separated by filtration and the filtrate was poured into a 2-layer solution of 15 ml of ethyl acetate and 10 ml of a saturated aqueous solution of sodium hydrogencarbonate. The organic layer was separated, washed with a saturated aqueous solution of sodium chloride and dried over anhydrous sodium sulfate, after which the solvent was removed by distillation under reduced pressure. The residue was purified by silica gel column chromatography, using a 2:1 by volume mixture of ethyl acetate and hexane as the eluent, to obtain 98 mg (yield 63%) of the title compound as a colorless viscous substance.

Rf=0.30 (20:1=methylene chloride:methanol). $[\alpha]_D^{25}$+2.2° (c=0.14, $CHCl_3$). Mass Spectrum (FAB) m/e 771 .($M^+$+H) $^1$H-Nuclear Magnetic Resonance Spectrum ($CDCl_3$, 270 MHz) δ (ppm): 0.80–0.95 (3H, singlet); 1.20–1.40 (24H, multiplet); 1.36 (3H, singlet); 1.41 (3H, singlet); 1.49 (9H, singlet); 1.50 (9H, singlet); 1.60–1.80 (2H, multiplet); 2.05 (3H, singlet); 4.10–4,70 (6H, multiplet); 5.20 (1H, doubled doublet of doublets, J=2.4, 7.5 & 7.5 Hz); 5.83 (1H, doublet, J=2.4 Hz); 5.65 (1H, doublet, J=7.0 Hz); 8.60 (1H, doublet, J=8.5 Hz).

7(iv) Tetradecyl 5-acetamido-4-guanidino-2,3,4,5,7-pentadeoxy-7-fluoro-D-glycero-D-galacto-non-2-enopyranosoate trifluoroacetic acid salt 80 mg (0.11 mmol) of tetradecyl 5-acetamido-4-(N, N'-bis-t-butoxycarbonyl-guanidino)-8,9-O-isopropylidene-2,3,4,5,7-pentadeoxy-7-fluoro-D-glycero-D-galacto-non-2-enopyranosoate [prepared as described in step (iii) above] were dissolved in of a 3:1 by volume mixture of methylene chloride and trifluoroacetic acid, and the mixture was stirred at room temperature for 4 hours. At the end of this time, the solvent was removed by distillation under reduced pressure, and the residue was purified by silica gel column chromatography, using a 2:8:1 by volume mixture of isopropanol, ethyl acetate and water as the eluent, to obtain 40 mg (yield 56%) of the title compound as a colorless solid.

Rf=0.35 (5:1:1=t-butanol:acetic acid:water). $[\alpha]_D^{25}$+22.4° (c=0.13, $CH_3OH$). Mass Spectrum (FAB) m/e 531 ($M^+$+H). $^1$H-Nuclear Magnetic Resonance Spectrum ($D_2O$, 270 MHz) δ (ppm): 0.70–0.85 (3H, singlet); 1.10–1.30

(24H, multiplet); 1.50–1.80 (2H, multiplet); 2.00 (3H, singlet); 3.60–3.80 (2H, multiplet); 4.10–4.30 (3H, multiplet); 4.40–4.60 (2H, multiplet); 5.88 (1H, singlet).

EXAMPLE 8

4-Guanidino-5-thioacetamido-2,3,4,5-tetradeoxy-D-glycero-D-galacto-non-2-enopyranosoic acid trifluoroacetic acid salt (Compound No. 31-1)

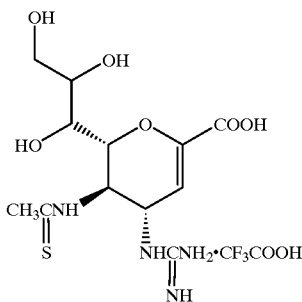

8(i) Methyl 5-acetamido-4-(N,N'-bis-t-butoxycarbonylguanidino)-7,8, 9-tri-O-acetyl-2,3,4,5-tetradeoxy-D-glycero-D-galacto-non-2-enopyranosoate 2.0 g (4.63 mmol) of 5-acetamido-4-amino-7,8,9-tri-O-acetyl-3,4, 5-tetradeoxy-D-glycero-D-galacto-non-2-enopyranosoate were dissolved in 40 ml of dimethylformamide, and 1.54 g (5.58 mmol) of N,N'-bis-t-butoxycarbonylthiourea, 1.1 g (11.2 mmol) of triethylamine and 1.54 g (5.58 mmol) of mercuric chloride were added to the resulting solution. The mixture was then stirred at room temperature for 2 hours. The insolubles were separated by filtration and the filtrate was poured into a 2-layer solution of 50 ml of ethyl acetate and 25 ml of a saturated aqueous solution of sodium hydrogencarbonate. The organic layer was separated, washed with a saturated aqueous solution of sodium chloride and dried over anhydrous sodium sulfate, after which the solvent was removed by distillation under reduced pressure. The resulting residue was purified by silica gel column chromatography, using a 1:1 by volume mixture of ethyl acetate and hexane as the eluent, to obtain 3.0 g (yield 96%) of the title compound as a colorless amorphous substance.

Rf=0.20 (1:1=ethyl acetate:hexane). $^1$H-Nuclear Magnetic Resonance Spectrum (CDCl$_3$, 270 MHz) δ (ppm): 1.49 (18H, singlet); 1.88 (3H, singlet); 2.07 (3H, singlet); 2.09 (3H, singlet); 2.13 (3H, singlet); 3.80 (3H, singlet); 4.15 (1H, doublet of doublets, J=8.0 & 13.0 Hz); 4.20–4.30 (2H, multiplet); 4.67 (1H, doublet of doublets, J=3.0 & 13.0 Hz); 5.15 (1H, doubled doublet of doublets, J=2.5, 8.5 & 8.5 Hz); 5.30 (1H, multiplet); 5.43 (1H, doublet of doublets, J=2.5 & 5.3 Hz); 5.90 (1H, doublet, J=2.5 Hz); 6.20 (1H, doublet, J=8.2 Hz); 8.50 (1H, doublet, J=8.5 Hz).

8(ii) Methyl 4-(N,N'-bis-t-butoxycarbonylguanidino)-5-thioacetamido-7,8, 9-tri-O-acetyl-2,3,4,5-tetradeoxy-D-glycero-D-galacto-non-2-enopyranosoate 1.95 g (2.89 mmol) of methyl 5-acetamido-4-(N, N'-bis-t-butoxycarbonyl-guanidino)-7,8,9-tri-O-acetyl-2,3,4,5-tetradeoxy-D-glycero-D-galacto-non-2-enopyranosoate [prepared as described in step (i) above] were dissolved in 40 ml of tetrahydrofuran, and 2.15 g (5.32 mmol) of Lawesson's reagent were added to the resulting solution. The mixture was then stirred at 60° C for 2 hours. The reaction mixture was then poured into a 2-layer solution of 50 ml of ethyl acetate and 30 ml of a saturated aqueous solution of sodium hydrogencarbonate. The organic layer was separated, washed with a saturated aqueous solution of sodium chloride and dried over anhydrous sodium sulfate, after which the solvent was removed by distillation under reduced pressure. The resulting residue was purified by silica gel column chromatography, using a 2:1 by volume mixture of ethyl acetate and hexane as the eluent, to obtain 1.0 g (yield 50%) of the title compound as a colorless amorphous substance.

Rf=0.40 (1:1=ethyl acetate:hexane). $[α]D^{25}$+19.0° (c=0.11, CHCl$_3$). Mass Spectrum (FAB) m/e 689 (M$^+$+H). $^1$H-Nuclear Magnetic Resonance Spectrum (CDCl$_3$, 270 MHz) δ (ppm): 1.46 (9H, singlet); 1.49 (9H, singlet); 1.95 (3H, singlet); 1.97 (3H, singlet); 1.99 (3H, singlet); 2.42 (3H, singlet); 3.80 (3H, singlet); 4.15 (1H, doublet of doublets, J=8.0 & 13.0 Hz); 4.45 (1H, doublet of doublets, J=3.0 & 8.5 Hz); 4.70 (1H, doublet of doublets, J=3.0 & 13.0 Hz); 5.20–5.35 (3H, multiplet); 5.40 (1H, doublet of doublets, J=2.5 & 4.5 Hz); 5.92 (1H, doublet, J=2.5 Hz); 7.95 (1H, doublet, J=8.2 Hz); 8.55 (1H, doublet, J=8.5 Hz).

8(iii) 4-Guanidino-5-thioacetamido-2,3, 4,5-tetradeoxy-D-glycero-D-galacto-non-2-enopyranosoic acid trifluoroacetic acid salt 800 mg (1.16 mmol) of methyl 4-(N,N'-bis-t-butoxycarbonylguanidino)-5-thioacetamido-7,8,9-tri-O-acetyl-2,3,4,5-tetradeoxy-D-glycero-D-galacto-non-2-enopyranosoate [prepared as described in step (ii) above] were dissolved in 10 ml methanol, and 1.5 ml of a 0.1 N methanolic solution of sodium methoxide were added to the resulting solution. The mixture was then stirred at room temperature for 2 hours, after which it was neutralized with a 4 M solution of hydrogen chloride in dioxane and the solvent was removed by distillation under reduced pressure. The resulting residue was dissolved in 20 ml of a 3:1 by volume mixture of methylene chloride and trifluoroacetic acid, and the resulting solution was stirred at room temperature for 5 hours. At the end of this time, the solvent was removed by distillation under reduced pressure, and the resulting residue was dissolved in 10 ml of distilled water and then 2.0 ml of a 1 N aqueous solution of sodium hydroxide were added to the resulting solution. The mixture was then stirred at room temperature for 1 hour. Dowex-50×8 (H$^+$) (Dowex is a trade mark) was then added to neutralize the reaction mixture, and water was removed by distillation under reduced pressure. The resulting residue was purified by silica gel column chromatography, using a 5:1:1 by volume mixture of isopropanol, ethyl acetate and water as the eluent, to obtain 215 mg (yield 40%) of the title compound as a colorless solid.

Rf=0.30 (4:1:1=isopropanol:ethyl acetate:water). $[α]D^{25}$+41.0° (c=0.11, H$_2$O). Mass Spectrum (FAB) m/e 349 (M$^+$+H). $^1$H-Nuclear Magnetic Resonance Spectrum (D$_2$O, 270 MHz) δ (ppm): 2.51 (3H, singlet); 3.55 (1H, doublet, J=10 Hz); 3.62 (1H, doublet of doublets, J=7.0 & 14.0 Hz); 3.85 (1H, doublet of doublets, J=3.5 & 14.0 Hz); 3.92 (1H, multiplet); 4.40–4.60 (2H, multiplet); 4.50 (1H, multiplet); 5.63 (1H, doublet, J=2.5 Hz).

EXAMPLE 9

Hexyl 5-thioacetamido-4-guanidino-2,3,4,5-tetradeoxy-D-glycero-D-galacto-non-2-enopyranosoate trifluoroacetic acid salt (Compound No. 31-3)

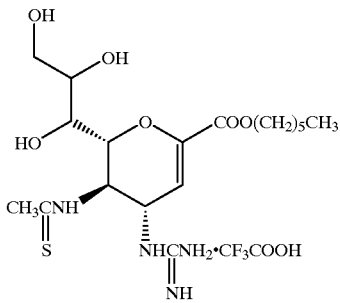

9(i) Methyl 5-thioacetamido-4-(N,N'-bis-t-butoxycarbonylguanidino8, 9-O-isopropylidene-2,3,4,5-tetradeoxy-D-glycero-D-galacto-non-2-enopyranosoate 700 mg (1.01 mmol) of methyl 4-N,N'-bis-t-butoxycarbonylguanidino)-5-thioacetamdo-7,8,9-tri-Q-acetyl-2,3,4,5-tetradeoxy-D-glycero-D-galacto-non-2-enopyranosoate [prepared as described in Example 8(ii)] were dissolved in 20 ml of methanol, and 0.2 ml of a 1 M methanolic solution of sodium methoxide was added to the resulting solution. The mixture was then stirred at room temperature for 1 hour. At the end of this time, the reaction mixture was neutralized with a 4 M solution of hydrogen chloride in dioxane, and the solvent was removed by distillation under reduced pressure. The resulting residue was dissolved in 30 ml of acetone, and 1.0 g (9.71 mmol) of 2,2-dimethoxypropane and 40 mg (0.22 mmol) of p-toluenesulfonic acid were added to the resulting solution. The mixture was then stirred at room temperature for 3 hours. 100 mg of solid sodium hydrogencarbonate were then added to the mixture, and the mixture was stirred for 30 minutes. The solids were then separated by filtration and the solvent was removed from the filtrate by distillation under reduced pressure. The resulting residue was purified by silica gel column chromatography, using a 50:1 by volume mixture of methylene chloride and methanol as the eluent, to obtain 450 mg (yield 74%) of the title compound as a colorless amorphous substance.

Rf=0.33 (20:1=methylene chloride:methanol). $[\alpha]_D^{25}$+14.4° (c=0.18, $CHCl_3$). Mass Spectrum (FAB) m/e 603 ($M^+$+H). $^1$H-Nuclear Magnetic Resonance Spectrum ($CDCl_3$, 270 MHz) δ (ppm): 1.37 (3H, singlet); 1.41 (3H, singlet); 1.48 (9H, singlet); 1.51 (9H, singlet); 2.55 (3H, singlet); 3.50 (1H, doublet of doublets, J=4.8 & 8.5 Hz); 3.80 (3H, singlet); 4.05 (1H, doublet of doublets, J=5.0 & 9.0 Hz); 4.13 (1H, doublet of doublets, J=7.3 & 9.2 Hz); 4.20 (1H, doublet, J=10.0 Hz); 4.40 (1H, multiplet); 4.55 (1H, doubled doublet of doublets, J=7.4, 10.0 & 10.0 Hz); 5.30 (1H, doubled doublet of doublets, J=2.4, 8.0 & 10.0 Hz); 5.84 (1H, doublet, J=2.8 Hz); 8.68 (1H, J=8.0 Hz); 9.04 (1H, J=7.2 Hz).

9(ii) Hexyl 5-thioacetamido-4-(N,N'-bis-t-butoxycarbonylguanidino)-8, 9-O-isopropylidene-2,3,4,5-tetradeoxy-D-glycero-D-galacto-non-2-enopyranosoate 190 mg (0.31 mmol) of methyl 5-thioacetamido-4-(N,N'-bis-t-butoxycarbonylguanidino)-8, 9-O-isopropylidene-2,3,4,5-tetradeoxy-D-glycero-D-galacto-non-2-enopyranosoate [prepared as described in step (i) above] were dissolved in 12 ml of a 6:1 by volume mixture of methanol and water, and 0.32 ml of a 1 M aqueous solution of potassium hydroxide was added to the resulting solution. The mixture was then stirred at room temperature for 3 hours. At the end of this time, the solvent was removed by distillation under reduced pressure, and the residue was dried under reduced pressure at room temperature for 2 hours to obtain a pale yellow solid. The solid was dissolved in 8 ml of acetonitrile, and 76 mg (0.29 mmol) of 18-crown-6 and 236 mg (1.43 mmol) of hexyl bromide were added to the resulting solution. The mixture was then stirred at 80° C. for 2 hours, after which it was poured into a 2-layer solution of 30 ml of ethyl acetate and 20 ml of a saturated aqueous solution of sodium hydrogencarbonate. The organic layer was separated, washed with a saturated aqueous solution of sodium chloride and dried over anhydrous sodium sulfate, after which the solvent was removed by distillation under reduced pressure. The residue was purified by silica gel column chromatography, using a 3:1 by volume mixture of ethyl acetate and hexane as the eluent, to obtain 73 mg (yield 35%) of the title compound as a colorless amorphous solid.

Rf=0.57 (20:1=methylene chloride:methanol). $[\alpha]_D^{25}$+19.2° (c=0.12, $CHCl_3$). Mass Spectrum (FAB) m/e 673 ($M^+$+H). $^1$H-Nuclear Magnetic Resonance Spectrum ($CDCl_3$, 270 MHz) δ (ppm): 0.85–0.95 (3H, singlet); 1.20–1.50 (8H, multiplet); 1.36 (3H, singlet); 1.41 (3H, singlet); 1.48 (9H, singlet); 1.51 (9H, singlet); 1.60–1.80 (2H, multiplet); 2.56 (3H, singlet); 3.52 (1H, doublet of doublets, J=4.8 & 8.5 Hz); 4.00–4.30 (3H, multiplet); 4.40 (1H, multiplet); 4.55 (1H, doubled doublet of doublets, J=7.4, 10.0 & 10.0 Hz); 5.30 (1H, doubled doublet of doublets, J=2.2, 8.0 & 10.0 Hz); 5.82 (1H, doublet, J=2.2 Hz); 8.68 (1H, J=8.0 Hz); 9.02 (1H, J=7.2 Hz).

9(iii) Hexyl 5-thioacetamido-4-guanidino-2,3, 4,5-tetradeoxy-D-glycero-D-galacto-non-2-enopyranosoate trifluoroacetic acid salt 100 mg (0.15 mmol) of hexyl 5-thioacetamido-4-(N,N'-bis-t-butoxycarbonylguanidino)-8, 9-isopropylidene-2,3,4, 5-tetradeoxy-D-glycero-D-galacto-non-2-enopyranosoate [prepared as described in step (ii) above] were dissolved in 12 ml of a 3 1 by volume mixture of methylene chloride and trifluoroacetic acid, and the mixture was stirred at room temperature for 4 hours. At the end of this time, the solvent was removed by distillation under reduced pressure, and the residue was purified by silica gel column chromatography, using a 15:1:1 by volume mixture of t-butanol, ethyl acetate and water as the eluent, to obtain 65 mg (yield 79%) of the title compound as a colorless solid.

Rf=0.75 (5 1:1=t-butanol:acetic acid:water). $[\alpha]_D^{25}$-1.9° (c=0.11, $CH_3OH$). Mass Spectrum (FAB) m/e 433 ($M^+$+H). $^1$H-Nuclear Magnetic Resonance Spectrum ($D_2O$, 270 MHz) δ (ppm: 0.70–0.85 (3H, singlet); 1.10–1.40 (8H, multiplet); 1.60–1.70 (2H, multiplet); 2.50 (3H, singlet); 3.51 (1H, doublet, J=8.5 Hz); 3.80 (1H, doublet, J=10.0 Hz); 4.20 (2H, multiplet); 4.40–4.70 (2H, multiplet); 5.10 (1H, multiplet); 5.98 (1H, broad singlet).

EXAMPLE 10

Tetradecyl 5-thioacetamido-4-guanidino-2,3,4,5-tetradeoxy-D-glycero-D-galacto-non-2-enopyranosoate trifluoroacetic acid salt (Compound No. 31-5)

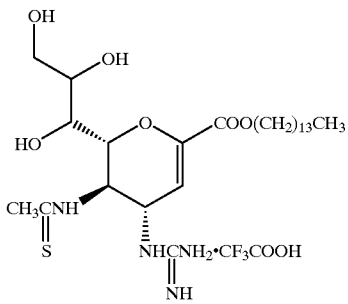

10(i) Tetradecyl 5-thioncetamido-4-(N,N'-bis-t-butoxycarbonylguanidino)-8, 9-O-isopropylidene-2,3,4,5-tetradeoxy-D-glycero-D-galacto-non-2-enopyranosoate 234 mg (0.39 mmol) of methyl 5-thioacetamido-4-(N,N'-bis-t-butoxycarbonylguanidino)-8, 9-O-isopropyhdene-2,3,4,5-tetradeoxy-,D-glycero-D-galacto-non-2-enopyranosoate [prepared as described in Example 9(i)] were dissolved in 12 ml of a 6:1 by volume mixture of methanol and water, and 0.43 ml of a 1 M aqueous solution of potassium hydroxide was added to the resulting solution. The mixture was then stirred at room temperature for 3 hours. At the end of this time, the solvent was removed by distillation under reduced pressure and the residue was dried under reduced pressure at room temperature for 2 hours to obtain a pale yellow solid. The solid was dissolved in 8 ml of acetonitrile and 103 mg (0.39 mmol) of 1 8-crown-6 and 593 mg (1.94 mmol) of tetradecyl bromide were added to the resulting solution. The mixture was then stirred at 80° C. for 2 hours. At the end of this time, the reaction mixture was poured into a 2-layer solution of 30 ml of ethyl acetate and 20 ml of a saturated aqueous solution of sodium hydrogencarbonate. The organic layer was separated, washed with a saturated aqueous solution of sodium chloride and dried over anhydrous sodium sulfate, after which the solvent was removed by distillation under reduced pressure. The resulting residue was purified by silica gel column chromatography, using a 3:1 by volume mixture of ethyl acetate and hexane as the eluent, to obtain 100 mg (yield 33%) of the title compound as a colorless amorphous substance.

Rf=0.45 (2:1=hexane:ethyl acetate). $[\alpha]D^{25}+18.2°$ (c=0.11, $CHCl_3$). Mass Spectrum (FAB) m/e 785 ($M^++H$). $^1$H-Nuclear Magnetic Resonance Spectrum ($CDCl_3$, 270 MHz) δ (ppm) 0.85–0.95 (3H, singlet); 1.20–1.50 (24H, multiplet); 1.36 (3H, singlet); 1.40 (3H, singlet); 1.48 (9H, singlet); 1.51 (9H, singlet); 1.60–1.80 (2H, multiplet); 2.54 (3H, singlet); 3.51 (1H, doublet of doublets, J=4.8 & 8.5 Hz); 4.00–4.30 (3H, multiplet); 4.40 (1H, multiplet); 4.55 (1H, doubled doublet of doublets, J=7.4, 10.0 & 10.0 Hz); 5.30 (1H, doubled doublet of doublets, J=2.2, 8.0 & 10.0 Hz); 5.82 (1H, doublet, J=2.2 Hz); 8.66 (1H, J=8.0 Hz); 9.00 (1H, J=7.2 Hz).

10(ii) Tetradecyl 5-thioacetamido-4-guanidino-2,3, 4,5-tetradeoxy-D-glycero-D-galacto-non-2-enopyranosoate trifluoroacetic acid salt 90 mg (0.11 mmol) of tetradecyl 5-thioacetamido-4-(N, N'-bis-t-butoxycarbonylguanidino)-8, 9-O-isopropylidene-2,3,4,5-tetradeoxy-D-glycero-D-galacto-non-2-enopyranosoate [prepared as described in step (i) above] were dissolved in 12 ml of a 3:1 by volume mixture of methylene chloride and trifluoroacetic acid, and the mixture was stirred at room temperature for 4 hours. At the end of this time, the solvent was removed by distillation under reduced pressure and the resulting residue was purified by silica gel column chromatography, using a 5:1:1 by volume mixture of t-butanol, ethyl acetate and water as the eluent, to obtain 40 mg (yield 47%) of the title compound as a colorless solid.

Rf=0.80 (5:1:1=t-butanol:acetic acid: water). $[\alpha]D^{25}-1.4°$ (c=0.15, $CH_3OH$). Mass Spectrum (FAB) m/e 545 ($M^++H$). $^1$H-Nuclear Magnetic Resonance Spectrum ($D_2O$, 270 MHz) δ (ppm): 0.70–0.85 (3H, singlet); 1.10–1.40 (24H, multiplet); 1.60–1.70 (2H, multiplet); 2.50 (3H, singlet); 3.60–3.90 (2H, multiplet); 4.15 (2H, multiplet); 4.40–4.70 (2H, multiplet); 5.10 (1H, multiplet); 5.90 (1H, broad singlet).

EXAMPLE 11

4Guanidino-9-O-hexanoyl-5-thioacetamido-2,3,4,5-tetradeoxy-D-glycero-D-galacto-non-2-enopyranosoic acid trifluoroacetic acid salt (Compound No. 31-36)

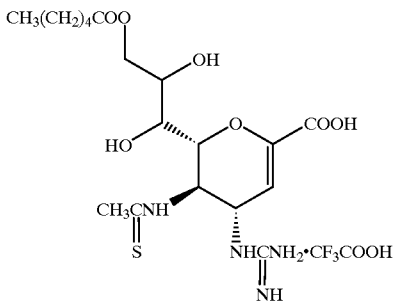

11(i) Methyl 5-thioacetamido-4-N,N'-bis-t-butoxycarbonylguanidino)-7-O-hexanoyl-8, 9-O-isopropylidene-2,3,4,5-tetradeoxy-D-glycero-D-galacto-non-2-enopyranosoate 500 mg (0.83 mmol) of methyl 5-thioacetamido-4-(N,N'-bis-t-butoxycarbonylguanidino)-8, 9-O-isopropylidene-2,3, 4,5-tetradeoxy-D-glycero-D-galacto-non-2-enopyranosoate [prepared as described in Example 9(i)] were dissolved in 15 ml of methylene chloride, and 110 mg (0.91 mmol) of dimethylaminopyridine and 122 mg (0.91 mmol) of hexanoyl chloride were added to the resulting solution. The mixture was then stirred at room temperature for 30 minutes. 92 mg (0.91 mmol) of triethylamine were then added to the resulting mixture and the mixture was stirred for 15 hours. At the end of this time, the reaction mixture was poured into a 2-layer solution of 30 ml of ethyl acetate and 15 ml of a saturated aqueous solution of sodium hydrogencazbonate. The organic layer was separated, washed with a saturated aqueous solution of sodium chloride and dried over anhydrous sodium sulfate, after which the solvent was removed by distillation under reduced pressure. The residue was purified by silica gel column chromatography, using a 50:1 by volume mixture of methylene chloride and methanol as the eluent, to obtain 432 mg (yield 74%) of the title compound as a colorless amorphous substance.

Rf=0.30 (20:1=methylene chloride:methanol). $[\alpha]D^{25}-18.0°$ (c=0.10, $CHCl_3$). Mass Spectrum (FAB) m/e 701 ($M^++H$). $^1$H-Nuclear Magnetic Resonance Spectrum ($CDCl_3$, 270 MHz) δ (ppm): 0.85–0.95 (3H, singlet);

1.20–1.70 (6H, multiplet); 1.35 (3H, singlet); 1.38 (3H, singlet); 1.47 (9H, singlet); 1.48 (9H, singlet); 2.20–2.50 (2H, multiplet); 2.42 (3H, singlet); 3.80 (3H, singlet); 3.92 (1H, doublet of doublets, J=6.6 & 8.5 Hz); 4.10 (1H, doublet of doublets, J=6.2 & 8.5 Hz); 4.35–4.45 (2H, multiplet); 5.15–5.35 (2H, multiplet); 5.90 (1H, doublet, J=2.0 Hz); 7.55 (1H, J=10.0 Hz); 8.55 (1H, J=9.5 Hz).

11 (ii) 4-(N,N'-Bis-t-butoxycarbonylguanidino)-7-O-hexanoyl-8, 9-O-isopropylidene-5-thioacetamido-2,3,4,5-tetradeoxy-D-glyclero-D-galacto-non-2-enopyranosoic acid 89 mg (0.13 mmol) of methyl 5-thioacetamido-4-(N,N'-bis-t-butoxycarbonylguanidino)-7-Ghexanoyl-8,9-O-isopropylidene-2,3, 4,5-tetradeoxy-D-glycero-D-galacto-non-2-enopyranosoate [prepared as described in step (i) above] were dissolved in 3 ml of a 6:1 by volume mixture of methanol and water, and 5.5 mg (0.13 mmol) of lithium hydroxide 1 hydrate were added to the resulting solution. The mixture was then stirred at room temperature for 3 hours. At the end of this time, the reaction mixture was neutralized with a 4 N solution of hydrogen chloride in dioxane , and the solvent was removed by distillation under reduced pressure. The residue was purified by silica gel column chromatography, using a 2:5:1 by volume mixture of isopropanol, ethyl acetate and water as the eluent, to obtain 48 mg (yield 64%) of the title compound as a colorless solid.

Rf=0.67 (2:5:1=isopropanol:ethyl acetate:water). $[\alpha]D^{25}$–25.0° (c=0.10, CHCl$_3$). Mass Spectrum (FAB) m/e 687 (M$^+$+H). $^1$H-Nuclear Magnetic Resonance Spectrum (CD$_3$OD, 270 MHz) δ (ppm): 0.85–0.95 (3H, singlet); 1.20–1.70 (6H, multiplet); 1.32 (3H, singlet); 1.35 (3H, singlet); 1.45 (9H, singlet); 1.51 (9H, singlet); 2.20–2.50 (2H, multiplet); 2.35 (3H, singlet); 3.40 (1H, multiplet); 4.20 (1H, doublet of doublets, J=6.2 & 8.5 Hz); 4.40 (1H, doublet of doublets, J=1.5 & 10.0 Hz); 4.55 (1H, multiplet); 5.00 (1H, doublet of doublets, J=10.0 & 10.0 Hz); 5.10 (1H, doublet of doublets, J=2.1 & 10.0 Hz); 5.30 (1H, doublet of doublets, J=2.0 & 5.5 Hz); 5.73 (1H, doublet, J=2.1 Hz).

11(iii) 4-Guanidino9-O-hexantal-5-thioacetamido-2,3,4,5-teadeoxy-D-glycero-D-galacto-non-2-enopyranosoic acid trifluoroacetic acid salt 100 mg (0.15 mmol) of 4-(N,N'-bis-t-butoxycarbonylguanidino)-7-O-hexanoyl-8,9-O-isopropylidene-5-thioacetamido-2,3,4,5-tetradeoxy-D-glycero-D-galacto-non-2-enopyranosoic acid [prepared as described in step (ii) above] were dissolved in 12 ml of a 2:6:1 by volume mixture of methylene chloride, trifluoroacetic acid and thiophenol, and the mixture was stirred at room temperature for 8 hours. At the end of this time, the solvent was removed by distillation under reduced pressure, and the resulting residue was purified by silica gel column chromatography, using a 2:5:1 by volume mixture of isopropanol, ethyl acetate and water as the eluent, to obtain 54 mg (yield 53%) of the title compound as a colorless solid.

Rf=0.55 (5:1:1=t-butanol:acetic acid:water). $[\alpha]D^{25}$+2.3° (c=0.10, CH$_3$OH). Mass Spectrum (FAB) m/e 447 (M$^+$+H). $^1$H-Nuclear Magnetic Resonance Spectrum (D$_2$O, 270 MHz) δ (ppm): 0.70–0.85 (3H, singlet); 1.20–1.70 (6H, multiplet); 2.30–2.50 (2H, multiplet); 2.52 (3H, singlet); 3.51 (1H, doublet, J=8.5 Hz); 4.15 (1H, multiplet); 4.23 (1H, doublet of doublets, J=5.5 & 12.0 Hz); 4.35 (1H, doublet of doublets, J=2.5 & 12.0 Hz); 4.40–4.60 (2H, multiplet); 5.10 (1H, multiplet); 5.63 (1H, doublet, J=2.4 Hz).

EXAMPLE 12

4-Guanidino-9-O-tetradecanoyl-5-thioacetamido-2,3,4,5-tetradeoxy-D-glycero-D-galacto-non-2-enopyranoso acid trifluoroacetic acid salt
(Compound No. 31-41)

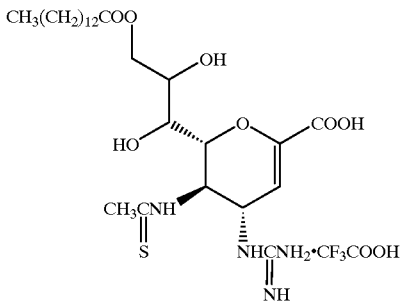

12(i) Methyl 4-(N,N'-bis-t-butoxycarbonylguanidino)-7-O-tetradecanoyl-8, 9-O-isopropylidene-5-thioacetamido-2,3,4, 5-tetradeoxy-D-glycero-D-galacto-non-2-enopyranosoate 440 mg (0.73 mmol) of methyl 5-thioacetamido-4-(N,N'-bis-t-butoxycarbonylguanidino)-8, 9-Sisopropylidene-2,3,4, 5-tetradeoxy-D-glycero-D-galacto-non-2-enopyranosoate [prepared as described in Example 9(i)] were dissolved in 15 ml of methylene chloride, and 132 mg (1.08 mmol) of dimethylaminopyridine and 247 mg (1.0 mmol) of tetradecanoyl chloride were added to the resulting solution. The mixture was then stirred at room temperature for 30 minutes, after which 109 mg (1.08 mmol) of triethylamine were added, and the mixture was stirred for 15 hours. The reaction mixture was then poured into a 2-layer solution of 30 ml of ethyl acetate and 15 ml of a saturated aqueous solution of sodium hydrogencarbonate. The organic layer was separated, washed with a saturated aqueous solution of sodium chloride and dried over anhydrous sodium sulfate, after which the solvent was removed by distillation under reduced pressure. The residue was purified by silica gel column chromatography, using a 50:1 by volume mixture of methylene chloride and methanol as the eluent, to obtain 350 mg (yield 59%) of the title compound as a colorless amorphous substance.

Rf=0.35 (1:1=ethyl acetate:hexane). $[\alpha]D^{25}$–17.60 (c=0.15, CHCl$_3$). Mass Spectrum (FAB) m/e 813 (M$^+$+H). 1H-Nuclear Magnetic Resonance Spectrum (CDCl$_3$, 270 MHz) δ (ppm): 0.85–0.95 (3H, singlet); 1.20–1.70 (22H, multiplet); 1.35 (3H, singlet); 1.38 (3H, singlet); 1.47 (9H, singlet); 1.49 (9H, singlet); 2.20–2.50 (2H, multiplet); 2.42 (3H, singlet); 3.80 (3H, singlet); 3.92 (1H, doublet of doublets, J=6.6 & 8.5 Hz); 4.10 (1H, doublet of doublets, J=6.2 & 8.5 Hz); 4.35–4.45 (2H, multiplet); 5.15–5.35 (2H, multiplet); 5.90 (1H, doublet, J=2.0 Hz); 7.55 (1H, J=10.0 Hz); 8.55 (1H, J=9.5 Hz).

12(ii) 4-(N,N'-Bis-t-butoxycarbonylguanidino)-7-O-tetradecanoyl-8, 9-O-isopropylidene-5-thioacetamido-2,3,4, 5-tetradeoxy-D-glycero-D-galacto-non-2-enopyranosoic acid 320 mg (0.39 mmol) of methyl 4-(N,N'-bis-t-butoxycarbonylguanidino)-7-O-tetradecanoyl-8, 9-O-isopropylidene-5-thioacetamido-2,3,4,5-tetradeoxy-D-glycero-D-galacto-non-2-enopyranosoate [prepared as described in step (i) above] were dissolved in 7 ml of a 6:1 by volume mixture of methanol and water, and 18 mg (0.41 mmol) of lithium hydroxide 1 hydrate were added to the resulting solution. The mixture was then stirred at room temperature for 3 hours. At the end of his time, the reaction mixture was neutralized with a 4 N solution of hydrogen chloride in dioxane, and the solvent was removed by distillation under reduced pressure. The resulting residue was purified by silica gel column chromatography, using a 5:1 by volume mixture of methylene chloride and methanol as the eluent, to obtain 240 mg (yield 77%) of the title compound as a colorless solid.

Rf=0.30 (10:1=methylene chloride:methanol). $[\alpha]D^{25}$ −25.0° (c=0.12, $CHCl_3$). Mass Spectrum (FAB) m/e 799 ($M^+$+H). $^1$H-Nuclear Magnetic Resonance Spectrum ($CD_3OD$, 270 Mz) δ (ppm): 0.85–0.95 (3H, singlet); 1.20–1.70 (22H, multiplet); 1.32 (3H, singlet); 1.35 (3H, singlet); 1.45 (9H, singlet); 1.50 (9H, singlet); 2.20–2.50 (2H, multiplet); 2.35 (3H, singlet); 3.95 (1H, doublet of doublets, J=6.2 & 8.5 Hz); 4.20 (1H, doublet of doublets, J=6.2 & 8.5 Hz); 4.40 (1H, doublet of doublets, J=1.5 & 10.0 Hz); 4.55 (1H, multiplet); 5.00 (1H, doublet of doublets, J=10.0 & 10.0 Hz); 5.10 (1H, doublet of doublets, J=2.1 & 10.0 Hz); 5.30 (1H, doublet of doublets, J=2.0 & 5.5 Hz); 5.73 (1H, doublet, J=2.1 Hz).

12(iii) 4-Guanidino-9-O-tetradecanoyl-5-thioacetamido-2, 3, 4,5-tetradeoxy-D-glycero-D-galacto-non-2-enopyranosoic acid trifluoroacetic acid salt 220 mg (0.27 mmol) of 4-(N,N'-bis-t-butoxycarbonylguanidino)-7-O-tetradecanoyl-8,9-O-isopropylidene-5-thioacetido-2,3, 4,5-teteoxy-D-glycero-D-galacto-non- 2-enopyranosoic acid [prepared as described in step (ii) above] were dissolved in 12 ml of a 2:6:1 by volume mixture of methylene chloride, trifluoroacetic acid and thiophenol, and the mixture was stirred at room temperature for 8 hours. At the end of this time, the solvent was removed by distillation under reduced pressure and the resulting residue was purified by silica gel column chromatography, using a 2:5:1 by volume mixture of isopropanol, ethyl acetate and water as the eluent, to obtain 120 mg (yield 56%) of the title compound as a colorless solid.

Rf=0.60 (5:1:1=t-butanol:acetic acid:water). $[\alpha]D^{25}$+2.2° (c=0.10, $CH_3OH$). Mass Spectrum (FAB) m/e 559 ($M^+$+H). 1H-Nuclear Magnetic Resonance Spectrum ($D_2O$, 270 MHz) δ (ppm): 0.70–0.85 (3H, singlet); 1.20–1.70 (22H, multiplet); 2.30–2.50 (2H, multiplet); 2.54 (3H, singlet); 3.61 (1H, doublet, J=8.5 Hz); 4.15 (1H, multiplet); 4.20 (1H, doublet of doublets, J=5.5 & 12.0 Hz); 4.30 (1H, doublet of doublets, J=2.5 & 12.0 Hz); 4.40–4.60 (2H, multiplet); 5.10 (1H, multiplet); 5.60 (1H, broad singlet).

EXAMPLE 13

5-Acetamido4-guanidino-9-hexanoyl-2,3, 4,5,7-pentadeoxy-7-fluoro-D-glycero-D-galacto-non-2-enopyranosoic acid trifluoroacetic acid salt
(Compound No. 1-36)

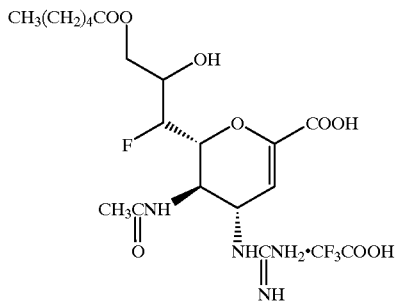

13(i) Diphenylmethyl 5-acetamido-4-(N,N'-bis-t-butoxycarbonylguanidino)-2,3, 4,5,7-pentadeoxy-7-fluoro-D-glycero-D-galacto-non-2-enopyranosoate 100 mg (0.24 mmol) of methyl 5-acetamido-4-(N,N'-bis-t-butoxycarbonylguanidino)-8, 9-di-O-acetyl-2,3,4,5,7-pentadeoxy-7-fluoro-D-glycero-D-galacto-non-2-enopyranosoate [prepared as described in Example 6(ii)] were dissolved in 3 ml of methanol, and 0.5 ml of a 0.1 N methanolic solution of sodium methoxide was added to the resulting solution. The mixture was then stirred at room temperature for 1 hour, after which the reaction mixture was neutralized with a 4 M solution of hydrogen chloride in dioxane, and the solvent was removed by distillation under reduced pressure. The resulting residue was dissolved in 1 ml of distilled water and 280 ml of a 1 N aqueous solution of sodium hydroxide were added to the resulting solution. The mixture was then stirred at room temperature for 1 hour, after which the reaction mixture was neutralized with a 4 M solution of hydrogen chloride in dioxane and then the water was removed by distillation. The resulting residue was dissolved in 3 ml of a 6:1 by volume mixture of methanol and water, and 100 mg (0.52 mmol) of diphenyldiazomethane and 8 mg (0.06 mmol) of a boron trifluoride-diethyl ether complex were added to the resulting solution. The mixture was then stirred at room temperature for 2 hours. At the end of this time, acetic acid was added to the reaction mixture, and the solvent was removed by distillation under reduced pressure. The residue was purified by silica gel column chromatography, using a 20:1 by volume mixture of methylene chloride and methanol as the eluent, to obtain 82 mg (yield 50%) of the title compound as a colorless amorphous substance.

Rf=0.45 (20:1=methylene chloride:methanol). $[\alpha]D^{25}$=−12.2° (c=0.1, $CHCl_3$). Mass Spectrum (FAB) m/e 701 ($M^+$+H). 1H-Nuclear Magnetic Resonance Spectrum ($CDCl_3$, 270 MHz) δ (ppm): 1.50 (9H, singlet); 1.51 (9H, singlet); 1.95 (3H, singlet); 3.25 (2H, multiplet); 3.90 (2H, multiplet); 4.20–4.70 (3H, multiplet); 5.25 (1H, multiplet); 5.95 (1H, doublet, J=2.5 Hz); 6.93 (1H, singlet); 7.10 (1H, doublet, J=8.5 Hz); 7.20–7.40 (10H, multiplet); 8.60 (1H, doublet, J=8.5 Hz).

13(ii) Diphenylmethyl 5-acetamido-4-(N,N'-bis-t-butoxycarbonylguanidino) 9-O-hexanoyl-2,3,4,5,7-pentadeoxy-7-fluoro-D-glycero-D-galacto-non-7-enopyranosoate 50 mg (0.072 mmol) of diphenylmethyl 5-acetamido-4-(N,N'-bis-t-butoxycarbonylguanidino)-2,3, 4,5,7-pentadeoxy-7-fluoro-D-glycero-D-galacto-non-2-enopyranosoate [prepared as described in step (i) above] were dissolved in 2 ml of methylene chloride, and 11 mg (0.11 mmol) of triethylamine and 11 mg (0.086 mmol) of hexanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 47 mg (yield 83%) of the title compound as a colorless amorphous substance.

Rf=0.6 (20:1=methylene chloride:methanol). $[\alpha]D^{25}$=−4.0° (c=0.1, $CHCl_3$). Mass Spectrum (FAB) m/e 786 ($M^+$+H). $^1$H-Nuclear Magnetic Resonance Spectrum ($CDCl_3$, 270 Mz) δ (ppm): 0.90 (3H, multiplet); 1.20–1.40 (6H, multiplet); 1.48 (9H, singlet); 1.50 (9H, singlet); 1.97 (3H, singlet); 2.35 (2H, triplet, J=7.5 Hz); 2.95 (1H, doublet, J=5.0 Hz); 4.20–4.60 (6H, multiplet); 5.25 (1H, multiplet); 5.97 (1H, doublet, J=2.6 Hz); 6.65 (1H, doublet, J=8.5 Hz); 6.93 (1H, singlet); 7.20–7.40 (10H, multiplet); 8.60 (1H, doublet, J=8.5 Hz).

13(iii) 5-Acetamido-4-guanidino-9-O-hexanoyl-2,3,4,5,7-pentadeoxy-7-fluoro-D-glycero-D-galacto-non-2-enopyranosoic acid trifluoroacetic acid salt 40 mg (0.05 mmol) of diphenylmethyl 5-acetamido-4-(N,N'-bis-t-butoxycarbonylguanidino)-9-O-hexanoyl-2,3,4,5,7-pentadeoxy-7-fluoro-D-glycero-D-galacto-non-2-enopyranosoate [prepared as described in step (ii) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 18 mg (yield 65%) of the title compound as a colorless solid.

Rf=0.3 (2:5:1=isopropanol:ethyl acetate:water). $[\alpha]_D^{25}$=+60.0° (c=0.1, $CH_3OH$). Mass Spectrum (FAB) m/e 433 ($M^+$+H). $^1$H-Nuclear Magnetic Resonance Spectrum ($CD_3OD$, 270 MHz) δ (ppm): 0.85–0.95 (3H, multiplet); 1.25–1.40 (4H, multiplet); 1.55–1.70 (2H, multiplet); 2.00 (3H, singlet); 2.35 (2H, triplet, J=4.5 Hz); 4.10–4.40 (5H, multiplet); 4.45–4.70 (2H, multiplet); 5.60 (1H, doublet, J=2.4 Hz).

EXAMPLE 14

5-Acetamido-4-guanidino-9-O-octanyl-2,3,4,5,7-pentadeoxy-7-fluoro-D-glyero-D-galacto-non-2-enopyranosoic acid trifluoroacetic acid salt
(Compound No;1-38)

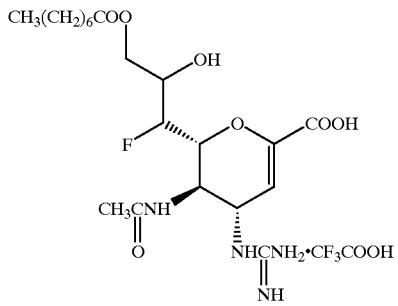

14-(i) Diphenylmethyl 5-acetamido-4-(N,N'-bis-t-butoxycarbonylguanidino)-9-O-octanoyl-2,3,4,5,7-pentadeoxy-7-fluoro-D-glycero-D-galacto-non-2-enopyranosoate 50 mg (0.072 mmol) of diphenylmethyl 5-acetamido-4-(N,N'-bis-t-butoxycarbonylguanidino)-2,3, 4,5,7-pentadeoxy-7-fluoro-D-glycero-D-galacto-non-2-enopyranosoate [prepared as described in Example 13(i)] were dissolved in 2 ml methylene chloride, and 11 mg (0.11 mmol) of triethylamine and 16 mg (0.086 mmol) of octanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 45 mg (yield 77%) of the title compound as a colorless amorphous substance.

Rf=0.5 (20:1=methylene chloride:methanol). $[\alpha]_D^{25}$=−5.2° (c=0.2, $CHCl_3$). Mass Spectrum (FAB) m/e 814 ($M^+$+H). $^1$H-Nuclear Magnetic Resonance Spectrum ($CDCl_3$, 270 MHz) δ (ppm): 1.48 (9H, singlet); 1.50 (9H, singlet); 1.95 (3H, singlet); 3.65 (1H, doublet of doublets, J=5.0 & 18 Hz); 3.80 (1H, doublet of doublets, J=1.8 & 18 Hz); 4.15 (1H, multiplet); 4.23 (1H, doublet, J=8.5 Hz); 4.30–4.60 (3H, multiplet); 5.95 (1H, doublet, J=2.3 Hz).

14(ii) 5-Acetamido-4-guanidino-9-O-octanoyl-2,3,4,5,7-pentadeoxy-7-fluoro-D-glycero-D-galacto-non-2-enopyranosoic acid trifluoroacetic acid salt 40 mg (0.05 mmol) of diphenylmethyl 5-acetamido-4-(N,N'-bis-t-butoxycarbonylguanidino)-9-O-octanoyl-2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 18 mg (yield 64%) of the title compound as a colorless solid Rf=0.3 (2 :5:1=isopropanol:ethyl acetate:water). $[\alpha]_D^{25}$=+56° (c=0.2 $CH_3OH$). Mass Spectrum (FAB) m/e 461 ($M^+$+H). $^1$H-Nuclear Magnetic Resonance Spectrum ($CD_3OD$, 270 MHz) δ (ppm): 0.85–0.95 (3H, multiplet); 1.25–1.40 (8H, multiplet); 1.55–1.70 (2H, multiplet); 2.00 (3H, singlet); 2.35 (2H, triplet, J=4.5 Hz); 4.10–4.40 (5H, multiplet); 4.45–4.70 (2H, multiplet); 5.60 (1H, doublet, J=2.4 Hz).

EXAMPLE 15

5-Acetamido-4-guanidino-9-O-dodecanoyl-2,3,4,5,7-pentadeoxy-7-fluoro-D-glycero-D-galacto-non-2-enopyranosoic acid trifluoroacetic acid salt
(Compound No. 1-40)

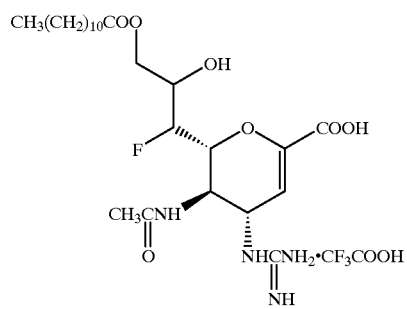

15(i) Diphenylmethyl 5-acetamido-4-(N,N'-bis-t-butoxycarbonylguanidino)-9-O-dodecangyl-2,3,4,5,7-pentadeoxy-7-fluoro-D-galycero-D-galacto-non-2-enopyrnosoate 55 mg (0.078 mmol) of diphenylmethyl 5-acetamido-4-(N,N'-bis-t-butoxycarbonylguanidino)-2,3, 4,5,7-pentadeoxy-7-fluoro-D-glycero-D-galacto-non-2-enopyranosoate [prepared as described in Example 13(i)] were dissolved in 2 ml of methylene chloride, 10 mg (0.10 mmol) of triethylamine and 21 mg (0.094 mmol) of dodecanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 1:1 by volume mixture of ethyl acetate and hexane as the eluent, to obtain 48 mg (yield 69%) of the title compound as a colorless amorphous substance.

Rf=0.4 (1:1=ethyl acetate:hexane). $[\alpha]_D^{25}$=−5.7° (c=0.12, CHCl$_3$). Mass Spectrum (FAB) m/e 883 (M$^+$+H). $^1$H-Nuclear Magnetic Resonance Spectrum (CDCl$_3$, 270 MHz) δ (ppm): 0.90 (3H, multiplet); 1.20–1.40 (18H, multiplet); 1.48 (9H, singlet); 1.50 (9H, singlet); 1.97 (3H, singlet); 2.35 (2H, triplet, J=7.5 Hz); 2.95 (1H, doublet, J=5.0 Hz); 4.20–4.60 (6H, multiplet); 5.25 (1H, multiplet); 5.97 (1H, doublet, J=2.6 Hz); 6.65 (1H, doublet, J=8.5 Hz); 6.93 (1H, singlet); 7.20–7.40 (10H, multiplet); 8.60 (1H, doublet, J=8.5 Hz).

15(ii) 5-Acetamido-4-guanidino-9-O-dodecanoyl-2,3,4,5,7-pentadeoxy-7-fluoro-D-glycero-D-galacto-non-2-enopyranosoic acid trifluoroacetic acid salt 43 mg (0.05 mmol) of diphenylmethyl 5-acetamido-4-(N,N'-bis-t-butoxycarbonylguanidino)-9-O-Udodecanoyl-2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol ethyl acetate and water as the eluent, to obtain 33 mg (yield 91%) of the title compound as a colorless solid Rf=0.4 (2 :5:1=isopropanol:ethyl acetate:water). $[\alpha]_D^{25}$=+22.70 (c=0.1, CH$_3$OH). Mass Spectrum (FAB) m/e 517 (M$^+$+H). $^1$H-Nuclear Magnetic Resonance Spectrum (CD$_3$OD, 270 MHz) δ (ppm): 0.85–0.95 (3H, multiplet); 1.25–1.40 (16H, multiplet); 1.55–1.70 (2H, multiplet); 2.00 (3H, singlet); 2.35 (2H, triplet, J=7.0 Hz); 4.10–4.40 (5H, multiplet); 4.45–4.70 (2H, multiplet); 5.60 (1H, doublet, J=2.4 Hz).

EXAMPLE 16

5-Acetamido-4-guanidino-9-O-tetradecanoyl-2,3,4,5,7-pentadeoxy-7-fluoro-D-glycero-D-galacto-non-2-enopyranosoic acid trifluoroacetic acid salt (Compound No. (1-41))

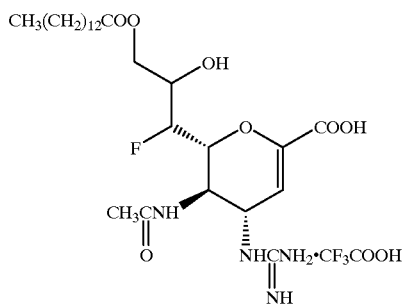

16(i) Diphenylmethyl 5-acetamido-4-(N,N'-bis-t-butoxycarbonylguanidino)-9-O-tetradecanoyl-2,3,4,5,7-pentadeoxy-7-fluoro-D-glycero-D-galacto-non-2-enopyranosoate 50 mg (0.072 mmol) of diphenylmethyl 5-acetamido-4-(N,N'-bis-t-butoxycarbonylguanidino)-2,3, 4,5,7-pentadeoxy-7-fluoro-D-glycero-D-galacto-non-2-enopyranosoate [prepared as described in Example 13(i)] were dissolved in 2 ml of methylene chloride, and 11 mg (0.11 mmol) of triethylamine and 21 mg (0.086 mmol) of tetradecanoyl chloride were added to the resulting solution, whilst ice-cooling. The mixture was then stirred at 0° C. for 1 hour. At the end of this time, the reaction mixture was poured into a 2-layer solution of 5 ml of ethyl-acetate and 3 ml of a saturated aqueous solution of sodium hydrogencarbonate, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 50 mg (yield 77%) of the title compound as a colorless amorphous substance.

Rf=0.4 (1:1=ethyl acetate:hexane). $[\alpha]_D^{25}$=−7.0° (c=0.10, CHCl$_3$). Mass Spectrum (FAB) m/e 898 (M$^+$+H). 1H-Nuclear Magnetic Resonance Spectrum (CDCl$_3$, 270 MHz) δ (ppm): 0.90 (3H, multiplet); 1.20–1.40 (22H, multiplet); 1.48 (9H, singlet); 1.50 (9H, singlet); 1.97 (3H, singlet); 2.35 (2H, triplet, J=7.5 Hz); 2.95 (1H, doublet, J=5.0 Hz); 4.20–4.60 (6H, multiplet); 5.25 (1H, multiplet); 5.97 (1H, doublet, J=2.6 Hz); 6.65 (1H, doublet, J=8.5 Hz); 6.93 (1H, singlet); 7.20–7.40 (10H, multiplet); 8.60 (1H, doublet, J=8.5 Hz).

16(ii) 5-Acetamido-4-guanidino-9-O-tetradecanoyl-2,3,4,5, 7-pentadeoxy-7-fluoro-D-glycero-D-galacto-non-2-enopyranosoic acid trifluoroacetic acid salt 40 mg (0.05 mmol) of diphenylmethyl 5-acetamido-4-(N, N'-bis-t-butoxycarbonylguanidino)-9-O-tetradecanoyl-2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 21 mg (yield 64%) of the title compound as a colorless solid.

Rf=0.4 (2:5:1=isopropanol:ethyl acetate:water). $[\alpha]_D^{25}$=+22.0° (c=0.06, $CH_3OH$). Mass Spectrum (FAB) m/e 545 ($M^+$+H). 1H-Nuclear Magnetic Resonance spectrum ($CD_3OD$, 270 MHz) δ (ppm): 0.85–0.95 (3H, multiplet); 1.25–1.70 (20H, multiplet); 1.55–1.70 (2H, multiplet); 2.00 (3H, singlet); 2.35 (2H, triplet, J=4.5 Hz); 4.10–4.40 (5H, multiplet); 4.45–4.70 (1H, multiplet); 5.60 (1H, doublet, J=2.4 Hz).

EXAMPLE 17

5-Acetamido-4-guanidino-9-O-hexadecanoyl-2,3,4,5,7-pentadeoxy-7-fluoro-D-glycero-D-galacto-non-2-enopyranosoic acid trifluoroacetic acid salt
(Compound No. 1-42)

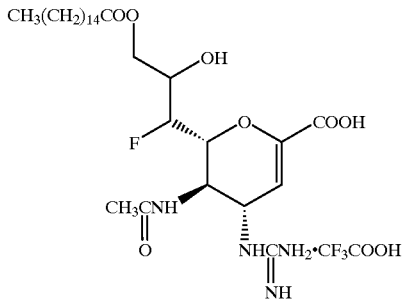

17(i) Diphenylmethyl 5-acetamido-4-(N,N'-bis-t-butoxycarbonylguanidino)-9-O-hexadecanoyl-2,3,4,5,7-pentadeoxy-7-fluoro-D-glycero-D-galacto-non-2-enopyranosoate 58 mg (0.08 mmol) of diphenylmethyl 5-acetamido 4-(N, N'-bis-t-butoxy-carbonylguanidino)-2,3, 4,5,7-pentadeoxy-7-fluoro-D-glycero-D-galacto-non-2-enopyranosoate [prepared as described in Example 13(i)] were dissolved in 2 ml of methylene chloride, and 10 mg (0.10 mmol) of triethylamine and 26 mg (0.0946 mmol) of hexadecanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 1:1 by volume mixture of ethyl acetate and hexane as the eluent, to obtain 50 mg (yield 67%) of the title compound as a colorless amorphous substance.

Rf=0.4 (1:1=ethyl acetate:hexane). $[\alpha]_D^{25}$=−11.0° (c=0.11, $CHCl_3$). Mass Spectrum (FAB) m/e 939 ($M^+$+H). 1H-Nuclear Magnetic Resonance Spectrum ($CDCl_3$, 270 MHz) δ (ppm): 0.90 (3H, multiplet); 1.20–1.40 (22H, multiplet); 1.48 (9H, singlet); 1.50 (9H, singlet); 1.97 (3H, singlet); 2.35 (2H, triplet, J=7.5 Hz); 2.95 (1H, doublet, J=5.0 Hz); 4.20–4.60 (6H, multiplet); 5.25 (1H, multiplet); 5.97 (1H, doublet, J=2.6 Hz); 6.65 (1H, doublet, J=8.5 Hz); 6.93 (1H, singlet); 7.20–7.40 (10H, multiplet); 8.60 (1H, doublet, J=8.5 Hz).

17(ii) 5-Acetamodo-4-guanidino-9-O-hexadecanoyl-2,3,4,5,7-pentadeoxy-7-fluro-D-glycero-D-galacto-non-2-enopyranosoic acid trifluoroacetic acid salt 45 mg (0.05 mmol) of diphenylmethyl 5-acetamido-4-(N, N'-bis-t-butoxycarbonylguanidino)-9-O-hexadecanoyl-2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 28 mg (yield 73%) of the title compound as a colorless solid.

Rf=0.4 (2:5:1=isopropanol:ethyl acetate:water). $[\alpha]_D^{25}$=+19.7° (c=0.1, $CH_3OH$). Mass Spectrum (FAB) m/e 573 ($M^+$+H). $^1$H-Nuclear Magnetic Resonance Spectrum ($CD_3OD$, 270 MHz) δ (ppm): 0.85–0.95 (3H, multiplet); 1.25–1.40 (16H, multiplet); 1.55–1.70 (2H, multiplet); 2.00 (3H, singlet); 2.35 (2H, triplet, J=7.0 Hz); 4.10–4.40 (5H, multiplet); 4.45–4.70 (2H, multiplet); 5.60 (1H, doublet, J=2.4 Hz).

EXAMPLE 18

5-Acetamido-4-guanidino-9-O-octadecanoyl2,3,4,5,7-pentadeoxy-7-fluoro-D-glycero-D-galacto-non-2-enopyranosoic acid trifluoroacetic acid salt
(Compound No. 1-43)

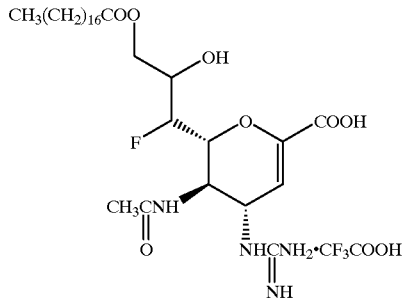

18(i) Diphenylmethyl 5-acetamido-4-(N,N'-bis-t-butoxycarbonvyguanidino)-9-O-octadecanoyl-2,3,4,5,7-pentadeoxy-7-fluoro-D-glycero-D-galacto-non-2-enopyranosoate 55 mg (0.08 mmol) of diphenylmethyl 5-acetamido-4-(N, N'-bis-t-butoxycarbonylguanidino)-2,3, 4,5,7-pentadeoxy-7-fluoro-D-glycero-D-galacto-non-2-enopyranosoate [prepared as described in Example 13(i)] were dissolved in 2 ml of methylene chloride, and 10 mg (0.10 mmol) of triethylamine and 29 mg (0.094 mmol) of octadecanoyl chloride were added to the resulting solution, whilst ice-cooling. The mixture was then stirred at 0° C. for 1 hour. At the end of this time, the reaction mixture was poured into a 2-layer solution of 5 ml of ethyl-acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 1:1 by volume mixture of ethyl acetate and hexane as the eluent, to obtain 51 mg (yield 67%) of the title compound as a colorless amorphous substance.

Rf=0.5 (1:1=ethyl acetate:hexane). $[\alpha]_D^{25}=-8.1°$ (c=0.16, CHCl$_3$). Mass Spectrum (FAB) m/e 967 (M$^+$+H). $^1$H-Nuclear Magnetic Resonance Spectrum (CDCl$_3$, 270 MHz) δ (ppm): 0.90 (3H, multiplet); 1.20–1.40 (30H, multiplet); 1.48 (9H, singlet); 1.50 (9H, singlet); 1.97 (3H, singlet); 2.35 (2H, triplet, J=7.5 Hz); 2.95 (1H, doublet, J=5.0 Hz); 4.20–4.60 (6H, multiplet); 5.25 (1H, multiplet); 5.97 (1H, doublet, J=2.6 Hz); 6.65 (1H, doublet, J=8.5 Hz); 6.93 (1H, singlet); 7.20–7.40 (10H, multiplet); 8.60 (1H, doublet, J=8.5 Hz).

18(i) 5-Acetamido-4-guanidino-9-O-octadecanoyl-2,3,4,5,7-pentadeoxy-7-fluoro-D-glyero-D-galacto-non-2-enopyranosoic acid trifluoroacetic acid salt 45 mg (0.047 mmol) of diphenylmethyl 5-acetamido-4-(N,N'-bis-t-butoxycarbonylguanidino)-9-O-octadecanoyl-2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 24 mg (yield 62%) of the title compound as a colorless solid.

Rf=0.4 (2:5:1=isopropanol:ethyl acetate:water). $[\alpha]_D^{25}=+14.3°$ (c=0.15, CH$_3$OH). Mass Spectrum (FAB) m/e 601 (M$^+$+H). $^1$H-Nuclear Magnetic Resonance Spectrum (CD$_3$OD, 270 MHz) δ (ppm): 0.85–0.95 (3H, multiplet); 1.25–1.40 (28H, multiplet); 1.55–1.70 (2H, multiplet); 2.00 (3H, singlet); 2.35 (2H, triplet, J=7.0 Hz); 4.10–4.40 (5H, multiplet); 4.45–4.70 (2H, multiplet); 5.60 (1H, doublet, J=2.4 Hz).

EXAMPLE 19

5-Acetamido 4guanidino-8,9-di-O-acetyl-2,3,4,5,7-pentadeoxy-7-fluoro-D-glycero-D-galacto-non-2-enopyranosoic acid trifluoroacetic acid salt
(Compound No. 1-54)

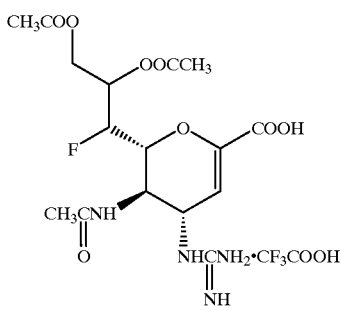

19(i) Diphenylmethyl 5-acetamido-4-(N,N'-bis-t-butoxycarbonylguanidino)-8,9-di-O-acetyl-2,3,4,5,7-pentadeoxy-7-fluoro-D-glycero-D-galacto-non-2-enopyranosoate 58 mg (0.083 mmnol) of diphenylmethyl 5-acetamido-4-(N,N'-bis-t-butoxycarbonylguanidino)-2,3,4,5,7-pentadeoxy-7-fluoro-D-glycero-D-galacto-non-2-enopyranosoate [prepared as described in Example 13(i)] were dissolved in 2 ml of pyridine, and 0.5 ml of acetic anhydride was added to the resulting solution, whilst ice-cooling. The mixture was then stirred at room temperature for 3 hours. At the end of this time, the reaction mixture was poured into a 2-layer solution of 5 ml of ethyl acetate and 3 ml of a 1 N aqueous hydrochloric acid solution, and the organic layer was separated and washed with a saturated aqueous solution of sodium hydrogencarbonate and then with a saturated aqueous solution of sodium chloride. It was then dried over anhydrous sodium sulfate, and the solvent was removed by distillation under reduced pressure. The resulting residue was purified by silica gel column chromatography, using a 1:1 by volume mixture of hexane and ethyl acetate as the eluent, to obtain 59 mg (yield 91%) of the title compound as a colorless amorphous substance.

Rf=0.47 (1:1=hexane:ethyl acetate). $[\alpha]_D^{25}=+2.5°$ (c=0.12, CHCl$_3$). Mass Spectrum (FAB) m/e 785 (M$^+$+H). $^1$H-Nuclear Magnetic Resonance Spectrum (CDCl$_3$, 270 MHz) δ (ppm): 1.48 (9H, singlet); 1.49 (9H, singlet); 1.99 (3H, singlet); 2.04 (3H, singlet); 2.07 (3H, singlet); 4.00–4.30 (3H, multiplet); 4.75 (1H, doublet, J=13 Hz); 4.80 (1H, doublet of doublets, J=7.5 & 45 Hz); 5.20 (1H, doubled doublet of doublets, J=1.0, 9.0 & 9.0 Hz); 5.50 (1H, multiplet); 5.92 (1H, doublet, J=2.4 Hz); 6.72 (1H, doublet, J=7.5 Hz); 6.94 (1H, singlet); 7.20–7.50 (10H, multiplet); 8.60 (1H, doublet, J=8.5 Hz).

19(ii) 5-Acetamido-4-guanidino-8,9-di-O-acetyl-2,3,4,5,7-pentadeoxy-7-fluoro-D-glycero-D-galacto-non-2-enopyranosoic acid trifluoroacetic acid salt 50 mg (0.064 mmol) of diphenylmethyl 5-acetamido-4-(N,N'-bis-t-butoxycarbonylguanidino)-8,9-di-O-acetyl-2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 23 mg (yield 56%) of the title compound as a colorless solid.

Rf=0.16 (2:5:1=isopropanol:ethyl acetate:water). $[\alpha]_D^{25}=+36.9°$ (c=0.15, CH$_3$OH). Mass Spectrum (FAB) m/e 419 (M$^+$+H). $^1$H-Nuclear Magnetic Resonance Spectrum (CD$_3$OD, 270 MHz) δ (ppm): 2.00 (3H, singlet); 2.03 (3H, singlet); 2.05 (3H, singlet); 4.10–4.40 (4H, multiplet); 4.70–5.00 (2H, multiplet); 5.50 (1H, multiplet); 5.70 (1H, doublet, J=3.0 Hz).

EXAMPLE 20

5-Acetamido-4-guanidino-8,9-di-O-propionyl-2,3,4,
5,7-pentadeoxy-7-fluoro-D-glycero-D-galacto-non-
2-enopyranosoic acid trifluoroacetic acid salt
(Compound No. 1-50)

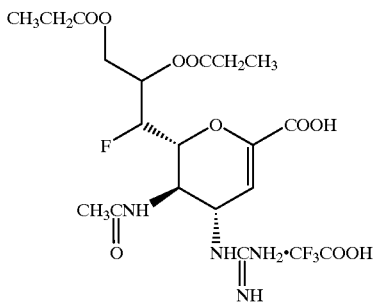

20(i) Diphenylmethyl 5-acetamido-4-(N,N'-bis-t-butoxycarbonylguanidino)-8,9-di-O-propionyl-2,3,4,5,7-pentadeoxy-7-fluoro-D-glycero-D-galacto-non-2-enopyranosoate 52 mg (0.074 mmol) of diphenylmethyl 5-acetamido-4-(N,N'-bis-t-butoxycarbonylguanidino)-2,3,4,5,7-pentadeoxy-7-fluoro-D-glycero-D-galacto-non-2-enopyranosoate [prepared as described in Example 13(i)] were dissolved in 2 ml of pyridine, and 0.5 ml of propionic anhydride was added to the resulting solution, whilst ice-cooling. The mixture was then stirred at room temperature for 3 hours. At the end of this time, the reaction mixture was poured into a 2-layer solution of 5 ml of ethyl acetate and 3 ml of a I N aqueous hydrochloric acid solution, and the organic layer was separated and washed with a saturated aqueous solution of sodium hydrogencarbonate and then with a saturated aqueous solution of sodium chloride. It was then dried over anhydrous sodium sulfate, and the solvent was removed by distillation under reduced pressure. The resulting residue was purified by silica gel column chromatography, using a 1:1 by volume mixture of hexane and ethyl acetate as the eluent, to obtain 54 mg (yield 90%/o) of the title compound as a colorless amorphous substance.

Rf=0.54 (1:1=hexane:ethyl acetate). $[\alpha]D^{25}$=+9.6° (c=0.14, $CHCl_3$). Mass Spectrum (FAB) m/e 813 ($M^+$+H). $^1$H-Nuclear Magnetic Resonance Spectrum ($CDCl_3$, 270 MHz) δ (ppm): 1.11 (9H, triplet, 7.5 Hz); 1.48 (9H, singlet); 1.49 (9H, singlet); 2.04 (3H, singlet); 2.20–2.35 (4H, multiplet); 4.00–4.30 (3H, multiplet); 4.75 (1H, doublet, J=13 Hz); 4.80 (1H, doublet of doublets, J=7.5 & 45 Hz); 5.20 (1H, doubled doublet of doublets, J=1.0, 9.0 & 9.0 Hz); 5.50 (1H, multiplet); 5.92 (1H, doublet, J=2.4 Hz); 6.72 (1H, doublet, J=7.5 Hz); 6.94 (1H, singlet); 7.20–7.50 (10H, multiplet); 8.60 (1H, doublet, J=8.5 Hz).

20(ii) 5-Acetamido-4-guanidino-8,9-di-O-propionyl-2,3,4,5,7-pentadeoxy-7-fluoro-D-glycero-D-galacto-non-2-enopyranosoic acid trifluoroacetic acid salt 46 mg (0.057 mmol) of diphenylmethyl 5-acetamido-4-(N,N'-bis-t-butoxycarbonylguanidino)-8,9-di-O-propionyl-2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 24 mg (yield 63%) of the title compound as a colorless solid.

Rf=0.25 (2:5:1=isopropanol:ethyl acetate:water). $[\alpha]D^{25}$=+32.3° (c=0.14, $CH_3OH$). Mass Spectrum (FAB) m/e 447 ($M^+$+H). $^1$H-Nuclear Magnetic Resonance Spectrum ($CD_3OD$, 270 MHz) δ (ppm): 1.10 (6H, triplet, J=7.5 Hz); 2.00 (3H, singlet); 2.35 (4H, quartet, J=7.5 Hz); 4.10–4.40 (4H, multiplet); 4.70–5.00 (2H, multiplet); 5.50 (1H, multiplet); 5.60 (1H, doublet, J=3.0 Hz).

EXAMPLE 21

5-Acetamido-4-guanidino-8,9-di-O-hexanoyl-3,4,5,
7-pentadeoxy-7-fluoro-D-glycero-D-galacto-non-2-
enopyranosoic acid trifluoroacetic acid salt
(Compound No. 1-58)

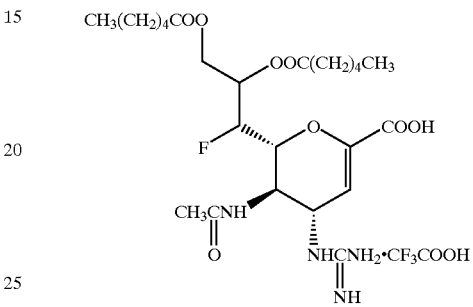

21(i) Diphenylmethyl 5-acetamido-4(N,N'-bis-t-butoxycarbonylguanidino)-8,9-di-O-hexanoyl-2,3,4,5,7-pentadeoxy-7-fluoro-D-glycero-D-galacto-non-2-enopyranosoate 44 mg (0.063 mmol) of diphenylmethyl 5-acetamido-4-bis-t-butoxycarbonylguanidino)-2,3,4,5,7-pentadeoxy-7-fluoro-D-glycero-D-galacto-non-2-enopyranosoate [prepared as described in Example 13(i)] were dissolved in 2 ml of methylene chloride, and 19 mg (0.17 mmol) of 4-dimethylaminopyridine and 19 mg (0.14 mmol) of hexanoyl chloride were added to the resulting solution, whilst ice-cooling. The mixture was then stirred at room temperature for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 3:1 by volume mixture of hexane and ethyl acetate as the eluent, to obtain 49 mg (yield 87%) of the title compound as a colorless amorphous substance.

Rf=0.28 (3:1=hexane:ethyl acetate). $[\alpha]D^{25}$=+6.5° (c=0.10, $CHCl_3$). Mass Spectrum (FAB) m/e 897 ($M^+$+H). $^1$H-Nuclear Magnetic Resonance Spectrum ($CDCl_3$, 270 MHz) δ (ppm): 0.80–1.00 (6H, multiplet); 1.20–1.40 (8H, multiplet); 1.48 (9H, singlet); 1.49 (9H, singlet); 1.50–1.70 (4H, multiplet); 1.98 (3H, singlet); 2.20–2.30 (4H, multiplet); 4.00–4.30 (3H, multiplet); 4.75 (1H, doublet, J=13 Hz); 4.80 (1H, doublet of doublets, J=7.4 & 45 Hz); 5.18 (1H, doubled doublet of doublets, J=1.0, 9.0 & 9.0 Hz); 5.50 (1H, multiplet); 5.93 (1H, doublet, J=2.4 Hz); 6.70 (1H, doublet, J=7.5 Hz); 6.93 (1H, singlet); 7.20–7.50 (10H, multiplet); 8.60 (1H, doublet, J=8.5 Hz).

21(ii) 5-Acetamido-4guanidino-8,9-di-O-hexanoyl-2,34,5,7-pentadeoxy-7-fluoro-D-glycero-D-galacto-non-2-enopyranosoic acid trifluoroacetic acid salt 42 mg (0.047 mmol) of diphenylmethyl 5-acetamido-4-(N,N'-bis-t-butoxycarbonylguanidino)-8,9-di-O-hexanoyl- 2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 21 mg (yield 59%) of the title compound as a colorless solid.

Rf=0.34 (2:5:1=isopropanol:ethyl acetate:water). $[\alpha]D^{25}$=+23.7° (c=0.11, $CH_3OH$). Mass Spectrum (FAB) m/e 531 ($M^++H$). $^1$H-Nuclear Magnetic Resonance Spectrum ($CD_3OD$, 270 MHz) δ (ppm): 0.85–0.95 (6H, multiplet); 1.20–1.40 (8H, multiplet); 1.55–1.70 (4H, multiplet); 2.00 (3H, singlet); 2.30 (2H, triplet, J=7.5 Hz); 4.10–4.40 (4H, multiplet); 4.70–5.00 (2H, multiplet); 5.55 (1H, multiplet); 5.65 (1H, doublet, J=3.0 Hz).

EXAMPLE 22

5Acetamido-4guanidino-8,9-di-O-decanoyl-2,3,4,5,7-pentadeoxy-7-fluoro-D-glycero-D-galacto-non-2-enopyranosoic acid trifluoroacetic acid salt
(Compound No. 1-61)

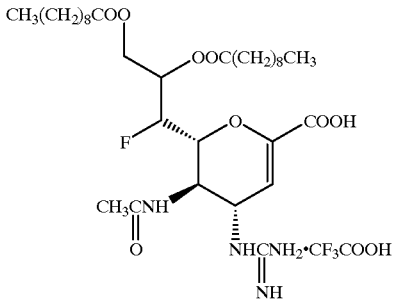

22(i) Diphenylmethyl 5-acetamido-4-(N,N'-bis-t-butoxycarbonylguanidino)-8,9-di-O-decanoyl-2,3,4,5,7-pentadeoxy-7-fluoro-D-glycero-D-galacto-non-2-enopyranosoate 42 mg (0.06 mmol) of diphenylmethyl 5-acetamido-4-(N,N'-bis-t-butoxycarbonylguanidino)-2,3,4,5,7-pentadeoxy-7-fluoro-D-glycero-D-galacto-non-2-enopyranosoate [prepared as described in Example 13(i)] were dissolved in 2 ml of methylene chloride, and 18 mg (0.15 mmol) of 4-dimethylaminopyridine and 26 mg (0.14 mmol) of decanoyl chloride were added to the resulting solution, whilst ice-cooling. The mixture was then stirred at room temperature for 1 hour. At the end of this time, the reaction mixture was poured into a 2-layer solution of 5 ml of ethyl acetate and 3 ml of a saturated aqueous solution of sodium hydrogen carbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 3:1 by volume mixture of hexane and ethyl acetate as the eluent, to obtain 52 mg (yield 86%) of the title compound as a colorless amorphous substance.

Rf=0.28 (3:1=hexane:ethyl acetate). $[\alpha]D^{25}$=+13.3° (c=0.17, $CHCl_3$). Mass Spectrum (FAB) m/e 1009 ($M^++H$). $^1$H-Nuclear Magnetic Resonance Spectrum ($CDCl_3$, 270 MHz) δ (ppm): 0.80–0.90 (6H, multiplet); 1.20–1.40 (24H, multiplet); 1.48 (9H, singlet); 1.49 (9H, singlet); 1.50–1.65 (4H, multiplet); 1.98 (3H, singlet); 2.20–2.30 (4H, multiplet); 4.00–4.30 (3H, multiplet); 4.75 (1H, doublet, J=13 Hz); 4.80 (1H, doublet of doublets, J=7.5 & 45 Hz); 5.20 (1H, doubled doublet of doublets, J=1.0, 9.0 & 9.0 Hz); 5.50 (1H, multiplet); 5.92 (1H, doublet, J=2.4 Hz); 6.65 (1H, doublet, J=7.5 Hz); 6.93 (1H, singlet); 7.20–7.50 (10H, multiplet); 8.60 (1H, doublet, J=8.5 Hz).

22(ii) 5Acetamido-4-guanidino-8,9-di-O-decanoyl-2,3,4,5,7-pentadeoxy-7-fluoro-D-glycero-D-galacto-non-2-enopyranosoic acid trifluoroacetic acid salt 45 mg (0.045 mmol) of diphenylmethyl 5-acetamido-4-(N,N'-bis-t-butoxycarbonylguanidino)-8,9-di-O-decanoyl-2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 29 mg (yield 75%) of the title compound as a colorless solid.

Rf=0.3 (2:5:1=isopropanol:ethyl acetate:water). $[\alpha]D^{25}$=+20.6° (c=0.14, $CH_3OH$). Mass Spectrum n(FAB) m/e 643 ($M^++H$). $^1$H-Nuclear Magnetic Resonance Spectrum ($CD_3OD$, 270 MHz) δ (ppm): 0.85–0.95 (6H, multiplet); 1.20–1.40 (24H, multiplet); 1.55–1.70 (4H, multiplet); 2.00 (3H, singlet); 2.30 (2H, triplet, J=7.0 Hz); 4.10–4.40 (4H, multiplet); 4.70–5.00 (2H, multiplet); 5.55 (1H, multiplet); 5.70 (1H, doublet, J=3.0 Hz).

EXAMPLE 23

5-Acetamido-4-guanidino-8,9-di-O-tetradecanoyl-2,3,4,5,7-pentadeoxy-7-fluoro-D-glycero-D-galacto-non-2-enopyranosoic acid trifluoroacetic acid salt
(Compound No. 1-63)

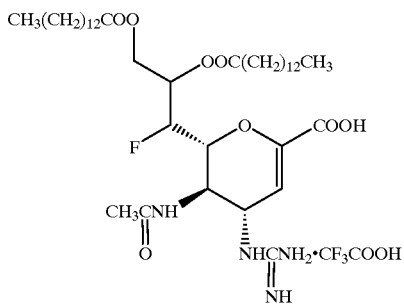

23(i) Diphenylmethyl 5-acetamido-4-(N,N'-bis-t-butoxycarbonylguanidino)-8,9-di-O-tetradecanoyl-2,3,4,5,7-pentadeoxy-7-fluoro-D-glycero-D-galacto-non-2-enopyranosoate 43 mg (0.06 mmol) of diphenylmethyl 5-acetamido-4(N,N'-bis-t-butoxycarbonylguanidino)-2,3,4,5,7-pentadeoxy-7-fluoro-D-glycero-D-galacto-non-2-enopyranosoate [prepared as described in Example 13(i)] were dissolved in 2 ml of methylene chloride, and 19 mg (0.15 mmol) of 4-dimethylaminopyridine and 26 mg (0.14 mmol) of tetradecanoyl chloride were added to the resulting solution, whilst ice-cooling. The mixture was then stirred at room temperature for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 3:1 by volume mixture of hexane and ethyl acetate as the eluent, to obtain 60 mg (yield 87%) of the title compound as a colorless amorphous substance.

Rf=0.28 (3:1=hexane:ethyl acetate). $[\alpha]D^{25}=+15.5°$ (c=0.11, $CHCl_3$). Mass Spectrum (FAB) m/e 1121 ($M^++H$). $^1$H-Nuclear Magnetic Resonance Spectrum ($CDCl_3$, 270 MHz) δ (ppm): 0.80–0.90 (6H, multiplet); 1.20–1.40 (40H, multiplet); 1.48 (9H, singlet); 1.49 (9H, singlet); 1.50–1.65 (4H, multiplet); 1.98 (3H, singlet); 2.20–2.30 (4H, multiplet); 4.00–4.30 (3H, multiplet); 4.75 (1H, doublet, J=13 Hz); 4.80 (1H, doublet of doublets, J=7.5 & 45 Hz); 5.18 (1H, doubled doublet of doublets, J=1.0, 9.0 & 9.0 Hz); 5.50 (1H, multiplet); 5.93 (1H, doublet, J=2.4 Hz); 6.66 (1H, doublet, J=7.5 Hz); 6.93 (1H, singlet); 7.20–7.50 (10H, multiplet); 8.60 (1H, doublet, J=8.5 Hz).

23(ii) 5Acetamido-4-guanidino-8,9-di-O-tetradecanoyl-2,3,4,5,7-pentadeoxy-7-fluoro-D-glycero-D-galacto-non-2-enopyranosoic acid trifluoroacetic acid salt 52 mg (0.046 mmol) of diphenylmethyl 5-acetamido-4-(N,N'-bis-t-butoxycarbonylguanidino)-8,9-di-O-tetradecanoyl-2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 38 mg (yield 83%) of the title compound as a colorless solid.

Rf=0.3 (2:5:1=isopropanol:ethyl acetate:water). $[\alpha]D^{25}=+28.0°$ (c=0.16, $CH_3OH$). Mass Spectrum 755 (FAB) m/e 545 ($M^++H$). $^1$H-Nuclear Magnetic Resonance Spectrum ($CD_3OD$, 270 MHz) δ (ppm): 0.85–0.95 (6H, multiplet); 1.20–1.40 (40H, multiplet); 1.55–1.70 (4H, multiplet); 2.00 (3H, singlet); 2.30 (2H, triplet, J=7.0 Hz); 4.10–4.40 (4H, multiplet); 4.70–5.00 (2H, multiplet); 5.55 (1H, multiplet); 5.70 (1H, doublet, J=3.0 Hz).

EXAMPLE 24

5-Acetamido-4-guanidino-8,9-di-O-hexadecanoyl-2,3,4,5,7-pentadeoxy-7-fluoro-D-glycero-D-galacto-non-2-enopyranosoic acid trifluoroacetic acid salt
(Compound No. 1-64)

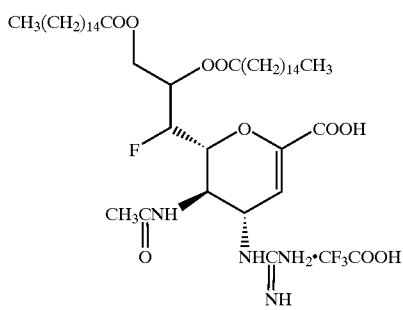

24(i) Diphenylmethyl 5-acetamido-4-(N,N'-bis-t-butoxycarbonylguanidino)-8,9-di-O-hexadecanoyl-2,3,4,5,7-pentadeoxy-7-fluoro-D-glycero-D-galacto-non-2-enopyranosoate 37 mg (0.053 mmol) of diphenylmethyl 5-acetamido-4-(N,N'-bis-t-butoxycarbonylguanidino)-2,3,4,5,7-pentadeoxy-7-fluoro-D-glycero-D-galacto-non-2-enopyranosoate [prepared as described in Example 13(i)] were dissolved in 2 ml of methylene chloride, and 16 mg (0.13 mmol) of 4-dimethylaminopyridine and 34 mg (0.12 mmol) of hexadecanoyl chloride were added to the resulting solution, whilst ice-cooling. The mixture was then stirred at room temperature for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 3:1 by volume mixture of hexane and ethyl acetate as the eluent, to obtain 52 mg (yield 84%) of the title compound as a colorless amorphous substance.

Rf=0.3 (3:1=hexane:ethyl acetate). $[\alpha]D^{25}=+10.9°$ (c=0.11, $CHCl_3$). Mass Spectrum (FAB) m/e 1177 ($M^++H$). $^1$H-Nuclear Magnetic Resonance Specter ($CDCl_3$, 270 MHz) δ (ppm): 0.80–0.90 (6H, multiplet); 1.20–1.40 (48H, multiplet); 1.48 (9H, singlet); 1.49 (9H, singlet); 1.50–1.65 (4H, multiplet); 1.98 (3H, singlet); 2.20–2.30 (4H, multiplet); 4.20–4.30 (3H, multiplet); 4.75 (1H, doublet, J=13 Hz); 4.80 (1H, doublet of doublets, J=7.5 & 45 Hz); 5.20 (1H, doubled doublet of doublets, J=1.0, 9.0 & 9.0 Hz); 5.50 (1H, multiplet); 5.92 (1H, doublet, J=2.4 Hz); 6.65 (1H, doublet, J=7.5 Hz); 6.93 (1H, singlet); 7.20–7.50 (10H, multiplet); 8.60 (1H, doublet, J=8.5 Hz).

24(in 5-Acetamido-4-guanidino-8,9-di-O-hexadecanoyl-2,3,4,5,7-pentadeoxy-7-fluoro-D-glycero-D-galacto-non-2-enopyranosoic acid trifluoroacetic acid salt 42 mg (0.036 mmol) of diphenylmethyl 5-acetamido-4-(N,N'-bis-t-butoxycarbonylguanidino)-8,9-di-O-hexadecanoyl-2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 22 mg (yield 59%) of the title compound as a colorless solid.

Rf=0.4 (2:5:1=isopropanol:ethyl acetate:water). $[\alpha]D^{25}=+15.3°$ (c=0.11, $CH_3OH$). Mass Spectrum (FAB) m/e 811 ($M^++H$). $^1$H-Nuclear Magnetic Resonance Spectrum ($CD_3OD$, 270 MHz) δ (ppm): 0.85–0.95 (6H, multiplet); 1.20–1.40 (48H, multiplet); 1.55–1.70 (4H, multiplet); 2.00 (3H, singlet); 2.30 (2H, triplet, J=7.0 Hz); 4.10–4.40 (4H, multiplet); 4.70–5.00 (2H, multiplet); 5.55 (1H, multiplet); 5.70 (1H, doublet, J=3.0 Hz).

EXAMPLE 25

5-Acetamido-4-guanidino-8,9-di-O-octadecanoyl-2,3,4,5,7-pentadeoxy-7-fluoro-D-glycero-D-galacto-non-2-enopyranosoic acid trifluoroacetic acid salt (Compound No. 65-1)

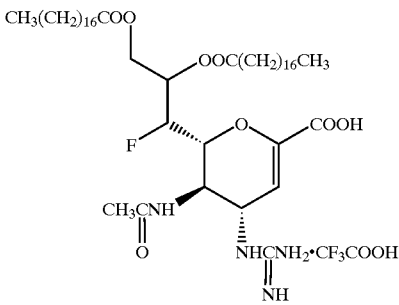

25(i) Diphenylmethyl 5-acetamido-4-(N,N'-bis-t-butolycarbonylguanidino)-8,9-di-O-octadecanoyl-2,3,4,5,7-pentadeoxy-7-fluoro-D-glycero-D-galacto-non-2-enopyranosoate 35 mg (0.05 mmol) of diphenylmethyl 5-acetamido4-(N,N'-bis-t-butoxycarbonylguanidino)-2,3,4,5,7-pentadeoxy-7-fluoro-D-glycero-D-galacto-non-2-enopyranosoate [prepared as described in Example 13(i)] were dissolved in 2 ml of methylene chloride, and 15 mg (0.13 mmol) of triethylamine and 35 mg (0.115 mmol) of octadecanoyl chloride were added to the resulting solution, whilst ice-cooling. The mixture was then stirred at room temperature for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 3:1 by volume mixture of hexane and ethyl acetate as the eluent, to obtain 57 mg (yield 93%) of the title compound as a colorless amorphous substance.

Rf=0.3 (3:1=hexane:ethyl acetate). $[\alpha]D^{25}$=+11.2° (c=0.18, $CHCl_3$). Mass Spectrum (FAB) m/e 1233 ($M^++H$). $^1$H-Nuclear Magnetic Resonance Spectrum ($CDCl_3$, 270 MHz) δ (ppm): 0.80–0.90 (6H, multiplet); 1.20–1.40 (56H, multiplet); 1.48 (9H, singlet); 1.49 (9H, singlet); 1.50–1.65 (4H, multiplet); 1.98 (3H, singlet); 2.20–2.30 (4H, multiplet); 4.00–4.30 (3H, multiplet); 4.75 (1H, doublet, J=13 Hz); 4.80 (1H, doublet of doublets, J=7.5 & 45 Hz); 5.20 (1H, doubled doublet of doublets, J=1.0, 9.0 & 9.0 Hz); 5.50 (1H, multiplet); 5.92 (1H, doublet, J=2.4 Hz); 6.65 (1H, doublet, J 7.5 Hz); 6.93 (1H, singlet); 7.20–7.50 (10H, multiplet); 8.60 (1H, doublet, J=8.5 Hz).

25(ii) 5Acetamido-4-guanidino-8,9-di-O-octadecanoyl-2,3,4,5,7-pentadeoxy-7-fluoro-D-glycero-D-galacto-non-2-enopyranosoic acid trifluoroacetic acid salt 47 mg (0.04 mmol) of diphenylmethyl 5-acetamido-4-(N,N'-bis-t-butoxycarbonylguanidino)-8,9-di-O-octadecanoyl-2,3,4,5,7-pentadeoxy-7-fluoro-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 28 mg (yield 67%) of the title compound as a colorless solid.

Rf=0.4 (2:5:1=isopropanol:ethyl acetate:water). $[\alpha]D^{25}$=+14.5° (c=0.14, $CH_3OH$). Mass Spectrum (FAB) m/e 867 ($M^++H$). $^1$H-Nuclear Magnetic Resonance Spectrum ($CD_3OD$, 270 MHz) δ (ppm): 0.85–0.95 (6H, multiplet); 1.20–1.40 (56H, multiplet); 1.55–1.70 (4H, multiplet); 2.00 (3H, singlet); 2.30 (2H, triplet, J=7.0 Hz); 4.10–4.40 (4H, multiplet); 4.70–5.00 (2H, multiplet); 5.55 (1H, multiplet); 5.70 (1H, doublet, J=3.0 Hz).

EXAMPLE 26

Hexadecyl 5-acetamido-4-guanidino-2,3,4,5,7-pentadeoxy-7-fluoro-D-glycero-D-galacto-non-2-enopyranosoate trifluoroacetic acid salt (Compound No. 1-6

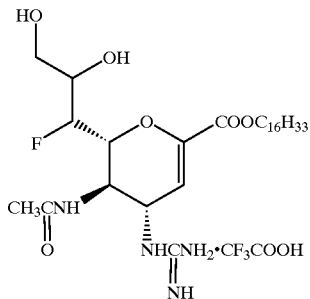

26(i) Hexadecyl 5-acetamido-4-azido-8,9-O-isopropylidene-2,3,4,5,7-pentadeoxy-7-fluoro-D-glycero-D-galacto-non-2-enopyranosoate 275 mg (0.74 mmol) of methyl 5-acetamido-4-azido-8,9-O-isopropylidene-2,3,4,5,7-pentadeoxy-7-fluoro-D-glycero-D-galacto-non-2-enopyranosoate [prepared as described in Example 7(i)] were dissolved in 7 ml of a 6:1 by volume mixture of methanol and water, and 0.82 ml of a 1 M aqueous solution of potassium hydroxide was added to the resulting solution. The mixture was then stirred at room temperature for 2 hours. At the end of this time, the solvent was removed by distillation under reduced pressure, and dried under reduced pressure at room temperature for 2 hours to obtain a pale yellow solid. This solid was dissolved in 8 ml of acetonitrile, and 195 mg (0.74 mmol) of 18-crown-6 and 677 mg (2.2 mmol) of hexadecyl bromide were added to the resulting solution. The mixture was then stirred at 80° C. for 30 minutes. At the end of this time, the solvent was removed by distillation under reduced pressure. A 2-layer solution of 15 ml of ethyl acetate and 10 ml of a saturated aqueous solution of sodium hydrogencarbonate was poured onto the resulting residue, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 240 mg (yield 56%) of the title compound as a colorless amorphous substance.

Rf=0.50 (20:1=methylene chloride:methanol). $[\alpha]D^{25}$=+65.0° (c=0.5, $CHCl_3$). Mass Spectrum (FAB) m/e 583 ($M^++H$). $^1$H-Nuclear Magnetic Resonance Spectrum ($CDCl_3$, 270 MHz) δ (ppm): 0.80–0.95 (3H, multiplet); 1.20–1.40 (28H, multiplet); 1.37 (3H, singlet); 1.42 (3H, singlet); 1.60–1.80 (2H, multiplet); 2.05 (3H, singlet); 4.10–4.30 (3H, multiplet); 4.40 (1H, multiplet); 4.72 (1H, doubled doublet of doublets, J=1.3, 5.3 & 47.0 Hz); 4.90 (1H, doublet of doublets, J=2.4 & 9.3 Hz); 4.92 (1H, doubled doublet of doublets, J=1.4, 10.0 & 28.0 Hz); 5.92 (1H, doublet, J=7.2 Hz); 5.94 (1H, doublet, J=2.6 Hz).

26(ii) Hexadecyl 5-acetamido-4-(N,N'-bis-t-butoxycarbonylguanidino)-8,9-O-isopropylidene-2,3,4,5,7-pentadeoxy-7-fluoro-D-glycero-D-galacto-non-2-enopyranosoate 240 mg (0.41 mmol) of hexadecyl 5-acetamido-4-azido-8,9-O-isopropylidene-2,3,4,5,7-pentadeoxy-7-fluoro-D-glycero-D-galacto-non-2-enopyranosoate [prepared as described in step (i) above] were dissolved in 10 ml of methanol, and 60 mg of a Lindlar catalyst were added to the resulting solution. The mixture was then stirred under a hydrogen atmosphere for 2 hours. At the end of this time, the catalyst was separated by filtration, and the solvent was removed by distillation under reduced pressure. The resulting residue was dissolved in 4 ml of dimethylformamide, and 145 mg (0.53 mmol) of N,N-di-t-butoxycarbonylthiourea, 106 mg (1.05 mmol) of triethylamine and 142 mg (0.53 mmol) of mercuric chloride were added to the resulting solution. The mixture was then stirred at room temperature for 1 hour. At the end of this time, the solid was separated by filtration, and the filtrate was poured into a 2-layer solution of 15 ml of ethyl acetate and 10 ml of a saturated aqueous solution of sodium hydrogencarbonate. The organic layer was washed with a saturated aqueous solution of sodium chloride, and dried over anhydrous sodium sulfate, after which the solvent was removed by distillation under reduced pressure. The resulting residue was purified by silica gel column chromatography, using a 1:2 by volume mixture of ethyl acetate and hexane as the eluent, to obtain 220 mg (yield 67%) of the title compound as a colorless viscous substance.

Rf=0.40 (20:1=methylene chloride:methanol). [α]$_D^{25}$=−11.6° (c=0.06, CHCl$_3$). Mass Spectrum (FAB) m/e 799 (M$^+$+H). $^1$H-Nuclear Magnetic Resonance Spectrum (CDCl$_3$, 270 MHz) δ (ppm): 0.80–0.95 (3H, multiplet); 1.20–1.40 (28H, multiplet); 1.37 (3H, singlet); 1.41 (3H, singlet); 1.49 (9H, singlet); 1.50 (9H, singlet); 1.60–1.80 (2H, multiplet); 1.97 (3H, singlet); 4.10–4.30 (4H, multiplet); 4.40–4.65 (2H, multiplet); 5.20 (1H, doubled doublet of doublets, J 2.4, 7.5 & 7.5 Hz); 5.83 (1 H, doublet, J=2.4 Hz); 5.65 (1H, doublet, J=7.0 Hz); 8.60 (1H, doublet, J=8.5 Hz).

26(iii) Hexadecyl 5-acetamido-4-guanidino-2,3,4,5,7-pentadeoxy-7-fluoro-D-glycero-D-galacto-non-2-enopyranosoate trifluoroacetic acid salt 200 mg (0.25 mmol) of hexadecyl 5-acetamido-4-(N,N'-bis-t-butoxycarbonylguanidino)-8,9-O-isopropylidene-2,3,4,5,7-pentadeoxy-7-fluoro-D-glycero-D-galacto-non-2-enopyranosoate [prepared as described in step (i) above] were dissolved in 10 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:8:1 by volume mixture of isopropanol, ethyl acetate and water as the eluent, to obtain 130 mg (yield 77%) of the title compound as a colorless solid.

Rf=0.55 (5:1:1=t-butanol:acetic acid:water). [α]$_D^{25}$=+14.7° (c=0.1, CH$_3$OH). Mass Spectrum (FAB) m/e 559 (M$^+$+H). $^1$H-Nuclear Magnetic Resonance Spectrum (D$_2$O, 270 MHz) δ (ppm): 0.70–0.85 (3H, multiplet); 1.10–1.30 (28H, multiplet); 1.60–1.80 (2H, multiplet); 2.00 (3H, singlet); 3.60–3.85 (2H, multiplet); 4.00–4.30 (3H, multiplet); 4.50–4.80 (2H, multiplet); 5.88 (1H, singlet).

EXAMPLE 27

Octadecyl 5-acetamido-4-guanidino-2,3,4,5,7-pentadeoxy-7-fluoro-D-glycero-D-galacto-non-2-enopyranosoate trifluoroacetic acid salt (Compound No. 1-7)

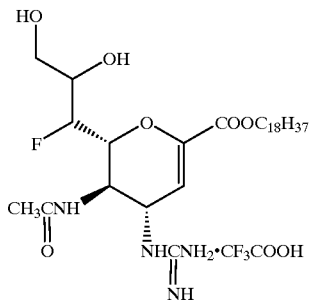

27(i) Octadecyl 5-acetamido-4-azido-8,9-O-isopropylidene-2,3,4,5,7-pentadeoxy-7-fluoro-D-glycero-D-galacto-2-enopyranosoate 45 mg (0.12 mmol) of methyl 5-acetamido-4azido-8,9-O-isopropylidene-2,3,4,5 ,7-pentadeoxy-7-fluoro-D-glycero-D-galacto-non-2-enopyranosoate [prepared as described in Example 7(i)] were dissolved in 4 ml of a 6:1 by volume mixture of methanol and water, and 0.13 ml of a 1 M aqueous solution of potassium hydroxide was added to the resulting solution. The mixture was then stirred at room temperature for 2 hours. At the end of this time, the solvent was removed by distillation under reduced pressure, and the residue was dried under reduced pressure at room temperature for 2 hours to obtain a pale yellow solid. This solid was dissolved in 2 ml of acetonitrile, and 32 mg (0.12 mmol) of 18-crown-6 and 121 mg (0.36 mmol) of octadecyl bromide were added to the resulting solution. The mixture was then stirred at 80° C. for 30 minutes. The resulting residue was poured into a 2-layer solution of 7 ml of ethyl acetate and 5 ml of a saturated aqueous solution of sodium hydrogencarbonate, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 2:1 by volume mixture of hexane and ethyl acetate as the eluent, to obtain 42 mg (yield 58%) of the title compound as a colorless amorphous substance.

Rf=0.50 (20:1=methylene chloride:methanol). [[|g]a] D$^{25}$=+76° (c=0.05, CHCl$_3$). Mass Spectrum (FAB) m/e 611 (M$^+$+H). $^1$H-Nuclear Magnetic Resonance Spectrum (CDCl$_3$, 270 MHz) δ (ppm): 0.85–0.95 (3H, multiplet); 1.20–1.40 (32H, multiplet); 1.37 (3H, singlet); 1.42 (3H, singlet); 1.60–1.80 (2H, multiplet); 2.05 (3H, singlet); 4.10–4.30 (3H, multiplet); 4.40 (1H, multiplet); 4.72 (1H, doubled doublet of doublets, J=1.3, 5.3 & 47.0 Hz); 4.90 (1H, doublet of doublets, J=2.6 & 9.5 Hz); 4.92 (1H, doubled doublet of doublets, J=1.4, 10.0 & 28.0 Hz); 5.94 (1H, doublet, J=7.2 Hz); 5.91 (1H, doublet, J=2.6 Hz).

27(ii) Octadecyl 5-acetamido-4-(N,N'-bis-t-butoxycarbonylguanidino)-8,9-O-isopropylidene-2,3,4.5.7-pentadeoxy-7-fluoro-D-glycero-D-galacto-non-2-enopyranosoate 40 mg (0.066 mmol) of octadecyl 5-acetamido-4-azido-8,9-O-isopropylidene-2,3,4,5,7-pentadeoxy-7-fluoro-D-glycero-D-galacto-non-2-enopyranosoate [prepared as described in step (i) above] were dissolved in 3 ml of methanol, and 10 mg of a Lindlar catalyst were added thereto. The mixture was then stirred under a hydrogen atmosphere for 2 hours. At the end of this time, the catalyst was separated by filtration, and the solvent was removed by distillation under reduced pressure. The resulting residue was dissolved in 2 ml of dimethylformamide, and then 25 mg (0.09 mmol) of N,N'-di-t-butoxycarbonylthiourea, 18 mg (0.18 mmol) of triethylamine and 25 mg (0.09 mmol) of mercuric chloride were added to the resulting solution. The mixture was then stirred at room temperature for I hour. At the end of this time, the solid produced was separated by filtration. The filtrate was poured into a 2-layer solution of 5 ml of ethyl acetate and 3 ml of a saturated aqueous solution of sodium hydrogencarbonate, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 1:1 by volume mixture of hexane and ethyl acetate as the eluent, to obtain 39 mg (yield 71%) of the title compound as a colorless viscous substance.

Rf=0.40 (20:1=methylene chloride:methanol). $[\alpha]D^{25}$=−7.4° (c=0.10, $CHCl_3$). Mass Spectrum (FAB) m/e 827 ($M^+$+H). $^1$H-Nuclear Magnetic Resonance Spectrum ($CDCl_3$, 270 MHz) δ (ppm): 0.80–0.95 (3H, multiplet); 1.20–1.40 (32H, multiplet); 1.37 (3H, singlet); 1.41 (3H, singlet); 1.49 (9H, singlet); 1.50 (9H, singlet); 1.60–1.80 (2H, multiplet); 1.97 (3H, singlet); 4.10–4.30 (4H, multiplet); 4.40–4.65 (2H, multiplet); 5.20 (1H, doubled doublet of doublets, J=2.4, 7.5 & 7.5 Hz); 5.83 (1H, doublet, J=2.3 Hz); 5.65 (1H, doublet, J=7.0 Hz); 8.60 (1H, doublet, J=8.5 Hz).

27(iii) Octadecyl 5-acetamido-4-guanidino-2,3,4,5,7-pentadeoxy-7-fluoro-D-glycero-D-galacto-non-2-enopyranosoate trifluoroacetic acid salt 30 mg (0.04 mmol) of octadecyl 5-acetamido-4-(N,N'-bis-t-butoxycarbonylguanidino)-8,9-O-isopropylidene-2,3,4,5,7-pentadeoxy-7-fluoro-D-glycero-D-galacto-non-2-enopyranosoate [prepared as described in step (ii) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:8:1 by volume mixture of isopropanol, ethyl acetate and water as the eluent, to obtain 20 mg (yield 79%) of the title compound as a colorless solid.

Rf=0.55 (5:1:1=t-butanol:acetic acid:water). $[\alpha]D^{25}$=+14.0° (c=0.10, $CH_3OH$). Mass Spectrum (FAB) m/e 587 ($M^+$+H). $^1$H-Nuclear Magnetic Resonance Spectrum ($D_2O$, 270 MH) δ (ppm): 0.70–0.85 (3H, multiplet); 1.10–1.30 (32H, multiplet); 1.60–1.80 (2H, multiplet); 2.00 (3H, singlet); 3.60–3.85 (2H, multiplet); 4.00–4.30 (3H, multiplet); 4.50–4.80 (2H, multiplet); 5.88 (1H, singlet).

EXAMPLE 28

5-Acetamido-4-guanidino-2,3,4,5,7-pentadeoxy-7-methoxy-D-glycero-D-galacto-non-2-enopyranosoic acid trifluoroacetic acid salt (Compound No. 163-1)

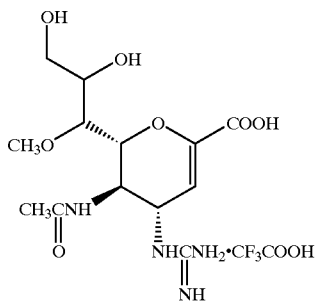

28(i) Benzyl N-acetyl-3,6-di-O-benzyl-O-methyl-α-D-glucosamine 4.48 g (9.12 mmol) of benzyl N-acetyl-3,6-di-O-benzyl-α-D-glucosamine [prepared according to the procedure described in Carbohydrate Res. 83, 163–169 (1980)] were dissolved in 50 ml of dimethylformamide, and 1.0 g (22.5 mmol) of sodium hydride was added to the resulting solution. The mixture was then stirred at room temperature for 30 minutes, after which 1.42 g (10.0 mmol) of methyl iodide were added at 0° C., and the mixture was stirred at room temperature for a further 5 hours. At the end of this time, the reaction mixture was poured into a 2-layer solution of 100 ml of ethyl acetate and 50 ml of a saturated aqueous solution of sodium hydrogencarbonate, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 4:1 by volume mixture of methylene chloride and ethyl acetate as the eluent, to obtain 3.6 g (yield 78%) of the title compound as a colorless solid.

Rf=0.55 (20:1=methylene chloride:methanol). $[\alpha]D^{25}$=+126° (c=1.15, $CHCl_3$). Mass Spectrum (FAB) m/e 506 ($M^+$+H). $^1$H-Nuclear Magnetic Resonance Spectrum ($CDCl_3$, 270 MHz) δ (ppm): 1.80 (3H, singlet); 3.48 (3H, singlet); 3.40–3.80 (5H, multiplet); 4.23 (1H, doubled doublet of doublets, J=3.5, 10.0 & 10.0 Hz); 4.40–4.90 (7H, multiplet); 5.25 (1H, doublet, J=10.0 Hz); 7.20–7.40 (15H, multiplet).

28(ii) N-Acetyl-4-O-methyl-α-D-glucosamine 3.6 g (7.12 mmol) of benzyl N-acetyl-3,6-di-O-benzyl-4-O-methyl-α-D-glucosamine [prepared as described in step (i) above] were dissolved in 40 ml of acetic acid, and 5.0 g of palladium-on-carbon were added to the resulting solution. The mixture was then stirred under a hydrogen atmosphere at 3 atmospheres. for 30 hours. At the end of this time, the catalyst was separated by filtration, and the solvent was removed by distillation under reduced pressure. The resulting residue was purified by silica gel column chromatography, using a gradient elution method, with mixtures of methylene chloride and methanol ranging from 10:1 to 5:1 by volume as the eluent, to obtain 1.42 g (yield 83%) of the title compound as a colorless solid.

Rf=0.35 (5:1=methylene chloride:methanol). $[\alpha]D^{25}$=+72.2° (c=2.9, $CH_3OH$). Mass Spectrum (FAB) m/e 236 ($M^+$+H). $^1$H-Nuclear Magnetic Resonance Spectrum (CD₃OD, 270 MHz) δ (ppm): 1.98 (3H, singlet); 3.57 (3H, singlet); 3.60–3.80 (6H, multiplet); 5.05 (1H, doublet, J=3.2 Hz).

28(iii) 5-Acetamido-3,5-dideoxy-7-O-methyl-D-glycero-O-galacto-2-nonuropyranosoic acid 5.0 g (21.3 mmol) of N-acetyl-4-O-methyl-α-D-glucosamine [prepared as described in step (ii) above] were dissolved in distilled water, and 100 mg of sodium azide and 5.0 g (45.5 mmol) of sodium pyruvate were added to the resulting solution. The pH of the reaction mixture was then adjusted to a value of 10 to 11 by the addition of a 1 N aqueous solution of sodium hydroxide, after which 25 mg (660U) of N-acetyl-neuraminic acid aldolase (produced by TOYOBO K.K.) were added to the mixture, and the mixture was stirred at 20° C. for 3 days. At the end of this time, the reaction mixture was desalted using a Dowex 50×8 (H⁺) resin (Dowex is a trade mark) and purified by column chromatography through Dowex 1 (HCOOH), eluted with a 1.0 M aqueous solution of formic acid, to obtain 1.8 g (yield 26%) of the title compound as a colorless viscous substance.

Rf=0.30 (4:1:1=isopropanol:acetic acid:water). $[\alpha]_D^{25}$=−19.7° (c=1.2, H₂O). Mass Spectrum (FAB) m/e 324 (M⁺+H). ¹H-Nuclear Magnetic Resonance Spectrum (D₂O, 270 MHz) δ (ppm): 1.80 (1H, doublet of doublets, J=12.0 & 12.0 Hz); 2.00 (3H, singlet); 2.10 (1H, doublet of doublets, J=4.5 & 12.0 Hz); 3.48 (3H, singlet); 3.50–3.80 (7H, multiplet).

28(iv) Methyl 5-acetamido-3,5-dideoxy-7-O-methyl-D-glycero-D-galacto-2-nonuropyranosoic 680 mg (2.10 mmol) of 5-acetamido-3,5-dideoxy-7-O-methyl-D-glycero-D-galacto-2-nonuropyranosoic acid [prepared as described in step (iii) above] were dissolved in 20 ml of methanol, and 500 mg of a Dowex 50×8 (H⁺) cation exchange resin (Dowex is a trade mark) were added to the resulting solution. The mixture was then stirred at room temperature for 15 hours. At the end of this time, the cation exchange resin was separated by filtration, and the solvent was removed by distillation under reduced pressure. The resulting residue was purified by silica gel column chromatography, using a 5:1 by volume mixture of methylene chloride and methanol as the eluent, to obtain 340 mg (yield 48%) of the title compound as a colorless amorphous substance.

Rf=0.15 (5:1=methylene chloride:methanol). $[\alpha]_D^{25}$=+30.2° (c=1.1, CH₃OH). Mass Spectrum (FAB) m/e 338 (M⁺+H). ¹H-Nuclear Magnetic Resonance Spectrum (CD₃OD, 270 MHz) δ (ppm): 1.90 (1H, doublet of doublets, J=12.0 & 14.0 Hz); 2.00 (3H, singlet); 2.16 (1H, doublet of doublets, J=4.5 & 12.0 Hz); 3.40 (1H, multiplet); 3.45 (3H, singlet); 3.50–3.80 (3H, multiplet); 3.77 (3H, singlet); 3.80–4.00 (2H, multiplet); 4.20 (1H, doublet of doublets, J=1.5 & 9.5 Hz).

28(v) Methyl 5-acetamido-4,8,9-tri-O-acetyl-2,3,5-trideoxy-7-O-methyl-D-glycero-D-galacto-non-2-enopyranosoate 686 mg (2.03 mmol) of methyl 5-acetamido-3,5-dideoxy-7-O-methyl-D-glycero-D-galacto-2-nonuropyranosoic [prepared as described in step (iv) above] were dissolved in a mixture of 10 ml of pyridine and 10 ml of acetic anhydride, and the mixture was stirred at room temperature for 15 hours. At the end of this time, the solvent was removed by distillation under reduced pressure, and the residue was dissolved in 20 ml of a 4 M solution of hydrogen chloride in dioxane, after which it was stirred at room temperature for 15 hours. At the end of this time, the solvent was dissolved in benzene, and 182 mg (1.20 mmol) of 1,8-diazabicyclo[5.4.0]-7-undecene were added to the resulting solution, and the mixture was stirred at room temperature for 2 hours. The reaction mixture was then poured into a 2-layer solution of 30 ml of methylene chloride and 15 ml of a saturated aqueous ammonium chloride solution, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 310 mg (yield 34%) of the title compound as a colorless amorphous substance.

Rf=0.30 (20:1=methylene chloride:methanol). $[\alpha]_D^{25}$=+206° (c=0.15, CHCl₃). Mass Spectrum (FAB) m/e 446 (M⁺+H). ¹H-Nuclear Magnetic Resonance Spectrum (CDCl₃, 270 MHz) δ (ppm): 2.00 (3H, singlet); 2.06 (3H, singlet); 2.08 (3H, singlet); 2.10 (3H, singlet); 3.50 (3H, singlet); 3.65 (1H, doublet of doublets, J=3.0 & 3.0 Hz); 3.80 (3H, singlet); 4.20–4.35 (2H, multiplet); 4.45 (1H, multiplet); 4.70 (1H, doublet of doublets, J=3.0 & 12.0 Hz); 5.35 (1H, multiplet); 5.50 (1H, doublet of doublets, J=3.0 & 7.0 Hz); 5.55 (1H, doublet, J=8.0 Hz); 6.00 (1H, doublet, J=2.8 Hz).

28(vi) Methyl 5-acetamido-4-azido-8,9-di-O-acetyl-2,3,4,5,7-pentadeoxy-7-methoxy-D-glycero-D-galacto-non-2-enopyranosoate 303 mg (0.67 mmol) of methyl 5-acetamido-4,8,9-tri-O-acetyl-2,3,5-trideoxy-7-O-methyl-2-glycero-D-galacto-non-2-enopyranosoate [prepared as described in step (v) above] were dissolved in 10 ml of anhydrous methylene chloride, and 22 mg (0.67 mmol) of methanol were added to the resulting solution. 956 mg (6.74 mmol) of a boron trifluoride-diethyl ether complex were added to the resulting mixture under a nitrogen atmosphere, and the mixture was stirred at room temperature for 24 hours. At the end of this time, the reaction mixture was poured into a mixture of 20 ml of water, 10 g of ice, 5 g of solid sodium hydrogencarbonate and 20 ml of ethyl acetate, and the mixture was vigorously stirred for 10 minutes. The organic layer was then separated, washed with 10 ml of a saturated aqueous solution of sodium chloride, and dried over anhydrous sodium sulfate, after which the solvent was removed by distillation under reduced pressure. The resulting residue (270 mg) was dissolved in 10 ml of dimethylformamide, and 270 mg of a cation exchange resin [Dowex 50×8 (H⁺)—Dowex is a trade mark] and 90 mg (1.37 mmol) of sodium azide were added to the resulting solution. The mixture was then stirred at 90° C. for 4 hours. At the end of this time, the Dowex 50×8 (H⁺) resin was separated by filtration, and the solvent was removed by distillation under reduced pressure. The resulting residue was dissolved in a 2-layer solution of 20 ml of ethyl acetate and 10 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 250 mg (yield 70%) of the title compound as a colorless viscous substance.

Rf=0.30 (20:1=methylene chloride:methanol). $[\alpha]_D^{25}$=+97.2° (c=0.25, CHCl₃). Mass Spectrum (FAB) m/e 429 (M⁺+H). ¹H-Nuclear Magnetic Resonance Spectrum (CDCl₃, 270 MHz) δ (ppm): 2.06 (6H, singlet); 2.10 (3H, singlet); 3.50 (3H, singlet); 3.65 (1H, doublet of doublets, J=1.8 & 4.0 Hz); 3.80 (3H, singlet); 4.25 (1H, doublet of doublets, J=5.0 & 12.0 Hz); 4.45–4.55 (2H, multiplet); 4.75

(1H, doublet of doublets, J=3.2 & 12.0 Hz); 5.35 (1H, multiplet); 5.52 (1H, doublet, J=8.2 Hz); 5.98 (1H, doublet, J=2.7 Hz).

28(vii) Methyl 5-acetamido-4-(N,N'-bis-t-butoxycarbonylguanidino)-8,9-di-O-acetyl-2,3,4,5,7-pentadeoxy-7-methoxy-D-glycero-D-galacto-non-2-enopyranosoate 80 mg (0.42 mmol) of methyl 5 acetamido-4-azido-8,9-di-O-acetyl-2,3,4,5,7-pentadeoxy-7-methoxy-D-glycero-D-galacto-non-2-enopyranosoate [prepared as described in step (vi) above] were dissolved in 10 ml of methanol, and 130 mg of a Lindlar catalyst were added to the resulting solution. The mixture was then stirred under a hydrogen atmosphere for 2 hours. At the end of this time, the catalyst was separated by filtration, and the solvent was removed by distillation under reduced pressure. The resulting residue (120 mg) was dissolved in 10 ml of dimethylformamide, and 100 mg (0.37 mmol) of N,N'-di-t-butoxycarbonylthiourea, 75 mg (0.74 mmol) of triethylamine and 100 mg (0.37 mmol) of mercuric chloride were added to the resulting solution. The mixture was then stirred at room temperature for 1 hour. At the end of this time, the solid was separated by filtration, and the filtrate was poured into a 2-layer solution of 10 ml of ethyl .acetate and 50 ml of a saturated aqueous solution of sodium hydrogencarbonate. The organic layer was separated, washed with a saturated aqueous solution of sodium chloride and dried over anhydrous sodium sulfate, after which the solvent was removed by distillation under reduced pressure. The resulting residue was purified by silica gel column chromatography, using a 2:1 by volume mixture of hexane and ethyl acetate as the eluent, to obtain 180 mg (yield 64 %/o) of the title compound as a colorless amorphous substance.

Rf=0.50 (20:1=methylene chloride:methanol). $[\alpha]D^{25}$=+2.8° (c=0.65, CHCl$_3$). Mass Spectrum (FAB) m/e 645 (M$^+$+H). 1H-Nuclear Magnetic Resonance Spectrum (CDCl$_3$, 270 MHz) δ (ppm): 1.49 (9H, singlet); 1.50 (9H, singlet); 1.97 (3H, singlet); 2.05 (3H, singlet); 2.07 (3H, singlet); 3.52 (3H, singlet); 3.55 (1H, multiplet); 3.78 (3H, singlet); 4.10 (1H, doublet of doublets, J=1.0 & 10.5 Hz); 4.25–4.40 (2H, multiplet); 4.82 (1H, doublet of doublets, J=3.2 & 12.0 Hz); 5.12 (1H, doubleted doublet of doublets, J=2.5 & 11.0 & 11.0 Hz); 5.30 (1H, multiplet); 5.85 (1H, doublet, J=2.3 Hz); 6.35 (1H, doublet, J=8.8 Hz).

28(viii) 5-Acetamido-4-guanidino-2,3,4,5,7-pentadeoxy-7-methoxy-D-glycero-galacto-non-2-enopyranosoic acid trifluoroacetic acid salt 53 mg (0.083 mmol;) of methyl 5 acetamido-4-(N,N'-bis-t-butoxycarbonylguanidino)-8,9-di-O-acetyl-2,3,4,5,7-pentadeoxy-7-methoxy-D-glycero-D-galacto-non-2-enopyranosoate [prepared as described in step (vii) above] were dissolved in 2 ml of methanol, and 0.2 ml of a 0.1 N methanolic solution of sodium methoxide was added to the resulting solution. The mixture was then stirred at room temperature for 1 hour. At the end of this time, the reaction mixture was neutralized with a 4 M solution of hydrogen chloride in dioxane, and the solvent was removed by distillation under reduced pressure. The resulting residue was dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was dissolved in 1 ml of distilled water. 72 μl of a 1N aqueous solution of sodium hydroxide were then added to the reaction mixture, which was then stirred at room temperature for 1 hour. At the end of this time, the reaction mixture was neutralized with a Dowex 50×8 (H$^+$) resin (Dowex is a trade mark), and then the water was removed by distillation. The resulting residue was purified by silica gel column chromatography, using a 5:1:1: by volume mixture of isopropanol, ethyl acetate and water as the eluent, to obtain 24 mg (yield 85%) of the title compound as a colorless solid.

Rf=0.30 (4:1:1=isopropanol:acetic acid:water). $[\alpha]D^{25}$=−9.3° (c=0.1, CH$_3$OH). Mass Spectrum (FAB) m/e 347 (M$^+$+H). 1H-Nuclear Magnetic Resonance Spectrum (CDCl$_3$, 270 Hz) δ (ppm): 2.00 (3H, singlet); 3.37 (3H, singlet); 3.55 (1H, doublet, J=8.5 Hz); 3.65 (1H, doublet of doublets, J 5.0 & 12 Hz); 3.90 (3H, multiplet); 4.20 (1H, doublet of doublets, J=10 & 10 Hz); 4.40–4.50(2H, multiplet); 5.85 (1H, doublet, J=1.8 Hz).

EXAMPLE 29

5-Acetamido-4-guanidino-9-O-tetradecanoyl-2,3,4,5, 7-pentadeoxy-7-methoxy-D-glycero-D-galacto-non-2-enopyranosoic acid trifluoroacetic acid salt
(Compound No. 163-41)

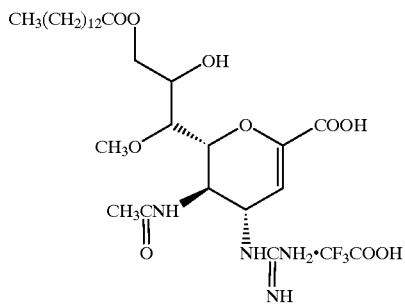

29(i) Diphenylmethyl 5-acetamido-4(N,N'-bis-t-butoxycarbonylguanidino)-2,3,4,5,7-pentadeoxy-7-methoxy-D-glycero-D-galacto-non-2-enopyranosoate 87 mg (0.14 mmol) of methyl 5 acetamido-4-(N,N'-bis-t-butoxycarbonylguanidino)-8,9-di-O-acetyl-2,3,4,5,7-pentadeoxy-7-methoxy-D-glycero-D-galacto-non-2-enopyranosoate [prepared as described in Example 28(vii)] were dissolved in 5 ml of methanol, and 2 ml of a 0.4 N methanolic solution of sodium methoxide were added to the resulting solution. The mixture was then stirred at room temperature for 1 hour. At the end of this time, the reaction mixture was neutralized with a 4 M solution of hydrogen chloride in dioxane, and the solvent was removed by distillation under reduced pressure. The resulting residue was dissolved in 4 ml of distilled water and 0.2 ml of a 1 N aqueous solution of sodium hydroxide was added to the resulting solution. The mixture was then stirred at room temperature for 1 hour. At the end of this time, the reaction mixture was neutralized with a 4 M solution of hydrogen chloride in dioxane, and then the water was removed by distillation, after which the residue was dissolved in a 1:1 by volume mixture of methanol and methylene chloride, and 47 mg (0.24 mmol) of diphenyldiazomethane and 50 mg (0.38 mmol) of a boron trifluoride-diethyl ether complex were added to the resulting solution. The mixture was then stirred at room temperature for 2 hours. At the end of this time, acetic acid was added, and the solvent was removed by distillation under reduced pressure. The resulting residue was purified by silica gel column chromatography, using a 20:1 by volume mixture of methylene chloride and methanol as the eluent, to obtain 29 mg (yield 30%) of the title compound as a colorless amorphous substance.

Rf=0.3 (20:1=methylene chloride:methanol). $[\alpha]D^{25}$=+22.0° (c=0.4, CHCl$_3$). Mass Spectrum (FAB) m/e 713 (M$^+$+

H). $^1$H-Nuclear Magnetic Resonance Spectrum (CD$_3$OD, 270 MHz) δ (ppm): 1.46 (9H, singlet); 1.52 (9H, singlet); 1.95 (3H, singlet); 3.48 (1H, doublet, J=9.0 Hz); 3.68 (1H, doublet of doublets, J=4.0 & 12 Hz); 3.85 (1H, doublet of doublets, J=2.5 & 12 Hz); 3.95 (1H, multiplet); 4.32 (1H, doublet of doublets, J=10 & 10 Hz); 4.43 (1H, doublet, J=10 Hz); 5.05 (1H, doublet of doublets, J=2.2 & 10 Hz); 6.02 (1H, doublet, J=2.2 Hz); 6.90 (1H, singlet); 7.20–7.50 (10H, multiplet).

29(ii) Diphenylmethyl 5-acetamido-4(N,N'-bis-t-butoxycarbonylguanidino)-9-O-tetradecanoyl-2,3,4,5,7-pentadeoxy-7-methoxy-D-glycero-D-galacto-non-2-enopyranosoate 28 mg (0.039 mmol) of diphenylmethyl 5-acetamido-4-(N,N'-bis-t-butoxycarbonylguanidino)-2,3,4,5,7-pentadeoxy-7-methoxy-D-glycero-D-galacto-non-2-enopyranosoate [prepared as described in step (i) above] were dissolved in 2 ml of methylene chloride, and 6 mg (0.06 mmol) of triethylamine and 8 mg (0.05 mmol) of tetradecanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 22 mg (yield 61%) of the title compound as a colorless amorphous substance.

Rf=0.45 (20:1=methylene chloride:methanol). [α]$D^{25}$=+40.5° (c=0.2, CHCl$_3$). Mass Spectrum (FAB) m/e 923 (M$^+$+H). $^1$H-Nuclear Magnetic Resonance Spectrum (CDCl$_3$, 270 MHz) δ (ppm): 0.85 (3H, multiplet); 1.20–1.30 (20H, multiplet); 1.48 (9H, singlet); 1.50 (9H, singlet); 1.55–1.70 (2H, multiplet); 1.98 (3H, singlet); 2.33 (2H, triplet, J=7.5 Hz); 3.40 (1H, multiplet); 3.48 (3H, singlet); 4.10–4.50 (5H, multiplet); 5.18 (1H, doubled doublet of doublets, J=2.4, 9.0 & 9.0 Hz); 5.95 (1H, doublet, J=2.3 Hz); 6.18 (1H, doublet, J=8.7 Hz); 6.92 (1H, singlet); 7.20–7.50 (10H, multiplet); 8.55 (1H, doublet, J=8.7 Hz).

29(iii) 5-Acetamido-4-guanidino-9-O-tetradecanoyl-2,3,4,5,7-pentadeoxy-7-methoxy-D-glycero-D-galacto-non-2-enopyranosoic acid trifluoroacetic acid salt 22 mg (0.024 mmol) of diphenylmethyl 5-acetamido-4-(N,N'-bis-t-butoxycarbonylguanidino)-9-O-tetradecanoyl-2,3,4,5,7-pentadeoxy-7-methoxy-D-glycero-D-galacto-non-2-enopyranosoate [prepared as described in step (ii) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 10 mg (yield 74%) of the title compound as a colorless solid.

Rf=0.4 (2:5:1=isopropanol:ethyl acetate:water). [α]$D^{25}$=+24.0° (c=0.1, CH$_3$OH). Mass Spectrum (FAB) m/e 557 (M$^+$+H). $^1$H-Nuclear Magnetic Resonance Spectrum (CD$_3$OD, 270 MHz) δ (ppm): 0.90 (3H, multiplet); 1.25–1.40 (20H, multiplet); 1.60–1.70 (2H, multiplet); 2.00 (3H, singlet); 2.37 (2H, triplet, J=7.5 Hz); 3.38 (3H, singlet); 3.45 (1H, multiplet); 4.10–4.40 (6H, multiplet); 5.53 (1H, doublet, J=1.8 Hz).

EXAMPLE 30

5-Acetamido-4-guanidino-2,3,4,5,7-pentadeoxy-7-ethoxy-D-glycero-D-galacto-non-2-enoic acid trifluoroacetic acid salt (Compound No. 199-1)

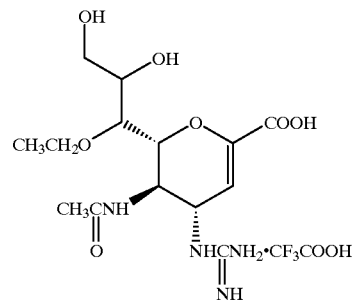

30(i) Benzyl N-acetyl-3,6di-O-benzyl-4-O-ethyl-α-D-glucosamine 8.35 g (16.8 mmol) of benzyl N-acetyl-3,6-di-O-benzyl-α-D-glucosamine [prepared according to the procedure described in Carbohydrate Res. 83, 163–169 (1980)] were dissolved in 80 ml of dimethylformamide, and 1.84 g (42.2 mmol) sodium hydride were added to the resulting solution. The mixture was then stirred at room temperature for 30 minutes, after which 2.86 g (18.5 mmol) of ethyl iodide were added to the mixture at 0° C., and the mixture was stirred at room temperature for 5 hours. At the end of this time, the reaction mixture was poured into a 2-layer solution of 200 ml of ethyl acetate and 100 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 4: 1 by volume mixture of methylene chloride and ethyl acetate as the eluent, to obtain 7.0 g (yield 80%) of the title compound as a colorless solid.

Rf=0.55 (20:1=methylene chloride:methanol). [α]$D^{25}$=+123° (c=2.3, CHCl$_3$). Mass Spectrum (FAB) m/e 520 (M$^+$+H). $^1$H-Nuclear Magnetic Resonance Spectrum (CDCl$_3$, 270 MHz) δ (ppm): 1.10 (3H, triplet, J=7.0 Hz); 1.80 (3H, singlet); 3.40–3.90 (7H, multiplet); 4.21 (1H, doubled doublet of doublets, J=3.5, 10.0 & 10.0 Hz); 4.40–4.90 (7H, multiplet); 5.22 (1H, doublet, J=10.0 Hz); 7.20–7.40 (15H, multiplet).

30(ii) N-Acetyl-4-O-ethyl-α-glucosamine 7.0 g (13.4 mmol) of benzyl N-acetyl-3,6-di-O-benzyl-4-O-ethyl-α-D-glucosamine [prepared as described in step (i) above] were dissolved in 60 ml of acetic acid, and 10 g of palladium-on-carbon were added to the resulting solution. The mixture was then stirred under hydrogen atmosphere at 3 atmospheres pressure for 30 hours. At the end of this time, the catalyst was separated by filtration, and the solvent was removed by distillation under reduced pressure. The resulting residue was purified by silica gel column chromatography, using a gradient elution method, with mixtures of methylene chloride and methanol ranging from 10:1 to 5:1 by volume as the eluent, to obtain 2.4 g (yield 81%) of the title compound as a colorless solid.

Rf=0.35 (5:1=methylene chloride:methanol). [α]$D^{25}$=+66.1° (c=2.1, CH$_3$OH). Mass Spectrum (FAB) m/e 250 (M$^+$+H). $^1$H-Nuclear Magnetic Resonance Spectrum (D$_2$O, 270 MHz) δ (ppm): 1.15 (3H, triplet, J=7.0 Hz); 2.00 (3H, singlet); 3.33 (2H, quartet, J=7.0 Hz); 3.60–3.90 (6H, multiplet); 5.15 (1H, singlet).

30(ii) 5-Acetamido-3,5-dideoxy-7-O-ethyl-D-glycero-D-galacto-2-nonuropyranosoic acid 5.0 g (20.1 mmol) of N-acetyl-4-O-ethyl-α-D-glucosamine [prepared as described in step (iii) above] were dissolved in distilled water, and 100 mg of sodium azide and 5.0 g (45.5 mmol) of sodium pyruvate were added to the resulting solution. The pH of the reaction mixture was adjusted to a value of 10 to 11 using a 1 N aqueous solution of sodium hydroxide, after which 25 mg (660U) of N-acetylneuraminic acid aldolase (produced by TOYOBO K.K.) were added, and the mixture was stirred at 20° C. for 3 days. At the end of this time, the reaction mixture was desalted using a Dowex 50×8 (H$^+$) resin (Dowex is a trade mark) and purified over chromatography using a Dowex 1 (HCOOH) resin with a 1.0 M aqueous solution of formic acid as the eluent, to obtain 500 mg (yield 7.4%) of the title compound as a colorless viscous substance.

Rf=0.20 (4:1:1=isopropanol:acetic acid:water). $[\alpha]D^{25}$=−8.4° (c=0.19, CH$_3$OH). Mass Spectrum (FAB) m/e 338 (M$^+$+H). $^1$H-Nuclear Magnetic Resonance Spectrum (D$_2$O, 270 MHz) δ (ppm): 1.05 (3H, triplet, J=7.0 Hz); 1.80 (1H, doublet of doublets, J=12.0 & 12.0 Hz); 2.00 (3H, singlet); 2.20 (1H, doublet of doublets, J=4.5 & 12.0 Hz); 3.50–3.80 (7H, multiplet).

30(iv) Methyl 5-acetamido-3,5-dideoxy-7-O-ethyl-D-glycero-D-galacto-2-nonuropyranosoate 1.9 g (5.64 mmol) of 5-acetamido-3,5-dideoxy-7-O-ethyl-D-glycero-D-galacto-2-nonuropyranosoic acid [prepared as described in step (iii) above] were dissolved in 60 ml of methanol, and 600 mg of a cation exchange resin [Dowex 50×8 (H$^+$)—Dowex is a trade mark] were added to the resulting solution. The mixture was then stirred at room temperature for 15 hours. At the end of this time, the Dowex 50×8 (H$^+$) was separated by filtration, and the solvent was removed by distillation under reduced pressure. The resulting residue was purified by silica gel column chromatography, using a 5:1 by volume mixture of methylene chloride and methanol as the eluent, to obtain 1.4 g (yield 71%) of the title compound as an amorphous substance.

Rf=0.3 (5:1=methylene chloride:methanol). $[\alpha]D^{25}$=−7.5° (c=0.10, CHCl$_3$). Mass Spectrum (FAB) m/e 352 (M$^+$+H). $^1$H-Nuclear Magnetic Resonance Spectrum (CD$_3$OD, 270 MHz) δ (ppm): 1.17 (3H, triplet, J=7.0 Hz); 1.95 (1H, doublet of doublets, J=12.0 & 14.0 Hz); 2.00 (3H, singlet); 2.16 (1H, doublet of doublets, J=4.5 & 12.0 Hz); 3.42 (1H, doublet of doublets, J=1.5 & 8.0 Hz); 3.60 (2H, quartet, J=7.0 Hz); 3.77 (3H, singlet); 3.70–4.00 (4H, multiplet); 4.15 (1H, doublet of doublets, J=1.5 & 9.5 Hz).

30(v) Methyl 5-acetamido-4,8,9,-tri-O-acetyl-2,3,5,7-tetradeoxy-7-ethoxy-D-glycero-D-galacto-non-2-enopyranosoate 1.4 g (3.99 mmol) of methyl 5-acetamido-3,5-dideoxy-7-O-ethyl-D-glycero-D-galacto-2-nonuropyranosoate [prepared as described in step (iv) above] were dissolved in a mixture of 20 ml of pyridine and 10 ml of acetic anhydride, and the mixture was stirred at room temperature for 15 hours. At the end of this time, the solvent was removed by distillation under reduced pressure, and the residue was dissolved in 50 ml of a 4 M solution of hydrogen chloride in dioxane. The mixture was then stirred at room temperature for 15 hours. At the end of this time, the solvent was removed by distillation under reduced pressure, and the residue was dissolved in benzene. 952 mg (6.30 mmol) of 1,8-diazabicyclo[5.4.0]-7-undecene were then added to the reaction mixture, and the mixture was stirred at room temperature for 2 hours. At the end of this time, the reaction mixture was poured into a 2-layer solution of 30 ml of methylene chloride and 15 ml of a saturated aqueous ammonium chloride solution, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 1.1 g (yield 60%) of the title compound as a colorless amorphous substance.

Rf=0.30 (20:1=methylene chloride:methanol). $[\alpha]D^{25}$=+24.1° (c=0.5, CHCl$_3$). Mass Spectrum (FAB) m/e 460 (M$^+$+H). $^1$H-Nuclear Magnetic Resonance Spectrum (CDCl$_3$, 270 MHz) δ (ppm): 1.20 (3H, triplet, J=7.0 Hz); 1.98 (3H, singlet); 2.05 (3H, singlet); 2.08 (3H, singlet); 3.50–3.80 (3H, multiplet); 3.80 (3H, singlet); 4.20–4.35 (2H, multiplet); 4.45 (1H, multiplet); 4.70 (1H, doublet of doublets, J=3.2 & 12.0 Hz); 2 5.33 (1H, multiplet); 5.47 (1H, doublet of doublets, J=3.3 & 7.0 Hz); 5.51 (1H, doublet, J=7.0 Hz); 6.00 (1H, doublet, J=3.3 Hz).

30(vi) Methyl 5-acetamido-4-azido-8,9-di-O-acetyl-2,3,4,5,7-pentadeoxy-7-ethoxy-D-glycero-D-galacto-non-2-enopyranosoate 1000 mg (2.18 mmol) of methyl 5-acetamido4,8,9-tri-O-acetyl-2,3,5,7-tetradeoxy-7-ethoxy-D-glycero-D-galacto-non-2-enopyranosoate [prepared as described in step (v) above] were dissolved in 20 ml of anhydrous methylene chloride, and 25 mg (0.78 mmol) of methanol were added to the resulting solution, after which 3.1 g (21.8 mmol) of a boron trifluoride-diethyl ether complex were added under a nitrogen atmosphere, and the mixture was stirred at room temperature for 24 hours. At the end of this time, the reaction mixture was poured into a mixture of 50 ml of water, 10 g of ice, 10 g of solid sodium hydrogencarbonate and 50 ml of ethyl acetate, and the mixture was vigorously stirred for 10 minutes. The organic layer was then washed with 10 ml of a saturated aqueous solution of sodium chloride and dried over anhydrous sodium sulfate, after which the solvent was removed by distillation under reduced pressure. The resulting residue (800 mg) was dissolved in 10 ml of dimethylformamide, and 800 mg of a cation exchange resin [Dowex 50×8 (H$^+$)—Dowex is a trade mark] and 400 mg (6.15 mmol) of sodium azide were added. The mixture was then stirred at 90° C. for 4 hours. At the end of this time, the Dowex 50×8 (H$^+$) was separated by filtration, and the solvent was removed by distillation under reduced pressure. The resulting residue was dissolved in a 2-layer solution of 30 ml of ethyl acetate and 20 ml of a saturated aqueous solution of sodium hydrogencarbonate, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 50: 1 by volume mixture of methylene chloride and methanol as the eluent, to obtain 600 mg (yield 63%) of the title compound as a colorless viscous substance.

Rf=0.30 (20:1=methylene chloride:methanol). $[\alpha]D^{25}$=+72.6° (c=0.05, CHCl$_3$). Mass Spectrum (FAB) m/e 443 (M$^+$+H). $^1$H-Nuclear Magnetic Resonance Spectrum (CDCl$_3$, 270 MHz) δ (ppm): 1.25 (3H, triplet, J 7.0 Hz); 2.09 (3H, singlet); 2.10 (3H, singlet); 2.13 (3H, singlet); 3.50–3.80 (3H, multiplet); 3.80 (3H, singlet); 4.05 (1H, multiplet); 4.25 (1H, doublet of doublets, J=5.0 & 12.0 Hz); 4.45–4.55 (2H, multiplet); 4.80 (1H, doublet of doublets, J=3.2 & 12.0 Hz); 5.35 (1H, multiplet); 5.51 (1H, doublet, J=8.2 Hz); 6.00 (1H, doublet, J=2.7 Hz).

30(vii) Methyl 5-acetamido-4-(N,N'-bis-t-butoxycarbonylguanidino)-8,9-di-O-acetyl-2,3,4,5,7-pentadeoxy-7-ethoxy-D-glycero-D-galacto-non-2-enopyranosoate 580 mg (1.31 mmol) of methyl 5-acetamido-4azido-8,9-di-O-acetyl-2,3,4,5,7-pentadeoxy-7-ethoxy-D-glycero-D-galacto-non-2-enopyranosoate [prepared as described in step (vi) above] were dissolved in 10 ml of methanol, and 270 mg of a Lindlar catalyst were added to the resulting solution. The mixture was then stirred under a hydrogen atmosphere for 2 hours. At the end of this time, the catalyst was separated by filtration, and the solvent was removed by distillation under reduced pressure. The resulting residue (400 mg) was dissolved in 10 ml of dimethylformamide, and 408 mg (1.48 mmol) of N,N-di-t-butoxycarbonylthiourea, 300 mg(2.95 mmol) of triethylamine and 402 mg (1.48 mmol) of mercuric chloride were added to the resulting solution. The mixture was then stirred at room temperature for 1 hour. At the end of this time, the solid was separated by filtration and the filtrate was poured into a 2-layer solution of 20 ml of ethyl acetate and 10 ml of a saturated aqueous solution of sodium hydrogencarbonate. The organic layer was separated, washed with a saturated aqueous solution of sodium chloride and dried over anhydrous sodium sulfate, after which the solvent was removed by distillation under reduced pressure. The resulting residue was purified by silica gel column chromatography, using a 2:1 by volume mixture of hexane and ethyl acetate as the eluent, to obtain 530 mg (yield 61%) of the title compound as a colorless amorphous substance.

Rf=0.40 (20:1=methylene chloride:methanol). $[\alpha]_D^{25}$=+2.8° (c=0.05, $CHCl_3$). Mass Spectrum (FAB) m/e 659 ($M^+$+H). $^1$H-Nuclear Magnetic Resonance Spectrum ($CDCl_3$, 270 MHz) δ (ppm): 1.20 (3H, triplet, J=7.0 Hz); 1.49 (9H, singlet); 1.50 (9H, singlet); 1.95 (3H, singlet); 2.06 (3H, singlet); 2.09 (3H, singlet); 3.50–3.80 (3H, multiplet); 3.80 (3H, singlet); 4.10 (1H, doublet of doublets, J=1.0 & 10.5 Hz); 4.25–4.40 (2H, multiplet); 4.80 (1H, doublet of doublets, J=3.2 & 12.0 Hz); 5.10 (1H, doubled doublet of doublets, J=2.5, 11.0 & 11.0 Hz); 5.30 (1H, multiplet); 5.83 (1H, doublet, J=2.3 Hz); 6.20 (1H, doublet, J=8.8 Hz).

30(viii) 5-Acetamido-4-guanidino-2,3,4,5,7-pentadeoxy-7-ethoxy-D-glycero-D-galacto-non-2-enopyranosoic acid trifluoroacetic acid salt 50 mg (0.076 mmol) of methyl 5-acetamido-4-(N,N'-bis-t-butoxycarbonylguanidino)-8,9-di-O-acetyl-2,3,4,5,7-pentadeoxy-7-ethoxy-D-glycero-D-galacto-non-2-enopyranosoate [prepared as described in step (vii) above] were dissolved in 2 ml of methanol, and 0.2 ml of a 0.1 N methanolic solution of sodium methoxide was added to the resulting solution. The mixture was then stirred at room temperature for 1 hour. At the end of this time, the reaction mixture was neutralized with a 4 M solution of hydrogen chloride in dioxane, and the solvent was removed by distillation under reduced pressure. The resulting residue was dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was dissolved in 1 ml of distilled water. 110 μl of a 1 N aqueous solution of sodium hydroxide were then added to the reaction mixture, which was then stirred at room temperature for 1 hour. At the end of this time, the reaction mixture was neutralized with a Dowex 50×8 ($H^+$) resin (Dowex is a trade mark), and then the water was removed by distillation. The resulting residue was purified by silica gel column chromatography, using a 5:1:1 by volume mixture of isopropanol, ethyl acetate and water as the eluent, to obtain 27 mg (yield 75%) of the title compound as a colorless solid.

Rf=0.30 (4:1:1=isopropanol:acetic acid:water). $[\alpha]_D^{25}$=+32.5° (c=0. 1, $CH_3OH$). Mass Spectrum (FAB) m/e 361 ($M^+$+H). $^1$H-Nuclear Magnetic Resonance Spectrum ($D_2O$, 270 MHz) δ (ppm): 1.05 (3H, triplet, J=7.0 Hz); 1.97 (3H, singlet); 3.40 (1H, multiplet); 3.50–3.65 (3H, multiplet); 3.80 (1H, doublet of doublets, J=5.0 & 12 Hz); 3.90 (1H, multiplet); 4.15 (1H, doublet of doublets, J=10 & 10 Hz); 4.40–4.50 (2H, multiplet); 5.55 (1H, doublet, J=1.8 Hz).

EXAMPLE 31

5-Acetamido-4-guanidino-9-O-octanoyl-2,3,4,5,7-pentadeoxy-7-ethoxy-D-glycero-D-galacto-non-2-enopyranosoic acid trifluoroacetic acid salt
(Compound No. 199-38)

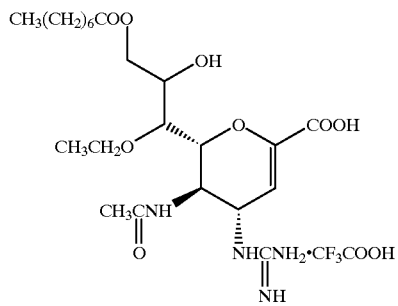

31(i) Diphenylmethyl 5-acetamido-4-(N,N'-bis-t-butolycarbonylguanidino)-2,3,4,5,7-pentadeoxy-7-ethoxy-D-glycero-D-galacto-non-2enopyranosoate 495 mg (0.75 mmol) of methyl 5-acetamido-4-(N,N'-bis-t-butoxycarbonylguanidino)-8,9-di-O-acetyl-2,3,4,5,7-pentadeoxy-7-ethoxy-D-glycero-D-galacto-non-2-enopyranosoate [prepared as described in Example 30(vii)] were dissolved in 10 ml of methanol, and 2 ml of a 0.1 N methanolic solution of sodium methoxide were added to the resulting solution. The mixture was then stirred at room temperature for 1 hour. At the end of this time, the reaction mixture was neutralized with a 4 M solution of hydrogen chloride in dioxane, and the solvent was removed by distillation under reduced pressure. The resulting residue was dissolved in 10 ml of distilled water, and 1.0 ml of a 1 N aqueous solution of sodium hydroxide was added thereto. The mixture was then stirred at room temperature for 1 hour. At the end of this time, the reaction mixture was neutralized with a 4 M solution of hydrogen chloride in dioxane, and then the water was removed by distillation. The resulting residue was dissolved in a 6: 1 by volume mixture of methanol and methylene chloride, and 500 mg (2.60 mmol) of diphenyldiazomethane and 50 mg (0.38 mmol) of a boron trifluoride-diethyl ether complex were added to the resulting solution. The mixture was then stirred at room temperature for 2 hours, after which acetic acid was added thereto, and the solvent was removed by distillation under reduced pressure. The resulting residue was purified by silica gel column chromatography, using a 20: 1 by volume mixture of methylene chloride and methanol as the eluent, to obtain 450 mg (yield 82%) of the title compound as a colorless amorphous substance.

Rf=0.25 (10:1=methylene chloride:methanol). $[\alpha]_D^{25}$=−10.7° (c=0.13, $CHCl_3$). Mass Spectrum (FAB) m/e 727 ($M^+$+H). $^1$H-Nuclear Magnetic Resonance Spectrum ($CDCl_3$, 270 MHz) δ (ppm): 1.20 (3H, triplet, J=7.0 Hz);

1.48 (9H, singlet); 1.50 (9H, singlet); 1.95 (3H, singlet); 3.60–4.10 (6H, multiplet); 4.30–4.50 (2H, multiplet); 5.10 (1H, multiplet); 5.95 (1H, doublet, J=2.7 Hz); 6.55 (1H, doublet, J=8.0 Hz); 6.95 (1H, singlet); 7.20–7.50 (10H, multiplet); 8.50 (1H, doublet, J=8.5 Hz).

31(ii) Diphenylmethyl 5-acetamido-4-(N,N'-bis-t-butoxycarbonylguanidino)-9-O-octanoyl-2,3,4,5,7-pentadeoxy-7-ethoxy-glycero-D-galacto-non-2-enopyranosoate 30 mg (0.041 mmol) of diphenylmethyl 5-acetamido-4-(N,N'-bis-t-butoxycarbonylguanidino)-2,3,4,5,7-pentadeoxy-7-ethoxy-D-glycero-D-galacto-non-2-enopyranosoate [prepared as described in step (i) above] were dissolved in 2 ml of methylene chloride, and 6 mg (0.06 mmol) of triethylamine and 8 mg (0.05 mmol) of octanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 24 mg (yield 69%) of the title compound as a colorless amorphous substance.

Rf=0.30 (20:1=methylene chloride:methanol). $[\alpha]D^{25}$ =–14.0° (c=0.05, $CHCl_3$). Mass Spectrum (FAB) m/e 854 ($M^+$+H). $^1$H-Nuclear Magnetic Resonance Spectrum ($CDCl_3$, 270 MHz)δ (ppm): 0.85 (3H, multiplet); 1.20 (3H, triplet, J=7.0 Hz); 1.20–1.30 (8H, multiplet); 1.48 (9H, singlet); 1.50 (9H, singlet); 1.55–1.70 (2H, multiplet); 1.95 (3H, singlet); 2.33 (2H, triplet, J=7.5 Hz); 3.50 (1H, triplet, J=5.5 Hz); 3.59 (2H, quartet, J=7.0 Hz); 4.10–4.50 (5H, multiplet); 5.10 (1H, doubled doublet of doublets, J=2.4, 9.0 & 9.0 Hz); 5.95 (1H, doublet, J=2.3 Hz); 6.10 (1H, doublet, J=8.7 Hz); 6.94 (1H, singlet); 7.20–7.50 (10H, multiplet); 8.55 (1H, doublet, J=8.7 Hz).

31 (iii) 5-Acetamido-4-guanidino-9-O-octanoyl-2,3,4,5,7-pentadeoxy-7-ethoxy-D-glycero-D-galacto-non-2-enopyranosoic acid trifluoroacetic acid salt 20 mg (0.023 mmol) of diphenylmethyl 5-acetamido-4-(N,N'-bis-t-butoxycarbonylguanidino)-9-O-octanoyl-2,3,4,5,7-pentadeoxy-7-ethoxy-D-glycero-D-galacto-non-2-enopyranosoate [prepared as described in step (ii) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 10 mg (yield 73%) of the title compound as a colorless solid.

Rf=0.3 (2:5:1=isopropanol:ethyl acetate:water). $[\alpha]D^{25}$=+55° (c=0.10, $CH_3OH$). Mass Spectrum (FAB) m/e 487 ($M^+$+H). $^1$H-Nuclear Magnetic Resonance Spectrum ($CD_3OD$, 270 M ) δ (ppm): 0.90 (3H, multiplet); 1.15 (3H, triplet, J=7.0 Hz); 1.20–1.40 (8H, multiplet); 1.55–1.70 (2H, multiplet); 2.00 (3H, singlet); 2.35 (2H, triplet, J=7.5 Hz); 3.45–3.60 (3H, multiplet); 4.10–4.40 (6H, multiplet); 5.53 (1H, doublet, J=1.8 Hz).

EXAMPLE 32

5-Acetamido-4-guanidino-9-O-dodecanoyl-2,3,4,5, 7-pentadeoxy-7-ethoxy-D-glycero-D-galacto-non-2-enopyranosoic acid trifluoroacetic acid salt
(Compound No. 199-40)

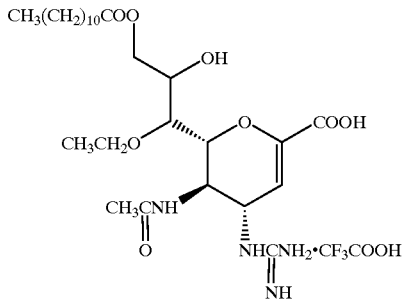

32(i) Diphenylmethyl 5-acetamido-4-(N,N'-bis-t-butoxycarbonylguanidino)-9-O-dodecanoyl-2,3,4,5,7-pentadeoxy-7-ethoxy-D-glycero-D-galacto-non-2-enopyranosoate 30 mg (0.041 mmol) of diphenylmethyl 5-acetamido-4-(N,N'-bis-t-butoxycarbonylguanidino)-2,3,4,5,7-pentadeoxy-7-ethoxy-D-glycero-D-galacto-non-2-enopyranosoate [prepared as described in Example 31(i)] were dissolved in 2 ml of methylene chloride, and 6 mg (0.06 mmol) of triethylamine and 11 mg (0.05 mmol) of dodecanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 29 mg (yield 78%) of the title compound as a colorless amorphous substance.

Rf=0.35 (20:1=methylene chloride:methanol). $[\alpha]D^{25}$=–9.0° (c=0.1, $CHCl_3$). Mass Spectrum (FAB) m/e 910 ($M^+$+H). $^1$H-Nuclear Magnetic Resonance Spectrum ($CDCl_3$, 270 MHz) δ (ppm): 0.85 (3H, multiplet); 1.20 (3H, triplet, J=7.0 Hz); 1.20–1.30 (16H, multiplet); 1.48 (9H, singlet); 1.50 (9H, singlet); 1.55–1.70 (2H, multiplet); 1.95 (3H, singlet); 2.33 (2H, triplet, J=7.5 Hz); 3.50 (1H, triplet, J=5.5 Hz); 3.59 (2H, quartet, J=7.0 Hz); 4.10–4.50 (5H, multiplet); 5.10 (1H, doubled doublet of doublets, J=2.4, 9.0 & 9.0 Hz); 5.95 (1H, doublet, J=2.3 Hz); 6.10 (1H, doublet, J=8.7 Hz); 6.94 (1H, singlet); 7.20–7.50 (10H, multiplet); 8.55 (1H, doublet, J=8.7 Hz).

32(ii) 5-Acetamido-4-guanidino-9-O-dodecanoyl-2,3,4,5,7-pentadeoxy-7-ethoxy-D-glycero-D-galacto-non-2-enopyranosoic acid trifluoroacetic acid salt 28 mg (0.03 mmol) of diphenylmethyl 5-acetamido-4-(N, N'-bis-t-butoxycarbonylguanidino)-9-D-dodecanoyl-2,3,4, 5,7-pentadeoxy-7-ethoxy-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 12 mg (yield 61 %) of the title compound as a colorless solid.

Rf=0.3 (2:5:1=isopropanol:ethyl acetate:water). $[\alpha]D^{25}$=+50° (c=0.05, $CH_3OH$). Mass Spectrum (FAB) m/e 543 ($M^+$+H). $^1$H-Nuclear Magnetic Resonance Spectrum ($CD_3OD$, 270 MHz) δ (ppm): 0.90 (3H, multiplet); 1.15 (3H, triplet, J=7.0 Hz); 1.20–1.40 (16H, multiplet); 1.55–1.70 (2H, multiplet); 2.00 (3H, singlet); 2.35 (2H, triplet, J=7.5 Hz); 3.45–3.60 (3H, multiplet); 4.10–4.40 (6H, multiplet); 5.53 (1H, doublet, J=1.8 Hz).

EXAMPLE 33

5-Acetamido-4-guanidino-9-O-tetradecanoyl2,3,4,5, 7-pentadeoxy-7-ethoxy-D-glycero-D-galacto-non-2-enopyranosoic acid trifluoroacetic acid salt
(Compound No. 199-41)

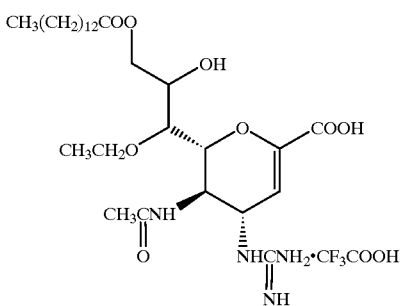

33(i) Diphenylmethyl 5-acetamido-4-(N,N'-bis-t-butoxycarbonylguanidino)-9-O-tetradecanoyl-2,3,4,5,7-pentadeoxy-7-ethoxy-D-glycero-D-galacto-non-2-enopyranosoate 30 mg (0.041 mmol) of diphenylmethyl 5-acetamido-4-(N,N'-bis-t-butoxycarbonylguanidino)-2,3,4,5,7-pentadeoxy-7-ethoxy-D-glycero-D-galacto-non-2-enopyranosoate [prepared as described in Example 31(i)] were dissolved in 2 ml of methylene chloride, and 6 mg (0.06 mmol) of triethylamine and 12 mg (0.05 mmol) of tetradecanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 30 mg (yield 78%) of the title compound as a colorless amorphous substance.

Rf=0.35 (20:1=methylene chloride:methanol). $[\alpha]D^{25}$=−8.0° (c=0.1, $CHCl_3$). Mass Spectrum (FAB) m/e 938 ($M^+$+H). $^1$H-Nuclear Magnetic Resonance Spectrum ($CDCl_3$, 270 Mz) δ (ppm): 0.85 (3H, multiplet); 1.20 (3H, triplet, J=7.0 Hz); 1.20–1.30 (20H, multiplet); 1.48 (9H, singlet); 1.50 (9H, singlet); 1.55–1.70 (2H, multiplet); 1.95 (3H, singlet); 2.33 (2H, triplet, J=7.5 Hz); 3.50 (1H, triplet, J=5.5 Hz); 3.59 (2H, quartet, J=7.0 Hz); 4.10–4.50 (5H, multiplet); 5.10 (1H, doubled doublet of doublets, J=2.4,9.0 & 9.0 Hz); 5.95 (1H, doublet, J=2.3 Hz); 6.10 (1H, doublet, J=8.7 Hz); 6.94 (1H, singlet); 7.20–7.50 (10H, multiplet); 8.55 (1H, doublet, J=8.7 Hz).

33(ii) 5-Acetamido-4-guanidino9-O-tetradecanoyl-2,3,4,5, 7-pentadeoxy-7-ethoxy-D-glycero-D-galacto-non-2enopyranosoic acid trifluoroacetic acid salt 28 mg (0.03 mmol) of diphenylmethyl 5-acetamido-4-(N, N'-bis-t-butoxycarbonylguanidino)-9-O-tetradecanoyl-2,3, 4,5,7-pentadeoxy-7-ethoxy-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 13 mg (yield 74%) of the title compound as a colorless solid.

Rf=0.3 (2:5:1=isopropanol:ethyl acetate:water). $[\alpha]D^{25}$=+38.0° (c=0.05, $CH_3OH$). Mass Spectrum (FAB) m/e 571 ($M^+$+H). $^1$H-Nuclear Magnetic Resonance Spectrum ($CD_3OD$, 270 MHz) δ (ppm): 0.90 (3H, multiplet); 1.15 (3H, triplet, J=7.0 Hz); 1.20–1.40 (20H, multiplet); 1.55–1.70 (2H, multiplet); 2.00 (3H, singlet); 2.35 (2H, triplet, J=7.5 Hz); 3.45–3.60 (3H, multiplet); 4.10–4.40 (6H, multiplet); 5.53 (1H, doublet, J=1.8 Hz).

EXAMPLE 34

5-Acetamido-4-guanidino-9-O-hexadecanoyl-2,3,4, 5,7-pentadeoxy-7-ethoxy-D-glycero-D-galacto-non-2-enopyranosoic acid trifluoroacetic acid salt
(Compound No; 199-42)

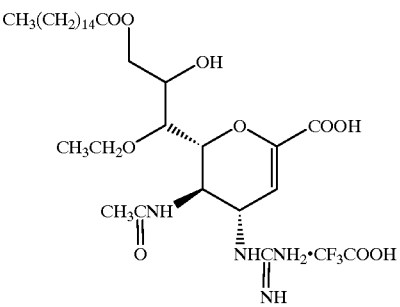

34(i) Diphenylmethyl 5-acetamido-4-N,N'-bis-t-butoxycarbonylguanidino)-9-O-hexadecanoyl-2,3,4,5,7-pentadeoxy-7-ethoxy-D-glycero-D-galacto-non-2-enopyranosoate 30 mg (0.041 mmol) of diphenylmethyl 5-acetamido-4-(N,N'-bis-t-butoxycarbonylguanidino)-2,3,4,5,7-pentadeoxy-7-ethoxy-D-glycero-D-galacto-non-2-enopyranosoate [prepared as described in Example 31(i)] were dissolved in 2 ml of methylene chloride, and 6 mg (0.06 mmol) of triethylamine and 14 mg (0.05 mmol) of hexadecanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 31 mg (yield 78%) of the title compound as a colorless amorphous substance.

Rf=0.35 (20:1=methylene chloride:methanol). $[\alpha]D^{25}$=−7.5° (c=0.1, CHCl$_3$). Mass Spectrum (FAB) m/e 966 (M$^+$+H). $^1$H-Nuclear Magnetic Resonance Spectrum (CDCl$_3$, 270 MHz) δ (ppm): 0.85 (3H, multiplet); 1.20 (3H, triplet, J=7.0 Hz); 1.20–1.30 (24H, multiplet); 1.48 (9H, singlet); 1.50 (9H, singlet); 1.55–1.70 (2H, multiplet); 1.95 (3H, singlet); 2.33 (2H, triplet, J=7.5 Hz); 3.50 (1H, triplet, J=5.5 Hz); 3.59 (2H, quartet, J=7.0 Hz); 4.10–4.50 (5H, multiplet); 5.10 (1H, doubled doublet of doublets, J=2.4, 9.0 & 9.0 Hz); 5.95 (1H, doublet, J=2.3 Hz); 6.10 (1H, doublet, J=8.7 Hz); 6.94 (1H, singlet); 7.20–7.50 (10H, multiplet); 8.55 (1H, doublet, J=8.7 Hz).

34(ii) 5-Acetamido-4-guanidino-9-O-hexadecanoyl-2,3,4,5,7-pentadeoxy-7-ethoxy-D-glycero-D-galacto-non-2-enopyranosoic acid trifluoroacetic acid salt 28 mg (0.029 mmol) of diphenylmethyl 5-acetamido-4-(N,N'-bis-t-butoxycarbonylguanidino)-9-O-hexadecanoyl-2,3,4,5,7-pentadeoxy-7-ethoxy-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 12 mg (yield 58%) of the title compound as a colorless solid.

Rf=0.3 (2:5:1=isopropanol:ethyl acetate:water). $[\alpha]D^{25}$=+30.0° (c=0.1, CH$_3$OH). Mass Spectrum (FAB) m/e 599 (M$^+$+H). $^1$H-Nuclear Magnetic Resonance Spectrum (CD$_3$OD, 270 MHz) δ (ppm): 0.90 (3H, multiplet); 1.15 (3H, triplet, J=7.0 Hz); 1.20–1.40 (24H, multiplet); 1.55–1.70 (2H, multiplet); 2.00 (3H, singlet); 2.35 (2H, triplet, J=7.5 Hz); 3.45–3.60 (3H, multiplet); 4.10–4.40 (6H, multiplet); 5.53 (1H, doublet, J=1.8 Hz).

EXAMPLE 35

5-Acetamido-4-guanidino-9-O-octanoyl-2,3,4,5,7-pentadeoxy-7-methoxy-D-glycero-D-galacto-non-2-enopyranosoic acid trifluoroacetic acid salt
(Compound No. 163-38)

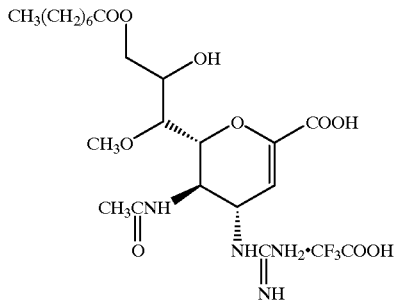

35(i) Diphenylmethyl 5-acetamido-4-(N,N'-bis-t-butoxycarbonylguanidino)-9-O-octanoyl-2,3,4,5,7-pentadeoxy-7-methoxy-D-glycero-D-galacto-non-2-enopyranosoate 57 mg (0.08 mmol) of diphenylmethyl 5-acetamido-4-(N,N'-bis-t-butoxycarbonylguanidino)-2,3,4,5,7-pentadeoxy-7-methoxy-D-glycero-D-galacto-non-2-enopyranosoate [prepared as described in Example 29(i)] were dissolved in 2 ml of methylene chloride, and 11 mg (0.10 mmol) of triethylamine and 16 mg (0.09 mmol) of octanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 38 mg (yield 58%) of the title compound as a colorless amorphous substance.

Rf=0.5 (10:1=methylene chloride:methanol). $[\alpha]D^{25}$=+2.7° (c=0.11, CHCl$_3$). Mass Spectrum (FAB) m/e 839 (M$^+$+H). $^1$H-Nuclear Magnetic Resonance Spectrum (CDCl$_3$, 270 MHz) δ (ppm): 0.85 (3H, multiplet); 1.20–1.30 (8H, multiplet); 1.48 (9H, singlet); 1.50 (9H, singlet); 1.55–1.70 (2H, multiplet); 1.98 (3H, singlet); 2.33 (2H, triplet, J=7.5 Hz); 3.40 (1H, multiplet); 3.48 (3H, singlet); 4.10–4.50 (5H, multiplet); 5.18 (1H, doubled doublet of doublets, J=2.4, 9.0 & 9.0 Hz); 5.95 (1H, doublet, J=2.3 Hz); 6.18 (1H, doublet, J=8.7 Hz); 6.92 (1H, singlet); 7.20–7.50 (10H, multiplet); 8.55 (1H, doublet, J=8.7 Hz).

35(ii) 5-Acetamido-4-guanidino9-O-octanoyl-2,3,4,5,7-pentadeoxy-7 methoxy-D-glycero-D-galacto-non-2-enopyranosoic acid trifluoroacetic acid salt 31 mg (0.037 mmol) of diphenylmethyl 5-acetamido-4-(N,N'-bis-t-butoxycarbonylguanidino)-9-O-octanoyl-2,3,4,5,7-pentadeoxy-7-methoxy-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 15 mg (yield 69%) of the title compound as a colorless solid.

Rf=0.34 (2:5:1=isopropanol:ethyl acetate:water). $[\alpha]D^{25}$=+38.2° (c=0.11, CH$_3$OH) Mass Spectrum (FAB) m/e 473 (M$^+$+H) $^1$H-Nuclear Magnetic Resonance Spectrum (CD$_3$OD, 270 MHz) δ (ppm): 0.90 (3H, multiplet); 1.25–1.40 (8H, multiplet); 1.60–1.70 (2H, multiplet); 2.00 (3H, singlet); 2.37 (2H, triplet, J=7.5 Hz); 3.38 (3H, singlet); 3.45 (1H, multiplet); 4.10–4.40 (6H, multiplet); 5.53 (1H, doublet, J=1.8 Hz).

EXAMPLE 36

5-Acetamido-4-guanidino-9-O-decanoyl-2,3,4,5,7-pentadeoxy-7-methoxy-D-glycero-D-galacto-non-2-enopyranosoic acid trifluoroacetic acid salt
(Compound No. 163-39)

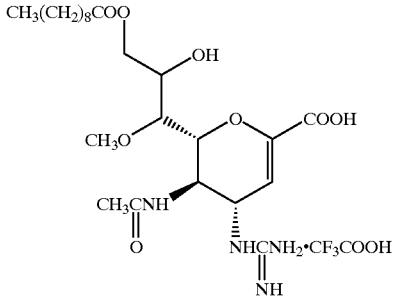

36(i) Diphenylmethyl 5-acetamido-4-(N,N'-bis-t-butoxycarbonylguanidino)-9-O-decanoyl-2,3,4,5,7- pentadeoxy-7-methoxy-D-glycero-D-galacto-non2-enopyranosoate 56 mg (0.08 mmol) of diphenylmethyl 5-acetamido-4-(N,N'-bis-t-butoxycarbonylguanidino)-2,3,4,5,7-pentadeoxy-7-methoxy-D-glycero-D-galacto-non-2-enopyranosoate [prepared as described in Example 29(i)] were dissolved in 2 ml of methylene chloride, and 11 mg (0.10 mmol) of triethylamine and 18 mg (0.09 mmol) of decanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 40 mg (yield 50%) of the title compound as a colorless amorphous substance.

Rf=0.5 (10:1=methylene chloride:methanol). $[\alpha]D^{25}$=+13.9° (c=0.11, $CHCl_3$) Mass Spectrum (FAB) m/e 867 ($M^+$+H) $^1$H-Nuclear Magnetic Resonance Spectrum ($CDCl_3$, 270 MHz) δ (ppm): 0.85 (3H, multiplet); 1.20–1.30 (12H, multiplet); 1.48 (9H, singlet); 1.50 (9H, singlet); 1.55–1.70 (2H, multiplet); 1.98 (3H, singlet); 2.33 (2H, triplet, J=7.5 Hz); 3.40 (1H, multiplet); 3.48 (3H, singlet); 4.10–4.50 (5H, multiplet); 5.18 (1H, doubled doublet of doublets, J 2.4, 9.0 & 9.0 Hz); 5.95 (1H, doublet, J=2.3 Hz); 6.18 (1H, doublet, J=8.7 Hz); 6.92 (1H, singlet); 7.20–7.50 (10H, multiplet); 8.55 (1H, doublet, J=8.7 Hz).

36(ii) 5-Acetamido-4-guanidino-9-O-decanoyl-2,3,4,5,7pentadeoxy-7-methoxy-D-glycero-D-galacto-non-2-enopyranosoic acid trifluoroacetic acid salt 33 mg (0.04 mmol) of diphenylmethyl 5-acetamido-4(N,N'-bis-t-butoxy- carbonylguanidino)-9-O-decanoyl-2,3,4,5,7-pentadeoxy7-methoxy-D-glycero-D-galacto-non-2-enopyranosoate [prepared as described in Example 36(i)] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 20 mg (yield 85%) of the title compound as a colorless solid.

Rf=0.34 (2:5:1=isopropanol:ethyl acetate:water). $[\alpha]D^{25}$=+33.30° (c=0.11, $CH_3OH$). Mass Spectrum (FAB) m/e 501 ($M^+$+H). $^1$H-Nuclear Magnetic Resonance Spectrum ($CD_3OD$, 270 MHz) δ (ppm): 0.90 (3H, multiplet); 1.25–1.40 (12H, multiplet); 1.60–1.70 (2H, multiplet); 2.00 (3H, singlet); 2.37 (2H, triplet, J=7.5 Hz); 3.38 (3H, singlet); 3.45 (1H, multiplet); 4.10–4.40 (6H, multiplet); 5.53 (1H, doublet, J=1.8 Hz).

EXAMPLE 37

5-Acetamido-4-guanidino-9-O-dodecanoyl-2,3,4,5,7-pentadeoxy-7methoxy-D-glycero-D-galacto-non-2enopyranosoic acid trifluoroacetic acid salt (Compound No. 163-40)

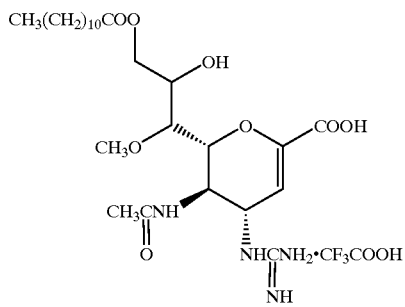

37(i) Diphenylmethyl 5-acetamido-4-(N,N'-bis-t-butoxycarbonylguanidino)-9-O-dodecanoyl-2,3,4,5,7-pentadeoxy-7methoxy-D-glycero-D-galacto-non-2-enopyranosoate 51 mg (0.07 mmol) of diphenylmethyl 5-acetamido-4-(N,N'-bis-t-butoxycarbonylguanidino)-2,3,4,5,7-pentadeoxy-7-methodoxy-D-glycero-D-galacto-non-2-enopyranosoate [prepared as described in Example 29(i)] were dissolved in 2 ml of methylene chloride, and 9 mg (0.09 mmol) of triethylamine and 19 mg (0.09 mmol) of dodecanoyl chloride were added to the resulting solution, whilst ice-cooling. The mixture was then stirred at 0° C. for 1 hour. At the end of this time, the reaction mixture was poured into a 2-layer solution of 5 ml of ethyl acetate and 3 ml of a saturated aqueous solution of sodium hydrogencarbonate, and the organic layer was washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 39 mg (yield 61%) of the title compound as a colorless amorphous substance.

Rf=0.6 (20:1=methylene chloride:methanol). $[\alpha]D^{25}$=+2.4° (c=0.13, $CHCl_3$) Mass Spectrum (FAB) m/e 895 ($M^+$+H) $^1$H-Nuclear Magnetic Resonance Spectrum ($CDCl_3$, 270 MHz) δ (ppm): 0.85 (3H, multiplet); 1.20–1.30 (16H, multiplet); 1.48 (9H, singlet); 1.50 (9H, singlet); 1.55–1.70 (2H, multiplet); 1.98 (3H, singlet); 2.33 (2H, triplet, J=7.5 Hz); 3.40 (1H, multiplet); 3.48 (3H, singlet); 4.10–4.50 (5H, multiplet); 5.18 (1H, doubled doublet of doublets, J=2.4, 9.0 & 9.0 Hz); 5.95 (1H, doublet, J=2.3 Hz); 6.18 (1H, doublet, J=8.7 Hz); 6.92 (1H, singlet); 7.20–7.50 (10H, multiplet); 8.55 (1H, doublet, J=8.7 Hz).

37(ii) 5-Acetamido-4-guanidino9-O-dodecanoyl-2,3,4,5,7-pentadeoxy-7-methoxy-D-glycero-D-galacto-non-2-enopyranosoic acid trifluoroacetic acid salt 31 mg (0.035 mmol) of diphenylmethyl 5-acetamido-4-(N,N'-bis-t-butoxycarbonylguanidino)-9-O-dodecanoyl-2,3,4,5,7-pentadeoxy-7-methoxy-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 22 mg (yield 98%) of the title compound as a colorless solid.

Rf=0.31 (2:5:1=isopropanol:ethyl acetate:water). [α]$_D^{25}$=+25.8° (c=0.16, CH$_3$OH). Mass Spectrum (FAB) m/e 529 (M$^+$+H). $^1$H-Nuclear Magnetic Resonance Spectrum (CD$_3$OD, 270 MHz) δ (ppm): 0.90 (3H, multiplet); 1.25–1.40 (16H, multiplet); 1.60–1.70 (2H, multiplet); 2.00 (3H, singlet); 2.37 (2H, triplet, J=7.5 Hz); 3.38 (3H, singlet); 3.45 (1H, multiplet); 4.10–4.40 (6H, multiplet); 5.53 (1H, doublet, J=1.8 Hz).

EXAMPLE 38

5-Acetamido-4-guanidino-9-O-hexadecanoyl-2,3,4,5,7-pentadeoxy-7-methoxy-D-glycero-D-galacto-non-2-enopyranosoic acid trifluoroacetic acid salt
(Compound No. 163-421)

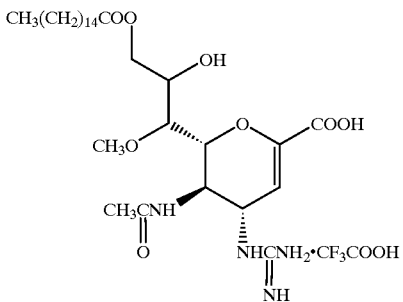

38(i) Diphenylmethyl 5-acetamido-4-(N,N'-bis-t-butoxycarbonylguanidino)-9-O-hexadecanoyl-2,3,4,5,7-pentadeoxy-7-methoxy-D-glycero-D-galacto-non-2-enopyranosoate 50 mg (0.07 mmol) of diphenylmethyl 5-acetamido-4-(N,N'-bis-t-butoxycarbonylguanidino)-2,3,4,5,7-pentadeoxy-7-methoxy-D-glycero-D-galacto-non-2-enopyranosoate [prepared as described in Example 29(i)] were dissolved in 2 ml of methylene chloride, and 9 mg (0.09 mmol) of triethylamine and 23 mg (0.084 mmol) of hexadecanoyl chloride were added to the resulting solution, whilst ice-cooling. The mixture was then stirred at 0° C. for 1 hour. At the end of this 10 time, the reaction mixture was poured into a 2-layer solution of 5 ml of ethyl acetate and 3 ml of a saturated aqueous solution of sodium hydrogencarbonate, and the organic layer was separated and washed with a saturated aqueous solution of sodium chloride. It was then dried over anhydrous sodium sulfate, and the solvent was removed by distillation under reduced pressure. The resulting residue was purified by silica gel column chromatography, using a 50:1 by volume mixture of methylene chloride and methanol as the eluent, to obtain 40 mg (yield 60%) of the title compound as a colorless amorphous substance.

Rf=0.6 (10:1=methylene chloride:methanol). [α]$_D^{25}$=+5.5° (c=0.11, CHCl$_3$). Mass Spectrum (FAB) m/e 951 (M$^+$+H). $^1$H-Nuclear Magnetic Resonance Spectrum (CDCl$_3$, 270 MHz) δ (ppm): 0.85 (3H, multiplet); 1.20–1.30 (24H, multiplet); 1.48 (9H, singlet); 1.50 (9H, singlet); 1.55–1.70 (2H, multiplet); 1.98 (3H, singlet); 2.33 (2H, triplet, J=7.5 Hz); 3.40 (1H, multiplet); 3.48 (3H, singlet); 4.10–4.50 (5H, multiplet); 5.18 (1H, doubled doublet of doublets, J=2.4, 9.0 & 9.0 Hz); 5.95 (1H, doublet, J=2.3 Hz); 6.18 (1H, doublet, J=8.7 Hz); 6.92 (1H, singlet); 7.20–7.50 (10H, multiplet); 8.55 (1H, doublet, J=8.7 Hz).

38(ii) 5-Acetamido-4guanidino-9-O-hexadecanoyl-2,3,4,5,7-pentadeoxy-7-methoxy-D-glycero-D-galacto-non-2-enopyranosoic acid trifluoroacetic acid salt 34 mg (0.036 mmol) of diphenylmethyl 5-acetamido-4-(N,N'-bis-t-butoxycarbonylguanidino)-9-O-hexadecanoyl-2,3,4,5,7-pentadeoxy-7-methoxy-D-glycero-D-galacto-non-2-enopyranosoate [prepared as described in step (i) above] were dissolved in 3 ml of a 3:1 by volume mixture of methylene chloride and trifluoroacetic acid, and the mixture was stirred at room temperature for 5 hours. At the end of this time, the solvent was removed by distillation under reduced pressure, and the residue was purified by silica gel column chromatography, using a 2:5:1 by volume mixture of isopropanol, ethyl acetate and water as the eluent, to obtain 23 mg (yield 92%) of the title compound as a colorless solid.

Rf=0.47 (2:5:1=isopropanol:ethyl acetate:water). [α]$_D^{25}$=+21.6° (c=0.12, CH$_3$OH). Mass Spectrum (FAB) m/e 585 (M$^+$+H). $^1$H-Nuclear Magnetic Resonance Spectrums (CD$_3$OD, 270 MHz) δ (ppm): 0.90 (3H, multiplet); 1.25–1.40 (24H, multiplet); 1.60–1.70 (2H, multiplet); 2.00 (3H, singlet); 2.37 (2H, triplet, J=7.5 Hz); 3.38 (3H, singlet); 3.45 (1H, multiplet); 4.10–4.40 (6H, multiplet); 5.53 (1H, doublet, J=1.8 Hz).

The present inventors found that acyl derivatives of the hydroxyl group at the 7- and 8- positions and/or the 9-position and ester derivatives of the carboxyl group at the 1- position of Compound A (GG-167) described in WO91/16320 (Japanese PCT Application (Kokai) No. Hei 5-507068) exhibit excellent in vivo viral replication inhibitory activity and sialidase inhibitory activity similar to Compound A, while also exhibiting infection therapeutic effects superior to Compound A when administered to mice infected with influenza virus, therefore being useful as an anti-influenza drug, and they accomplished the present invention. Therefore, in a further embodiment of the invention wherein formula I is in the ester form, the neuraminic acid of the present invention has the formula:

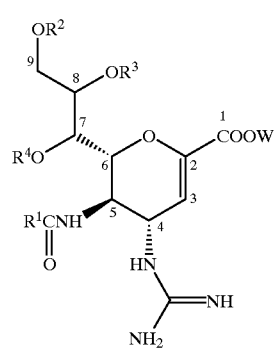

(1)

[wherein R$^1$ represents an alkyl group having from 1 to 4 carbon atoms which may be substituted with a halogen atom; R$^2$, R$^3$ and R$^4$ are the same or different and each represents a hydrogen atom or an aliphatic acyl group having from 3 to 25 carbon atoms, and W represents a hydrogen atom or an ester residue, provided that the case where R$^1$ is a methyl group and each of R$^2$, R$^3$, R$^4$ and W is a hydrogen atom is excluded].

In the above general formula (1):

"The alkyl group having from 1 to 4 carbon atoms" of "the alkyl group having from 1 to 4 carbon atoms which may be substituted with a halogen atom" of R$^1$ includes, for example, methyl, ethyl, n-propyl, isopropyl, n-butyl, isobutyl, s-butyl and tert-butyl groups, preferably a methyl group.

"The halogen atom" of "the alkyl group having from 1 to 4 carbon atoms which may be substituted with a halogen atom" of R$^1$ includes, for example, fluorine, chlorine and bromine atoms, preferably a fluorine atom.

"The alkyl group having from 1 to 4 carbon atoms substituted with a halogen atom" of "the alkyl group having from 1 to 4 carbon atoms which may be substituted with a halogen atom" of $R^1$ includes, for example, monofluoromethyl, difluoromethyl, trifluoromethyl, 1-fluoroethyl, 2-fluoroethyl, 1-fluoropropyl, 2-fluoropropyl, 3-fluoropropyl, 4fluorobutyl, monochloromethyl, dichloromethyl, trichloromethyl, 1-chloroethyl, 2-chloroethyl, 1-chloropropyl, 2-chloropropyl, 3-chloropropyl, 4-chlorobutyl, monobromomethyl, 1-bromoethyl, 2-bromoethyl, 1-bromopropyl, 2-bromopropyl, 3-bromopropyl, 4-bromobutyl and fluorochloromethyl groups, preferably a methyl group substituted with a fluorine atom, more preferably monofluoromethyl and difluoromethyl groups.

Therefore, "the alkyl group having from 1 to 4 carbon atoms which may be substituted with a halogen atom" of $R^1$ as a whole includes preferably a methyl group which may be substituted with a fluorine atom, more preferably methyl, monofluoromethyl and difluoromethyl groups, most preferably a methyl group, "The aliphatic acyl group having from 3 to 25 carbon atoms" of $R^2$, $R^3$ and $R^4$ includes, for example, an alkylcarbonyl group such as propionyl, butyryl, isobutyryl, pentanoyl, pivaloyl, valeryl, isovaleryl, octanoyl, nonylcarbonyl, decylcarbonyl, 3-methylnonylcarbonyl, 8-methylnonylcarbonyl, 3-ethyloctylcarbonyl, 3,7-dimethyloctylcarbonyl, undecylcarbonyl, dodecylcarbonyl, tridecylcarbonyl, tetradecylcarbonyl, pentadecylcarbonyl, hexadecylcarbonyl, 1-methylpentadecylcarbonyl, 14-methylpentadecylcarbonyl, 13,13-dimethyltetradecylcarbonyl, heptadecylcarbonyl, 15-methylhexadecylcarbonyl, octadecylcarbonyl, 1-methylheptadecylcarbonyl, nonadecylcarbonyl, eicosylcarbonyl, tricosylcarbonyl and tetracosylcarbonyl, preferably an aliphatic acyl group having from 6 to 25 carbon atoms, more preferably an aliphatic acyl group having from 6 to 20 carbon atoms, particularly preferably a hexanoyl, octanoyl, decanoyl, dodecanoyl, myristoyl, palmitoyl or stearoyl group.

$R^2$, $R^3$ and $R^4$ as a whole each are preferably a hydrogen atom or an aliphatic acyl group having from 6 to 25 carbon atoms, more preferably a hydrogen atom or an aliphatic acyl group having from 6 to 20 carbon atoms, particularly preferably a hydrogen atom or a hexanoyl, octanoyl, decanoyl, dodecanoyl, myristoyl, palmitoyl or stearoyl group.

As the combination of $R^2$, $R^3$ and $R^4$, (a) the combination wherein $R^2$ is an aliphatic acyl group having from 3 to 25 carbon atoms (preferably an aliphatic acyl group having from 6 to 25 carbon atoms, more preferably an aliphatic acyl group having from 6 to 20 carbon atoms, particularly preferably a hexanoyl, octanoyl, decanoyl, dodecanoyl, myristoyl, palmitoyl or stearoyl group), and each of $R^3$ and $R^4$ is a hydrogen atom, (b) the combination wherein $R^3$ is an aliphatic acyl group having from 3 to 25 carbon atoms preferably an aliphatic acyl group having from 6 to 25 carbon atoms, more preferably an aliphatic acyl group having from 6 to 20 carbon atoms, particularly preferably a hexanoyl, octanoyl, decanoyl, dodecanoyl, myristoyl, palmitoyl or stearoyl group), and each of $R^2$ and $R^4$ is a hydrogen atom, (c) the combination wherein $R^4$ is an aliphatic acyl group having from 3 to 25 carbon atoms (preferably an aliphatic acyl group having from 6 to 25 carbon atoms, more preferably an aliphatic acyl group having from 6 to 20 carbon atoms, particularly preferably a hexanoyl, octanoyl, decanoyl, dodecanoyl, myristoyl, palmitoyl or stearoyl group), and each of $R^2$ and $R^3$ is a hydrogen atom, (d) the combination wherein each of $R^2$ and $R^3$ is an aliphatic acyl group having from 3 to 25 carbon atoms (preferably an aliphatic acyl group having from 6 to 25 carbon atoms, more preferably an aliphatic acyl group having from 6 to 20 carbon atoms, particularly preferably a hexanoyl, octanoyl, decanoyl, dodecanoyl, myristoyl, palmitoyl or stearoyl group), and $R^4$ is a hydrogen atom, (e) the combination wherein each of $R^2$ and $R^4$ is an aliphatic acyl group having from 3 to 25 carbon atoms (preferably an aliphatic acyl group having from 6 to 25 carbon atoms, more preferably an aliphatic acyl group having from 6 to 20 carbon atoms, particularly preferably a hexanoyl, octanoyl, decanoyl, dodecanoyl myristoyl, palmitoyl or stearoyl group), and $R^3$ is a hydrogen atom, (f) the combination wherein each of $R^3$ and $R^4$ is an aliphatic acyl group having from 3 to 25 carbon atoms (preferably an aliphatic acyl group having from 6 to 25 carbon atoms, more preferably an aliphatic acyl group having from 6 to 20 carbon atoms, particularly preferably a hexanoyl, octanoyl, decanoyl, dodecanoyl, myristoyl, palmitoyl or stearoyl group), and $R^2$ is a hydrogen atom, (g) the combination wherein each of $R^2$, $R^3$ and $R^4$ is an aliphatic acyl group having from 3 to 25 carbon atoms (preferably the aliphatic acyl group having from 6 to 25 carbon atoms, more preferably the aliphatic acyl group having from 6 to 20 carbon atoms, particularly preferably hexanoyl, octanoyl, decanoyl, dodecanoyl, myristoyl, palmitoyl and stearoyl groups), and (h) the combination wherein each of $R^2$, $R^3$ and $R^4$ is a hydrogen atom.

Of these combinations, the combination of (a) or (h) is preferred.

"The ester residue" of W includes, for example, "an alkyl group" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1-methylhexyl, 2-methylhexyl, 3-methylhexyl, 4 methylhexyl, 5-methylhexyl, 1-propylbutyl, 4,4-dimethylpentyl, octyl, 1-methylheptyl, 2-methylheptyl, 3-methylheptyl, 4-methylheptyl, 5-methylheptyl, 6-methylheptyl, 1-propylpentyl, 2-ethylhexyl, 5,5-diethylhexyl, nonyl, 3-methyloctyl, 4-methyloctyl, 5-methyloctyl, 6-methyloctyl, 1-propylhexyl, 2-ethylheptyl, 6,6-dimethylheptyl, decyl, 1-methylnonyl, 3-methylnonyl, 8-methylnonyl, 3-ethyloctyl, 3,7-dimethyloctyl, 7,7-dimethyloctyl, undecyl, 4,8-dimethylnonyl, dodecyl, tridecyl, tetradecyl, pentadecyl, 3,7,11-trimethyldodecyl, hexadecyl, 4,8,12-trimethyltridecyl, 1-methylpentadecyl, 14-methylpentadecyl, 13,13-dimethyltetradecyl, heptadecyl, 15-methylhexadecyl, octadecyl, 1-methylheptadecyl, nonadecyl, eicosyl, 3,7,11,15-tetramethylhexadecyl, heneicosyl, docosyl, tricosyl and tetracosyl groups; "an alkenyl group" such as ethenyl, 1-propenyl, 2-propenyl, 1-methyl-2-propenyl, 1-methyl-1-propenyl, 2-methyl-1- propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl4-pentenyl, 2-methyl-4pentenyl, 1-hexenyl, 2-hexenyl, 3-hexenyl, 4-hexenyl and 5-hexenyl; "an alkynyl group" such as ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3 -butynyl, 2-methyl-3-butynyl, 1-ethyl-3-butynyl, 2-pentynyl, 1-methyl-2-pentynyl, 2-methyl-2-pentynyl, 3-pentynyl, 1-methyl-3-pentynyl, 2-methyl-3-pentynyl, 4-pentynyl, 1-methyl-4-pentynyl, 2-methyl4-pentynyl, 2-hexynyl, 3-hexynyl, 4-hexynyl and 5-hexynyl; "a halogeno lower alkyl group" such as trifluoromethyl, trichloromethyl difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl and 2,2-dibromoethyl; "a hydroxy lower alkyl group" such as 2-hydroxyethyl, 2,3-dihydroxypropyl, 3-hydroxypropyl, 3,4-dihydroxybutyl and 4-hydroxybutyl; "an aliphatic acyl lower alkyl group" such as acetylmethyl; "a lower alkyl group substituted with from 1 to 3 aryls" such as benzyl, phenethyl, 3-phenylpropyl, α-naphthylmethyl, β-naphthylmethyl, diphenylmethyl, triphenylmethyl, 6-phenylhexyl, α-naphthyldiphenylmethyl and 9-anthrylmethyl; "an aralkyl group of which the aryl ring is substituted with lower alkyl, lower alkoxy, nitro, halogen, cyano or alkoxycarbonyl" such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, bis(2-nitrophenyl)methyl, piperonyl and 4-methoxycarbonylbenzyl; "a tri(alkyl and/or phenyl)silyl group" such as trimethylsilyl, triethylsilyl, isopropyldimethylsilyl, tert-butyldimethylsilyl, methyldiisopropylsilyl, methyldi-tert-butylsilyl, triisopropylsilyl, methyldiphenylsilyl, isopropyldiphenylsilyl, butyldiphenylsilyl and phenyldiisopropylsilyl; "a protecting group which is cleavable according to a biological method such as hydrolysis in a living body", that is, an ester which produces a free acid or a salt thereof by being hydrolized in a human body, for example, "a lower alkoxy lower alkyl group" such as methoxymethyl, 1-ethoxyethyl, 1-methyl-1-methoxyethyl, 1-(isopropoxy) ethyl, 2-methoxyethyl, 2-ethoxyethyl, 1,1-dimethyl-1-methoxymethyl, ethoxymethyl, n-propoxymethyl, isopropoxymethyl, n-butoxymethyl and tert-butoxymethyl; "a lower alkoxylated lower alkoxy lower alkyl group" such as 2-methoxyethoxymethyl; "an aryloxy lower alkyl group" such as phenoxymethyl; "a halogenated lower alkoxy lower alkyl group" such as 2,2,2-trichloroethoxymethyl and bis(2-chloroethoxy)methyl; "a lower alkoxycarbonyl lower alkyl group" such as methoxycarbonylmethyl; "a cyano lower alkyl group" such as cyanomethyl and 2-cyanoethyl; "a lower alkylthiomethyl group" such as methylthiomethyl and ethylthiomethyl; "an arylthiomethyl group" such as phenylthiomethyl and naphthylthiomethyl; "a lower alkylsulfonyl lower alkyl group which may be substituted with halogen" such as 2-methanesulfonylethyl and 2-trifluoromethanesulfonylethyl; "an arylsulfonyl lower alkyl group" such as 2-benzenesulfonylethyl and 2-toluenesulfonylethyl; "an aliphatic acyloxy lower alkyl group" such as formyloxymethyl, acetoxymethyl, propionyloxymethyl, butyryloxymethyl, pivaloyloxymethyl valeryloxymethyl isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl and 1-pivaloyloxyhexyl; "a cycloalkylcarbonyloxy lower alkyl group" such as cyclopentanoyloxymethyl, cyclohexanoyloxymethyl, 1-cyclopentanoyloxyethyl, 1-cyclohexanoyloxyethyl, 1-cyclopentanoyloxypropyl, 1-cyclohexanoyloxypropyl, 1-cyclopentanoyloxybutyl and 1-cyclohexanoyloxybutyl; "an aromatic acyloxy lower alkyl group" such as benzoyloxymethyl; "an (alkoxycarbonyloxy) alkyl group" such as methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cyclohexyloxycarbonyloxymethyl, cyclohexyloxycarbonyloxy(cyclohexyl)methyl, 1methoxycarbonyloxy)ethyl, 1-(ethoxycarbonyloxy)ethyl, 1-propoxycarbonyloxymethyl, 1-(isopropoxycarbonyloxy) ethyl, 1-butoxycarbonyloxyethyl, 1-isobutoxycarbonyloxyethyl, 1-(tert-butoxycarbonyloxy) ethyl, 1-pentyloxycarbonyloxyethyl, 1-hexyloxycarbonyloxyethyl, 1-cyclopentyloxycarbonyloxyethyl, 1-cyclopentyloxycarbonyloxypropyl, 1-cyclohexyloxycarbonyloxypropyl, 1-cyclopentyloxycarbonyloxybutyl, 1-cyclohexyloxycarbonyloxybutyl, 1(cyclohexyloxycarbonyloxy)ethyl, 1-(ethoxycarbonyloxy) propyl, 2-methoxycarbonyloxyethyl, 2-ethoxycarbonyloxyethyl, 2-propoxycarbonyloxyethyl, 2-isopropoxycarbonyloxyethyl, 2-butoxycarbonyloxyethyl, 2-isobutoxycarbonyloxyethyl, 2-pentyloxycarbonyloxyethyl, 2-hexyloxycarbonyloxyethyl, 1-methoxycarbonyloxypropyl, 1-ethoxycarbonyloxypropyl, 1-propoxycarbonyloxypropyl, 1-isopropoxycarbonyloxypropyl, 1-butoxycarbonyloxypropyl, 1-isobutoxycarbonyloxypropyl, 1-pentyloxycarbonyloxypropyl, 1-hexyloxycarbonyloxypropyl, 1-methoxycarbonyloxybutyl, 1-ethoxycarbonyloxybutyl, 1-propoxycarbonyloxybutyl, 1-isopropoxycarbonyloxybutyl, 1-butoxycarbonyloxybutyl, 1-isobutoxycarbonyloxybutyl, 1-methoxycarbonyloxypentyl, 1-ethoxycarbonyloxypentyl, 1-methoxycarbonyloxyhexyl and 1-ethoxycarbonyloxyhexyl; "an oxodioxolenylmethyl group" such as (5-phenyl-2-oxo-1,3-dioxolen-4-yl)methyl, [5-(4-methylphenyl)-2-oxo-1,3-dioxolen-4 yl]methyl, [5-(4-methoxyphenyl)-2-oxo-1,3-dioxolen-4-yl]methyl, [5-(4- fluorophenyl)-2-oxo-1,3-dioxolen 4yl]methyl, [5-(4chlorophenyl)-2-oxo-1,3-dioxolen4-yl]methyl, (2-oxo-1,3-dioxolen4-yl)methyl, (5-methyl-2-oxo-1,3-dioxolen4yl)methyl, (5-ethyl-2-oxo-1,3-dioxolen4yl)methyl, (5-propyl-2-oxo-1,3-dioxolen4-yl)methyl, (5-isopropyl-2-oxo-1,3-dioxolen4-yl)methyl and (5-butyl-2-oxo-1,3-dioxolen4-yl)methyl; "a phthalidyl group" such as phthalidyl, dimethylphthalidyl and dimethoxyphthalidyl; "an aryl group" such as phenyl and indanyl; and "a carboxyalkyl group" such as carboxymethyl, preferably "an alkyl group", more preferably an alkyl group having from 1 to 18 carbon atoms.

In the case where at least one of $R^2$, $R^3$ and $R^4$ is an aliphatic acyl group having from 3 to 25 carbon atoms, "the ester residue" of W is preferably an alkyl group having from 1 to 18 carbon atoms. In this case, W is, as a whole, preferably a hydrogen atom or an alkyl group having from 1 to 18 carbon atoms, more preferably a hydrogen atom.

In the case where each of $R^2$, $R^3$ and $R^4$ is a hydrogen atom, "the ester residue" of W is preferably an alkyl group having from 1 to 18 carbon atoms, more preferably an alkyl group having from 6 to 18 carbon atoms. In this case, W is, as a whole, preferably an ester residue, more preferably an alkyl group having from 6 to 18 carbon atoms.

"The pharmacologically acceptable salt thereof" includes alkali metal salts such as salts of sodium, potassium and lithium, alkali earth metal salts such as salts of calcium and magnesium, metal salts such as salts of aluminium, iron, zinc, copper, nickel and cobalt; inorganic amine salts such as ammonium salts, organic amine salts such as salts of t-octylamine, dibenzylamine, morpholine, glucosamine, phenylglycinealkyl ester, ethylenediamine, N-methylglucamine, guanidine, diethylamine, triethylamine, dicyclohexylamine, N,N'-dibenzylethylenediamine, chloroprocaine, procaine, diethanolamine, N-benzylphenethylamine, piperazine, tetra methylammonium and tris(hydroxymethyl)aminomethane; halogenated hydroacid salts such as hydrofluoride, hydrochloride, hydrobromide and hydroiodide, inorganic acid salts such as nitrate, perchlorate, sulfate and phosphate; organic acid salts including lower alkanesulfonates such as methanesulfonate, trifluoromethanesulfonate and ethanesulfonate, arylsulfonates such as benzenesulfonate and p-toluenesulfonate, acetate, trifluoroacetate, malate, fumarate, succinate, citrate, tartrate, oxalate and maleate; and amino acid salts such as glycine salt, lysine salt, arginine salt, ornithine salt, glutamate and aspartate, preferably alkali metal salts such as sodium, potassium and lithium salts, and organic acid salts such as acetate and trifluoroacetate, and inorganic acid salts such as hydrochloride and sulfate.

Of the compounds of the present invention, the preferable one includes the following:

(1) compounds in which $R^1$ is a methyl group which may be substituted with a fluorine atom,
(2) compounds in which $R^1$ is a methyl, monofluoromethyl or difluoromethyl group,
(3) compounds in which $R^1$ is a methyl group,
(4) compounds in which $R^2$ is a hydrogen atom or an aliphatic acyl group having from 6 to 25 carbon atoms,
(5) compounds in which $R^2$ is a hydrogen atom or an aliphatic acyl group having from 6 to 20 carbon atoms,
(6) compounds in which $R^2$ is a hydrogen atom, or a hexanoyl, octanoyl, decanoyl, dodecanoyl, myristoyl, palmitoyl or stearoyl group,
(7) compounds in which $R^3$ is a hydrogen atom or an aliphatic acyl group having from 6 to 25 carbon atoms,
(8) compounds in which $R^3$ is a hydrogen atom or an aliphatic acyl group having from 6 to 20 carbon atoms,
(9) compounds in which $R^3$ is a hydrogen atom, or a hexanoyl octanoyl, decanoyl, dodecanoyl, myristoyl, palmitoyl or stearoyl group,
(10) compounds in which $R^4$ is a hydrogen atom or an aliphatic acyl group having from 6 to 25 carbon atoms,
(11) compounds in which $R^4$ is a hydrogen atom or an aliphatic acyl group having from 6 to 20 carbon atoms,
(12) compounds in which $R^4$ is a hydrogen atom, or a hexanoyl, octanoyl, decanoyl, dodecanoyl, myristoyl, palmitoyl or stearoyl group,
(13) compounds in which $R^2$ is an aliphatic acyl group having from 3 to 25 carbon atoms, and each of $R^3$ and $R^4$ is a hydrogen atom,
(14) compounds in which $R^2$ is an aliphatic acyl group having from 6 to 25 carbon atoms, and each of $R^3$ and $R^4$ is a hydrogen atom,
(15) compounds in which $R^2$ is an aliphatic acyl group having from 6 to 20 carbon atoms, and each of $R^3$ and $R^4$ is a hydrogen atom.
(16) compounds in which $R^2$ is a hexanoyl, octanoyl, decanoyl, dodecanoyl, myristoyl, palmitoyl or stearoyl group, and each of $R^3$ and $R^4$ is a hydrogen atom,
(17) compounds in which W is a hydrogen atom or an alkyl group having from 1 to 18 carbon atoms,
(18) compounds in which W is a hydrogen atom,
(19) compounds in which W is an ester residue,
(20) compounds in which W is an alkyl group having from 6 to 18 carbon atoms.

Further, the compounds obtained by combining the substituents $R^1$, $R^2$, $R^3$, $R^4$ and W selected in the compounds of the above (1) to (20) are more preferable and includes, for example, the following compounds.

(21) compounds in which each of $R^2$, $R^3$ and $R^4$ is a hydrogen atom, and W is ana ester residue,
(22) compounds in which each of $R^2$, $R^3$ and $R^4$ is a hydrogen atom, and W is an alkyl group having from 6 to 18 carbon atoms,
(23) compounds in which $R^1$ is a methyl group which may be substituted with a fluorine atom, $R^2$ is an aliphatic acyl group having from 3 to 25 carbon atoms, each of $R^3$ and $R^4$ is a hydrogen atom, and W is a hydrogen atom or an ester residue,
(24) compounds in which $R^1$ is a methyl group, $R^2$ is an aliphatic acyl group having from 6 to 25 carbon atoms, each of $R^3$ and $R^4$ is a hydrogen atom, and W is a hydrogen atom or an alkyl group having from 1 to 18 carbon atoms,
(25) compounds in which $R^1$ is a methyl group, $R^2$ is an aliphatic acyl group having from 6 to 20 carbon atoms, and each of $R^3$, $R^4$ and W is a hydrogen atom,
(26) compounds in which $R^1$ is a methyl group which may be substituted with a fluorine atom, each of $R^2$, $R^3$ and $R^4$ is a hydrogen atom, and W is an ester residue, and
(27) compounds in which $R^1$ is a methyl group, each of $R^2$, $R^3$ and $R^4$ is a hydrogen atom, and W is an alkyl group having from 6 to 18 carbon atoms.

In the following, the compounds of the present invention are exemplified but the present invention is not limited to these.

TABLE 1'

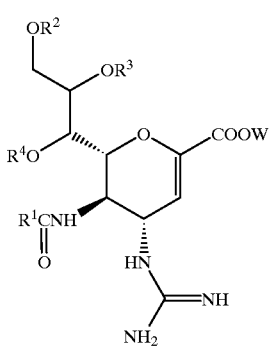

| No. | R¹ | R² | R³ | R⁴ | W |
|---|---|---|---|---|---|
| 1' | $CH_3$ | H | H | H | H |
| 2' | $CH_3$ | H | H | $CH_3CO$ | H |
| 3' | $CH_3$ | H | H | $CH_3(CH_2)_5CO$ | H |
| 4' | $CH_3$ | H | H | $CH_3(CH_2)_{10}CO$ | H |
| 5' | $CH_3$ | H | H | $CH_3(CH_2)_{13}CO$ | H |
| 6' | $CH_3$ | H | H | $CH_3(CH_2)_{15}CO$ | H |
| 7' | $CH_3$ | H | H | $CH_3(CH_2)_{17}CO$ | H |
| 8' | $CH_3$ | H | H | $CH_3(CH_2)_{21}CO$ | H |
| 9' | $CH_3$ | H | $CH_3CO$ | H | H |
| 10' | $CH_3$ | H | $CH_3CH_2CO$ | H | H |
| 11' | $CH_3$ | H | $CH_3(CH_2)_2CO$ | H | H |
| 12' | $CH_3$ | H | $CH_3(CH_2)_3CO$ | H | H |
| 13' | $CH_3$ | H | $CH_3(CH_2)_4CO$ | H | H |
| 14' | $CH_3$ | H | $CH_3(CH_2)_5CO$ | H | H |
| 15' | $CH_3$ | H | $CH_3(CH_2)_6CO$ | H | H |
| 16' | $CH_3$ | H | $CH_3(CH_2)_8CO$ | H | H |
| 17' | $CH_3$ | H | $CH_3(CH_2)_{10}CO$ | H | H |
| 18' | $CH_3$ | H | $CH_3(CH_2)_{12}CO$ | H | H |
| 19' | $CH_3$ | H | $CH_3(CH_2)_{14}CO$ | H | H |
| 20' | $CH_3$ | H | $CH_3(CH_2)_{16}CO$ | H | H |
| 21' | $CH_3$ | H | $CH_3(CH_2)_{18}CO$ | H | H |
| 22' | $CH_3$ | H | $CH_3(CH_2)_{20}CO$ | H | H |
| 23' | $CH_3$ | H | $CH_3(CH_2)_{22}CO$ | H | H |
| 24' | $CH_3$ | H | $CH_3(CH_2)_4CO$ | $CH_3CO$ | H |
| 25' | $CH_3$ | H | $CH_3(CH_2)_4CO$ | $CH_3(CH_2)_5CO$ | H |
| 26' | $CH_3$ | H | $CH_3(CH_2)_4CO$ | $CH_3(CH_2)_{10}CO$ | H |
| 27' | $CH_3$ | H | $CH_3(CH_2)_4CO$ | $CH_3(CH_2)_{13}CO$ | H |
| 28' | $CH_3$ | H | $CH_3(CH_2)_{12}CO$ | $CH_3CO$ | H |
| 29' | $CH_3$ | H | $CH_3(CH_2)_{12}CO$ | $CH_3(CH_2)_5CO$ | H |
| 30' | $CH_3$ | H | $CH_3(CH_2)_{12}CO$ | $CH_3(CH_2)_{10}CO$ | H |
| 31' | $CH_3$ | H | $CH_3(CH_2)_{12}CO$ | $CH_3(CH_2)_{13}CO$ | H |
| 32' | $CH_3$ | $CH_3CO$ | H | H | H |
| 33' | $CH_3$ | $CH_3CH_2CO$ | H | H | H |
| 34' | $CH_3$ | $CH_3(CH_2)_2CO$ | H | H | H |
| 35' | $CH_3$ | $CH_3(CH_2)_3CO$ | H | H | H |
| 36' | $CH_3$ | $CH_3(CH_2)_4CO$ | H | H | H |
| 37' | $CH_3$ | $CH_3(CH_2)_5CO$ | H | H | H |
| 38' | $CH_3$ | $CH_3(CH_2)_6CO$ | H | H | H |
| 38a' | $CH_3$ | $CH_3(CH_2)_7CO$ | H | H | H |
| 39' | $CH_3$ | $CH_3(CH_2)_8CO$ | H | H | H |
| 39a' | $CH_3$ | $CH_3(CH_2)_9CO$ | H | H | H |
| 40' | $CH_3$ | $CH_3(CH_2)_{10}CO$ | H | H | H |
| 40a' | $CH_3$ | $CH_3(CH_2)_{11}CO$ | H | H | H |
| 41' | $CH_3$ | $CH_3(CH_2)_{12}CO$ | H | H | H |
| 41a' | $CH_3$ | $CH_3(CH_2)_{13}CO$ | H | H | H |
| 42' | $CH_3$ | $CH_3(CH_2)_{14}CO$ | H | H | H |
| 42a' | $CH_3$ | $CH_3(CH_2)_{15}CO$ | H | H | H |
| 43' | $CH_3$ | $CH_3(CH_2)_{16}CO$ | H | H | H |
| 43a' | $CH_3$ | $CH_3(CH_2)_{17}CO$ | H | H | H |
| 44' | $CH_3$ | $CH_3(CH_2)_{18}CO$ | H | H | H |
| 44a' | $CH_3$ | $CH_3(CH_2)_{19}CO$ | H | H | H |
| 45' | $CH_3$ | $CH_3(CH_2)_{20}CO$ | H | H | H |
| 45a' | $CH_3$ | $CH_3(CH_2)_{21}CO$ | H | H | H |
| 45b' | $CH_3$ | $CH_3(CH_2)_{22}CO$ | H | H | H |
| 45c' | $CH_3$ | $CH_3(CH_2)_{23}CO$ | H | H | H |
| 46' | $CH_3$ | $CH_3(CH_2)_4CO$ | H | $CH_3CO$ | H |
| 47' | $CH_3$ | $CH_3(CH_2)_4CO$ | H | $CH_3(CH_2)_5CO$ | H |
| 48' | $CH_3$ | $CH_3(CH_2)_4CO$ | H | $CH_3(CH_2)_{10}CO$ | H |
| 49' | $CH_3$ | $CH_3(CH_2)_4CO$ | H | $CH_3(CH_2)_{13}CO$ | H |

TABLE 1'-continued

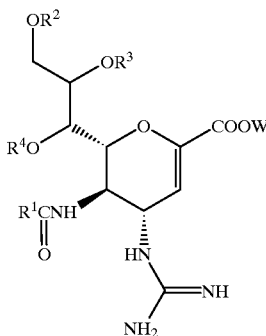

| No. | R¹ | R² | R³ | R⁴ | W |
|---|---|---|---|---|---|
| 50' | $CH_3$ | $CH_3(CH_2)_{12}CO$ | H | $CH_3CO$ | H |
| 51' | $CH_3$ | $CH_3(CH_2)_{12}CO$ | H | $CH_3(CH_2)_5CO$ | H |
| 52' | $CH_3$ | $CH_3(CH_2)_{12}CO$ | H | $CH_3(CH_2)_{10}CO$ | H |
| 53' | $CH_3$ | $CH_3(CH_2)_{12}CO$ | H | $CH_3(CH_2)_{13}CO$ | H |
| 54' | $CH_3$ | $CH_3CO$ | $CH_3CO$ | H | H |
| 55' | $CH_3$ | $CH_3CH_2CO$ | $CH_3CH_2CO$ | H | H |
| 56' | $CH_3$ | $CH_3(CH_2)_2CO$ | $CH_3(CH_2)_2CO$ | H | H |
| 57' | $CH_3$ | $CH_3(CH_2)_3CO$ | $CH_3(CH_2)_3CO$ | H | H |
| 58' | $CH_3$ | $CH_3(CH_2)_4CO$ | $CH_3(CH_2)_4CO$ | H | H |
| 59' | $CH_3$ | $CH_3(CH_2)_5CO$ | $CH_3(CH_2)_5CO$ | H | H |
| 60' | $CH_3$ | $CH_3(CH_2)_6CO$ | $CH_3(CH_2)_6CO$ | H | H |
| 61' | $CH_3$ | $CH_3(CH_2)_8CO$ | $CH_3(CH_2)_8CO$ | H | H |
| 62' | $CH_3$ | $CH_3(CH_2)_{10}CO$ | $CH_3(CH_2)_{10}CO$ | H | H |
| 63' | $CH_3$ | $CH_3(CH_2)_{12}CO$ | $CH_3(CH_2)_{12}CO$ | H | H |
| 64' | $CH_3$ | $CH_3(CH_2)_{14}CO$ | $CH_3(CH_2)_{14}CO$ | H | H |
| 65' | $CH_3$ | $CH_3(CH_2)_{16}CO$ | $CH_3(CH_2)_{16}CO$ | H | H |
| 66' | $CH_3$ | $CH_3(CH_2)_{18}CO$ | $CH_3(CH_2)_{18}CO$ | H | H |
| 67' | $CH_3$ | $CH_3(CH_2)_{20}CO$ | $CH_3(CH_2)_{20}CO$ | H | H |
| 68' | $CH_3$ | $CH_3(CH_2)_{22}CO$ | $CH_3(CH_2)_{22}CO$ | H | H |
| 69' | $CH_3$ | $CH_3(CH_2)_{12}CO$ | $CH_3(CH_2)_6CO$ | H | H |
| 70' | $CH_3$ | $CH_3(CH_2)_4CO$ | $CH_3(CH_2)_{12}CO$ | H | H |
| 71' | $CH_3$ | $CH_3(CH_2)_4CO$ | $CH_3(CH_2)_4CO$ | $CH_3CO$ | H |
| 72' | $CH_3$ | $CH_3(CH_2)_4CO$ | $CH_3(CH_2)_4CO$ | $CH_3(CH_2)_5CO$ | H |
| 73' | $CH_3$ | $CH_3(CH_2)_4CO$ | $CH_3(CH_2)_4CO$ | $CH_3(CH_2)_{10}CO$ | H |
| 74' | $CH_3$ | $CH_3(CH_2)_4CO$ | $CH_3(CH_2)_4CO$ | $CH_3(CH_2)_{13}CO$ | H |
| 75' | $CH_3$ | $CH_3(CH_2)_{12}CO$ | $CH_3(CH_2)_{12}CO$ | $CH_3CO$ | H |
| 76' | $CH_3$ | $CH_3(CH_2)_{12}CO$ | $CH_3(CH_2)_{12}CO$ | $CH_3(CH_2)_5CO$ | H |
| 77' | $CH_3$ | $CH_3(CH_2)_{12}CO$ | $CH_3(CH_2)_{12}CO$ | $CH_3(CH_2)_{10}CO$ | H |
| 78' | $CH_3$ | $CH_3(CH_2)_{12}CO$ | $CH_3(CH_2)_{12}CO$ | $CH_3(CH_2)_{13}CO$ | H |
| 79' | $CH_3$ | $CH_3(CH_2)_4CO$ | $CH_3(CH_2)_{12}CO$ | $CH_3COO$ | H |
| 80' | $CH_3$ | $CH_3(CH_2)_4CO$ | $CH_3(CH_2)_{12}CO$ | $CH_3(CH_2)_5CO$ | H |
| 81' | $CH_3$ | $CH_3(CH_2)_4CO$ | $CH_3(CH_2)_{12}CO$ | $CH_3(CH_2)_{10}CO$ | H |
| 82' | $CH_3$ | $CH_3(CH_2)_4CO$ | $CH_3(CH_2)_{12}CO$ | $CH_3(CH_2)_{13}CO$ | H |
| 83' | $CH_3$ | $CH_3(CH_2)_{12}CO$ | $CH_3(CH_2)_4CO$ | $CH_3CO$ | H |
| 84' | $CH_3$ | $CH_3(CH_2)_{12}CO$ | $CH_3(CH_2)_4CO$ | $CH_3(CH_2)_5CO$ | H |
| 85' | $CH_3$ | $CH_3(CH_2)_{12}CO$ | $CH_3(CH_2)_4CO$ | $CH_3(CH_2)_{10}CO$ | H |
| 86' | $CH_3$ | $CH_3(CH_2)_{12}CO$ | $CH_3(CH_2)_4CO$ | $CH_3(CH_2)_{13}CO$ | H |
| 87' | $CH_3$ | H | H | H | $(CH_2)_5CH_3$ |
| 87a' | $CH_3$ | H | H | H | $(CH_2)_6CH_3$ |
| 87b' | $CH_3$ | H | H | H | $(CH_2)_7CH_3$ |
| 87c' | $CH_3$ | H | H | H | $(CH_2)_8CH_3$ |
| 87d' | $CH_3$ | H | H | H | $(CH_2)_9CH_3$ |
| 87e' | $CH_3$ | H | H | H | $(CH_2)_{10}CH_3$ |
| 87f' | $CH_3$ | H | H | H | $(CH_2)_{11}CH_3$ |
| 87g' | $CH_3$ | H | H | H | $(CH_2)_{12}CH_3$ |
| 88' | $CH_3$ | H | H | H | $(CH_2)_{13}CH_3$ |
| 88a' | $CH_3$ | H | H | H | $(CH_2)_{14}CH_3$ |
| 89' | $CH_3$ | H | H | H | $(CH_2)_{15}CH_3$ |
| 90' | $CH_3$ | H | H | H | $(CH_2)_{16}CH_3$ |
| 91' | $CH_3$ | H | H | H | $(CH_2)_{17}CH_3$ |
| 92' | $CH_3$ | H | H | H | $(CH_2)_{18}CH_3$ |
| 92a' | $CH_3$ | H | H | H | $(CH_2)_{19}CH_3$ |
| 93' | $CH_3$ | H | H | H | $(CH_2)_{20}CH_3$ |
| 94' | $CH_3$ | H | H | H | $(CH_2)_{21}CH_3$ |
| 94a' | $CH_3$ | H | H | H | $(CH_2)_{22}CH_3$ |
| 94b' | $CH_3$ | H | H | H | $(CH_2)_{23}CH_3$ |
| 95' | $CH_3$ | H | H | $CH_3(CH_2)_5CO$ | $(CH_2)_5CH_3$ |
| 96' | $CH_3$ | H | H | $CH_3(CH_2)_{10}CO$ | $(CH_2)_{13}CH_3$ |
| 97' | $CH_3$ | H | H | $CH_3(CH_2)_{13}CO$ | $(CH_2)_5CH_3$ |

TABLE 1'-continued $$\text{Structure with } OR^2, OR^3, R^4O, R^1CNH, COOW, \text{guanidino group}$$

| No. | $R^1$ | $R^2$ | $R^3$ | $R^4$ | W |
|---|---|---|---|---|---|
| 98' | $CH_3$ | H | H | $CH_3(CH_2)_{15}CO$ | $(CH_2)_{13}CH_3$ |
| 99' | $CH_3$ | H | H | $CH_3(CH_2)_{17}CO$ | $(CH_2)_5CH_3$ |
| 100' | $CH_3$ | H | H | $CH_3(CH_2)_{21}CO$ | $(CH_2)_{13}CH_3$ |
| 101' | $CH_3$ | H | $CH_3CO$ | H | $(CH_2)_5CH_3$ |
| 102' | $CH_3$ | H | $CH_3CH_2CO$ | H | $(CH_2)_{13}CH_3$ |
| 103' | $CH_3$ | H | $CH_3(CH_2)_2CO$ | H | $(CH_2)_5CH_3$ |
| 104' | $CH_3$ | H | $CH_3(CH_2)_3CO$ | H | $(CH_2)_{13}CH_3$ |
| 105' | $CH_3$ | H | $CH_3(CH_2)_4CO$ | H | $(CH_2)_5CH_3$ |
| 106' | $CH_3$ | H | $CH_3(CH_2)_5CO$ | H | $(CH_2)_{13}CH_3$ |
| 107' | $CH_3$ | H | $CH_3(CH_2)_6CO$ | H | $(CH_2)_5CH_3$ |
| 108' | $CH_3$ | H | $CH_3(CH_2)_8CO$ | H | $(CH_2)_{13}CH_3$ |
| 109' | $CH_3$ | H | $CH_3(CH_2)_{10}CO$ | H | $(CH_2)_5CH_3$ |
| 110' | $CH_3$ | H | $CH_3(CH_2)_{12}CO$ | H | $(CH_2)_{13}CH_3$ |
| 111' | $CH_3$ | H | $CH_3(CH_2)_{14}CO$ | H | $(CH_2)_5CH_3$ |
| 112' | $CH_3$ | H | $CH_3(CH_2)_{16}CO$ | H | $(CH_2)_{13}CH_3$ |
| 113' | $CH_3$ | H | $CH_3(CH_2)_{18}CO$ | H | $(CH_2)_5CH_3$ |
| 114' | $CH_3$ | H | $CH_3(CH_2)_{20}CO$ | H | $(CH_2)_{13}CH_3$ |
| 115' | $CH_3$ | H | $CH_3(CH_2)_{22}CO$ | H | $(CH_2)_5CH_3$ |
| 116' | $CH_3$ | H | $CH_3(CH_2)_4CO$ | $CH_3CO$ | $(CH_2)_{13}CH_3$ |
| 117' | $CH_3$ | H | $CH_3(CH_2)_4CO$ | $CH_3(CH_2)_5CO$ | $(CH_2)_5CH_3$ |
| 118' | $CH_3$ | H | $CH_3(CH_2)_4CO$ | $CH_3(CH_2)_{10}CO$ | $(CH_2)_{13}CH_3$ |
| 119' | $CH_3$ | H | $CH_3(CH_2)_4CO$ | $CH_3(CH_2)_{13}CO$ | $(CH_2)_5CH_3$ |
| 120' | $CH_3$ | H | $CH_3(CH_2)_{12}CO$ | $CH_3CO$ | $(CH_2)_{13}CH_3$ |
| 121' | $CH_3$ | H | $CH_3(CH_2)_{12}CO$ | $CH_3(CH_2)_5CO$ | $(CH_2)_5CH_3$ |
| 122' | $CH_3$ | H | $CH_3(CH_2)_{12}CO$ | $CH_3(CH_2)_{10}CO$ | $(CH_2)_{13}CH_3$ |
| 123' | $CH_3$ | H | $CH_3(CH_2)_{12}CO$ | $CH_3(CH_2)_{13}CO$ | $(CH_2)_5CH_3$ |
| 124' | $CH_3$ | $CH_3CO$ | H | H | $(CH_2)_{13}CH_3$ |
| 125' | $CH_3$ | $CH_3CH_2CO$ | H | H | $(CH_2)_5CH_3$ |
| 126' | $CH_3$ | $CH_3(CH_2)_2CO$ | H | H | $(CH_2)_{13}CH_3$ |
| 127' | $CH_3$ | $CH_3(CH_2)_3CO$ | H | H | $(CH_2)_5CH_3$ |
| 128' | $CH_3$ | $CH_3(CH_2)_4CO$ | H | H | $(CH_2)_{13}CH_3$ |
| 129' | $CH_3$ | $CH_3(CH_2)_5CO$ | H | H | $(CH_2)_5CH_3$ |
| 130' | $CH_3$ | $CH_3(CH_2)_6CO$ | H | H | $(CH_2)_{13}CH_3$ |
| 131' | $CH_3$ | $CH_3(CH_2)_8CO$ | H | H | $(CH_2)_5CH_3$ |
| 132' | $CH_3$ | $CH_3(CH_2)_{10}CO$ | H | H | $(CH_2)_{13}CH_3$ |
| 133' | $CH_3$ | $CH_3(CH_2)_{12}CO$ | H | H | $(CH_2)_5CH_3$ |
| 134' | $CH_3$ | $CH_3(CH_2)_{14}CO$ | H | H | $(CH_2)_{13}CH_3$ |
| 135' | $CH_3$ | $CH_3(CH_2)_{16}CO$ | H | H | $(CH_2)_5CH_3$ |
| 136' | $CH_3$ | $CH_3(CH_2)_{18}CO$ | H | H | $(CH_2)_{13}CH_3$ |
| 137' | $CH_3$ | $CH_3(CH_2)_{20}CO$ | H | H | $(CH_2)_5CH_3$ |
| 138' | $CH_3$ | $CH_3(CH_2)_4CO$ | H | $CH_3CO$ | $(CH_2)_{13}CH_3$ |
| 139' | $CH_3$ | $CH_3(CH_2)_4CO$ | H | $CH_3(CH_2)_5CO$ | $(CH_2)_5CH_3$ |
| 140' | $CH_3$ | $CH_3(CH_2)_4CO$ | H | $CH_3(CH_2)_{10}CO$ | $(CH_2)_{13}CH_3$ |
| 141' | $CH_3$ | $CH_3(CH_2)_4CO$ | H | $CH_3(CH_2)_{13}CO$ | $(CH_2)_5CH_3$ |
| 142' | $CH_3$ | $CH_3(CH_2)_{12}CO$ | H | $CH_3CO$ | $(CH_2)_{13}CH_3$ |
| 143' | $CH_3$ | $CH_3(CH_2)_{12}CO$ | H | $CH_3(CH_2)_5CO$ | $(CH_2)_5CH_3$ |
| 144' | $CH_3$ | $CH_3(CH_2)_{12}CO$ | H | $CH_3(CH_2)_{10}CO$ | $(CH_2)_{13}CH_3$ |
| 145' | $CH_3$ | $CH_3(CH_2)_{12}CO$ | H | $CH_3(CH_2)_{13}CO$ | $(CH_2)_5CH_3$ |
| 146' | $CH_3$ | $CH_3CO$ | $CH_3CO$ | H | $(CH_2)_{13}CH_3$ |
| 147' | $CH_3$ | $CH_3CH_2CO$ | $CH_3CH_2CO$ | H | $CH_3$ |
| 148' | $CH_3$ | $CH_3(CH_2)_2CO$ | $CH_3(CH_2)_2CO$ | H | $(CH_2)_5CH_3$ |
| 149' | $CH_3$ | $CH_3(CH_2)_3CO$ | $CH_3(CH_2)_3CO$ | H | $(CH_2)_{10}CH_3$ |
| 150' | $CH_3$ | $CH_3(CH_2)_4CO$ | $CH_3(CH_2)_4CO$ | H | $(CH_2)_{13}CH_3$ |
| 151' | $CH_3$ | $CH_3(CH_2)_5CO$ | $CH_3(CH_2)_5CO$ | H | $(CH_2)_{15}CH_3$ |
| 152' | $CH_3$ | $CH_3(CH_2)_6CO$ | $CH_3(CH_2)_6CO$ | H | $(CH_2)_{17}CH_3$ |
| 153' | $CH_3$ | $CH_3(CH_2)_8CO$ | $CH_3(CH_2)_8CO$ | H | $(CH_2)_{21}CH_3$ |
| 154' | $CH_3$ | $CH_3(CH_2)_{10}CO$ | $CH_3(CH_2)_{10}CO$ | H | $CH_3$ |
| 155' | $CH_3$ | $CH_3(CH_2)_{12}CO$ | $CH_3(CH_2)_{12}CO$ | H | $(CH_2)_5CH_3$ |
| 156' | $CH_3$ | $CH_3(CH_2)_{14}CO$ | $CH_3(CH_2)_{14}CO$ | H | $(CH_2)_{10}CH_3$ |

TABLE 1'-continued

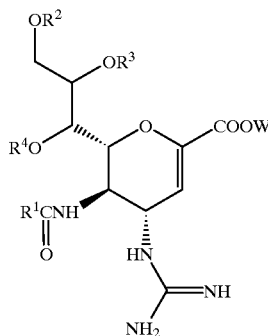

| No. | R¹ | R² | R³ | R⁴ | W |
|---|---|---|---|---|---|
| 157' | $CH_3$ | $CH_3(CH_2)_{16}CO$ | $CH_3(CH_2)_{16}CO$ | H | $(CH_2)_{13}CH_3$ |
| 158' | $CH_3$ | $CH_3(CH_2)_{18}CO$ | $CH_3(CH_2)_{18}CO$ | H | $(CH_2)_{15}CH_3$ |
| 159' | $CH_3$ | $CH_3(CH_2)_{20}CO$ | $CH_3(CH_2)_{20}CO$ | H | $(CH_2)_{17}CH_3$ |
| 160' | $CH_3$ | $CH_3(CH_2)_{22}CO$ | $CH_3(CH_2)_{22}CO$ | H | $(CH_2)_{21}CH_3$ |
| 161' | $CH_3$ | $CH_3(CH_2)_{12}CO$ | $CH_3(CH_2)_6CO$ | H | $CH_3$ |
| 162' | $CH_3$ | $CH_3(CH_2)_4CO$ | $CH_3(CH_2)_{12}CO$ | H | $(CH_2)_5CH_3$ |
| 163' | $CH_3$ | $CH_3(CH_2)_4CO$ | $CH_3(CH_2)_4CO$ | $CH_3CO$ | $(CH_2)_{10}CH_3$ |
| 164' | $CH_3$ | $CH_3(CH_2)_4CO$ | $CH_3(CH_2)_4CO$ | $CH_3(CH_2)_5CO$ | $(CH_2)_{13}CH_3$ |
| 165' | $CH_3$ | $CH_3(CH_2)_4CO$ | $CH_3(CH_2)_4CO$ | $CH_3(CH_2)_{10}CO$ | $(CH_2)_{15}CH_3$ |
| 166' | $CH_3$ | $CH_3(CH_2)_4CO$ | $CH_3(CH_2)_4CO$ | $CH_3(CH_2)_{13}CO$ | $(CH_2)_{17}CH_3$ |
| 167' | $CH_3$ | $CH_3(CH_2)_{12}CO$ | $CH_3(CH_2)_{12}CO$ | $CH_3CO$ | $(CH_2)_{21}CH_3$ |
| 168' | $CH_3$ | $CH_3(CH_2)_{12}CO$ | $CH_3(CH_2)_{12}CO$ | $CH_3(CH_2)_5CO$ | $CH_3$ |
| 169' | $CH_3$ | $CH_3(CH_2)_{12}CO$ | $CH_3(CH_2)_{12}CO$ | $CH_3(CH_2)_{10}CO$ | $(CH_2)_5CH_3$ |
| 170' | $CH_3$ | $CH_3(CH_2)_{12}CO$ | $CH_3(CH_2)_{12}CO$ | $CH_3(CH_2)_{13}CO$ | $(CH_2)_{10}CH_3$ |
| 171' | $CH_3$ | $CH_3(CH_2)_4CO$ | $CH_3(CH_2)_{12}CO$ | $CH_3COO$ | $(CH_2)_{13}CH_3$ |
| 172' | $CH_3$ | $CH_3(CH_2)_4CO$ | $CH_3(CH_2)_{12}CO$ | $CH_3(CH_2)_5CO$ | $(CH_2)_{15}CH_3$ |
| 173' | $CH_3$ | $CH_3(CH_2)_4CO$ | $CH_3(CH_2)_{12}CO$ | $CH_3(CH_2)_{10}CO$ | $(CH_2)_{17}CH_3$ |
| 174' | $CH_3$ | $CH_3(CH_2)_4CO$ | $CH_3(CH_2)_{12}CO$ | $CH_3(CH_2)_{13}CO$ | $(CH_2)_{21}CH_3$ |
| 175' | $CH_3$ | $CH_3(CH_2)_{12}CO$ | $CH_3(CH_2)_4CO$ | $CH_3CO$ | $CH_3$ |
| 176' | $CH_3$ | $CH_3(CH_2)_{12}CO$ | $CH_3(CH_2)_4CO$ | $CH_3(CH_2)_5CO$ | $(CH_2)_5CH_3$ |
| 177' | $CH_3$ | $CH_3(CH_2)_{12}CO$ | $CH_3(CH_2)_4CO$ | $CH_3(CH_2)_{10}CO$ | $(CH_2)_{10}CH_3$ |
| 178' | $CH_3$ | $CH_3(CH_2)_{12}CO$ | $CH_3(CH_2)_4CO$ | $CH_3(CH_2)_{13}CO$ | $(CH_2)_{13}CH_3$ |
| 179' | $CH_2F$ | H | H | H | H |
| 180' | $CH_2F$ | H | H | $CH_3CO$ | H |
| 181' | $CH_2F$ | H | H | $CH_3(CH_2)_5CO$ | H |
| 182' | $CH_2F$ | H | H | $CH_3(CH_2)_{10}CO$ | H |
| 183' | $CH_2F$ | H | H | $CH_3(CH_2)_{13}CO$ | H |
| 184' | $CH_2F$ | H | H | $CH_3(CH_2)_{15}CO$ | H |
| 185' | $CH_2F$ | H | H | $CH_3(CH_2)_{17}CO$ | H |
| 186' | $CH_2F$ | H | H | $CH_3(CH_2)_{21}CO$ | H |
| 187' | $CH_2F$ | H | $CH_3CO$ | H | H |
| 188' | $CH_2F$ | H | $CH_3CH_2CO$ | H | H |
| 189' | $CH_2F$ | H | $CH_3(CH_2)_2CO$ | H | H |
| 190' | $CH_2F$ | H | $CH_3(CH_2)_3CO$ | H | H |
| 191' | $CH_2F$ | H | $CH_3(CH_2)_4CO$ | H | H |
| 192' | $CH_2F$ | H | $CH_3(CH_2)_5CO$ | H | H |
| 193' | $CH_2F$ | H | $CH_3(CH_2)_6CO$ | H | H |
| 194' | $CH_2F$ | H | $CH_3(CH_2)_8CO$ | H | H |
| 195' | $CH_2F$ | H | $CH_3(CH_2)_{10}CO$ | H | H |
| 196' | $CH_2F$ | H | $CH_3(CH_2)_{12}CO$ | H | H |
| 197' | $CH_2F$ | H | $CH_3(CH_2)_{14}CO$ | H | H |
| 198' | $CH_2F$ | H | $CH_3(CH_2)_{16}CO$ | H | H |
| 199' | $CH_2F$ | H | $CH_3(CH_2)_{18}CO$ | H | H |
| 200' | $CH_2F$ | H | $CH_3(CH_2)_{20}CO$ | H | H |
| 201' | $CH_2F$ | H | $CH_3(CH_2)_{22}CO$ | H | H |
| 202' | $CH_2F$ | H | $CH_3(CH_2)_4CO$ | $CH_3CO$ | H |
| 203' | $CH_2F$ | H | $CH_3(CH_2)_4CO$ | $CH_3(CH_2)_5CO$ | H |
| 204' | $CH_2F$ | H | $CH_3(CH_2)_4CO$ | $CH_3(CH_2)_{10}CO$ | H |
| 205' | $CH_2F$ | H | $CH_3(CH_2)_4CO$ | $CH_3(CH_2)_{13}CO$ | H |
| 206' | $CH_2F$ | H | $CH_3(CH_2)_{12}CO$ | $CH_3CO$ | H |
| 207' | $CH_2F$ | H | $CH_3(CH_2)_{12}CO$ | $CH_3(CH_2)_5CO$ | H |
| 208' | $CH_2F$ | H | $CH_3(CH_2)_{12}CO$ | $CH_3(CH_2)_{10}CO$ | H |
| 209' | $CH_2F$ | H | $CH_3(CH_2)_{12}CO$ | $CH_3(CH_2)_{13}CO$ | H |
| 210' | $CH_2F$ | $CH_3CO$ | H | H | H |
| 211' | $CH_2F$ | $CH_3CH_2CO$ | H | H | H |
| 212' | $CH_2F$ | $CH_3(CH_2)_2CO$ | H | H | H |
| 213' | $CH_2F$ | $CH_3(CH_2)_3CO$ | H | H | H |
| 214' | $CH_2F$ | $CH_3(CH_2)_4CO$ | H | H | H |
| 215' | $CH_2F$ | $CH_3(CH_2)_5CO$ | H | H | H |

TABLE 1'-continued

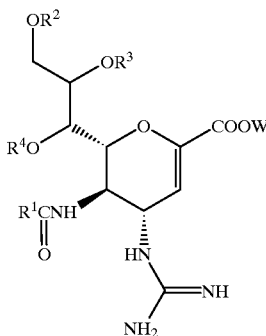

| No. | R¹ | R² | R³ | R⁴ | W |
|---|---|---|---|---|---|
| 216' | $CH_2F$ | $CH_3(CH_2)_6CO$ | H | H | H |
| 217' | $CH_2F$ | $CH_3(CH_2)_8CO$ | H | H | H |
| 218' | $CH_2F$ | $CH_3(CH_2)_{10}CO$ | H | H | H |
| 219' | $CH_2F$ | $CH_3(CH_2)_{12}CO$ | H | H | H |
| 220' | $CH_2F$ | $CH_3(CH_2)_{14}CO$ | H | H | H |
| 221' | $CH_2F$ | $CH_3(CH_2)_{16}CO$ | H | H | H |
| 222' | $CH_2F$ | $CH_3(CH_2)_{18}CO$ | H | H | H |
| 223' | $CH_2F$ | $CH_3(CH_2)_{20}CO$ | H | H | H |
| 224' | $CH_2F$ | $CH_3(CH_2)_4CO$ | H | $CH_3CO$ | H |
| 225' | $CH_2F$ | $CH_3(CH_2)_4CO$ | H | $CH_3(CH_2)_5CO$ | H |
| 226' | $CH_2F$ | $CH_3(CH_2)_4CO$ | H | $CH_3(CH_2)_{10}CO$ | H |
| 227' | $CH_2F$ | $CH_3(CH_2)_4CO$ | H | $CH_3(CH_2)_{13}CO$ | H |
| 228' | $CH_2F$ | $CH_3(CH_2)_{12}CO$ | H | $CH_3CO$ | H |
| 229' | $CH_2F$ | $CH_3(CH_2)_{12}CO$ | H | $CH_3(CH_2)_5CO$ | H |
| 230' | $CH_2F$ | $CH_3(CH_2)_{12}CO$ | H | $CH_3(CH_2)_{10}CO$ | H |
| 231' | $CH_2F$ | $CH_3(CH_2)_{12}CO$ | H | $CH_3(CH_2)_{13}CO$ | H |
| 232' | $CH_2F$ | $CH_3CO$ | $CH_3CO$ | H | H |
| 233' | $CH_2F$ | $CH_3CH_2CO$ | $CH_3CH_2CO$ | H | H |
| 234' | $CH_2F$ | $CH_3(CH_2)_2CO$ | $CH_3(CH_2)_2CO$ | H | H |
| 235' | $CH_2F$ | $CH_3(CH_2)_3CO$ | $CH_3(CH_2)_3CO$ | H | H |
| 236' | $CH_2F$ | $CH_3(CH_2)_4CO$ | $CH_3(CH_2)_4CO$ | H | H |
| 237' | $CH_2F$ | $CH_3(CH_2)_5CO$ | $CH_3(CH_2)_5CO$ | H | H |
| 238' | $CH_2F$ | $CH_3(CH_2)_6CO$ | $CH_3(CH_2)_6CO$ | H | H |
| 239' | $CH_2F$ | $CH_3(CH_2)_8CO$ | $CH_3(CH_2)_8CO$ | H | H |
| 240' | $CH_2F$ | $CH_3(CH_2)_{10}CO$ | $CH_3(CH_2)_{10}CO$ | H | H |
| 241' | $CH_2F$ | $CH_3(CH_2)_{12}CO$ | $CH_3(CH_2)_{12}CO$ | H | H |
| 242' | $CH_2F$ | $CH_3(CH_2)_{14}CO$ | $CH_3(CH_2)_{14}CO$ | H | H |
| 243' | $CH_2F$ | $CH_3(CH_2)_{16}CO$ | $CH_3(CH_2)_{16}CO$ | H | H |
| 244' | $CH_2F$ | $CH_3(CH_2)_{18}CO$ | $CH_3(CH_2)_{18}CO$ | H | H |
| 245' | $CH_2F$ | $CH_3(CH_2)_{20}CO$ | $CH_3(CH_2)_{20}CO$ | H | H |
| 246' | $CH_2F$ | $CH_3(CH_2)_{22}CO$ | $CH_3(CH_2)_{22}CO$ | H | H |
| 247' | $CH_2F$ | $CH_3(CH_2)_{12}CO$ | $CH_3(CH_2)_6CO$ | H | H |
| 248' | $CH_2F$ | $CH_3(CH_2)_4CO$ | $CH_3(CH_2)_{12}CO$ | H | H |
| 249' | $CH_2F$ | $CH_3(CH_2)_4CO$ | $CH_3(CH_2)_4CO$ | $CH_3CO$ | H |
| 250' | $CH_2F$ | $CH_3(CH_2)_4CO$ | $CH_3(CH_2)_4CO$ | $CH_3(CH_2)_5CO$ | H |
| 251' | $CH_2F$ | $CH_3(CH_2)_4CO$ | $CH_3(CH_2)_4CO$ | $CH_3(CH_2)_{10}CO$ | H |
| 252' | $CH_2F$ | $CH_3(CH_2)_4CO$ | $CH_3(CH_2)_4CO$ | $CH_3(CH_2)_{13}CO$ | H |
| 253' | $CH_2F$ | $CH_3(CH_2)_{12}CO$ | $CH_3(CH_2)_{12}CO$ | $CH_3CO$ | H |
| 254' | $CH_2F$ | $CH_3(CH_2)_{12}CO$ | $CH_3(CH_2)_{12}CO$ | $CH_3(CH_2)_5CO$ | H |
| 255' | $CH_2F$ | $CH_3(CH_2)_{12}CO$ | $CH_3(CH_2)_{12}CO$ | $CH_3(CH_2)_{10}CO$ | H |
| 256' | $CH_2F$ | $CH_3(CH_2)_{12}CO$ | $CH_3(CH_2)_{12}CO$ | $CH_3(CH_2)_{13}CO$ | H |
| 257' | $CH_2F$ | $CH_3(CH_2)_4CO$ | $CH_3(CH_2)_{12}CO$ | $CH_3CO$ | H |
| 258' | $CH_2F$ | $CH_3(CH_2)_4CO$ | $CH_3(CH_2)_{12}CO$ | $CH_3(CH_2)_5CO$ | H |
| 259' | $CH_2F$ | $CH_3(CH_2)_4CO$ | $CH_3(CH_2)_{12}CO$ | $CH_3(CH_2)_{10}CO$ | H |
| 260' | $CH_2F$ | $CH_3(CH_2)_4CO$ | $CH_3(CH_2)_{12}CO$ | $CH_3(CH_2)_{13}CO$ | H |
| 261' | $CH_2F$ | $CH_3(CH_2)_{12}CO$ | $CH_3(CH_2)_4CO$ | $CH_3CO$ | H |
| 262' | $CH_2F$ | $CH_3(CH_2)_{12}CO$ | $CH_3(CH_2)_4CO$ | $CH_3(CH_2)_5CO$ | H |
| 263' | $CH_2F$ | $CH_3(CH_2)_{12}CO$ | $CH_3(CH_2)_4CO$ | $CH_3(CH_2)_{10}CO$ | H |
| 264' | $CH_2F$ | $CH_3(CH_2)_{12}CO$ | $CH_3(CH_2)_4CO$ | $CH_3(CH_2)_{13}CO$ | H |
| 265' | $CH_2F$ | H | H | H | $(CH_2)_5CH_3$ |
| 266' | $CH_2F$ | H | H | H | $(CH_2)_{13}CH_3$ |
| 267' | $CH_2F$ | H | H | H | $(CH_2)_{15}CH_3$ |
| 268' | $CH_2F$ | H | H | H | $(CH_2)_{16}CH_3$ |
| 269' | $CH_2F$ | H | H | H | $(CH_2)_{17}CH_3$ |
| 270' | $CH_2F$ | H | H | H | $(CH_2)_{18}CH_3$ |
| 271' | $CH_2F$ | H | H | H | $(CH_2)_{20}CH_3$ |
| 272' | $CH_2F$ | H | H | H | $(CH_2)_{21}CH_3$ |
| 273' | $CH_2F$ | H | H | $CH_3CO$ | $(CH_2)_{13}CH_3$ |
| 274' | $CH_2F$ | H | H | $CH_3(CH_2)_5CO$ | $(CH_2)_5CH_3$ |

TABLE 1'-continued

| No. | R¹ | R² | R³ | R⁴ | W |
|---|---|---|---|---|---|
| 275' | $CH_2F$ | H | H | $CH_3(CH_2)_{10}CO$ | $(CH_2)_{13}CH_3$ |
| 276' | $CH_2F$ | H | H | $CH_3(CH_2)_{13}CO$ | $(CH_2)_5CH_3$ |
| 277' | $CH_2F$ | H | H | $CH_3(CH_2)_{15}CO$ | $(CH_2)_{13}CH_3$ |
| 278' | $CH_2F$ | H | H | $CH_3(CH_2)_{17}CO$ | $(CH_2)_5CH_3$ |
| 279' | $CH_2F$ | H | H | $CH_3(CH_2)_{21}CO$ | $(CH_2)_{13}CH_3$ |
| 280' | $CH_2F$ | H | $CH_3CO$ | H | $(CH_2)_5CH_3$ |
| 281' | $CH_2F$ | H | $CH_3CH_2CO$ | H | $(CH_2)_{13}CH_3$ |
| 282' | $CH_2F$ | H | $CH_3(CH_2)_2CO$ | H | $(CH_2)_5CH_3$ |
| 283' | $CH_2F$ | H | $CH_3(CH_2)_3CO$ | H | $(CH_2)_{13}CH_3$ |
| 284' | $CH_2F$ | H | $CH_3(CH_2)_4CO$ | H | $(CH_2)_5CH_3$ |
| 285' | $CH_2F$ | H | $CH_3(CH_2)_5CO$ | H | $(CH_2)_{13}CH_3$ |
| 286' | $CH_2F$ | H | $CH_3(CH_2)_6CO$ | H | $(CH_2)_5CH_3$ |
| 287' | $CH_2F$ | H | $CH_3(CH_2)_8CO$ | H | $(CH_2)_{13}CH_3$ |
| 288' | $CH_2F$ | H | $CH_3(CH_2)_{10}CO$ | H | $(CH_2)_5CH_3$ |
| 289' | $CH_2F$ | H | $CH_3(CH_2)_{12}CO$ | H | $(CH_2)_{13}CH_3$ |
| 290' | $CH_2F$ | H | $CH_3(CH_2)_{14}CO$ | H | $(CH_2)_5CH_3$ |
| 291' | $CH_2F$ | H | $CH_3(CH_2)_{16}CO$ | H | $(CH_2)_{13}CH_3$ |
| 292' | $CH_2F$ | H | $CH_3(CH_2)_{18}CO$ | H | $(CH_2)_5CH_3$ |
| 293' | $CH_2F$ | H | $CH_3(CH_2)_{20}CO$ | H | $(CH_2)_{13}CH_3$ |
| 294' | $CH_2F$ | H | $CH_3(CH_2)_{22}CO$ | H | $(CH_2)_5CH_3$ |
| 295' | $CH_2F$ | H | $CH_3(CH_2)_4CO$ | $CH_3CO$ | $(CH_2)_{13}CH_3$ |
| 296' | $CH_2F$ | H | $CH_3(CH_2)_4CO$ | $CH_3(CH_2)_5CO$ | $(CH_2)_5CH_3$ |
| 297' | $CH_2F$ | H | $CH_3(CH_2)_4CO$ | $CH_3(CH_2)_{10}CO$ | $(CH_2)_{13}CH_3$ |
| 298' | $CH_2F$ | H | $CH_3(CH_2)_4CO$ | $CH_3(CH_2)_{13}CO$ | $(CH_2)_5CH_3$ |
| 299' | $CH_2F$ | H | $CH_3(CH_2)_{12}CO$ | $CH_3CO$ | $(CH_2)_{13}CH_3$ |
| 300' | $CH_2F$ | H | $CH_3(CH_2)_{12}CO$ | $CH_3(CH_2)_5CO$ | $(CH_2)_5CH_3$ |
| 301' | $CH_2F$ | H | $CH_3(CH_2)_{12}CO$ | $CH_3(CH_2)_{10}CO$ | $(CH_2)_{13}CH_3$ |
| 302' | $CH_2F$ | H | $CH_3(CH_2)_{12}CO$ | $CH_3(CH_2)_{13}CO$ | $(CH_2)_5CH_3$ |
| 303' | $CH_2F$ | $CH_3CO$ | H | H | $(CH_2)_{13}CH_3$ |
| 304' | $CH_2F$ | $CH_3CH_2CO$ | H | H | $(CH_2)_5CH_3$ |
| 305' | $CH_2F$ | $CH_3(CH_2)_2CO$ | H | H | $(CH_2)_{13}CH_3$ |
| 306' | $CH_2F$ | $CH_3(CH_2)_3CO$ | H | H | $(CH_2)_5CH_3$ |
| 307' | $CH_2F$ | $CH_3(CH_2)_4CO$ | H | H | $(CH_2)_{13}CH_3$ |
| 308' | $CH_2F$ | $CH_3(CH_2)_5CO$ | H | H | $(CH_2)_5CH_3$ |
| 309' | $CH_2F$ | $CH_3(CH_2)_6CO$ | H | H | $(CH_2)_{13}CH_3$ |
| 310' | $CH_2F$ | $CH_3(CH_2)_8CO$ | H | H | $(CH_2)_5CH_3$ |
| 311' | $CH_2F$ | $CH_3(CH_2)_{10}CO$ | H | H | $(CH_2)_{13}CH_3$ |
| 312' | $CH_2F$ | $CH_3(CH_2)_{12}CO$ | H | H | $(CH_2)_5CH_3$ |
| 313' | $CH_2F$ | $CH_3(CH_2)_{14}CO$ | H | H | $(CH_2)_{13}CH_3$ |
| 314' | $CH_2F$ | $CH_3(CH_2)_{16}CO$ | H | H | $(CH_2)_5CH_3$ |
| 315' | $CH_2F$ | $CH_3(CH_2)_{18}CO$ | H | H | $(CH_2)_{13}CH_3$ |
| 316' | $CH_2F$ | $CH_3(CH_2)_{20}CO$ | H | H | $(CH_2)_5CH_3$ |
| 317' | $CH_2F$ | $CH_3(CH_2)_4CO$ | H | $CH_3CO$ | $(CH_2)_{13}CH_3$ |
| 318' | $CH_2F$ | $CH_3(CH_2)_4CO$ | H | $CH_3(CH_2)_5CO$ | $(CH_2)_5CH_3$ |
| 319' | $CH_2F$ | $CH_3(CH_2)_4CO$ | H | $CH_3(CH_2)_{10}CO$ | $(CH_2)_{13}CH_3$ |
| 320' | $CH_2F$ | $CH_3(CH_2)_4CO$ | H | $CH_3(CH_2)_{13}CO$ | $(CH_2)_5CH_3$ |
| 321' | $CH_2F$ | $CH_3(CH_2)_{12}CO$ | H | $CH_3CO$ | $(CH_2)_{13}CH_3$ |
| 322' | $CH_2F$ | $CH_3(CH_2)_{12}CO$ | H | $CH_3(CH_2)_5CO$ | $(CH_2)_5CH_3$ |
| 323' | $CH_2F$ | $CH_3(CH_2)_{12}CO$ | H | $CH_3(CH_2)_{10}CO$ | $(CH_2)_{13}CH_3$ |
| 324' | $CH_2F$ | $CH_3(CH_2)_{12}CO$ | H | $CH_3(CH_2)_{13}CO$ | $(CH_2)_5CH_3$ |
| 325' | $CH_2F$ | $CH_3CO$ | $CH_3CO$ | H | $(CH_2)_{13}CH_3$ |
| 326' | $CH_2F$ | $CH_3CH_2CO$ | $CH_3CH_2CO$ | H | $CH_3$ |
| 327' | $CH_2F$ | $CH_3(CH_2)_2CO$ | $CH_3(CH_2)_2CO$ | H | $(CH_2)_5CH_3$ |
| 328' | $CH_2F$ | $CH_3(CH_2)_3CO$ | $CH_3(CH_2)_3CO$ | H | $(CH_2)_{10}CH_3$ |
| 329' | $CH_2F$ | $CH_3(CH_2)_4CO$ | $CH_3(CH_2)_4CO$ | H | $(CH_2)_{13}CH_3$ |
| 330' | $CH_2F$ | $CH_3(CH_2)_5CO$ | $CH_3(CH_2)_5CO$ | H | $(CH_2)_{15}CH_3$ |
| 331' | $CH_2F$ | $CH_3(CH_2)_6CO$ | $CH_3(CH_2)_6CO$ | H | $(CH_2)_{17}CH_3$ |
| 332' | $CH_2F$ | $CH_3(CH_2)_8CO$ | $CH_3(CH_2)_8CO$ | H | $(CH_2)_{21}CH_3$ |
| 333' | $CH_2F$ | $CH_3(CH_2)_{10}CO$ | $CH_3(CH_2)_{10}CO$ | H | $CH_3$ |

TABLE 1'-continued

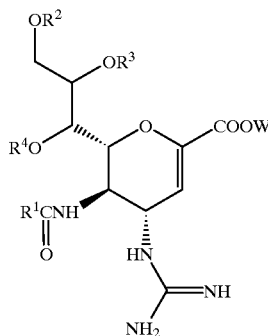

| No. | R$^1$ | R$^2$ | R$^3$ | R$^4$ | W |
|---|---|---|---|---|---|
| 334' | CH$_2$F | CH$_3$(CH$_2$)$_{12}$CO | CH$_3$(CH$_2$)$_{12}$CO | H | (CH$_2$)$_5$CH$_3$ |
| 335' | CH$_2$F | CH$_3$(CH$_2$)$_{14}$CO | CH$_3$(CH$_2$)$_{14}$CO | H | (CH$_2$)$_{10}$CH$_3$ |
| 336' | CH$_2$F | CH$_3$(CH$_2$)$_{16}$CO | CH$_3$(CH$_2$)$_{16}$CO | H | (CH$_2$)$_{13}$CH$_3$ |
| 337' | CH$_2$F | CH$_3$(CH$_2$)$_{18}$CO | CH$_3$(CH$_2$)$_{18}$CO | H | (CH$_2$)$_{15}$CH$_3$ |
| 338' | CH$_2$F | CH$_3$(CH$_2$)$_{20}$CO | CH$_3$(CH$_2$)$_{20}$CO | H | (CH$_2$)$_{17}$CH$_3$ |
| 339' | CH$_2$F | CH$_3$(CH$_2$)$_{22}$CO | CH$_3$(CH$_2$)$_{22}$CO | H | (CH$_2$)$_{21}$CH$_3$ |
| 340' | CH$_2$F | CH$_3$(CH$_2$)$_{12}$CO | CH$_3$(CH$_2$)$_6$CO | H | CH$_3$ |
| 341' | CH$_2$F | CH$_3$(CH$_2$)$_4$CO | CH$_3$(CH$_2$)$_{12}$CO | H | (CH$_2$)$_5$CH$_3$ |
| 342' | CH$_2$F | CH$_3$(CH$_2$)$_4$CO | CH$_3$(CH$_2$)$_4$CO | CH$_3$CO | (CH$_2$)$_{10}$CH$_3$ |
| 343' | CH$_2$F | CH$_3$(CH$_2$)$_4$CO | CH$_3$(CH$_2$)$_4$CO | CH$_3$(CH$_2$)$_5$CO | (CH$_2$)$_{13}$CH$_3$ |
| 344' | CH$_2$F | CH$_3$(CH$_2$)$_4$CO | CH$_3$(CH$_2$)$_4$CO | CH$_3$(CH$_2$)$_{10}$CO | (CH$_2$)$_{15}$CH$_3$ |
| 345' | CH$_2$F | CH$_3$(CH$_2$)$_4$CO | CH$_3$(CH$_2$)$_4$CO | CH$_3$(CH$_2$)$_{13}$CO | (CH$_2$)$_{17}$CH$_3$ |
| 346' | CH$_2$F | CH$_3$(CH$_2$)$_{12}$CO | CH$_3$(CH$_2$)$_{12}$CO | CH$_3$CO | (CH$_2$)$_{21}$CH$_3$ |
| 347' | CH$_2$F | CH$_3$(CH$_2$)$_{12}$CO | CH$_3$(CH$_2$)$_{12}$CO | CH$_3$(CH$_2$)$_5$CO | CH$_3$ |
| 348' | CH$_2$F | CH$_3$(CH$_2$)$_{12}$CO | CH$_3$(CH$_2$)$_{12}$CO | CH$_3$(CH$_2$)$_{10}$CO | (CH$_2$)$_5$CH$_3$ |
| 349' | CH$_2$F | CH$_3$(CH$_2$)$_{12}$CO | CH$_3$(CH$_2$)$_{12}$CO | CH$_3$(CH$_2$)$_{13}$CO | (CH$_2$)$_{10}$CH$_3$ |
| 350' | CH$_2$F | CH$_3$(CH$_2$)$_4$CO | CH$_3$(CH$_2$)$_{12}$CO | CH$_3$CO | (CH$_2$)$_{13}$CH$_3$ |
| 351' | CH$_2$F | CH$_3$(CH$_2$)$_4$CO | CH$_3$(CH$_2$)$_{12}$CO | CH$_3$(CH$_2$)$_5$CO | (CH$_2$)$_{15}$CH$_3$ |
| 352' | CH$_2$F | CH$_3$(CH$_2$)$_4$CO | CH$_3$(CH$_2$)$_{12}$CO | CH$_3$(CH$_2$)$_{10}$CO | (CH$_2$)$_{17}$CH$_3$ |
| 353' | CH$_2$F | CH$_3$(CH$_2$)$_4$CO | CH$_3$(CH$_2$)$_{12}$CO | CH$_3$(CH$_2$)$_{13}$CO | (CH$_2$)$_{21}$CH$_3$ |
| 354' | CH$_2$F | CH$_3$(CH$_2$)$_{12}$CO | CH$_3$(CH$_2$)$_4$CO | CH$_3$CO | CH$_3$ |
| 355' | CH$_2$F | CH$_3$(CH$_2$)$_{12}$CO | CH$_3$(CH$_2$)$_4$CO | CH$_3$(CH$_2$)$_5$CO | (CH$_2$)$_5$CH$_3$ |
| 356' | CH$_2$F | CH$_3$(CH$_2$)$_{12}$CO | CH$_3$(CH$_2$)$_4$CO | CH$_3$(CH$_2$)$_{10}$CO | (CH$_2$)$_{10}$CH$_3$ |
| 357' | CH$_2$F | CH$_3$(CH$_2$)$_{12}$CO | CH$_3$(CH$_2$)$_4$CO | CH$_3$(CH$_2$)$_{13}$CO | (CH$_2$)$_{13}$CH$_3$ |
| 358' | CHF$_2$ | H | H | H | H |
| 359' | CHF$_2$ | H | H | CH$_3$CO | H |
| 360' | CHF$_2$ | H | H | CH$_3$(CH$_2$)$_5$CO | H |
| 361' | CHF$_2$ | H | H | CH$_3$(CH$_2$)$_{10}$CO | H |
| 362' | CHF$_2$ | H | H | CH$_3$(CH$_2$)$_{13}$CO | H |
| 363' | CHF$_2$ | H | H | CH$_3$(CH$_2$)$_{15}$CO | H |
| 364' | CHF$_2$ | H | H | CH$_3$(CH$_2$)$_{17}$CO | H |
| 365' | CHF$_2$ | H | H | CH$_3$(CH$_2$)$_{21}$CO | H |
| 366' | CHF$_2$ | H | CH$_3$CO | H | H |
| 367' | CHF$_2$ | H | CH$_3$CH$_2$CO | H | H |
| 368' | CHF$_2$ | H | CH$_3$(CH$_2$)$_2$CO | H | H |
| 369' | CHF$_2$ | H | CH$_3$(CH$_2$)$_3$CO | H | H |
| 370' | CHF$_2$ | H | CH$_3$(CH$_2$)$_4$CO | H | H |
| 371' | CHF$_2$ | H | CH$_3$(CH$_2$)$_5$CO | H | H |
| 372' | CHF$_2$ | H | CH$_3$(CH$_2$)$_6$CO | H | H |
| 373' | CHF$_2$ | H | CH$_3$(CH$_2$)$_8$CO | H | H |
| 374' | CHF$_2$ | H | CH$_3$(CH$_2$)$_{10}$CO | H | H |
| 375' | CHF$_2$ | H | CH$_3$(CH$_2$)$_{12}$CO | H | H |
| 376' | CHF$_2$ | H | CH$_3$(CH$_2$)$_{14}$CO | H | H |
| 377' | CHF$_2$ | H | CH$_3$(CH$_2$)$_{16}$CO | H | H |
| 378' | CHF$_2$ | H | CH$_3$(CH$_2$)$_{18}$CO | H | H |
| 379' | CHF$_2$ | H | CH$_3$(CH$_2$)$_{20}$CO | H | H |
| 380' | CHF$_2$ | H | CH$_3$(CH$_2$)$_{22}$CO | H | H |
| 381' | CHF$_2$ | H | CH$_3$(CH$_2$)$_4$CO | CH$_3$CO | H |
| 382' | CHF$_2$ | H | CH$_3$(CH$_2$)$_4$CO | CH$_3$(CH$_2$)$_5$CO | H |
| 383' | CHF$_2$ | H | CH$_3$(CH$_2$)$_4$CO | CH$_3$(CH$_2$)$_{10}$CO | H |
| 384' | CHF$_2$ | H | CH$_3$(CH$_2$)$_4$CO | CH$_3$(CH$_2$)$_{13}$CO | H |
| 385' | CHF$_2$ | H | CH$_3$(CH$_2$)$_{12}$CO | CH$_3$CO | H |
| 386' | CHF$_2$ | H | CH$_3$(CH$_2$)$_{12}$CO | CH$_3$(CH$_2$)$_5$CO | H |
| 387' | CHF$_2$ | H | CH$_3$(CH$_2$)$_{12}$CO | CH$_3$(CH$_2$)$_{10}$CO | H |
| 388' | CHF$_2$ | H | CH$_3$(CH$_2$)$_{12}$CO | CH$_3$(CH$_2$)$_{13}$CO | H |
| 389' | CHF$_2$ | CH$_3$CO | H | H | H |
| 390' | CHF$_2$ | CH$_3$CH$_2$CO | H | H | H |
| 391' | CHF$_2$ | CH$_3$(CH$_2$)$_2$CO | H | H | H |
| 392' | CHF$_2$ | CH$_3$(CH$_2$)$_3$CO | H | H | H |

TABLE 1'-continued

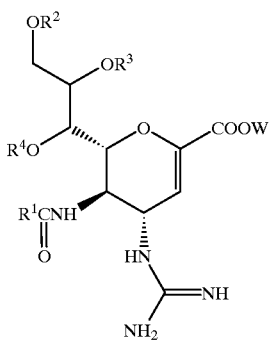

| No. | $R^1$ | $R^2$ | $R^3$ | $R^4$ | W |
|---|---|---|---|---|---|
| 393' | $CHF_2$ | $CH_3(CH_2)_4CO$ | H | H | H |
| 394' | $CHF_2$ | $CH_3(CH_2)_5CO$ | H | H | H |
| 395' | $CHF_2$ | $CH_3(CH_2)_6CO$ | H | H | H |
| 396' | $CHF_2$ | $CH_3(CH_2)_8CO$ | H | H | H |
| 397' | $CHF_2$ | $CH_3(CH_2)_{10}CO$ | H | H | H |
| 398' | $CHF_2$ | $CH_3(CH_2)_{12}CO$ | H | H | H |
| 399' | $CHF_2$ | $CH_3(CH_2)_{14}CO$ | H | H | H |
| 400' | $CHF_2$ | $CH_3(CH_2)_{16}CO$ | H | H | H |
| 401' | $CHF_2$ | $CH_3(CH_2)_{18}CO$ | H | H | H |
| 402' | $CHF_2$ | $CH_3(CH_2)_{20}CO$ | H | H | H |
| 403' | $CHF_2$ | $CH_3(CH_2)_4CO$ | H | $CH_3CO$ | H |
| 404' | $CHF_2$ | $CH_3(CH_2)_4CO$ | H | $CH_3(CH_2)_5CO$ | H |
| 405' | $CHF_2$ | $CH_3(CH_2)_4CO$ | H | $CH_3(CH_2)_{10}CO$ | H |
| 406' | $CHF_2$ | $CH_3(CH_2)_4CO$ | H | $CH_3(CH_2)_{13}CO$ | H |
| 407' | $CHF_2$ | $CH_3(CH_2)_{12}CO$ | H | $CH_3CO$ | H |
| 408' | $CHF_2$ | $CH_3(CH_2)_{12}CO$ | H | $CH_3(CH_2)_5CO$ | H |
| 409' | $CHF_2$ | $CH_3(CH_2)_{12}CO$ | H | $CH_3(CH_2)_{10}CO$ | H |
| 410' | $CHF_2$ | $CH_3(CH_2)_{12}CO$ | H | $CH_3(CH_2)_{13}CO$ | H |
| 411' | $CHF_2$ | $CH_3CO$ | $CH_3CO$ | H | H |
| 412' | $CHF_2$ | $CH_3CH_2CO$ | $CH_3CH_2CO$ | H | H |
| 413' | $CHF_2$ | $CH_3(CH_2)_2CO$ | $CH_3(CH_2)_2CO$ | H | H |
| 414' | $CHF_2$ | $CH_3(CH_2)_3CO$ | $CH_3(CH_2)_3CO$ | H | H |
| 415' | $CHF_2$ | $CH_3(CH_2)_4CO$ | $CH_3(CH_2)_4CO$ | H | H |
| 416' | $CHF_2$ | $CH_3(CH_2)_5CO$ | $CH_3(CH_2)_5CO$ | H | H |
| 417' | $CHF_2$ | $CH_3(CH_2)_6CO$ | $CH_3(CH_2)_6CO$ | H | H |
| 418' | $CHF_2$ | $CH_3(CH_2)_8CO$ | $CH_3(CH_2)_8CO$ | H | H |
| 419' | $CHF_2$ | $CH_3(CH_2)_{10}CO$ | $CH_3(CH_2)_{10}CO$ | H | H |
| 420' | $CHF_2$ | $CH_3(CH_2)_{12}CO$ | $CH_3(CH_2)_{12}CO$ | H | H |
| 421' | $CHF_2$ | $CH_3(CH_2)_{14}CO$ | $CH_3(CH_2)_{14}CO$ | H | H |
| 422' | $CHF_2$ | $CH_3(CH_2)_{16}CO$ | $CH_3(CH_2)_{16}CO$ | H | H |
| 423' | $CHF_2$ | $CH_3(CH_2)_{18}CO$ | $CH_3(CH_2)_{18}CO$ | H | H |
| 424' | $CHF_2$ | $CH_3(CH_2)_{20}CO$ | $CH_3(CH_2)_{20}CO$ | H | H |
| 425' | $CHF_2$ | $CH_3(CH_2)_{22}CO$ | $CH_3(CH_2)_{22}CO$ | H | H |
| 426' | $CHF_2$ | $CH_3(CH_2)_{12}CO$ | $CH_3(CH_2)_6CO$ | H | H |
| 427' | $CHF_2$ | $CH_3(CH_2)_4CO$ | $CH_3(CH_2)_{12}CO$ | H | H |
| 428' | $CHF_2$ | $CH_3(CH_2)_4CO$ | $CH_3(CH_2)_4CO$ | $CH_3CO$ | H |
| 429' | $CHF_2$ | $CH_3(CH_2)_4CO$ | $CH_3(CH_2)_4CO$ | $CH_3(CH_2)_5CO$ | H |
| 430' | $CHF_2$ | $CH_3(CH_2)_4CO$ | $CH_3(CH_2)_4CO$ | $CH_3(CH_2)_{10}CO$ | H |
| 431' | $CHF_2$ | $CH_3(CH_2)_4CO$ | $CH_3(CH_2)_4CO$ | $CH_3(CH_2)_{13}CO$ | H |
| 432' | $CHF_2$ | $CH_3(CH_2)_{12}CO$ | $CH_3(CH_2)_{12}CO$ | $CH_3CO$ | H |
| 433' | $CHF_2$ | $CH_3(CH_2)_{12}CO$ | $CH_3(CH_2)_{12}CO$ | $CH_3(CH_2)_5CO$ | H |
| 434' | $CHF_2$ | $CH_3(CH_2)_{12}CO$ | $CH_3(CH_2)_{12}CO$ | $CH_3(CH_2)_{10}CO$ | H |
| 435' | $CHF_2$ | $CH_3(CH_2)_{12}CO$ | $CH_3(CH_2)_{12}CO$ | $CH_3(CH_2)_{13}CO$ | H |
| 436' | $CHF_2$ | $CH_3(CH_2)_4CO$ | $CH_3(CH_2)_{12}CO$ | $CH_3CO$ | H |
| 437' | $CHF_2$ | $CH_3(CH_2)_4CO$ | $CH_3(CH_2)_{12}CO$ | $CH_3(CH_2)_5CO$ | H |
| 438' | $CHF_2$ | $CH_3(CH_2)_4CO$ | $CH_3(CH_2)_{12}CO$ | $CH_3(CH_2)_{10}CO$ | H |
| 439' | $CHF_2$ | $CH_3(CH_2)_4CO$ | $CH_3(CH_2)_{12}CO$ | $CH_3(CH_2)_{13}CO$ | H |
| 440' | $CHF_2$ | $CH_3(CH_2)_{12}CO$ | $CH_3(CH_2)_4CO$ | $CH_3CO$ | H |
| 441' | $CHF_2$ | $CH_3(CH_2)_{12}CO$ | $CH_3(CH_2)_4CO$ | $CH_3(CH_2)_5CO$ | H |
| 442' | $CHF_2$ | $CH_3(CH_2)_{12}CO$ | $CH_3(CH_2)_4CO$ | $CH_3(CH_2)_{10}CO$ | H |
| 443' | $CHF_2$ | $CH_3(CH_2)_{12}CO$ | $CH_3(CH_2)_4CO$ | $CH_3(CH_2)_{13}CO$ | H |
| 444' | $CHF_2$ | H | H | H | $(CH_2)_5CH_3$ |
| 445' | $CHF_2$ | H | H | H | $(CH_2)_{13}CH_3$ |
| 446' | $CHF_2$ | H | H | H | $(CH_2)_{15}CH_3$ |
| 447' | $CHF_2$ | H | H | H | $(CH_2)_{16}CH_3$ |
| 448' | $CHF_2$ | H | H | H | $(CH_2)_{17}CH_3$ |
| 449' | $CHF_2$ | H | H | H | $(CH_2)_{18}CH_3$ |
| 450' | $CHF_2$ | H | H | H | $(CH_2)_{20}CH_3$ |
| 451' | $CHF_2$ | H | H | H | $(CH_2)_{21}CH_3$ |

TABLE 1'-continued

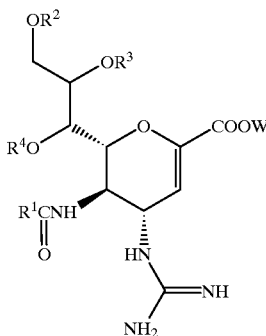

| No. | R$^1$ | R$^2$ | R$^3$ | R$^4$ | W |
|---|---|---|---|---|---|
| 452' | CHF$_2$ | H | H | CH$_3$CO | (CH$_2$)$_{13}$CH$_3$ |
| 453' | CHF$_2$ | H | H | CH$_3$(CH$_2$)$_5$CO | (CH$_2$)$_5$CH$_3$ |
| 454' | CHF$_2$ | H | H | CH$_3$(CH$_2$)$_{10}$CO | (CH$_2$)$_{13}$CH$_3$ |
| 455' | CHF$_2$ | H | H | CH$_3$(CH$_2$)$_{13}$CO | (CH$_2$)$_5$CH$_3$ |
| 456' | CHF$_2$ | H | H | CH$_3$(CH$_2$)$_{15}$CO | (CH$_2$)$_{13}$CH$_3$ |
| 457' | CHF$_2$ | H | H | CH$_3$(CH$_2$)$_{17}$CO | (CH$_2$)$_5$CH$_3$ |
| 458' | CHF$_2$ | H | H | CH$_3$(CH$_2$)$_{21}$CO | (CH$_2$)$_{13}$CH$_3$ |
| 459' | CHF$_2$ | H | CH$_3$CO | H | (CH$_2$)$_5$CH$_3$ |
| 460' | CHF$_2$ | H | CH$_3$CH$_2$CO | H | (CH$_2$)$_{13}$CH$_3$ |
| 461' | CHF$_2$ | H | CH$_3$(CH$_2$)$_2$CO | H | (CH$_2$)$_5$CH$_3$ |
| 462' | CHF$_2$ | H | CH$_3$(CH$_2$)$_3$CO | H | (CH$_2$)$_{13}$CH$_3$ |
| 463' | CHF$_2$ | H | CH$_3$(CH$_2$)$_4$CO | H | (CH$_2$)$_5$CH$_3$ |
| 464' | CHF$_2$ | H | CH$_3$(CH$_2$)$_5$CO | H | (CH$_2$)$_{13}$CH$_3$ |
| 465' | CHF$_2$ | H | CH$_3$(CH$_2$)$_6$CO | H | (CH$_2$)$_5$CH$_3$ |
| 466' | CHF$_2$ | H | CH$_3$(CH$_2$)$_8$CO | H | (CH$_2$)$_{13}$CH$_3$ |
| 467' | CHF$_2$ | H | CH$_3$(CH$_2$)$_{10}$CO | H | (CH$_2$)$_5$CH$_3$ |
| 468' | CHF$_2$ | H | CH$_3$(CH$_2$)$_{12}$CO | H | (CH$_2$)$_{13}$CH$_3$ |
| 469' | CHF$_2$ | H | CH$_3$(CH$_2$)$_{14}$CO | H | (CH$_2$)$_5$CH$_3$ |
| 470' | CHF$_2$ | H | CH$_3$(CH$_2$)$_{16}$CO | H | (CH$_2$)$_{13}$CH$_3$ |
| 471' | CHF$_2$ | H | CH$_3$(CH$_2$)$_{18}$CO | H | (CH$_2$)$_5$CH$_3$ |
| 472' | CHF$_2$ | H | CH$_3$(CH$_2$)$_{20}$CO | H | (CH$_2$)$_{13}$CH$_3$ |
| 473' | CHF$_2$ | H | CH$_3$(CH$_2$)$_{22}$CO | H | (CH$_2$)$_5$CH$_3$ |
| 474' | CHF$_2$ | H | CH$_3$(CH$_2$)$_4$CO | CH$_3$CO | (CH$_2$)$_{13}$CH$_3$ |
| 475' | CHF$_2$ | H | CH$_3$(CH$_2$)$_4$CO | CH$_3$(CH$_2$)$_5$CO | (CH$_2$)$_5$CH$_3$ |
| 476' | CHF$_2$ | H | CH$_3$(CH$_2$)$_4$CO | CH$_3$(CH$_2$)$_{10}$CO | (CH$_2$)$_{13}$CH$_3$ |
| 477' | CHF$_2$ | H | CH$_3$(CH$_2$)$_4$CO | CH$_3$(CH$_2$)$_{13}$CO | (CH$_2$)$_5$CH$_3$ |
| 478' | CHF$_2$ | H | CH$_3$(CH$_2$)$_{12}$CO | CH$_3$CO | (CH$_2$)$_{13}$CH$_3$ |
| 479' | CHF$_2$ | H | CH$_3$(CH$_2$)$_{12}$CO | CH$_3$(CH$_2$)$_5$CO | (CH$_2$)$_5$CH$_3$ |
| 480' | CHF$_2$ | H | CH$_3$(CH$_2$)$_{12}$CO | CH$_3$(CH$_2$)$_{10}$CO | (CH$_2$)$_{13}$CH$_3$ |
| 481' | CHF$_2$ | H | CH$_3$(CH$_2$)$_{12}$CO | CH$_3$(CH$_2$)$_{13}$CO | (CH$_2$)$_5$CH$_3$ |
| 482' | CHF$_2$ | CH$_3$CO | H | H | (CH$_2$)$_{13}$CH$_3$ |
| 483' | CHF$_2$ | CH$_3$CH$_2$CO | H | H | (CH$_2$)$_5$CH$_3$ |
| 484' | CHF$_2$ | CH$_3$(CH$_2$)$_2$CO | H | H | (CH$_2$)$_{13}$CH$_3$ |
| 485' | CHF$_2$ | CH$_3$(CH$_2$)$_3$CO | H | H | (CH$_2$)$_5$CH$_3$ |
| 486' | CHF$_2$ | CH$_3$(CH$_2$)$_4$CO | H | H | (CH$_2$)$_{13}$CH$_3$ |
| 487' | CHF$_2$ | CH$_3$(CH$_2$)$_5$CO | H | H | (CH$_2$)$_5$CH$_3$ |
| 488' | CHF$_2$ | CH$_3$(CH$_2$)$_6$CO | H | H | (CH$_2$)$_{13}$CH$_3$ |
| 489' | CHF$_2$ | CH$_3$(CH$_2$)$_8$CO | H | H | (CH$_2$)$_5$CH$_3$ |
| 490' | CHF$_2$ | CH$_3$(CH$_2$)$_{10}$CO | H | H | (CH$_2$)$_{13}$CH$_3$ |
| 491' | CHF$_2$ | CH$_3$(CH$_2$)$_{12}$CO | H | H | (CH$_2$)$_5$CH$_3$ |
| 492' | CHF$_2$ | CH$_3$(CH$_2$)$_{14}$CO | H | H | (CH$_2$)$_{13}$CH$_3$ |
| 493' | CHF$_2$ | CH$_3$(CH$_2$)$_{16}$CO | H | H | (CH$_2$)$_5$CH$_3$ |
| 494' | CHF$_2$ | CH$_3$(CH$_2$)$_{18}$CO | H | H | (CH$_2$)$_{13}$CH$_3$ |
| 495' | CHF$_2$ | CH$_3$(CH$_2$)$_{20}$CO | H | H | (CH$_2$)$_5$CH$_3$ |
| 496' | CHF$_2$ | CH$_3$(CH$_2$)$_4$CO | H | CH$_3$CO | (CH$_2$)$_{13}$CH$_3$ |
| 497' | CHF$_2$ | CH$_3$(CH$_2$)$_4$CO | H | CH$_3$(CH$_2$)$_5$CO | (CH$_2$)$_5$CH$_3$ |
| 498' | CHF$_2$ | CH$_3$(CH$_2$)$_4$CO | H | CH$_3$(CH$_2$)$_{10}$CO | (CH$_2$)$_{13}$CH$_3$ |
| 499' | CHF$_2$ | CH$_3$(CH$_2$)$_4$CO | H | CH$_3$(CH$_2$)$_{13}$CO | (CH$_2$)$_5$CH$_3$ |
| 500' | CHF$_2$ | CH$_3$(CH$_2$)$_{12}$CO | H | CH$_3$CO | (CH$_2$)$_{13}$CH$_3$ |
| 501' | CHF$_2$ | CH$_3$(CH$_2$)$_{12}$CO | H | CH$_3$(CH$_2$)$_5$CO | (CH$_2$)$_5$CH$_3$ |
| 502' | CHF$_2$ | CH$_3$(CH$_2$)$_{12}$CO | H | CH$_3$(CH$_2$)$_{10}$CO | (CH$_2$)$_{13}$CH$_3$ |
| 503' | CHF$_2$ | CH$_3$(CH$_2$)$_{12}$CO | H | CH$_3$(CH$_2$)$_{13}$CO | (CH$_2$)$_5$CH$_3$ |
| 504' | CHF$_2$ | CH$_3$CO | CH$_3$CO | H | (CH$_2$)$_{13}$CH$_3$ |
| 505' | CHF$_2$ | CH$_3$CH$_2$CO | CH$_3$CH$_2$CO | H | CH$_3$ |
| 506' | CHF$_2$ | CH$_3$(CH$_2$)$_2$CO | CH$_3$(CH$_2$)$_2$CO | H | (CH$_2$)$_5$CH$_3$ |
| 507' | CHF$_2$ | CH$_3$(CH$_2$)$_3$CO | CH$_3$(CH$_2$)$_3$CO | H | (CH$_2$)$_{10}$CH$_3$ |
| 508' | CHF$_2$ | CH$_3$(CH$_2$)$_4$CO | CH$_3$(CH$_2$)$_4$CO | H | (CH$_2$)$_{13}$CH$_3$ |
| 509' | CHF$_2$ | CH$_3$(CH$_2$)$_5$CO | CH$_3$(CH$_2$)$_5$CO | H | (CH$_2$)$_{15}$CH$_3$ |
| 510' | CHF$_2$ | CH$_3$(CH$_2$)$_6$CO | CH$_3$(CH$_2$)$_6$CO | H | (CH$_2$)$_{17}$CH$_3$ |

TABLE 1'-continued

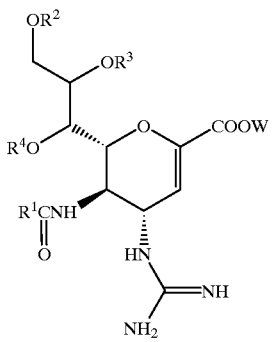

| No. | $R^1$ | $R^2$ | $R^3$ | $R^4$ | W |
|---|---|---|---|---|---|
| 511' | $CHF_2$ | $CH_3(CH_2)_8CO$ | $CH_3(CH_2)_8CO$ | H | $(CH_2)_{21}CH_3$ |
| 512' | $CHF_2$ | $CH_3(CH_2)_{10}CO$ | $CH_3(CH_2)_{10}CO$ | H | $CH_3$ |
| 513' | $CHF_2$ | $CH_3(CH_2)_{12}CO$ | $CH_3(CH_2)_{12}CO$ | H | $(CH_2)_5CH_3$ |
| 514' | $CHF_2$ | $CH_3(CH_2)_{14}CO$ | $CH_3(CH_2)_{14}CO$ | H | $(CH_2)_{10}CH_3$ |
| 515' | $CHF_2$ | $CH_3(CH_2)_{16}CO$ | $CH_3(CH_2)_{16}CO$ | H | $(CH_2)_{13}CH_3$ |
| 516' | $CHF_2$ | $CH_3(CH_2)_{18}CO$ | $CH_3(CH_2)_{18}CO$ | H | $(CH_2)_{15}CH_3$ |
| 517' | $CHF_2$ | $CH_3(CH_2)_{20}CO$ | $CH_3(CH_2)_{20}CO$ | H | $(CH_2)_{17}CH_3$ |
| 518' | $CHF_2$ | $CH_3(CH_2)_{22}CO$ | $CH_3(CH_2)_{22}CO$ | H | $(CH_2)_{21}CH_3$ |
| 519' | $CHF_2$ | $CH_3(CH_2)_{12}CO$ | $CH_3(CH_2)_6CO$ | H | $CH_3$ |
| 520' | $CHF_2$ | $CH_3(CH_2)_4CO$ | $CH_3(CH_2)_{12}CO$ | H | $(CH_2)_5CH_3$ |
| 521' | $CHF_2$ | $CH_3(CH_2)_4CO$ | $CH_3(CH_2)_4CO$ | $CH_3CO$ | $(CH_2)_{10}CH_3$ |
| 522' | $CHF_2$ | $CH_3(CH_2)_4CO$ | $CH_3(CH_2)_4CO$ | $CH_3(CH_2)_5CO$ | $(CH_2)_{13}CH_3$ |
| 523' | $CHF_2$ | $CH_3(CH_2)_4CO$ | $CH_3(CH_2)_4CO$ | $CH_3(CH_2)_{10}CO$ | $(CH_2)_{15}CH_3$ |
| 524' | $CHF_2$ | $CH_3(CH_2)_4CO$ | $CH_3(CH_2)_4CO$ | $CH_3(CH_2)_{13}CO$ | $(CH_2)_{17}CH_3$ |
| 525' | $CHF_2$ | $CH_3(CH_2)_{12}CO$ | $CH_3(CH_2)_{12}CO$ | $CH_3CO$ | $(CH_2)_{21}CH_3$ |
| 526' | $CHF_2$ | $CH_3(CH_2)_{12}CO$ | $CH_3(CH_2)_{12}CO$ | $CH_3(CH_2)_5CO$ | $CH_3$ |
| 527' | $CHF_2$ | $CH_3(CH_2)_{12}CO$ | $CH_3(CH_2)_{12}CO$ | $CH_3(CH_2)_{10}CO$ | $(CH_2)_5CH_3$ |
| 528' | $CHF_2$ | $CH_3(CH_2)_{12}CO$ | $CH_3(CH_2)_{12}CO$ | $CH_3(CH_2)_{13}CO$ | $(CH_2)_{10}CH_3$ |
| 529' | $CHF_2$ | $CH_3(CH_2)_4CO$ | $CH_3(CH_2)_{12}CO$ | $CH_3CO$ | $(CH_2)_{13}CH_3$ |
| 530' | $CHF_2$ | $CH_3(CH_2)_4CO$ | $CH_3(CH_2)_{12}CO$ | $CH_3(CH_2)_5CO$ | $(CH_2)_{15}CH_3$ |
| 531' | $CHF_2$ | $CH_3(CH_2)_4CO$ | $CH_3(CH_2)_{12}CO$ | $CH_3(CH_2)_{10}CO$ | $(CH_2)_{17}CH_3$ |
| 532' | $CHF_2$ | $CH_3(CH_2)_4CO$ | $CH_3(CH_2)_{12}CO$ | $CH_3(CH_2)_{13}CO$ | $(CH_2)_{21}CH_3$ |
| 533' | $CHF_2$ | $CH_3(CH_2)_{12}CO$ | $CH_3(CH_2)_4CO$ | $CH_3CO$ | $CH_3$ |
| 534' | $CHF_2$ | $CH_3(CH_2)_{12}CO$ | $CH_3(CH_2)_4CO$ | $CH_3(CH_2)_5CO$ | $(CH_2)_5CH_3$ |
| 535' | $CHF_2$ | $CH_3(CH_2)_{12}CO$ | $CH_3(CH_2)_4CO$ | $CH_3(CH_2)_{10}CO$ | $(CH_2)_{10}CH_3$ |
| 536' | $CHF_2$ | $CH_3(CH_2)_{12}CO$ | $CH_3(CH_2)_4CO$ | $CH_3(CH_2)_{13}CO$ | $(CH_2)_{13}CH_3$ |

Of the above exemplary compounds, preferred are Compounds 36', 37', 38', 38a', 39', 39a', 40', 40a', 41', 41a', 42', 42a', 43', 43a', 44', 44a', 45', 45a', 45b', 45c', 87', 87a', 87b', 87c'', 87d', 87e', 87f', 87g', 88', 88a', 90', 91', 92', 92a', 93', 94', 94a', 94b', 214', 215', 216', 217', 218', 219', 220', 221', 222', 223', 265', 266', 267', 268', 269', 270', 271', 272', 393', 394', 395', 396', 397', 398', 399', 400', 401', 402', 444', 445', 446', 447', 448', 449', 450' and 451'.

Of the above exemplary compounds, preferred are Compounds 36', 37', 38', 38a', 39', 39a', 40', 40a', 41', 41a', 42', 42a', 43', 43a', 44', 44a', 45', 45a', 45b', 45c', 87', 87a', 87b', 87c', 87d', 87e', 87f', 87g', 88', 88a', 89', 90', 91', 92', 92a', 93', 94', 94a', 94b', 214', 215', 216', 217', 218', 219', 220', 221', 222', 223', 265', 266', 267', 268', 269', 270', 271', 272', 393', 394', 395', 396', 397',397', 398', 399', 400', 401', 402', 444', 445', 446', 447', 448', 449', 450' and 451'.

More preferred are Compounds 36', 37', 38', 38a', 39', 39a', 40', 40a', 41', 41a', 42', 42a', 43', 43a', 44', 44a', 45', 45a', 45b', 45c', 87', 87a', 87b', 87c', 87d', 87e', 87f', 87g', 88', 88a', 89', 90', 91', 92', 92a', 93', 94', 94a', 94b', 219', 220', 221', 222', 269', 270', 271', 272', 398', 399', 400', 401', 448', 449', 450' and 451'.

The following compounds are most preferred.

5-acetamido-2,3,4,5-tetradeoxy-4-guanidino-9-O-hexanoyl-D-glycero-D-galacto-non-2-enopyranosoic acid (Exemplary compound No. 36')

5-acetamido-2,3,4,5-tetradeoxy-4-guanidino-9-O-octanoyl-D-glycero-D-galacto-non-2-enopyranosoic acid (Exemplary compound No. 38')

5-acetamido-2,3,4,5-tetradeoxy-4-guanidino-9-O-decanoyl-D-glycero-D-galacto-non-2-enopyranosoic acid (Exemplary compound No. 39')

5-acetamido-2,3,4,5-tetradeoxy-4-guanidino-9-O-dodecanoyl-D-glycero-D-galacto-non-2-enopyranosoic acid (Exemplary compound No. 40')

5-acetamido-2,3,4,5-tetradeoxy-4-guanidino-9-O-myristoyl-D-glycero-D-galacto-non-2-enopyranosoic acid (Exemplary compound No. 41')

5-acetamido-2,3,4,5-tetradeoxy-4-guanidino-9-O-palmitoyl-D-glycero-D-galacto-non-2-enopyranosoic acid (Exemplary compound No. 42')

5-acetamido-2,3,4,5-tetradeoxy-4-guanidino-9-O-stearoyl-D-glycero-D-galacto-non-2-enopyranosoic acid (Exemplary compound No. 43')

hexyl 5-acetamido-2,3,4,5-tetradeoxy-4-guanidino-D-glycero-D-galacto-non-2-enopyranosoate (Exemplary compound No. 87')

myristyl 5-acetamido-2,3,4,5-tetradeoxy-4-guanidino-D-glycero-D-galacto-non-2-enopyranosoate (Exemplary compound No. 88')

cetyl 5-acetamido-2,3,4,5-tetradeoxy-4-guanidino-D-glycero-D-galacto-non-2-enopyranosoate (Exemplary compound No. 89')

stearyl 5-acetamido-2,3,4,5-tetradeoxy-4-guanidino-D-glycero-D-galacto-non-2-enopyranosoate (Exemplary compound No. 91')

In the following, the process for preparing the compound (1') of the present invention will be described.

The compound (1') of the present invention can be prepared according to the process described in Process A', B' or C' shown below. Further, the compound (1') can be also prepared according to Process J' described later.

The raw material compound (2') used in Processes A' and B' can be prepared according to the processes described in Process D', E', F', or G' shown below. Further, the raw material compound (5') used in Process C' can be prepared according to the process described in Process H' shown below.

The meanings of $R^1$, $R^2$, $R^{2a}$, $R^{2b}$, $R^3$, $R^{3a}$, $R^4$, $R^{4a}$, $R^6$, $R^7$, $R^8$, W, $W^a$, Me, Ac and Boc used in the steps of Processes A' to J' are shown below.

That is, $R^1$, $R^2$, $R^3$, $R^4$ and W have the same meanings as defined above, $R^{2a}$ has the same meaning as defined for the above $R^2$ or represents a protecting group of the hydroxyl group (preferably a t-butyldimethylsilyl group or an isopropylidene group taken together with the protecting group of the hydroxyl group of $R^{3a}$), $R^{2b}$ represents a protecting group of the hydroxyl group (preferably a t-butyldimethylsilyl group), $R^{3a}$ has the same meaning as defined for the above $R^3$ or represents a protecting group of the hydroxyl group (preferably a t-butyldimethylsilyl group or an isopropylidene group taken together with the protecting group of the hydroxyl group of $R^{2a}$), $R^{4a}$ has the same meaning as defined for the above $R^4$ or represents a protected hydroxyl group (preferably a t-butyldimethylsilyl group), $R^6$, $R^7$ and $R^8$ may be the same or different and each represent an aliphatic acyl group having from 3 to 25 carbon atoms, $W^a$ has the same meaning as defined for the above W or represents a protecting group of the carboxyl group (preferably a methyl, ethyl, benzyl, allyl, methoxymethyl, methylthiomethyl, 2-(trimethylsilyl) ethoxymethoxy or diphenylmethyl group, more preferably a methyl, benzyl or diphenylmethyl group), Ac represents an acetyl group, Boc represents a t-butoxycarbonyl group, and Me represents a methyl group.

In the following, each Process will be described in detail.

(Process A')

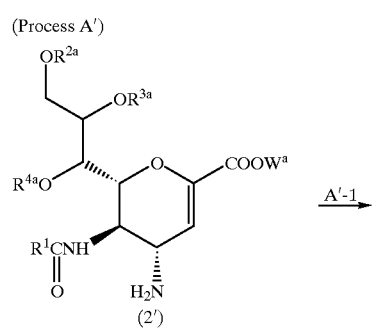

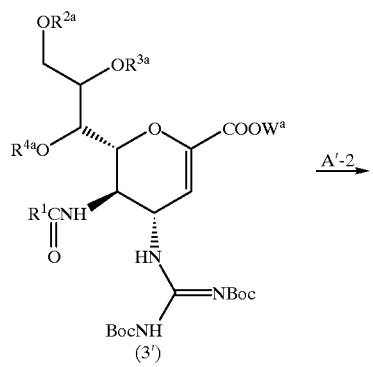

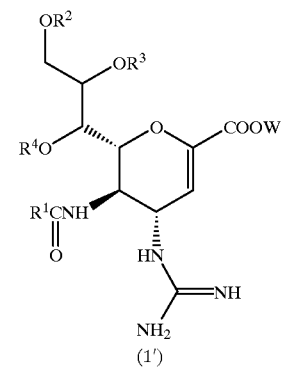

Process A' is a process for preparing the compound (1') of the present invention by eliminating the protecting group of the compound (3') obtained by reacting the raw material compound (2') which is easily available according to the method described later with N,N'-di-t-butoxycarbonylthiourea.

(Step A'-1)

The present step is to prepare the compound (3') by reacting the compound (2') with N,N'-di-t-butoxycarbonylthiourea in an inert solvent in the presence of a base and mercuric chloride.

The solvent employable is not particularly limited so long as it does not affect the reaction and includes aromatic hydrocarbons such as benzene, toluene and xylene; ethers such as diethyl ether, diisopropyl ether, tetrahydrofuran, dioxane, dimethoxyethane and diethylene glycol dimethyl ether, and amides such as N,N-dimethylacetamide and dimethylformamide, preferably amides (particularly N,N-dimethylacetamide and dimethylformamide).

The base employable here includes preferably organic bases such as triethylamine and dimethylaminopyridine.

The reaction temperature is usually from −10 to 50° C., preferably from 10 to 30° C.

The reaction time varies depending on the material used, the base, the reaction temperature, etc. and is usually from 1 to 24 hours, preferably from 5 to 10 hours.

After the reaction, the desired compound is obtained, for example, by filtering the reaction mixture under reduced pressure to remove insolubles, adding a water-immiscible organic solvent such as ethyl acetate thereto, washing the mixture with water, separating the organic layer containing the desired compound, drying the layer over anhydrous magnesium sulfate, and distilling off the solvent.

If necessary, the desired compound can be further purified by recrystalization or various kinds of chromatographies.
(Step A'-2)

The present step is to prepare the compound (1') of the present invention by reacting the compound (3') with a reagent for eliminating the tert-butoxycarbonyl group in an inert solvent.

The solvent employable is not particularly limited so long as it does not affect the reaction and includes preferably alcohols such as methanol and ethanol, water and a mixture thereof.

The reagent for elimination is preferably an acid, and the acid is not particularly limited so long as it is used as an acid catalyst in the usual reaction and includes Bronsted acids such as inorganic acids, e.g. hydrochloric acid, hydrobromic acid, sulfuric acid, perchloric acid and phosphoric acid, and organic acids, e.g. acetic acid, formic acid, oxalic acid, methanesulfonic acid, para-toluenesulfonic acid, trifluoroacetic acid and trifluoromethanesulfonic acid; Lewis acids such as zinc chloride, tin tetrachloride, boron trichloride, boron trriluoride and boron tribromide; and acidic ion exchange resins, preferably organic acids (particularly acetic acid and trifluoroacetic acid).

The reaction temperature is usually from −10 to 50° C., preferably from 10 to 30° C.

The reaction time varies depending on the material, the base, the reaction temperature, etc. and is usually from 15 minutes to 10 hours, preferably from 1 to 5 hours.

After the reaction, the desired compound can be obtained, for example, by neutralizing the reaction mixture, distilling off the solvent under reduced pressure, and then purifying the residue over silica gel column chromatography.

Further, in the case where $R^{2a}$, $R^{3a}$ or $R^{4a}$ is a protecting group of a hydroxyl group or $W^a$ is a protecting group of a carboxyl group, they are further eliminated to obtain the compound (1') of the present invention.

The method for eliminating the protecting group varies depending on the kind of the protecting group and can be carried out according to the methods usually used, for example, the methods described in Protective Groups in Organic Synthesis, Second Edition (1991, Green et al.).

In the case where the protecting group of a hydroxyl group is a trialkylsilyl group such as a tert-butyldimethylsilyl group, acetic acid is preferably used in a mixture of water and tetrahydrofuran, or tetrabutylammonium fluoride is used in tetrahydrofuran.

In the case where the protecting group of a hydroxyl group is an isopropylidene group, the method of Step E'-2 or E'-4 described later is used.

In the case where the protecting group of a carboxyl group is a diphenylmethyl group, catalytic reduction is carried out, an acid such as acetic acid and trifluoroacetic acid is used or trifluoroboran-diethyl ether complex is used.

In the case where the protecting group of a carboxyl group is a benzyl group, catalytic reduction is carried out, and in the case where the protecting group is the methyl group, hydrolysis is carried out.

(Process B')

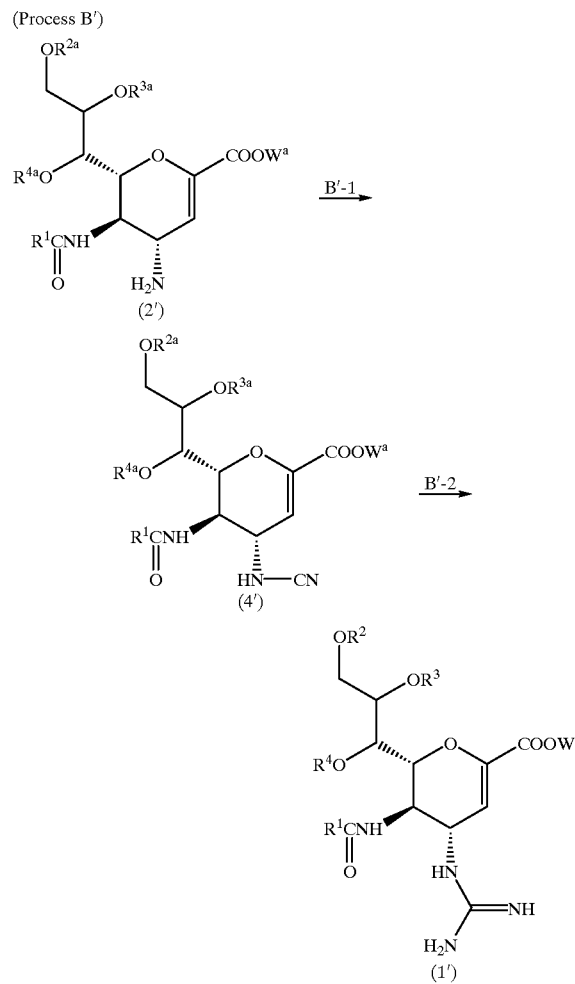

Process B' is a process for preparing the compound (1') of the present invention by reacting the raw material compound (2'), which is easily available according to the method described later, with a cyanating agent, reacting the resulting compound with ammonia, and further, if necessary, eliminating the protecting group.
(Step B'-1)

The present step is to prepare a compound (4') by reacting the compound (2') with a cyanating agent in an inert solvent.

The solvent employable is not particularly limited so long as it does not affect the reaction and includes alcohols such as methanol, ethanol n-propanol, isopropanol, n-butanol, isobutanol, t-butanol, isoamyl alcohol, diethylene glycol, glycerin, octanol, cyclohexanol and methyl cellosolve; amides such as formamide, N,N-dimethylformamide, N,N-dimethylacetamide, N-methyl-2-pyrrolidone, N-methylpyrrolidinone and hexamethylphosphoric triamide; and sulfoxides such as dimethyl sulfoxide and sulfolane, preferably alcohols (particularly methanol).

The cyanating agent employable includes preferably cyanogen bromide, and sodium acetate is simultaneously employed as a base.

The reaction temperature is usually from −10 to 50° C., preferably from 10 to 40° C.

The reaction time varies depending on the material used, the base, the reaction temperature, etc. and is usually from 15 minutes to 10 hours, preferably from 1 to 5 hours.

After the reaction, the desired compound can be obtained, for example, by distilling off the solvent and then purifying the residue by recrystalization or silica gel column chromatography.

(Step B'-2)

The present step is to prepare the compound (1') of the present invention by reacting the compound (4') with ammonia in an inert solvent.

The solvent employable is not particularly limited so long as it does not affect the reaction and includes preferably alcohols (particularly methanol).

The reaction temperature is usually from −10 to 50° C., preferably from 10 to 40° C.

The reaction time varies depending on the material used, the base, the reaction temperature, etc. and is usually from 15 minutes to 10 hours, preferably from 1 to 5 hours.

After the reaction, the desired compound can be obtained, for example, by distilling off the solvent and then purifying the residue by recrystalization or silica gel column chromatography.

Incidentally, in the case where $R^{2a}$, $R^{3a}$ or $R^{4a}$ is a protecting group of a hydroxyl group, or $W^a$ is a protecting group of a carboxyl group, the compound of the present invention is obtained by eliminating the protecting group in a similar manner to Process A'.

(Process C')

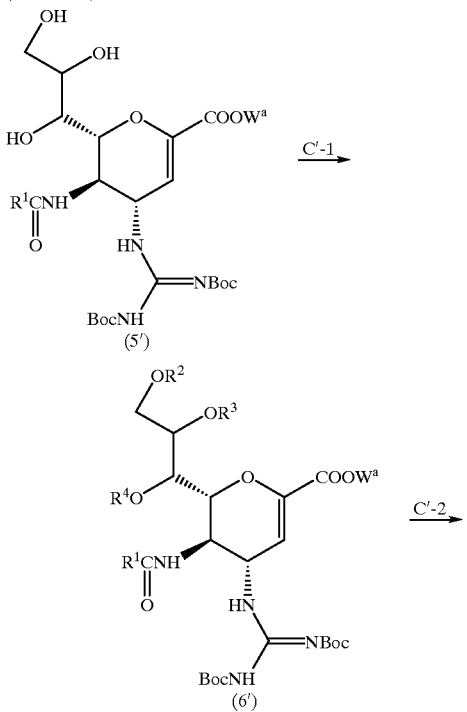

-continued

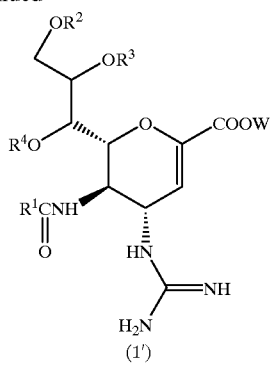

Process C' is a process for preparing the compound (1') of the present invention by acylating partly or entirely the hydroxyl groups of the raw material compound (5') which is easily available according to the method described later, and then eliminating the protecting group of the resulting compound.

(Step C'-1)

The present step is to prepare the compound (6') by introducing a desired acyl group to the compound (5') in an inert solvent.

The acylation method includes the following methods 1 to 3.

Method 1'

Method 1' is to react a compound of the general formula: RCO-Hal or a compound of the general formula: RCO—O—COR

[wherein,

R represents an alkyl group, Hal represents a group to be eliminated, and the group to be eliminated is not particularly limited so long as it is a group to be eliminated as a nucleophilic residue and includes preferably a halogen atom such as chlorine, bromine and iodine; a lower alkoxycarbonyloxy group such as methoxycarbonyloxy and ethoxycarbonyloxy; a halogenated alkylcarbonyloxy group such as chloroacetyloxy, dichloroacetyloxy, trichloroacetyloxy and trifluoroacetyloxy; a lower alkanesulfonyloxy group such as methanesulfonyloxy and ethanesulfonyloxy; a halogeno lower alkanesulfonyloxy group such as trifluoromethanesulfonyloxy and pentafluoroethanesulfonyloxy; and an arylsulfonyloxy group such as benzenesulfonyloxy, p-toluenesulfonyloxy and p-nitrobenzenesulfonyloxy, more preferably a halogen atom, a halogeno lower alkanesulfonyloxy group and an arylsulfonyloxy group]

with the compound (5') in a solvent in the presence or absence of a base.

The solvent employable is not particularly limited so long as it does not inhibit the reaction and dissolves the starting material to some extent, and includes preferably aliphatic hydrocarbons such as hexane and heptane; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutyronitrile; and amides such as formamide, N,N-dimethylformamide, N,N- dimethylacetamide, N-methyl-2-pyrrolidone, N-methylpyrrolidinone and hexamethylphosphoric triamide.

The base employable is not particularly limited so long as it is used as a base in the usual reaction and includes preferably organic bases such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino) pyridine, 2,6-di(tert-butyl)-4-methylpyridine, quinoline, N,N-dimethylaniline and N,N-diethylaniline.

Incidentally, 4-(N,N-dimethylamino)pyridine and 4-pyrrolidinopyridine can be used at a catalytic amount by combining it with other bases, and further quaternary ammonium salts such as benzyltriethylammonium chloride and tetrabutylammonium chloride and crown ethers such as dibenzo-18-crown-6 can be also added thereto in order to effectively carry out the reaction.

The reaction is usually carried out at from −20° C. to the refluxing temperature of the solvent used, preferably from 0° C. to the refluxing temperature of the solvent used.

The reaction time varies mainly depending on the reaction temperature, the raw material compound, the base used or the kind of the solvent used, and is usually from 10 minutes to 3 days, preferably from 1 to 6 hours.

Method 2'

Method 2' is to react a compound of the general formula: RCOOH [wherein R has the same meaning as defined above] with the compound (5') in a solvent in the presence or absence of "an esterifying agent" and a catalytic amount of base.

The "esterifying agent" employable includes a condensing agent; halogenated formates such as methyl chloroformate and ethyl chloroformate; and cyanophosphoric acid diesters such as diethyl cyanophosphate. Such "condensing agents" includes N-hydroxy derivatives such as N-hydroxysuccinimide, 1-hydroxybenzotriazole and N-hydroxy-5-norbomene-2,3-dicarboxyimide; disulfide compounds such as 2,2'-dipyridyl disulfide; succinic acid compounds such as N,N'-disuccinimidyl carbonate; phosphinic chloride compounds such as N,N'-bis(2-oxo-3-oxazolidinyl)phosphinic chloride; oxalate derivatives such as N,N'-disuccinimidyl oxalate (DSO), N,N'-diphthalimide oxalate (DPO), N,N'-bis(norbornenylsuccinimidyl)oxalate (BNO), 1,1'-bis(benzotriazolyl)oxalate (BBTO), 1,1'-bis(6-chlorobenzotriazolyl)oxalate (BCTO) and 1,1'-bis(6-trifluoromethylbenzotriazolyl)oxalate (BTBO); triarylphosphines such as triarylphosphines, e.g. triphenylphosphine and azodicarboxylic acid di-lower alkyl-triarylphosphines such as diethyl azodicarboxylate-triphenylphosphine; N-lower alkyl-5-arylisoxazolium-3'-sulfonates such as N-ethyl-5-phenylisoxazolium-3'-sulfonate; carbodiimide derivatives such as N',N'-dicycloalkylcarbodiimides, e.g. N',N'-dicyclohexylcarbodiimide (DCC) and 1-ethyl-3-(3-dimethylaminopropyl)carbodiimide (EDAPC); diheteroaryldiselenides such as di-2-pyridyldiselenide; arylsulfonyltriazolides such as p-nitrobenzenesulfonyltriazolide; 2-halo-1-lower alkylpyridinium halides such as 2-chloro-1-methylpyridinium iodide; diarylphosphorylazides such as diphenylphosphorylazide (DPPA); and imidazole derivatives such as 1,1'-oxazolyldiimidazole and N,N'-carbonyldiimidazole, preferably diarylphosphorylazides.

The solvent employable is not particularly limited so long as it does not inhibit the reaction and dissolves the starting material to some extent, and includes preferably aliphatic hydrocarbons such as hexane and heptane; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether, nitriles such as acetonitrile and isobutyronitrile; amides such as formamide, N,N-dimethylformamide, N,N-dimethylacetamide, N-methyl-2-pyrrolidone, N-methylpyrrolidinone and hexamethylphosphoric triamide.

As the base to be used, similar bases to those described in the above <Method 1'> can be employed.

The reaction is carried out at from −20° C. to 80° C., preferably from 0° C. to room temperature.

The reaction time varies depending mainly on the reaction temperature, the raw material compound, the reaction reagent or the kind of solvent used, and is usually from 10 minutes to 3 days, preferably from 30 minutes to one day.

Method 3'

Method 3' is to react the compound of the general formula: RCOOH [wherein R has the same meaning as defined above] with the compound (5') in a solvent in the presence of halogenated phosphoric acid dialkyl ester such as diethyl chlorophosphate and a base.

The solvent employable is not particularly limited so long as it does not inhibit the reaction and dissolves the starting material to some extent, and includes preferably aliphatic hydrocarbons such as hexane and heptane; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether, nitrites such as acetonitrile and isobutyronitrile; amides such as fornamide, N,N-dimethylformamide, N,N-dimethylacetamide, N-methyl-2-pyrrolidone, N-methylpyrrolidinone and hexamethylphosphoric triamide.

As the base used, similar bases to those described in the above <Method 1> can be employed.

The reaction is carried out at from 0° C. to the refluxing temperature of the solvent used, preferably from room temperature to 50° C.

The reaction time varies depending mainly on the reaction temperature, the raw material compound, the reaction reagent or the kind of solvent used, and is usually from 10 minutes to 3 days, preferably from 30 minutes to one day.

In the above <Method 1'>, <Method 2'> and <Method 3'>, the compound (6') in which from 1 to 3 acyl groups are introduced to the compound (5') can be obtained by appropriately controlling an equivalent amount of the acylating agent used relative to the compound (5').

After the reaction, the desired compound (6') of the present reaction is collected from the reaction mixture according to the conventional method.

For example, the desired compound can be obtained by appropriately neutralizing the reaction mixture, eliminating insolubles by filtration if they exist, adding a water-immiscible organic solvent such as ethyl acetate thereto, washing it with water, separating the organic layer containing the desired compound, drying the layer over anhydrous magnesium sulfate and distilling off the solvent.

The desired compound thus obtained can be separated and purified, if necessary, by appropriately combining the conventional methods, for example, recrystalization, reprecipitation or a method usually employable for separation and purification of organic compounds, for example, adsorption column chromatography using carriers such as silica gel, alumina, Florisil of magnesium-silica gel system; a method using a synthesized adsorbing agent such as partition column chromatography using carriers such as Sephadex LH-20 (manufactured by Pharmacia Co., Ltd.), Amberlite XAD-11 (manufactured by Rohm & Haas Co., Ltd.) and Diaion HP-20 (Mitsubishi Chemical Corp.), or normal phase-reversed phase column chromatography using silica gel or alkylated silica gel (preferably high performance liquid chromatography), and eluting it with appropriate eluting solutions.

(Step C'-2)

The present step is to prepare the compound (1') of the present invention by eliminating a t-butoxycarbonyl group in the compound (6') in an inert solvent.

The present step can be carried out similarly to the procedures of Step A'-2.

Further, in the case where $W^a$ is a protecting group of a carboxyl group, the compound (1') of the present invention can be obtained by fiwer eliminating them similarly to the procedures of Step A'-2.

(Process D')

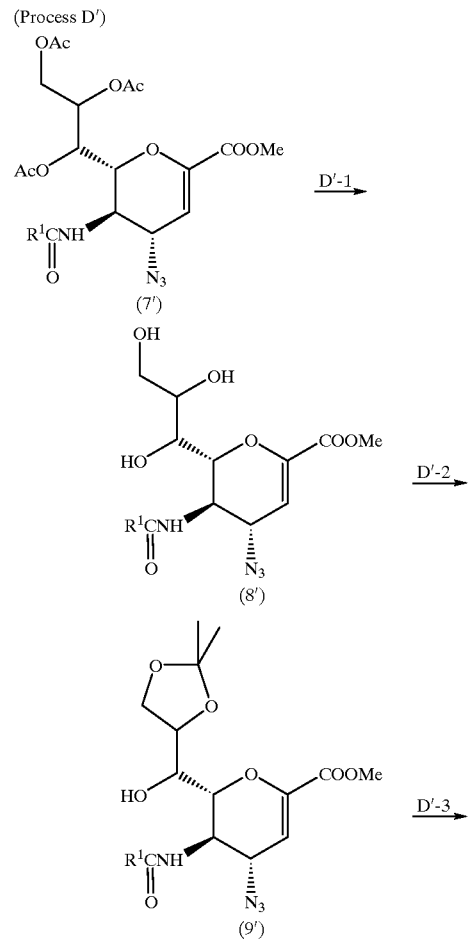

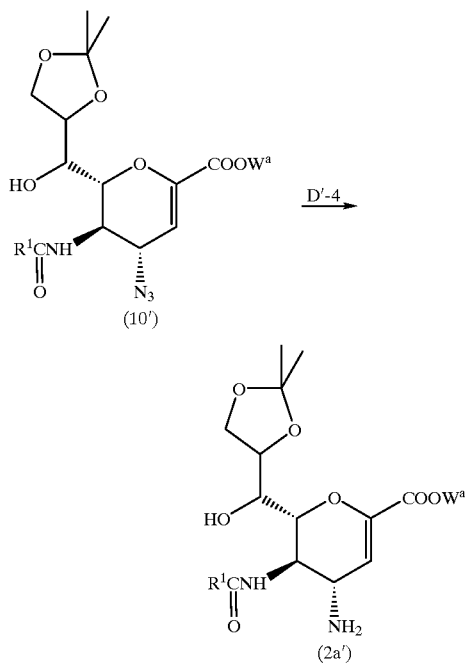

Process D' is to prepare the compound (2a') which is one of the raw material compounds in Processes A' and B' using the raw material compound (7') easily available according to the method described later.

(Step D'-1)

The present step is to prepare a compound (8') by reacting the compound (7') with a base in an inert solvent.

The solvent employable is not particularly limited so long as it does not inhibit the reaction and dissolves the starting material to some extent, and includes preferably aliphatic hydrocarbons such as hexane, heptane, ligroin and petroleum ether, aromatic hydrocarbons such as benzene, toluene and xylene; halogenated hydrocarbons such as methylene chloride, chloroform, carbon tetrachloride, dichloroethane, chlorobenzene and dichlorobenzene; ethers such as diethyl ether, diisopropyl ether, tetrahydrofuran, dioxane, dimethoxyethane and diethylene glycol dimethyl ether; and methanol, preferably halogenated hydrocarbons and methanol.

The base employable is not particularly limited so long as it does not affect other functional groups (for example, methyl ester) and includes preferably alkali metal methoxides such as sodium methoxide and potassium methoxide.

The reaction temperature is usually from −10 to 50° C., preferably from 10 to 30° C.

The reaction time varies depending on the material used, the base, the reaction temperature, etc., and is usually from 15 minutes to 10 hours, preferably from 1 to 5 hours.

After the reaction, the desired compound can be obtained, for example, by neutralizing the reaction mixture with hydrochloric acid/dioxane solution, distilling off the solvent under reduced pressure, and then purifying the residue over silica gel column chromatography.

(Step D'-2)

The present step is to prepare the compound (9') by reacting the compound (8') with a reagent for introducing an isopropylidene group in an inert solvent.

The solvent employable is not particularly limited so long as it does not inhibit the reaction and dissolves the starting material to some extent, and includes aliphatic hydrocarbons such as hexane, heptane, ligroin and petroleum ether; aromatic hydrocarbons such as benzene, toluene and xylene; ethers such as diethyl ether, diisopropyl ether, tetrahydrofuran, dioxane, dimethoxyethane and diethylene glycol dimethyl ether; and ketones such as acetone, methyl ethyl ketone, methyl isobutyl ketone, isophorone and cyclohexanone, preferably ketones (particularly acetone).

The reagent employable includes preferably 2,2-dimethoxypropane and acids such as p-toluenesulfonic acid are used as a catalyst.

The reaction temperature is usually from −10 to 50° C., preferably from 10 to 30° C.

The reaction time varies depending on the material used, the base, the reaction temperature, etc., and is usually from 15 minutes to 10 hours, preferably from 1 to 5 hours.

After the reaction, the desired compound can be obtained, for example, by adding a water-immiscible solvent such as ethyl acetate and an aqueous sodium hydrogencarbonate solution to the reaction mixture, extracting the desired compound with ethyl acetate, and distilling off the solvent. The desired compound can be further purified, if necessary, by recrystalization or various kinds of chromatographies.

(Step D'-3)

The present step is, if necessary, 1) to substitute the methyl group of the methyl carboxylate portion with other ester residue, 2) to hydrolize the methyl carboxylate portion or 3) to introduce a protecting group of the carboxyl group or the ester residue after hydrolysis of 2).

(Ester interchange)

The present step is to prepare the compound (10') by reacting the compound (9') with an alcohol which can give the desired ester group in an inert solvent in the presence of a base.

The solvent employable is not particularly limited so long as it does not inhibit the reaction and includes, for example, aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; ethers such as diethyl ether, diisopropyl ether, tetrahydrofliran, dioxane, dimethoxyethane and diethylene glycol dimethyl ether, and alcohols such as methanol, ethanol, n-propanol, isopropanol, n-butanol isobutanol, t-butanol, isoamyl alcohol diethylene glycol, glycerin, octanol, cyclohexanol and methyl cellosolve. Preferably, an alcohol forming the desired ester group may be employed as the solvent.

The base employable includes preferably organic bases such as pyridine, triethylamine, diethylamine and 4-N,N-dimethylaminopyridine.

After the reaction, the desired compound can be obtained, for example, by neutralizing the reaction mixture with an acid, adding a water-immiscible solvent such as ethyl acetate to the mixture, extracting the desired compound with ethyl acetate, etc., washing it with water, and distilling off the solvent. The desired compound can be further purified, if necessary, by recrystalization or various kinds of chromatographies.

(Diphenylmethylation)

The present step is to prepare the compound (10') by reacting the compound (9') with diphenyldiazomethane in an inert solvent in the presence of Lewis acid.

The solvent employable is not particularly limited so long as it does not inhibit the reaction and dissolves the starting material to some extent, and includes preferably aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane and chlorobenzene; ethers such as diethyl ether, diisopropyl ether, tetrahydrofuran, dioxane, dimethoxyethane and ethylene glycol dimethyl ether, and alcohols such as methanol, ethanol, n-propanol, isopropanol, n-butanol, isobutanol, t-butanol, isoamyl alcohol, diethylene glycol, glycerin, octanol, cyclohexanol and methyl cellosolve, more preferably alcohols (artcularly methanol), halogenated hydrocarbons (dichloromethane); and mixtures thereof.

The Lewis acid employable includes preferably boron trifluoride-ether complex.

The reaction temperature is usually from 0 to 50° C., preferably room temperature.

The reaction time varies depending on the starting material, Lewis acid and the reaction temperature, and is usually from 10 minutes to 5 hours, preferably from 1 to 3 hours.

After the reaction, the solvent is distilled off and purification by recrystalization or chromatography is carried out to obtain the desired compound.

(Hydrolysis)

The present step is to prepare the compound (10') in which $W^a$ is a hydrogen atom by hydrolizing the compound (9') in an inert solvent in the presence of a base.

The solvent employable is not particularly limited so long as it does not inhibit the reaction and dissolves the starting material to some extent, and includes aromatic hydrocarbons such as benzene and toluene; ethers such as diethyl ether and tetrahydrofuran; halogenated hydrocarbons such as dichloromethane and chloroform; ketones such as acetone and methyl ethyl ketone; water, and mixtures of these organic solvents and water.

The base employable includes alkali metal hydroxides such as lithium hydroxide, sodium hydroxide and potassium hydroxide; and alkali metal hydrogencarbonates such as sodium hydrogencarbonate and potassium hydrogencarbonate.

The reaction temperature is usually from −10 to 50° C., preferably from 10 to 30° C.

The reaction time varies depending on the raw material used, the base, the reaction temperature, etc., and is usually from 15 minutes to 10 hours, preferably from 1 to 5 hours.

After the reaction, the desired compound can be obtained, for example, by cooling the reaction mixture, making it weakly acidic using dilute hydrochloric acid, adding a water-immiscible solvent such as ethyl acetate to the reaction mixture, extracting the desired compound with ethyl acetate, and distilling off the solvent. The tdesired compound can be further purified by recrystalization or various kinds of chromatographies.

(Introduction of the protecting group of carboxyl group or the ester residue)

The present step is to prepare the compound (10') by introducing the protecting group or the ester residue to the carboxyl group at the 1-position of the compound (9') in which $W^a$ is a hydrogen atom.

Introduction of the protecting group or the ester residue varies depending on the kind of ester residue or the protecting group, and can be carried out according to the methods generally used in the field of organic synthesis chemistry, for example, the methods described in Protective Groups in Organic Synthesis, Second Edition (1991, Green et al.).

(Step D'-4)

The present step is to prepare the compound (2a') from the compound (10') using a reducing agent in an inert solvent.

The solvent employable is not particularly limited so long as it does not inhibit the reaction and dissolves the starting material to some extent, and includes preferably aliphatic hydrocarbons such as hexane, heptane, ligroin and petroleum ether, aromatic hydrocarbons such as benzene, toluene and xylene; ethers such as diethyl ether, diisopropyl ether, tetrahydrofaran, dioxane, dimethoxyethane and diethylene glycol dimethyl ether, alcohols such as methanol, ethanol, n-propanol, isopropanol, n-butanol, isobutanol, t-butanol, isoamyl alcohol, diethylene glycol, glycerin, octanol, cyclohexanol and methyl cellosolve; ketones such as acetone, methyl ethyl ketone, methyl isobutyl ketone, isophorone and cyclohexanone; nitriles such as acetonitfile and isobutyronitrile; amides such as formamide, N,N-dimethylformamide, N,N-dimethylacetamide, N-methyl-2-pyrrolidone, N-methylpyrrolidinone and hexamethylphosphoric triamide; sulfoxides such as dimethyl sulfoxide and sulfolane; aliphatic carboxylic acids such as acetic acid; and mixtures of these organic solvents and water, preferably the alcohols (particularly methanol), the ethers such as tetrahydrofuran and dioxane, the aliphatic carboxylic acids such as acetic acid, and mixtures of these organic solvents and water.

As the reducing agent used, a catalyst such as palladium-carbon, platinum and Raney nickel may be employed in the presence of hydrogen gas, and a Lindlar catalyst (Pd-BaSO$_4$ or Pd-CaCO$_3$ and quinoline or lead acetate are employed in combination) is particularly preferably employed.

The reaction temperature is usually from –10C to 50° C., preferably from 10 to 30° C.

The reaction time varies depending on the raw material used, the base, the reaction temperature, etc., and is usually from 15 minutes to 10 hours, preferably from 1 to 5 hours.

After the reaction, the desired compound can be obtained, for example, by filtering the reaction mixture under reduced pressure to remove the catalyst, and distilling off the solvent under reduced pressure. The desired compound can be further purified, if necessary, by recrystalization or various kinds of chromatographies.

(Process E')

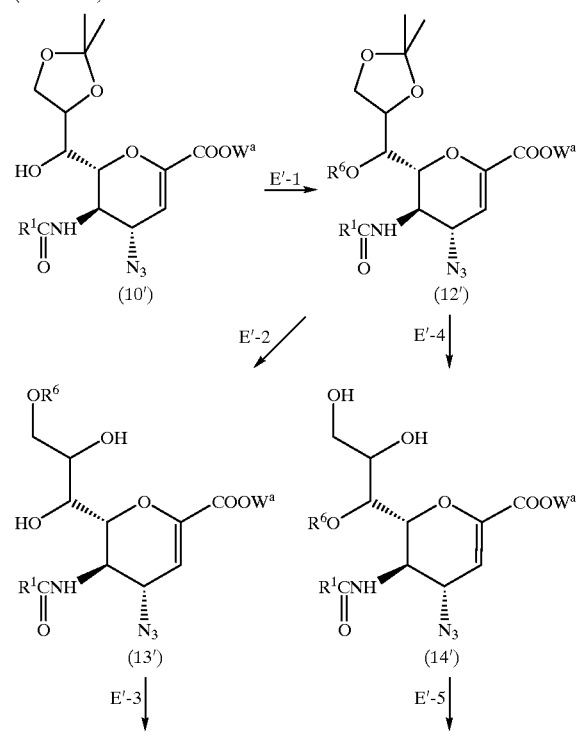

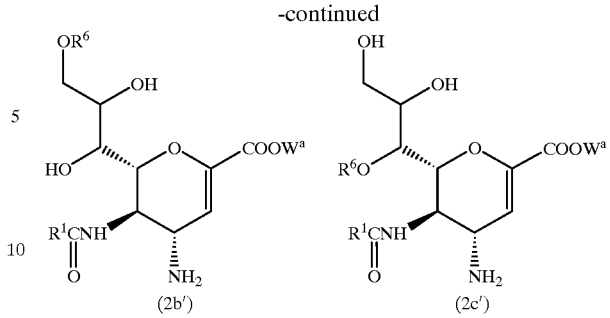

Process E is a process for preparing the compound (2b') or (2c') which is one of the raw material compounds in Processes A' and B' using the raw material compound (10') which is easily available according to the above method.

(Step E'-1)

The present step is to prepare the compound (12') by introducing the desired acyl group to the compound (10') in an inert solvent.

Further, the present step can be carried out similarly to the procedures of the above Step C'-1.

(Step E'-2)

The present step is to prepare the compound (13') by treating the compound (12') with a reagent for eliminating the isopropylidene group in an inert solvent.

The solvent employable is not particularly limited so long as it does not inhibit the reaction and dissolves the starting material to some extent, and includes preferably halogenated hydrocarbons such as methylene chloride and chloroform.

As the reagent used for the elimination, an acid is preferable, and the acid is not particularly limited so long as it is used as an acid catalyst in the usual reaction and includes Bronsted acids such as inorganic acids, e.g. hydrochloric acid, hydrobromic acid, sulfuric acid, perchloric acid and phosphoric acid, and organic acids such as formic acid, oxalic acid, methanesulfonic acid, p-toluenesulfonic acid, trifluoroacetic acid and trifluoromethanesulfonic acid; and Lewis acids such as zinc chloride, tin tetrachloride, boron trichloride, boron trifluoride and boron tribromide and acidic ion exchange resins, preferably organic acids (particularly the trifluoroacetic acid).

The reaction temperature is usually from –10 to 50° C., preferably from 10 to 30° C.

The reaction time varies depending on the raw material used, the base, the reaction temperature, etc., and is usually from 15 minutes to 10 hours, preferably from 1 to 5 hours.

After the reaction, the desired compound can be obtained, for example, by neutralizing the reaction mixture, distilling off the solvent under reduced pressure, and then purifying the residue over silica gel chromatography.

Further, in the present step, the acyl group (R$^{6'}$) at the 7-position is transferred to the 9-position.

(Step E'-3)

The present step is to prepare the desired raw material compound (2b') from the compound (13') using a reducing agent in an inert solvent.

The present step can be carried out similarly to the procedures of the above Step D'-4.

(Step E'-4)

The present step is to prepare the compound (14') of the present invention by treating the compound (12') with a reagent for eliminating the isopropylidene group in an inert solvent in the presence of an acid catalyst.

The solvent employable is not particularly limited so long as it does not inhibit the reaction and dissolves the starting material to some extent, and includes preferably a mixture of acetic acid (which is simultaneously utilized as the acid catalyst) and water.

The reaction temperature is usually from 10 to 70° C., preferably from 30 to 60° C.

The reaction time varies depending on the raw material used, the base, the reaction temperature, etc., and is usually from 15 minutes to 24 hours, preferably from 10 to 20 hours.

After the reaction, the desired compound can be obtained, for example, by distilling off the solvent under reduced pressure, adding a water-immiscible solvent such as ethyl acetate and an aqueous sodium hydrogencarbonate solution to the reaction mixture, extracting the desired compound with ethyl acetate, and distilling off the solvent. The desired compound can be further purified, if necessary, by recrystalization or various kinds of chromatographies.

(Step E'-5)

The present step is to prepare the desired raw material compound (2c') from the compound (14') using a reducing agent in an inert solvent.

The present step can be carried out similarly to the procedures in the above Step D'-4.

(Process F')

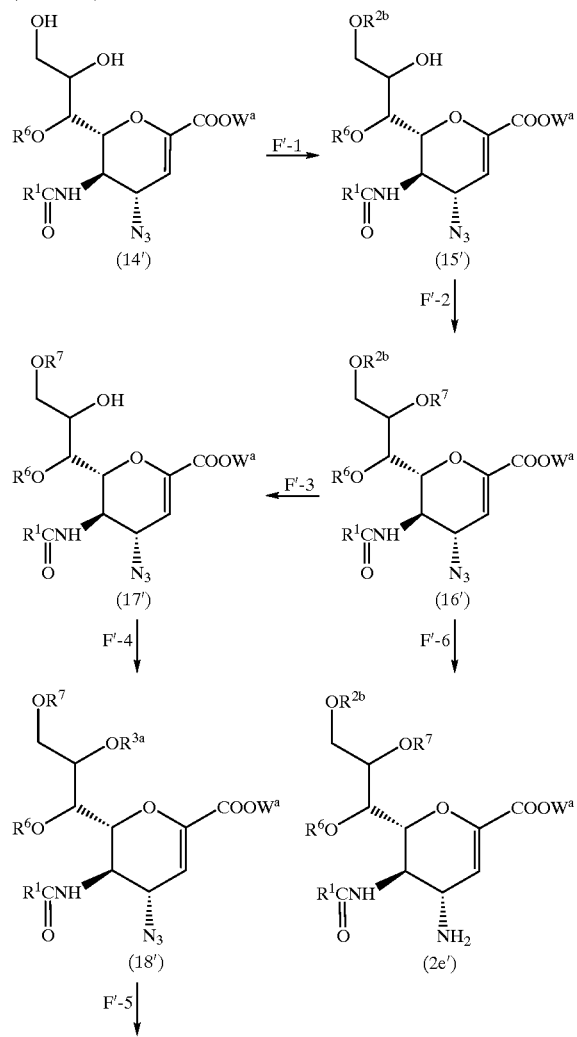
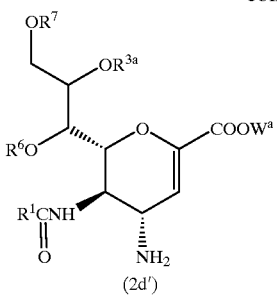

Process F' is a process for preparing the compound (2d') or (2c') which is one of the raw material compounds in Processes A' and B' using the raw material compound (14') which is easily available according to the above method.

(Step F'-1)

The present step is to prepare the compound (15') by reacting the compound (14') with a reagent for protecting the hydroxyl group in an inert solvent.

The protecting group is not particularly limited and includes preferably a tert-butyldimethylsilyl group and a tert-butyldiphenylsilyl group.

Silylation can be carried out according to the usual methods. For example, silylation can be carried out by reacting tert-butyldimethylsilyl halide (particularly chloride) in dimethylformamide in the presence of a base such as triethylamine and 4-(N,N-dimethylamino)pyridine.

The reaction temperature is usually from −10 to 50° C., preferably from 10 to 40° C.

The reaction time varies depending on the raw material used, the base, the reaction temperature, etc., and is usually from 15 minutes to 24 hours, preferably from 10 to 20 hours.

After the reaction, the desired compound can be obtained, for example, by adding a water-immiscible solvent such as ethyl acetate and an aqueous sodium hydrogencarbonate solution to the reaction mixture, extracting the desired compound with ethyl acetate, and distilling off the solvent The desired compound can be further purified, if necessary, by recrystalization or various kinds of chromatographies.

(Step F'-2)

The present step is to prepare the compound (16') by introducing the desired acyl group to the compound (15') in an inert solvent.

The present step can be carried out similarly to the procedures of Step C'-1.

(Step F'-3)

The present step is to prepare the compound (17') by reacting the compound (16') with a reagent for eliminating the protecting group (preferably a tert-butyldimethylsilyl group or a tert-butyldiphenylsilyl group) of the hydroxyl group in an inert solvent.

The solvent employable includes preferably alcohols such as methanol and ethanol, water and mixtures thereof.

Acids are preferably used as the reagent for the elimination, and the acid is not particularly limited so long as it is used as the acid catalyst in the usual reactions and includes Bronsted acids such as inorganic acids, e.g. hydrochloric acid, hydrobromic acid, sulfuric acid, perchloric acid and phosphoric acid, and organic acids, e.g. acetic acid, formic acid, oxalic acid, methanesulfonic acid, p-toluenesulfonic acid, trifluoroacetic acid and trifluoromethanesulfonic acid, and Lewis acids such as zinc chloride, tin tetrachloride, boron trichloride, boron trifluoride and boron tribromide, and acidic ion exchange resins, preferably organic acids (particularly acetic acid and trifluoroacetic acid).

Reagents which produce a fluoride ion such as tetrabutylammonium fluoride can be also used, as desired.

The reaction temperature is usually from −10 to 50° C., preferably from 10 to 30° C.

The reaction time varies depending on the raw material used, the base, the reaction temperature, etc., and is usually from 15 minutes to 10 hours, preferably from 1 to 5 hours.

After the reaction, the desired compound can be obtained, for example, by neutralizing the reaction mixture, distilling off the solvent under reduced pressure, and then purifying the residue over silica gel chromatography.

In the present step, the acyl group ($R^7$) at the 8-position is transferred to the 9-position.

(Step F'-4)

The present step is to prepare the compound (18') by 1) protecting the hydroxyl group at the 8-position of the compound (17') or 2) introducing the desired acyl group, as desired.

(Introduction of the acyl group)

The present step can be carried out similarly to the procedures of Step C'-1.

(Introduction of the protecting group)

As the protecting group, tert-butyldimethylsilyl group is preferable, and introduction of the protecting group is carried out using tert-butyldimethylsilyl triflate and lutidine in methylene chloride.

(Step F'-5)

The present step is to prepare the desired raw material compound (2d') from the compound (18') using a reducing agent in an inert solvent.

The present step can be carried out similarly to the procedures of Step D'-4.

(Step F'-6)

The present step is to prepare the desired raw material compound (2e') from the compound (16') using a reducing agent in an inert solvent.

The present step can be carried out similarly to the procedures of Step D'-4.

(Process G')

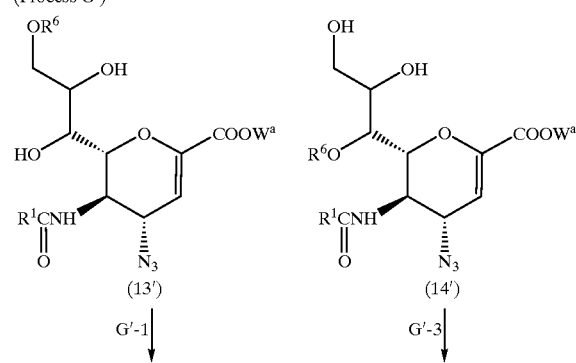

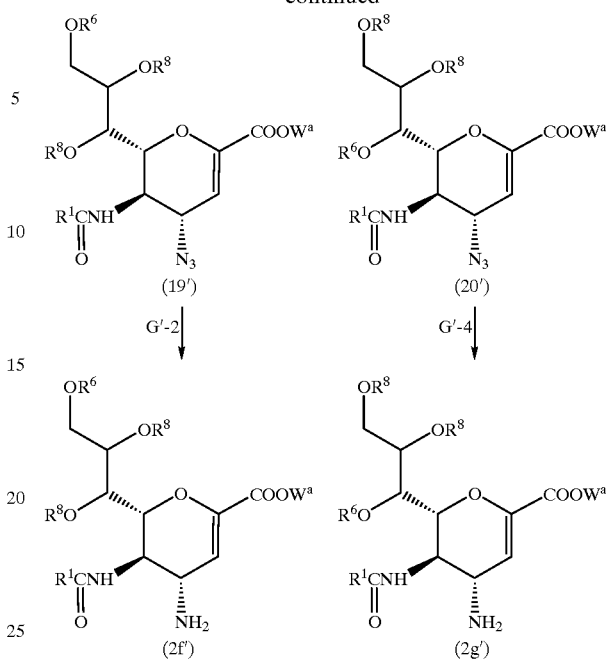

Process G' is a process for preparing the compound (2f') or (2g') which is one of the raw material compounds in Processes A' and B' using the above compound (13') or (14') described above.

(Step G'-1)

The present step is to prepare the compound (19') by introducing the desired acyl group to the compound (13') in an inert solvent.

The present step can be carried out similarly to the procedures of Step C'-1.

(Step G'-2)

The present step is to prepare the desired raw material compound (2f') from the compound (19') using a reducing agent in an inert solvent.

The present step can be carried out similarly to the procedures of Step D'-4.

(Step G'-3)

The present step is to prepare the compound (20') by introducing the desired acyl group to the compound (14') in an inert solvent.

The present step can be carried out similarly to the procedures of Step C'-1.

(Step G'-4)

The present step is to prepare the desired raw material compound (2g') from the compound (20') using a reducing agent in an inert solvent.

The present step can be carried out similarly to the procedures of Step D'-4.

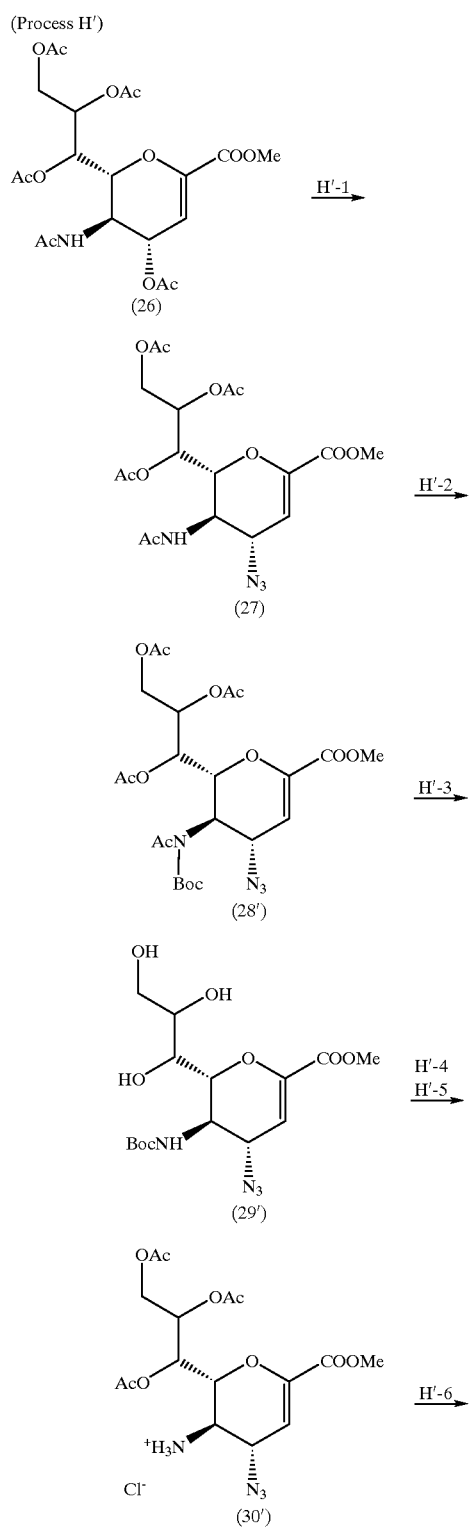
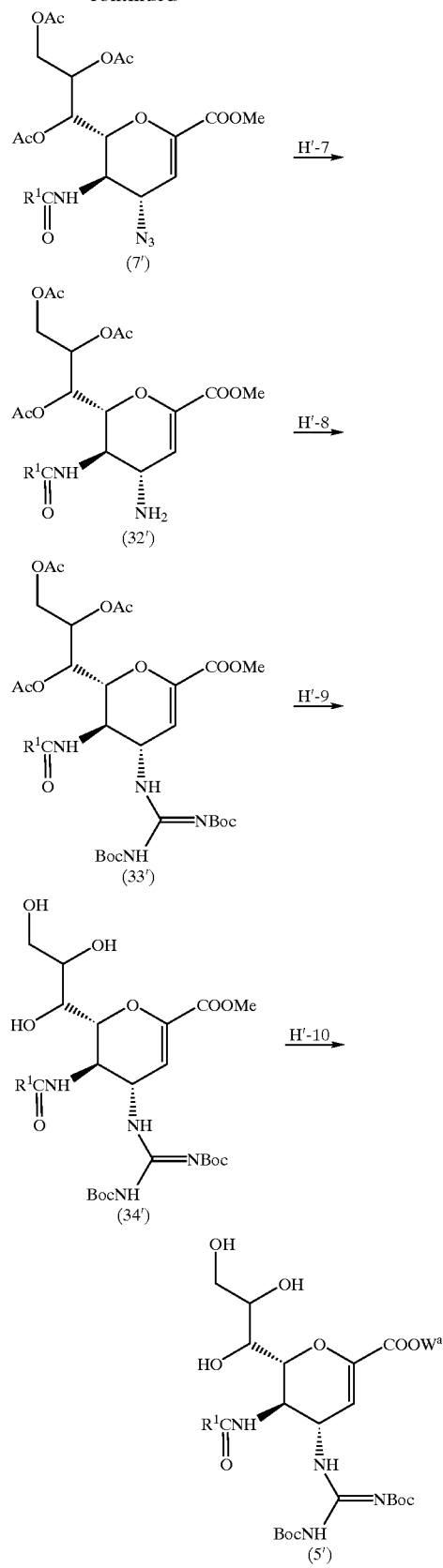

Process H' is a process for preparing the compound (5') which is the raw material compound in Process C using the well known compound (26') described in Carbohydrate Research, 83, 163–169 (1980) or WO 95/32955.
(Step H'-1)

The present step is to prepare the compound (27') by reacting the known compound (26') with an azidating agent in an inert solvent.

The solvent employable is not particularly limited so long as it does not inhibit the reaction and dissolves the starting material to some extent, and includes preferably aromatic hydrocarbons such as benzene, toluene and xylene; halogenated hydrocarbons such as methylene chloride and chloroform; ethers such as diethyl ether, tetrahydrofuran, dioxane and dimethoxyethane; and nitrites such as acetonitrile.

The reagent employable is not particularly limited so long as it is usually used for azidation and includes preferably diaryl phosphoric azide derivatives such as diphenyl phosphoric azide; trialkylsilylazides such as trimethylsilylazide and triethylsilylazide and azidated alkali metal salts such as sodium azide and potassium azide, preferably the sodium azide.

The reaction temperature is usually from −10 to 50° C., preferably from 10 to 30° C.

The reaction time varies depending on the raw material used, the base, the reaction temperature, etc., and is usually from 15 minutes to 10 hours, preferably from 1 to 5 hours.

After the reaction, the desired compound can be obtained, for example, by neutralizing the reaction mixture with a hydrochloric acid/dioxane solution, and purifying the residue obtained by distilling off the solvent under reduced pressure over silica gel chromatography.
(Step H'-2)

The present step is to prepare the compound (28') by reacting the compound (27') with a t-butoxycarbonylating agent in an inert solvent.

The t-butoxycarbonylation can be carried out by reacting di-tert-butyl dicarbonate or 2-(tert-butoxycarbonyloxyimino)-2-phenylacetonitrile in an inert solvent (for example, aromatic hydrocarbons such as benzene and toluene; halogenated hydrocarbons such as methylene chloride and chloroform; ethers such as diethyl ether, tetrahydrofuran and dioxane; and amides such as dimethylformamide) in the presence of a base (for example, 4-(N,N-dimethylamino)pyridine).

After the reaction, the desired compound can be obtained, for example, by neutralizing the reaction mixture, distilling off the solvent under reduced pressure, adding a water-immiscible solvent such as ethyl acetate thereto, extracting the desired compound with ethyl acetate, and distilling off the solvent. The desired compound can be further purified, if necessary, by recrystalization or various kinds of chromatographies.
(Step H'-3)

The present step is to prepare the compound (29') by reacting the compound (28') with a base in an inert solvent.

The present step can be carried out similarly to the procedures of Step D-1. (Step H'-4)

The present step is to acetylate the compound (29') in an inert solvent. The acetylation is carried out according to the usual method for protecting a hydroxyl group. For example, the acetylation can be carried out by 1) reacting with acetic anhydride in pyridine or 2) reacting with acetyl halide (particularly chloride) in methylene chloride in the presence of a base catalyst (for example, triethylamine and 4-N,N-dimethylaminopyridine).

After the reaction, the desired compound can be obtained by distilling off the solvent under reduced pressure, adding a water-immiscible solvent such as ethyl acetate and an aqueous sodium hydrogencarbonate solution to the residue, extracting the desired compound with ethyl acetate, and distilling off the solvent. The desired compound can be further purified, if necessary, by recrystalization or various kinds of chromatographies.
(Step H'-5)

The present step is to prepare the compound (30') by treating the compound obtained in Step H'-4 with a reagent which eliminates a t-butoxycarbonyl group in an inert solvent.

The elimination of the t-butoxycarbonyl group is carried out according to the usual methods.

The solvent employable is not particularly limited so long as it does not inhibit the reaction and dissolves the staring material to some extent, and includes preferably aliphatic hydrocarbons such as hexane, heptane, ligroin and petroleum ether; aromatic hydrocarbons such as benzene, toluene and xylene; halogenated hydrocarbons such as methylene chloride, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; amides such as formamide, N,N-dimethylformamide, N,N-dimethylacetamide, N-methyl-2-pyrrolidone, N-methylpyrrolidinone and hexamethylphosphoric triamide; and sulfoxides such as dimethyl sulfoxide and sulfolane, preferably the halogenated hydrocarbons (particularly methylene chloride).

The reagent employable is not particularly limited so long as it is usually used and includes preferably hydrochloric acid.

The reaction temperature is usually from −10 to 50° C., preferably from 10 to 30° C.

The reaction time varies depending on the raw material used, the base, the reaction temperature, etc., and is usually from 15 minutes to 24 hours, preferably from 1 to 10 hours.

After the reaction, the desired compound can be obtained, for example, by distilling off the solvent under reduced pressure, adding a water-immiscible solvent such as ethyl acetate and an aqueous sodium hydrogencarbonate solution to the reaction mixture, extracting the desired compound with ethyl acetate, and distilling off the solvent. The desired compound can be further purified, if necessary, by recrystalization or various kinds of chromatographies.
(Step H'-6)

The present step is to prepare the compound (7') by introducing the desired acyl group to the compound (30') in an inert solvent.

The present step can be carried out similarly to the procedures of Step C'-1.
(Step H'-7)

The present step is to prepare the compound (32') from the compound (7') using a reducing agent in an inert solvent.

The present step can be carried out similarly to the procedures of Step D'-4.
(Step H'-8)

The present step is to prepare the compound (33') by reacting the compound (32') with N,N'-di-t-butoxycarbonylthiourea in an inert solvent in the presence of a base and mercuric chloride.

The present step can be carried out similarly to the procedures of Step A'-1.
(Step H'-9)

The present step is to prepare the compound (34') by reacting the compound (33') with a base in an inert solvent.

The present step can be carried out similarly to the procedures of Step D'-1.

(Step H'-10) Ester interchange, hydrolysis, protection or esterification

The present step is 1) to substitute the methyl group of the methyl carboxylate portion with another ester residue, 2) to hydrolize the methyl carboxylate portion, or 3) to introduce a protecting group of the carboxyl group or an ester residue after hydrolysis in 2), as desired.

The present step can be carried out similarly to the procedures of Step D'-3.

The compound (1') of the present invention can be also prepared according to processes other than those described above. Particularly, it is possible to prepare the compound (1') of the present invention by changing the order of the steps of Processes A' to H' described above depending on the situations. For example, the compound (1') of the present invention can be prepared according to Process J' shown below using the compound (10') obtained as an intermediate in Process D'.

(Process J')

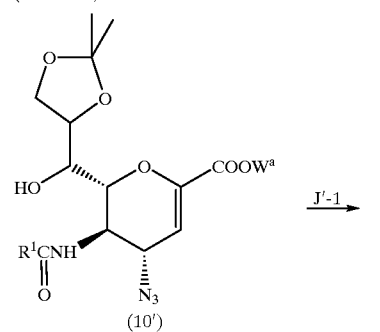

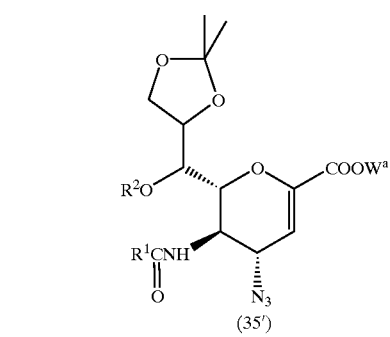

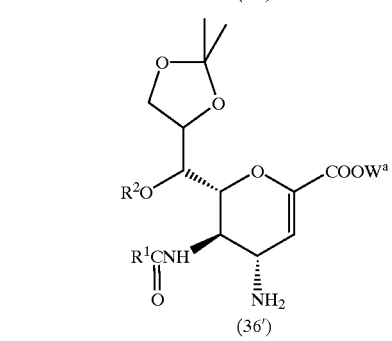

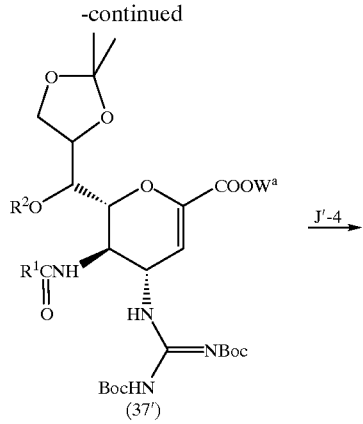

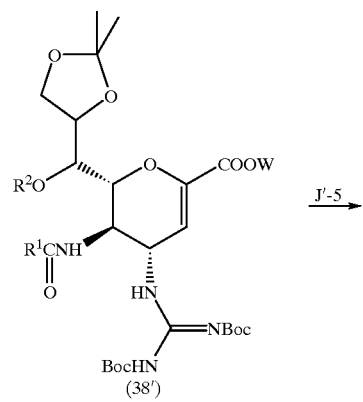

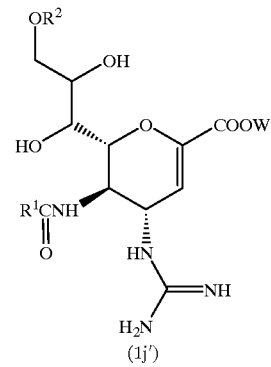

(Step J'-1)
The present step is carried out if necessary, and is to prepare the compound (35') by introducing the desired acyl group to the compound (10') in an inert solvent.
The present step can be carried out similarly to the procedures of Step C'-1 described above.

(Step J'-2)
The present step is to prepare the compound (36') by reacting the compound (35') with a reducing agent in an inert solvent.
The present step can be carried out similarly to the procedures of Step D'-4 described above.

(Step J'-3)
The present step is to prepare the compound (37') by reacting the compound (36') with N,N'-di-t-butoxycarbonylthiourea in an inert solvent in the presence of a base and mercuric chloride.
The present step can be carried out similarly to the procedures of Step A'-1 described above.

(Step J'-4)

The present step is carried out if necessary, and is to prepare the compound (38') by eliminating the protecting group of the carboxyl group of the compound (37').

The elimination method of the protecting group varies depending on the kind of the protecting group, and can be carried out according to the methods usually used, for example, the methods described in Protective Groups in Organic Synthesis, Second Edition (1991, Green et al.).

In the case where the protecting group is a diphenylmethyl group, catalytic reduction is carried out, acids such as acetic acid and trifluoroacetic acid are used or a boron trifluoride-diethyl ether complex is used.

In the case where the protecting group of the carboxyl group is a benzyl group, catalytic reduction is carried out, and in the case where the protecting group is an alkyl group such as methyl and ethyl, hydrolysis is carried out.

(Step J'-5)

The present step is to prepare the compound (1j') of the present invention by reacting the compound (38') with a reagent for eliminating the tert-butoxycarbonyl group and isopropylidene group in an inert solvent.

The present step can be carried out similarly to the procedures of Step E'-2.

The neuraminic acid compound (1') thus obtained or the salt thereof can be converted, if necessary, to other pharmacologically acceptable salts.

The neuraminic acid compound (1') of the present invention undergoes hydrolysis by hydrolase present in a living body and exhibits excellent viral replication inhibitory activity and sialidase inhibitory activity. In addition, if the neuraminic acid compound (1') is administered to mice infected with influenza virus, the compound exhibits infection therapeutic effects superior to Compound A'(GG-167) described in WO91/16320 (Japanese PCT application (Kokai) No. Hei 5-507068. Thus, the neuraminic acid compound (1') of the present invention is useful as a therapeutic agent or a preventive agent (preferably a therapeutic agent) for viral infections (preferably influenza viral infections).

The administration form of the neuraminic acid compound of the present invention includes, for example, oral administration or intranasal administration by solutions such as liquid agents, aqueous co-solvents, etc., aerosols, powders, etc. Of these preparations, solutions such as liquid agents and aqueous co-solvents are prepared by the well known methods using purified water, pharmacologically acceptable organic solvents (for example, ethanol, propylene glycol, PEG 400, etc.), and stabilizers (paraoxybenzoates such as methylparaben and propylparaben; alcohols such as chlorobutanol, benzyl alcohol and phenylethyl alcohol; benzalkonium chloride; phenols such as phenol and cresol; thimerosal; dehydroacetic acid, etc.). The aerosols are prepared by the well known methods using a propellant such as various kinds of Freon gases and nitrogen gas, and a surface active agent such as lecitin. The powders are prepared by the well known methods using excipients (for example, organic excipients such as sugars, e.g. lactose, sucrose, glucose, mannitol and sorbitol; starches, e.g. corn starch, potato starch, α-starch, dextrin and carboxymethyl starch; celluloses, e.g. crystalline cellulose, low-substituted hydroxypropyl cellulose, hydroxypropyl cellulose, hydroxypropylmethyl cellulose, carboxymethyl cellulose, carboxymethyl cellulose calcium and internally bridged carboxymethyl cellulose sodium; gum arabic; dextran; and Pullulan, and inorganic excipients such as silicates, e.g. light silicic anhydride, synthesized aluminium silicate and magnesium aluminate metasilicate; phosphates, e.g. calcium phosphate; carbonates, e.g. calcium carbonate; and sulfates, e.g. calcium sulfate), lubricants (for example, stearic acid, stearic acid metal salts such as calcium stearate and magnesium stearate; talc; colloidal silica; waxes such as bee gum and spermaceti; boric acid; adipic acid; sulfates, e.g. sodium sulfate; glycol; filmaric acid; sodium benzoate; DL-leucine; fatty acid sodium salt; laurylsulfates such as sodium laurylsulfate and magnesium laurylsulfate; silicic acids such as silicic anhydride and silicic acid hydrate; and the above starches), stabilizers (paraoxybenzoates such as methylparaben and propylparaben; alcohols such as chlorobutanol, benzyl alcohol and phenylethyl alcohol; benzalkonium chloride; phenols such as phenol and cresol; thimerosal; dehydroacetic acid; and sorbic acid), corrigents (for example, sweeteners, vinegars, perfumes, etc. usually used), diluents, etc.

While the dose of the active ingredients will vary depending on the condition of disease, age of the patient, administration methods, etc., for example, in the case of solutions, it is desirable to administer the active ingredient in an amount of 0.1 mg (preferably 1 mg) as a lower limit and 1000 mg (preferably 500 mg) as an upper limit, in the case of dry powders, it is desirable to administer the active ingredient in an amount of 0.1 mg (preferably 1 mg) as a lower limit and 1000 mg (preferably 500 mg) as an upper limit, and in the case of aerosols, it is desirable to administer the active ingredient in an amount of 0.1 mg (preferably 1 mg) as a lower limit and 1000 mg (preferably 500 mg) as an upper limit, once or several times a day in the above administration methods, depending on the condition of disease.

The present invention will be described in more detail by way of Examples, Preparation examples and Test examples below but the scope of the present invention is not limited to these.

EXAMPLE 1'

Myristyl 5-acetamido-2,3,4,5-tetradeoxy-4-guanidino-D-glycero-D-galacto-non-2-enopyranosoate trifluoroacetic acid salt (E'8)
(Exemplary compound No. 88')

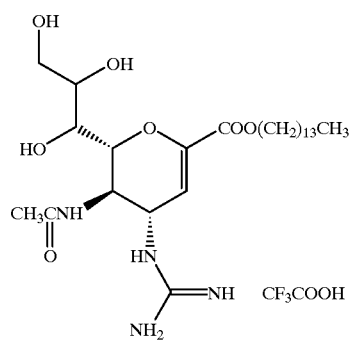

i) Methyl 5-acetamido-4-azido-2,3,4,5-tetradeoxy-8,9-O-isopropylidene-D-glycero-D-galacto-non-2-enopyranosoate (E'3)

1.3 g (2.8 mmol) of methyl 5-acetamido-7,8,9-tri-O-acetyl-4-azido-2,3,4,5-tetradeoxy-D-glycero-D-galacto-non-2-enopiranosonate (E'1) (which was synthesized according to the processes described in Mark von Itzstein et al., Carbohydr. Res., 244, 181–185 (1993) and Carbohydr. Res., 259, 293–299 (1993)) were dissolved in 26 ml (20-times volume) at room temperature, and a catalytic amount of sodium methoxide was added to the system under the same conditions, followed by further stirring of the mixture for 1 hour. After confirmation of completion of the reaction, Dowex-50×8 (H⁺) was added to the system to neutralize the mixture. The reaction mixture was filtered and the filtered product was washed with methanol. The filtrate and the washing water were distilled off under reduced pressure, and the residue was purified over silica gel column chromatography (Kiesel gel 60, 100 g, methylene chloride:methanol= 5:1) to obtain 620 mg (yield: 66%) of the compound (E'2) as a pale yellow solid.

Rf value: 0.3 (methylene chloride:methanol=5:1).

580 mg (1.8 mmol) of the resulting compound (E'2) were dissolved in 29 ml (50-times volume) of acetone at room temperature, and subsequently 0.7 ml (5.2 mmol) of 2,2-dimethoxypropane and 42 mg (0.18 mmol) of DL-10-camphorsulfonic acid were added to the system under ice-cooling, followed by stirring of the mixture at room temperature for 1 hour. After confirmation of completion of the reaction, triethylamine was poured into the system to neutralize the mixture. The reaction mixture was distilled off under reduced pressure, and the residue was purified over silica gel column chromatography (Kiesel gel 60, 60 g, benzene:acetonitrile=1:1) to obtain 540 mg (yield: 84%) of the title compound (E'3) as a white solid.

Rf value: 0.76 (benzene:acetonitrile=1:1). $^1$H-NMR (270 MHz, CDCl$_3$, TMS): δ (ppm) 5.97 (1H, d, J=2.4 Hz), 5.63 (1H, d, J=7.1 Hz), 4.36 (1H, ddd, J=7.9, 6.4, 4.8 Hz), 4.30–4.00 (6H, m), 3.81 (3H, s), 3.57 (1H, dd, J=7.9, 5.3 Hz), 2.12 (3H, s), 1.40 (3H, s), 1.36 (3H, s); $[α]_D^{24}$=+122.4° (c=1.0, CHCl$_3$).

ii) 5-Acetamido-4-azido-2,3,4,5-tetradeoxy-8,9-O-isopropylidene-D-glycero-D-galacto-non-2-enopyranosoic acid (E'4)

460 mg (1.2 mmol) of the compound (E'3) were dissolved in 24 ml (30-times volume) of methanol at room temperature, and subsequently 2.9 ml (1.4 mmol) of 1M aqueous sodium hydroxide solution were added to the system at room temperature, followed by stirring of the mixture at room temperature for 1 hour. After confirmation of completion of the reaction, Dowex-50W was added to the system to neutralize the mixture. The reaction mixture was filtered, and the filtered product was washed with water. The filtrate and the washing solution were combined and distilled off under reduced pressure. The residue was purified over silica gel column chromatography (Kiesel gel 60, 60 g, ethyl acetate:2-propanol:water=2:2:1) to obtain 0.44 g (yield: 100%) of the title compound (E'4) as a white solid.

Rf value: 0.25 (ethyl acetate:2-propanol:water=5:2:1); $^1$H-NMR (27 MHz, CD$_3$OD, TMS): δ (ppm) 5.72 (1H, d, J=2.1 Hz), 4.37 (1H, dt, J=8.8, 5.5 Hz), 4.27 (1H, dd, J=6.9, 1.4 Hz), 4.20–4.04 (3H, m), 4.00 (1H, dd, J=8.8, 5.0 Hz), 3.54 (1H, d, J=8.8 Hz), 2.03 (3H, s), 1.37 (3H, s), 1.32 (3H, s); $[α]_D^{24}$=+43.4° (c=0.53, MeOH).

iii) Myristyl 5-acetamido-4-azido-2,3,4,5-tetradeoxy-8,9-O-isopropylidene-D-glycero-D-galacto-non-2-enopyranosoate (E'5)

460 mg (1.2 mmol) of the compound (E'4), 530 mg (2.5 mmol) of myristyl alcohol and 510 mg (1.9 mmol) of 2-bromo-1-ethylpyridinium tetrafluoroborate were dissolved in 22 ml (50-times volume) of formamide. Subsequently, 0.9 ml (3.8 mmol) of tri-n-butylamine were poured into the system, and the mixture was stirred in an oil bath at 50° C. for 6 hours. The reaction mixture was separated with ethyl acetate and a saturated aqueous NaCl solution, and the aqueous layer was extracted with ethyl acetate. The organic layer was dried over magnesium sulfate and filtered, followed by distilling off under reduced pressure. The residue was purified over silica gel column chromatography (Kiesel gel 60, 100 g, benzene:ethyl acetate= 1:1) to obtain 0.19 g (yield: 28%) of the title compound (E'5) as a white solid.

Rf value: 0.4 (benzene:ethyl acetate=1:1); $^1$H-NMR (270 MHz, CDCl$_3$, TMS): δ (ppm) 5.95 (1H, d, J=2.4 Hz), 5.60 (1H, d, J=7.0 Hz), 4.36 (1H, dt, J=7.7, 5.7 Hz), 4.30–4.00 (8H, m), 3.58 (1H, d, J=7.7 Hz), 2.12 (3H, s), 1.69 (2H, quintet, J=6.3 Hz), 1.40 (3H, s), 1.35 (3H, s), 1.26 (22H, bs), 0.88 (3H, t, J=6.3 Hz); $[α]_D^{24}$=+83.3° (c=0.54, CHCl$_3$).

iv) Myristyl 5-acetamido-4-amino-2,3,4,5-tetradeoxy-8,9-O-isopropylidene-D-glycero-D-galacto-non-2-enopyranosoate (E'6)

134 mg (0.24 mmol) of the compound (E'5) were dissolved in 6.7 ml (50-times volume) of ethanol at room temperature, and subsequently 47 mg (0.35-times volume) of Lindlar catalyst were added to the system at room temperature, followed by stirring of the mixture at room temperature under a hydrogen atmosphere of 1 atm. for 2 hours. After confirmation of completion of the reaction, the reaction mixture was filtered, and the filtered product was washed with ethanol. The filtrate and the washing solution were combined and distilled off under reduced pressure. The residue thus obtained was purified over silica gel column chromatography (Kiesel gel 60, 60 g, ethyl acetate:2-propanol:water=5:2:1) to obtain 0.11 g (yield: 88%) of the title compound (E'6) as a white solid.

Rf value: 0.28 (ethyl acetate:2-propanol:water=8:2:1); $^1$H-NMR (270 MHz, CD$_3$OD, TMS): δ (ppm) 5.93 (1H, d, J=2.6 Hz), 4.31 (1H, quintet, J=6.9 Hz), 4.23–3.93 (5H, m), 3.88 (1H, t, J=9.0 Hz), 3.67–3.50 (2H, m), 2.05 (3H, s), 1.68 (2H, quintet, J=8.1 Hz), 1.37 (3H, s), 1.33 (3H, s), 1.27 (22H, bs), 0.88 (3H, t, J=8.1 Hz).

v) Myristyl 5-acetamido-4-(N,N'-bis-tert-butoxycarbonyl) guanidino-2,3,4,5-tetradeoxy-8,9-O-isopropylidene-D-glycero-D-galacto-non-2-enopyranosoate (E'7)

110 mg (0.21 mmol) of the compound (E'6), 72 mg (0.26 mmol) of N,N'-bis-tert-butoxycarbonylthiourea and 80 ml (0.57 mmol) of triethylamine were dissolved in 22 ml (50-times volume) of dimethylformamide at room temperature. Subsequently, 70.5 mg (0.26 mmol) of mercuric chloride were added to the system under ice-cooling, followed by stirring of the mixture at room temperature for 2 hours. The reaction mixture was diluted with ethyl acetate, and the mixture was filtered using Celite, and the filtered product was washed with ethyl acetate. The filtrate thus obtained and the washing solution were combined, and ethyl acetate and a saturated aqueous NaCl solution were added to the mixture, followed by separation. The organic layer was dried over magnesium sulfate and filtered, followed by distilling off of the solvent under reduced pressure. The residue was purified over silica gel column chromatography (Kiesel gel 60, 100 g, hexane:ethyl acetate=3:2) to obtain 120 mg (yield: 71%) of the title compound (E'7) as a white solid.

Rf value: 0.65 (hexane:ethyl acetate=3:2); $^1$H-NMR (270 MHz, CDCl$_3$, TMS): δ (ppm) 11.4 (1H, s), 8.63 (1H, d, J=7.8 Hz), 7.99 (1H, d, J=4.8 Hz), 5.78 (1H, d, J=2.4 Hz), 5.32 (1H, d, J=4.4 Hz), 5.14 (1H, tt, J=7.8, 1.6 Hz), 4.40 (1H, dt, J=10.6, 4.8 Hz), 4.33–3.90 (6H, m), 3.52 (1H, dd, J=8.7, 3.9 Hz), 2.02 (3H, s), 1.64 (2H, m), 1.52 (9H, s), 1.49 (9H, s), 1.43 (3H, s), 1.36 (3H, s), 1.26 (22H, bs), 0.88 (3H, t, J=6.7 Hz); $[α]_D^{24}$=−20.9° (c:0.58, CHCl$_3$).

vi) Myristyl 5-acetamido-2,3,4,5-tetradeoxy-4-guanidino-D-glycero-D-galacto-non-2-enopyranosoate trifluoroacetic acid salt (E'8)

84 mg (0.11 mmol) of the compound (E'7) were dissolved in 4.7 ml (50-times volume) of methylene chloride at room temperature, and subsequently 0.85 ml (10-times volume) of trifluoroacetic acid were added to the system at room temperature, followed by stirring of the mixture at room temperature for 22 hours. After confirmation of completion of the reaction, the reaction mixture was concentrated under reduced pressure. The residue was purified over silica gel column chromatography (Kiesel gel 60, 15 g, ethyl acetate:2-propanol:water=8:2:1) to obtain 82 mg (yield: 88%) of the title compound (E'8) as a white solid.

Rf value: 0.6 (ethyl acetate:2-propanol:water=8:2:1); $^1$H-NMR (270 MHz, CD$_3$OD): δ (ppm) 5.83 (1H, d, J=2.7 Hz), 4.44 (1H, dd, J=9.0, 2.7 Hz), 4.38 (1H, dd, J=9.0, <1 Hz), 4.18 (2H, t, J=6.2 Hz), 4.17 (1H, t, J=9.0 Hz), 3.90–3.74 (2H, m), 3.68 (1H, dd, J=12.0, 4.5 Hz), 3.65 (1H, d, J=9.0 Hz), 1.99 (3H, s), 1.67 (2H, quintet, J=6.2 Hz), 1.26 (24H, bs), 0.87 (3H, t, J=6.2 Hz); FAB-MS (positive): 529 (M+H)$^+$; HR-MS: Calcd. for C$_{26}$H$_{49}$N$_4$O$_7$, 529.3597, Found 529.3605 (M+H)$^+$.

EXAMPLE 2'

Hexyl 5-acetamido-2,3,4,5-tetradeoxy-4-guanidino-D-glycero-D-galacto-non-2-enopyranosoate trifluoroacetic acid salt (E'12) (Exemplary compound No. 87')

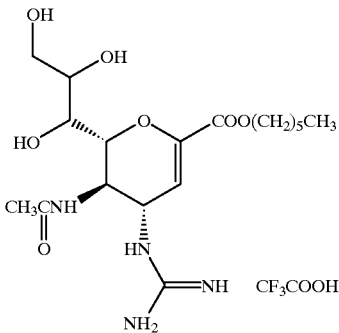

i) Hexyl 5-acetamido-4-azido-2,3,4,5-tetradeoxy-8,9-O-isopropylidene-D-glycero-D-galacto-non-2-enopyranosoate (E'9)

940 mg (2.6 mmol) of the compound (E'4), 0.66 ml (5.3 mmol) of 1-hexanol and 1.1 g (4.0 mmol) of 2-bromo-1-ethylpyridinium tetraluoroborate were dissolved in 47 ml (50-times volume) of dimethylformamide at room temperature. Subsequently, 1.9 ml (8.0 mmol) of tri-n-butylamine were poured into the system, and the mixture was stirred in an oil bath at 50° C. for 6 hours. Ethyl acetate and a saturated aqueous NaCl solution were added to the reaction mixture, and the mixture was separated. The organic layer thus obtained was dried over magnesium sulfate and filtered, followed by concentration under reduced pressure. The residue was purified over silica gel column chromatography (Kiesel gel 60, 150 g, benzene:acetonitrile=2:1) to obtain 560 mg (yield: 44%) of the title compound (E'9) as a pale brown solid.

Rf value: 0.43 (benzene:acetonitrile=2:1); $^1$H-NMR (270 MHz, CDCl$_3$, TMS): δ (ppm) 6.53 (1H, d, J=6.9 Hz), 5.92 (1H, d, J=2.5 Hz), 4.48 (1H, bs), 4.41–4.29 (2H, m), 4.24–4.00 (7H, m), 3.63 (1H, bd, J=7.3 Hz), 1.70 (2H, quintet, J=6.5 Hz), 1.40 (3H, s), 1.35 (9H, bs), 1.30 (3H, s), 0.89 (3H, t, J=6.5 Hz); $[α]_D^{24}$=+8° (c=0.4, CHCl$_3$).

ii) Hexyl 5-acetamido-4-(N,N'-bis-tert-butoxycarbonyl) guanidino-2,3,4,5-tetradeoxy-8,9-O-isopropylidene-D-glycero-D-galacto-non-2-enopyranosoate (E'11)

533 mg (1.1 mmol) of the compound (E'9) were dissolved in 25 ml (50-times volume) of ethanol at room temperature, and subsequently 190 mg (0.35-times volume) of Lindlar catalyst were added to the system at room temperature, followed by stirring of the mixture at room temperature under a hydrogen atmosphere of 1 atm. for 2.5 hours. After confirmation of completion of the reaction, the reaction mixture was filtered. The filtered product was washed with ethanol, and the filtrate and the washing solution were combined, followed by concentration under reduced pressure. The residue was purified over silica gel column chromatography (Kiesel gel 60, 50 g, ethyl acetate:2-propanol:water=5:2:1) to obtain 303 mg (yield: 60%) of the title compound (E'10) as a pale brown foamy solid.

Rf value: 0.44 (ethyl acetate:2-propanol:water=5:2:1).

290 mg (0.63 mmol) of the resulting compound (E10), 210 mg (0.75 mmol) of N,N'-bis-tert-butoxycarbonylthiourea and 0.22 ml (1.6 mmol) of triethylamine were dissolved in 15 ml (50-times volume) of dimethylformamide at room temperature. Subsequently, 220 mg (0.8 mmol) of mercury chloride were added to the system under ice-cooling and the mixture was stirred at room temperature for 2 hours. The reaction mixture was diluted with ethyl acetate and filtered using Celite, and the filtered product was washed with ethyl acetate. The filtrate thus obtained and the washing solution were combined, and ethyl acetate and a saturated aqueous NaCl solution were added thereto to separate the mixture, followed by extraction of the aqueous layer with ethyl acetate. The organic layer was dried over magnesium sulfate and filtered, followed by concentration under reduced pressure. The residue was purified over silica gel column chromatography (Kiesel gel 60, 75 g, hexane:ethyl acetate=1:1) to obtain 273 mg (yield: 66%) of the desired compound (E'11) as a white solid.

Rf value: 0.38 (benzene:ethyl acetate=5:1); $^1$H-NMR (270 MHz, CDCl$_3$, TMS): δ (ppm) 11.4 (1H, s), 8.64 (1H, d, J=7.7 Hz), 7.99 (1H, d, J=4.7 Hz), 5.78 (1H, d, J=2.4 Hz), 5.33 (1H, d, J=4.4 Hz), 5.14 (1H, tt, J=7.9, <1 Hz), 4.40 (1H, dt, J=7.8, 5.7 Hz), 4.23–3.90 (7H, m), 3.51 (1H, dd, J=8.2, 4.5 Hz), 2.01 (3H, s), 1.68 (2H, quintet, J=6.4 Hz), 1.51 (9H, s), 1.49 (9H, s), 1.43 (3H, s), 1.36 (3H, s), 1.35–1.20 (6H, m), 0.89 (3H, t, J=6.4 Hz); $[α]_D^{24}$=−22.0° (c:0.5, CHCl$_3$).

iii) Hexyl 5-acetamido-2,3,4,5-tetradeoxy-4-guanidino-D-glycero-D-galacto-non-2-enopyranosoate trifluoroacetic acid salt (E'12)

158 mg (0.24 mmol) of the compound (E'11) were dissolved in 8.0 ml (50-times volume) of methylene chloride at room temperature, and subsequently 1.6 ml (10-times volume) of trifluoroacetic acid were added to the system at room temperature, followed by stirring of the mixture at room temperature for 18 hours. After confirmation of completion of the reaction, the reaction mixture was concentrated under reduced pressure. The residue was purified over silica gel column chromatography (Kiesel gel 60, 15 g, ethyl acetate:2-propanol:water=5:2:1) to obtain 155 mg (yield: 100%) of the title compound (E'12) as a white solid.

Rf value: 0.8 (ethyl acetate:2-propanol:water=5:2:1); $^1$H-NMR (270 MHz, CD$_3$OD): δ (ppm) 5.94 (1H, d, J=2.4 Hz), 4.46 (1H, dd, J=9.3, 2.4 Hz), 4.38 (1H, dd, J=10.4, 1.3 Hz), 4.20 (1H, t, J=9.3 Hz), 4.20 (2H, t, J=6.2 Hz), 3.91–3.76 (2H, m), 3.66 (1H, bd, J=9.3 Hz), 3.61 (1H, dd, J=12.5, 6.3 Hz), 1.97 (3H, s), 1.63 (2H, quintet, J=6.3 Hz), 1.40–1.10 (6H, m), 0.80 (3H, t, J=6.3 Hz); $[α]_D^{24}$=+18.1° (c=0.48, CHCl$_3$).

EXAMPLE 3'

5-Acetamido-2,3,4,5-tetradeoxy-4-guanidino-9-O-myristoyl-D-glvcero-D-galacto-non-2-enopyranosoic acid trifluoroacetic acid salt (E'17) (Exemplary compound No. 41')

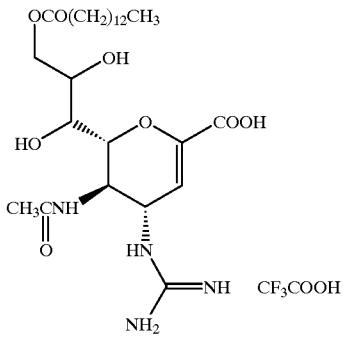

i) Methyl 5-acetamido-4-azido-2,3,4,5-tetradeoxy-8,9-O-isopropylidene-7-O-myristoyl-D-glycero-D-galacto-non-2-enopyranosoate (E'13)

61 mg (0.16 mmol) of the compound (E'3) were dissolved in 3.0 ml (50-times volume) of methylene chloride at room temperature, and subsequently 54 ml (0.2 mmol) of myristoyl chloride and 24.1 mg (0.2 mmol) of 4-dimethylaminopyridine were added to the system under ice-cooling, followed by stirring of the mixture at room temperature for 30 minutes. Next 27 ml (0.2 mmol) of triethylamine were poured into the reaction mixture at room temperature, followed by further stirring of the mixture for 6 hours. After confirmation of completion of the reaction, methanol was poured into the system, followed by stirring of the mixture for 30 minutes. Next, ethyl acetate and a saturated aqueous NaCl solution were added to the reaction mixture to separate the mixture. The organic layer thus obtained was dried over magnesium sulfate and filtered, followed by concentration under reduced pressure. The residue was purified over silica gel column chromatography (Kiesel gel 60, 15, benzene:ethyl acetate=1:1) to obtain 70 mg (yield: 74%) of the desired compound. (E'13) as a colorless transparent syrup.

Rf value: 0.42 (benzene:ethyl acetate=2:1); $^1$H-NMR (270 MHz, CDCl$_3$, TMS): δ (ppm) 5.95 (1H, d, J=2.7 Hz), 5.88 (1H, d, J=7.9 Hz), 5.35 (1H, dd, J=6.0, 1.8 Hz), 4.80 (1H, dd, J=9.1, 2.7 Hz), 4.71 (1H, dd, J=10.5, 1.8 Hz), 4.39 (1H, q, J=6.0 Hz), 4.14 (1H, dd, J=8.8, 6.0 Hz), 4.71 (1H, dd, J=10.5, 1.8 Hz), 4.39 (1H, q, J=6.0 Hz), 4.14 (1H, dd, J=8.8, 6.0 Hz) 3.945 (1H, dd, J=8.8, 6.0 Hz), 3.81 (3H, s), 3.45 (1H, ddd, J=10.5, 9.1, 7.9 Hz), 2.41 (1H, t, J=7.5 Hz), 2.39 (1H, t, J=7.5 Hz), 2.02 (3H, s), 1.63 (2H, quintet, J=7.5 Hz), 1.37 (3H, s), 1.35 (3H, s), 1.26 (20H, s), 0.88 (3H, t, J=7.5 Hz).

ii) Methyl 5-acetamido-4-amino-2,3,4,5-tetradeoxy-8,9-O-isopropylidene-7-O-myristoyl-D-glycero-D-galacto-non-2-enopyranosoate (E'14)

70 mg (0.12 mmol) of the compound (E'13) were dissolved in 3.5 ml (50-times volume) of ethanol at room temperature, and subsequently 25 mg (0.35-times volume) of Lindlar catalyst were added to the system at room temperature, followed by stirring of the mixture at room temperature under a hydrogen atmosphere of 1 atm. for 1.5 hours. After confirmation of completion of the reaction, the reaction mixture was filtered. The filtered product was washed with ethanol, and the filtrate and the washing solution were combined, followed by concentration under reduced pressure. The residue was purified over silica gel column chromatography (Kiesel gel 60, 15 g, ethyl acetate:2-propanol:water=5:2:1) to obtain 57 mg (yield: 84%) of the title compound (E'14) as a white solid.

Rf value: 0.49 (methylene chloride:methanol=10:1); $^1$H-NMR (270 MHz, CD$_3$OD, TMS): δ (ppm) 5.94 (1H, d, J=2.4 Hz), 5.42 (1H, dd, J=4.7, 1.8 Hz), 4.39 (1H, dt, J=7.1, 6.0 Hz), 4.18 (1H, dd, J=9.5, 1.6 Hz), 4.14 (1H, dd, J=8.7, 6.4 Hz), 3.93 (1H, dd, J=8.7, 6.4 Hz), 3.87 (1H, t, J=9.5 Hz), 3.78 (3H, s), 3.44 (1H, dd, J=9.5, 2.4 Hz), 2.35 (2H, q, J=7.3 Hz), 1.94 (3H, s), 1.60 (2H, quintet, J=7.3 Hz), 1.32 (3H, s), 1.31 (3H, s), 1.27 (20H, s), 0.88 (3H, t, J=7.3 Hz).

iii) Methyl 5-acetamido-4-(N,N'-bis-tert-butoxycarbonyl)guanidino-2,3,4,5-tetradeoxy-8,9-O-isopropylidene-7-O-myristoyl-D-glycero-D-galacto-non-2-enopyranosoate (E'15)

57 mg (0.1 mmol) of the compound (E'14), 34 mg (0.12 mmol) of N,N'-bis-tert-butoxycarbonylthiourea and 35 ml (0.25 mmol) of triethylamine were dissolveff in 28 ml (50-times volume) of dimethylformamide at room temperature. Subsequently, 35 mg (0.13 mmol) of mercury chloride were added to the system under ice-cooling, and the mixture was stirred at room temperature for 2 hours. Ethyl acetate was added to the reaction mixture to dilute it, followed by filtration using Celite. The filtered product was washed with ethyl acetate. The filtrate thus obtained and the washing solution were combined, and ethyl acetate and a saturated aqueous NaCl solution were added to the mixture to separate it. The organic layer was dried over magnesium sulfate and filtered, followed by concentration under reduced pressure. The residue was purified over silica gel column chromatography (Kiesel gel 60, 15 g, hexane:ethyl acetate=2:1) to obtain 75 mg (yield: 100%) of the title compound as a colorless transparent syrup.

Rf value: 0.33 (hexane:ethyl acetate=2:1); $^1$H-NMR (270 MHz, CDCl$_3$, TMS): δ (ppm) 11.4 (1H, s), 8.46 (1H, d, J=8.7 Hz), 6.06 (1H, d, J=8.7 Hz), 5.88 (1H, d, J=2.4 Hz), 5.37 (1H, dd, J=6.4, 1.5 Hz), 5.15 (1H, dt, J=8.7, 2.4 Hz), 4.38 (1H, q, J=6.4 Hz), 4.28 (1H, dd, J=8.7, 1.5 Hz), 4.23 (1H, t, J=8.7 Hz), 4.10 (1H, dd, J=9.6, 6.4 Hz), 3.95 (1H, dd, J=9.6, 6.4 Hz), 3.80 (3H, s), 2.453 (1H, dt, J=16.0, 7.5 Hz), 2.33 (1H, dt, J=16.0, 7.5 Hz), 1.87 (3H, s), 1.61 (2H, quintet, J=7.5 Hz), 1.49 (9H, s), 1.48 (9H, s), 1.38 (3H, s), 1.35 (3H, s), 1.25 (20H, bs), 0.88 (3H, t, J=7.5 Hz).

iv) 5-Acetamido-4-(N,N'-bis-tert-butoxycarbonyl)guanidino-2,3,4,5-tetradeoxy-8,9-O-isopropylidene-7-O-myristoyl-D-glycero-D-galacto-non-2-enopyranosoic acid (E'16)

51 mg (0.07 mmol) of the compound (E'15) were dissolved in a mixture of 2 ml (40-times volume) of methanol and 0.5 ml (10-times volume) of water, and 3.3 mg (0.078 mmol) of lithium hydroxide monohydrate were added to the system at room temperature, followed by stirring of the mixture at room temperature for 8 hours. After confirmation of completion of the reaction, Dowex-50W was added to the system to neutralize the mixture. The reaction mixture was filtered, and the filtered product was washed with methanol. The filtrate and the washing solution were combined and concentrated under reduced pressure. The residue was purified over silica gel column chromatography (Kiesel gel 60, 60 g, ethyl acetate:2-propanol:water=10:2:1) to obtain 33 mg (yield: 66%) of the desired compound (E'16) as a white solid.

Rf value: 0.45 (methylene chloride:methanol=10:1); $^1$H-NMR (270 MHz, CDCl$_3$, TMS): δ (ppm) 11.4 (1H, s), 8.48 (1H, d, J=8.0 Hz), 6.31 (1H, dull s), 5.90 (1H, bs), 5.30 (1H, bs), 5.10 (1H, bs), 4.60–3.30 (7H, m), 2.48 (1H, dt, J=13.5, 6.5 Hz), 2.32 (1H, dt, J=13.5, 6.5 Hz), 1.88 (3H, s), 1.60 (2H, quintet, J=6.5 Hz), 1.48 (18H, s), 1.39 (3H, s), 1.37 (3H, s), 1.25 (20H, bs), 0.88 (3H, t, J=6.5 Hz).

v) 5-Acetamido-2,3,4,5-tetradeoxy-4-guanidino-9-O-myristoyl-D-glycero-D-galacto-non-2-enopyranosoic acid trifluoroacetic acid salt (E'17)

33 mg (0.046 mmol) of the compound (E'16) were dissolved in 1.6 ml (50-times volume) of methylene chloride at room temperature, and subsequendy 60 ml (10-times volume) of trifluoroacetic acid were added to the system at room temperature, followed by stirring of the mixture at room temperature for 22 hours. After confirmation of completion of the reaction, the reaction mixture was concentrated under reduced pressure. The residue was purified over silica gel column chromatography (Kiesel gel 60, 5 g, 2-propanol:water=5:1) to obtain 30 mg (yield: 84%) of the title compound (E'17) as a pale yellow solid.

Rf value: 0.4 (2-propanol:water=5:1); $^1$H-NMR (270 MHz, CD$_3$OD): δ (ppm) 5.63 (1H, d, J=2.3 Hz), 4.49 (1H, dd, J=9.3, 2.3 Hz), 4.39 (1H, d, J=10.6 Hz), 4.25–4.00 (4H, m), 3.77 (1H, d, J=9.3 Hz), 2.36 (2H, t, J=7.4 Hz), 1.92 (3H, s), 1.70–1.50 (2H, m), 1.30 (20H, bs), 0.90 (3H, t, J=7.4 Hz); FAB-MS (positive): 543 (M+H)$^+$; HR-MS Calcd. for C$_{26}$H$_{47}$O$_8$N$_4$, 543.3378, Found 543.3412 (M+M)$^+$; $[\alpha]_D^{24}$=+25° (c=0.12, MeOH).

EXAMPLE 4'

5-Acetamido-2,3,4,5-tetradeoxy-4-guanidino-9-O-hexanoyl-D-glycero-D-galacto-non-2-enopyranosoic acid trifluoroacetic acid salt (E'22) (Exemplary compound No. 36')

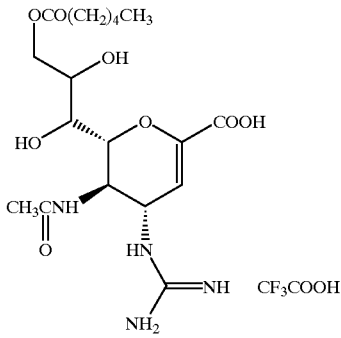

i) Methyl 5-acetamido-4-azido-2,3,4,5-tetradeoxy-8,9-O-isopropylidene-7-O-hexanoyl-D-glycero-D-galacto-non-2-enopyranosoate (E'18)

270 mg (0.73 mmol) of the compound (E'3) were dissolved in 13.5 ml (50-times volume) of methylene chloride, and subsequently 0.14 ml (1.0 mmol) of hexanoyl chloride and 110 mg (0.9 mmol) of 4-dimethylaminopyridine were added to the system under ice-cooling, followed by stirring of the mixture at room temperature for 30 minutes. Next, 0.13 ml (0.9 mmol) of triethylamine were poured into the reaction mixture at room temperature, followed by farther stirring of the mixture for 19 hours. After confirmation of completion of the reaction, methanol was poured into the system, followed by stirring of the mixture for 30 minutes. Next, ethyl acetate and a saturated aqueous NaCl solution were added to the reaction mixture to separate the mixture. The organic layer was dried over magnesium sulfate and filtered, followed by concentration under reduced pressure. The residue thus obtained was purified over silica gel column chromatography (Kiesel gel 60, 75 g, benzene:ethyl acetate=1:1) to obtain 220 mg (yield: 74%) of the title compound (E'18) as a colorless transparent syrup.

Rf value: 0.45 (benzene:ethyl acetate=1:1); $^1$H-NMR (270 MHz, CDCl$_3$, TMS): δ (ppm) 6.11 (1H, d, J=8.0 Hz), 5.95 (1H, d, J=2.6 Hz), 5.38 (1H, d, J=5.3, 2.0 Hz), 4.69 (1H, dd, J=9.2, 2.6 Hz), 4.65 (1H, dd, J=10.6, 2.0 Hz), 4.38 (1H, q, J=5.5 Hz), 4.14 (1H, dd, J=9.5, 5.5 Hz), 3.95 (1H, dd, J=9.5, 5.4 Hz), 3.81 (3H, s), 3.59 (1H, ddd, J=10.6, 9.2, 8.0 Hz), 2.44 (1H, dt, J=15.9, 7.4 Hz), 2.36 (1H, dt, J=15.9, 7.4 Hz), 2.01 (3H, s), 1.64 (2H, quintet, J=7.4 Hz), 1.37 (3H, s), 1.35 (3H, s), 1.35–1.30 (4H, m), 0.90 (3H, t, J=7.4 Hz); $[\alpha]_D^{24}$=+94.3° (c:0.35, CHCl$_3$).

ii) Methyl 5-acetamido-4-(N,N'-bis-tert-butoxycarbonyl)guanidino-2,3,4,5-tetradeoxy-8,9-O-isopropylidene-7-O-hexanoyl-D-glycero-D-galacto-non-2-enopyranosoate (E'20)

190 mg (0.41 mmol) of the compound (E'18) were dissolved in 9.3 ml (50-times volume) of ethanol at room temperature, and subsequently 70 mg (0.38-times volume) of Lindlar catalyst were added to the system at room temperature, followed by stirring of the mixture at room temperature under a hydrogen atmosphere of 1 atm. for 2.5 hours. After confirmation of completion of the reaction, the reaction mixture was filtered. The filtered product was washed with ethanol, and the filtrate and the washing solution were combined, followed by concentration under reduced pressure. The residue was purified over silica gel column chromatography (Kiesel gel 60, 60 g, ethyl acetate:2-propanol:water=5:2:1) to obtain 140 mg (yield: 80%) of the compound (E'19) as a pale yellow foamy solid.

Rf value: 0.4 (ethyl acetate:2-propanol=5:2:1).

140 mg (0.3 mmol) of the resulting compound (E'19), 120 mg (0.43 mmol) of N,N'-bis-tert-butoxycarbonylthiourea and 0.12 ml (0.86 mmol) of triethylamine were dissolved in 7 ml (50-times volume) of dimethylformamide at room temperature. Subsequently, 110 mg (0.41 mmol) of mercury chloride were added to the system under ice-cooling, followed by stirring of the mixture at room temperature for 1.5 hours. Ethyl acetate was added to the reaction mixture to dilute it and the mixture was filtered using Celite, followed by washing of the filtered product with ethyl acetate. The filtrate and the washing solution were combined, and ethyl acetate and a saturated aqueous NaCl solution were added thereto to separate it. The organic layer was dried over magnesium sulfate and filtered, followed by concentration under reduced pressure. The residue was purified over silica gel column chromatography Kiesel gel 60, 50 g, benzene::ethyl acetate=3:1) to obtain 220 mg (yield: 100%) of the title compound (E'20) as a white foamy solid.

Rf value: 0.5 (benzene:ethyl acetate=3:1); $^1$H-NMR (270 MHz, CDCl$_3$, TMS): δ (ppm) 11.4 (1H, s), 8.46 (1H, d, J=8.7 Hz), 5.97 (1H, d, J=8.7 Hz), 5.88 (1H, d, J=2.3 Hz), 5.37 (1H, dd, J=6.3, 1.6 Hz), 5.15 (1H, dt, J=8.7, 2.3 Hz), 4.37 (1H, q, J=6.4 Hz), 4.29 (1H, dd, J=8.7, 1.5 Hz), 4.24 (1H, t, J=8.7 Hz), 4.11 (1H, dd, J=8.8, 6.4 Hz), 3.96 (1H, dd, J=8.8, 6.4 Hz), 3.81 (3H, s), 2.46 (1H, dt, J=15.9, 7.4 Hz), 2.33 (1H, dt, J=15.9, 7.4 Hz), 1.88 (3H, s), 1.70–1.50 (2H, m), 1.49 (9H, s), 1.48 (9H, s), 1.38 (3H, s), 1.37 (3H, s), 1.40–1.25 (4H, m), 0.89 (3H, t, J=7.4 Hz); $[\alpha]_D^{24}$=−28.3° (c=0.4, CHCl$_3$).

iii) 5-Acetamido-4-(N,N'-bis-tert-butoxycarbonyl)guanidino-2,3,4,5-tetradeoxy-8,9-O-isopropylidene-7-O-hexanoyl-D-glycero-D-galacto-non-2-enopyranosoic acid (E'21)

180 mg (0.26 mmol) of the compound (E'20) were dissolved in a mixture of 10.8 ml (60-times volume) of methanol and 1.8 ml (10-times volume) of water, and 12 mg (0.29 mmol) of lithium hydroxide monohydrate were added to the system at room temperature, followed by stirring of the mixture at room temperature for 17 hours. After confirmation of completion of the reaction, Dowex-50W was added to the system to neutralize it. The reaction mixture was filtered, and the filtered product was washed with methanol. The filtrate and the washing solution were combined and concentrated under reduced pressure. The residue was purified over silica gel column chromatography (Kiesel gel 60, 50 g, methylene chloride:methanol=10:1) to obtain 0.13 g (yield: 75%) of the title compound (E'21) as a white foamy solid.

Rf value: 0.24 (methylene chloride:methanol=10:1); $^1$H-NMR (270 MHz, CDCl$_3$, TMS): δ (ppm) 11.4 (1H, bs), 8.52 (1H, bs), 5.95 (2H, bs), 5.32 (1H, bs), 5.15 (1H, bs), 4.60–4.10 (3H, m), 3.95 (1H, bs), 2.70–2.20 (2H, m), 1.89 (3H, s), 1.75–1.00 (28H, m), 0.85 (3H, m).

iv) 5-Acetamido-2,3,4,5-tetradeoxy-4-guanidino-9-O-hexanoyl-D-glycero-D-galacto-non-2-enopyranosoic acid trifluoroacetic acid salt (E'22)

95 mg (0.15 mmol) of the compound (E'21) were dissolved in 4.8 ml (50-times volume) of methylene chloride, and subsequently 0.95 ml (10-times volume) of trifluoroacetic acid were added to the system at room temperature, followed by stirring of the mixture at room temperature for 4.5 hours. After confirmation of completion of the reaction, the reaction mixture was concentrated under reduced pressure. The residue was purified over silica gel column chromatography (Kiesel gel 60, 20 g, ethyl acetate:2-propanol:water=4:2:1) to obtain 54 mg (yield: 57%) of the desired compound as a white solid.

Rf value: 0.3 (ethyl acetate:2-propanol:water=4:2:1); $^1$H-NMR (270 MHz, CD$_3$OD): δ (ppm) 5.53 (1H, d, J=2.2 Hz), 4.50–4.00 (6H, m), 3.59 (1H, d, J=9.2 Hz), 2.35 (2H, t, J=7.5 Hz), 2.01 (3H, s), 1.70–1.50 (2H, m), 1.40–1.20 (4H, m), 0.91 (3H, t, J=7.5 Hz); IR(KBr)(cm$^{-1}$)3333, 1665, 1617, 1401, 1385, 1176; FAB-MS (positive) 431 (M+H)$^+$; HR-MS Calcd. for C$_{18}$H$_{31}$N$_4$O$_8$ 431.2165, Found 431.2125 (M+H)$^+$; $[α]_D^{24}$=+29° (c=0.2, MeOH).

EXAMPLE 5'

5-Acetamido-2,3,4,5-tetradeoxy-4-guanidino-9-O-octanoyl-D-glycero-D-galacto-non-2-enopyranosoic acid trifluoroacetic acid salt (E'27) Exemplary compound No. 38')

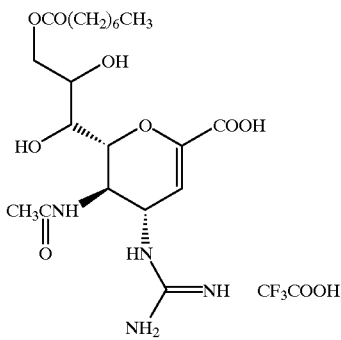

i) Methyl 5-acetamido-4-azido-2,3,4,5-tetradeoxy-8,9-O-isopropylidene-7-O-myristoyl-D-glycero-D-galacto-non-2-enopyranosoate (E'23)

185 mg (0.5 mmol) of the compound (E'3) were dissolved in 5.0 ml of methylene chloride at room temperature, and 132 μl (0.75 mmol) of octanoyl chloride and 91 mg (0.75 mmol) of 4-dimethylaminopyridine were added to the system under ice-cooling, followed by stirring of the mixture at room temperature for 30 minutes. Next, 104 μl (0.75 mmol) of triethylamine were poured into the reaction mixture at room temperature, followed by further stirring of the mixture for 6 hours. After confirmation of completion of the reaction, methanol was poured into the system, followed by stirring of the mixture for 30 minutes. Next, ethyl acetate and a saturated aqueous NaCl solution were added to the reaction mixture to separate it. The organic layer thus obtained was dried over magnesium sulfate and filtered, followed by concentration under reduced pressure. The residue was purified over silica gel column chromatography (Kiesel gel 60, methylene chloride:methanol=50:1) to obtain 150 mg (yield: 64%) of the desired compound (E'23) as a colorless transparent syrup.

Rf value: 0.50 (methylene chloride:methanol=20:1); $^1$H-NMR (270 MHz, CDCl$_3$, TMS): δ (ppm) 5.95 (1H, d, J=2.7 Hz), 5.88 (1H, d, J=7.9 Hz), 5.35 (1H, dd, J=6.0, 1.8 Hz), 4.80 (1H, dd, J=9.1, 2.7 Hz), 4.71 (1H, dd, J=10.5, 1.8 Hz), 4.39 (1H, q, J=6.0 Hz), 4.14 (1H, dd, J=8.8, 6.0 Hz), 4.71 (1H, dd, J=10.5, 1.8 Hz), 4.39 (1H, q, J=6.0 Hz), 4.14 (1H, dd, J=8.8, 6.0 Hz), 3.945 (1H, dd, J=8.8, 6.0 Hz), 3.81 (3H, s), 3.45 (1H, ddd, J=10.5, 9.1, 7.9 Hz), 2.41 (1H, t, J=7.5 Hz), 2.39 (1H, t, J=7.5 Hz), 2.02 (3H, s), 1.63 (2H, quintet, J=7.5 Hz), 1.37 (3H, s), 1.35 (3H, s), 1.26 (8H, s), 0.88 (3H, t, J=7.5 Hz).

ii) Methyl 5-acetamido-4-amino-2,3,4,5-tetradeoxy-8,9-O-isopropylidene-7-O-octanoyl-D-glycero-D-galacto-non-2-enopyranosoate (E'24)

130 mg (0.28 mmol) of the compound (E'23) were dissolved in 6.0 ml of ethanol at room temperature, and subsequently 46 mg (0.35-times volume) of Lindlar catalyst were added to the system at room temperature, followed by stirring of the mixture at room temperature under a hydrogen atmosphere of 1 atm. for 1.5 hours. After confirmation of completion of the reaction, the reaction mixture was filtered. The filtered product was washed with ethanol, and the filtrate and the washing solution were combined, followed by concentration under reduced pressure. The residue was purified over silica gel column chromatography (Kiesel gel 60, 15 g, ethyl acetate:2-propanol:water=5:2:1) to obtain 95 mg (yield: 77%) of the title compound (E'24) as a white solid.

Rf value: 0.35 (n-hexane:ethyl acetate=2:1); $^1$H-NMR (270 MHz, CD$_3$OD, TMS): δ (ppm) 5.94 (1H, d, J=2.4 Hz), 5.42 (1H, dd, J=4.7, 1.8 Hz), 4.39 (1H, dt, J=7.1, 6.0 Hz), 4.18 (1H, dd, J=9.5, 1.6 Hz), 4.14 (1H, dd, J=8.7, 6.4 Hz), 3.93 (1H, dd, J=8.7, 6.4 Hz), 3.87 (1H, t, J=9.5 Hz), 3.78 (3H, s), 3.44 (1H, dd, J=9.5, 2.4 Hz), 2.35 (2H, q, J=7.3 Hz), 1.94 (3H, s), 1.60 (2H, quintet, J=7.3 Hz), 1.32 (3H, s), 1.31 (3H, s), 1.27 (8H, s), 0.88 (3H, t, J=7.3 Hz).

iii) Methyl 5-acetamido-4-(N,N'-bis-tert-butoxycarbonyl)guanidino-2,3,4,5-tetradeoxy-8,9-O-isopropylidene-7-O-octanoyl-D-glycero-D-galacto-non-2-enopyranosoate (E'25)

90 mg (0.2 mmol) of the compound (E'24), 83 mg (0.30 mmol) of N,N'-bis-tert-butoxycarbonylthiourea and 84 μl (0.25 mmol) of triethylamine were dissolved in 5 ml of dimethylformamide at room temperature. Subsequently, 82 mg (0.30 mmol) of mercury chloride were added to the system under ice-cooling, followed by stirring of the mixture at room temperature for 2 hours. Ethyl acetate was added to the reaction mixture to dilute it and the mixture was filtered using Celite. The filtered product was washed with ethyl acetate. The filtrate thus obtained and the washing solution were combined, and ethyl acetate and a saturated aqueous NaCl solution were added to the mixture to separate it. The organic layer was dried over magnesium sulfate and filtered, followed by concentration under reduced pressure. The residue was purified over silica gel column chromatography (Kiesel gel 60, 15 g, hexane:ethyl acetate=2:1) to obtain 120 mg (yield: 88%) of the title compound (E'25) as a colorless transparent syrup.

Rf value: 0.30 (hexane:ethyl acetate=2:1); $^1$H-NMR (270 MHz, CDCl$_3$, TMS): δ (ppm) 11.4 (1H, s), 8.46 (1H, d, J=8.7 Hz), 6.06 (1H, d, J=8.7 Hz), 5.88 (1H, d, J=2.4 Hz), 5.37 (1H, dd, J=6.4, 1.5 Hz), 5.15 (1H, dt, J=8.7, 2.4 Hz), 4.38 (1H, q, J=6.4 Hz), 4.28 (1H, dd, J=8.7, 1.5 Hz), 4.23 (1H, t, J=8.7 Hz), 4.10 (1H, dd, J=9.6, 6.4 Hz), 3.95 (1H, dd, J=9.6, 6.4 Hz), 3.80 (3H, s), 2.453 (1H, dt, J=16.0, 7.5 Hz), 2.33 (1H, dt, J=16.0, 7.5 Hz), 1.87 (3H, s), 1.61 (2H, quintet, J=7.5 Hz), 1.49 (9H, s), 1.48 (9H, s), 1.38 (3H, s), 1.35 (3H, s), 1.25 (8H, bs), 0.88 (3H, t, J=7.5 Hz).

iv) 5-Acetamido-4-(N,N'-bis-tert-butoxycarbonyl)guanidino-2,3,4,5-tetradeoxy-8,9-O-isopropylidene-7-O-octanoyl-D-glycero-D-ealacto-non-2-enopyranosoic acid (E'26)

100 mg (0.15 mmol) of the compound (E'25) were dissolved in a mixture of 4 ml (40-times volume) of methanol and 1 ml (10-times volume) of water, and 7.0 mg (0.165 mmol) of lithium hydroxide monohydrate were added to the system at room temperature, followed by stirring of the mixture at room temperature for 8 hours. After confirmation of completion of the reaction, Dowex-50W was added to the system to neutralize it. The reaction mixture was filtered, and the filtered product was washed with methanol. The filtrate and the washing solution were combined and concentrated under reduced pressure. The residue thus obtained was purified over silica gel column chromatography (Kiesel gel 60, ethyl acetate:2-propanol:water=10:2:1) to obtain 56 mg (yield: 56%) of the desired compound (E'26) as a white solid.

Rf value: 0.35 (methylene chloride:meffianol=10:1); $^1$H-NMR (270 MHz, CDCl$_3$, TMS): δ (ppm) 11.4 (1H, s), 8.48 (1H, d, J=8.0 Hz), 6.31 (1H, dull s), 5.90 (1H, bs), 5.30 (1H, bs), 5.10 (1H, bs), 4.60–3.30 (7H, m), 2.48 (1H, dt, J=13.5, 6.5 Hz), 2.32 (1H, dt, J=13.5, 6.5 Hz), 1.88 (3H, s), 1.60 (2H, quintet, J=6.5 Hz), 1.48 (18H, s), 1.39 (3H, s), 1.37 (3H, s), 1.25 (8K bs), 0.88 (3H, t, J=6.5 Hz).

v) 5-Acetamido-2,3,4,5-tetradeoxy-4-guanidino-9-O-octanoyl-Dglycero-D-galacto-non-2-enopyranosoic acid trifluoroacetic acid salt (E'27)

50 mg (0.075 mmol) of the compound (E'26) were dissolved in 3 ml (50-times volume) of methylene chloride at room temperature, and subsequently 1 ml (10-times volume) of trifluoroacetic acid was added to the system at room temperature, followed by stirring of the mixture at room temperature for 22 hours. After confirmation of completion of the reaction, the reaction mixture was concentrated under reduced pressure. The residue was purified over silica gel column chromatography (Kiesel gel 60, 5 g, 2-propanol:water=5:1) to obtain 38 mg (yield: 88%) of the title compound (E'27) as a pale yellow solid.

Rf value: 0.3 (2-propanol:water=5:1); $^1$H-NMR (270 MHz, CD$_3$OD): δ (ppm) 5.55 (1H, bs), 4.40–4.10 (7H, m), 3.65 (1H, d, J=9.0 Hz), 2.36 (2H, t, J=7.0 Hz), 2.00 (3H, s), 1.70–1.50 (2H, m), 1.30 (8H, bs), 0.90 (3H, t, J=7.0 Hz); FAB-MS positive): 459 (M+H)$^+$; [α]$_D^{24}$=+19.2° (c=0.26, MeOH).

EXAMPLE 6

5-Acetamido-2,3,4,5-tetradeoxy-4-guanidino-9-O-decanoyl-D-glycero-D-galacto-non-2-enopyranosoic acid trifluoroacetic acid salt (E'32) (Exemplary compound No. 39')

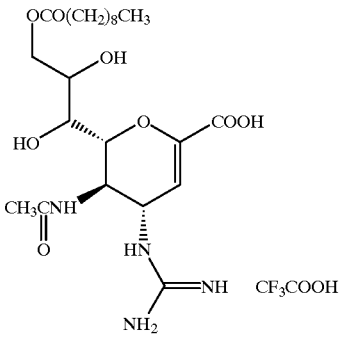

i) Methyl 5-acetamido-4-azido-2,3,4,5-tetradeoxy-8,9-O-isopropylidene-7-O-decanoyl-D-glycero-D-galacto-non-2-enopyranosoate (E'28)

214 mg (0.58 mmol) of the compound (E'3) were dissolved in 6.0 ml of methylene chloride at room temperature, and subsequently 152 μl (0.87 mmol) of decanoyl chloride and 106 mg (0.87 mmol) of 4-methylaminopyridine were added to the system under ice-cooling, followed by stirring of the mixture at room temperature for 30 minutes. Next, 106 μl (0.87 mmol) of trimethylamine were poured into the reaction mixture at room temperature, followed by further stirring of the mixture for 6 hours. After confirmation of completion of the reaction, methanol was poured into the system and the mixture was stirred for 30 minutes. Next, ethyl acetate and a saturated aqueous NaCl solution were added to the reaction mixture to separate it. The organic layer thus obtained was dried over magnesium sulfate and filtered, followed by concentration under reduced pressure. The residue was purified over silica gel column chromatography (Kiesel gel 60, methylene chloride:methanol=50:1) to obtain 180 mg (yield: 63%) of the desired compound (E'28) as a colorless transparent syrup.

Rf value: 0.56 (methylene chloride:methanol=20:1); $^1$H-NMR (270 MHz, CDCl$_3$, TMS): δ (ppm) 5.95 (1H, d, J=2.7 Hz), 5.88 (1H, d, J=7.9 Hz), 5.35 (1H, dd, J=6.0, 1.8 Hz), 4.80 (1H, dd, J=9.1, 2.7 Hz), 4.71 (1H, dd, J=10.5, 1.8 Hz), 4.39 (1H, q, J=6.0 Hz), 4.14 (1H, dd, J=8.8, 6.0 Hz), 3.945 (1H, dd, J=8.8, 6.0 Hz), 3.81 (3H, s), 3.45 (1H, ddd, J=10.5, 9.1, 7.9 Hz), 2.41 (1H, t, J=7.5 Hz), 2.39 (1H, t, J=7.5 Hz), 2.02 (3H, s), 1.63 (2H, quintet, J=7.5 Hz), 1.37 (3H, s), 1.35 (3H, s), 1.26 (12H, s), 0.88 (3H, t, J=7.5 Hz).

ii) Methyl 5-acetamido-4-amino-2,3,4,5-tetradeoxy-8,9-O-isopropylidene-7-O-decanoyl-D-glycero-D-galacto-non-2-enopyranosoate (E'29)

170 mg (0.32 mmol) of the compound (E'28) were dissolved in 10 ml of ethanol at room temperature, and subsequently 60 mg (0.35-times volume) of Lindlar catalyst were added to the system at room temperature, followed by stirring of the mixture at room temperature under a hydrogen atmosphere of 1 atm. for 1.5 hours. After confirmation of completion of the reaction, the reaction mixture was filtered. The filtered product was washed with ethanol, and the filtrate and the washing solution were combined, followed by concentration under reduced pressure. The residue was purified over silica gel column chromatography Kiesel gel 60, 15 g, ethyl acetate:2-propanol:water=5:2:1) to obtain 120 mg (yield: 80%) of the title compound (E'29) as a white solid.

Rf value: 0.40 (n-hexane:ethyl acetate=2:1); $^1$H-NMR (270 MHz, CD$_3$OD, TMS): δ (ppm) 5.94 (1H, d, J=2.4 Hz), 5.42 (1H, dd, J=4.7, 1.8 Hz), 4.39 (1H, dt, J=7.1, 6.0 Hz), 4.18 (1H, dd, J=9.5, 1.6 Hz), 4.14 (1H, dd, J=8.7, 6.4 Hz), 3.93 (1H, dd, J=8.7, 6.4 Hz), 3.87 (1H, t, J=9.5 Hz), 3.78 (3H, s), 3.44 (1H, dd, J=9.5, 2.4 Hz), 2.35 (2H, q, J=7.3 Hz), 1.94 (3H, s), 1.60 (2H, quintet, J=7.3 Hz), 1.32 (3H, s), 1.31 (3H, s), 1.27 (12H, s), 0.88 (3H, t, J=7.3 Hz).

iii) Methyl 5-acetamido-4-(N,N'-bis-tert-butoxycarbonyl)guanidino-2,3,4,5-tetradeoxy-8,9-O-isopropylidene-7-O-decanoyl-D-glycero-D-galacto-non-2-enopyranosoate (E'30)

100 mg (0.21 mmol) of the compound (E'29), 87 mg (0.31 mmol) of N,N'-bis-tert-butoxycarbonylthiourea and 87 μl (0.63 mmol) of triethylamine were dissolved in 5 ml of dimethylformamide at room temperature. Subsequently, 84 mg (0.31 mmol) of mercury chloride were added to the system under ice-cooling, and the mixture was stirred at room temperature for 2 hours. Ethyl acetate was added to the reaction mixture to dilute it and the mixture was filtered using Celite. The filtered product was washed with ethyl acetate. The filtrate thus obtained and the washing solution were combined, and ethyl acetate and a saturated aqueous NaCl solution were added thereto to separate the mixture. The organic layer was dried over magnesium sulfate and filtered, followed by concentration under reduced pressure. The residue was purified over silica gel column chromatography (Kiesel gel 60, hexane:ethyl acetate=2:1) to obtain 120 mg (yield: 87%) of the title compound (E'30) as a colorless transparent syrup.

Rf value: 0.30 (hexane:ethyl acetate=2:1); $^1$H-NMR (270 MHz, CDCl$_3$, TMS): δ (ppm) 11.4 (1H, s), 8.46 (1H, d, J=8.7 Hz), 6.06 (1H, d, J=8.7 Hz), 5.88 (1H, d, J=2.4 Hz), 5.37 (1H, dd, J=6.4, 1.5 Hz), 5.15 (1H, dt, J=8.7, 2.4 Hz), 4.38 (1H, q, J=6.4 Hz), 4.28 (1H, dd, J=8.7, 1.5 Hz), 4.23 (1H, t, J=8.7 Hz), 4.10 (1H, dd, J=9.6, 6.4 Hz), 3.95 (1H, dd, J=9.6, 6.4 Hz), 3.80 (3H, s), 2.453 (1H, dt, J=16.0, 7.5 Hz), 2.33 (1H, dt, J=16.0, 7.5 Hz), 1.87 (3H, s), 1.61 (2H, quintet, J=7.5 Hz), 1.49 (9H, s), 1.48 (9H, s), 1.38 (3H, s), 1.35 (3H, s), 1.25 (12H, bs), 0.88 (3H, t, J=7.5 Hz).

iv) 5-Acetamido-4-(N,N'-bis-tert-butoxycarbonyl)guanidino-2,3,4,5-tetradeoxy-8,9-O-isopropylidene-7-O-decanoyl-D-glycero-D-galacto-non-2-enopyranosoic acid (E'31)

100 mg (0.14 mmol) of the compound (E'30) were dissolved in a mixture of 4 ml (40-times volume) of methanol and 1 ml (10-times volume) of water, and 6.5 mg (0.154 mmol) of lithium hydroxide monohydrate were added to the system at room temperature, followed by stirring of the mixture at room temperature for 8 hours. After confirmation of completion of the reaction, Dowex-50W was added to the system to neutralize it. The reaction mixture was filtered, and the filtered product was washed with methanol. The filtrate and the washing solution were combined and concentrated under reduced pressure. The residue was purified over silica gel column chromatography (Kiesel gel 60, ethyl acetate:2-propanol:water=10:2:1) to obtain 53 mg (yield: 55%) of the desired compound (E'31) as a white solid.

Rf value: 0.38 (methylene chloride:methanol=10:1); $^1$H-NMR (270 MHz, CDCl$_3$, TMS): δ (ppm) 11.4 (1H, s), 8.48 (1H, d, J=8.0 Hz), 6.31 (1H, dull s), 5.90 (1H, bs), 5.30 (1H, bs), 5.10 (1H, bs), 4.60–3.30 (7H, m), 2.48 (1H, dt, J=13.5, 6.5 Hz), 2.32 (1H, dt, J=13.5, 6.5 Hz), 1.88 (3H, s), 1.60 (2H, quintet, J=6.5 Hz), 1.48 (18H, s), 1.39 (3H, s), 1.37 (3H, s), 1.25 (12H, bs), 0.88 (3H, t, J=6.5 Hz).

v) 5-Acetamido-2,3,4,5-tetradeoxy-4-guanidino-9-O-decanoyl-D-glycero-D-galacto-non-2-enopyranosoic acid trifluoroacetic acid salt (E'32)

40 mg (0.057 mmol) of the compound (E'31) were dissolved in 3 ml (50-times volume) of methylene chloride at room temperature, and subsequently 1 ml (10-times volume) of trifluoroacetic acid was added to the system at room temperature, followed by stirring of the mixture at room temperature for 22 hours. After confirmation of completion of the reaction, the reaction mixture was concentrated under reduced pressure. The residue was purified over silica gel column chromatography (Kiesel gel 60, 5 g, 2-propanol:water=5:1) to obtain 30 mg (yield: 87%) of the title compound (E'32) as a pale yellow solid.

Rf value: 0.3 (2-propanol:water 5:1); $^1$H-NMR (270 MHz, CD$_3$OD): δ (ppm) 5.55 (1H, bs), 4.40–4.10 (7H, m), 3.65 (1H, d, J=9.0 Hz), 2.36 (2H, t, J=7.0 Hz), 2.00 (3H, s), 1.70–1.50 (2H, m), 1.30 (12H, bs), 0.90 (3H, t, J=7.0 Hz); FAB-MS (positive): 487(M+H)$^+$; $[\alpha]_D^{24}$=+17.2° (c=0.15, MeOH).

EXAMPLE 7

5-Acetamido-2,3,4,5-tetradeoxy-4-guanidino-9-O-palmitoyl-D-glycero-D-galacto-non-2-enopyranosoic acid trifluoroacetic acid salt (E'37) (Exemplary compound No. 42')

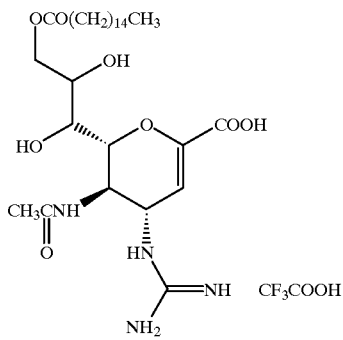

i) Methyl 5-acetamido-4-azido-2,3,4,5-tetradeoxy-8,9-O-isopropylidene-7-O-palmitoyl-D-glycero-D-galacto-non-2-enopyranosoate (E'33)

1.35 g (3.66 mmol) of the compound (E'3) were dissolved in 10 ml of methylene chloride at room temperature, and subsequently 1.88 ml (6.22 mmol) of palmitoyl chloride and 759 mg (4.33 mmol) of 4-dimethylaminopyridine were added to the system under ice-cooling, followed by stirring of the mixture at room temperature for 30 minutes. Next, 104 μl (6.21 mmol) of triethylamine were poured into the reaction mixture at room temperature, and the resulting mixture was further stirred for 15 hours. After confirmation of completion of the reaction, methanol was poured to the system, and the mixture was stirred for 30 minutes. Next, ethyl acetate and a saturated aqueous NaCl solution were added to the reaction mixture to separate it. The organic layer thus obtained was dried over magnesium sulfate and filtered, followed by concentration under reduced pressure. The residue was purified over silica gel column chromatography (Kiesel gel 60, n-hexane:ethyl acetate=2:1) to obtain 1.42 g (yield: 64%) of the desired compound (E'33) as a colorless foam.

Rf value: 0.53 (n-hexane:ethyl acetate=1:1); $^1$H-NMR (270 MHz, CDCl$_3$, TMS): δ (ppm) 5.95 (1H, d, J=2.7 Hz), 5.88 (1H, d, J=7.9 Hz), 5.35 (1H, dd, J=6.0, 1.8 Hz), 4.80 (1H, dd, J=9.1, 2.7 Hz), 4.71 (1H, dd, J=10.5, 1.8 Hz), 4.39 (1H, q, J=6.0 Hz) 4.14 (1H, dd, J=8.8, 6.0 Hz), 3.945 (1H, dd, J=8.8, 6.0 Hz), 3.81 (3H, s), 3.45 (1H, ddd, J=10.5, 9.1, 7.9 Hz), 2.41 (1H, t, J=7.5 Hz), 2.39 (1H, t, J=7.5 Hz), 2.02 (3H, s), 1.63 (2H, quintet, J=7.5 Hz), 1.37 (3H, s), 1.35 (3H, s), 1.26 (24H, s), 0.88 (3H, t, J=7.5 Hz).

ii) Methyl 5-acetamido-4-amino-2,3,4,5-tetradeoxy-8,9-O-isopropylidene-7-O-palmitoyl-D-glycero-D-galacto-non-2-enopyranosoate (E'34)

1.42 g (2.34 mmol) of the compound (E'33) were dissolved in 15 ml of ethanol at room temperature, and subsequently 477 mg (0.34-times volume) of Lindlar catalyst were added to the system at room temperature, followed by stirring of the mixture at room temperature under a hydrogen atmosphere of 1 atm. for 2 hours. After confirmation of completion of the reaction, the reaction mixture was filtered. The filtered product was washed with ethanol, and the filtrate and the washing solution were combined, followed by concentration under reduced pressure. The residue was purified over silica gel column chromatography (Kiesel gel 60, 15 g, ethyl acetate:methanol=10:1) to obtain 1.16 g (yield: 85%) of the title compound (E'34) as a colorless foam.

Rf value: 0.18 (ethyl acetate:methanol=5:1); $^1$H-NMR (270 MHz, CD$_3$OD, TMS): δ (ppm) 5.94 (1H, d, J=2.4 Hz), 5.42 (1H, dd, J=4.7, 1.8 Hz), 4.39 (1H, dt, J=7.1, 6.0 Hz), 4.18 (1H, dd, J=9.5, 1.6 Hz), 4.14 (1H, dd, J=8.7, 6.4 Hz), 3.93 (1H, dd, J=8.7, 6.4 Hz), 3.87 (1H, t, J=9.5 Hz), 3.78 (3H, s), 3.44 (1H, dd, J=9.5, 2.4 Hz), 2.35 (2H, q, J=7.3 Hz), 1.94 (3H, s), 1.60 (2H, quintet, J=7.3 Hz), 1.32 (3H, s), 1.31 (3H, s), 1.27 (24H, s), 0.88 (3H, t, J=7.3 Hz).

iii) Methyl 5-acetamido-4-(N,N'-bis-tert-butoxycarbonyl)guanidino-2,3,4,5-tetradeoxy-8,9-O-isopropylidene-7-O-palmitoyl-D-glycero-D-galacto-non-2-enopyranosoate (E'35)

1.16 g (2.0 mmol) of the compound (E'34), 828 mg (2.99 mmol) of N,N'-bis-tert-butoxycarbonylthiourea and 0.42 ml (3.03 mmol) of triethylamine were dissolved in 12 ml of dimethylformamide at room temperature. Subsequently, 813 mg (2.99 mmol) of mercury chloride were added to the system under ice-cooling, and the mixture was stirred at room temperature for 2 hours. Ethyl acetate was added to the reaction mixture to dilute it and the mixture was filtered using Celite. The filtered product was washed with ethyl acetate. The filtrate thus obtained and the washing solution were combined, and ethyl acetate and a saturated aqueous NaCl solution were added thereto to separate the mixture. The organic layer was dried over magnesium sulfate and filtered, followed by concentration under reduced pressure. The residue was purified over silica gel column chromatography (Kiesel gel 60, 15 g, hexane:ethyl acetate=2:1) to obtain 1.0 g (yield: 61%) of the title compound (E'35) as a colorless foam.

Rf value: 0.52 (hexane:ethyl acetate=2:1); $^1$H-NMR (270 MHz, CDCl$_3$, TMS): δ (ppm) 11.4 (1H, s), 8.46 (1H, d, J=8.7 Hz), 6.06 (1H, d, J=8.7 Hz), 5.88 (1H, d, J=2.4 Hz), 5.37 (1H, dd, J=6.4, 1.5 Hz), 5.15 (1H, dt, J=8.7, 2.4 Hz), 4.38 (1H, q, J=6.4 Hz), 4.28 (1H, dd, J=8.7, 1.5 Hz), 4.23 (1H, t, J=8.7 Hz), 4.10 (1H, dd, J=9.6, 6.4 Hz), 3.95 (1H, dd, J=9.6, 6.4 Hz), 3.80 (3H, s), 2.453 (1H, dt, J=16.0, 7.5 Hz), 2.33 (1H, dt, J=16.0, 7.5 Hz), 1.87 (3H, s), 1.61 (2H, quintet, J=7.5 Hz), 1.49 (9H, s), 1.48 (9H, s), 1.38 (3H, s), 1.35 (3H, s), 1.25 (24H, bs), 0.88 (3H, t, J=7.5 Hz).

iv) 5-Acetamido-4-(N,N'-bis-tert-butoxycarbonyl)guanidino-2,3,4,5-tetradeoxy-8,9-O-isopropylidene-7-O-palmitoyl-D-glycero-D-galacto-non-2-enopyranosoic acid (E'36)

61 mg (0.07 mmol) of the compound (E'35) were dissolved in a mixture of 1.2 ml (40-times volume) of methanol and 0.15 ml (10-times volume) of water, and 3.4 mg (0.08 mmol) of lithium hydroxide monohydrate were added to the system at room temperature, followed by stirring of the mixture at room temperature for 3 hours. After confirmation of completion of the reaction, Dowex-50W was added to the system to neutralize it, and the reaction mixture was filtered. The filtered product was washed with methanol. The filtrate and the washing solution were combined, and the mixture was concentrated under reduced pressure. The residue was purified over silica gel column chromatography (Kiesel gel 60, ethyl acetate:methanol=10:1) to obtain 33 mg (yield: 55%) of the desired compound (E'36) as a colorless foam.

Rf value: 0.61 (ethyl acetate:methanol=5:1); $^1$H-NMR (270 MHz, CDCl$_3$, TMS): δ (ppm) 11.4 (1H, s), 8.48 (1H, d, J=8.0 Hz), 6.31 (1H, dull s), 5.90 (1H, bs), 5.30 (1H, bs), 5.10 (1H, bs), 4.60–3.30 (7H, m), 2.48 (1H, dt, J=13.5, 6.5 Hz), 2.32 (1H, dt, J=13.5, 6.5 Hz), 1.88 (3H, s), 1.60 (2H, quintet, J=6.5 Hz), 1.48 (24H, s), 1.39 (3H, s), 1.37 (3H, s), 1.25 (8H, bs), 0.88 (3H, J=6.5 Hz).

v) 5-Acetamido-2,3,4,5-tetradeoxy-4-guanidino-9-O-palmitoyl-D-glycero-D-galacto-non-2-enopyranosoic acid trifluoroacetic acid salt (E'37)

289 mg (0.36 mmol) of the compound (E'36) were dissolved in 3 ml (50-times volume) of methylene chloride at room temperature, and subsequently 1 ml (10-times volume) of trifluoroacetic acid was added to the system at room temperature, followed by stirring of the mixture at room temperature for 22 hours. After confirmation of completion of the reaction, the reaction mixture was concentrated under reduced pressure. The residue was purified over silica gel column chromatography (Kiesel gel 60, 5 g, ethyl acetate:2-propanol:water=5:2:1) to obtain 206 mg (yield: 84%) of the title compound (E'37) as a colorless foam.

Rf value: 0.44 (2-propanol:water=5:1); $^1$H-NMR (270 MHz, CD$_3$OD): δ (ppm) 5.55 (1H, bs), 4.40–4.10 (7H, m), 3.65 (1H, d, J=9.0 Hz), 2.36 (2H, t, J=7.0 Hz), 2.00 (3H, s), 1.70–1.50 (2H, m), 1.30 (24H, bs), 0.90 (3H, t, J=7.0 Hz); FAB-MS (positive): 571 (M+H)$^+$; $[\alpha]_D^{24}$=+18.5° (c=0.12, MeOH).

EXAMPLE 8'

5-Acetamido-2,3,4,5-tetradeoxy-4-guanidino-9-O-dodecanoyl-D-glycero-D-galacto-non-2-enopyranosoic acid trifluoroacetic acid salt (E'42)
(Exemplary compound No. 40')

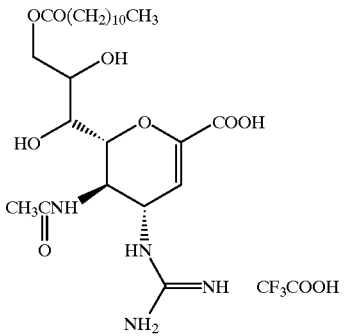

i) Methyl 5-acetamido-4-azido-2,3,4,5-tetradeoxy-8,9-O-isopropylidene-7-O-dodecanoyl-D-glycero-D-galacto-non-2-enopyranosoate (E'38)

1.07 g (2.89 mmol) of the compound (E'3) were dissolved in 11 ml of methylene chloride at room temperature, and subsequently 1.03 ml (4.33 mmol) of dodecanoyl chloride and 529 mg (4.33 mmol) of 4-dimethylaminopyridine were added to the system under ice-cooling, followed by stirring of the mixture at room temperature for 30 minutes. Next, 0.6 ml (4.33 mmol) of triethylamine were poured into the reaction mixture at room temperature, and the mixture was further stirred for 2.5 hours. After confirmation of completion of the reaction, methanol was poured into the system, and the mixture was stirred for 30 minutes. Next, ethyl acetate and a saturated aqueous NaCl solution were added to the reaction mixture to separate it. The organic layer thus obtained was dried over magnesium sulfate and filtered, followed by concentration under reduced pressure. The residue was purified over silica gel column chromatography (Kiesel gel 60, n-hexane:ethyl acetate=2:1) to obtain 1.07 mg (yield: 67%) of the desired compound (E'38) as a colorless foam.

Rf value: 0.44 (n-hexane:ethyl acetate=1:1); $^1$H-NMR (270 MHz, CDCl$_3$, TMS): δ (ppm) 5.95 (1H, d, J=2.7 Hz), 5.88 (1H, d, J=7.9 Hz), 5.35 (1H, dd, J=6.0, 1.8 Hz), 4.80 (1H, dd, J=9.1, 2.7 Hz), 4.71 (1H, dd, J=10.5, 1.8 Hz), 4.39 (1H, q, J=6.0 Hz), 4.14 (1H, dd, J=8.8, 6.0 Hz), 3.945 (1H, dd, J=8.8, 6.0 Hz), 3.81 (3H, s), 3.45 (1H, ddd, J=10.5, 9.1, 7.9 Hz), 2.41 (1H, t, J=7.5 Hz), 2.39 (1H, t, J=7.5 Hz), 2.02 (3H, s), 1.63 (2H, quintet, J=7.5 Hz), 1.37 (3H, s), 1.35 (3H, s), 1.26 (16H, s), 0.88 (3H, t, J=7.5 Hz).

ii) Methyl 5-acetamido-4-amino-2,3,4,5-tetradeoxy-8,9-O-isopropylidene-7-O-dodecanoyl-D-glycero-D-galacto-non-2-enopyranosoate (E'39)

1.06 g (1.92 mmol) of the compound (E'38) were dissolved in 10 ml of ethanol at room temperature, and subsequently 353 mg (0.33-times volume) of Lindlar catalyst were added to the system at room temperature, followed by stirring of the mixture at room temperature under a hydrogen atmosphere of 1 atm. for 1.5 hours. After confirmation of completion of the reaction, the reaction mixture was filtered. The filtered product was washed with ethanol, and the filtrate and the washing solution were combined, followed by concentration under reduced pressure. The residue was purified over silica gel column chromatography (Kiesel gel 60, 15 g, ethyl acetate:methanol=5:1) to obtain 871 mg (yield: 86%) of the title compound (E'39) as a colorless foam.

Rf value: 0.36 (ethyl acetate:methanol=5:1); $^1$H-NMR (270 MHz, CD$_3$OD, TMS): δ (ppm) 5.94 (1H, d, J=2.4 Hz), 5.42 (1H, dd, J=4.7, 1.8 Hz), 4.39 (1H, dt, J=7.1, 6.0 Hz), 4.18 (1H, dd, J=9.5, 1.6 Hz), 4.14 (1H, dd, J=8.7, 6.4 Hz), 3.93 (1H, dd, J=8.7, 6.4 Hz), 3.87 (1H, t, J=9.5 Hz), 3.78 (3H, s), 3.44 (1H, dd, J=9.5, 2.4 Hz), 2.35 (2H, q, J=7.3 Hz), 1.94 (3H, s), 1.60 (2H, quintet, J=7.3 Hz), 1.32 (3H, s), 1.31 (3H, s), 1.27 (16H, s), 0.88 (3H, t, J=7.3 Hz).

iii) Methyl 5-acetamido-4-N,N'-bis-tert-butoxycarbonyl) guanidino-2,3,4,5-tetradeoxy-8,9-O-isopropylidene-7-O-dodecanoyl-D-glycero-D-galacto-non-2-enopyranosoate (E'40)

868 mg (1.65 mmol) of the compound (E'39), 940 mg (3.4 mmol) of N,N'-bis-tert-butoxycarbonylthiourea and 0.95 ml (6.90 mmol) of triethylamine were dissolved in 10 ml of dimethylformamide at room temperature. Subsequently, 926 mg (3.4 mmol) of mercury chloride were added to the system under ice-cooling, and the mixture was stirred at room temperature for 2 hours. Ethyl acetate was added to the reaction mixture to dilute it and the mixture was filtered using Celite. The filtered product was washed with ethyl acetate. The filtrate and the washing solution were combined, and ethyl acetate and a saturated aqueous NaCl solution were added thereto to separate the mixture. The organic layer was dried over magnesium sulfate and filtered, followed by concentration under reduced pressure. The residue was purified over silica gel column chromatography (Kiesel gel 60, 15 g, hexane:ethyl acetate=2:1) to obtain 1.3 g (yield: 100%) of the title compound (E'40) as a colorless foam.

Rf value: 0.47 (hexane:ethyl acetate=2:1); $^1$H-NMR (270 MHz, CDCl$_3$, TMS): δ (ppm) 11.4 (1H, s), 8.46 (1H, d, J=8.7 Hz), 6.06 (1H, d, J=8.7 Hz), 5.88 (1H, d, J=2.4 Hz), 5.37 (1H, dd, J=6.4, 1.5 Hz), 5.15 (1H, dt, J=8.7, 2.4 Hz), 4.38 (1H, q, J=6.4 Hz), 4.28 (1H, dd, J=8.7, 1.5 Hz), 4.23 (1H, t, J=8.7 Hz), 4.10 (1H, dd, J=9.6, 6.4 Hz), 3.95 (1H, dd, J=9.6, 6.4 Hz), 3.80 (3H, s), 2.453 (1H, dt, J=16.0, 7.5 Hz), 2.33 (1H, dt, J=16.0, 7.5 Hz), 1.87 (3H, s), 1.61 (2H, quintet, J=7.5 Hz), 1.49 (9H, s), 1.48 (9H, s), 1.38 (3H, s), 1.35 (3H, s), 1.25 (16H, bs), 0.88 (3H, t, J=7.5 Hz).

iv) 5-Acetamido-4-(N,N'-bis-tert-butoxycarbonyl) guanidino-2,3,4,5-tetradeoxy-8,9-O-isopropylidene-7-O-dodecanoyl-D-glycero-D-galacto-non-2-enopyranosoic acid (E'41)

100 mg (0.15 mmol) of the compound (E'40) were dissolved in a mixture of 4 ml (40-times volume) of methanol and 1 ml (10-times volume) of water, and 7.0 mg (0.165 mmol) of lithium hydroxide monohydrate were added to the system at room temperature, followed by stirring of the mixture at room temperature for 8 hours. After confirmation of completion of the reaction, Dowex-50W was added to the system to neutralize it, and the reaction mixture was filtered. The filtered product was washed with methanol. The filtrate and the washing solution were combined, and the mixture was concentrated under reduced pressure. The residue was purified over silica gel column chromatography (Kiesel gel 60, ethyl acetate:2-propanol:water=10:2:1) to obtain 56 mg (yield: 56%) of the desired compound (E'41) as a white solid.

Rf value: 0.35 (methylene chloride:methanol=10:1); $^1$H-NMR (270 MHz, CDCl$_3$, TMS): δ (ppm) 11.4 (1H, s), 8.48 (1H, d, J=8.0 Hz), 6.31 (1H, dull s), 5.90 (1H, bs), 5.30 (1H, bs), 5.10 (1H, bs), 4.60–3.30 (7H, m), 2.48 (1H, dt, J=13.5, 6.5 Hz), 2.32 (1H, dt, J=13.5, 6.5 Hz), 1.88 (3H, s), 1.60 (2H, quintet, J=6.5 Hz), 1.48 (18H, s), 1.39 (3H, s), 1.37 (3H, s), 1.25 (8H, bs), 0.88 (3H, t, J=6.5 Hz).

v) 5-Acetamido-2,3,4,5-tetradeoxy-4-guanidino-9-O-dodecanoyl-D-glycero-D-galacto-non-2-enopyranosoic acid trifluoroacetic acid salt (E'42)

50 mg (0.075 mmol) of the compound (E'41) were dissolved in 3 ml (50-times volume) of methylene chloride at room temperature, and subsequently 1 ml (10-times volume) of trifluoroacetic acid was added to the system at room temperature, followed by stirring of the mixture at room temperature for 22 hours. After confirmation of completion of the reaction, the reaction mixture was concentrated under reduced pressure. The residue was purified over silica gel column chromatography (Kiesel gel 60, 5 g, 2-propanol:water=5:1) to obtain 38 mg (yield: 88%) of the title compound (E'42) as a pale yellow solid.

Rf value: 0.3 (2-propanol:water=5:1); $^1$H-NMR (270 MHz, CD$_3$OD): δ (ppm) 5.55 (1H, bs), 4.40–4.10 (7H, m), 3.65 (1H, d, J=9.0 Hz), 2.36 (2H, t, J=7.0 Hz), 2.00 (3H, s), 1.70–1.50 (2H, m), 1.30 (8H, bs), 0.90 (3H, t, J=7.0 Hz); FAB-MS (positive): 515 (M+H)$^+$; $[\alpha]_D^{24}$=+20.5° (c=0.08, MeOH).

EXAMPLE 9'

5-Acetamido-2,3,4,5-tetradeoxy-4-guanidino-9-O-octadecanoyl-D-glycero-D-galacto-non-2-enopyranosoic acid trifluoroacetic acid salt (E'47) (Exemplary compound No. 43')

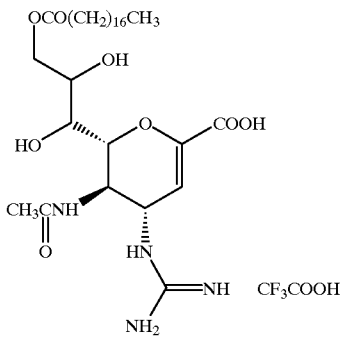

i) Methyl 5-acetamido-4-azido-2,3,4,5-tetradeoxy-8,9-O-isopropylidene-7-O-octadecanoyl-D-glycero-D-galacto-non-2-enopyranosoate (E'43)

1.10 g (2.98 mmol) of the compound (E'3) were dissolved in 11 ml of methylene chloride at room temperature, and subsequently 1.70 ml (5.03 mmol) of stearoyl chloride and 620 mg (5.07 mmol) of 4-dimethylaminopyridine were added to the system under ice-cooling, followed by stirring of the mixture at room temperature for 30 minutes. Next, 0.70 ml (5.05 mmol) of triethylamine were poured into the reaction mixture at room temperature, and the resulting mixture was further stirred for 15 hours. After confirmation of completion of the reaction, methanol was poured into the system, and the mixture was stirred for 30 minutes. Next, ethyl acetate and a saturated aqueous NaCl solution were added to the reaction mixture to separate it. The organic layer was dried over magnesium sulfate and filtered, followed by concentration under reduced pressure. The residue was purified over silica gel column chromatography (Kiesel gel 60, n-hexane:ethyl acetate=2:1) to obtain 1.21 g (yield: 64%) of the desired compound (E'43) as a colorless foam.

Rf value: 0.51 (n-hexane:ethyl acetate=1:1); $^1$H-NMR (270 MHz, CDCl$_3$, TMS): δ (ppm) 5.95 (1H, d, J=2.7 Hz), 5.88 (1H, d, J=7.9 Hz), 5.35 (1H, dd, J=6.0, 1.8 Hz), 4.80 (1H, dd, J=9.1, 2.7 Hz), 4.71 (1H, dd, J=10.5, 1.8 Hz), 4.39 (1H, q, J=6.0 Hz), 4.14 (1H, dd, J=8.8, 6.0 Hz), 3.945 (1H, dd, J=8.8, 6.0 Hz), 3.81 (3H, s), 3.45 (1H, ddd, J=10.5, 9.1, 7.9 Hz), 2.41 (1H, t, J=7.5 Hz), 2.39 (1H, t, J=7.5 Hz), 2.02 (3H, s), 1.63 (2H, quintet, J=7.5 Hz), 1.37 (3H, s), 1.35 (3H, s), 1.26 (28H, s), 0.88 (3H, t, J=7.5 Hz).

ii) Methyl 5-acetamido-4-amino-2,3,4,5-tetradeoxy-8,9-O-isopropylidene-7-O-octadecanoyl-D-glycero-D-galacto-non-2-enopyranosoate (E'44)

1.20 g (1.88 mmol) of the compound (E'43) were dissolved in 12 ml of ethanol at room temperature, and subsequently 399 mg (0.33-times volume) of Lindlar catalyst were added to the system at room temperature, followed by stirring of the mixture at room temperature under a hydrogen atmosphere of 1 atm. for 3 hours. After confirmation of completion of the reaction, the reaction mixture was filtered. The filtered product was washed with ethanol. The filtrate and the washing solution were combined, and the mixture was concentrated under reduced pressure. The residue was purified over silica gel column chromatography (Kiesel gel 60, 15 g, ethyl acetate:methanol=10:1) to obtain 924 mg (yield: 80%) of the title compound (E'44) as a colorless foam.

Rf value: 0.37 (ethyl acetate:methanol=4:1); $^1$H-NMR (270 MHz, CD$_3$OD, TMS): δ (ppm) 5.94 (1H, d, J=2.4 Hz), 5.42 (1H, dd, J=4.7, 1.8 Hz), 4.39 (1H, dt, J=7.1, 6.0 Hz), 4.18 (1H, dd, J=9.5, 1.6 Hz), 4.14 (1H, dd, J=8.7, 6.4 Hz), 3.93 (1H, dd, J=8.7, 6.4 Hz), 3.87 (1H, t, J=9.5 Hz), 3.78 (3H, s), 3.44 (1H, dd, J=9.5, 2.4 Hz), 2.35 (2H, q, J=7.3 Hz), 1.94 (3H, s), 1.60 (2H, quintet, J=7.3 Hz), 1.32 (3H, s), 1.31 (3H, s), 1.27 (28H, s), 0.88 (3H, t, J=7.3 Hz).

iii) Methyl 5-acetamido-4-(N,N'-bis-tert-butoxycarbonyl)guanidino-2,3,4,5-tetradeoxy-8,9-O-isopropylidene-7-O-octadecanoyl-D-glycero-D-galacto-non-2-enopyranosoate (E'45)

916 mg (1.50 mmol) of the compound (E'44), 539 mg (1.95 mmol) of N,N'-bis-tert-butoxycarbonylthiourea and 0.27 ml (1.95 mmol) of triethylamine were dissolved in 12 ml of dimethylformamide at room temperature. Subsequently, 529 mg (1.95 mmol) of mercury chloride were added to the system under ice-cooling, and the mixture was stirred at room temperature for 4 hours. Ethyl acetate was added to the reaction mixture to dilute it, and the mixture was filtered using Celite. The filtered product was washed with ethyl acetate. The filtrate and the washing solution were combined, and ethyl acetate and a saturated aqueous NaCl solution were added to the mixture separate it. The organic layer was dried over magnesium sulfate and filtered, followed by concentration under reduced pressure. The residue was purified over silica gel column chromatography (Kiesel gel 60, 15 g, hexane:ethyl acetate=2:1) to obtain 750 mg (yield: 59%) of the title compound (E'45) as a colorless foam.

Rf value: 0.29 (hexane:ethyl acetate=2:1); $^1$H-NMR (270 MHz, CDCl$_3$, TMS): δ (ppm) 11.4 (1H, s), 8.46 (1H, d, J=8.7 Hz), 6.06 (1H, d, J=8.7 Hz), 5.88 (1H, d, J=2.4 Hz), 5.37 (1H, dd, J=6.4, 1.5 Hz), 5.15 (1H, dt, J=8.7, 2.4 Hz), 4.38 (1H, q, J=6.4 Hz), 4.28 (1H, dd, J=8.7, 1.5 Hz), 4.23 (1H, J=8.7 Hz), 4.10 (1H, dd, J=9.6, 6.4 Hz), 3.95 (1H, dd, J=9.6, 6.4 Hz), 3.80 (3H, s), 2.453 (1H, dt, J=16.0, 7.5 Hz), 2.33 (1H, dt, J=16.0, 7.5 Hz), 1.87 (3H, s), 1.61 (2H, quintet, J=7.5 Hz), 1.49 (9H, s), 1.48 (9H, s), 1.38 (3H, s), 1.35 (3H, s), 1.25 (28H, bs), 0.88 (3H, t, J=7.5 Hz).

iv) 5-Acetamido-4-(N,N'-bis-tert-butoxycarbonyl)guanidino-2,3,4,5-tetradeoxy-8,9-O-isopropylidene-7-O-octadecanoyl-D-glycero-D-galacto-non-2-enopyranosoic acid (E'46)

741 mg (0.87 mmol) of the compound (E'45) were dissolved in a mixture of 15 ml of methanol and 1.5 ml of water, and 38 mg (0.91 mmol) of lithium hydroxide monohydrate were added to the system at room temperature, followed by stirring of the mixture at room temperature for 6 hours. After confirmation of completion of the reaction, a solution of 4N HCl in dioxane was added to the system to neutralize it, followed by concentration under reduced pressure. The residue was purified over silica gel column chromatography (Kiesel gel 60, ethyl acetate:metanol=10:1) to obtain 430 mg (yield: 59%) of the desired compound (E'46) as a colorless foam.

Rf value: 0.40 (ethyl acetate:methanol=5:1); $^1$H-NMR (270 MHz, CDCl$_3$, TMS): δ (ppm) 11.4 (1H, s), 8.48 (1H, d, J=8.0 Hz), 6.31 (1H, dull s), 5.90 (1H, bs), 5.30 (1H, bs), 5.10 (1H, bs), 4.60–3.30 (7H, m), 2.48 (1H, dt, J=13.5, 6.5 Hz), 2.32 (1H, dt, J=13.5, 6.5 Hz), 1.88 (3H, s), 1.60 (2H, quintet, J=6.5 Hz), 1.48 (24H, s), 1.39 (3H, s), 1.37 (3H, s), 1.25 (28H, bs), 0.88 (3H, t, J=6.5 Hz).

v) 5-Acetamido-2,3,4,5-tetradeoxy-4-guanidino-9-O-octadecanoyl-D-glycero-D-galacto-non-2-enopyranosoic acid trifluoroacetic acid salt (E'47)

422 mg (0.50 mmol) of the compound (E'46) were dissolved in 3 ml of methylene chloride at room temperature, and subsequently 1 ml of trifluoroacetic acid was added to the system at room temperature, followed by stirring of the mixture at room temperature for 22 hours. After confirmation of completion of the reaction, the reaction mixture was concentrated under reduced pressure. The residue was purified over silica gel column chromatography (Kiesel gel 60, 5 g, ethyl acetate: 2-propanol:water=5:2:1) to obtain 300 mg (yield: 84%) of the title compound (E'47) as a colorless foam.

Rf value: 0.44 (2-propanol:water=5:1); $^1$H-NMR (270 MHz, CD$_3$OD): δ (ppm) 5.55 (1H, bs), 4.40–4.10 (7H, m), 3.65 (1H, d, J=9.0 Hz), 2.36 (2H, t, J=7.0 Hz), 2.00 (3H, s), 1.70–1.50 (2H, m), 1.30 (28H, bs), 0.90 (3H, t, J=7.0 Hz); FAB-MS (positive): 599 (M+H)$^+$; $[α]_D^{24}$=+19.8° (c=0.15, MeOH).

EXAMPLE 10'

Cetyl 5-acetamido-2,3,4,5-tetradeoxy-4-guanidino-D-glycero-D-galacto-non-2-enopyranosoate trifluoroacetic acid salt (E'48) (Exemplary compound No. 89')

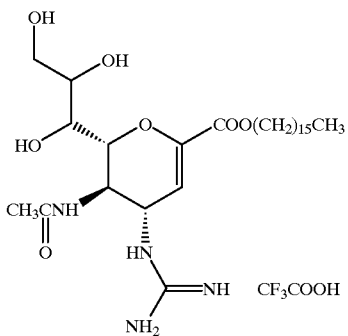

The procedures were carried out in a similar manner to those in Example 1' using cetyl alcohol instead of myristyl alcohol to obtain the title compound.

$^1$H-NMR (270 MHz, CD$_3$OD): δ (ppm) 5.83 (1H, d, J=2.7 Hz), 4.44 (1H, dd, J=9.0, 2.7 Hz), 4.38 (1H, dd, J=9.0, <1 Hz), 4.18 (2H, t, J=6.2 Hz), 4.17 (1H, t, J=9.0 Hz), 3.90–3.74 (2H, m), 3.68 (1H, dd, J=12.0, 4.5 Hz), 3.65 (1H, d, J=9.0 Hz), 1.99 (3H, s), 1.67 (2H, quintet, J=6.2 Hz), 1.26 (28H, bs), 0.87 (3H, t, J=6.2 Hz).

EXAMPLE 11'

Stearyl 5-acetamido-2,3,4,5-tetradeoxy-4-guanidino-D-glycero-D-galacto-non-2-enopyranosoate trifluoroacetic acid salt (E'49) (Exemplary compound No. 91')

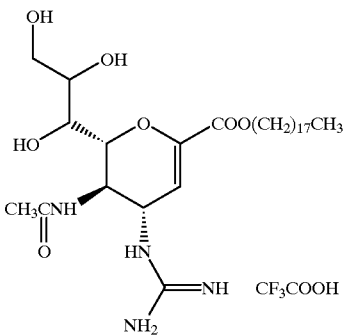

The procedures were carried out in a similar manner to those in Example 1' using stearyl alcohol instead of myristyl alcohol to obtain the title compound. $^1$H-NMR (270 MHz, CD$_3$OD): δ (ppm) 5.83 (1H, d, J=2.7 Hz), 4.44 (1H, dd, J=9.0, 2.7 Hz), 4.38 (1H, dd, J=9.0, <1Hz), 4.18 (2H, t, J=6.2 Hz), 4.17 (1H, t, J=9.0 Hz), 3.90–3.74 (2H, m), 3.68 (1H, dd, J=12.0, 4.5 Hz), 3.65 (1H, d, J=9.0 Hz), 1.99 (3H, s), 1.67 (2H, quintet, J=6.2 Hz), 1.26 (32H, bs), 0.87 (3H, J=6.2 Hz).

PREPARATION EXAMPLE 1'

An aqueous solution was prepared so that the compound of Example 4' was 10% (W/W), benzalkonium chloride 0.04% (W/W), phenylethyl alcohol 0.40% (W/W), and purified water 89.56% (W/W).

PREPARATION EXAMPLE 2'

An aqueous co-solvent solution was prepared so that the compound of Example 4' was 10% (W/W), benzalkonium chloride 0.04% (W/W), polyethylene glycol 400 10.0% (W/W), propylene glycol 30% (W/W), and purified water 39.96% (W/W).

PREPARATION EXAMPLE 3'

A dry powder was prepared so that the compound of Example 4' was 40% (W/W) and lactose was 60% (W/W).

PREPARATION EXAMPLE 4'

An aerosol agent was prepared so that the compound of Example 4' was 10% (W/W), lecithin 0.5% (W/W), Freon 11 34.5% and Freon 12 55%.

TEST EXAMPLE 1'

Influenza Virus Sialidase Inhibitory Activity

A cannula was inserted into the trachea of mice (BALB/C, females, 5 to 6 weeks old, body weight: 20 g) under anesthesia followed by injection of 0.5 ml of phosphate-buffered physiological saline. Lung washings were then obtained by collecting the liquid by aspiration, repeating the procedure three times. 1 μM of the test compound (sample), 10 μg of lung washings in terms of the amount of protein, and phosphate-buffered physiological saline were mixed and incubated at 37° C. for one to three days at a final volume of 100 μl. After sampling 10 μl of this reaction mixture, a sialidase reaction was carried out in 32.5 mM 2-(N-morpholino)ethanesulfonate buffer (pH 6.5) containing 40 mM calcium chloride using influenza virus A/PR/8/34 (equivalent to 5×10$^5$ plaque-forming units) as the sialidase enzyme and 0.1 mM ammonium 4-methylumbelliferyl-N-acetyl-α-D-neuraminate as the substrate. The fluorescence intensity of the 4-methylumbelliferone produced in the reaction mixture was measured at an excitation wavelength of 360 nm and measurement wavelength of 460 nm. On the other hand, a concentration vs. inhibition curve was prepared by carrying out similar reactions using as sample various concentrations of Compound A (GG-167). The amount of substance having sialidase inhibitory activity formed in the lung washings from the test compound was quantitatively determined as the amount of Compound A using the above inhibition curve.

Although the compound of the present invention did not exhibit influenza virus sialidase inhibitory activity directly, by treating with biological fractions containing hydrolase (e.g., mouse lung washings), the compound of the present invention exhibited influenza virus sialidase inhibitory activity similar to that of Compound A.

TEST EXAMPLE 2'

Mouse Infection Treatment Experiment 1'

A solution was prepared containing 500 pfu (plaque-forming units) of mouse-acclimated influenza virus A/PR/8/34 strain in 50 μl of phosphate buffer containing 0.42% bovine serum albumin which was then used to infect mice (BALB/C, females, 5–6 weeks old, 20 g) by dropping into the nose for infection. The compounds of the present invention were prepared to a dose level of 0.6 μmol/kg/50 μl by suspending in physiological saline, and administered to the animals by dropping into the nose on a total of 3 occasions at 4 hours before, 4 hours after and 17 hours after viral infection. The test was performed on groups of 7 or 8 animals, and results were indicated as the number of surviving mice divided by the number of test mice at 6, 8 and 10 days after infection. Incidentally, Compound A (GG-167) was used as the comparative compound.

TABLE 2

|  | Day 6 | Day 3 | Day 10 |
| --- | --- | --- | --- |
| Physiological saline only | 1/7 | 0/7 | 0/7 |
| Compound A | 7/7 | 3/7 | 0/7 |
| Compound of Example 1' | 8/8 | 5/8 | 3/8 |
| Compound of Example 2' | 8/8 | 2/8 | 1/8 |

Although all of the animals in the group dosed with Compound A were dead on day 10 after infection, 3 or 1 of the animals in the groups dosed with the compounds of Example 1' or Example 2' were still alive. These results indicate that the compound of Example 1' or Example 2' of the present invention possesses influenza infection therapeutic effects superior to those of Compound A.

TEST EXAMPLE 3'

Mouse Infection Treatment Experiment-2'

A solution was prepared containing 500 pfu (plaque-forming units) of mouse-acclimated influenza virus A/PR/8/34 strain in 50 μl of phosphate buffer containing 0.42% bovine serum albumin which was then used to infect mice (BALB/C, females, 5–6 weeks old, 20 g) by dropping into the nose for infection The compounds of the present invention were prepared to a dose level of 0.9 μmol/kg/50 μl by suspending in physiological saline, and administered to the animals by dropping into the nose on a total of 3 occasions at 4 hours before, 4 hours after and 17 hours after viral infection. The test was performed on groups of 4 to 12 animals, and results were indicated as the number of surviving mice divided by the number of test mice at 8 and 10 days after infection. Incidentally, Compound A (GG-167) was used as the comparative compound.

TABLE 3

|  | Day 8 | Day 10 |
| --- | --- | --- |
| Physiological saline only | 0/4 | 0/4 |
| Compound A | 0/8 | 0/8 |
| Compound of Example 1' | 4/12 | 2/12 |
| Compound of Example 10' | 10/12 | 5/12 |
| Compound of Example 11' | 11/11 | 5/11 |

Although all of the animals in the group dosed with Compound A were dead on day 10 after infection, 2 to 5 of the animals in the groups dosed with the compounds of Example 1', 10' or 11' were still alive. These results indicate that the compound of Example 1', Example 10' or Example 11' of the present invention possesses influenza infection therapeutic effects superior to those of Compound A.

TEST EXAMPLE 4'

Mouse Infection Treatment Experiment-3'

A solution was prepared containing 500 pfu (plaque-forming units) of mouse-acclimated influenza virus A/PR/8/34 strain in 50 μl of phosphate buffer containing 0.42% bovine serum albumin which was then used to infect mice (BALB/C, females, 5–6 weeks old, 20 g) by dropping into the nose for infection. The compounds of the present invention were prepared to a dose level of 0.3 μmol/kg/50 μl by suspending in physiological saline, and administered to the animals by dropping into the nose on a total of 3 occasions at 4 hours before, 4 hours after and 17 hours after viral infection. The test was performed on groups of 10 or 11 animals, and results were indicated as the number of surviving mice divided by the number of test mice at 6 and 8 days after infection. Incidentally, Compound A (GG-167) was used as the comparative compound.

TABLE 4

|  | Day 6 | Day 8 |
| --- | --- | --- |
| Physiological saline only | 0/10 | 0/10 |
| Compound A | 10/10 | 1/10 |
| Compound of Example 3' | 10/10 | 10/10 |
| Compound of Example 4' | 10/10 | 6/10 |
| Compound of Example 5' | 11/11 | 10/11 |
| Compound of Example 6' | 11/11 | 10/11 |
| Compound of Example 7' | 10/10 | 3/10 |
| Compound of Example 8' | 11/11 | 2/11 |
| Compound of Example 9' | 10/10 | 4/10 |

Although only one of the animals in the group dosed with Compound A was alive on day 8 after infection, 2 to 10 animals in the groups dosed with the compound of any one of Examples 3 to 9 were still alive. These results indicate that the compounds of Examples 3 to 9 of the present invention possess influenza infection therapeutic effects superior to those of Compound A.

Industrial Applicability

The neuraminic acid compound (1') of the present invention undergoes hydrolysis by hydrolase present in a living body and exhibits excellent viral replication inhibitory activity and sialidase inhibitory activity. In addition, if the neuraminic acid compound (1') is administered to mice infected with influenza virus, the compound exhibits infection therapeutic effects superior to Compound A (GG-167) described in WO91/16320 (Japanese PCT application (Kokai) No. Hei 5-507068. Thus, the neuraminic acid compound (1') of the present invention is useful as a therapeutic agent or preventive agent (preferably therapeutic agent) for viral infections (preferably influenza viral infections).

We claim:

1. A compound of formula (1):

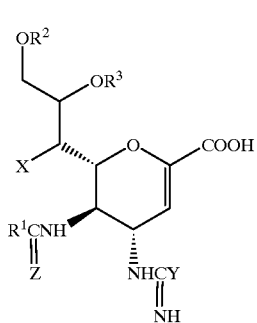

(I)

wherein:
$R^1$ represents an alkyl group having from 1 to 4 carbon atoms;
$R^2$ and $R^3$ are the same as or different from each other and each represents a hydrogen atom or an aliphatic acyl group having from 2 to 25 carbon atoms;
X represents a halogen atom or an alkoxy group having from 1 to 4 carbon atoms;
Y represents a group of formula $R^bR^cN$— or $R^bR^cN$—O—, where $R^b$ and $R^c$ are the same as or different from each other and each represents a hydrogen atom or an alkyl group having from 1 to 4 carbon atoms; and
Z represents an oxygen atom or a sulfur atom;
or a pharmaceutically acceptable salt or ester thereof.

2. The compound of claim 1, wherein $R^1$ represents a butyl group.

3. The compound of claim 1, wherein $R^1$ represents an ethyl group.

4. The compound of claim 1, wherein $R^1$ represents a propyl group.

5. The compound of claim 1, wherein $R^1$ represents a methyl group.

6. The compound of claim 1, wherein $R^2$ represents a hydrogen atom or an aliphatic carboxylic acyl group having from 6 to 25 carbon atoms.

7. The compound of claim 1, wherein $R^2$ represents a hydrogen atom or an aliphatic carboxylic acyl group having from 8 to 16 carbon atoms.

8. The compound of claim 1, wherein $R^2$ represents a hydrogen atom or an aliphatic carboxylic acyl group having from 8 to 16 carbon atoms and $R^3$ represents a hydrogen atom.

9. The compound of claim 1, wherein $R^2$ represents an octanoyl, decanoyl, dodecanoyl, myristoyl or palmitoyl group.

10. The compound of claim 1, wherein $R^2$ represents an octanoyl, decanoyl, dodecanoyl, myristoyl or palmitoyl group and $R^3$ represents a hydrogen atom.

11. The compound of claim 1, wherein $R^3$ represents a hydrogen atom or an aliphatic carboxylic acyl group having from 6 to 25 carbon atoms.

12. The compound of claim 1, wherein $R^3$ represents a hydrogen atom or an aliphatic carboxylic acyl group having from 8 to 16 carbon atoms.

13. The compound of claim 1, wherein $R^3$ represents a hydrogen atom, or an octanoyl, decanoyl, dodecanoyl, myristoyl or palmitoyl group.

14. The compound of claim 1, wherein X represents an alkoxy group having from 1 to 4 carbon atoms.

15. The compound of claim 1, wherein X represents a fluorine atom, a methoxy group or an ethoxy group.

16. The compound of claim 1, wherein Y represents an amino group or a group of formula $R^bR^cN$—O—, where $R^b$ and $R^c$ are as defined in claim 1.

17. The compound of claim 1, wherein Y represents an amino group or an aminooxy group.

18. The compound of claim 1, wherein Y represents an amino group.

19. The compound of claim 1, wherein Z represents an oxygen atom.

20. The compound of claim 1, wherein:
$R^1$ represents a methyl group;
$R^2$ represents a hydrogen atom or an aliphatic carboxylic acyl group having from 6 to 25 carbon atoms;
$R^3$ represents a hydrogen atom or an aliphatic carboxylic acyl group having from 6 to 25 carbon atoms;
X represents a halogen atom or an alkoxy group having from 1 to 4 carbon atoms;
Y represents an amino group or the group of formula $R^bR^cN$—O—; and
Z represents an oxygen atom.

21. The compound of claim 1, wherein:
$R^1$ represents a methyl group;
$R^2$ represents a hydrogen atom or an aliphatic carboxylic acyl group having from 8 to 16 carbon atoms;
$R^3$ represents a hydrogen atom or an aliphatic carboxylic acyl group having from 8 to 16 carbon atoms;
X represents a fluorine atom, a methoxy group or an ethoxy group;
Y represents an amino group or an aminooxy group; and
Z represents an oxygen atom.

22. The compound of claim 1, wherein:
$R^1$ represents a methyl group;
$R^2$ represents a hydrogen atom or an aliphatic carboxylic acyl group having from 8 to 16 carbon atoms;
$R^3$ represents a hydrogen atom;
X represents a fluorine atom, a methoxy group or an ethoxy group;
Y represents an amino group or an aminooxy group; and
Z represents an oxygen atom.

23. The compound of claim 1, wherein:
$R^1$ represents a methyl group;
$R^2$ represents an octanoyl, decanoyl, dodecanoyl, myristoyl or palmitoyl group;
$R^3$ represents a hydrogen atom, or an octanoyl, decanoyl, dodecanoyl, myristoyl or palmitoyl group;
X represents a fluorine atom, a methoxy group or an ethoxy group;

Y represents an amino group; and

Z represents an oxygen group.

24. The compound of claim 1, wherein:

$R^1$ represents a methyl group;

$R^2$ represents an octanoyl, decanoyl, dodecanoyl, myristoyl or palmitoyl group and $R^3$ represents a hydrogen atom;

X represents a fluorine atom, a methoxy group or an ethoxy group;

Y represents an amino group; and

Z represents an oxygen atom.

25. The compound of claim 1, selected from the group consisting of 5-acetamido-4-guanidino-2,3,4,5,7-pentadeoxy-7-fluoro-D-glycero-D-galacto-non-2-enopyranosoic acid and pharmaceutically acceptable salts and esters thereof.

26. The compound of claim 1, selected from the group consisting of 5-acetamido-4-guanidino-9-O-dodecanoyl-2,3,4,5,7-pentadeoxy-7-fluoro-D-glycero-D-galacto-non-2-enopyranosoic acid and pharmaceutically acceptable salts and esters thereof.

27. The compound of claim 1, selected from the group consisting of 5-acetamido-4-guanidino-9-O-myristoyl-2,3,4,5,7-pentadeoxy-7-fluoro-D-glycero-D-galacto-non-2-enopyranosoic acid and pharmaceutically acceptable salts and esters thereof.

28. The compound of claim 1, selected from the group consisting of 5-acetamido-4-guanidino-9-O-palmitoyl-2,3,4,5,7-pentadeoxy-7-fluoro-D-glycero-D-galacto-non-2-enopyranosoic acid and pharmaceutically acceptable salts and esters thereof.

29. The compound of claim 1, selected from the group consisting of 5-acetamido-4-guanidino-2,3,4,5,7-pentadeoxy-7-methoxy-D-glycero-D-galacto-non-2-enopyranosoic acid and pharmaceutically acceptable salts and esters thereof.

30. The compound of claim 1, selected from the group consisting of 5-acetamido-4-guanidino-9-O-myristoyl-2,3,4,5,7-pentadeoxy-7-methoxy-D-glycero-D-galacto-non-2-enopyranosoic acid and pharmaceutically acceptable salts and esters thereof.

31. The compound of claim 1, selected from the group consisting of 5-acetamido-4-guanidino-2,3,4,5,7-pentadeoxy-7-ethoxy-D-glycero-D-galacto-non-2-enopyranosoic acid and pharmaceutically acceptable salts and esters thereof.

32. The compound of claim 1, selected from the group consisting of 5-acetamido-4-guanidino-9-O-octanoyl-2,3,4,5,7-pentadeoxy-7-ethoxy-D-glycero-D-galacto-non-2-enopyranosoic acid and pharmaceutically acceptable salts and esters thereof.

33. The compound of claim 1, selected from the group consisting of 5-acetamido-4-guanidino-9-O-dodecanoyl-2,3,4,5,7-pentadeoxy-7-ethoxy-D-glycero-D-galacto-non-2-enopyranosoic acid and pharmaceutically acceptable salts and esters thereof.

34. The compound of claim 1, selected from the group consisting of 5-acetamido-4-guanidino-9-myristoyl-2,3,4,5,7-pentadeoxy-7-ethoxy-D-glycero-D-galacto-non-2-enopyranosoic acid and pharmaceutically acceptable salts and esters thereof.

35. The compound of claim 1, selected from the group consisting of 5-acetamido-4-guanidino-9-O-palmitoyl-2,3,4,5,7-pentadeoxy-7-ethoxy-D-glycero-D-galacto-non-2-enopyranosoic acid and pharmaceutically acceptable salts and esters thereof.

36. A method of treating or preventing an infection in a mammal caused by a sialidase-bearing virus, which method comprises administering to said mammal an effective amount of a sialidase inhibitory compound, wherein the sialidase inhibitory compound is at least one compound selected from the group consisting of compounds of formula (I) and pharmaceutically acceptable salts and esters thereof, as claimed in claim 1.

37. The method of claim 36, wherein:

$R^1$ represents a methyl group;

$R^2$ represents a hydrogen atom or an aliphatic carboxylic acyl group having from 6 to 25 carbon atoms;

$R^3$ represents a hydrogen atom or an aliphatic carboxylic acyl group having from 6 to 25 carbon atoms;

X represents a halogen atom or an alkoxy group having from 1 to 4 carbon atoms;

Y represents an amino group or the group of formula $R^bR^cN$—O—; and

Z represents an oxygen atom.

38. The method of claim 36, wherein:

$R^1$ represents a methyl group;

$R^2$ represents a hydrogen atom or an aliphatic carboxylic acyl group having from 8 to 16 carbon atoms;

$R^3$ represents a hydrogen atom or an aliphatic carboxylic acyl group having from 8 to 16 carbon atoms;

X represents a fluorine atom, a methoxy group or an ethoxy group;

Y represents an amino group or an aminooxy group; and

Z represents an oxygen atom.

39. The method of claim 36, wherein:

$R^1$ represents a methyl group;

$R^2$ represents a hydrogen atom or an aliphatic carboxylic acyl group having from 8 to 16 carbon atoms;

$R^3$ represents a hydrogen atom;

X represents a fluorine atom, a methoxy group or an ethoxy group;

Y represents an amino group or an aminooxy group; and

Z represents an oxygen atom.

40. The method of claim 36, wherein:

$R^1$ represents a methyl group;

$R^2$ represents an octanoyl, decanoyl, dodecanoyl, myristoyl or palmitoyl group;

$R^3$ represents a hydrogen atom, or an octanoyl, decanoyl, dodecanoyl, myristoyl or palmitoyl group;

X represents a fluorine atom, a methoxy group or an ethoxy group;

Y represents an amino group; and

Z represents an oxygen atom.

41. The method of claim 36, wherein:

$R^1$ represents a methyl group;

$R^2$ represents an octanoyl, decanoyl, dodecanoyl, myristoyl or palmitoyl group and $R^3$ represents a hydrogen atom;

X represents a fluorine atom, a methoxy group or an ethoxy group;

Y represents an amino group; and

Z represents an oxygen atom.

42. The method of claim 36, wherein the sialidase inhibitory compound is selected from the group consisting of:

5-acetamido-4-guanidino-2,3,4,5,7-pentadeoxy-7-fluoro-D-glycero-D-galacto-non-2-enopyranosoic acid;

5-acetamido-4-guanidino-9-O-dodecanoyl-2,3,4,5,7-pentadeoxy-7-fluoro-D-glycero-D-galacto-non-2-enopyranosoic acid;

5-acetamido-4-guanidino-9-O-myristoyl-2,3,4,5,7-pentadeoxy-7-fluoro-D-glycero-D-galacto-non-2-enopyranosoic acid;

5-acetamido-4-guanidino-9-O-palmitoyl-2,3,4,5,7-pentadeoxy-7-fluoro-D-glycero-D-galacto-non-2-enopyrmosoic acid;

5-acetamido-4-guanidino-2,3,4,5,7-pentadeoxy-7-methoxy-D-glycero-D-galacto-non-2-enopyranosoic acid;

5-acetamido-4-guanidino-9-O-myristoyl-2,3,4,5,7-pentadeoxy-7-methoxy-D-glycero-D-galacto-non-2-enopyranosoic acid;

5-acetamido-4-guanidino-2,3,4,5,7-pentadeoxy-7-ethoxy-D-glycero-D-galacto-non-2-enopyranosoic acid;

5-acetamido-4-guanidino-9-O-octanoyl-2,3,4,5,7-pentadeoxy-7-ethoxy-D-glycero-D-galacto-non-2-enopyranosoic acid;

5-acetamido-4-guanidino-9-O-dodecanoyl-2,3,4,5,7-pentadeoxy-7-ethoxy-D-glycero-D-galacto-non-2-enopyranosoic acid;

5-acetamido-4-guanidino-9-O-myristoyl-2,3,4,5,7-pentadeoxy-7-ethoy-D-glycero-D-galacto-non-2-enopyranosoic acid;

5-acetamido-4-guanidino-9-O-palmitoyl-2,3,4,5,7-pentadeoxy-7-ethoxy-D-glycero-D-galacto-non-2-enopyranosoic acid;

and pharmaceutically acceptable salts and esters thereof.

43. A pharmaceutical composition for the treatment or prevention of infections in a mammal caused by sialidase-bearing viruses, which composition comprises a sialidase inhibitory compound in admixture with a pharmaceutically acceptable carrier or diluent, wherein the sialidase inhibitory compound is at least one compound selected from the group consisting of compounds of formula (I) and pharmaceutically acceptable salts and esters thereof, as claimed in claim 1.

44. The composition of claim 43, wherein:

$R^1$ represents a methyl group;

$R^2$ represents a hydrogen atom or an aliphatic carboxylic acyl group having from 6 to 25 carbon atoms;

$R^3$ represents a hydrogen atom or an aliphatic carboxylic acyl group having from 6 to 25 carbon atoms;

X represents a halogen atom or an alkoxy group having from 1 to 4 carbon atoms;

Y represents an amino group or the group of formula $R^b R^c N$—O—; and

Z represents an oxygen atom.

45. The composition of claim 43, wherein:

$R^1$ represents a methyl group;

$R^2$ represents a hydrogen atom or an aliphatic carboxylic acyl group having from 8 to 16 carbon atoms;

$R^3$ represents a hydrogen atom or an aliphatic carboxylic acyl group having from 8 to 16 carbon atoms;

X represents a fluorine atom, a methoxy group or an ethoxy group;

Y represents an amino group or an aminooxy group; and

Z represents an oxygen atom.

46. The composition of claim 43, wherein:

$R^1$ represents a methyl group;

$R^2$ represents a hydrogen atom or an aliphatic carboxylic acyl group having from 8 to 16 carbon atoms;

$R^3$ represents a hydrogen atom;

X represents a fluorine atom, a methoxy group or an ethoxy group;

Y represents an amino group or an aminooxy group; and

Z represents an oxygen atom.

47. The composition of claim 43, wherein:

$R^1$ represents a methyl group;

$R^2$ represents an octanoyl, decanoyl, dodecanoyl, myristoyl or palmitoyl group $R^3$ represents a hydrogen atom, or an octanoyl, decanoyl, dodecanoyl, myristoyl or palmitoyl group;

X represents a fluorine atom, a methoxy group or an ethoxy group;

Y represents an amino group; and

Z represents an oxygen atom.

48. The composition of claim 43, wherein:

$R^1$ represents a methyl group;

$R^2$ represents an octanoyl, decanoyl, dodecanoyl, myristoyl or palmitoyl group and $R^3$ represents a hydrogen atom;

X represents a fluorine atom, a methoxy group or an ethoxy group;

Y represents an amino group; and

Z represents an oxygen atom.

49. The composition of claim 43, wherein the sialidase inhibitory compound is selected from the group consisting of:

5-acetamido-4-guanidino-2,3,4,5,7-pentadeoxy-7-fluoro-D-glycero-D-galacto-non-2-enopyranosoic acid;

5-acetamido-4-guanidino-9-O-dodecanoyl-2,3,4,5,7-pentadeoxy-7-fluoro-D-glycero-D-galacto-non-2-enopyranosoic acid;

5-acetamido-4-guanidino-9-O-myristoyl-2,3,4,5,7-pentadeoxy-7-fluoro-D-glycero-D-galacto-non-2-enopyranosoic acid;

5-acetamido-4-guanidino-9-O-palmitoyl-2,3,4,5,7-pentadeoxy-7-fluoro-D-glycero-D-galacto-non-2-enopyranosoic acid;

5-acetamido-4-guanidino-2,3,4,5,7-pentadeoxy-7-methoxy-D-glycero-D-galacto-non-2-enopyranosoic acid;

5-acetamido-4-guanidino-9-O-myristoyl-2,3,4,5,7-pentadeoxy-7-methoxy-D-glycero-D-galacto-non-2-enopyranosoic acid;

5-acetamido-4-guanidino-2,3,4,5,7-pentadeoxy-7-ethoxy-D-glycero-D-galacto-non-2-enopyranosoic acid;

5-acetamido-4-guanidino-9-O-octanoyl-2,3,4,5,7-pentadeoxy-7-ethoxy-D-glycero-D-galacto-non-2-enopyranosoic acid;

5-acetamido-4-guanidino-9-O-odecanoyl-2,3,4,5,7-pentadeoxy-7-ethoxy-D-glycero-D-galacto-non-2-enopyranosoic acid;

5-acetamido-4-guanidino-9-O-myirstoyl-2,3,4,5,7-pentadeoxy-7-ethoxy-D-glycero-D-galacto-non-2-enopyranosoic acid;

5-acetamido-4-guanidino-9-O-palmitoyl-2,3,4,5,7-pentadeoxy-7-ethoxy-D-glycero-D-galacto-non-2enopyranosoic acid;

and pharmaceutically acceptable salts and esters thereof.

50. The compound of claim 1, selected from the group consisting of 5-acetamido-4-guanidino-9-O-octanoyl-2,3,4,5,7-pentadeoxy-7-methoxy-D-glycero-D-galacto-non-2-enopyranosoic acid, and pharmaceutically acceptable salts and esters thereof.

51. The compound of claim 1, selected from the group consisting of 5-acetamido-4-guanidino-9-O-decanoyl-2,3,4,5,7-pentadeoxy-7-methoxy-D-glycero-D-galacto-non-2-enopyranosoic acid, and pharmaceutically acceptable salts and esters thereof.

52. The compound of claim 1, selected from the group consisting of 5-acetamido-4-guanidino-9-O-dodecanoyl-2,3,4,5,7-pentadeoxy-7-methoxy-D-glycero-D-galacto-non-2-enopyranosoic acid, and pharmaceutically acceptable salts and esters thereof.

53. The compound of claim 1, selected from the group consisting of 5-acetamido-4-guanidino-9-O-hexadecanoyl-2,3,4,5,7-pentadeoxy-7-methoxy-D-glycero-D-galacto-non-2-enopyranosoic acid, and pharmaceutically acceptable salts and esters thereof.

54. The method of claim 36, wherein the sialidase inhibitory compound is selected from the group consisting of 5-acetamido-4-guanidino-9-O-octanoyl-2,3,4,5,7-pentadeoxy-7-methoxy-D-glycero-D-galacto-non-2-enopyranosoic acid;

5-acetamido-4-guanidino-9-O-decanoyl-2,3,4,5,7-pentadeoxy-7-methoxy-D-glycero-D-galacto-non-2-enopyranosoic acid;

5-acetamido-4-guanidino-9-O-dodecanoyl-2,3,4,5,7-pentadeoxy-7-methoxy-D-glycero-D-galacto-non-2-enopyranosoic acid;

5-acetamido-4-guanidino-9-O-hexadecanoyl-2,3,4,5,7-pentadeoxy-7-methoxy-D-glycero-D-galacto-non-2-enopyranosoic acid; and pharmaceutically acceptable salts and esters thereof.

55. The composition of claim 43, wherein the sialidase inhibitory compound is selected from the group consisting of 5-acetamido-4-guanidino-9-O-octanoyl-2,3,4,5,7-pentadeoxy-7-methoxy-D-glycero-D-galacto-non-2-enopyranosoic acid;

5-acetamido-4-guanidino-9-O-decanoyl-2,3,4,5,7-pentadeoxy-7-methoxy-D-glycero-D-galacto-non-2-enopyranosoic acid;

5-acetamido-4-guanidino-9-O-dodecanoyl-2,3,4,5,7-pentadeoxy-7-methoxy-D-glycero-D-galacto-non-2-enopyranosoic acid;

5-acetamido-4-guanidino-9-O-hexadecanoyl-2,3,4,5,7-pentadeoxy-7-methoxy-D-glycero-D-galacto-non-2-enopyranosoic acid; and pharmaceutically acceptable salts and esters thereof.

56. A compound of formula (I'):

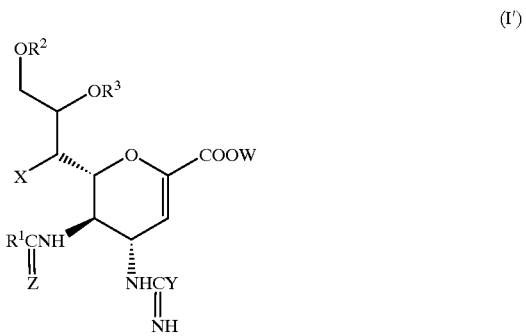

(I')

wherein:

$R^1$ represents an alkyl group having from 1 to 4 carbon atoms;

$R^2$ and $R^3$ are the same as or different from each other and each represents a hydrogen atom or an aliphatic acyl group having from 2 to 25 carbon atoms;

W represents alkyl having 1 to 30 carbon atoms;

X represents a halogen atom or an alkoxy group having from 1 to 4 carbon atoms;

Y represent a group of formula $R^bR^cN-$ or $R^bR^cN-O-$, where $R^b$ and $R^c$ are the same as or different from each other and each represents a hydrogen atom or an alkyl group having from 1 to 4 carbon atoms; and Z represents an oxygen atom or a sulfur atom;

or a pharmaceutically acceptable salt thereof.

57. The compound of claim 50, wherein W represents an alkyl group having 1 to 25 carbon atoms.

58. The compound of claim 56, wherein W represents an alkyl group having from 6 to 25 carbon atoms.

59. The compound of claim 56, wherein W represents a hexyl, undecyl, tetradecyl, hexadecyl or octadecyl group.

60. The compound of claim 56, wherein:

$R^1$ represents a methyl group;

$R^2$ represents a hydrogen atom or an aliphatic carboxylic acyl group having from 6 to 25 carbon atoms;

$R^3$ represents a hydrogen atom or an aliphatic carboxylic acyl group having from 6 to 25 carbon atoms;

X represents a fluorine atom, a methoxy group or an ethoxy group;

Y represents an amino group;

Z represents an oxygen atom; and

W represents an alkyl group having 6 to 25 carbon atoms.

61. The compound of claim 56 wherein:

$R^2$ and $R^3$ represent a hydrogen atom;

X represents methoxy; and

W represents an alkyl group having 6 to 22 carbon atoms.

62. The compound of claim 56 wherein:

W represents an alkyl group having 6 to 18 carbon atoms.

63. The compound of claim 56, selected from the group consisting of 5-acetamido-4-guanidino-2,3,4,5,7-pentadeoxy-7-methoxy-D-glycero-D-galacto-non-2-enopyranosoic acid hexyl ester and pharmaceutically acceptable salts thereof.

64. The compound of claim 56, selected from the group consisting of 5-acetamido-4-guanidino-2,3,4,5,7-pentadeoxy-7-methoxy-D-glycero-D-galacto-non-2-enopyranosoic acid undecyl ester and pharmaceutically acceptable salts thereof.

65. The compound of claim 56, selected from the group consisting of 5-acetamido-4-guanidino-2,3,4,5,7-pentadeoxy-7-methoxy-D-glycero-D-galacto-non-2-enopyranosoic acid tetradecyl ester and pharmaceutically acceptable salts thereof.

66. The compound of claim 56, selected from the group consisting of 5-acetamido-4-guanidino-2,3,4,5,7-pentadeoxy-7-methoxy-D-glycero-D-galacto-non-2-enopyranosoic acid hexadecyl ester and pharmaceutically acceptable salts thereof.

67. The compound of claim 56, selected from the group consisting of 5-acetamido-4-guanidino-2,3,4,5,7-pentadeoxy-7-methoxy-D-glycero-D-galacto-non-2-enopyranosoic acid octadecyl ester and pharmaceutically acceptable salts thereof.

68. A method for the treatment or prevention of viral infections, which method comprises administering a pharmacologically effective amount of an anti-viral compound to a mammal suffering from or susceptible to a viral infection, wherein said anti-viral compound is a compound as claimed in claim 56.

69. The method of claim 68, wherein the sialidase inhibitory compound is selected from the group consisting of 5-acetamido-4-guanidino-2,3,4,5,7-pentadeoxy-7-methoxy-D-glycero-D-galacto-non-2-enopyranosoic acid hexyl ester;

5-acetamido-4-guanidino-2,3,4,5,7-pentadeoxy-7-methoxy-D-glycero-D-galacto-non-2-enopyranosoic acid undecyl ester;

5-acetamido-4-guanidino-2,3,4,5,7-pentadeoxy-7-methoxy-D-glycero-D-galacto-non-2-enopyranosoic acid tetradecyl ester;

5-acetamido-4-guanidino-2,3,4,5,7-pentadeoxy-7-methoxy-D-glycero-D-galacto-non-2-enopyranosoic acid hexadecyl ester;

5-acetamido-4-guanidino-2,3,4,5,7-pentadeoxy-7-methoxy-D-glycero-D-galacto-non-2-enopyranosoic acid octadecyl ester;

and pharmaceutically acceptable salts thereof.

70. A pharmaceutical composition comprising an effective amount of a pharmacologically active compound as claimed in claim 56 together with a pharmacologically acceptable diluent or carrier therefor.

71. The composition of claim 70 wherein the sialidase inhibitory compound is selected from the group consisting of 5-acetamido-4-guanidino-2,3,4,5,7-pentadeoxy-7-methoxy-D-glycero-D-galacto-non-2-enopyranosoic acid hexyl ester;

5-acetamido-4-guanidino-2,3,4,5,7-pentadeoxy-7-methoxy-D-glycero-D-galacto-non-2-enopyranosoic acid undecyl ester;

5-acetamido-4-guanidino-2,3,4,5,7-pentadeoxy-7-methoxy-D-glycero-D-galacto-non-2-enopyranosoic acid tetradecyl ester;

5-acetamido-4-guanidino-2,3,4,5,7-pentadeoxy-7-methoxy-D-glycero-D-galacto-non-2-enopyranosoic acid hexadecyl ester;

5-acetamido-4-guanidino-2,3,4,5,7-pentadeoxy-7-methoxy-D-glycero-D-galacto-non-2-enopyranosoic acid octadecyl ester;

and pharmaceutically acceptable salts thereof.

* * * * *

UNITED STATES PATENT AND TRADEMARK OFFICE
CERTIFICATE OF CORRECTION

PATENT NO. : 6,340,702 B1
DATED : January 22, 2002
INVENTOR(S) : Honda et al.

Page 1 of 1

It is certified that error appears in the above-identified patent and that said Letters Patent is hereby corrected as shown below:

Column 102,
Line 6, after "cosolvent" delete "3".

Column 234,
Line 1, after "EXAMPLE" delete "6" and insert -- 6' --.

Column 236,
Line 19, after "EXAMPLE" delete "7" and insert -- 7' --.

Signed and Sealed this

Twenty-ninth Day of June, 2004

JON W. DUDAS
*Acting Director of the United States Patent and Trademark Office*